US007369946B2

(12) United States Patent
Bump et al.

(10) Patent No.: US 7,369,946 B2
(45) Date of Patent: May 6, 2008

(54) METHOD OF IDENTIFYING INHIBITORS OF TIE-2

(75) Inventors: Nancy J. Bump, Lowell, MA (US); Lee D. Arnold, Westborough, MA (US); Richard W. Dixon, Jefferson, MA (US); Hans Wolfgang Hoeffken, Ludwigshafen (DE); Karen Allen, Weston, MA (US); Cornelia Bellamacina, Dedham, MA (US)

(73) Assignee: Abbott GmbH & Co. KG, Wiesbaden (DE)

( * ) Notice: Subject to any disclaimer, the term of this patent is extended or adjusted under 35 U.S.C. 154(b) by 28 days.

(21) Appl. No.: 09/815,341

(22) Filed: Mar. 22, 2001

(65) Prior Publication Data

US 2003/0082622 A1 May 1, 2003

Related U.S. Application Data

(60) Provisional application No. 60/192,920, filed on Mar. 29, 2000.

(51) Int. Cl.
*G06F 19/00* (2006.01)
(52) U.S. Cl. .......................... 702/27; 702/19; 435/7.1; 435/69.2; 435/183
(58) Field of Classification Search ................ 702/27; 536/23.1; 436/7.1; 530/350; 544/280
See application file for complete search history.

(56) References Cited

U.S. PATENT DOCUMENTS

| 5,447,860 | A | * | 9/1995 | Ziegler ................... 435/240.1 |
| 6,001,839 | A |   | 12/1999 | Calderwood et al. ....... 514/258 |
| 6,160,092 | A | * | 12/2000 | Chen et al. ................. 530/350 |

FOREIGN PATENT DOCUMENTS

| WO | WO98/07835 | 2/1998 |
| WO | WO98/41525 | 9/1998 |
| WO | WO00/17202 | 3/2000 |
| WO | WO00/17203 | 3/2000 |
| WO | WO01/72761 | 10/2001 |

OTHER PUBLICATIONS

L06139, GENBANK, Jan. 14, 1995.*
Vikkula et al. Vascular Dysmorphogenesis Caused by an Activating Mutation in the Receptor Tyrosine Kinase TIE2. Cell, 1996, vol. 87, pp. 1181-1190.*
Drenth, Crystallizing a Protein, Principles of Protein X-ray Crystallography, 1994, Springer, pp. 1-19.*
Schlessinger and Ulrich, "Growth Factor Signaling by Receptor Tyrosine Kinases", Neuron, 9:383-391, (1992).
Yarden and Ullrich, "Growth Factor Receptor Tyrosine Kinases", Ann. Rev. Biochem. 57:443-478, (1988).
Ullrich & Schlessinger, "Signal Transduction by Receptors with Tyrosine Kinase Activity", Cell, 61:203-212, (1990).
Fantl et al., "Distinct Phosphotyrosines on a Growth Factor Receptor Bind to Specific Molecules that Mediate Different Signaling Pathways", Cell, 69:413-423, (1992).
Songyang et al., "Specific Motifs Recognized by the SH2 Domains of Csk, 3BP2, fps/fes, GRB-2, HCP, SHC, Syk and Vav", Mol. Cell. Biol., 14:2777-2785, (1994).
Songyang et al., "SH2 Domains Recognize Specific Phosphopeptide Sequences", Cell 72:767-778, (1993).
Koch et al., "SH2 and SH3 Domains: Elements that Control Interactions of Cytoplasmic Signaling Proteins", Science 252:668-674, (1991).
Shoelson, "SH2 and PTB Domain Interactions in Tyrosine Kinase Signal Transduction", Curr. Opin. Chem. Biol., 1(2), 227-234, (1997).
Cowburn, "Peptide Recognition by PTB and PDZ Domains", Curr. Opin. Struct. Biol., 7(6), 835-838, (1997).
Mustonen and Alitalo, "Endothelial Receptor Tyrosine Kinases Involved in Angiogenesis", J. Cell Biol. 129:895-898, (1995).
Ziegler, et al., "Molecular Cloning and Characterization of a Novel Receptor Protein Tyrosine Kinase from Human Placenta", Oncogene, 8:663, (1993).
Jones, N., et al., "Identification of Tek/Tie2 Binding Partners", J. Biol. Chem., 274(43):30896, (1999).
Needleman and Wunsch, "A General Method Applicable to the Search for Similarities in the Amino Acid Sequence of Two Proteins", J. Mol. Biol. (48):443-453 (1970).
Devereux, J., et al., "A Comprehensive Set of Sequence Analysis Programs for the VAX", Nucleic Acids Res. 12(1):387, (1984).
E. Meyers and W. Miller, "Optimal Alignments in Linear Space", CABIOS, 4:11-17, (1989).
Altschul, et al. "Basic Local Alignment Search Tool", J. Mol. Biol. 215:403-10, (1990).
Altschul et al., "Gapped BLAST and PSI-BLAST: A New Generation of Protein Database Search Programs", Nucleic Acids Res. 25(17):3389-3402, (1997).
Roger Sayle et al., "RASMOL: Biomolecular Graphic for All", Trends Biochem. Sci. 20: 374-376, (1995).
Nicholls et al., "Protein Folding and Association: Insights from the Interfacial and Thermodynamic Properties of Hydrocarbons", Proteins 11: 281-289, (1991).
Voller, et al., (1980) "Enzyme-Linked Immunosorbent Assay," In: Manual of Clinical Immunology, 2d ed., edited by Rose and Friedman, pp. 359-371 Am. Soc. of Microbiology, Washington, D.C.
Ferrin et al., "The MIDAS Display System", J. Mol. Graphics 6:13-27, (1988).

(Continued)

*Primary Examiner*—Carolyn L. Smith
(74) *Attorney, Agent, or Firm*—Kenneth P. Zwicker; Gayle B. O'Brien

(57) ABSTRACT

The present invention relates to polypeptides which comprise the ligand binding domain of Tie-2, crystalline forms of these polypeptides and the use of these crystalline forms to determine the three dimensional structure of the catalytic domain of Tie-2. The invention also relates to the use of the three dimensional structure of the Tie-2 catalytic domain both alone, or in complex with inhibitors, in methods of designing and/or identifying potential inhibitors of Tie-2 activity, for example, compounds which inhibit the binding of a native substrate to the Tie-2 catalytic domain.

15 Claims, 171 Drawing Sheets

OTHER PUBLICATIONS

Rarey et al., "A Fast Flexible Docking Method Using an Incremental Construction Algorithm", J. Mol. Biol. 261: 470-489, (1996).

Kuntz et al., "A Geometric Approach to Macromolecule-Ligand Interactions", J. Mol. Biol., 161: 269-288, (1982).

Boehm, "The Computer Program LUDI: A New Method for the De Novo Design of Enzyme Inhibitors", J Comp. Aid. Mol. Des. 6:61-78, (1992).

Bartlett et al. "CAVEAT: A Program to Facilitate the Structure-derived Design of Biologically Active Molecules" in Molecular Recognition in Chemical and Biological Problems, special publication of The Royal Chem. Soc., 78:182-196, (1989).

Miranker et al. "Functionality Maps of Binding Sites: A Multiple Copy Simultaneous Search Method", Proteins 11: 29-34, (1991).

Moon et al. "Computer Design of Bioactive Molecules: A Method for Receptor-Based de Novo Ligand Design", Proteins 11:314-328, (1991).

Gillet et al. "SPROUT: A Program for Structure Generation", J Comp. Aid. Mol. Des. 7:127, (1993).

Muegge et al., "A General and Fast Scoring Function for Protein-Ligand Interaction: A Simplified Potential Approach", J Med. Chem. 42:791-804, (1999).

Cohen et al., "Molecular Modeling Software and Methods for Medicinal Chemistry", J. Med. Chem. 33: 883-894, (1990).

Navia et al. "Use of Structural Information in Drug Design", Current Opinions in Structural Biology 2: 202-210, (1992).

Baldwin et al. "Thienothiopyran-2-sulfonamides: Novel Topically Active Carbonic Anhydrase Inhibitors for the Treatment of Glaucoma", J. Med. Chem. 32: 2510-2513, (1989).

Appelt et al. "Design of Enzyme Inhibitors Using Iterative Protein Crystallographic Analysis", J. Med. Chem. 34: 1925-1934, (1991).

Ealick et al. "Application of Crystallographic and Modeling Methods in the Design of Purine Nucleoside Phosphorylase Inhibitors", Proc. Nat. Acad. Sci. USA 88: 11540-11544, (1991).

Brunger et al., "Crystallography & NMR System: A New Suite for Macromolecular Structure Determination", Acta Cryst., D54, 905-921, (1998).

Collaborative Computational Project, No. 4, "The CCP4 Suite: Programs for Protein Crystallography", Acta Crys.t D50, 760-763, (1994).

Jones, A.T and Kjeldgaard, M. "Electron-Density Map Interpretation", Methods in Enzymology 277, 173-208, (1997).

Kleywegt G. J. and Jones, T.A. "Detecting Folding Motifs and Similarities in Protein Structures", Methods in Enzymology 277, 525-545, (1997).

Kleywegt G. J., "Dictionaries for Heteros", ESF/CCP4 Newsletter 31, 45-50, (1995).

Navaza, J., "AmoRe: An Automated Package for Molecular Replacement", Acta Cryst. A50, 157-163, (1994).

Z. Songyang et al., "Catalytic Specificity of Protein-Tyrosine Kinases is Critical for Selective Signalling", Nature. 373:536-539, 1995.

\* cited by examiner

MDSLASLVLC GVSLLLSGTV EGAMDLILIN SLPLVSDAET SLTCIASGWR PHEPITIGRD
FEALMNQHQD PLEVTQDVTR EWAKKVVWKR EKASKINGAY FCEGRVRGEA IRIRTMKMRQ
QASFLPATLT MTVDKGDNVN ISFKKVLIKE EDAVIYKNGS FIHSVPRHEV PDILEVHLPH
AQPQDAGVYS ARYIGGNLFT SAFTRLIVRR CEAQKWGPEC NHLCTACMNN GVCHEDTGEC
ICPPGFMGRT CEKACELHTF GRTCKERCSG QEGCKSYVFC LPDPYGCSCA TGWKGLQCNE
ACHPGFYGPD CKLRCSCNNG EMCDRFQGCL CSPGWQGLQC EREGIPRMTP KIVDLPDHIE
VNSGKFNPIC KASGWPLPTN EEMTLVKPDG TVLHPKDFNH TDHFSVAIFT IHRILPPDSG
VWVCSVNTVA GMVEKPFNIS VKVLPKPLNA PNVIDTGHNF AVINISSEPY FGDGPIKSKK
LLYKPVNHYE AWQHIQVTNE IVTLNYLEPR TEYELCVQLV RRGEGGEGHP GPVRRFTTAS
IGLPPPRGLN LLPKSQTTLN LTWQPIFPSS EDDFYVEVER RSVQKSDQQN IKVPGNLTSV
LLNNLHPREQ YVVRARVNTK AQGEWSEDLT AWTLSDILPP QPENIKISNI THSSAVISWT
ILDGYSISSI TIRYKVQGKN EDQHVDVKIK NATIIQYQLK GLEPETAYQV DIFAENNIGS
SNPAFSHELV TLPESQAPAD LGGGKMLLIA ILGSAGMTCL TVLLAFLIIL QLKRANVQRR
MAQAFQNVRE EPAVQFNSGT LALNRKVKNN PDPTIYPVLD WNDIKFQDVI GEGNFGQVLK
ARIKKDGLRM DAAIKRMKEY ASKDDHRDFA GELEVLCKLG HHPNIINLLG ACEHRGYLYL
AIEYAPHGNL LDFLRKSRVL ETDPAFAIAN STASTLSSQQ LLHFAADVAR GMDYLSQKQF
IHRDLAARNI LVGENYVAKI ADFGLSRGQE VYVKKTMGRL PVRWMAIESL NYSVYTTNSD
VWSYGVLLWE IVSLGGTPYC GMTCAELYEK LPQGYRLEKP LNCDDEVYDL MRQCWREKPY
ERPSFAQILV SLNRMLEERK TYVNTTLYEK FTYAGIDCSA EEAA

FIG. 1

ALNRKVKNN    PDPTIYPVLD    WNDIKFQDVI    GEGNFGQVLK
ARIKKDGLRM   DAAIKRMKEY    ASKDDHRDFA    GELEVLCKLG
HHPNIINLLG   ACEHRGYLYL    AIEYAPHGNL    LDFLRKSRVL
ETDPAFAIAN   STASTLSSQQ    LLHFAADVAR    GMDYLSQKQF
IHRNLAARNI   LVGENYVAKI    ADFGLSRGQE    VYVKKTMGRL
PVRWMAIESL   NYSVYTTNSD    VWSYGVLLWE    IVSLGGTPYC
GMTCAELYEK   LPQGYRLEKP    LNCDDEVYDL    MRQCWREKPY
ERPSFAQILV   SLNRMLEERK    TYVNTTLYEK    FTYAGIDCSA
EEAA

FIG. 2

```
CRYST1   95.604  117.589   78.214  90.00  90.00  90.00
ORIGX1       1.000000  0.000000  0.000000        0.00000
ORIGX2       0.000000  1.000000  0.000000        0.00000
ORIGX3       0.000000  0.000000  1.000000        0.00000
SCALE1       0.010460  0.000000  0.000000        0.00000
SCALE2       0.000000  0.008504  0.000000        0.00000
SCALE3       0.000000  0.000000  0.012785        0.00000
ATOM     1  CB  VAL   818       5.159  51.390 -17.822  1.00 65.41      6
ATOM     2  C   VAL   818       3.553  51.091 -15.926  1.00 99.70      6
ATOM     3  O   VAL   818       2.603  51.682 -16.444  1.00 99.70      8
ATOM     4  N   VAL   818       4.074  49.203 -17.428  1.00 99.70      7
ATOM     5  CA  VAL   818       4.628  50.419 -16.774  1.00 99.70      6
ATOM     6  N   LEU   819       3.729  50.991 -14.616  1.00100.00      7
ATOM     7  CA  LEU   819       2.912  51.555 -13.639  1.00100.00      6
ATOM     8  CB  LEU   819       3.310  51.175 -12.250  1.00 77.77      6
ATOM     9  CG  LEU   819       2.625  51.796 -11.045  1.00 67.90      6
ATOM    10  CD1 LEU   819       1.161  51.416 -11.022  1.00 67.90      6
ATOM    11  CD2 LEU   819       3.336  51.313  -9.810  1.00 67.90      6
ATOM    12  C   LEU   819       2.607  53.076 -13.729  1.00100.00      6
ATOM    13  O   LEU   819       3.568  53.838 -13.899  1.00100.00      8
ATOM    14  N   ASP   820       1.351  53.507 -13.602  1.00100.00      7
ATOM    15  CA  ASP   820       0.990  54.928 -13.659  1.00100.00      6
ATOM    16  CB  ASP   820      -0.505  55.084 -13.929  1.00100.00      6
ATOM    17  CG  ASP   820      -0.910  56.525 -14.140  1.00100.00      6
ATOM    18  OD1 ASP   820      -2.054  56.874 -13.785  1.00100.00      8
ATOM    19  OD2 ASP   820      -0.087  57.303 -14.663  1.00100.00      8
ATOM    20  C   ASP   820       1.314  55.593 -12.329  1.00100.00      6
ATOM    21  O   ASP   820       0.786  55.200 -11.290  1.00100.00      8
ATOM    22  N   TRP   821       2.171  56.605 -12.361  1.00100.00      7
ATOM    23  CA  TRP   821       2.558  57.278 -11.132  1.00100.00      6
ATOM    24  CB  TRP   821       3.291  58.582 -11.458  1.00 96.30      6
ATOM    25  CG  TRP   821       3.985  59.118 -10.263  1.00 96.04      6
ATOM    26  CD2 TRP   821       3.369  59.782  -9.149  1.00 96.04      6
ATOM    27  CE2 TRP   821       4.371  59.991  -8.185  1.00 96.04      6
ATOM    28  CE3 TRP   821       2.061  60.200  -8.869  1.00 96.04      6
ATOM    29  CD1 TRP   821       5.302  58.974  -9.938  1.00 96.04      6
ATOM    30  NE1 TRP   821       5.545  59.494  -8.689  1.00 96.04      7
ATOM    31  CZ2 TRP   821       4.106  60.614  -6.976  1.00 96.04      6
ATOM    32  CZ3 TRP   821       1.803  60.816  -7.657  1.00 96.04      6
ATOM    33  CH2 TRP   821       2.824  61.007  -6.733  1.00 96.04      6
ATOM    34  C   TRP   821       1.355  57.543 -10.207  1.00100.00      6
ATOM    35  O   TRP   821       1.462  57.434  -8.983  1.00100.00      8
ATOM    36  N   ASN   822       0.207  57.853 -10.801  1.00 78.55      7
ATOM    37  CA  ASN   822      -1.018  58.149 -10.061  1.00 78.55      6
ATOM    38  CB  ASN   822      -2.158  58.380 -11.037  1.00100.00      6
ATOM    39  CG  ASN   822      -3.126  59.416 -10.546  1.00100.00      6
ATOM    40  OD1 ASN   822      -3.508  60.321 -11.291  1.00100.00      8
ATOM    41  ND2 ASN   822      -3.536  59.303  -9.286  1.00100.00      7
ATOM    42  C   ASN   822      -1.453  57.094  -9.048  1.00 78.55      6
ATOM    43  O   ASN   822      -1.451  57.340  -7.842  1.00 78.55      8
ATOM    44  N   ASP   823      -1.854  55.933  -9.554  1.00 95.03      7
ATOM    45  CA  ASP   823      -2.308  54.841  -8.704  1.00 95.03      6
ATOM    46  CB  ASP   823      -2.991  53.775  -9.562  1.00 65.89      6
ATOM    47  C   ASP   823      -1.158  54.218  -7.916  1.00 95.03      6
```

FIG. 3A

| ATOM | 48 | O | ASP | 823 | -0.967 | 53.008 | -7.949 | 1.00 | 95.03 | 8 |
| ATOM | 49 | N | ILE | 824 | -0.384 | 55.043 | -7.221 | 1.00 | 88.67 | 7 |
| ATOM | 50 | CA | ILE | 824 | 0.729 | 54.531 | -6.426 | 1.00 | 88.67 | 6 |
| ATOM | 51 | CB | ILE | 824 | 2.112 | 54.819 | -7.082 | 1.00 | 53.67 | 6 |
| ATOM | 52 | CG2 | ILE | 824 | 3.202 | 54.080 | -6.326 | 1.00 | 56.64 | 6 |
| ATOM | 53 | CG1 | ILE | 824 | 2.161 | 54.314 | -8.526 | 1.00 | 56.64 | 6 |
| ATOM | 54 | CD1 | ILE | 824 | 3.503 | 54.615 | -9.196 | 1.00 | 56.64 | 6 |
| ATOM | 55 | C | ILE | 824 | 0.701 | 55.176 | -5.041 | 1.00 | 88.67 | 6 |
| ATOM | 56 | O | ILE | 824 | 1.617 | 55.912 | -4.665 | 1.00 | 88.67 | 8 |
| ATOM | 57 | N | LYS | 825 | -0.361 | 54.889 | -4.292 | 1.00 | 65.97 | 7 |
| ATOM | 58 | CA | LYS | 825 | -0.552 | 55.426 | -2.947 | 1.00 | 65.97 | 6 |
| ATOM | 59 | CB | LYS | 825 | -1.917 | 54.995 | -2.406 | 1.00 | 30.30 | 6 |
| ATOM | 60 | C | LYS | 825 | 0.544 | 55.003 | -1.973 | 1.00 | 65.97 | 6 |
| ATOM | 61 | O | LYS | 825 | 0.502 | 53.909 | -1.401 | 1.00 | 65.97 | 8 |
| ATOM | 62 | N | PHE | 826 | 1.526 | 55.879 | -1.788 | 1.00 | 96.52 | 7 |
| ATOM | 63 | CA | PHE | 826 | 2.632 | 55.608 | -0.878 | 1.00 | 96.52 | 6 |
| ATOM | 64 | CB | PHE | 826 | 3.784 | 56.586 | -1.112 | 1.00 | 96.59 | 6 |
| ATOM | 65 | CG | PHE | 826 | 4.397 | 56.474 | -2.463 | 1.00 | 100.00 | 6 |
| ATOM | 66 | CD1 | PHE | 826 | 3.989 | 57.310 | -3.489 | 1.00 | 100.00 | 6 |
| ATOM | 67 | CD2 | PHE | 826 | 5.351 | 55.500 | -2.726 | 1.00 | 100.00 | 6 |
| ATOM | 68 | CE1 | PHE | 826 | 4.518 | 57.181 | -4.764 | 1.00 | 100.00 | 6 |
| ATOM | 69 | CE2 | PHE | 826 | 5.888 | 55.358 | -4.001 | 1.00 | 100.00 | 6 |
| ATOM | 70 | CZ | PHE | 826 | 5.469 | 56.202 | -5.023 | 1.00 | 100.00 | 6 |
| ATOM | 71 | C | PHE | 826 | 2.158 | 55.727 | 0.565 | 1.00 | 96.52 | 6 |
| ATOM | 72 | O | PHE | 826 | 1.746 | 56.794 | 0.991 | 1.00 | 96.52 | 8 |
| ATOM | 73 | N | GLN | 827 | 2.247 | 54.651 | 1.332 | 1.00 | 100.00 | 7 |
| ATOM | 74 | CA | GLN | 827 | 1.769 | 54.708 | 2.698 | 1.00 | 100.00 | 6 |
| ATOM | 75 | CB | GLN | 827 | 0.886 | 53.484 | 2.937 | 1.00 | 100.00 | 6 |
| ATOM | 76 | CG | GLN | 827 | -0.252 | 53.407 | 1.903 | 1.00 | 100.00 | 6 |
| ATOM | 77 | CD | GLN | 827 | -1.539 | 52.860 | 2.488 | 1.00 | 100.00 | 6 |
| ATOM | 78 | OE1 | GLN | 827 | -1.553 | 51.771 | 3.060 | 1.00 | 100.00 | 8 |
| ATOM | 79 | NE2 | GLN | 827 | -2.633 | 53.615 | 2.349 | 1.00 | 100.00 | 7 |
| ATOM | 80 | C | GLN | 827 | 2.840 | 54.886 | 3.781 | 1.00 | 100.00 | 6 |
| ATOM | 81 | O | GLN | 827 | 2.892 | 55.942 | 4.395 | 1.00 | 100.00 | 8 |
| ATOM | 82 | N | ASP | 828 | 3.696 | 53.894 | 4.015 | 1.00 | 99.72 | 7 |
| ATOM | 83 | CA | ASP | 828 | 4.713 | 54.034 | 5.064 | 1.00 | 99.72 | 6 |
| ATOM | 84 | CB | ASP | 828 | 4.144 | 53.510 | 6.388 | 1.00 | 87.03 | 6 |
| ATOM | 85 | CG | ASP | 828 | 5.121 | 53.627 | 7.533 | 1.00 | 84.60 | 6 |
| ATOM | 86 | OD1 | ASP | 828 | 5.870 | 54.617 | 7.572 | 1.00 | 84.60 | 8 |
| ATOM | 87 | OD2 | ASP | 828 | 5.128 | 52.740 | 8.406 | 1.00 | 84.60 | 8 |
| ATOM | 88 | C | ASP | 828 | 6.003 | 53.286 | 4.720 | 1.00 | 99.72 | 6 |
| ATOM | 89 | O | ASP | 828 | 5.961 | 52.262 | 4.034 | 1.00 | 99.72 | 8 |
| ATOM | 90 | N | VAL | 829 | 7.154 | 53.772 | 5.178 | 1.00 | 85.45 | 7 |
| ATOM | 91 | CA | VAL | 829 | 8.408 | 53.075 | 4.863 | 1.00 | 85.45 | 6 |
| ATOM | 92 | CB | VAL | 829 | 9.606 | 53.874 | 5.391 | 1.00 | 51.35 | 6 |
| ATOM | 93 | C | VAL | 829 | 8.460 | 51.633 | 5.402 | 1.00 | 85.45 | 6 |
| ATOM | 94 | O | VAL | 829 | 8.437 | 51.418 | 6.615 | 1.00 | 85.45 | 8 |
| ATOM | 95 | N | ILE | 830 | 8.538 | 50.663 | 4.488 | 1.00 | 100.00 | 7 |
| ATOM | 96 | CA | ILE | 830 | 8.598 | 49.244 | 4.852 | 1.00 | 100.00 | 6 |
| ATOM | 97 | CB | ILE | 830 | 8.745 | 48.326 | 3.602 | 1.00 | 100.00 | 6 |
| ATOM | 98 | CG2 | ILE | 830 | 9.458 | 47.031 | 3.973 | 1.00 | 81.07 | 6 |
| ATOM | 99 | CG1 | ILE | 830 | 7.370 | 48.034 | 2.994 | 1.00 | 81.07 | 6 |
| ATOM | 100 | CD1 | ILE | 830 | 6.385 | 47.414 | 3.969 | 1.00 | 81.07 | 6 |
| ATOM | 101 | C | ILE | 830 | 9.788 | 49.013 | 5.769 | 1.00 | 100.00 | 6 |
| ATOM | 102 | O | ILE | 830 | 9.782 | 48.103 | 6.596 | 1.00 | 100.00 | 8 |
| ATOM | 103 | N | GLY | 831 | 10.821 | 49.834 | 5.605 | 1.00 | 95.79 | 7 |
| ATOM | 104 | CA | GLY | 831 | 11.992 | 49.713 | 6.453 | 1.00 | 95.79 | 6 |

FIG. 3B

| ATOM | 105 | C | GLY | 831 | 13.352 | 49.743 | 5.806 | 1.00 | 95.79 | 6 |
|------|-----|-----|-----|-----|--------|--------|-------|------|-------|---|
| ATOM | 106 | O | GLY | 831 | 13.497 | 50.005 | 4.613 | 1.00 | 95.79 | 8 |
| ATOM | 107 | N | GLU | 832 | 14.357 | 49.480 | 6.630 | 1.00 | 99.78 | 7 |
| ATOM | 108 | CA | GLU | 832 | 15.760 | 49.427 | 6.231 | 1.00 | 99.78 | 6 |
| ATOM | 109 | CB | GLU | 832 | 16.055 | 48.055 | 5.602 | 1.00 | 100.00 | 6 |
| ATOM | 110 | CG | GLU | 832 | 16.417 | 46.997 | 6.632 | 1.00 | 100.00 | 6 |
| ATOM | 111 | CD | GLU | 832 | 17.103 | 47.598 | 7.859 | 1.00 | 100.00 | 6 |
| ATOM | 112 | OE1 | GLU | 832 | 16.380 | 48.153 | 8.721 | 1.00 | 100.00 | 8 |
| ATOM | 113 | OE2 | GLU | 832 | 18.352 | 47.535 | 7.943 | 1.00 | 100.00 | 8 |
| ATOM | 114 | C | GLU | 832 | 16.376 | 50.502 | 5.339 | 1.00 | 99.78 | 6 |
| ATOM | 115 | O | GLU | 832 | 15.689 | 51.284 | 4.679 | 1.00 | 99.78 | 8 |
| ATOM | 116 | N | GLY | 833 | 17.708 | 50.501 | 5.333 | 1.00 | 100.00 | 7 |
| ATOM | 117 | CA | GLY | 833 | 18.494 | 51.424 | 4.536 | 1.00 | 100.00 | 6 |
| ATOM | 118 | C | GLY | 833 | 19.580 | 50.682 | 3.756 | 1.00 | 100.00 | 6 |
| ATOM | 119 | O | GLY | 833 | 19.557 | 49.446 | 3.693 | 1.00 | 100.00 | 8 |
| ATOM | 120 | N | ASN | 834 | 20.540 | 51.432 | 3.192 | 1.00 | 100.00 | 7 |
| ATOM | 121 | CA | ASN | 834 | 21.643 | 50.854 | 2.407 | 1.00 | 100.00 | 6 |
| ATOM | 122 | CB | ASN | 834 | 22.414 | 49.810 | 3.241 | 1.00 | 100.00 | 6 |
| ATOM | 123 | CG | ASN | 834 | 23.700 | 49.360 | 2.579 | 1.00 | 100.00 | 6 |
| ATOM | 124 | OD1 | ASN | 834 | 23.727 | 49.066 | 1.387 | 1.00 | 100.00 | 8 |
| ATOM | 125 | ND2 | ASN | 834 | 24.778 | 49.302 | 3.354 | 1.00 | 100.00 | 7 |
| ATOM | 126 | C | ASN | 834 | 21.094 | 50.179 | 1.149 | 1.00 | 100.00 | 6 |
| ATOM | 127 | O | ASN | 834 | 20.299 | 49.228 | 1.240 | 1.00 | 100.00 | 8 |
| ATOM | 128 | N | PHE | 835 | 21.519 | 50.650 | -0.030 | 1.00 | 100.00 | 7 |
| ATOM | 129 | CA | PHE | 835 | 21.056 | 50.117 | -1.328 | 1.00 | 100.00 | 6 |
| ATOM | 130 | CB | PHE | 835 | 22.041 | 49.061 | -1.877 | 1.00 | 100.00 | 6 |
| ATOM | 131 | CG | PHE | 835 | 23.383 | 49.629 | -2.294 | 1.00 | 100.00 | 6 |
| ATOM | 132 | CD1 | PHE | 835 | 24.562 | 48.976 | -1.954 | 1.00 | 100.00 | 6 |
| ATOM | 133 | CD2 | PHE | 835 | 23.465 | 50.835 | -2.996 | 1.00 | 100.00 | 6 |
| ATOM | 134 | CE1 | PHE | 835 | 25.808 | 49.509 | -2.291 | 1.00 | 100.00 | 6 |
| ATOM | 135 | CE2 | PHE | 835 | 24.706 | 51.380 | -3.342 | 1.00 | 100.00 | 6 |
| ATOM | 136 | CZ | PHE | 835 | 25.879 | 50.718 | -2.987 | 1.00 | 100.00 | 6 |
| ATOM | 137 | C | PHE | 835 | 19.641 | 49.519 | -1.261 | 1.00 | 100.00 | 6 |
| ATOM | 138 | O | PHE | 835 | 19.380 | 48.467 | -1.841 | 1.00 | 100.00 | 8 |
| ATOM | 139 | N | GLY | 836 | 18.748 | 50.228 | -0.570 | 1.00 | 100.00 | 7 |
| ATOM | 140 | CA | GLY | 836 | 17.369 | 49.813 | -0.397 | 1.00 | 100.00 | 6 |
| ATOM | 141 | C | GLY | 836 | 16.689 | 50.596 | 0.720 | 1.00 | 100.00 | 6 |
| ATOM | 142 | O | GLY | 836 | 17.188 | 50.622 | 1.840 | 1.00 | 100.00 | 8 |
| ATOM | 143 | N | GLN | 837 | 15.571 | 51.261 | 0.418 | 1.00 | 100.00 | 7 |
| ATOM | 144 | CA | GLN | 837 | 14.831 | 52.043 | 1.420 | 1.00 | 100.00 | 6 |
| ATOM | 145 | CB | GLN | 837 | 15.333 | 53.505 | 1.397 | 1.00 | 100.00 | 6 |
| ATOM | 146 | CG | GLN | 837 | 14.344 | 54.609 | 1.081 | 1.00 | 100.00 | 6 |
| ATOM | 147 | CD | GLN | 837 | 15.041 | 55.948 | 0.852 | 1.00 | 100.00 | 6 |
| ATOM | 148 | OE1 | GLN | 837 | 15.798 | 56.108 | -0.108 | 1.00 | 100.00 | 8 |
| ATOM | 149 | NE2 | GLN | 837 | 14.796 | 56.912 | 1.739 | 1.00 | 100.00 | 7 |
| ATOM | 150 | C | GLN | 837 | 13.327 | 51.889 | 1.138 | 1.00 | 100.00 | 6 |
| ATOM | 151 | O | GLN | 837 | 12.525 | 52.818 | 1.236 | 1.00 | 100.00 | 8 |
| ATOM | 152 | N | VAL | 838 | 12.993 | 50.652 | 0.789 | 1.00 | 49.78 | 7 |
| ATOM | 153 | CA | VAL | 838 | 11.645 | 50.199 | 0.469 | 1.00 | 49.78 | 6 |
| ATOM | 154 | CB | VAL | 838 | 11.565 | 48.683 | 0.604 | 1.00 | 54.51 | 6 |
| ATOM | 155 | CG1 | VAL | 838 | 11.159 | 48.064 | -0.703 | 1.00 | 54.51 | 6 |
| ATOM | 156 | CG2 | VAL | 838 | 12.902 | 48.146 | 1.071 | 1.00 | 54.51 | 6 |
| ATOM | 157 | C | VAL | 838 | 10.515 | 50.785 | 1.303 | 1.00 | 49.78 | 6 |
| ATOM | 158 | O | VAL | 838 | 10.694 | 51.096 | 2.481 | 1.00 | 49.78 | 8 |
| ATOM | 159 | N | LEU | 839 | 9.344 | 50.916 | 0.684 | 1.00 | 44.19 | 7 |
| ATOM | 160 | CA | LEU | 839 | 8.171 | 51.461 | 1.369 | 1.00 | 44.19 | 6 |
| ATOM | 161 | CB | LEU | 839 | 7.935 | 52.921 | 0.962 | 1.00 | 90.21 | 6 |

FIG. 3C

```
ATOM    162  CG   LEU    839       9.039   53.975    1.060  1.00  84.90      6
ATOM    163  CD1  LEU    839      10.061   53.788   -0.028  1.00  84.90      6
ATOM    164  CD2  LEU    839       8.417   55.343    0.924  1.00  84.90      6
ATOM    165  C    LEU    839       6.900   50.671    1.061  1.00  44.19      6
ATOM    166  O    LEU    839       6.814   50.010    0.033  1.00  44.19      8
ATOM    167  N    LYS    840       5.920   50.740    1.959  1.00  64.49      7
ATOM    168  CA   LYS    840       4.642   50.068    1.744  1.00  64.49      6
ATOM    169  CB   LYS    840       3.953   49.727    3.066  1.00  84.80      6
ATOM    170  CG   LYS    840       2.531   49.222    2.900  1.00  81.21      6
ATOM    171  CD   LYS    840       2.073   48.506    4.142  1.00  81.21      6
ATOM    172  CE   LYS    840       0.582   48.660    4.331  1.00  81.21      6
ATOM    173  NZ   LYS    840      -0.153   48.279    3.096  1.00  81.21      7
ATOM    174  C    LYS    840       3.798   51.053    0.951  1.00  64.49      6
ATOM    175  O    LYS    840       3.854   52.260    1.176  1.00  64.49      8
ATOM    176  N    ALA    841       3.021   50.538    0.016  1.00  53.58      7
ATOM    177  CA   ALA    841       2.219   51.409   -0.814  1.00  53.58      6
ATOM    178  CB   ALA    841       3.082   51.913   -1.961  1.00  25.05      6
ATOM    179  C    ALA    841       1.003   50.670   -1.353  1.00  53.58      6
ATOM    180  O    ALA    841       1.144   49.616   -1.966  1.00  53.58      8
ATOM    181  N    ARG    842      -0.189   51.212   -1.135  1.00  86.10      7
ATOM    182  CA   ARG    842      -1.385   50.551   -1.637  1.00  86.10      6
ATOM    183  CB   ARG    842      -2.630   51.062   -0.905  1.00  40.66      6
ATOM    184  C    ARG    842      -1.514   50.804   -3.137  1.00  86.10      6
ATOM    185  O    ARG    842      -2.277   51.662   -3.572  1.00  86.10      8
ATOM    186  N    ILE    843      -0.763   50.040   -3.918  1.00  81.66      7
ATOM    187  CA   ILE    843      -0.773   50.176   -5.372  1.00  81.66      6
ATOM    188  CB   ILE    843       0.612   49.831   -5.984  1.00 100.00      6
ATOM    189  CG2  ILE    843       0.443   49.166   -7.362  1.00 100.00      6
ATOM    190  CG1  ILE    843       1.469   51.092   -6.056  1.00 100.00      6
ATOM    191  CD1  ILE    843       1.562   51.810   -4.732  1.00 100.00      6
ATOM    192  C    ILE    843      -1.796   49.337   -6.116  1.00  81.66      6
ATOM    193  O    ILE    843      -1.940   48.137   -5.884  1.00  81.66      8
ATOM    194  N    LYS    844      -2.482   49.988   -7.041  1.00  89.28      7
ATOM    195  CA   LYS    844      -3.449   49.324   -7.893  1.00  89.28      6
ATOM    196  CB   LYS    844      -4.657   50.218   -8.114  1.00  80.56      6
ATOM    197  C    LYS    844      -2.695   49.129   -9.205  1.00  89.28      6
ATOM    198  O    LYS    844      -1.818   49.928   -9.538  1.00  89.28      8
ATOM    199  N    LYS    845      -3.022   48.079   -9.944  1.00 100.00      7
ATOM    200  CA   LYS    845      -2.339   47.828  -11.208  1.00 100.00      6
ATOM    201  CB   LYS    845      -1.937   46.355  -11.305  1.00 100.00      6
ATOM    202  C    LYS    845      -3.232   48.203  -12.376  1.00 100.00      6
ATOM    203  O    LYS    845      -3.957   49.206  -12.324  1.00 100.00      8
ATOM    204  N    ASP    846      -2.834   47.343  -13.559  1.00 100.00      7
ATOM    205  CA   ASP    846      -3.726   47.631  -14.691  1.00 100.00      6
ATOM    206  CB   ASP    846      -3.314   46.796  -15.906  1.00 100.00      6
ATOM    207  CG   ASP    846      -3.993   47.249  -17.201  1.00 100.00      6
ATOM    208  OD1  ASP    846      -4.145   48.507  -17.444  1.00 100.00      8
ATOM    209  OD2  ASP    846      -4.414   46.373  -18.049  1.00 100.00      8
ATOM    210  C    ASP    846      -5.170   47.288  -14.320  1.00 100.00      6
ATOM    211  O    ASP    846      -5.989   46.948  -15.186  1.00 100.00      8
ATOM    212  N    GLY    847      -5.433   47.392  -13.030  1.00 100.00      7
ATOM    213  CA   GLY    847      -6.758   47.112  -12.459  1.00 100.00      6
ATOM    214  C    GLY    847      -6.612   46.491  -11.067  1.00 100.00      6
ATOM    215  O    GLY    847      -5.794   45.583  -10.856  1.00 100.00      8
ATOM    216  N    LEU    848      -7.419   47.011  -10.161  1.00  86.45      7
ATOM    217  CA   LEU    848      -7.450   46.563   -8.761  1.00  86.45      6
ATOM    218  CB   LEU    848      -7.206   45.055   -8.687  1.00  99.14      6
```

FIG. 3D

```
ATOM   219  CG   LEU   848    -6.201  44.560  -9.729  1.00 92.74    6
ATOM   220  CD1  LEU   848    -5.757  43.115  -9.491  1.00 92.74    6
ATOM   221  CD2  LEU   848    -6.753  44.595 -11.155  1.00 92.74    6
ATOM   222  C    LEU   848    -6.366  47.280  -7.954  1.00 86.45    6
ATOM   223  O    LEU   848    -5.717  48.215  -8.445  1.00 86.45    8
ATOM   224  N    ARG   849    -6.211  46.809  -6.730  1.00 99.60    7
ATOM   225  CA   ARG   849    -5.226  47.347  -5.780  1.00 99.60    6
ATOM   226  CB   ARG   849    -5.877  48.415  -4.899  1.00100.00    6
ATOM   227  CG   ARG   849    -6.736  49.403  -5.692  1.00 99.93    6
ATOM   228  CD   ARG   849    -8.059  49.736  -4.998  1.00 99.93    6
ATOM   229  NE   ARG   849    -7.887  50.134  -3.594  1.00 99.93    7
ATOM   230  CZ   ARG   849    -8.903  50.347  -2.746  1.00 99.93    6
ATOM   231  NH1  ARG   849   -10.175  50.205  -3.143  1.00 99.93    7
ATOM   232  NH2  ARG   849    -8.747  50.710  -1.465  1.00 99.93    7
ATOM   233  C    ARG   849    -4.694  46.224  -4.887  1.00 99.60    6
ATOM   234  O    ARG   849    -5.398  45.242  -4.608  1.00 99.60    8
ATOM   235  N    MET   850    -3.457  46.411  -4.467  1.00 80.73    7
ATOM   236  CA   MET   850    -2.754  45.456  -3.599  1.00 80.73    6
ATOM   237  CB   MET   850    -1.967  44.457  -4.450  1.00100.00    6
ATOM   238  CG   MET   850    -2.734  43.994  -5.690  1.00 68.64    6
ATOM   239  SD   MET   850    -1.849  44.290  -7.206  1.00 68.64   16
ATOM   240  CE   MET   850    -0.189  43.661  -7.074  1.00 68.64    6
ATOM   241  C    MET   850    -1.782  46.199  -2.681  1.00 80.73    6
ATOM   242  O    MET   850    -1.937  47.403  -2.426  1.00 80.73    8
ATOM   243  N    ASP   851    -1.168  45.352  -2.147  1.00 74.44    7
ATOM   244  CA   ASP   851    -0.137  45.775  -1.223  1.00 74.44    6
ATOM   245  CB   ASP   851    -0.163  44.913   0.034  1.00100.00    6
ATOM   246  CG   ASP   851    -0.724  45.642   1.229  1.00100.00    6
ATOM   247  OD1  ASP   851    -1.307  46.731   1.026  1.00100.00    8
ATOM   248  OD2  ASP   851    -0.588  45.124   2.360  1.00100.00    8
ATOM   249  C    ASP   851     1.159  45.518  -1.967  1.00 74.44    6
ATOM   250  O    ASP   851     1.583  44.367  -2.118  1.00 74.44    8
ATOM   251  N    ALA   852     1.775  46.581  -2.456  1.00 26.66    7
ATOM   252  CA   ALA   852     3.023  46.431  -3.173  1.00 26.66    6
ATOM   253  CB   ALA   852     2.984  47.212  -4.475  1.00 11.17    6
ATOM   254  C    ALA   852     4.155  46.921  -2.313  1.00 26.66    6
ATOM   255  O    ALA   852     3.957  47.275  -1.154  1.00 26.66    8
ATOM   256  N    ALA   853     5.346  46.931  -2.890  1.00 89.52    7
ATOM   257  CA   ALA   853     6.532  47.410  -2.204  1.00 89.52    6
ATOM   258  CB   ALA   853     7.355  46.243  -1.675  1.00 23.28    6
ATOM   259  C    ALA   853     7.324  48.210  -3.229  1.00 89.52    6
ATOM   260  O    ALA   853     7.765  47.668  -4.240  1.00 89.52    8
ATOM   261  N    ILE   854     7.417  49.467  -3.319  1.00 41.73    7
ATOM   262  CA   ILE   854     8.279  50.444  -3.999  1.00 41.73    6
ATOM   263  CB   ILE   854     7.851  51.866  -3.630  1.00 71.42    6
ATOM   264  CG2  ILE   854     8.539  52.937  -4.479  1.00 83.27    6
ATOM   265  CG1  ILE   854     6.349  52.102  -3.802  1.00 83.27    6
ATOM   266  CD1  ILE   854     5.768  51.388  -5.024  1.00 83.27    6
ATOM   267  C    ILE   854     9.736  50.239  -3.577  1.00 41.73    6
ATOM   268  O    ILE   854    10.035  50.042  -2.390  1.00 41.73    8
ATOM   269  N    LYS   855    10.597  50.294  -4.576  1.00 62.34    7
ATOM   270  CA   LYS   855    12.045  50.123  -4.395  1.00 62.34    6
ATOM   271  CB   LYS   855    12.496  48.792  -5.001  1.00 99.81    6
ATOM   272  CG   LYS   855    13.652  48.147  -4.235  1.00 99.81    6
ATOM   273  CD   LYS   855    13.741  46.635  -4.449  1.00 99.81    6
ATOM   274  CE   LYS   855    13.407  46.212  -5.881  1.00 99.81    6
ATOM   275  NZ   LYS   855    14.507  46.460  -6.824  1.00 99.81    7
```

FIG. 3E

```
ATOM    276  C   LYS   855     12.797  51.263  -5.085  1.00 62.34       6
ATOM    277  O   LYS   855     12.216  52.028  -5.869  1.00 62.34       8
ATOM    278  N   ARG   856     14.076  51.334  -4.765  1.00100.00       7
ATOM    279  CA  ARG   856     14.982  52.353  -5.313  1.00100.00       6
ATOM    280  CB  ARG   856     14.324  53.733  -5.241  1.00 95.22       6
ATOM    281  CG  ARG   856     15.161  54.829  -5.903  1.00 95.22       6
ATOM    282  CD  ARG   856     14.465  56.192  -5.906  1.00 95.22       6
ATOM    283  NE  ARG   856     15.316  57.271  -6.428  1.00 95.22       7
ATOM    284  CZ  ARG   856     14.938  58.554  -6.503  1.00 95.22       6
ATOM    285  NH1 ARG   856     13.723  58.940  -6.093  1.00 95.22       7
ATOM    286  NH2 ARG   856     15.715  59.537  -6.979  1.00 95.22       7
ATOM    287  C   ARG   856     16.284  52.382  -4.510  1.00100.00       6
ATOM    288  O   ARG   856     16.269  52.404  -3.270  1.00100.00       8
ATOM    289  N   MET   857     17.443  52.378  -5.338  1.00100.00       7
ATOM    290  CA  MET   857     18.288  53.750  -3.743  1.00100.00       6
ATOM    291  CB  MET   857     18.449  53.097  -2.384  1.00100.00       6
ATOM    292  CG  MET   857     17.994  54.017  -1.306  1.00100.00       6
ATOM    293  SD  MET   857     18.352  53.350   0.258  1.00100.00      16
ATOM    294  CE  MET   857     20.116  53.447   0.204  1.00100.00       6
ATOM    295  C   MET   857     19.646  53.843  -4.450  1.00100.00       6
ATOM    296  O   MET   857     20.497  52.937  -4.253  1.00100.00       8
ATOM    297  OXT MET   857     19.839  54.838  -5.196  1.00 82.10       8
TER
ATOM    298  CB  ASP   864     22.499  59.975 -11.088  1.00 55.87       6
ATOM    299  C   ASP   864     23.323  58.318 -12.792  1.00100.00       6
ATOM    300  O   ASP   864     22.981  58.052 -13.940  1.00100.00       8
ATOM    301  N   ASP   864     22.263  57.542 -10.688  1.00100.00       7
ATOM    302  CA  ASP   864     22.263  58.615 -11.734  1.00100.00       6
ATOM    303  N   ASP   865     24.599  58.333 -12.412  1.00100.00       7
ATOM    304  CA  ASP   865     25.670  57.988 -13.347  1.00100.00       6
ATOM    305  CB  ASP   865     26.925  58.842 -13.098  1.00 87.31       6
ATOM    306  C   ASP   865     25.951  56.494 -13.073  1.00100.00       6
ATOM    307  O   ASP   865     26.537  55.781 -13.902  1.00100.00       8
ATOM    308  N   HIS   866     25.485  56.080 -11.889  1.00 99.63       7
ATOM    309  CA  HIS   866     25.554  54.713 -11.357  1.00 99.63       6
ATOM    310  CB  HIS   866     25.728  54.726  -9.827  1.00100.00       6
ATOM    311  CG  HIS   866     24.600  55.378  -9.079  1.00100.00       6
ATOM    312  CD2 HIS   866     23.472  54.858  -8.543  1.00100.00       6
ATOM    313  ND1 HIS   866     24.593  56.720  -8.769  1.00100.00       7
ATOM    314  CE1 HIS   866     23.509  57.002  -8.065  1.00100.00       6
ATOM    315  NE2 HIS   866     22.811  55.888  -7.915  1.00100.00       7
ATOM    316  C   HIS   866     24.196  54.120 -11.715  1.00 99.63       6
ATOM    317  O   HIS   866     23.599  53.339 -10.964  1.00 99.63       8
ATOM    318  N   ARG   867     23.732  54.498 -12.904  1.00100.00       7
ATOM    319  CA  ARG   867     22.419  54.106 -13.405  1.00100.00       6
ATOM    320  CB  ARG   867     21.700  55.371 -13.954  1.00100.00       6
ATOM    321  CG  ARG   867     21.971  55.721 -15.445  1.00100.00       6
ATOM    322  CD  ARG   867     23.460  55.680 -15.790  1.00100.00       6
ATOM    323  NE  ARG   867     23.698  55.859 -17.219  1.00100.00       7
ATOM    324  CZ  ARG   867     24.794  55.439 -17.837  1.00100.00       6
ATOM    325  NH1 ARG   867     25.733  54.810 -17.137  1.00100.00       7
ATOM    326  NH2 ARG   867     24.940  55.628 -19.145  1.00100.00       7
ATOM    327  C   ARG   867     22.524  53.015 -14.480  1.00100.00       6
ATOM    328  O   ARG   867     21.980  53.140 -15.575  1.00100.00       8
ATOM    329  N   ASP   868     23.225  51.934 -14.164  1.00100.00       7
ATOM    330  CA  ASP   868     23.393  50.867 -15.146  1.00100.00       6
ATOM    331  CB  ASP   868     24.591  49.998 -14.773  1.00100.00       6
```

FIG. 3F

| ATOM | 332 | CG  | ASP | 868 | 24.412 | 49.314 | -13.435 | 1.00 | 100.00 | 6 |
| ATOM | 333 | OD1 | ASP | 868 | 24.613 | 49.980 | -12.391 | 1.00 | 100.00 | 8 |
| ATOM | 334 | OD2 | ASP | 868 | 24.027 | 48.130 | -13.442 | 1.00 | 100.00 | 8 |
| ATOM | 335 | C   | ASP | 868 | 22.154 | 49.960 | -15.282 | 1.00 | 100.00 | 6 |
| ATOM | 336 | O   | ASP | 868 | 22.293 | 48.750 | -15.504 | 1.00 | 100.00 | 8 |
| ATOM | 337 | N   | PHE | 869 | 20.955 | 50.538 | -15.156 | 1.00 | 100.00 | 7 |
| ATOM | 338 | CA  | PHE | 869 | 19.717 | 49.746 | -15.259 | 1.00 | 100.00 | 6 |
| ATOM | 339 | CB  | PHE | 869 | 18.424 | 50.554 | -15.017 | 1.00 | 99.62  | 6 |
| ATOM | 340 | CG  | PHE | 869 | 18.595 | 52.044 | -14.986 | 1.00 | 99.62  | 6 |
| ATOM | 341 | CD1 | PHE | 869 | 18.716 | 52.692 | -13.761 | 1.00 | 99.62  | 6 |
| ATOM | 342 | CD2 | PHE | 869 | 18.498 | 52.813 | -16.148 | 1.00 | 99.62  | 6 |
| ATOM | 343 | CE1 | PHE | 869 | 18.734 | 54.068 | -13.681 | 1.00 | 99.62  | 6 |
| ATOM | 344 | CE2 | PHE | 869 | 18.515 | 54.204 | -16.077 | 1.00 | 99.62  | 6 |
| ATOM | 345 | CZ  | PHE | 869 | 18.630 | 54.834 | -14.843 | 1.00 | 99.62  | 6 |
| ATOM | 346 | C   | PHE | 869 | 19.576 | 49.080 | -16.612 | 1.00 | 100.00 | 6 |
| ATOM | 347 | O   | PHE | 869 | 20.380 | 49.305 | -17.508 | 1.00 | 100.00 | 8 |
| ATOM | 348 | N   | ALA | 870 | 18.524 | 48.278 | -16.746 | 1.00 | 100.00 | 7 |
| ATOM | 349 | CA  | ALA | 870 | 18.206 | 47.512 | -17.951 | 1.00 | 100.00 | 6 |
| ATOM | 350 | CB  | ALA | 870 | 19.005 | 48.006 | -19.156 | 1.00 | 97.10  | 6 |
| ATOM | 351 | C   | ALA | 870 | 18.532 | 46.061 | -17.670 | 1.00 | 100.00 | 6 |
| ATOM | 352 | O   | ALA | 870 | 17.644 | 45.222 | -17.671 | 1.00 | 100.00 | 8 |
| ATOM | 353 | N   | GLY | 871 | 19.810 | 45.775 | -17.434 | 1.00 | 100.00 | 7 |
| ATOM | 354 | CA  | GLY | 871 | 20.221 | 44.419 | -17.133 | 1.00 | 100.00 | 6 |
| ATOM | 355 | C   | GLY | 871 | 19.602 | 44.044 | -15.804 | 1.00 | 100.00 | 6 |
| ATOM | 356 | O   | GLY | 871 | 19.400 | 42.871 | -15.506 | 1.00 | 100.00 | 8 |
| ATOM | 357 | N   | GLU | 872 | 19.305 | 45.055 | -14.996 | 1.00 | 99.97  | 7 |
| ATOM | 358 | CA  | GLU | 872 | 18.669 | 44.813 | -13.718 | 1.00 | 99.97  | 6 |
| ATOM | 359 | CB  | GLU | 872 | 18.811 | 46.023 | -12.787 | 1.00 | 100.00 | 6 |
| ATOM | 360 | CG  | GLU | 872 | 17.496 | 46.495 | -12.182 | 1.00 | 100.00 | 6 |
| ATOM | 361 | CD  | GLU | 872 | 17.571 | 46.692 | -10.675 | 1.00 | 100.00 | 6 |
| ATOM | 362 | OE1 | GLU | 872 | 18.323 | 47.585 | -10.230 | 1.00 | 100.00 | 8 |
| ATOM | 363 | OE2 | GLU | 872 | 16.882 | 45.946 | -9.940  | 1.00 | 100.00 | 8 |
| ATOM | 364 | C   | GLU | 872 | 17.200 | 44.565 | -14.033 | 1.00 | 99.97  | 6 |
| ATOM | 365 | O   | GLU | 872 | 16.575 | 43.673 | -13.465 | 1.00 | 99.97  | 8 |
| ATOM | 366 | N   | LEU | 873 | 16.659 | 45.350 | -14.961 | 1.00 | 63.02  | 7 |
| ATOM | 367 | CA  | LEU | 873 | 15.255 | 45.213 | -15.327 | 1.00 | 63.02  | 6 |
| ATOM | 368 | CB  | LEU | 873 | 14.756 | 46.482 | -15.955 | 1.00 | 69.97  | 6 |
| ATOM | 369 | C   | LEU | 873 | 14.977 | 44.032 | -16.243 | 1.00 | 63.02  | 6 |
| ATOM | 370 | O   | LEU | 873 | 13.990 | 43.323 | -16.052 | 1.00 | 63.02  | 8 |
| ATOM | 371 | N   | GLU | 874 | 15.847 | 43.819 | -17.227 | 1.00 | 100.00 | 7 |
| ATOM | 372 | CA  | GLU | 874 | 15.687 | 42.716 | -18.164 | 1.00 | 100.00 | 6 |
| ATOM | 373 | CB  | GLU | 874 | 16.645 | 42.862 | -19.331 | 1.00 | 19.50  | 6 |
| ATOM | 374 | C   | GLU | 874 | 15.923 | 41.394 | -17.454 | 1.00 | 100.00 | 6 |
| ATOM | 375 | O   | GLU | 874 | 15.103 | 40.482 | -17.547 | 1.00 | 100.00 | 8 |
| ATOM | 376 | N   | VAL | 875 | 17.040 | 41.298 | -16.737 | 1.00 | 69.27  | 7 |
| ATOM | 377 | CA  | VAL | 875 | 17.383 | 40.082 | -16.002 | 1.00 | 69.27  | 6 |
| ATOM | 378 | CB  | VAL | 875 | 18.763 | 40.218 | -15.359 | 1.00 | 39.27  | 6 |
| ATOM | 379 | C   | VAL | 875 | 16.344 | 39.755 | -14.934 | 1.00 | 69.27  | 6 |
| ATOM | 380 | O   | VAL | 875 | 16.338 | 38.651 | -14.399 | 1.00 | 69.27  | 8 |
| ATOM | 381 | N   | LEU | 876 | 15.493 | 40.728 | -14.613 | 1.00 | 78.00  | 7 |
| ATOM | 382 | CA  | LEU | 876 | 14.438 | 40.543 | -13.616 | 1.00 | 78.00  | 6 |
| ATOM | 383 | CB  | LEU | 876 | 14.169 | 41.853 | -12.843 | 1.00 | 53.20  | 6 |
| ATOM | 384 | CG  | LEU | 876 | 14.939 | 42.141 | -11.537 | 1.00 | 29.26  | 6 |
| ATOM | 385 | CD1 | LEU | 876 | 14.466 | 43.420 | -10.852 | 1.00 | 29.26  | 6 |
| ATOM | 386 | CD2 | LEU | 876 | 14.715 | 40.969 | -10.608 | 1.00 | 29.26  | 6 |
| ATOM | 387 | C   | LEU | 876 | 13.147 | 40.076 | -14.290 | 1.00 | 78.00  | 6 |
| ATOM | 388 | O   | LEU | 876 | 12.410 | 39.262 | -13.737 | 1.00 | 78.00  | 8 |

FIG. 3G

```
ATOM    389  N   CYS   877      12.870  40.591 -15.486  1.00 60.18      7
ATOM    390  CA  CYS   877      11.652  40.208 -16.191  1.00 60.18      6
ATOM    391  CB  CYS   877      11.199  41.317 -17.164  1.00100.00      6
ATOM    392  SG  CYS   877      12.370  41.807 -18.447  1.00100.00     16
ATOM    393  C   CYS   877      11.857  38.886 -16.916  1.00 60.18      6
ATOM    394  O   CYS   877      11.194  38.591 -17.909  1.00 60.18      8
ATOM    395  N   LYS   878      12.788  38.094 -16.398  1.00 65.17      7
ATOM    396  CA  LYS   878      13.088  36.788 -16.964  1.00 65.17      6
ATOM    397  CB  LYS   878      14.593  36.609 -17.078  1.00 89.20      6
ATOM    398  CG  LYS   878      15.190  37.551 -18.092  1.00 52.09      6
ATOM    399  CD  LYS   878      16.693  37.453 -18.128  1.00 52.09      6
ATOM    400  CE  LYS   878      17.289  38.360 -19.216  1.00 52.09      6
ATOM    401  NZ  LYS   878      16.965  37.922 -20.614  1.00 52.09      7
ATOM    402  C   LYS   878      12.473  35.703 -16.091  1.00 65.17      6
ATOM    403  O   LYS   878      12.100  34.632 -16.572  1.00 65.17      8
ATOM    404  N   LEU   879      12.365  35.982 -14.801  1.00100.00      7
ATOM    405  CA  LEU   879      11.752  35.044 -13.879  1.00100.00      6
ATOM    406  CB  LEU   879      12.480  35.052 -12.526  1.00 45.22      6
ATOM    407  CG  LEU   879      12.801  36.419 -11.904  1.00 46.30      6
ATOM    408  CD1 LEU   879      13.226  36.250 -10.462  1.00 46.30      6
ATOM    409  CD2 LEU   879      13.892  37.109 -12.704  1.00 46.30      6
ATOM    410  C   LEU   879      10.301  35.492 -13.717  1.00100.00      6
ATOM    411  O   LEU   879      10.019  36.656 -13.405  1.00100.00      8
ATOM    412  N   GLY   880       9.381  34.572 -13.972  1.00 96.05      7
ATOM    413  CA  GLY   880       7.980  34.903 -13.848  1.00 96.05      6
ATOM    414  C   GLY   880       7.540  34.784 -12.409  1.00 96.05      6
ATOM    415  O   GLY   880       8.358  34.825 -11.483  1.00 96.05      8
ATOM    416  N   HIS   881       6.236  34.641 -12.216  1.00 70.51      7
ATOM    417  CA  HIS   881       5.693  34.496 -10.876  1.00 70.51      6
ATOM    418  CB  HIS   881       4.178  34.726 -10.843  1.00 99.80      6
ATOM    419  CG  HIS   881       3.498  34.160  -9.629  1.00 99.80      6
ATOM    420  CD2 HIS   881       3.000  32.924  -9.383  1.00 99.80      6
ATOM    421  ND1 HIS   881       3.264  34.897  -8.484  1.00 99.80      7
ATOM    422  CE1 HIS   881       2.648  34.142  -7.592  1.00 99.80      6
ATOM    423  NE2 HIS   881       2.477  32.939  -8.110  1.00 99.80      7
ATOM    424  C   HIS   881       5.952  33.094 -10.384  1.00 70.51      6
ATOM    425  O   HIS   881       5.908  32.134 -11.147  1.00 70.51      8
ATOM    426  N   HIS   882       6.231  32.982  -9.104  1.00 45.83      7
ATOM    427  CA  HIS   882       6.404  31.672  -8.546  1.00 45.83      6
ATOM    428  CB  HIS   882       7.866  31.289  -8.449  1.00 14.81      6
ATOM    429  CG  HIS   882       8.076  29.813  -8.295  1.00 29.81      6
ATOM    430  CD2 HIS   882       7.783  28.782  -9.126  1.00 29.81      6
ATOM    431  ND1 HIS   882       8.608  29.244  -7.167  1.00 29.81      7
ATOM    432  CE1 HIS   882       8.638  27.932  -7.299  1.00 29.81      6
ATOM    433  NE2 HIS   882       8.142  27.626  -8.484  1.00 29.81      7
ATOM    434  C   HIS   882       5.773  31.719  -7.182  1.00 45.83      6
ATOM    435  O   HIS   882       5.987  32.655  -6.411  1.00 45.83      8
ATOM    436  N   PRO   883       4.959  30.711  -6.873  1.00 37.21      7
ATOM    437  CD  PRO   883       4.747  29.405  -7.508  1.00 52.55      6
ATOM    438  CA  PRO   883       4.353  30.762  -5.556  1.00 37.21      6
ATOM    439  CB  PRO   883       3.821  29.336  -5.373  1.00 47.02      6
ATOM    440  CG  PRO   883       4.591  28.493  -6.316  1.00 52.55      6
ATOM    441  C   PRO   883       5.359  31.209  -4.487  1.00 37.21      6
ATOM    442  O   PRO   883       4.990  31.958  -3.579  1.00 37.21      8
ATOM    443  N   ASN   884       6.628  30.800  -4.601  1.00 24.86      7
ATOM    444  CA  ASN   884       7.619  31.198  -3.582  1.00 24.86      6
ATOM    445  CB  ASN   884       8.077  29.996  -2.714  1.00 18.47      6
```

FIG. 3H

```
ATOM  446  CG   ASN  884   7.553  28.671  -3.203  1.00  33.47  6
ATOM  447  OD1  ASN  884   7.951  28.205  -4.243  1.00  33.47  8
ATOM  448  ND2  ASN  884   6.674  28.052  -2.443  1.00  33.47  7
ATOM  449  C    ASN  884   8.860  31.986  -4.022  1.00  24.86  6
ATOM  450  O    ASN  884   9.996  31.540  -3.862  1.00  24.86  8
ATOM  451  N    ILE  885   8.603  33.191  -4.518  1.00  46.00  7
ATOM  452  CA   ILE  885   9.616  34.125  -4.986  1.00  46.00  6
ATOM  453  CB   ILE  885  10.063  33.811  -6.435  1.00  25.68  6
ATOM  454  CG2  ILE  885  10.616  35.056  -7.119  1.00  21.87  6
ATOM  455  CG1  ILE  885  11.101  32.696  -6.451  1.00  21.87  6
ATOM  456  CD1  ILE  885  11.855  32.614  -7.727  1.00  21.87  6
ATOM  457  C    ILE  885   8.924  35.476  -5.013  1.00  46.00  6
ATOM  458  O    ILE  885   7.845  35.596  -5.601  1.00  46.00  8
ATOM  459  N    ILE  886   9.501  36.488  -4.373  1.00  36.62  7
ATOM  460  CA   ILE  886   8.857  37.785  -4.434  1.00  36.62  6
ATOM  461  CB   ILE  886   9.462  38.768  -3.414  1.00  17.99  6
ATOM  462  CG2  ILE  886   9.259  40.221  -3.846  1.00  27.09  6
ATOM  463  CG1  ILE  886   8.764  38.531  -2.075  1.00  27.09  6
ATOM  464  CD1  ILE  886   9.230  39.402  -1.000  1.00  27.09  6
ATOM  465  C    ILE  886   8.969  38.250  -5.881  1.00  36.62  6
ATOM  466  O    ILE  886  10.040  38.615  -6.363  1.00  36.62  8
ATOM  467  N    ASN  887   7.832  38.163  -6.566  1.00  39.60  7
ATOM  468  CA   ASN  887   7.716  38.506  -7.975  1.00  39.60  6
ATOM  469  CB   ASN  887   6.531  37.759  -8.603  1.00  82.94  6
ATOM  470  CG   ASN  887   6.602  36.250  -8.406  1.00  82.94  6
ATOM  471  OD1  ASN  887   7.490  35.584  -8.932  1.00  82.94  8
ATOM  472  ND2  ASN  887   5.665  35.710  -7.637  1.00  82.94  7
ATOM  473  C    ASN  887   7.535  39.990  -8.222  1.00  39.60  6
ATOM  474  O    ASN  887   6.893  40.687  -7.432  1.00  39.60  8
ATOM  475  N    LEU  888   8.125  40.438  -9.332  1.00  73.28  7
ATOM  476  CA   LEU  888   8.067  41.822  -9.789  1.00  73.28  6
ATOM  477  CB   LEU  888   9.044  42.055 -10.953  1.00  34.36  6
ATOM  478  CG   LEU  888   9.064  43.390 -11.721  1.00  18.51  6
ATOM  479  CD1  LEU  888   9.760  44.444 -10.873  1.00  18.51  6
ATOM  480  CD2  LEU  888   9.809  43.220 -13.035  1.00  18.51  6
ATOM  481  C    LEU  888   6.651  42.083 -10.274  1.00  73.28  6
ATOM  482  O    LEU  888   6.083  41.282 -11.022  1.00  73.28  8
ATOM  483  N    LEU  889   6.091  43.210  -9.853  1.00  99.59  7
ATOM  484  CA   LEU  889   4.731  43.573 -10.235  1.00  99.59  6
ATOM  485  CB   LEU  889   3.936  43.972  -8.975  1.00  97.88  6
ATOM  486  CG   LEU  889   3.874  42.924  -7.838  1.00  59.80  6
ATOM  487  CD1  LEU  889   2.923  43.357  -6.733  1.00  59.80  6
ATOM  488  CD2  LEU  889   3.419  41.589  -8.413  1.00  59.80  6
ATOM  489  C    LEU  889   4.676  44.676 -11.304  1.00  99.59  6
ATOM  490  O    LEU  889   3.805  44.645 -12.167  1.00  99.59  8
ATOM  491  N    GLY  890   5.599  45.636 -11.266  1.00  54.35  7
ATOM  492  CA   GLY  890   5.597  46.699 -12.264  1.00  54.35  6
ATOM  493  C    GLY  890   6.668  47.737 -11.986  1.00  54.35  6
ATOM  494  O    GLY  890   7.617  47.466 -11.259  1.00  54.35  8
ATOM  495  N    ALA  891   6.534  48.926 -12.560  1.00  66.65  7
ATOM  496  CA   ALA  891   7.515  49.985 -12.328  1.00  66.65  6
ATOM  497  CB   ALA  891   8.872  49.590 -12.911  1.00  68.11  6
ATOM  498  C    ALA  891   7.055  51.299 -12.937  1.00  66.65  6
ATOM  499  O    ALA  891   6.176  51.318 -13.789  1.00  66.65  8
ATOM  500  N    CYS  892   7.656  52.393 -12.485  1.00  99.57  7
ATOM  501  CA   CYS  892   7.322  53.720 -12.984  1.00  99.57  6
ATOM  502  CB   CYS  892   6.872  54.619 -11.833  1.00  98.88  6
```

FIG. 3I

| | | | | | | | | |
|---|---|---|---|---|---|---|---|---|
| ATOM | 503 | SG | CYS | 892 | 5.614 | 55.803 | -12.345 | 1.00 92.24 | 16 |
| ATOM | 504 | C | CYS | 892 | 8.579 | 54.284 | -13.611 | 1.00 99.57 | 6 |
| ATOM | 505 | O | CYS | 892 | 9.610 | 53.625 | -13.607 | 1.00 99.57 | 8 |
| ATOM | 506 | N | GLU | 893 | 8.503 | 55.485 | -14.165 | 1.00 99.69 | 7 |
| ATOM | 507 | CA | GLU | 893 | 9.676 | 56.130 | -14.759 | 1.00 99.69 | 6 |
| ATOM | 508 | CB | GLU | 893 | 9.687 | 55.991 | -16.289 | 1.00100.00 | 6 |
| ATOM | 509 | CG | GLU | 893 | 10.439 | 54.776 | -16.825 | 1.00100.00 | 6 |
| ATOM | 510 | CD | GLU | 893 | 10.793 | 54.883 | -18.308 | 1.00100.00 | 6 |
| ATOM | 511 | OE1 | GLU | 893 | 11.715 | 55.657 | -18.646 | 1.00100.00 | 8 |
| ATOM | 512 | OE2 | GLU | 893 | 10.123 | 54.219 | -19.128 | 1.00100.00 | 8 |
| ATOM | 513 | C | GLU | 893 | 9.616 | 57.594 | -14.387 | 1.00 99.69 | 6 |
| ATOM | 514 | O | GLU | 893 | 9.817 | 58.469 | -15.215 | 1.00 99.69 | 8 |
| ATOM | 515 | N | HIS | 894 | 9.516 | 57.779 | -12.908 | 1.00 96.96 | 7 |
| ATOM | 516 | CA | HIS | 894 | 9.344 | 59.158 | -12.428 | 1.00 96.96 | 6 |
| ATOM | 517 | CB | HIS | 894 | 8.697 | 59.154 | -11.042 | 1.00100.00 | 6 |
| ATOM | 518 | CG | HIS | 894 | 8.186 | 60.532 | -10.618 | 1.00100.00 | 6 |
| ATOM | 519 | CD2 | HIS | 894 | 7.291 | 61.381 | -11.187 | 1.00100.00 | 6 |
| ATOM | 520 | ND1 | HIS | 894 | 8.631 | 61.157 | -9.457 | 1.00100.00 | 7 |
| ATOM | 521 | CE1 | HIS | 894 | 8.019 | 62.323 | -9.357 | 1.00100.00 | 6 |
| ATOM | 522 | NE2 | HIS | 894 | 7.216 | 62.472 | -10.381 | 1.00100.00 | 7 |
| ATOM | 523 | C | HIS | 894 | 10.703 | 59.854 | -12.336 | 1.00 96.96 | 6 |
| ATOM | 524 | O | HIS | 894 | 11.756 | 59.200 | -12.319 | 1.00 96.96 | 8 |
| ATOM | 525 | N | ARG | 895 | 10.631 | 61.171 | -12.278 | 1.00100.00 | 7 |
| ATOM | 526 | CA | ARG | 895 | 11.818 | 62.033 | -12.182 | 1.00100.00 | 6 |
| ATOM | 527 | CB | ARG | 895 | 11.408 | 63.440 | -11.741 | 1.00100.00 | 6 |
| ATOM | 528 | CG | ARG | 895 | 10.703 | 64.230 | -12.846 | 1.00100.00 | 6 |
| ATOM | 529 | CD | ARG | 895 | 10.357 | 65.661 | -12.430 | 1.00100.00 | 6 |
| ATOM | 530 | NE | ARG | 895 | 10.896 | 66.673 | -13.350 | 1.00100.00 | 7 |
| ATOM | 531 | CZ | ARG | 895 | 10.138 | 67.483 | -14.101 | 1.00100.00 | 6 |
| ATOM | 532 | NH1 | ARG | 895 | 8.801 | 67.415 | -14.056 | 1.00100.00 | 7 |
| ATOM | 533 | NH2 | ARG | 895 | 10.630 | 68.406 | -14.939 | 1.00100.00 | 7 |
| ATOM | 534 | C | ARG | 895 | 12.796 | 61.452 | -11.159 | 1.00100.00 | 6 |
| ATOM | 535 | O | ARG | 895 | 12.399 | 60.726 | -10.236 | 1.00100.00 | 8 |
| ATOM | 536 | N | GLY | 896 | 14.055 | 61.795 | -11.359 | 1.00100.00 | 7 |
| ATOM | 537 | CA | GLY | 896 | 15.150 | 61.337 | -10.493 | 1.00100.00 | 6 |
| ATOM | 538 | C | GLY | 896 | 14.949 | 59.861 | -10.145 | 1.00100.00 | 6 |
| ATOM | 539 | O | GLY | 896 | 14.575 | 59.517 | -9.013 | 1.00100.00 | 8 |
| ATOM | 540 | N | TYR | 897 | 15.205 | 59.037 | -11.143 | 1.00100.00 | 7 |
| ATOM | 541 | CA | TYR | 897 | 15.068 | 57.578 | -11.033 | 1.00100.00 | 6 |
| ATOM | 542 | CB | TYR | 897 | 15.624 | 57.096 | -9.692 | 1.00100.00 | 6 |
| ATOM | 543 | CG | TYR | 897 | 15.964 | 55.604 | -9.688 | 1.00100.00 | 6 |
| ATOM | 544 | CD1 | TYR | 897 | 17.195 | 55.165 | -10.192 | 1.00100.00 | 6 |
| ATOM | 545 | CE1 | TYR | 897 | 17.506 | 53.800 | -10.190 | 1.00100.00 | 6 |
| ATOM | 546 | CD2 | TYR | 897 | 15.045 | 54.676 | -9.182 | 1.00100.00 | 6 |
| ATOM | 547 | CE2 | TYR | 897 | 15.357 | 53.311 | -9.179 | 1.00100.00 | 6 |
| ATOM | 548 | CZ | TYR | 897 | 16.587 | 52.873 | -9.684 | 1.00100.00 | 6 |
| ATOM | 549 | OH | TYR | 897 | 16.890 | 51.547 | -9.682 | 1.00100.00 | 8 |
| ATOM | 550 | C | TYR | 897 | 13.592 | 57.190 | -11.131 | 1.00100.00 | 6 |
| ATOM | 551 | O | TYR | 897 | 12.714 | 58.051 | -11.293 | 1.00100.00 | 8 |
| ATOM | 552 | N | LEU | 898 | 13.367 | 55.894 | -11.027 | 1.00100.00 | 7 |
| ATOM | 553 | CA | LEU | 898 | 12.020 | 55.310 | -11.093 | 1.00100.00 | 6 |
| ATOM | 554 | CB | LEU | 898 | 11.960 | 54.258 | -12.202 | 1.00 41.85 | 6 |
| ATOM | 555 | C | LEU | 898 | 11.672 | 54.648 | -9.759 | 1.00100.00 | 6 |
| ATOM | 556 | O | LEU | 898 | 12.234 | 54.992 | -8.709 | 1.00100.00 | 8 |
| ATOM | 557 | N | TYR | 899 | 10.747 | 53.711 | -9.850 | 1.00 72.77 | 7 |
| ATOM | 558 | CA | TYR | 899 | 10.267 | 52.951 | -8.688 | 1.00 72.77 | 6 |
| ATOM | 559 | CB | TYR | 899 | 9.153 | 53.725 | -7.982 | 1.00100.00 | 6 |

FIG. 3J

```
ATOM    560  CG   TYR   899       9.685  54.728  -6.958  1.00100.00      6
ATOM    561  CD1  TYR   899       9.394  56.090  -7.096  1.00100.00      6
ATOM    562  CE1  TYR   899       9.884  57.008  -6.159  1.00100.00      6
ATOM    563  CD2  TYR   899      10.465  54.283  -5.884  1.00100.00      6
ATOM    564  CE2  TYR   899      10.955  55.201  -4.948  1.00100.00      6
ATOM    565  CZ   TYR   899      10.664  56.564  -5.085  1.00100.00      6
ATOM    566  OH   TYR   899      11.140  57.456  -4.175  1.00100.00      8
ATOM    567  C    TYR   899       9.726  51.592  -9.136  1.00 72.77      6
ATOM    568  O    TYR   899       8.785  51.513  -9.940  1.00 72.77      8
ATOM    569  N    LEU   900      10.350  50.565  -8.591  1.00 78.27      7
ATOM    570  CA   LEU   900       9.996  49.168  -8.876  1.00 78.27      6
ATOM    571  CB   LEU   900      11.233  48.277  -8.738  1.00 79.18      6
ATOM    572  CG   LEU   900      11.566  47.512 -10.020  1.00 54.43      6
ATOM    573  CD1  LEU   900      11.602  48.408 -11.259  1.00 54.43      6
ATOM    574  CD2  LEU   900      12.931  46.823  -9.967  1.00 54.43      6
ATOM    575  C    LEU   900       8.927  48.689  -7.892  1.00 78.27      6
ATOM    576  O    LEU   900       9.079  48.823  -6.669  1.00 78.27      8
ATOM    577  N    ALA   901       7.874  48.141  -8.468  1.00 72.23      7
ATOM    578  CA   ALA   901       6.731  47.614  -7.708  1.00 72.23      6
ATOM    579  CB   ALA   901       5.424  47.944  -8.433  1.00 33.79      6
ATOM    580  C    ALA   901       6.851  46.095  -7.568  1.00 72.23      6
ATOM    581  O    ALA   901       7.121  45.383  -8.546  1.00 72.23      8
ATOM    582  N    ILE   902       6.929  45.582  -6.293  1.00 59.87      7
ATOM    583  CA   ILE   902       7.104  44.154  -6.059  1.00 59.87      6
ATOM    584  CB   ILE   902       8.550  43.900  -5.623  1.00 34.80      6
ATOM    585  CG2  ILE   902       9.522  44.289  -6.729  1.00 35.77      6
ATOM    586  CG1  ILE   902       8.846  44.755  -4.397  1.00 35.77      6
ATOM    587  CD1  ILE   902      10.311  45.018  -4.169  1.00 35.77      6
ATOM    588  C    ILE   902       6.165  43.633  -4.969  1.00 59.87      6
ATOM    589  O    ILE   902       5.750  44.390  -4.093  1.00 59.87      8
ATOM    590  N    GLU   903       5.835  42.344  -5.030  1.00 34.73      7
ATOM    591  CA   GLU   903       4.967  41.716  -4.036  1.00 34.73      6
ATOM    592  CB   GLU   903       5.047  40.197  -4.119  1.00 38.01      6
ATOM    593  CG   GLU   903       4.180  39.568  -5.170  1.00 49.25      6
ATOM    594  CD   GLU   903       4.216  38.043  -5.112  1.00 49.25      6
ATOM    595  OE1  GLU   903       4.310  37.497  -3.985  1.00 49.25      8
ATOM    596  OE2  GLU   903       4.141  37.403  -6.191  1.00 49.25      8
ATOM    597  C    GLU   903       5.343  42.124  -2.627  1.00 34.73      6
ATOM    598  O    GLU   903       6.514  42.378  -2.330  1.00 34.73      8
ATOM    599  N    TYR   904       4.328  42.169  -1.770  1.00 31.03      7
ATOM    600  CA   TYR   904       4.469  42.530  -0.370  1.00 31.03      6
ATOM    601  CB   TYR   904       3.411  43.577  -0.003  1.00 13.64      6
ATOM    602  CG   TYR   904       3.419  43.950   1.459  1.00 23.21      6
ATOM    603  CD1  TYR   904       4.598  44.344   2.086  1.00 23.21      6
ATOM    604  CE1  TYR   904       4.647  44.606   3.448  1.00 23.21      6
ATOM    605  CD2  TYR   904       2.276  43.840   2.236  1.00 23.21      6
ATOM    606  CE2  TYR   904       2.315  44.102   3.608  1.00 23.21      6
ATOM    607  CZ   TYR   904       3.509  44.477   4.204  1.00 23.21      6
ATOM    608  OH   TYR   904       3.575  44.663   5.569  1.00 23.21      8
ATOM    609  C    TYR   904       4.328  41.291   0.532  1.00 31.03      6
ATOM    610  O    TYR   904       3.388  40.494   0.393  1.00 31.03      8
ATOM    611  N    ALA   905       5.284  41.154   1.447  1.00 31.20      7
ATOM    612  CA   ALA   905       5.334  40.063   2.409  1.00 31.20      6
ATOM    613  CB   ALA   905       6.733  39.460   2.430  1.00 28.71      6
ATOM    614  C    ALA   905       4.990  40.633   3.781  1.00 31.20      6
ATOM    615  O    ALA   905       5.853  41.091   4.514  1.00 31.20      8
ATOM    616  N    PRO   906       3.716  40.600   4.151  1.00 17.48      7
```

FIG. 3K

```
ATOM    617  CD   PRO   906      2.597   40.048    3.370  1.00  32.19      6
ATOM    618  CA   PRO   906      3.241   41.121    5.427  1.00  17.48      6
ATOM    619  CB   PRO   906      1.728   40.964    5.314  1.00  32.19      6
ATOM    620  CG   PRO   906      1.580   39.762    4.442  1.00  32.19      6
ATOM    621  C    PRO   906      3.774   40.564    6.724  1.00  17.48      6
ATOM    622  O    PRO   906      3.408   41.072    7.788  1.00  17.48      8
ATOM    623  N    HIS   907      4.636   39.550    6.683  1.00  30.66      7
ATOM    624  CA   HIS   907      5.123   38.987    7.954  1.00  30.66      6
ATOM    625  CB   HIS   907      4.657   37.543    8.130  1.00   5.00      6
ATOM    626  CG   HIS   907      3.174   37.357    8.048  1.00   5.00      6
ATOM    627  CD2  HIS   907      2.219   37.353    9.011  1.00   5.00      6
ATOM    628  ND1  HIS   907      2.517   37.103    6.865  1.00   5.00      7
ATOM    629  CE1  HIS   907      1.224   36.945    7.097  1.00   5.00      6
ATOM    630  NE2  HIS   907      1.021   37.091    8.393  1.00   5.00      7
ATOM    631  C    HIS   907      6.622   39.004    8.229  1.00  30.66      6
ATOM    632  O    HIS   907      7.130   38.115    8.926  1.00  30.66      8
ATOM    633  N    GLY   908      7.326   40.009    7.718  1.00  38.98      7
ATOM    634  CA   GLY   908      8.756   40.081    7.947  1.00  38.98      6
ATOM    635  C    GLY   908      9.483   38.924    7.298  1.00  38.98      6
ATOM    636  O    GLY   908      8.935   38.235    6.436  1.00  38.98      8
ATOM    637  N    ASN   909     10.719   38.698    7.718  1.00  31.42      7
ATOM    638  CA   ASN   909     11.517   37.620    7.140  1.00  31.42      6
ATOM    639  CB   ASN   909     12.963   38.068    6.941  1.00  41.70      6
ATOM    640  CG   ASN   909     13.566   38.630    8.197  1.00  41.70      6
ATOM    641  OD1  ASN   909     14.196   39.684    8.168  1.00  41.70      8
ATOM    642  ND2  ASN   909     13.381   37.931    9.316  1.00  41.70      7
ATOM    643  C    ASN   909     11.488   36.349    7.964  1.00  31.42      6
ATOM    644  O    ASN   909     11.094   36.340    9.132  1.00  31.42      8
ATOM    645  N    LEU   910     11.937   35.275    7.347  1.00  17.12      7
ATOM    646  CA   LEU   910     11.930   34.014    8.019  1.00  17.12      6
ATOM    647  CB   LEU   910     12.524   32.962    7.139  1.00  20.29      6
ATOM    648  CG   LEU   910     12.192   31.558    7.604  1.00  20.29      6
ATOM    649  CD1  LEU   910     10.687   31.274    7.677  1.00  20.29      6
ATOM    650  CD2  LEU   910     12.850   30.696    6.590  1.00  20.29      6
ATOM    651  C    LEU   910     12.679   34.039    9.332  1.00  17.12      6
ATOM    652  O    LEU   910     12.183   33.554   10.355  1.00  17.12      8
ATOM    653  N    LEU   911     13.885   34.579    9.319  1.00  21.04      7
ATOM    654  CA   LEU   911     14.646   34.644   10.551  1.00  21.04      6
ATOM    655  CB   LEU   911     15.865   35.523   10.363  1.00  23.99      6
ATOM    656  CG   LEU   911     16.744   35.463   11.596  1.00  23.99      6
ATOM    657  CD1  LEU   911     17.326   34.053   11.797  1.00  23.99      6
ATOM    658  CD2  LEU   911     17.833   36.483   11.399  1.00  23.99      6
ATOM    659  C    LEU   911     13.791   35.199   11.697  1.00  21.04      6
ATOM    660  O    LEU   911     13.565   34.515   12.692  1.00  21.04      8
ATOM    661  N    ASP   912     13.305   36.429   11.557  1.00  16.81      7
ATOM    662  CA   ASP   912     12.489   37.041   12.618  1.00  16.81      6
ATOM    663  CB   ASP   912     11.973   38.399   12.177  1.00  39.39      6
ATOM    664  CG   ASP   912     12.996   39.463   12.327  1.00  39.39      6
ATOM    665  OD1  ASP   912     12.794   40.557   11.777  1.00  39.39      8
ATOM    666  OD2  ASP   912     14.005   39.185   12.989  1.00  39.39      8
ATOM    667  C    ASP   912     11.311   36.214   13.031  1.00  16.81      6
ATOM    668  O    ASP   912     11.020   36.079   14.215  1.00  16.81      8
ATOM    669  N    PHE   913     10.623   35.698   12.027  1.00  39.11      7
ATOM    670  CA   PHE   913      9.462   34.884   12.255  1.00  39.11      6
ATOM    671  CB   PHE   913      8.850   34.495   10.937  1.00  34.21      6
ATOM    672  CG   PHE   913      7.458   34.005   11.055  1.00  34.21      6
ATOM    673  CD1  PHE   913      6.412   34.897   11.233  1.00  34.21      6
```

FIG. 3L

| | | | | | | | | | |
|---|---|---|---|---|---|---|---|---|---|
| ATOM | 674 | CD2 | PHE | 913 | 7.181 | 32.647 | 10.986 | 1.00 34.21 | 6 |
| ATOM | 675 | CE1 | PHE | 913 | 5.109 | 34.450 | 11.343 | 1.00 34.21 | 6 |
| ATOM | 676 | CE2 | PHE | 913 | 5.885 | 32.185 | 11.094 | 1.00 34.21 | 6 |
| ATOM | 677 | CZ | PHE | 913 | 4.843 | 33.089 | 11.271 | 1.00 34.21 | 6 |
| ATOM | 678 | C | PHE | 913 | 9.846 | 33.636 | 13.026 | 1.00 39.11 | 6 |
| ATOM | 679 | O | PHE | 913 | 9.073 | 33.166 | 13.843 | 1.00 39.11 | 8 |
| ATOM | 680 | N | LEU | 914 | 11.018 | 33.076 | 12.770 | 1.00 29.14 | 7 |
| ATOM | 681 | CA | LEU | 914 | 11.389 | 31.895 | 13.527 | 1.00 29.14 | 6 |
| ATOM | 682 | CB | LEU | 914 | 12.622 | 31.212 | 12.916 | 1.00 10.91 | 6 |
| ATOM | 683 | CG | LEU | 914 | 12.407 | 30.445 | 11.606 | 1.00 10.91 | 6 |
| ATOM | 684 | CD1 | LEU | 914 | 13.709 | 29.936 | 11.066 | 1.00 10.91 | 6 |
| ATOM | 685 | CD2 | LEU | 914 | 11.430 | 29.310 | 11.861 | 1.00 10.91 | 6 |
| ATOM | 686 | C | LEU | 914 | 11.659 | 32.247 | 14.994 | 1.00 29.14 | 6 |
| ATOM | 687 | O | LEU | 914 | 11.215 | 31.551 | 15.893 | 1.00 29.14 | 8 |
| ATOM | 688 | N | ARG | 915 | 12.377 | 33.337 | 15.228 | 1.00 18.56 | 7 |
| ATOM | 689 | CA | ARG | 915 | 12.750 | 33.766 | 16.569 | 1.00 18.56 | 6 |
| ATOM | 690 | CB | ARG | 915 | 13.829 | 34.844 | 16.463 | 1.00 29.12 | 6 |
| ATOM | 691 | CG | ARG | 915 | 15.088 | 34.300 | 15.887 | 1.00 29.12 | 6 |
| ATOM | 692 | CD | ARG | 915 | 16.140 | 35.354 | 15.729 | 1.00 29.12 | 6 |
| ATOM | 693 | NE | ARG | 915 | 17.459 | 34.736 | 15.660 | 1.00 29.12 | 7 |
| ATOM | 694 | CZ | ARG | 915 | 18.580 | 35.352 | 15.285 | 1.00 29.12 | 6 |
| ATOM | 695 | NH1 | ARG | 915 | 18.545 | 36.630 | 14.924 | 1.00 29.12 | 7 |
| ATOM | 696 | NH2 | ARG | 915 | 19.745 | 34.689 | 15.287 | 1.00 29.12 | 7 |
| ATOM | 697 | C | ARG | 915 | 11.609 | 34.256 | 17.439 | 1.00 18.56 | 6 |
| ATOM | 698 | O | ARG | 915 | 11.641 | 34.094 | 18.665 | 1.00 18.56 | 8 |
| ATOM | 699 | N | LYS | 916 | 10.605 | 34.841 | 16.788 | 1.00 22.66 | 7 |
| ATOM | 700 | CA | LYS | 916 | 9.426 | 35.406 | 17.441 | 1.00 22.66 | 6 |
| ATOM | 701 | CB | LYS | 916 | 8.816 | 36.463 | 16.501 | 1.00 51.60 | 6 |
| ATOM | 702 | CG | LYS | 916 | 7.369 | 36.228 | 16.021 | 1.00 51.60 | 6 |
| ATOM | 703 | CD | LYS | 916 | 7.163 | 34.999 | 15.123 | 1.00 51.60 | 6 |
| ATOM | 704 | CE | LYS | 916 | 5.699 | 34.865 | 14.684 | 1.00 51.60 | 6 |
| ATOM | 705 | NZ | LYS | 916 | 4.772 | 34.565 | 15.811 | 1.00 51.60 | 7 |
| ATOM | 706 | C | LYS | 916 | 8.377 | 34.360 | 17.848 | 1.00 22.66 | 6 |
| ATOM | 707 | O | LYS | 916 | 7.332 | 34.718 | 18.366 | 1.00 22.66 | 8 |
| ATOM | 708 | N | SER | 917 | 8.677 | 33.082 | 17.633 | 1.00 22.66 | 7 |
| ATOM | 709 | CA | SER | 917 | 7.773 | 31.979 | 17.957 | 1.00 22.66 | 6 |
| ATOM | 710 | CB | SER | 917 | 7.623 | 31.070 | 16.741 | 1.00 19.58 | 6 |
| ATOM | 711 | OG | SER | 917 | 8.890 | 30.564 | 16.328 | 1.00 19.58 | 8 |
| ATOM | 712 | C | SER | 917 | 8.272 | 31.143 | 19.135 | 1.00 22.66 | 6 |
| ATOM | 713 | O | SER | 917 | 7.720 | 30.078 | 19.436 | 1.00 22.66 | 8 |
| ATOM | 714 | N | ARG | 918 | 9.339 | 31.602 | 19.780 | 1.00 32.97 | 7 |
| ATOM | 715 | CA | ARG | 918 | 9.906 | 30.908 | 20.934 | 1.00 32.97 | 6 |
| ATOM | 716 | CB | ARG | 918 | 11.372 | 31.305 | 21.132 | 1.00 9.93 | 6 |
| ATOM | 717 | CG | ARG | 918 | 12.287 | 31.089 | 19.973 | 1.00 9.93 | 6 |
| ATOM | 718 | CD | ARG | 918 | 13.751 | 31.230 | 20.402 | 1.00 9.93 | 6 |
| ATOM | 719 | NE | ARG | 918 | 14.633 | 30.604 | 19.413 | 1.00 9.93 | 7 |
| ATOM | 720 | CZ | ARG | 918 | 15.957 | 30.509 | 19.504 | 1.00 9.93 | 6 |
| ATOM | 721 | NH1 | ARG | 918 | 16.610 | 31.007 | 20.533 | 1.00 9.93 | 7 |
| ATOM | 722 | NH2 | ARG | 918 | 16.637 | 29.872 | 18.565 | 1.00 9.93 | 7 |
| ATOM | 723 | C | ARG | 918 | 9.110 | 31.323 | 22.177 | 1.00 32.97 | 6 |
| ATOM | 724 | O | ARG | 918 | 9.547 | 32.189 | 22.925 | 1.00 32.97 | 8 |
| ATOM | 725 | N | VAL | 919 | 7.943 | 30.704 | 22.365 | 1.00 29.42 | 7 |
| ATOM | 726 | CA | VAL | 919 | 7.026 | 30.973 | 23.484 | 1.00 29.42 | 6 |
| ATOM | 727 | CB | VAL | 919 | 5.878 | 29.970 | 23.518 | 1.00 31.60 | 6 |
| ATOM | 728 | CG1 | VAL | 919 | 4.650 | 30.613 | 24.113 | 1.00 31.60 | 6 |
| ATOM | 729 | CG2 | VAL | 919 | 5.620 | 29.426 | 22.134 | 1.00 31.60 | 6 |
| ATOM | 730 | C | VAL | 919 | 7.635 | 30.893 | 24.867 | 1.00 29.42 | 6 |

FIG. 3M

| | | | | | | | | | |
|---|---|---|---|---|---|---|---|---|---|
| ATOM | 731 | O | VAL | 919 | 7.173 | 31.537 | 25.793 | 1.00 29.42 | 8 |
| ATOM | 732 | N | LEU | 920 | 8.635 | 30.048 | 25.020 | 1.00 34.37 | 7 |
| ATOM | 733 | CA | LEU | 920 | 9.260 | 29.900 | 26.305 | 1.00 34.37 | 6 |
| ATOM | 734 | CB | LEU | 920 | 10.093 | 28.629 | 26.324 | 1.00 36.03 | 6 |
| ATOM | 735 | CG | LEU | 920 | 10.688 | 28.310 | 27.688 | 1.00 36.03 | 6 |
| ATOM | 736 | CD1 | LEU | 920 | 9.559 | 28.061 | 28.676 | 1.00 36.03 | 6 |
| ATOM | 737 | CD2 | LEU | 920 | 11.592 | 27.104 | 27.587 | 1.00 36.03 | 6 |
| ATOM | 738 | C | LEU | 920 | 10.138 | 31.117 | 26.552 | 1.00 34.37 | 6 |
| ATOM | 739 | O | LEU | 920 | 10.523 | 31.393 | 27.676 | 1.00 34.37 | 8 |
| ATOM | 740 | N | GLU | 921 | 10.472 | 31.851 | 25.503 | 1.00 29.12 | 7 |
| ATOM | 741 | CA | GLU | 921 | 11.301 | 33.025 | 25.693 | 1.00 29.12 | 6 |
| ATOM | 742 | CB | GLU | 921 | 12.215 | 33.237 | 24.485 | 1.00 99.98 | 6 |
| ATOM | 743 | CG | GLU | 921 | 13.435 | 34.081 | 24.798 | 1.00 99.98 | 6 |
| ATOM | 744 | CD | GLU | 921 | 13.165 | 35.574 | 24.753 | 1.00 99.98 | 6 |
| ATOM | 745 | OE1 | GLU | 921 | 12.935 | 36.086 | 23.638 | 1.00 99.98 | 8 |
| ATOM | 746 | OE2 | GLU | 921 | 13.156 | 36.228 | 25.824 | 1.00 99.98 | 8 |
| ATOM | 747 | C | GLU | 921 | 10.362 | 34.207 | 25.885 | 1.00 29.12 | 6 |
| ATOM | 748 | O | GLU | 921 | 10.452 | 34.929 | 26.869 | 1.00 29.12 | 8 |
| ATOM | 749 | N | THR | 922 | 9.455 | 34.375 | 24.932 | 1.00 52.74 | 7 |
| ATOM | 750 | CA | THR | 922 | 8.463 | 35.437 | 24.944 | 1.00 52.74 | 6 |
| ATOM | 751 | CB | THR | 922 | 7.450 | 35.207 | 23.800 | 1.00 53.34 | 6 |
| ATOM | 752 | OG1 | THR | 922 | 8.038 | 35.598 | 22.558 | 1.00 53.34 | 8 |
| ATOM | 753 | CG2 | THR | 922 | 6.167 | 35.977 | 24.026 | 1.00 53.34 | 6 |
| ATOM | 754 | C | THR | 922 | 7.706 | 35.498 | 26.265 | 1.00 52.74 | 6 |
| ATOM | 755 | O | THR | 922 | 7.923 | 36.398 | 27.077 | 1.00 52.74 | 8 |
| ATOM | 756 | N | ASP | 923 | 6.827 | 34.515 | 26.461 | 1.00 32.25 | 7 |
| ATOM | 757 | CA | ASP | 923 | 5.981 | 34.391 | 27.651 | 1.00 32.25 | 6 |
| ATOM | 758 | CB | ASP | 923 | 4.509 | 34.434 | 27.231 | 1.00 60.93 | 6 |
| ATOM | 759 | CG | ASP | 923 | 3.558 | 34.328 | 28.404 | 1.00 60.93 | 6 |
| ATOM | 760 | OD1 | ASP | 923 | 3.762 | 35.032 | 29.415 | 1.00 60.93 | 8 |
| ATOM | 761 | OD2 | ASP | 923 | 2.593 | 33.545 | 28.309 | 1.00 60.93 | 8 |
| ATOM | 762 | C | ASP | 923 | 6.295 | 33.083 | 28.361 | 1.00 32.25 | 6 |
| ATOM | 763 | O | ASP | 923 | 5.711 | 32.034 | 28.055 | 1.00 32.25 | 8 |
| ATOM | 764 | N | PRO | 924 | 7.216 | 33.146 | 29.346 | 1.00 33.34 | 7 |
| ATOM | 765 | CD | PRO | 924 | 7.426 | 34.381 | 30.130 | 1.00 100.00 | 6 |
| ATOM | 766 | CA | PRO | 924 | 7.637 | 31.978 | 30.125 | 1.00 33.34 | 6 |
| ATOM | 767 | CB | PRO | 924 | 8.263 | 32.605 | 31.366 | 1.00 100.00 | 6 |
| ATOM | 768 | CG | PRO | 924 | 7.488 | 33.863 | 31.535 | 1.00 100.00 | 6 |
| ATOM | 769 | C | PRO | 924 | 6.464 | 31.030 | 30.456 | 1.00 33.34 | 6 |
| ATOM | 770 | O | PRO | 924 | 6.470 | 29.873 | 30.053 | 1.00 33.34 | 8 |
| ATOM | 771 | N | ALA | 925 | 5.460 | 31.543 | 31.164 | 1.00 69.10 | 7 |
| ATOM | 772 | CA | ALA | 925 | 4.282 | 30.781 | 31.603 | 1.00 69.10 | 6 |
| ATOM | 773 | CB | ALA | 925 | 3.311 | 31.735 | 32.255 | 1.00 73.73 | 6 |
| ATOM | 774 | C | ALA | 925 | 3.562 | 29.976 | 30.531 | 1.00 69.10 | 6 |
| ATOM | 775 | O | ALA | 925 | 3.802 | 28.779 | 30.384 | 1.00 69.10 | 8 |
| ATOM | 776 | N | PHE | 926 | 2.662 | 30.639 | 29.806 | 1.00 48.64 | 7 |
| ATOM | 777 | CA | PHE | 926 | 1.877 | 30.013 | 28.743 | 1.00 48.64 | 6 |
| ATOM | 778 | CB | PHE | 926 | 1.766 | 30.975 | 27.558 | 1.00 37.88 | 6 |
| ATOM | 779 | CG | PHE | 926 | 0.669 | 30.632 | 26.605 | 1.00 37.88 | 6 |
| ATOM | 780 | CD1 | PHE | 926 | -0.646 | 30.983 | 26.893 | 1.00 37.88 | 6 |
| ATOM | 781 | CD2 | PHE | 926 | 0.926 | 29.853 | 25.479 | 1.00 37.88 | 6 |
| ATOM | 782 | CE1 | PHE | 926 | -1.679 | 30.560 | 26.089 | 1.00 37.88 | 6 |
| ATOM | 783 | CE2 | PHE | 926 | -0.106 | 29.420 | 24.668 | 1.00 37.88 | 6 |
| ATOM | 784 | CZ | PHE | 926 | -1.406 | 29.774 | 24.977 | 1.00 37.88 | 6 |
| ATOM | 785 | C | PHE | 926 | 2.439 | 28.673 | 28.267 | 1.00 48.64 | 6 |
| ATOM | 786 | O | PHE | 926 | 1.752 | 27.656 | 28.298 | 1.00 48.64 | 8 |
| ATOM | 787 | N | ALA | 927 | 3.688 | 28.681 | 27.812 | 1.00 47.80 | 7 |

FIG. 3N

| | | | | | | | | | |
|---|---|---|---|---|---|---|---|---|---|
| ATOM | 788 | CA | ALA | 927 | 4.337 | 27.467 | 27.340 | 1.00 47.80 | 6 |
| ATOM | 789 | CB | ALA | 927 | 5.786 | 27.752 | 26.970 | 1.00 31.97 | 6 |
| ATOM | 790 | C | ALA | 927 | 4.272 | 26.297 | 28.314 | 1.00 47.80 | 6 |
| ATOM | 791 | O | ALA | 927 | 3.725 | 25.256 | 27.984 | 1.00 47.80 | 8 |
| ATOM | 792 | N | ILE | 928 | 4.850 | 26.439 | 29.499 | 1.00 44.35 | 7 |
| ATOM | 793 | CA | ILE | 928 | 4.810 | 25.346 | 30.457 | 1.00 44.35 | 6 |
| ATOM | 794 | CB | ILE | 928 | 5.155 | 25.837 | 31.868 | 1.00 67.81 | 6 |
| ATOM | 795 | CG2 | ILE | 928 | 5.834 | 24.735 | 32.641 | 1.00 29.96 | 6 |
| ATOM | 796 | CG1 | ILE | 928 | 6.130 | 27.004 | 31.806 | 1.00 29.96 | 6 |
| ATOM | 797 | CD1 | ILE | 928 | 7.542 | 26.594 | 31.485 | 1.00 29.96 | 6 |
| ATOM | 798 | C | ILE | 928 | 3.410 | 24.718 | 30.494 | 1.00 44.35 | 6 |
| ATOM | 799 | O | ILE | 928 | 3.266 | 23.499 | 30.626 | 1.00 44.35 | 8 |
| ATOM | 800 | N | ALA | 929 | 2.390 | 25.562 | 30.346 | 1.00 42.29 | 7 |
| ATOM | 801 | CA | ALA | 929 | 0.984 | 25.135 | 30.390 | 1.00 42.29 | 6 |
| ATOM | 802 | CB | ALA | 929 | 0.118 | 26.315 | 30.676 | 1.00 5.26 | 6 |
| ATOM | 803 | C | ALA | 929 | 0.457 | 24.440 | 29.156 | 1.00 42.29 | 6 |
| ATOM | 804 | O | ALA | 929 | -0.225 | 23.429 | 29.252 | 1.00 42.29 | 8 |
| ATOM | 805 | N | ASN | 930 | 0.745 | 24.995 | 27.994 | 1.00 36.17 | 7 |
| ATOM | 806 | CA | ASN | 930 | 0.259 | 24.398 | 26.775 | 1.00 36.17 | 6 |
| ATOM | 807 | CB | ASN | 930 | -0.230 | 25.506 | 25.852 | 1.00 57.20 | 6 |
| ATOM | 808 | CG | ASN | 930 | -1.444 | 26.223 | 26.430 | 1.00 57.20 | 6 |
| ATOM | 809 | OD1 | ASN | 930 | -2.586 | 25.742 | 26.344 | 1.00 57.20 | 8 |
| ATOM | 810 | ND2 | ASN | 930 | -1.202 | 27.360 | 27.057 | 1.00 57.20 | 7 |
| ATOM | 811 | C | ASN | 930 | 1.295 | 23.486 | 26.128 | 1.00 36.17 | 6 |
| ATOM | 812 | O | ASN | 930 | 1.088 | 22.976 | 25.028 | 1.00 36.17 | 8 |
| ATOM | 813 | N | SER | 931 | 2.401 | 23.259 | 26.834 | 1.00 50.28 | 7 |
| ATOM | 814 | CA | SER | 931 | 3.468 | 22.383 | 26.353 | 1.00 50.28 | 6 |
| ATOM | 815 | CB | SER | 931 | 2.986 | 20.930 | 26.341 | 1.00 90.81 | 6 |
| ATOM | 816 | OG | SER | 931 | 2.790 | 20.433 | 27.659 | 1.00 90.81 | 8 |
| ATOM | 817 | C | SER | 931 | 4.006 | 22.748 | 24.979 | 1.00 50.28 | 6 |
| ATOM | 818 | O | SER | 931 | 4.484 | 21.889 | 24.258 | 1.00 50.28 | 8 |
| ATOM | 819 | N | THR | 932 | 3.918 | 24.023 | 24.622 | 1.00 48.32 | 7 |
| ATOM | 820 | CA | THR | 932 | 4.397 | 24.510 | 23.334 | 1.00 48.32 | 6 |
| ATOM | 821 | CB | THR | 932 | 3.443 | 25.591 | 22.749 | 1.00 79.61 | 6 |
| ATOM | 822 | OG1 | THR | 932 | 3.247 | 26.634 | 23.711 | 1.00 79.61 | 8 |
| ATOM | 823 | CG2 | THR | 932 | 2.108 | 24.989 | 22.374 | 1.00 79.61 | 6 |
| ATOM | 824 | C | THR | 932 | 5.784 | 25.127 | 23.483 | 1.00 48.32 | 6 |
| ATOM | 825 | O | THR | 932 | 6.046 | 25.841 | 24.449 | 1.00 48.32 | 8 |
| ATOM | 826 | N | ALA | 933 | 6.667 | 24.854 | 22.527 | 1.00 55.05 | 7 |
| ATOM | 827 | CA | ALA | 933 | 8.009 | 25.436 | 22.552 | 1.00 55.05 | 6 |
| ATOM | 828 | CB | ALA | 933 | 9.057 | 24.378 | 22.297 | 1.00 28.55 | 6 |
| ATOM | 829 | C | ALA | 933 | 8.051 | 26.489 | 21.461 | 1.00 55.05 | 6 |
| ATOM | 830 | O | ALA | 933 | 8.936 | 27.339 | 21.437 | 1.00 55.05 | 8 |
| ATOM | 831 | N | SER | 934 | 7.098 | 26.393 | 20.543 | 1.00 27.13 | 7 |
| ATOM | 832 | CA | SER | 934 | 6.978 | 27.340 | 19.469 | 1.00 27.13 | 6 |
| ATOM | 833 | CB | SER | 934 | 7.937 | 27.003 | 18.341 | 1.00 36.98 | 6 |
| ATOM | 834 | OG | SER | 934 | 7.630 | 27.748 | 17.167 | 1.00 36.98 | 8 |
| ATOM | 835 | C | SER | 934 | 5.552 | 27.315 | 18.959 | 1.00 27.13 | 6 |
| ATOM | 836 | O | SER | 934 | 4.897 | 26.270 | 19.001 | 1.00 27.13 | 8 |
| ATOM | 837 | N | THR | 935 | 5.080 | 28.468 | 18.488 | 1.00 15.04 | 7 |
| ATOM | 838 | CA | THR | 935 | 3.740 | 28.582 | 17.963 | 1.00 15.04 | 6 |
| ATOM | 839 | CB | THR | 935 | 3.387 | 30.101 | 17.642 | 1.00 26.85 | 6 |
| ATOM | 840 | OG1 | THR | 935 | 4.301 | 30.658 | 16.680 | 1.00 26.85 | 8 |
| ATOM | 841 | CG2 | THR | 935 | 3.432 | 30.930 | 18.917 | 1.00 26.85 | 6 |
| ATOM | 842 | C | THR | 935 | 3.652 | 27.696 | 16.712 | 1.00 15.04 | 6 |
| ATOM | 843 | O | THR | 935 | 2.594 | 27.154 | 16.407 | 1.00 15.04 | 8 |
| ATOM | 844 | N | LEU | 936 | 4.778 | 27.530 | 16.015 | 1.00 41.56 | 7 |

FIG. 30

| | | | | | | | | | |
|---|---|---|---|---|---|---|---|---|---|
| ATOM | 845 | CA | LEU | 936 | 4.839 | 26.720 | 14.788 | 1.00 41.56 | 6 |
| ATOM | 846 | CB | LEU | 936 | 6.005 | 27.210 | 13.915 | 1.00 16.11 | 6 |
| ATOM | 847 | CG | LEU | 936 | 5.980 | 28.713 | 13.613 | 1.00 16.11 | 6 |
| ATOM | 848 | CD1 | LEU | 936 | 7.108 | 29.067 | 12.679 | 1.00 16.11 | 6 |
| ATOM | 849 | CD2 | LEU | 936 | 4.640 | 29.083 | 13.020 | 1.00 16.11 | 6 |
| ATOM | 850 | C | LEU | 936 | 4.958 | 25.203 | 15.018 | 1.00 41.56 | 6 |
| ATOM | 851 | O | LEU | 936 | 5.433 | 24.744 | 16.063 | 1.00 41.56 | 8 |
| ATOM | 852 | N | SER | 937 | 4.524 | 24.440 | 14.021 | 1.00 27.35 | 7 |
| ATOM | 853 | CA | SER | 937 | 4.551 | 22.989 | 14.081 | 1.00 27.35 | 6 |
| ATOM | 854 | CB | SER | 937 | 3.167 | 22.438 | 13.764 | 1.00 9.94 | 6 |
| ATOM | 855 | OG | SER | 937 | 2.884 | 22.429 | 12.374 | 1.00 9.94 | 8 |
| ATOM | 856 | C | SER | 937 | 5.574 | 22.357 | 13.128 | 1.00 27.35 | 6 |
| ATOM | 857 | O | SER | 937 | 6.180 | 23.041 | 12.291 | 1.00 27.35 | 8 |
| ATOM | 858 | N | SER | 938 | 5.752 | 21.043 | 13.257 | 1.00 23.83 | 7 |
| ATOM | 859 | CA | SER | 938 | 6.689 | 20.294 | 12.431 | 1.00 23.83 | 6 |
| ATOM | 860 | CB | SER | 938 | 6.578 | 18.813 | 12.838 | 1.00 31.90 | 6 |
| ATOM | 861 | OG | SER | 938 | 7.011 | 17.966 | 11.741 | 1.00 31.90 | 8 |
| ATOM | 862 | C | SER | 938 | 6.362 | 20.431 | 10.943 | 1.00 23.83 | 6 |
| ATOM | 863 | O | SER | 938 | 7.256 | 20.590 | 10.121 | 1.00 23.83 | 8 |
| ATOM | 864 | N | GLN | 939 | 5.083 | 20.382 | 10.597 | 1.00 34.70 | 7 |
| ATOM | 865 | CA | GLN | 939 | 4.704 | 20.491 | 9.206 | 1.00 34.70 | 6 |
| ATOM | 866 | CB | GLN | 939 | 3.296 | 19.955 | 9.022 | 1.00 40.81 | 6 |
| ATOM | 867 | CG | GLN | 939 | 3.189 | 18.544 | 9.538 | 1.00 40.81 | 6 |
| ATOM | 868 | CD | GLN | 939 | 4.026 | 17.558 | 8.732 | 1.00 40.81 | 6 |
| ATOM | 869 | OE1 | GLN | 939 | 3.584 | 17.084 | 7.675 | 1.00 40.81 | 8 |
| ATOM | 870 | NE2 | GLN | 939 | 5.243 | 17.254 | 9.216 | 1.00 40.81 | 7 |
| ATOM | 871 | C | GLN | 939 | 4.838 | 21.906 | 8.685 | 1.00 34.70 | 6 |
| ATOM | 872 | O | GLN | 939 | 5.352 | 22.096 | 7.592 | 1.00 34.70 | 8 |
| ATOM | 873 | N | GLN | 940 | 4.388 | 22.906 | 9.435 | 1.00 22.70 | 7 |
| ATOM | 874 | CA | GLN | 940 | 4.556 | 24.267 | 8.950 | 1.00 22.70 | 6 |
| ATOM | 875 | CB | GLN | 940 | 4.094 | 25.286 | 9.986 | 1.00 30.92 | 6 |
| ATOM | 876 | CG | GLN | 940 | 4.588 | 26.679 | 9.679 | 1.00 30.92 | 6 |
| ATOM | 877 | CD | GLN | 940 | 3.663 | 27.483 | 8.790 | 1.00 30.92 | 6 |
| ATOM | 878 | OE1 | GLN | 940 | 2.738 | 28.141 | 9.277 | 1.00 30.92 | 8 |
| ATOM | 879 | NE2 | GLN | 940 | 3.891 | 27.427 | 7.482 | 1.00 30.92 | 7 |
| ATOM | 880 | C | GLN | 940 | 6.047 | 24.501 | 8.632 | 1.00 22.70 | 6 |
| ATOM | 881 | O | GLN | 940 | 6.381 | 25.050 | 7.574 | 1.00 22.70 | 8 |
| ATOM | 882 | N | LEU | 941 | 6.934 | 24.076 | 9.535 | 1.00 22.33 | 7 |
| ATOM | 883 | CA | LEU | 941 | 8.377 | 24.242 | 9.348 | 1.00 22.33 | 6 |
| ATOM | 884 | CB | LEU | 941 | 9.137 | 23.858 | 10.599 | 1.00 19.37 | 6 |
| ATOM | 885 | CG | LEU | 941 | 8.939 | 24.738 | 11.806 | 1.00 19.37 | 6 |
| ATOM | 886 | CD1 | LEU | 941 | 9.540 | 23.981 | 12.995 | 1.00 19.37 | 6 |
| ATOM | 887 | CD2 | LEU | 941 | 9.613 | 26.094 | 11.606 | 1.00 19.37 | 6 |
| ATOM | 888 | C | LEU | 941 | 8.956 | 23.427 | 8.202 | 1.00 22.33 | 6 |
| ATOM | 889 | O | LEU | 941 | 9.994 | 23.781 | 7.648 | 1.00 22.33 | 8 |
| ATOM | 890 | N | LEU | 942 | 8.334 | 22.308 | 7.869 | 1.00 30.49 | 7 |
| ATOM | 891 | CA | LEU | 942 | 8.877 | 21.545 | 6.765 | 1.00 30.49 | 6 |
| ATOM | 892 | CB | LEU | 942 | 8.370 | 20.098 | 6.748 | 1.00 27.17 | 6 |
| ATOM | 893 | CG | LEU | 942 | 8.901 | 19.138 | 7.816 | 1.00 27.17 | 6 |
| ATOM | 894 | CD1 | LEU | 942 | 8.244 | 17.799 | 7.576 | 1.00 27.17 | 6 |
| ATOM | 895 | CD2 | LEU | 942 | 10.399 | 18.997 | 7.776 | 1.00 27.17 | 6 |
| ATOM | 896 | C | LEU | 942 | 8.445 | 22.285 | 5.517 | 1.00 30.49 | 6 |
| ATOM | 897 | O | LEU | 942 | 9.211 | 22.408 | 4.582 | 1.00 30.49 | 8 |
| ATOM | 898 | N | HIS | 943 | 7.224 | 22.805 | 5.502 | 1.00 24.87 | 7 |
| ATOM | 899 | CA | HIS | 943 | 6.766 | 23.543 | 4.331 | 1.00 24.87 | 6 |
| ATOM | 900 | CB | HIS | 943 | 5.393 | 24.127 | 4.565 | 1.00 75.69 | 6 |
| ATOM | 901 | CG | HIS | 943 | 4.306 | 23.142 | 4.316 | 1.00 75.69 | 6 |

FIG. 3P

```
ATOM    902  CD2 HIS   943       3.224  23.187   3.507  1.00 75.69      6
ATOM    903  ND1 HIS   943       4.317  21.892   4.884  1.00 75.69      7
ATOM    904  CE1 HIS   943       3.284  21.198   4.431  1.00 75.69      6
ATOM    905  NE2 HIS   943       2.608  21.960   3.596  1.00 75.69      7
ATOM    906  C   HIS   943       7.727  24.644   3.967  1.00 24.87      6
ATOM    907  O   HIS   943       8.112  24.794   2.815  1.00 24.87      8
ATOM    908  N   PHE   944       8.107  25.412   4.976  1.00 23.28      7
ATOM    909  CA  PHE   944       9.049  26.499   4.812  1.00 23.28      6
ATOM    910  CB  PHE   944       9.379  27.069   6.196  1.00 24.44      6
ATOM    911  CG  PHE   944       8.293  27.953   6.782  1.00 24.44      6
ATOM    912  CD1 PHE   944       8.361  28.370   8.101  1.00 24.44      6
ATOM    913  CD2 PHE   944       7.282  28.477   5.983  1.00 24.44      6
ATOM    914  CE1 PHE   944       7.449  29.299   8.598  1.00 24.44      6
ATOM    915  CE2 PHE   944       6.372  29.406   6.489  1.00 24.44      6
ATOM    916  CZ  PHE   944       6.466  29.815   7.792  1.00 24.44      6
ATOM    917  C   PHE   944      10.301  26.011   4.079  1.00 23.28      6
ATOM    918  O   PHE   944      10.778  26.675   3.164  1.00 23.28      8
ATOM    919  N   ALA   945      10.829  24.855   4.470  1.00 15.27      7
ATOM    920  CA  ALA   945      11.996  24.310   3.799  1.00 15.27      6
ATOM    921  CB  ALA   945      12.627  23.197   4.645  1.00 55.81      6
ATOM    922  C   ALA   945      11.644  23.804   2.386  1.00 15.27      6
ATOM    923  O   ALA   945      12.493  23.819   1.517  1.00 15.27      8
ATOM    924  N   ALA   946      10.408  23.368   2.139  1.00  9.68      7
ATOM    925  CA  ALA   946      10.011  22.897   0.795  1.00  9.68      6
ATOM    926  CB  ALA   946       8.734  22.042   0.869  1.00 20.69      6
ATOM    927  C   ALA   946       9.760  24.088  -0.114  1.00  9.68      6
ATOM    928  O   ALA   946      10.026  24.032  -1.319  1.00  9.68      8
ATOM    929  N   ASP   947       9.205  25.149   0.471  1.00 24.26      7
ATOM    930  CA  ASP   947       8.922  26.379  -0.245  1.00 24.26      6
ATOM    931  CB  ASP   947       8.300  27.430   0.671  1.00 51.33      6
ATOM    932  CG  ASP   947       6.870  27.122   1.021  1.00 51.33      6
ATOM    933  OD1 ASP   947       6.378  26.066   0.572  1.00 51.33      8
ATOM    934  OD2 ASP   947       6.248  27.934   1.740  1.00 51.33      8
ATOM    935  C   ASP   947      10.231  26.909  -0.772  1.00 24.26      6
ATOM    936  O   ASP   947      10.378  27.109  -1.979  1.00 24.26      8
ATOM    937  N   VAL   948      11.192  27.120   0.123  1.00 17.83      7
ATOM    938  CA  VAL   948      12.458  27.641  -0.335  1.00 17.83      6
ATOM    939  CB  VAL   948      13.483  27.833   0.788  1.00  5.04      6
ATOM    940  CG1 VAL   948      14.786  28.296   0.175  1.00  5.04      6
ATOM    941  CG2 VAL   948      13.012  28.856   1.801  1.00  5.04      6
ATOM    942  C   VAL   948      13.078  26.766  -1.412  1.00 17.83      6
ATOM    943  O   VAL   948      13.514  27.304  -2.425  1.00 17.83      8
ATOM    944  N   ALA   949      13.115  25.442  -1.219  1.00 24.98      7
ATOM    945  CA  ALA   949      13.697  24.531  -2.221  1.00 24.98      6
ATOM    946  CB  ALA   949      13.827  23.129  -1.666  1.00 53.47      6
ATOM    947  C   ALA   949      12.882  24.505  -3.505  1.00 24.98      6
ATOM    948  O   ALA   949      13.440  24.313  -4.576  1.00 24.98      8
ATOM    949  N   ARG   950      11.570  24.716  -3.413  1.00 23.96      7
ATOM    950  CA  ARG   950      10.742  24.733  -4.617  1.00 23.96      6
ATOM    951  CB  ARG   950       9.239  24.736  -4.282  1.00 30.38      6
ATOM    952  CG  ARG   950       8.302  24.244  -5.419  1.00 30.38      6
ATOM    953  CD  ARG   950       6.829  24.454  -5.081  1.00 30.38      6
ATOM    954  NE  ARG   950       6.567  24.306  -3.648  1.00 30.38      7
ATOM    955  CZ  ARG   950       6.313  23.154  -3.030  1.00 30.38      6
ATOM    956  NH1 ARG   950       6.270  22.013  -3.723  1.00 30.38      7
ATOM    957  NH2 ARG   950       6.132  23.146  -1.708  1.00 30.38      7
ATOM    958  C   ARG   950      11.091  25.997  -5.391  1.00 23.96      6
```

FIG. 3Q

| | | | | | | | | | |
|---|---|---|---|---|---|---|---|---|---|
| ATOM | 959 | O | ARG | 950 | 11.089 | 26.003 | -6.617 | 1.00 23.96 | 8 |
| ATOM | 960 | N | GLY | 951 | 11.409 | 27.064 | -4.667 | 1.00 35.74 | 7 |
| ATOM | 961 | CA | GLY | 951 | 11.749 | 28.315 | -5.323 | 1.00 35.74 | 6 |
| ATOM | 962 | C | GLY | 951 | 13.156 | 28.338 | -5.890 | 1.00 35.74 | 6 |
| ATOM | 963 | O | GLY | 951 | 13.439 | 29.046 | -6.850 | 1.00 35.74 | 8 |
| ATOM | 964 | N | MET | 952 | 14.050 | 27.562 | -5.294 | 1.00 35.49 | 7 |
| ATOM | 965 | CA | MET | 952 | 15.430 | 27.512 | -5.755 | 1.00 35.49 | 6 |
| ATOM | 966 | CB | MET | 952 | 16.335 | 26.979 | -4.656 | 1.00 28.83 | 6 |
| ATOM | 967 | CG | MET | 952 | 16.616 | 27.981 | -3.562 | 1.00 28.83 | 6 |
| ATOM | 968 | SD | MET | 952 | 17.396 | 29.511 | -4.180 | 1.00 28.83 | 16 |
| ATOM | 969 | CE | MET | 952 | 18.963 | 28.883 | -4.732 | 1.00 28.83 | 6 |
| ATOM | 970 | C | MET | 952 | 15.553 | 26.645 | -6.972 | 1.00 35.49 | 6 |
| ATOM | 971 | O | MET | 952 | 16.480 | 26.786 | -7.759 | 1.00 35.49 | 8 |
| ATOM | 972 | N | ASP | 953 | 14.623 | 25.723 | -7.119 | 1.00 22.04 | 7 |
| ATOM | 973 | CA | ASP | 953 | 14.658 | 24.863 | -8.277 | 1.00 22.04 | 6 |
| ATOM | 974 | CB | ASP | 953 | 13.701 | 23.708 | -8.065 | 1.00 46.74 | 6 |
| ATOM | 975 | CG | ASP | 953 | 13.868 | 22.649 | -9.095 | 1.00 46.74 | 6 |
| ATOM | 976 | OD1 | ASP | 953 | 14.938 | 22.016 | -9.119 | 1.00 46.74 | 8 |
| ATOM | 977 | OD2 | ASP | 953 | 12.934 | 22.479 | -9.894 | 1.00 46.74 | 8 |
| ATOM | 978 | C | ASP | 953 | 14.285 | 25.650 | -9.534 | 1.00 22.04 | 6 |
| ATOM | 979 | O | ASP | 953 | 14.796 | 25.378 | -10.600 | 1.00 22.04 | 8 |
| ATOM | 980 | N | TYR | 954 | 13.388 | 26.620 | -9.391 | 1.00 30.73 | 7 |
| ATOM | 981 | CA | TYR | 954 | 12.969 | 27.454 | -10.506 | 1.00 30.73 | 6 |
| ATOM | 982 | CB | TYR | 954 | 11.735 | 28.261 | -10.120 | 1.00 46.88 | 6 |
| ATOM | 983 | CG | TYR | 954 | 11.212 | 29.222 | -11.180 | 1.00 46.88 | 6 |
| ATOM | 984 | CD1 | TYR | 954 | 10.358 | 28.777 | -12.198 | 1.00 46.88 | 6 |
| ATOM | 985 | CE1 | TYR | 954 | 9.817 | 29.675 | -13.139 | 1.00 46.88 | 6 |
| ATOM | 986 | CD2 | TYR | 954 | 11.523 | 30.596 | -11.131 | 1.00 46.88 | 6 |
| ATOM | 987 | CE2 | TYR | 954 | 10.987 | 31.498 | -12.071 | 1.00 46.88 | 6 |
| ATOM | 988 | CZ | TYR | 954 | 10.139 | 31.023 | -13.062 | 1.00 46.88 | 6 |
| ATOM | 989 | OH | TYR | 954 | 9.618 | 31.893 | -13.980 | 1.00 46.88 | 8 |
| ATOM | 990 | C | TYR | 954 | 14.104 | 28.406 | -10.820 | 1.00 30.73 | 6 |
| ATOM | 991 | O | TYR | 954 | 14.484 | 28.556 | -11.961 | 1.00 30.73 | 8 |
| ATOM | 992 | N | LEU | 955 | 14.654 | 29.048 | -9.801 | 1.00 22.51 | 7 |
| ATOM | 993 | CA | LEU | 955 | 15.727 | 29.991 | -10.043 | 1.00 22.51 | 6 |
| ATOM | 994 | CB | LEU | 955 | 16.100 | 30.747 | -8.771 | 1.00 36.85 | 6 |
| ATOM | 995 | CG | LEU | 955 | 15.064 | 31.699 | -8.184 | 1.00 36.85 | 6 |
| ATOM | 996 | CD1 | LEU | 955 | 15.708 | 32.365 | -7.021 | 1.00 36.85 | 6 |
| ATOM | 997 | CD2 | LEU | 955 | 14.586 | 32.734 | -9.210 | 1.00 36.85 | 6 |
| ATOM | 998 | C | LEU | 955 | 16.963 | 29.355 | -10.619 | 1.00 22.51 | 6 |
| ATOM | 999 | O | LEU | 955 | 17.530 | 29.885 | -11.560 | 1.00 22.51 | 8 |
| ATOM | 1000 | N | SER | 956 | 17.403 | 28.229 | -10.080 | 1.00 31.05 | 7 |
| ATOM | 1001 | CA | SER | 956 | 18.608 | 27.602 | -10.615 | 1.00 31.05 | 6 |
| ATOM | 1002 | CB | SER | 956 | 18.998 | 26.380 | -9.778 | 1.00 57.17 | 6 |
| ATOM | 1003 | OG | SER | 956 | 18.077 | 25.324 | -9.989 | 1.00 57.17 | 8 |
| ATOM | 1004 | C | SER | 956 | 18.439 | 27.207 | -12.084 | 1.00 31.05 | 6 |
| ATOM | 1005 | O | SER | 956 | 19.379 | 27.348 | -12.858 | 1.00 31.05 | 8 |
| ATOM | 1006 | N | GLN | 957 | 17.247 | 26.732 | -12.462 | 1.00 19.64 | 7 |
| ATOM | 1007 | CA | GLN | 957 | 16.932 | 26.307 | -13.841 | 1.00 19.64 | 6 |
| ATOM | 1008 | CB | GLN | 957 | 15.580 | 25.587 | -13.899 | 1.00 97.55 | 6 |
| ATOM | 1009 | CG | GLN | 957 | 15.565 | 24.175 | -13.366 | 1.00 97.55 | 6 |
| ATOM | 1010 | CD | GLN | 957 | 16.884 | 23.460 | -13.539 | 1.00 97.55 | 6 |
| ATOM | 1011 | OE1 | GLN | 957 | 17.543 | 23.597 | -14.568 | 1.00 97.55 | 8 |
| ATOM | 1012 | NE2 | GLN | 957 | 17.275 | 22.679 | -12.532 | 1.00 97.55 | 7 |
| ATOM | 1013 | C | GLN | 957 | 16.901 | 27.437 | -14.860 | 1.00 19.64 | 6 |
| ATOM | 1014 | O | GLN | 957 | 16.903 | 27.191 | -16.054 | 1.00 19.64 | 8 |
| ATOM | 1015 | N | LYS | 958 | 16.815 | 28.666 | -14.370 | 1.00 37.82 | 7 |

FIG. 3R

```
ATOM   1016  CA   LYS   958      16.801  29.851  -15.205  1.00  37.82     6
ATOM   1017  CB   LYS   958      15.881  30.918  -14.601  1.00  51.85     6
ATOM   1018  CG   LYS   958      14.374  30.580  -14.569  1.00  51.85     6
ATOM   1019  CD   LYS   958      13.831  30.551  -15.986  1.00  51.85     6
ATOM   1020  CE   LYS   958      12.345  30.408  -16.083  1.00  51.85     6
ATOM   1021  NZ   LYS   958      12.076  30.168  -17.526  1.00  51.85     7
ATOM   1022  C    LYS   958      18.236  30.355  -15.192  1.00  37.82     6
ATOM   1023  O    LYS   958      18.528  31.466  -15.641  1.00  37.82     8
ATOM   1024  N    GLN   959      19.129  29.546  -14.634  1.00  37.14     7
ATOM   1025  CA   GLN   959      20.543  29.885  -14.550  1.00  37.14     6
ATOM   1026  CB   GLN   959      21.078  30.229  -15.942  1.00  59.23     6
ATOM   1027  CG   GLN   959      20.943  29.096  -16.925  1.00  59.23     6
ATOM   1028  CD   GLN   959      21.605  27.827  -16.441  1.00  59.23     6
ATOM   1029  OE1  GLN   959      22.832  27.742  -16.372  1.00  59.23     8
ATOM   1030  NE2  GLN   959      20.790  26.844  -16.047  1.00  59.23     7
ATOM   1031  C    GLN   959      20.914  31.004  -13.559  1.00  37.14     6
ATOM   1032  O    GLN   959      21.937  31.669  -13.751  1.00  37.14     8
ATOM   1033  N    PHE   960      20.097  31.201  -12.519  1.00  48.69     7
ATOM   1034  CA   PHE   960      20.369  32.208  -11.492  1.00  48.69     6
ATOM   1035  CB   PHE   960      19.067  32.712  -10.840  1.00  18.22     6
ATOM   1036  CG   PHE   960      18.261  33.647  -11.686  1.00  18.22     6
ATOM   1037  CD1  PHE   960      17.426  33.166  -12.686  1.00  18.22     6
ATOM   1038  CD2  PHE   960      18.343  35.023  -11.493  1.00  18.22     6
ATOM   1039  CE1  PHE   960      16.677  34.044  -13.502  1.00  18.22     6
ATOM   1040  CE2  PHE   960      17.607  35.908  -12.296  1.00  18.22     6
ATOM   1041  CZ   PHE   960      16.777  35.415  -13.301  1.00  18.22     6
ATOM   1042  C    PHE   960      21.225  31.549  -10.402  1.00  48.69     6
ATOM   1043  O    PHE   960      21.203  30.329  -10.251  1.00  48.69     8
ATOM   1044  N    ILE   961      22.000  32.348   -9.674  1.00  25.93     7
ATOM   1045  CA   ILE   961      22.814  31.840   -8.561  1.00  25.93     6
ATOM   1046  CB   ILE   961      24.347  31.827   -8.883  1.00   5.00     6
ATOM   1047  CG2  ILE   961      25.140  31.201   -7.756  1.00   5.00     6
ATOM   1048  CG1  ILE   961      24.610  31.048  -10.132  1.00   5.00     6
ATOM   1049  CD1  ILE   961      25.990  31.281  -10.676  1.00   5.00     6
ATOM   1050  C    ILE   961      22.542  32.864   -7.449  1.00  25.93     6
ATOM   1051  O    ILE   961      22.658  34.061   -7.689  1.00  25.93     8
ATOM   1052  N    HIS   962      22.193  32.412   -6.247  1.00  38.00     7
ATOM   1053  CA   HIS   962      21.871  33.355   -5.180  1.00  38.00     6
ATOM   1054  CB   HIS   962      21.093  32.661   -4.072  1.00  25.73     6
ATOM   1055  CG   HIS   962      20.206  33.579   -3.289  1.00  25.73     6
ATOM   1056  CD2  HIS   962      20.482  34.461   -2.308  1.00  25.73     6
ATOM   1057  ND1  HIS   962      18.846  33.614   -3.475  1.00  25.73     7
ATOM   1058  CE1  HIS   962      18.315  34.478   -2.625  1.00  25.73     6
ATOM   1059  NE2  HIS   962      19.282  35.004   -1.903  1.00  25.73     7
ATOM   1060  C    HIS   962      23.054  34.079   -4.573  1.00  38.00     6
ATOM   1061  O    HIS   962      23.119  35.303   -4.637  1.00  38.00     8
ATOM   1062  N    ARG   963      23.972  33.338   -3.958  1.00  61.33     7
ATOM   1063  CA   ARG   963      25.152  33.932   -3.334  1.00  61.33     6
ATOM   1064  CB   ARG   963      25.855  34.907   -4.306  1.00  42.94     6
ATOM   1065  CG   ARG   963      25.864  34.466   -5.753  1.00  42.94     6
ATOM   1066  CD   ARG   963      26.986  35.078   -6.571  1.00  42.94     6
ATOM   1067  NE   ARG   963      26.799  36.481   -6.929  1.00  42.94     7
ATOM   1068  CZ   ARG   963      26.940  37.488   -6.079  1.00  42.94     6
ATOM   1069  NH1  ARG   963      27.268  37.258   -4.809  1.00  42.94     7
ATOM   1070  NH2  ARG   963      26.752  38.723   -6.508  1.00  42.94     7
ATOM   1071  C    ARG   963      24.756  34.688   -2.062  1.00  61.33     6
ATOM   1072  O    ARG   963      25.543  35.464   -1.528  1.00  61.33     8
```

FIG. 3S

| ATOM | 1073 | N   | ASN | 964 | 23.549 | 34.460 | -1.561 | 1.00 | 37.36 | 7 |
| ATOM | 1074 | CA  | ASN | 964 | 23.111 | 35.212 | -0.384 | 1.00 | 37.36 | 6 |
| ATOM | 1075 | CB  | ASN | 964 | 22.742 | 36.636 | -0.805 | 1.00 | 69.75 | 6 |
| ATOM | 1076 | CG  | ASN | 964 | 23.319 | 37.670 | 0.107  | 1.00 | 69.75 | 6 |
| ATOM | 1077 | OD1 | ASN | 964 | 23.337 | 37.499 | 1.324  | 1.00 | 69.75 | 8 |
| ATOM | 1078 | ND2 | ASN | 964 | 23.792 | 38.761 | -0.468 | 1.00 | 69.75 | 7 |
| ATOM | 1079 | C   | ASN | 964 | 21.909 | 34.573 | 0.273  | 1.00 | 37.36 | 6 |
| ATOM | 1080 | O   | ASN | 964 | 21.096 | 35.251 | 0.890  | 1.00 | 37.36 | 8 |
| ATOM | 1081 | N   | LEU | 965 | 21.812 | 33.258 | 0.133  | 1.00 | 45.72 | 7 |
| ATOM | 1082 | CA  | LEU | 965 | 20.691 | 32.503 | 0.666  | 1.00 | 45.72 | 6 |
| ATOM | 1083 | CB  | LEU | 965 | 20.515 | 31.230 | -0.182 | 1.00 | 22.49 | 6 |
| ATOM | 1084 | CG  | LEU | 965 | 19.348 | 30.261 | -0.002 | 1.00 | 22.49 | 6 |
| ATOM | 1085 | CD1 | LEU | 965 | 19.237 | 29.344 | -1.189 | 1.00 | 22.49 | 6 |
| ATOM | 1086 | CD2 | LEU | 965 | 19.565 | 29.461 | 1.252  | 1.00 | 22.49 | 6 |
| ATOM | 1087 | C   | LEU | 965 | 20.867 | 32.180 | 2.151  | 1.00 | 45.72 | 6 |
| ATOM | 1088 | O   | LEU | 965 | 21.862 | 31.584 | 2.564  | 1.00 | 45.72 | 8 |
| ATOM | 1089 | N   | ALA | 966 | 19.898 | 32.605 | 2.948  | 1.00 | 9.29  | 7 |
| ATOM | 1090 | CA  | ALA | 966 | 19.899 | 32.364 | 4.386  | 1.00 | 9.29  | 6 |
| ATOM | 1091 | CB  | ALA | 966 | 20.870 | 33.291 | 5.057  | 1.00 | 5.00  | 6 |
| ATOM | 1092 | C   | ALA | 966 | 18.474 | 32.615 | 4.891  | 1.00 | 9.29  | 6 |
| ATOM | 1093 | O   | ALA | 966 | 17.613 | 32.963 | 4.107  | 1.00 | 9.29  | 8 |
| ATOM | 1094 | N   | ALA | 967 | 18.209 | 32.464 | 6.181  | 1.00 | 20.93 | 7 |
| ATOM | 1095 | CA  | ALA | 967 | 16.855 | 32.698 | 6.627  | 1.00 | 20.93 | 6 |
| ATOM | 1096 | CB  | ALA | 967 | 16.627 | 32.084 | 7.989  | 1.00 | 8.30  | 6 |
| ATOM | 1097 | C   | ALA | 967 | 16.481 | 34.170 | 6.630  | 1.00 | 20.93 | 6 |
| ATOM | 1098 | O   | ALA | 967 | 15.335 | 34.486 | 6.393  | 1.00 | 20.93 | 8 |
| ATOM | 1099 | N   | ARG | 968 | 17.423 | 35.077 | 6.875  | 1.00 | 18.97 | 7 |
| ATOM | 1100 | CA  | ARG | 968 | 17.100 | 36.503 | 6.901  | 1.00 | 18.97 | 6 |
| ATOM | 1101 | CB  | ARG | 968 | 18.298 | 37.322 | 7.381  | 1.00 | 55.21 | 6 |
| ATOM | 1102 | CG  | ARG | 968 | 19.596 | 36.932 | 6.747  | 1.00 | 55.21 | 6 |
| ATOM | 1103 | CD  | ARG | 968 | 20.653 | 38.006 | 6.946  | 1.00 | 55.21 | 6 |
| ATOM | 1104 | NE  | ARG | 968 | 21.881 | 37.608 | 6.275  | 1.00 | 55.21 | 7 |
| ATOM | 1105 | CZ  | ARG | 968 | 22.617 | 36.572 | 6.652  | 1.00 | 55.21 | 6 |
| ATOM | 1106 | NH1 | ARG | 968 | 22.246 | 35.846 | 7.704  | 1.00 | 55.21 | 7 |
| ATOM | 1107 | NH2 | ARG | 968 | 23.697 | 36.244 | 5.954  | 1.00 | 55.21 | 7 |
| ATOM | 1108 | C   | ARG | 968 | 16.632 | 37.016 | 5.548  | 1.00 | 18.97 | 6 |
| ATOM | 1109 | O   | ARG | 968 | 15.790 | 37.915 | 5.477  | 1.00 | 18.97 | 8 |
| ATOM | 1110 | N   | ASN | 969 | 17.165 | 36.427 | 4.481  | 1.00 | 17.09 | 7 |
| ATOM | 1111 | CA  | ASN | 969 | 16.820 | 36.815 | 3.109  | 1.00 | 17.09 | 6 |
| ATOM | 1112 | CB  | ASN | 969 | 18.008 | 36.589 | 2.179  | 1.00 | 47.15 | 6 |
| ATOM | 1113 | CG  | ASN | 969 | 19.028 | 37.700 | 2.240  | 1.00 | 47.15 | 6 |
| ATOM | 1114 | OD1 | ASN | 969 | 20.137 | 37.547 | 1.739  | 1.00 | 47.15 | 8 |
| ATOM | 1115 | ND2 | ASN | 969 | 18.661 | 38.831 | 2.842  | 1.00 | 47.15 | 7 |
| ATOM | 1116 | C   | ASN | 969 | 15.619 | 36.088 | 2.526  | 1.00 | 17.09 | 6 |
| ATOM | 1117 | O   | ASN | 969 | 15.524 | 35.926 | 1.318  | 1.00 | 17.09 | 8 |
| ATOM | 1118 | N   | ILE | 970 | 14.725 | 35.625 | 3.385  | 1.00 | 17.16 | 7 |
| ATOM | 1119 | CA  | ILE | 970 | 13.527 | 34.939 | 2.933  | 1.00 | 17.16 | 6 |
| ATOM | 1120 | CB  | ILE | 970 | 13.521 | 33.425 | 3.353  | 1.00 | 5.00  | 6 |
| ATOM | 1121 | CG2 | ILE | 970 | 12.211 | 32.763 | 2.943  | 1.00 | 5.00  | 6 |
| ATOM | 1122 | CG1 | ILE | 970 | 14.716 | 32.686 | 2.742  | 1.00 | 5.00  | 6 |
| ATOM | 1123 | CD1 | ILE | 970 | 14.542 | 32.175 | 1.313  | 1.00 | 5.00  | 6 |
| ATOM | 1124 | C   | ILE | 970 | 12.395 | 35.687 | 3.653  | 1.00 | 17.16 | 6 |
| ATOM | 1125 | O   | ILE | 970 | 12.454 | 35.923 | 4.864  | 1.00 | 17.16 | 8 |
| ATOM | 1126 | N   | LEU | 971 | 11.365 | 36.047 | 2.903  | 1.00 | 27.06 | 7 |
| ATOM | 1127 | CA  | LEU | 971 | 10.234 | 36.784 | 3.443  | 1.00 | 27.06 | 6 |
| ATOM | 1128 | CB  | LEU | 971 | 10.000 | 38.039 | 2.584  | 1.00 | 23.00 | 6 |
| ATOM | 1129 | CG  | LEU | 971 | 11.152 | 39.063 | 2.555  | 1.00 | 23.00 | 6 |

FIG. 3T

```
ATOM  1130  CD1  LEU  971   11.197  39.762   1.249  1.00  23.00  6
ATOM  1131  CD2  LEU  971   10.990  40.054   3.689  1.00  23.00  6
ATOM  1132  C    LEU  971    8.984  35.910   3.465  1.00  27.06  6
ATOM  1133  O    LEU  971    8.730  35.192   2.511  1.00  27.06  8
ATOM  1134  N    VAL  972    8.218  35.967   4.558  1.00  35.27  7
ATOM  1135  CA   VAL  972    6.974  35.188   4.710  1.00  35.27  6
ATOM  1136  CB   VAL  972    6.641  34.916   6.237  1.00  15.12  6
ATOM  1137  CG1  VAL  972    5.384  34.069   6.387  1.00  15.12  6
ATOM  1138  CG2  VAL  972    7.806  34.239   6.917  1.00  15.12  6
ATOM  1139  C    VAL  972    5.805  35.979   4.086  1.00  35.27  6
ATOM  1140  O    VAL  972    5.220  36.848   4.727  1.00  35.27  8
ATOM  1141  N    GLY  973    5.466  35.686   2.841  1.00  28.86  7
ATOM  1142  CA   GLY  973    4.378  36.404   2.212  1.00  28.86  6
ATOM  1143  C    GLY  973    3.021  35.983   2.743  1.00  28.86  6
ATOM  1144  O    GLY  973    2.933  35.251   3.734  1.00  28.86  8
ATOM  1145  N    GLU  974    1.954  36.429   2.092  1.00  36.97  7
ATOM  1146  CA   GLU  974    0.621  36.081   2.554  1.00  36.97  6
ATOM  1147  CB   GLU  974   -0.434  36.662   1.619  1.00  98.72  6
ATOM  1148  CG   GLU  974   -1.001  37.980   2.107  1.00  98.72  6
ATOM  1149  CD   GLU  974   -1.619  37.873   3.503  1.00  98.72  6
ATOM  1150  OE1  GLU  974   -2.364  36.904   3.759  1.00  98.72  8
ATOM  1151  OE2  GLU  974   -1.368  38.763   4.342  1.00  98.72  8
ATOM  1152  C    GLU  974    0.418  34.585   2.720  1.00  36.97  6
ATOM  1153  O    GLU  974    1.049  33.768   2.034  1.00  36.97  8
ATOM  1154  N    ASN  975   -0.474  34.253   3.649  1.00  50.17  7
ATOM  1155  CA   ASN  975   -0.811  32.878   3.980  1.00  50.17  6
ATOM  1156  CB   ASN  975   -1.496  32.190   2.812  1.00  49.51  6
ATOM  1157  CG   ASN  975   -2.900  32.725   2.577  1.00  49.51  6
ATOM  1158  OD1  ASN  975   -3.688  32.145   1.834  1.00  49.51  8
ATOM  1159  ND2  ASN  975   -3.218  33.851   3.213  1.00  49.51  7
ATOM  1160  C    ASN  975    0.432  32.122   4.392  1.00  50.17  6
ATOM  1161  O    ASN  975    0.528  30.910   4.222  1.00  50.17  8
ATOM  1162  N    TYR  976    1.386  32.871   4.931  1.00  34.67  7
ATOM  1163  CA   TYR  976    2.637  32.335   5.427  1.00  34.67  6
ATOM  1164  CB   TYR  976    2.386  31.613   6.734  1.00  32.84  6
ATOM  1165  CG   TYR  976    1.690  32.497   7.736  1.00  32.84  6
ATOM  1166  CD1  TYR  976    0.309  32.654   7.715  1.00  32.84  6
ATOM  1167  CE1  TYR  976   -0.328  33.464   8.625  1.00  32.84  6
ATOM  1168  CD2  TYR  976    2.411  33.182   8.693  1.00  32.84  6
ATOM  1169  CE2  TYR  976    1.792  33.991   9.602  1.00  32.84  6
ATOM  1170  CZ   TYR  976    0.422  34.129   9.571  1.00  32.84  6
ATOM  1171  OH   TYR  976   -0.210  34.897  10.515  1.00  32.84  8
ATOM  1172  C    TYR  976    3.376  31.440   4.475  1.00  34.67  6
ATOM  1173  O    TYR  976    3.903  30.410   4.875  1.00  34.67  8
ATOM  1174  N    VAL  977    3.436  31.857   3.217  1.00  16.20  7
ATOM  1175  CA   VAL  977    4.135  31.111   2.181  1.00  16.20  6
ATOM  1176  CB   VAL  977    3.297  31.091   0.876  1.00   9.07  6
ATOM  1177  CG1  VAL  977    4.187  30.767  -0.331  1.00   9.07  6
ATOM  1178  CG2  VAL  977    2.153  30.102   1.005  1.00   9.07  6
ATOM  1179  C    VAL  977    5.490  31.755   1.900  1.00  16.20  6
ATOM  1180  O    VAL  977    5.545  32.795   1.284  1.00  16.20  8
ATOM  1181  N    ALA  978    6.571  31.126   2.337  1.00  15.88  7
ATOM  1182  CA   ALA  978    7.924  31.643   2.141  1.00  15.88  6
ATOM  1183  CB   ALA  978    8.940  30.547   2.489  1.00  21.88  6
ATOM  1184  C    ALA  978    8.238  32.215   0.757  1.00  15.88  6
ATOM  1185  O    ALA  978    7.905  31.630  -0.268  1.00  15.88  8
ATOM  1186  N    LYS  979    8.920  33.352   0.736  1.00  28.57  7
```

FIG. 3U

| | | | | | | | | | |
|---|---|---|---|---|---|---|---|---|---|
| ATOM | 1187 | CA | LYS | 979 | 9.284 | 34.011 | -0.508 | 1.00 28.57 | 6 |
| ATOM | 1188 | CB | LYS | 979 | 8.468 | 35.289 | -0.621 | 1.00 15.51 | 6 |
| ATOM | 1189 | CG | LYS | 979 | 6.969 | 35.078 | -0.838 | 1.00 15.51 | 6 |
| ATOM | 1190 | CD | LYS | 979 | 6.698 | 34.786 | -2.297 | 1.00 15.51 | 6 |
| ATOM | 1191 | CE | LYS | 979 | 5.254 | 35.044 | -2.662 | 1.00 15.51 | 6 |
| ATOM | 1192 | NZ | LYS | 979 | 4.388 | 34.606 | -1.545 | 1.00 15.51 | 7 |
| ATOM | 1193 | C | LYS | 979 | 10.800 | 34.294 | -0.506 | 1.00 28.57 | 6 |
| ATOM | 1194 | O | LYS | 979 | 11.348 | 34.679 | 0.525 | 1.00 28.57 | 8 |
| ATOM | 1195 | N | ILE | 980 | 11.458 | 34.082 | -1.655 | 1.00 23.28 | 7 |
| ATOM | 1196 | CA | ILE | 980 | 12.914 | 34.271 | -1.815 | 1.00 23.28 | 6 |
| ATOM | 1197 | CB | ILE | 980 | 13.507 | 33.236 | -2.812 | 1.00 12.16 | 6 |
| ATOM | 1198 | CG2 | ILE | 980 | 14.986 | 33.535 | -3.046 | 1.00 12.16 | 6 |
| ATOM | 1199 | CG1 | ILE | 980 | 13.309 | 31.804 | -2.268 | 1.00 12.16 | 6 |
| ATOM | 1200 | CD1 | ILE | 980 | 13.475 | 30.688 | -3.319 | 1.00 12.16 | 6 |
| ATOM | 1201 | C | ILE | 980 | 13.270 | 35.665 | -2.301 | 1.00 23.28 | 6 |
| ATOM | 1202 | O | ILE | 980 | 12.739 | 36.135 | -3.292 | 1.00 23.28 | 8 |
| ATOM | 1203 | N | ALA | 981 | 14.185 | 36.335 | -1.623 | 1.00 30.98 | 7 |
| ATOM | 1204 | CA | ALA | 981 | 14.538 | 37.683 | -2.040 | 1.00 30.98 | 6 |
| ATOM | 1205 | CB | ALA | 981 | 13.810 | 38.664 | -1.156 | 1.00 12.02 | 6 |
| ATOM | 1206 | C | ALA | 981 | 16.047 | 37.959 | -2.021 | 1.00 30.98 | 6 |
| ATOM | 1207 | O | ALA | 981 | 16.840 | 37.172 | -1.499 | 1.00 30.98 | 8 |
| ATOM | 1208 | N | ASP | 982 | 16.433 | 39.094 | -2.589 | 1.00 70.73 | 7 |
| ATOM | 1209 | CA | ASP | 982 | 17.834 | 39.511 | -2.652 | 1.00 70.73 | 6 |
| ATOM | 1210 | CB | ASP | 982 | 18.327 | 39.939 | -1.272 | 1.00 99.58 | 6 |
| ATOM | 1211 | CG | ASP | 982 | 19.512 | 40.861 | -1.358 | 1.00 99.58 | 6 |
| ATOM | 1212 | OD1 | ASP | 982 | 19.287 | 42.012 | -1.783 | 1.00 99.58 | 8 |
| ATOM | 1213 | OD2 | ASP | 982 | 20.646 | 40.436 | -1.039 | 1.00 99.58 | 8 |
| ATOM | 1214 | C | ASP | 982 | 18.821 | 38.488 | -3.199 | 1.00 70.73 | 6 |
| ATOM | 1215 | O | ASP | 982 | 19.686 | 38.005 | -2.477 | 1.00 70.73 | 8 |
| ATOM | 1216 | N | PHE | 983 | 18.703 | 38.184 | -4.479 | 1.00 67.82 | 7 |
| ATOM | 1217 | CA | PHE | 983 | 19.595 | 37.229 | -5.095 | 1.00 67.82 | 6 |
| ATOM | 1218 | CB | PHE | 983 | 18.781 | 36.124 | -5.784 | 1.00 46.69 | 6 |
| ATOM | 1219 | CG | PHE | 983 | 17.480 | 36.593 | -6.382 | 1.00 46.69 | 6 |
| ATOM | 1220 | CD1 | PHE | 983 | 17.423 | 37.752 | -7.143 | 1.00 46.69 | 6 |
| ATOM | 1221 | CD2 | PHE | 983 | 16.317 | 35.852 | -6.222 | 1.00 46.69 | 6 |
| ATOM | 1222 | CE1 | PHE | 983 | 16.229 | 38.166 | -7.737 | 1.00 46.69 | 6 |
| ATOM | 1223 | CE2 | PHE | 983 | 15.122 | 36.259 | -6.814 | 1.00 46.69 | 6 |
| ATOM | 1224 | CZ | PHE | 983 | 15.080 | 37.413 | -7.570 | 1.00 46.69 | 6 |
| ATOM | 1225 | C | PHE | 983 | 20.552 | 37.905 | -6.081 | 1.00 67.82 | 6 |
| ATOM | 1226 | O | PHE | 983 | 20.451 | 39.112 | -6.338 | 1.00 67.82 | 8 |
| ATOM | 1227 | N | GLY | 984 | 21.497 | 37.128 | -6.599 | 1.00 44.02 | 7 |
| ATOM | 1228 | CA | GLY | 984 | 22.467 | 37.644 | -7.543 | 1.00 44.02 | 6 |
| ATOM | 1229 | C | GLY | 984 | 21.911 | 37.639 | -8.954 | 1.00 44.02 | 6 |
| ATOM | 1230 | O | GLY | 984 | 21.520 | 36.599 | -9.488 | 1.00 44.02 | 8 |
| ATOM | 1231 | N | LEU | 985 | 21.875 | 38.816 | -9.562 | 1.00100.00 | 7 |
| ATOM | 1232 | CA | LEU | 985 | 21.363 | 38.951 | -10.917 | 1.00100.00 | 6 |
| ATOM | 1233 | CB | LEU | 985 | 20.792 | 40.360 | -11.126 | 1.00 41.04 | 6 |
| ATOM | 1234 | CG | LEU | 985 | 19.455 | 40.644 | -10.434 | 1.00 41.04 | 6 |
| ATOM | 1235 | CD1 | LEU | 985 | 18.448 | 39.621 | -10.945 | 1.00 41.04 | 6 |
| ATOM | 1236 | CD2 | LEU | 985 | 19.577 | 40.549 | -8.925 | 1.00 41.04 | 6 |
| ATOM | 1237 | C | LEU | 985 | 22.473 | 38.670 | -11.920 | 1.00100.00 | 6 |
| ATOM | 1238 | O | LEU | 985 | 22.517 | 39.253 | -13.004 | 1.00100.00 | 8 |
| ATOM | 1239 | N | SER | 986 | 23.383 | 37.785 | -11.539 | 1.00 42.70 | 7 |
| ATOM | 1240 | CA | SER | 986 | 24.484 | 37.421 | -12.416 | 1.00 42.70 | 6 |
| ATOM | 1241 | CB | SER | 986 | 25.818 | 37.625 | -11.697 | 1.00 68.70 | 6 |
| ATOM | 1242 | OG | SER | 986 | 25.996 | 38.984 | -11.346 | 1.00 68.70 | 8 |
| ATOM | 1243 | C | SER | 986 | 24.295 | 35.955 | -12.780 | 1.00 42.70 | 6 |

FIG. 3V

```
ATOM   1244  O    SER  986      24.956  35.078 -12.238  1.00 42.70       8
ATOM   1245  N    ARG  987      23.381  35.697 -13.703  1.00 47.12       7
ATOM   1246  CA   ARG  987      23.068  34.336 -14.124  1.00 47.12       6
ATOM   1247  CB   ARG  987      21.873  34.383 -15.045  1.00 55.43       6
ATOM   1248  CG   ARG  987      20.828  35.354 -14.585  1.00 55.43       6
ATOM   1249  CD   ARG  987      19.927  35.581 -15.728  1.00 55.43       6
ATOM   1250  NE   ARG  987      19.371  34.311 -16.169  1.00 55.43       7
ATOM   1251  CZ   ARG  987      18.891  34.116 -17.385  1.00 55.43       6
ATOM   1252  NH1  ARG  987      18.924  35.110 -18.261  1.00 55.43       7
ATOM   1253  NH2  ARG  987      18.364  32.946 -17.713  1.00 55.43       7
ATOM   1254  C    ARG  987      24.204  33.608 -14.823  1.00 47.12       6
ATOM   1255  O    ARG  987      24.990  34.223 -15.535  1.00 47.12       8
ATOM   1256  N    GLY  988      24.281  32.294 -14.629  1.00 32.39       7
ATOM   1257  CA   GLY  988      25.330  31.512 -15.274  1.00 32.39       6
ATOM   1258  C    GLY  988      25.704  30.203 -14.592  1.00 32.39       6
ATOM   1259  O    GLY  988      24.832  29.393 -14.275  1.00 32.39       8
ATOM   1260  N    GLN  989      26.999  29.978 -14.382  1.00 53.32       7
ATOM   1261  CA   GLN  989      27.473  28.756 -13.738  1.00 53.32       6
ATOM   1262  CB   GLN  989      28.063  27.789 -14.761  1.00 52.63       6
ATOM   1263  CG   GLN  989      27.056  26.759 -15.207  1.00 52.63       6
ATOM   1264  CD   GLN  989      27.583  25.337 -15.120  1.00 52.63       6
ATOM   1265  OE1  GLN  989      28.219  24.855 -16.052  1.00 52.63       8
ATOM   1266  NE2  GLN  989      27.355  24.672 -13.985  1.00 52.63       7
ATOM   1267  C    GLN  989      28.473  28.926 -12.631  1.00 53.32       6
ATOM   1268  O    GLN  989      28.683  28.002 -11.861  1.00 53.32       8
ATOM   1269  N    GLU  990      29.082  30.096 -12.532  1.00 57.00       7
ATOM   1270  CA   GLU  990      30.072  30.328 -11.503  1.00 57.00       6
ATOM   1271  CB   GLU  990      31.320  29.532 -11.858  1.00 60.46       6
ATOM   1272  CG   GLU  990      32.281  29.295 -10.745  1.00 60.46       6
ATOM   1273  CD   GLU  990      32.976  27.979 -10.927  1.00 60.46       6
ATOM   1274  OE1  GLU  990      33.448  27.718 -12.049  1.00 60.46       8
ATOM   1275  OE2  GLU  990      33.044  27.198  -9.960  1.00 60.46       8
ATOM   1276  C    GLU  990      30.368  31.814 -11.523  1.00 57.00       6
ATOM   1277  O    GLU  990      30.639  32.363 -12.589  1.00 57.00       8
ATOM   1278  N    VAL  991      30.269  32.470 -10.367  1.00 47.34       7
ATOM   1279  CA   VAL  991      30.567  33.904 -10.285  1.00 47.34       6
ATOM   1280  CB   VAL  991      29.423  34.745  -9.575  1.00 25.98       6
ATOM   1281  CG1  VAL  991      29.646  36.247  -9.822  1.00 25.98       6
ATOM   1282  CG2  VAL  991      28.029  34.365 -10.094  1.00 25.98       6
ATOM   1283  C    VAL  991      31.878  34.057  -9.493  1.00 47.34       6
ATOM   1284  O    VAL  991      32.387  33.090  -8.924  1.00 47.34       8
ATOM   1285  N    TYR  992      32.437  35.262  -9.483  1.00 68.84       7
ATOM   1286  CA   TYR  992      33.683  35.517  -8.774  1.00 68.84       6
ATOM   1287  CB   TYR  992      34.849  35.554  -9.765  1.00 49.61       6
ATOM   1288  CG   TYR  992      36.187  35.817  -9.103  1.00 49.61       6
ATOM   1289  CD1  TYR  992      36.680  34.950  -8.127  1.00 49.61       6
ATOM   1290  CE1  TYR  992      37.886  35.201  -7.465  1.00 49.61       6
ATOM   1291  CD2  TYR  992      36.941  36.947  -9.410  1.00 49.61       6
ATOM   1292  CE2  TYR  992      38.154  37.210  -8.750  1.00 49.61       6
ATOM   1293  CZ   TYR  992      38.614  36.333  -7.780  1.00 49.61       6
ATOM   1294  OH   TYR  992      39.785  36.607  -7.115  1.00 49.61       8
ATOM   1295  C    TYR  992      33.653  36.836  -7.999  1.00 68.84       6
ATOM   1296  O    TYR  992      33.941  37.886  -8.565  1.00 68.84       8
ATOM   1297  N    VAL  993      33.312  36.802  -6.718  1.00 73.45       7
ATOM   1298  CA   VAL  993      33.293  38.048  -5.964  1.00 73.45       6
ATOM   1299  CB   VAL  993      32.078  38.110  -5.043  1.00 77.88       6
ATOM   1300  CG1  VAL  993      30.812  38.281  -5.857  1.00 77.88       6
```

FIG. 3W

```
ATOM   1301  CG2 VAL   993      32.012  36.866  -4.236  1.00 77.88       6
ATOM   1302  C   VAL   993      34.585  38.227  -5.162  1.00 73.45       6
ATOM   1303  O   VAL   993      35.222  37.248  -4.762  1.00 73.45       8
ATOM   1304  N   LYS   994      34.965  39.483  -4.946  1.00100.00       7
ATOM   1305  CA  LYS   994      36.190  39.825  -4.225  1.00100.00       6
ATOM   1306  CB  LYS   994      37.340  39.934  -5.227  1.00 96.49       6
ATOM   1307  CG  LYS   994      38.693  40.258  -4.635  1.00 96.49       6
ATOM   1308  CD  LYS   994      39.679  40.656  -5.728  1.00 96.49       6
ATOM   1309  CE  LYS   994      40.977  39.891  -5.576  1.00 96.49       6
ATOM   1310  NZ  LYS   994      41.937  40.208  -6.655  1.00 96.49       7
ATOM   1311  C   LYS   994      35.981  41.170  -3.525  1.00100.00       6
ATOM   1312  O   LYS   994      36.298  42.217  -4.089  1.00100.00       8
ATOM   1313  N   LYS   995      35.456  41.135  -2.299  1.00100.00       7
ATOM   1314  CA  LYS   995      35.173  42.337  -1.505  1.00100.00       6
ATOM   1315  CB  LYS   995      36.432  43.233  -1.423  1.00100.00       6
ATOM   1316  C   LYS   995      33.996  43.132  -2.094  1.00100.00       6
ATOM   1317  O   LYS   995      34.079  44.383  -2.139  1.00100.00       8
ATOM   1318  OXT LYS   995      33.001  42.485  -2.484  1.00 85.30       8
TER
ATOM   1319  CB  PRO  1001      26.968  35.804   4.979  1.00 23.69       6
ATOM   1320  CG  PRO  1001      26.527  36.525   3.738  1.00 23.69       6
ATOM   1321  C   PRO  1001      29.219  34.895   5.215  1.00 43.97       6
ATOM   1322  O   PRO  1001      28.910  33.885   4.598  1.00 43.97       8
ATOM   1323  N   PRO  1001      28.835  36.609   3.692  1.00 43.97       7
ATOM   1324  CD  PRO  1001      27.692  36.488   2.779  1.00 23.69       6
ATOM   1325  CA  PRO  1001      28.434  36.157   5.028  1.00 43.97       6
ATOM   1326  N   VAL  1002      30.217  34.937   6.077  1.00 30.46       7
ATOM   1327  CA  VAL  1002      31.040  33.763   6.267  1.00 30.46       6
ATOM   1328  CB  VAL  1002      32.241  34.137   7.118  1.00 49.80       6
ATOM   1329  CG1 VAL  1002      32.805  35.456   6.632  1.00 49.80       6
ATOM   1330  CG2 VAL  1002      31.852  34.219   8.578  1.00 49.80       6
ATOM   1331  C   VAL  1002      30.360  32.503   6.834  1.00 30.46       6
ATOM   1332  O   VAL  1002      30.790  31.389   6.553  1.00 30.46       8
ATOM   1333  N   ARG  1003      29.292  32.669   7.596  1.00 40.35       7
ATOM   1334  CA  ARG  1003      28.643  31.505   8.207  1.00 40.35       6
ATOM   1335  CB  ARG  1003      27.872  31.924   9.444  1.00 42.33       6
ATOM   1336  CG  ARG  1003      28.755  32.265  10.626  1.00 42.33       6
ATOM   1337  CD  ARG  1003      27.857  32.633  11.767  1.00 42.33       6
ATOM   1338  NE  ARG  1003      28.533  32.694  13.047  1.00 42.33       7
ATOM   1339  CZ  ARG  1003      29.508  33.544  13.336  1.00 42.33       6
ATOM   1340  NH1 ARG  1003      29.932  34.417  12.428  1.00 42.33       7
ATOM   1341  NH2 ARG  1003      30.067  33.516  14.535  1.00 42.33       7
ATOM   1342  C   ARG  1003      27.737  30.626   7.370  1.00 40.35       6
ATOM   1343  O   ARG  1003      27.262  29.606   7.865  1.00 40.35       8
ATOM   1344  N   TRP  1004      27.495  31.011   6.121  1.00 26.04       7
ATOM   1345  CA  TRP  1004      26.632  30.250   5.221  1.00 26.04       6
ATOM   1346  CB  TRP  1004      25.459  31.141   4.768  1.00 50.68       6
ATOM   1347  CG  TRP  1004      24.332  31.279   5.776  1.00 50.68       6
ATOM   1348  CD2 TRP  1004      24.261  32.186   6.885  1.00 50.68       6
ATOM   1349  CE2 TRP  1004      23.066  31.901   7.585  1.00 50.68       6
ATOM   1350  CE3 TRP  1004      25.093  33.208   7.363  1.00 50.68       6
ATOM   1351  CD1 TRP  1004      23.207  30.513   5.843  1.00 50.68       6
ATOM   1352  NE1 TRP  1004      22.445  30.880   6.924  1.00 50.68       7
ATOM   1353  CZ2 TRP  1004      22.681  32.601   8.737  1.00 50.68       6
ATOM   1354  CZ3 TRP  1004      24.704  33.905   8.515  1.00 50.68       6
ATOM   1355  CH2 TRP  1004      23.510  33.594   9.186  1.00 50.68       6
ATOM   1356  C   TRP  1004      27.409  29.747   4.006  1.00 26.04       6
```

FIG. 3X

| | | | | | | | | | |
|---|---|---|---|---|---|---|---|---|---|
| ATOM | 1357 | O | TRP | 1004 | 27.003 | 28.794 | 3.356 | 1.00 26.04 | 8 |
| ATOM | 1358 | N | MET | 1005 | 28.535 | 30.382 | 3.706 | 1.00 37.80 | 7 |
| ATOM | 1359 | CA | MET | 1005 | 29.329 | 30.009 | 2.543 | 1.00 37.80 | 6 |
| ATOM | 1360 | CB | MET | 1005 | 30.502 | 30.949 | 2.412 | 1.00 40.16 | 6 |
| ATOM | 1361 | CG | MET | 1005 | 30.063 | 32.299 | 1.973 | 1.00 40.16 | 6 |
| ATOM | 1362 | SD | MET | 1005 | 31.319 | 33.493 | 2.212 | 1.00 40.16 | 16 |
| ATOM | 1363 | CE | MET | 1005 | 32.621 | 32.780 | 1.246 | 1.00 40.16 | 6 |
| ATOM | 1364 | C | MET | 1005 | 29.827 | 28.584 | 2.473 | 1.00 37.80 | 6 |
| ATOM | 1365 | O | MET | 1005 | 30.268 | 28.011 | 3.465 | 1.00 37.80 | 8 |
| ATOM | 1366 | N | ALA | 1006 | 29.753 | 28.008 | 1.283 | 1.00 45.98 | 7 |
| ATOM | 1367 | CA | ALA | 1006 | 30.230 | 26.654 | 1.092 | 1.00 45.98 | 6 |
| ATOM | 1368 | CB | ALA | 1006 | 29.797 | 26.138 | -0.284 | 1.00 10.86 | 6 |
| ATOM | 1369 | C | ALA | 1006 | 31.764 | 26.736 | 1.196 | 1.00 45.98 | 6 |
| ATOM | 1370 | O | ALA | 1006 | 32.322 | 27.830 | 1.151 | 1.00 45.98 | 8 |
| ATOM | 1371 | N | ILE | 1007 | 32.448 | 25.604 | 1.326 | 1.00 44.58 | 7 |
| ATOM | 1372 | CA | ILE | 1007 | 33.909 | 25.657 | 1.446 | 1.00 44.58 | 6 |
| ATOM | 1373 | CB | ILE | 1007 | 34.528 | 24.267 | 1.753 | 1.00 25.13 | 6 |
| ATOM | 1374 | CG2 | ILE | 1007 | 34.415 | 23.969 | 3.224 | 1.00 25.13 | 6 |
| ATOM | 1375 | CG1 | ILE | 1007 | 33.880 | 23.182 | 0.886 | 1.00 25.13 | 6 |
| ATOM | 1376 | CD1 | ILE | 1007 | 34.418 | 23.123 | -0.571 | 1.00 25.13 | 6 |
| ATOM | 1377 | C | ILE | 1007 | 34.619 | 26.244 | 0.234 | 1.00 44.58 | 6 |
| ATOM | 1378 | O | ILE | 1007 | 35.585 | 26.988 | 0.379 | 1.00 44.58 | 8 |
| ATOM | 1379 | N | GLU | 1008 | 34.137 | 25.915 | -0.957 | 1.00 31.07 | 7 |
| ATOM | 1380 | CA | GLU | 1008 | 34.743 | 26.402 | -2.188 | 1.00 31.07 | 6 |
| ATOM | 1381 | CB | GLU | 1008 | 34.089 | 25.710 | -3.378 | 1.00 43.81 | 6 |
| ATOM | 1382 | CG | GLU | 1008 | 32.595 | 25.941 | -3.415 | 1.00 43.81 | 6 |
| ATOM | 1383 | CD | GLU | 1008 | 31.795 | 24.661 | -3.241 | 1.00 43.81 | 6 |
| ATOM | 1384 | OE1 | GLU | 1008 | 31.967 | 23.953 | -2.216 | 1.00 43.81 | 8 |
| ATOM | 1385 | OE2 | GLU | 1008 | 30.965 | 24.377 | -4.125 | 1.00 43.81 | 8 |
| ATOM | 1386 | C | GLU | 1008 | 34.578 | 27.914 | -2.308 | 1.00 31.07 | 6 |
| ATOM | 1387 | O | GLU | 1008 | 35.377 | 28.583 | -2.967 | 1.00 31.07 | 8 |
| ATOM | 1388 | N | SER | 1009 | 33.546 | 28.447 | -1.660 | 1.00 30.15 | 7 |
| ATOM | 1389 | CA | SER | 1009 | 33.259 | 29.873 | -1.711 | 1.00 30.15 | 6 |
| ATOM | 1390 | CB | SER | 1009 | 31.802 | 30.117 | -1.366 | 1.00 23.09 | 6 |
| ATOM | 1391 | OG | SER | 1009 | 30.984 | 29.274 | -2.034 | 1.00 23.09 | 8 |
| ATOM | 1392 | C | SER | 1009 | 34.150 | 30.622 | -0.743 | 1.00 30.15 | 6 |
| ATOM | 1393 | O | SER | 1009 | 34.565 | 31.760 | -0.995 | 1.00 30.15 | 8 |
| ATOM | 1394 | N | LEU | 1010 | 34.428 | 29.977 | 0.381 | 1.00 29.90 | 7 |
| ATOM | 1395 | CA | LEU | 1010 | 35.293 | 30.566 | 1.380 | 1.00 29.90 | 6 |
| ATOM | 1396 | CB | LEU | 1010 | 35.402 | 29.629 | 2.585 | 1.00 44.65 | 6 |
| ATOM | 1397 | CG | LEU | 1010 | 34.152 | 29.450 | 3.460 | 1.00 44.65 | 6 |
| ATOM | 1398 | CD1 | LEU | 1010 | 34.435 | 28.420 | 4.534 | 1.00 44.65 | 6 |
| ATOM | 1399 | CD2 | LEU | 1010 | 33.752 | 30.781 | 4.101 | 1.00 44.65 | 6 |
| ATOM | 1400 | C | LEU | 1010 | 36.663 | 30.771 | 0.726 | 1.00 29.90 | 6 |
| ATOM | 1401 | O | LEU | 1010 | 37.082 | 31.912 | 0.503 | 1.00 29.90 | 8 |
| ATOM | 1402 | N | ASN | 1011 | 37.327 | 29.661 | 0.397 | 1.00 34.23 | 7 |
| ATOM | 1403 | CA | ASN | 1011 | 38.652 | 29.638 | -0.230 | 1.00 34.23 | 6 |
| ATOM | 1404 | CB | ASN | 1011 | 39.105 | 28.205 | -0.511 | 1.00 32.72 | 6 |
| ATOM | 1405 | CG | ASN | 1011 | 38.990 | 27.287 | 0.679 | 1.00 32.72 | 6 |
| ATOM | 1406 | OD1 | ASN | 1011 | 39.433 | 27.600 | 1.783 | 1.00 32.72 | 8 |
| ATOM | 1407 | ND2 | ASN | 1011 | 38.404 | 26.117 | 0.450 | 1.00 32.72 | 7 |
| ATOM | 1408 | C | ASN | 1011 | 38.801 | 30.353 | -1.560 | 1.00 34.23 | 6 |
| ATOM | 1409 | O | ASN | 1011 | 39.728 | 31.137 | -1.748 | 1.00 34.23 | 8 |
| ATOM | 1410 | N | TYR | 1012 | 37.914 | 30.041 | -2.494 | 1.00 35.06 | 7 |
| ATOM | 1411 | CA | TYR | 1012 | 38.018 | 30.611 | -3.822 | 1.00 35.06 | 6 |
| ATOM | 1412 | CB | TYR | 1012 | 37.824 | 29.521 | -4.845 | 1.00 40.77 | 6 |
| ATOM | 1413 | CG | TYR | 1012 | 38.705 | 28.358 | -4.552 | 1.00 40.77 | 6 |

FIG. 3Y

| | | | | | | | | | |
|---|---|---|---|---|---|---|---|---|---|
| ATOM | 1414 | CD1 | TYR | 1012 | 38.167 | 27.093 | -4.400 | 1.00 40.77 | 6 |
| ATOM | 1415 | CE1 | TYR | 1012 | 38.961 | 26.024 | -4.105 | 1.00 40.77 | 6 |
| ATOM | 1416 | CD2 | TYR | 1012 | 40.077 | 28.531 | -4.397 | 1.00 40.77 | 6 |
| ATOM | 1417 | CE2 | TYR | 1012 | 40.896 | 27.472 | -4.098 | 1.00 40.77 | 6 |
| ATOM | 1418 | CZ | TYR | 1012 | 40.336 | 26.208 | -3.957 | 1.00 40.77 | 6 |
| ATOM | 1419 | OH | TYR | 1012 | 41.152 | 25.119 | -3.717 | 1.00 40.77 | 8 |
| ATOM | 1420 | C | TYR | 1012 | 37.161 | 31.787 | -4.193 | 1.00 35.06 | 6 |
| ATOM | 1421 | O | TYR | 1012 | 37.443 | 32.440 | -5.195 | 1.00 35.06 | 8 |
| ATOM | 1422 | N | SER | 1013 | 36.109 | 32.060 | -3.433 | 1.00 42.36 | 7 |
| ATOM | 1423 | CA | SER | 1013 | 35.278 | 33.209 | -3.746 | 1.00 42.36 | 6 |
| ATOM | 1424 | CB | SER | 1013 | 36.159 | 34.439 | -3.983 | 1.00 39.37 | 6 |
| ATOM | 1425 | OG | SER | 1013 | 37.157 | 34.576 | -2.983 | 1.00 39.37 | 8 |
| ATOM | 1426 | C | SER | 1013 | 34.433 | 32.973 | -4.982 | 1.00 42.36 | 6 |
| ATOM | 1427 | O | SER | 1013 | 34.291 | 33.865 | -5.807 | 1.00 42.36 | 8 |
| ATOM | 1428 | N | VAL | 1014 | 33.890 | 31.772 | -5.121 | 1.00 22.55 | 7 |
| ATOM | 1429 | CA | VAL | 1014 | 33.045 | 31.467 | -6.260 | 1.00 22.55 | 6 |
| ATOM | 1430 | CB | VAL | 1014 | 33.653 | 30.369 | -7.143 | 1.00 31.51 | 6 |
| ATOM | 1431 | CG1 | VAL | 1014 | 35.048 | 30.791 | -7.599 | 1.00 31.51 | 6 |
| ATOM | 1432 | CG2 | VAL | 1014 | 33.701 | 29.054 | -6.383 | 1.00 31.51 | 6 |
| ATOM | 1433 | C | VAL | 1014 | 31.720 | 30.999 | -5.712 | 1.00 22.55 | 6 |
| ATOM | 1434 | O | VAL | 1014 | 31.644 | 30.562 | -4.577 | 1.00 22.55 | 8 |
| ATOM | 1435 | N | TYR | 1015 | 30.671 | 31.121 | -6.507 | 1.00 26.01 | 7 |
| ATOM | 1436 | CA | TYR | 1015 | 29.338 | 30.712 | -6.101 | 1.00 26.01 | 6 |
| ATOM | 1437 | CB | TYR | 1015 | 28.501 | 31.938 | -5.753 | 1.00 41.40 | 6 |
| ATOM | 1438 | CG | TYR | 1015 | 29.116 | 32.782 | -4.672 | 1.00 41.40 | 6 |
| ATOM | 1439 | CD1 | TYR | 1015 | 30.233 | 33.560 | -4.922 | 1.00 41.40 | 6 |
| ATOM | 1440 | CE1 | TYR | 1015 | 30.854 | 34.235 | -3.904 | 1.00 41.40 | 6 |
| ATOM | 1441 | CD2 | TYR | 1015 | 28.638 | 32.709 | -3.365 | 1.00 41.40 | 6 |
| ATOM | 1442 | CE2 | TYR | 1015 | 29.257 | 33.388 | -2.330 | 1.00 41.40 | 6 |
| ATOM | 1443 | CZ | TYR | 1015 | 30.361 | 34.139 | -2.605 | 1.00 41.40 | 6 |
| ATOM | 1444 | OH | TYR | 1015 | 30.968 | 34.830 | -1.588 | 1.00 41.40 | 8 |
| ATOM | 1445 | C | TYR | 1015 | 28.674 | 29.998 | -7.252 | 1.00 26.01 | 6 |
| ATOM | 1446 | O | TYR | 1015 | 28.513 | 30.572 | -8.324 | 1.00 26.01 | 8 |
| ATOM | 1447 | N | THR | 1016 | 28.311 | 28.741 | -7.043 | 1.00 17.46 | 7 |
| ATOM | 1448 | CA | THR | 1016 | 27.610 | 27.971 | -8.082 | 1.00 17.46 | 6 |
| ATOM | 1449 | CB | THR | 1016 | 28.317 | 26.625 | -8.456 | 1.00 15.11 | 6 |
| ATOM | 1450 | OG1 | THR | 1016 | 28.649 | 25.909 | -7.262 | 1.00 15.11 | 8 |
| ATOM | 1451 | CG2 | THR | 1016 | 29.540 | 26.855 | -9.283 | 1.00 15.11 | 6 |
| ATOM | 1452 | C | THR | 1016 | 26.257 | 27.590 | -7.487 | 1.00 17.46 | 6 |
| ATOM | 1453 | O | THR | 1016 | 25.919 | 28.038 | -6.408 | 1.00 17.46 | 8 |
| ATOM | 1454 | N | THR | 1017 | 25.489 | 26.752 | -8.171 | 1.00 10.55 | 7 |
| ATOM | 1455 | CA | THR | 1017 | 24.229 | 26.325 | -7.585 | 1.00 10.55 | 6 |
| ATOM | 1456 | CB | THR | 1017 | 23.346 | 25.602 | -8.600 | 1.00 29.18 | 6 |
| ATOM | 1457 | OG1 | THR | 1017 | 22.913 | 26.533 | -9.600 | 1.00 29.18 | 8 |
| ATOM | 1458 | CG2 | THR | 1017 | 22.138 | 25.017 | -7.906 | 1.00 29.18 | 6 |
| ATOM | 1459 | C | THR | 1017 | 24.563 | 25.381 | -6.419 | 1.00 10.55 | 6 |
| ATOM | 1460 | O | THR | 1017 | 23.802 | 25.287 | -5.466 | 1.00 10.55 | 8 |
| ATOM | 1461 | N | ASN | 1018 | 25.740 | 24.743 | -6.500 | 1.00 41.35 | 7 |
| ATOM | 1462 | CA | ASN | 1018 | 26.266 | 23.772 | -5.505 | 1.00 41.35 | 6 |
| ATOM | 1463 | CB | ASN | 1018 | 27.522 | 23.095 | -6.033 | 1.00 49.00 | 6 |
| ATOM | 1464 | CG | ASN | 1018 | 27.234 | 22.010 | -7.015 | 1.00 49.00 | 6 |
| ATOM | 1465 | OD1 | ASN | 1018 | 28.100 | 21.630 | -7.788 | 1.00 49.00 | 8 |
| ATOM | 1466 | ND2 | ASN | 1018 | 26.025 | 21.477 | -6.981 | 1.00 49.00 | 7 |
| ATOM | 1467 | C | ASN | 1018 | 26.646 | 24.371 | -4.156 | 1.00 41.35 | 6 |
| ATOM | 1468 | O | ASN | 1018 | 26.773 | 23.647 | -3.160 | 1.00 41.35 | 8 |
| ATOM | 1469 | N | SER | 1019 | 26.887 | 25.680 | -4.148 | 1.00 46.21 | 7 |
| ATOM | 1470 | CA | SER | 1019 | 27.247 | 26.400 | -2.935 | 1.00 46.21 | 6 |

FIG. 3Z

| ATOM | 1471 | CB | SER | 1019 | 28.179 | 27.570 | -3.247 | 1.00 | 35.31 | 6 |
|---|---|---|---|---|---|---|---|---|---|---|
| ATOM | 1472 | OG | SER | 1019 | 27.517 | 28.561 | -3.996 | 1.00 | 35.31 | 8 |
| ATOM | 1473 | C | SER | 1019 | 25.936 | 26.919 | -2.392 | 1.00 | 46.21 | 6 |
| ATOM | 1474 | O | SER | 1019 | 25.835 | 27.281 | -1.225 | 1.00 | 46.21 | 8 |
| ATOM | 1475 | N | ASP | 1020 | 24.929 | 26.965 | -3.253 | 1.00 | 42.68 | 7 |
| ATOM | 1476 | CA | ASP | 1020 | 23.640 | 27.426 | -2.808 | 1.00 | 42.68 | 6 |
| ATOM | 1477 | CB | ASP | 1020 | 22.826 | 28.008 | -3.951 | 1.00 | 34.86 | 6 |
| ATOM | 1478 | CG | ASP | 1020 | 22.962 | 29.508 | -4.032 | 1.00 | 34.86 | 6 |
| ATOM | 1479 | OD1 | ASP | 1020 | 23.242 | 30.127 | -2.972 | 1.00 | 34.86 | 8 |
| ATOM | 1480 | OD2 | ASP | 1020 | 22.788 | 30.046 | -5.149 | 1.00 | 34.86 | 8 |
| ATOM | 1481 | C | ASP | 1020 | 22.912 | 26.281 | -2.171 | 1.00 | 42.68 | 6 |
| ATOM | 1482 | O | ASP | 1020 | 21.925 | 26.487 | -1.480 | 1.00 | 42.68 | 8 |
| ATOM | 1483 | N | VAL | 1021 | 23.401 | 25.071 | -2.398 | 1.00 | 33.68 | 7 |
| ATOM | 1484 | CA | VAL | 1021 | 22.751 | 23.944 | -1.787 | 1.00 | 33.68 | 6 |
| ATOM | 1485 | CB | VAL | 1021 | 22.872 | 22.690 | -2.628 | 1.00 | 9.47 | 6 |
| ATOM | 1486 | CG1 | VAL | 1021 | 22.096 | 21.575 | -1.962 | 1.00 | 9.47 | 6 |
| ATOM | 1487 | CG2 | VAL | 1021 | 22.328 | 22.940 | -4.008 | 1.00 | 9.47 | 6 |
| ATOM | 1488 | C | VAL | 1021 | 23.403 | 23.746 | -0.444 | 1.00 | 33.68 | 6 |
| ATOM | 1489 | O | VAL | 1021 | 22.872 | 23.061 | 0.422 | 1.00 | 33.68 | 8 |
| ATOM | 1490 | N | TRP | 1022 | 24.565 | 24.355 | -0.268 | 1.00 | 49.04 | 7 |
| ATOM | 1491 | CA | TRP | 1022 | 25.247 | 24.284 | 1.011 | 1.00 | 49.04 | 6 |
| ATOM | 1492 | CB | TRP | 1022 | 26.732 | 24.600 | 0.868 | 1.00 | 36.23 | 6 |
| ATOM | 1493 | CG | TRP | 1022 | 27.463 | 24.712 | 2.164 | 1.00 | 36.23 | 6 |
| ATOM | 1494 | CD2 | TRP | 1022 | 28.575 | 23.920 | 2.583 | 1.00 | 36.23 | 6 |
| ATOM | 1495 | CE2 | TRP | 1022 | 28.985 | 24.411 | 3.836 | 1.00 | 36.23 | 6 |
| ATOM | 1496 | CE3 | TRP | 1022 | 29.269 | 22.843 | 2.019 | 1.00 | 36.23 | 6 |
| ATOM | 1497 | CD1 | TRP | 1022 | 27.246 | 25.623 | 3.158 | 1.00 | 36.23 | 6 |
| ATOM | 1498 | NE1 | TRP | 1022 | 28.155 | 25.452 | 4.165 | 1.00 | 36.23 | 7 |
| ATOM | 1499 | CZ2 | TRP | 1022 | 30.061 | 23.862 | 4.532 | 1.00 | 36.23 | 6 |
| ATOM | 1500 | CZ3 | TRP | 1022 | 30.338 | 22.300 | 2.710 | 1.00 | 36.23 | 6 |
| ATOM | 1501 | CH2 | TRP | 1022 | 30.721 | 22.808 | 3.951 | 1.00 | 36.23 | 6 |
| ATOM | 1502 | C | TRP | 1022 | 24.558 | 25.391 | 1.777 | 1.00 | 49.04 | 6 |
| ATOM | 1503 | O | TRP | 1022 | 23.962 | 25.164 | 2.822 | 1.00 | 49.04 | 8 |
| ATOM | 1504 | N | SER | 1023 | 24.599 | 26.598 | 1.244 | 1.00 | 20.71 | 7 |
| ATOM | 1505 | CA | SER | 1023 | 23.946 | 27.666 | 1.954 | 1.00 | 20.71 | 6 |
| ATOM | 1506 | CB | SER | 1023 | 24.032 | 28.977 | 1.181 | 1.00 | 17.98 | 6 |
| ATOM | 1507 | OG | SER | 1023 | 25.377 | 29.363 | 1.081 | 1.00 | 17.98 | 8 |
| ATOM | 1508 | C | SER | 1023 | 22.516 | 27.305 | 2.265 | 1.00 | 20.71 | 6 |
| ATOM | 1509 | O | SER | 1023 | 22.009 | 27.705 | 3.298 | 1.00 | 20.71 | 8 |
| ATOM | 1510 | N | TYR | 1024 | 21.842 | 26.557 | 1.400 | 1.00 | 27.47 | 7 |
| ATOM | 1511 | CA | TYR | 1024 | 20.474 | 26.200 | 1.758 | 1.00 | 27.47 | 6 |
| ATOM | 1512 | CB | TYR | 1024 | 19.728 | 25.580 | 0.590 | 1.00 | 25.94 | 6 |
| ATOM | 1513 | CG | TYR | 1024 | 18.447 | 24.902 | 1.003 | 1.00 | 25.94 | 6 |
| ATOM | 1514 | CD1 | TYR | 1024 | 17.222 | 25.512 | 0.847 | 1.00 | 25.94 | 6 |
| ATOM | 1515 | CE1 | TYR | 1024 | 16.037 | 24.846 | 1.170 | 1.00 | 25.94 | 6 |
| ATOM | 1516 | CD2 | TYR | 1024 | 18.465 | 23.611 | 1.506 | 1.00 | 25.94 | 6 |
| ATOM | 1517 | CE2 | TYR | 1024 | 17.288 | 22.954 | 1.833 | 1.00 | 25.94 | 6 |
| ATOM | 1518 | CZ | TYR | 1024 | 16.089 | 23.579 | 1.656 | 1.00 | 25.94 | 6 |
| ATOM | 1519 | OH | TYR | 1024 | 14.949 | 22.909 | 1.953 | 1.00 | 25.94 | 8 |
| ATOM | 1520 | C | TYR | 1024 | 20.502 | 25.233 | 2.942 | 1.00 | 27.47 | 6 |
| ATOM | 1521 | O | TYR | 1024 | 19.712 | 25.368 | 3.873 | 1.00 | 27.47 | 8 |
| ATOM | 1522 | N | GLY | 1025 | 21.419 | 24.273 | 2.917 | 1.00 | 24.43 | 7 |
| ATOM | 1523 | CA | GLY | 1025 | 21.505 | 23.344 | 4.025 | 1.00 | 24.43 | 6 |
| ATOM | 1524 | C | GLY | 1025 | 21.593 | 24.073 | 5.356 | 1.00 | 24.43 | 6 |
| ATOM | 1525 | O | GLY | 1025 | 21.032 | 23.619 | 6.356 | 1.00 | 24.43 | 8 |
| ATOM | 1526 | N | VAL | 1026 | 22.307 | 25.195 | 5.384 | 1.00 | 31.88 | 7 |
| ATOM | 1527 | CA | VAL | 1026 | 22.417 | 25.947 | 6.632 | 1.00 | 31.88 | 6 |

FIG. 3AA

```
ATOM  1528  CB   VAL  1026   23.566  26.979   6.609  1.00  14.56  6
ATOM  1529  CG1  VAL  1026   23.783  27.551   8.015  1.00  14.56  6
ATOM  1530  CG2  VAL  1026   24.835  26.301   6.132  1.00  14.56  6
ATOM  1531  C    VAL  1026   21.077  26.636   6.908  1.00  31.88  6
ATOM  1532  O    VAL  1026   20.691  26.833   8.062  1.00  31.88  8
ATOM  1533  N    LEU  1027   20.348  26.978   5.855  1.00  36.84  7
ATOM  1534  CA   LEU  1027   19.063  27.591   6.078  1.00  36.84  6
ATOM  1535  CB   LEU  1027   18.470  28.110   4.777  1.00   5.00  6
ATOM  1536  CG   LEU  1027   17.030  28.620   4.806  1.00   5.00  6
ATOM  1537  CD1  LEU  1027   16.683  29.318   6.095  1.00   5.00  6
ATOM  1538  CD2  LEU  1027   16.893  29.549   3.640  1.00   5.00  6
ATOM  1539  C    LEU  1027   18.149  26.556   6.711  1.00  36.84  6
ATOM  1540  O    LEU  1027   17.383  26.885   7.606  1.00  36.84  8
ATOM  1541  N    LEU  1028   18.234  25.304   6.272  1.00  19.77  7
ATOM  1542  CA   LEU  1028   17.390  24.264   6.848  1.00  19.77  6
ATOM  1543  CB   LEU  1028   17.645  22.931   6.147  1.00  24.80  6
ATOM  1544  CG   LEU  1028   16.802  21.696   6.487  1.00  24.80  6
ATOM  1545  CD1  LEU  1028   15.298  21.976   6.507  1.00  24.80  6
ATOM  1546  CD2  LEU  1028   17.117  20.681   5.417  1.00  24.80  6
ATOM  1547  C    LEU  1028   17.681  24.145   8.339  1.00  19.77  6
ATOM  1548  O    LEU  1028   16.779  23.912   9.136  1.00  19.77  8
ATOM  1549  N    TRP  1029   18.944  24.309   8.714  1.00  26.73  7
ATOM  1550  CA   TRP  1029   19.318  24.241  10.114  1.00  26.73  6
ATOM  1551  CB   TRP  1029   20.836  24.229  10.257  1.00  36.84  6
ATOM  1552  CG   TRP  1029   21.363  24.082  11.678  1.00  36.84  6
ATOM  1553  CD2  TRP  1029   21.634  25.145  12.611  1.00  36.84  6
ATOM  1554  CE2  TRP  1029   22.215  24.556  13.757  1.00  36.84  6
ATOM  1555  CE3  TRP  1029   21.438  26.536  12.588  1.00  36.84  6
ATOM  1556  CD1  TRP  1029   21.774  22.926  12.292  1.00  36.84  6
ATOM  1557  NE1  TRP  1029   22.292  23.202  13.539  1.00  36.84  7
ATOM  1558  CZ2  TRP  1029   22.613  25.310  14.860  1.00  36.84  6
ATOM  1559  CZ3  TRP  1029   21.830  27.283  13.682  1.00  36.84  6
ATOM  1560  CH2  TRP  1029   22.409  26.670  14.803  1.00  36.84  6
ATOM  1561  C    TRP  1029   18.736  25.435  10.898  1.00  26.73  6
ATOM  1562  O    TRP  1029   18.498  25.314  12.089  1.00  26.73  8
ATOM  1563  N    GLU  1030   18.520  26.590  10.266  1.00  28.62  7
ATOM  1564  CA   GLU  1030   17.958  27.734  10.996  1.00  28.62  6
ATOM  1565  CB   GLU  1030   18.082  29.020  10.177  1.00  33.13  6
ATOM  1566  CG   GLU  1030   19.486  29.535  10.077  1.00  33.13  6
ATOM  1567  CD   GLU  1030   19.635  30.718   9.135  1.00  33.13  6
ATOM  1568  OE1  GLU  1030   19.628  30.498   7.909  1.00  33.13  8
ATOM  1569  OE2  GLU  1030   19.756  31.865   9.625  1.00  33.13  8
ATOM  1570  C    GLU  1030   16.494  27.467  11.333  1.00  28.62  6
ATOM  1571  O    GLU  1030   16.066  27.619  12.470  1.00  28.62  8
ATOM  1572  N    ILE  1031   15.746  27.065  10.314  1.00  23.86  7
ATOM  1573  CA   ILE  1031   14.328  26.733  10.413  1.00  23.86  6
ATOM  1574  CB   ILE  1031   13.845  26.094   9.083  1.00   5.00  6
ATOM  1575  CG2  ILE  1031   12.626  25.263   9.308  1.00   5.00  6
ATOM  1576  CG1  ILE  1031   13.660  27.181   8.029  1.00   5.00  6
ATOM  1577  CD1  ILE  1031   13.157  26.703   6.709  1.00   5.00  6
ATOM  1578  C    ILE  1031   14.085  25.760  11.544  1.00  23.86  6
ATOM  1579  O    ILE  1031   13.202  25.946  12.357  1.00  23.86  8
ATOM  1580  N    VAL  1032   14.894  24.723  11.595  1.00  16.66  7
ATOM  1581  CA   VAL  1032   14.745  23.717  12.611  1.00  16.66  6
ATOM  1582  CB   VAL  1032   15.538  22.452  12.184  1.00  12.88  6
ATOM  1583  CG1  VAL  1032   15.873  21.594  13.367  1.00  12.88  6
ATOM  1584  CG2  VAL  1032   14.713  21.662  11.163  1.00  12.88  6
```

FIG. 3BB

| | | | | | | | | | |
|---|---|---|---|---|---|---|---|---|---|
| ATOM | 1585 | C | VAL | 1032 | 15.155 | 24.252 | 13.977 | 1.00 16.66 | 6 |
| ATOM | 1586 | O | VAL | 1032 | 14.456 | 24.032 | 14.952 | 1.00 16.66 | 8 |
| ATOM | 1587 | N | SER | 1033 | 16.258 | 24.986 | 14.058 | 1.00 33.94 | 7 |
| ATOM | 1588 | CA | SER | 1033 | 16.732 | 25.551 | 15.331 | 1.00 33.94 | 6 |
| ATOM | 1589 | CB | SER | 1033 | 18.173 | 25.982 | 15.197 | 1.00 27.55 | 6 |
| ATOM | 1590 | OG | SER | 1033 | 18.203 | 27.172 | 14.452 | 1.00 27.55 | 8 |
| ATOM | 1591 | C | SER | 1033 | 15.937 | 26.791 | 15.793 | 1.00 33.94 | 6 |
| ATOM | 1592 | O | SER | 1033 | 16.275 | 27.415 | 16.801 | 1.00 33.94 | 8 |
| ATOM | 1593 | N | LEU | 1034 | 14.913 | 27.165 | 15.035 | 1.00 25.63 | 7 |
| ATOM | 1594 | CA | LEU | 1034 | 14.075 | 28.313 | 15.353 | 1.00 25.63 | 6 |
| ATOM | 1595 | CB | LEU | 1034 | 13.382 | 28.107 | 16.707 | 1.00 16.09 | 6 |
| ATOM | 1596 | CG | LEU | 1034 | 12.545 | 26.834 | 16.882 | 1.00 16.09 | 6 |
| ATOM | 1597 | CD1 | LEU | 1034 | 11.931 | 26.831 | 18.286 | 1.00 16.09 | 6 |
| ATOM | 1598 | CD2 | LEU | 1034 | 11.456 | 26.758 | 15.839 | 1.00 16.09 | 6 |
| ATOM | 1599 | C | LEU | 1034 | 14.777 | 29.676 | 15.328 | 1.00 25.63 | 6 |
| ATOM | 1600 | O | LEU | 1034 | 14.641 | 30.476 | 16.254 | 1.00 25.63 | 8 |
| ATOM | 1601 | N | GLY | 1035 | 15.519 | 29.927 | 14.256 | 1.00 32.06 | 7 |
| ATOM | 1602 | CA | GLY | 1035 | 16.185 | 31.202 | 14.092 | 1.00 32.06 | 6 |
| ATOM | 1603 | C | GLY | 1035 | 17.458 | 31.404 | 14.866 | 1.00 32.06 | 6 |
| ATOM | 1604 | O | GLY | 1035 | 17.832 | 32.537 | 15.149 | 1.00 32.06 | 8 |
| ATOM | 1605 | N | GLY | 1036 | 18.124 | 30.316 | 15.224 | 1.00 12.96 | 7 |
| ATOM | 1606 | CA | GLY | 1036 | 19.371 | 30.430 | 15.957 | 1.00 12.96 | 6 |
| ATOM | 1607 | C | GLY | 1036 | 20.486 | 30.704 | 14.974 | 1.00 12.96 | 6 |
| ATOM | 1608 | O | GLY | 1036 | 20.355 | 30.393 | 13.789 | 1.00 12.96 | 8 |
| ATOM | 1609 | N | THR | 1037 | 21.572 | 31.293 | 15.457 | 1.00 38.43 | 7 |
| ATOM | 1610 | CA | THR | 1037 | 22.712 | 31.608 | 14.609 | 1.00 38.43 | 6 |
| ATOM | 1611 | CB | THR | 1037 | 23.593 | 32.723 | 15.266 | 1.00 32.45 | 6 |
| ATOM | 1612 | OG1 | THR | 1037 | 22.813 | 33.907 | 15.442 | 1.00 32.45 | 8 |
| ATOM | 1613 | CG2 | THR | 1037 | 24.754 | 33.076 | 14.387 | 1.00 32.45 | 6 |
| ATOM | 1614 | C | THR | 1037 | 23.519 | 30.323 | 14.418 | 1.00 38.43 | 6 |
| ATOM | 1615 | O | THR | 1037 | 23.687 | 29.555 | 15.359 | 1.00 38.43 | 8 |
| ATOM | 1616 | N | PRO | 1038 | 24.003 | 30.054 | 13.193 | 1.00 51.13 | 7 |
| ATOM | 1617 | CD | PRO | 1038 | 23.734 | 30.837 | 11.973 | 1.00 42.78 | 6 |
| ATOM | 1618 | CA | PRO | 1038 | 24.791 | 28.859 | 12.863 | 1.00 51.13 | 6 |
| ATOM | 1619 | CB | PRO | 1038 | 24.677 | 28.776 | 11.354 | 1.00 42.78 | 6 |
| ATOM | 1620 | CG | PRO | 1038 | 24.691 | 30.218 | 10.977 | 1.00 42.78 | 6 |
| ATOM | 1621 | C | PRO | 1038 | 26.233 | 28.968 | 13.308 | 1.00 51.13 | 6 |
| ATOM | 1622 | O | PRO | 1038 | 26.873 | 30.002 | 13.113 | 1.00 51.13 | 8 |
| ATOM | 1623 | N | TYR | 1039 | 26.753 | 27.895 | 13.886 | 1.00 44.91 | 7 |
| ATOM | 1624 | CA | TYR | 1039 | 28.124 | 27.909 | 14.349 | 1.00 44.91 | 6 |
| ATOM | 1625 | CB | TYR | 1039 | 29.082 | 28.341 | 13.221 | 1.00 38.97 | 6 |
| ATOM | 1626 | CG | TYR | 1039 | 28.980 | 27.544 | 11.933 | 1.00 38.97 | 6 |
| ATOM | 1627 | CD1 | TYR | 1039 | 28.593 | 28.161 | 10.739 | 1.00 38.97 | 6 |
| ATOM | 1628 | CE1 | TYR | 1039 | 28.487 | 27.434 | 9.545 | 1.00 38.97 | 6 |
| ATOM | 1629 | CD2 | TYR | 1039 | 29.263 | 26.185 | 11.907 | 1.00 38.97 | 6 |
| ATOM | 1630 | CE2 | TYR | 1039 | 29.165 | 25.455 | 10.730 | 1.00 38.97 | 6 |
| ATOM | 1631 | CZ | TYR | 1039 | 28.773 | 26.082 | 9.553 | 1.00 38.97 | 6 |
| ATOM | 1632 | OH | TYR | 1039 | 28.647 | 25.353 | 8.396 | 1.00 38.97 | 8 |
| ATOM | 1633 | C | TYR | 1039 | 28.176 | 28.932 | 15.479 | 1.00 44.91 | 6 |
| ATOM | 1634 | O | TYR | 1039 | 29.152 | 29.674 | 15.601 | 1.00 44.91 | 8 |
| ATOM | 1635 | N | CYS | 1040 | 27.120 | 28.989 | 16.293 | 1.00 52.33 | 7 |
| ATOM | 1636 | CA | CYS | 1040 | 27.093 | 29.933 | 17.411 | 1.00 52.33 | 6 |
| ATOM | 1637 | CB | CYS | 1040 | 25.700 | 30.015 | 18.046 | 1.00 51.31 | 6 |
| ATOM | 1638 | SG | CYS | 1040 | 25.484 | 31.409 | 19.213 | 1.00 51.31 | 16 |
| ATOM | 1639 | C | CYS | 1040 | 28.094 | 29.416 | 18.424 | 1.00 52.33 | 6 |
| ATOM | 1640 | O | CYS | 1040 | 28.113 | 28.224 | 18.729 | 1.00 52.33 | 8 |
| ATOM | 1641 | N | GLY | 1041 | 28.930 | 30.315 | 18.928 | 1.00 33.04 | 7 |

FIG. 3CC

```
ATOM   1642  CA   GLY  1041      29.930  29.917  19.895  1.00 33.04      6
ATOM   1643  C    GLY  1041      31.293  29.745  19.257  1.00 33.04      6
ATOM   1644  O    GLY  1041      32.207  29.176  19.855  1.00 33.04      8
ATOM   1645  N    MET  1042      31.435  30.206  18.024  1.00 54.51      7
ATOM   1646  CA   MET  1042      32.718  30.129  17.350  1.00 54.51      6
ATOM   1647  CB   MET  1042      32.703  29.085  16.241  1.00 40.53      6
ATOM   1648  CG   MET  1042      33.032  27.691  16.710  1.00 40.53      6
ATOM   1649  SD   MET  1042      32.920  26.501  15.349  1.00 40.53     16
ATOM   1650  CE   MET  1042      31.539  25.362  15.966  1.00 40.53      6
ATOM   1651  C    MET  1042      33.029  31.492  16.785  1.00 54.51      6
ATOM   1652  O    MET  1042      32.195  32.395  16.804  1.00 54.51      8
ATOM   1653  N    THR  1043      34.241  31.633  16.286  1.00 54.86      7
ATOM   1654  CA   THR  1043      34.677  32.894  15.726  1.00 54.86      6
ATOM   1655  CB   THR  1043      36.055  33.252  16.229  1.00 82.76      6
ATOM   1656  OG1  THR  1043      36.987  32.269  15.763  1.00 82.76      8
ATOM   1657  CG2  THR  1043      36.069  33.282  17.735  1.00 82.76      6
ATOM   1658  C    THR  1043      34.780  32.796  14.227  1.00 54.86      6
ATOM   1659  O    THR  1043      34.695  31.710  13.659  1.00 54.86      8
ATOM   1660  N    CYS  1044      35.002  33.943  13.599  1.00 95.17      7
ATOM   1661  CA   CYS  1044      35.142  34.000  12.158  1.00 95.17      6
ATOM   1662  CB   CYS  1044      35.205  35.453  11.692  1.00 93.17      6
ATOM   1663  SG   CYS  1044      33.676  36.379  11.856  1.00 93.17     16
ATOM   1664  C    CYS  1044      36.396  33.272  11.681  1.00 95.17      6
ATOM   1665  O    CYS  1044      36.622  33.174  10.483  1.00 95.17      8
ATOM   1666  N    ALA  1045      37.215  32.773  12.603  1.00 38.28      7
ATOM   1667  CA   ALA  1045      38.428  32.079  12.197  1.00 38.28      6
ATOM   1668  CB   ALA  1045      39.618  32.633  12.941  1.00 50.33      6
ATOM   1669  C    ALA  1045      38.348  30.571  12.387  1.00 38.28      6
ATOM   1670  O    ALA  1045      38.780  29.817  11.517  1.00 38.28      8
ATOM   1671  N    GLU  1046      37.822  30.131  13.526  1.00 39.84      7
ATOM   1672  CA   GLU  1046      37.712  28.702  13.787  1.00 39.84      6
ATOM   1673  CB   GLU  1046      36.911  28.460  15.068  1.00 83.44      6
ATOM   1674  CG   GLU  1046      37.622  28.995  16.300  1.00 83.44      6
ATOM   1675  CD   GLU  1046      36.997  28.556  17.607  1.00 83.44      6
ATOM   1676  OE1  GLU  1046      36.872  27.334  17.835  1.00 83.44      8
ATOM   1677  OE2  GLU  1046      36.635  29.442  18.408  1.00 83.44      8
ATOM   1678  C    GLU  1046      37.051  28.027  12.591  1.00 39.84      6
ATOM   1679  O    GLU  1046      37.370  26.884  12.245  1.00 39.84      8
ATOM   1680  N    LEU  1047      36.148  28.772  11.953  1.00 55.18      7
ATOM   1681  CA   LEU  1047      35.412  28.312  10.771  1.00 55.18      6
ATOM   1682  CB   LEU  1047      34.315  29.319  10.424  1.00 58.88      6
ATOM   1683  CG   LEU  1047      33.325  29.563  11.565  1.00 58.88      6
ATOM   1684  CD1  LEU  1047      32.333  30.619  11.148  1.00 58.88      6
ATOM   1685  CD2  LEU  1047      32.610  28.260  11.906  1.00 58.88      6
ATOM   1686  C    LEU  1047      36.307  28.092   9.548  1.00 55.18      6
ATOM   1687  O    LEU  1047      36.106  27.157   8.786  1.00 55.18      8
ATOM   1688  N    TYR  1048      37.283  28.967   9.352  1.00 49.08      7
ATOM   1689  CA   TYR  1048      38.203  28.820   8.234  1.00 49.08      6
ATOM   1690  CB   TYR  1048      39.033  30.097   8.078  1.00 62.53      6
ATOM   1691  CG   TYR  1048      38.422  31.088   7.123  1.00 62.53      6
ATOM   1692  CD1  TYR  1048      37.554  32.092   7.559  1.00 62.53      6
ATOM   1693  CE1  TYR  1048      36.956  32.963   6.644  1.00 62.53      6
ATOM   1694  CD2  TYR  1048      38.678  30.981   5.765  1.00 62.53      6
ATOM   1695  CE2  TYR  1048      38.096  31.829   4.851  1.00 62.53      6
ATOM   1696  CZ   TYR  1048      37.233  32.820   5.280  1.00 62.53      6
ATOM   1697  OH   TYR  1048      36.649  33.642   4.333  1.00 62.53      8
ATOM   1698  C    TYR  1048      39.112  27.618   8.525  1.00 49.08      6
```

FIG. 3DD

```
ATOM   1699  O    TYR  1048      39.661  27.008   7.603  1.00 49.08       8
ATOM   1700  N    GLU  1049      39.224  27.293   9.817  1.00 50.97       7
ATOM   1701  CA   GLU  1049      40.047  26.196  10.341  1.00 50.97       6
ATOM   1702  CB   GLU  1049      40.532  26.543  11.761  1.00 95.40       6
ATOM   1703  CG   GLU  1049      41.455  25.483  12.408  1.00 95.40       6
ATOM   1704  CD   GLU  1049      41.583  25.610  13.940  1.00 95.40       6
ATOM   1705  OE1  GLU  1049      41.872  26.717  14.445  1.00 95.40       8
ATOM   1706  OE2  GLU  1049      41.397  24.589  14.641  1.00 95.40       8
ATOM   1707  C    GLU  1049      39.347  24.829  10.395  1.00 50.97       6
ATOM   1708  O    GLU  1049      39.581  23.962   9.543  1.00 50.97       8
ATOM   1709  N    LYS  1050      38.499  24.659  11.416  1.00 80.24       7
ATOM   1710  CA   LYS  1050      37.750  23.420  11.683  1.00 80.24       6
ATOM   1711  CB   LYS  1050      37.217  23.446  13.105  1.00 32.58       6
ATOM   1712  C    LYS  1050      36.603  23.121  10.729  1.00 80.24       6
ATOM   1713  O    LYS  1050      35.910  22.112  10.874  1.00 80.24       8
ATOM   1714  N    LEU  1051      36.394  23.993   9.757  1.00 50.22       7
ATOM   1715  CA   LEU  1051      35.323  23.769   8.810  1.00 50.22       6
ATOM   1716  CB   LEU  1051      34.627  25.081   8.449  1.00 21.77       6
ATOM   1717  CG   LEU  1051      33.258  24.954   7.780  1.00 21.77       6
ATOM   1718  CD1  LEU  1051      32.248  24.632   8.834  1.00 21.77       6
ATOM   1719  CD2  LEU  1051      32.900  26.226   7.065  1.00 21.77       6
ATOM   1720  C    LEU  1051      35.827  23.121   7.540  1.00 50.22       6
ATOM   1721  O    LEU  1051      35.308  22.098   7.123  1.00 50.22       8
ATOM   1722  N    PRO  1052      36.860  23.692   6.913  1.00 73.14       7
ATOM   1723  CD   PRO  1052      37.819  24.695   7.400  1.00 57.36       6
ATOM   1724  CA   PRO  1052      37.372  23.122   5.675  1.00 73.14       6
ATOM   1725  CB   PRO  1052      38.669  23.898   5.460  1.00 57.36       6
ATOM   1726  CG   PRO  1052      38.368  25.214   6.097  1.00 57.36       6
ATOM   1727  C    PRO  1052      37.600  21.638   5.814  1.00 73.14       6
ATOM   1728  O    PRO  1052      36.747  20.823   5.474  1.00 73.14       8
ATOM   1729  N    GLN  1053      38.756  21.308   6.359  1.00 77.10       7
ATOM   1730  CA   GLN  1053      39.139  19.932   6.542  1.00 77.10       6
ATOM   1731  CB   GLN  1053      40.574  19.886   7.003  1.00100.00       6
ATOM   1732  C    GLN  1053      38.256  19.137   7.504  1.00 77.10       6
ATOM   1733  O    GLN  1053      38.279  17.904   7.479  1.00 77.10       8
ATOM   1734  N    GLY  1054      37.475  19.815   8.341  1.00 78.88       7
ATOM   1735  CA   GLY  1054      36.658  19.075   9.293  1.00 78.88       6
ATOM   1736  C    GLY  1054      35.160  18.960   9.074  1.00 78.88       6
ATOM   1737  O    GLY  1054      34.644  19.099   7.965  1.00 78.88       8
ATOM   1738  N    TYR  1055      34.460  18.683  10.164  1.00 61.80       7
ATOM   1739  CA   TYR  1055      33.018  18.525  10.146  1.00 61.80       6
ATOM   1740  CB   TYR  1055      32.547  17.902  11.458  1.00100.00       6
ATOM   1741  CG   TYR  1055      32.642  18.897  12.598  1.00100.00       6
ATOM   1742  CD1  TYR  1055      31.499  19.464  13.161  1.00100.00       6
ATOM   1743  CE1  TYR  1055      31.592  20.444  14.144  1.00100.00       6
ATOM   1744  CD2  TYR  1055      33.885  19.337  13.057  1.00100.00       6
ATOM   1745  CE2  TYR  1055      33.985  20.316  14.039  1.00100.00       6
ATOM   1746  CZ   TYR  1055      32.835  20.860  14.571  1.00100.00       6
ATOM   1747  OH   TYR  1055      32.928  21.827  15.531  1.00100.00       8
ATOM   1748  C    TYR  1055      32.344  19.891  10.001  1.00 61.80       6
ATOM   1749  O    TYR  1055      32.982  20.912   9.728  1.00 61.80       8
ATOM   1750  N    ARG  1056      31.038  19.885  10.231  1.00 78.80       7
ATOM   1751  CA   ARG  1056      30.216  21.079  10.155  1.00 78.80       6
ATOM   1752  CB   ARG  1056      29.674  21.216   8.729  1.00 56.27       6
ATOM   1753  CG   ARG  1056      29.456  19.890   8.001  1.00 56.27       6
ATOM   1754  CD   ARG  1056      29.992  19.943   6.563  1.00 56.27       6
ATOM   1755  NE   ARG  1056      31.444  19.832   6.494  1.00 56.27       7
```

FIG. 3EE

| | | | | | | | | | |
|---|---|---|---|---|---|---|---|---|---|
| ATOM | 1756 | CZ | ARG | 1056 | 32.115 | 19.413 | 5.425 | 1.00 56.27 | 6 |
| ATOM | 1757 | NH1 | ARG | 1056 | 31.468 | 19.062 | 4.323 | 1.00 56.27 | 7 |
| ATOM | 1758 | NH2 | ARG | 1056 | 33.441 | 19.327 | 5.464 | 1.00 56.27 | 7 |
| ATOM | 1759 | C | ARG | 1056 | 29.074 | 21.074 | 11.192 | 1.00 78.80 | 6 |
| ATOM | 1760 | O | ARG | 1056 | 29.031 | 20.212 | 12.068 | 1.00 78.80 | 8 |
| ATOM | 1761 | N | LEU | 1057 | 28.149 | 22.030 | 11.081 | 1.00 52.45 | 7 |
| ATOM | 1762 | CA | LEU | 1057 | 27.019 | 22.181 | 12.016 | 1.00 52.45 | 6 |
| ATOM | 1763 | CB | LEU | 1057 | 25.915 | 23.018 | 11.375 | 1.00 37.29 | 6 |
| ATOM | 1764 | CG | LEU | 1057 | 26.218 | 24.496 | 11.647 | 1.00 37.29 | 6 |
| ATOM | 1765 | CD1 | LEU | 1057 | 25.208 | 25.439 | 10.966 | 1.00 37.29 | 6 |
| ATOM | 1766 | CD2 | LEU | 1057 | 26.201 | 24.676 | 13.134 | 1.00 37.29 | 6 |
| ATOM | 1767 | C | LEU | 1057 | 26.429 | 20.921 | 12.635 | 1.00 52.45 | 6 |
| ATOM | 1768 | O | LEU | 1057 | 26.147 | 19.948 | 11.957 | 1.00 52.45 | 8 |
| ATOM | 1769 | N | GLU | 1058 | 26.264 | 20.978 | 13.955 | 1.00 65.26 | 7 |
| ATOM | 1770 | CA | GLU | 1058 | 25.730 | 19.856 | 14.739 | 1.00 65.26 | 6 |
| ATOM | 1771 | CB | GLU | 1058 | 26.251 | 19.940 | 16.182 | 1.00 73.19 | 6 |
| ATOM | 1772 | CG | GLU | 1058 | 25.940 | 21.232 | 16.943 | 1.00 73.19 | 6 |
| ATOM | 1773 | CD | GLU | 1058 | 26.617 | 22.490 | 16.375 | 1.00 73.19 | 6 |
| ATOM | 1774 | OE1 | GLU | 1058 | 27.625 | 22.354 | 15.641 | 1.00 73.19 | 8 |
| ATOM | 1775 | OE2 | GLU | 1058 | 26.158 | 23.611 | 16.679 | 1.00 73.19 | 8 |
| ATOM | 1776 | C | GLU | 1058 | 24.207 | 19.746 | 14.738 | 1.00 65.26 | 6 |
| ATOM | 1777 | O | GLU | 1058 | 23.497 | 20.746 | 14.708 | 1.00 65.26 | 8 |
| ATOM | 1778 | N | LYS | 1059 | 23.721 | 18.509 | 14.777 | 1.00 77.52 | 7 |
| ATOM | 1779 | CA | LYS | 1059 | 22.282 | 18.230 | 14.756 | 1.00 77.52 | 6 |
| ATOM | 1780 | CB | LYS | 1059 | 22.021 | 16.720 | 14.580 | 1.00 63.67 | 6 |
| ATOM | 1781 | CG | LYS | 1059 | 20.563 | 16.341 | 14.799 | 1.00 63.67 | 6 |
| ATOM | 1782 | CD | LYS | 1059 | 20.206 | 15.034 | 14.104 | 1.00 63.67 | 6 |
| ATOM | 1783 | CE | LYS | 1059 | 20.288 | 13.847 | 15.043 | 1.00 63.67 | 6 |
| ATOM | 1784 | NZ | LYS | 1059 | 19.240 | 13.976 | 16.098 | 1.00 63.67 | 7 |
| ATOM | 1785 | C | LYS | 1059 | 21.507 | 18.697 | 15.978 | 1.00 77.52 | 6 |
| ATOM | 1786 | O | LYS | 1059 | 21.765 | 18.261 | 17.093 | 1.00 77.52 | 8 |
| ATOM | 1787 | N | PRO | 1060 | 20.530 | 19.587 | 15.780 | 1.00 65.64 | 7 |
| ATOM | 1788 | CD | PRO | 1060 | 20.131 | 20.220 | 14.513 | 1.00 37.22 | 6 |
| ATOM | 1789 | CA | PRO | 1060 | 19.725 | 20.087 | 16.894 | 1.00 65.64 | 6 |
| ATOM | 1790 | CB | PRO | 1060 | 18.724 | 21.016 | 16.219 | 1.00 37.22 | 6 |
| ATOM | 1791 | CG | PRO | 1060 | 19.416 | 21.473 | 14.984 | 1.00 37.22 | 6 |
| ATOM | 1792 | C | PRO | 1060 | 19.030 | 18.898 | 17.567 | 1.00 65.64 | 6 |
| ATOM | 1793 | O | PRO | 1060 | 18.860 | 17.840 | 16.956 | 1.00 65.64 | 8 |
| ATOM | 1794 | N | LEU | 1061 | 18.637 | 19.074 | 18.820 | 1.00 79.51 | 7 |
| ATOM | 1795 | CA | LEU | 1061 | 17.962 | 18.017 | 19.564 | 1.00 79.51 | 6 |
| ATOM | 1796 | CB | LEU | 1061 | 17.893 | 18.413 | 21.044 | 1.00 82.15 | 6 |
| ATOM | 1797 | CG | LEU | 1061 | 17.476 | 19.851 | 21.443 | 1.00 82.15 | 6 |
| ATOM | 1798 | CD1 | LEU | 1061 | 18.413 | 20.859 | 20.777 | 1.00 82.15 | 6 |
| ATOM | 1799 | CD2 | LEU | 1061 | 16.033 | 20.116 | 21.048 | 1.00 82.15 | 6 |
| ATOM | 1800 | C | LEU | 1061 | 16.562 | 17.680 | 19.047 | 1.00 79.51 | 6 |
| ATOM | 1801 | O | LEU | 1061 | 16.187 | 16.513 | 19.026 | 1.00 79.51 | 8 |
| ATOM | 1802 | N | ASN | 1062 | 15.802 | 18.696 | 18.631 | 1.00 43.98 | 7 |
| ATOM | 1803 | CA | ASN | 1062 | 14.437 | 18.512 | 18.124 | 1.00 43.98 | 6 |
| ATOM | 1804 | CB | ASN | 1062 | 13.689 | 19.843 | 18.124 | 1.00 26.42 | 6 |
| ATOM | 1805 | CG | ASN | 1062 | 14.462 | 20.938 | 17.404 | 1.00 26.42 | 6 |
| ATOM | 1806 | OD1 | ASN | 1062 | 15.554 | 21.327 | 17.834 | 1.00 26.42 | 8 |
| ATOM | 1807 | ND2 | ASN | 1062 | 13.908 | 21.430 | 16.294 | 1.00 26.42 | 7 |
| ATOM | 1808 | C | ASN | 1062 | 14.459 | 17.989 | 16.718 | 1.00 43.98 | 6 |
| ATOM | 1809 | O | ASN | 1062 | 13.422 | 17.665 | 16.156 | 1.00 43.98 | 8 |
| ATOM | 1810 | N | CYS | 1063 | 15.646 | 17.914 | 16.143 | 1.00 48.23 | 7 |
| ATOM | 1811 | CA | CYS | 1063 | 15.767 | 17.460 | 14.769 | 1.00 48.23 | 6 |
| ATOM | 1812 | CB | CYS | 1063 | 16.914 | 18.199 | 14.103 | 1.00 49.76 | 6 |

FIG. 3FF

| | | | | | | | | | |
|---|---|---|---|---|---|---|---|---|---|
| ATOM | 1813 | SG | CYS | 1063 | 16.932 | 17.981 | 12.363 | 1.00 49.76 | 16 |
| ATOM | 1814 | C | CYS | 1063 | 15.943 | 15.948 | 14.559 | 1.00 48.23 | 6 |
| ATOM | 1815 | O | CYS | 1063 | 16.912 | 15.361 | 15.039 | 1.00 48.23 | 8 |
| ATOM | 1816 | N | ASP | 1064 | 15.001 | 15.338 | 13.834 | 1.00 41.84 | 7 |
| ATOM | 1817 | CA | ASP | 1064 | 15.029 | 13.907 | 13.522 | 1.00 41.84 | 6 |
| ATOM | 1818 | CB | ASP | 1064 | 13.788 | 13.487 | 12.715 | 1.00 55.35 | 6 |
| ATOM | 1819 | CG | ASP | 1064 | 13.829 | 12.012 | 12.290 | 1.00 55.35 | 6 |
| ATOM | 1820 | OD1 | ASP | 1064 | 13.977 | 11.154 | 13.175 | 1.00 55.35 | 8 |
| ATOM | 1821 | OD2 | ASP | 1064 | 13.712 | 11.710 | 11.086 | 1.00 55.35 | 8 |
| ATOM | 1822 | C | ASP | 1064 | 16.273 | 13.599 | 12.702 | 1.00 41.84 | 6 |
| ATOM | 1823 | O | ASP | 1064 | 16.918 | 14.521 | 12.181 | 1.00 41.84 | 8 |
| ATOM | 1824 | N | ASP | 1065 | 16.602 | 12.309 | 12.576 | 1.00 68.56 | 7 |
| ATOM | 1825 | CA | ASP | 1065 | 17.789 | 11.871 | 11.825 | 1.00 68.56 | 6 |
| ATOM | 1826 | CB | ASP | 1065 | 18.094 | 10.391 | 12.086 | 1.00100.00 | 6 |
| ATOM | 1827 | CG | ASP | 1065 | 18.357 | 10.088 | 13.549 | 1.00100.00 | 6 |
| ATOM | 1828 | OD1 | ASP | 1065 | 17.400 | 10.124 | 14.341 | 1.00100.00 | 8 |
| ATOM | 1829 | OD2 | ASP | 1065 | 19.524 | 9.820 | 13.894 | 1.00100.00 | 8 |
| ATOM | 1830 | C | ASP | 1065 | 17.654 | 12.072 | 10.321 | 1.00 68.56 | 6 |
| ATOM | 1831 | O | ASP | 1065 | 18.627 | 12.404 | 9.644 | 1.00 68.56 | 8 |
| ATOM | 1832 | N | GLU | 1066 | 16.457 | 11.850 | 9.797 | 1.00 54.29 | 7 |
| ATOM | 1833 | CA | GLU | 1066 | 16.247 | 12.025 | 8.378 | 1.00 54.29 | 6 |
| ATOM | 1834 | CB | GLU | 1066 | 14.843 | 11.583 | 8.001 | 1.00 91.86 | 6 |
| ATOM | 1835 | CG | GLU | 1066 | 14.550 | 10.152 | 8.383 | 1.00 91.86 | 6 |
| ATOM | 1836 | CD | GLU | 1066 | 13.252 | 9.651 | 7.787 | 1.00 91.86 | 6 |
| ATOM | 1837 | OE1 | GLU | 1066 | 12.729 | 8.615 | 8.258 | 1.00 91.86 | 8 |
| ATOM | 1838 | OE2 | GLU | 1066 | 12.755 | 10.296 | 6.840 | 1.00 91.86 | 8 |
| ATOM | 1839 | C | GLU | 1066 | 16.481 | 13.479 | 7.989 | 1.00 54.29 | 6 |
| ATOM | 1840 | O | GLU | 1066 | 17.223 | 13.758 | 7.048 | 1.00 54.29 | 8 |
| ATOM | 1841 | N | VAL | 1067 | 15.878 | 14.408 | 8.727 | 1.00 46.62 | 7 |
| ATOM | 1842 | CA | VAL | 1067 | 16.032 | 15.836 | 8.426 | 1.00 46.62 | 6 |
| ATOM | 1843 | CB | VAL | 1067 | 15.277 | 16.712 | 9.430 | 1.00 20.69 | 6 |
| ATOM | 1844 | CG1 | VAL | 1067 | 15.286 | 18.154 | 8.957 | 1.00 20.69 | 6 |
| ATOM | 1845 | CG2 | VAL | 1067 | 13.879 | 16.208 | 9.595 | 1.00 20.69 | 6 |
| ATOM | 1846 | C | VAL | 1067 | 17.484 | 16.314 | 8.400 | 1.00 46.62 | 6 |
| ATOM | 1847 | O | VAL | 1067 | 17.892 | 17.076 | 7.526 | 1.00 46.62 | 8 |
| ATOM | 1848 | N | TYR | 1068 | 18.261 | 15.858 | 9.367 | 1.00 49.64 | 7 |
| ATOM | 1849 | CA | TYR | 1068 | 19.654 | 16.240 | 9.459 | 1.00 49.64 | 6 |
| ATOM | 1850 | CB | TYR | 1068 | 20.195 | 15.811 | 10.813 | 1.00 42.96 | 6 |
| ATOM | 1851 | CG | TYR | 1068 | 21.604 | 16.239 | 11.074 | 1.00 42.96 | 6 |
| ATOM | 1852 | CD1 | TYR | 1068 | 21.947 | 17.594 | 11.093 | 1.00 42.96 | 6 |
| ATOM | 1853 | CE1 | TYR | 1068 | 23.236 | 18.006 | 11.387 | 1.00 42.96 | 6 |
| ATOM | 1854 | CD2 | TYR | 1068 | 22.593 | 15.301 | 11.348 | 1.00 42.96 | 6 |
| ATOM | 1855 | CE2 | TYR | 1068 | 23.882 | 15.701 | 11.640 | 1.00 42.96 | 6 |
| ATOM | 1856 | CZ | TYR | 1068 | 24.198 | 17.055 | 11.662 | 1.00 42.96 | 6 |
| ATOM | 1857 | OH | TYR | 1068 | 25.470 | 17.451 | 11.985 | 1.00 42.96 | 8 |
| ATOM | 1858 | C | TYR | 1068 | 20.424 | 15.557 | 8.338 | 1.00 49.64 | 6 |
| ATOM | 1859 | O | TYR | 1068 | 21.239 | 16.176 | 7.663 | 1.00 49.64 | 8 |
| ATOM | 1860 | N | ASP | 1069 | 20.148 | 14.275 | 8.144 | 1.00 54.25 | 7 |
| ATOM | 1861 | CA | ASP | 1069 | 20.808 | 13.495 | 7.112 | 1.00 54.25 | 6 |
| ATOM | 1862 | CB | ASP | 1069 | 20.056 | 12.188 | 6.905 | 1.00100.00 | 6 |
| ATOM | 1863 | CG | ASP | 1069 | 20.812 | 11.231 | 6.043 | 1.00100.00 | 6 |
| ATOM | 1864 | OD1 | ASP | 1069 | 21.225 | 11.635 | 4.937 | 1.00100.00 | 8 |
| ATOM | 1865 | OD2 | ASP | 1069 | 20.986 | 10.076 | 6.479 | 1.00100.00 | 8 |
| ATOM | 1866 | C | ASP | 1069 | 20.815 | 14.279 | 5.803 | 1.00 54.25 | 6 |
| ATOM | 1867 | O | ASP | 1069 | 21.779 | 14.247 | 5.037 | 1.00 54.25 | 8 |
| ATOM | 1868 | N | LEU | 1070 | 19.697 | 14.956 | 5.562 | 1.00 40.31 | 7 |
| ATOM | 1869 | CA | LEU | 1070 | 19.496 | 15.777 | 4.371 | 1.00 40.31 | 6 |

FIG. 3GG

| | | | | | | | | |
|---|---|---|---|---|---|---|---|---|
| ATOM | 1870 | CB | LEU | 1070 | 18.009 | 16.075 | 4.195 | 1.00 25.05 | 6 |
| ATOM | 1871 | CG | LEU | 1070 | 17.581 | 16.966 | 3.048 | 1.00 25.05 | 6 |
| ATOM | 1872 | CD1 | LEU | 1070 | 17.865 | 16.291 | 1.720 | 1.00 25.05 | 6 |
| ATOM | 1873 | CD2 | LEU | 1070 | 16.114 | 17.219 | 3.219 | 1.00 25.05 | 6 |
| ATOM | 1874 | C | LEU | 1070 | 20.290 | 17.079 | 4.447 | 1.00 40.31 | 6 |
| ATOM | 1875 | O | LEU | 1070 | 20.561 | 17.688 | 3.423 | 1.00 40.31 | 8 |
| ATOM | 1876 | N | MET | 1071 | 20.639 | 17.510 | 5.655 | 1.00 23.05 | 7 |
| ATOM | 1877 | CA | MET | 1071 | 21.452 | 18.703 | 5.785 | 1.00 23.05 | 6 |
| ATOM | 1878 | CB | MET | 1071 | 21.367 | 19.310 | 7.201 | 1.00 19.93 | 6 |
| ATOM | 1879 | CG | MET | 1071 | 20.030 | 19.910 | 7.631 | 1.00 19.93 | 6 |
| ATOM | 1880 | SD | MET | 1071 | 20.077 | 20.344 | 9.411 | 1.00 19.93 | 16 |
| ATOM | 1881 | CE | MET | 1071 | 18.390 | 20.649 | 9.751 | 1.00 19.93 | 6 |
| ATOM | 1882 | C | MET | 1071 | 22.888 | 18.243 | 5.504 | 1.00 23.05 | 6 |
| ATOM | 1883 | O | MET | 1071 | 23.591 | 18.880 | 4.744 | 1.00 23.05 | 8 |
| ATOM | 1884 | N | ARG | 1072 | 23.319 | 17.124 | 6.082 | 1.00 51.65 | 7 |
| ATOM | 1885 | CA | ARG | 1072 | 24.689 | 16.669 | 5.864 | 1.00 51.65 | 6 |
| ATOM | 1886 | CB | ARG | 1072 | 24.978 | 15.434 | 6.696 | 1.00 98.84 | 6 |
| ATOM | 1887 | CG | ARG | 1072 | 24.870 | 15.716 | 8.162 | 1.00 98.84 | 6 |
| ATOM | 1888 | CD | ARG | 1072 | 26.125 | 16.339 | 8.727 | 1.00 98.84 | 6 |
| ATOM | 1889 | NE | ARG | 1072 | 27.004 | 15.305 | 9.271 | 1.00 98.84 | 7 |
| ATOM | 1890 | CZ | ARG | 1072 | 27.992 | 15.530 | 10.131 | 1.00 98.84 | 6 |
| ATOM | 1891 | NH1 | ARG | 1072 | 28.232 | 16.767 | 10.546 | 1.00 98.84 | 7 |
| ATOM | 1892 | NH2 | ARG | 1072 | 28.724 | 14.521 | 10.593 | 1.00 98.84 | 7 |
| ATOM | 1893 | C | ARG | 1072 | 25.023 | 16.404 | 4.401 | 1.00 51.65 | 6 |
| ATOM | 1894 | O | ARG | 1072 | 26.150 | 16.659 | 3.973 | 1.00 51.65 | 8 |
| ATOM | 1895 | N | GLN | 1073 | 24.073 | 15.900 | 3.617 | 1.00 27.54 | 7 |
| ATOM | 1896 | CA | GLN | 1073 | 24.376 | 15.679 | 2.211 | 1.00 27.54 | 6 |
| ATOM | 1897 | CB | GLN | 1073 | 23.347 | 14.746 | 1.568 | 1.00 67.93 | 6 |
| ATOM | 1898 | CG | GLN | 1073 | 21.934 | 15.149 | 1.789 | 1.00 67.93 | 6 |
| ATOM | 1899 | CD | GLN | 1073 | 20.972 | 14.026 | 1.527 | 1.00 67.93 | 6 |
| ATOM | 1900 | OE1 | GLN | 1073 | 20.889 | 13.066 | 2.298 | 1.00 67.93 | 8 |
| ATOM | 1901 | NE2 | GLN | 1073 | 20.238 | 14.127 | 0.422 | 1.00 67.93 | 7 |
| ATOM | 1902 | C | GLN | 1073 | 24.449 | 17.041 | 1.500 | 1.00 27.54 | 6 |
| ATOM | 1903 | O | GLN | 1073 | 25.088 | 17.162 | 0.453 | 1.00 27.54 | 8 |
| ATOM | 1904 | N | CYS | 1074 | 23.816 | 18.070 | 2.072 | 1.00 36.16 | 7 |
| ATOM | 1905 | CA | CYS | 1074 | 23.858 | 19.423 | 1.497 | 1.00 36.16 | 6 |
| ATOM | 1906 | CB | CYS | 1074 | 22.925 | 20.393 | 2.243 | 1.00 40.38 | 6 |
| ATOM | 1907 | SG | CYS | 1074 | 21.201 | 20.463 | 1.797 | 1.00 40.38 | 16 |
| ATOM | 1908 | C | CYS | 1074 | 25.282 | 19.995 | 1.627 | 1.00 36.16 | 6 |
| ATOM | 1909 | O | CYS | 1074 | 25.746 | 20.748 | 0.767 | 1.00 36.16 | 8 |
| ATOM | 1910 | N | TRP | 1075 | 25.958 | 19.619 | 2.716 | 1.00 26.48 | 7 |
| ATOM | 1911 | CA | TRP | 1075 | 27.302 | 20.120 | 3.049 | 1.00 26.48 | 6 |
| ATOM | 1912 | CB | TRP | 1075 | 27.413 | 20.389 | 4.570 | 1.00 32.15 | 6 |
| ATOM | 1913 | CG | TRP | 1075 | 26.260 | 21.224 | 5.181 | 1.00 32.15 | 6 |
| ATOM | 1914 | CD2 | TRP | 1075 | 25.679 | 21.080 | 6.485 | 1.00 32.15 | 6 |
| ATOM | 1915 | CE2 | TRP | 1075 | 24.682 | 22.075 | 6.613 | 1.00 32.15 | 6 |
| ATOM | 1916 | CE3 | TRP | 1075 | 25.901 | 20.211 | 7.553 | 1.00 32.15 | 6 |
| ATOM | 1917 | CD1 | TRP | 1075 | 25.607 | 22.272 | 4.597 | 1.00 32.15 | 6 |
| ATOM | 1918 | NE1 | TRP | 1075 | 24.662 | 22.783 | 5.449 | 1.00 32.15 | 7 |
| ATOM | 1919 | CZ2 | TRP | 1075 | 23.909 | 22.222 | 7.774 | 1.00 32.15 | 6 |
| ATOM | 1920 | CZ3 | TRP | 1075 | 25.133 | 20.361 | 8.703 | 1.00 32.15 | 6 |
| ATOM | 1921 | CH2 | TRP | 1075 | 24.148 | 21.357 | 8.807 | 1.00 32.15 | 6 |
| ATOM | 1922 | C | TRP | 1075 | 28.471 | 19.236 | 2.622 | 1.00 26.48 | 6 |
| ATOM | 1923 | O | TRP | 1075 | 29.599 | 19.447 | 3.071 | 1.00 26.48 | 8 |
| ATOM | 1924 | N | ARG | 1076 | 28.209 | 18.265 | 1.751 | 1.00 51.58 | 7 |
| ATOM | 1925 | CA | ARG | 1076 | 29.258 | 17.367 | 1.279 | 1.00 51.58 | 6 |
| ATOM | 1926 | CB | ARG | 1076 | 28.683 | 16.391 | 0.249 | 1.00 67.56 | 6 |

FIG. 3HH

```
ATOM   1927  CG   ARG  1076    27.618  15.509   0.847  1.00 67.56     6
ATOM   1928  CD   ARG  1076    27.279  14.291   0.009  1.00 67.56     6
ATOM   1929  NE   ARG  1076    26.267  13.485   0.690  1.00 67.56     7
ATOM   1930  CZ   ARG  1076    25.731  12.365   0.215  1.00 67.56     6
ATOM   1931  NH1  ARG  1076    26.104  11.891  -0.966  1.00 67.56     7
ATOM   1932  NH2  ARG  1076    24.819  11.714   0.929  1.00 67.56     7
ATOM   1933  C    ARG  1076    30.431  18.157   0.710  1.00 51.58     6
ATOM   1934  O    ARG  1076    30.238  19.206   0.103  1.00 51.58     8
ATOM   1935  N    GLU  1077    31.642  17.651   0.941  1.00 50.74     7
ATOM   1936  CA   GLU  1077    32.885  18.281   0.488  1.00 50.74     6
ATOM   1937  CB   GLU  1077    34.059  17.419   0.893  1.00 91.21     6
ATOM   1938  C    GLU  1077    32.927  18.540  -1.013  1.00 50.74     6
ATOM   1939  O    GLU  1077    33.213  19.657  -1.450  1.00 50.74     8
ATOM   1940  N    LYS  1078    32.656  17.494  -1.790  1.00 49.20     7
ATOM   1941  CA   LYS  1078    32.657  17.579  -3.240  1.00 49.20     6
ATOM   1942  CB   LYS  1078    32.895  16.197  -3.847  1.00 93.58     6
ATOM   1943  CG   LYS  1078    34.289  15.666  -3.640  1.00 93.51     6
ATOM   1944  CD   LYS  1078    34.458  14.341  -4.346  1.00 93.51     6
ATOM   1945  CE   LYS  1078    35.872  13.806  -4.191  1.00 93.51     6
ATOM   1946  NZ   LYS  1078    36.025  12.476  -4.860  1.00 93.51     7
ATOM   1947  C    LYS  1078    31.345  18.145  -3.760  1.00 49.20     6
ATOM   1948  O    LYS  1078    30.290  17.528  -3.617  1.00 49.20     8
ATOM   1949  N    PRO  1079    31.390  19.341  -4.366  1.00 30.47     7
ATOM   1950  CD   PRO  1079    32.592  20.190  -4.459  1.00 29.67     6
ATOM   1951  CA   PRO  1079    30.236  20.040  -4.931  1.00 30.47     6
ATOM   1952  CB   PRO  1079    30.887  21.098  -5.791  1.00 29.67     6
ATOM   1953  CG   PRO  1079    32.024  21.511  -4.914  1.00 29.67     6
ATOM   1954  C    PRO  1079    29.235  19.190  -5.711  1.00 30.47     6
ATOM   1955  O    PRO  1079    28.040  19.221  -5.420  1.00 30.47     8
ATOM   1956  N    TYR  1080    29.708  18.462  -6.718  1.00 44.53     7
ATOM   1957  CA   TYR  1080    28.821  17.616  -7.520  1.00 44.53     6
ATOM   1958  CB   TYR  1080    29.576  17.054  -8.730  1.00 62.16     6
ATOM   1959  CG   TYR  1080    30.938  16.479  -8.412  1.00 62.16     6
ATOM   1960  CD1  TYR  1080    31.072  15.207  -7.859  1.00 62.16     6
ATOM   1961  CE1  TYR  1080    32.329  14.691  -7.531  1.00 62.16     6
ATOM   1962  CD2  TYR  1080    32.095  17.223  -8.636  1.00 62.16     6
ATOM   1963  CE2  TYR  1080    33.351  16.722  -8.312  1.00 62.16     6
ATOM   1964  CZ   TYR  1080    33.462  15.458  -7.757  1.00 62.16     6
ATOM   1965  OH   TYR  1080    34.701  14.970  -7.409  1.00 62.16     8
ATOM   1966  C    TYR  1080    28.232  16.490  -6.672  1.00 44.53     6
ATOM   1967  O    TYR  1080    27.282  15.833  -7.087  1.00 44.53     8
ATOM   1968  N    GLU  1081    28.792  16.285  -5.484  1.00 41.53     7
ATOM   1969  CA   GLU  1081    28.285  15.257  -4.588  1.00 41.53     6
ATOM   1970  CB   GLU  1081    29.373  14.767  -3.638  1.00 60.45     6
ATOM   1971  CG   GLU  1081    30.292  13.713  -4.220  1.00 60.45     6
ATOM   1972  CD   GLU  1081    31.240  13.143  -3.182  1.00 60.45     6
ATOM   1973  OE1  GLU  1081    31.903  12.119  -3.470  1.00 60.45     8
ATOM   1974  OE2  GLU  1081    31.323  13.726  -2.079  1.00 60.45     8
ATOM   1975  C    GLU  1081    27.114  15.809  -3.778  1.00 41.53     6
ATOM   1976  O    GLU  1081    26.512  15.099  -2.972  1.00 41.53     8
ATOM   1977  N    ARG  1082    26.812  17.087  -3.975  1.00 50.75     7
ATOM   1978  CA   ARG  1082    25.702  17.706  -3.280  1.00 50.75     6
ATOM   1979  CB   ARG  1082    25.979  19.207  -3.053  1.00 30.76     6
ATOM   1980  CG   ARG  1082    26.429  19.535  -1.624  1.00 30.76     6
ATOM   1981  CD   ARG  1082    27.857  20.100  -1.505  1.00 30.76     6
ATOM   1982  NE   ARG  1082    27.939  21.540  -1.743  1.00 30.76     7
ATOM   1983  CZ   ARG  1082    29.060  22.258  -1.663  1.00 30.76     6
```

FIG. 3II

```
ATOM   1984  NH1  ARG  1082     30.225  21.698  -1.358  1.00  30.76   7
ATOM   1985  NH2  ARG  1082     29.007  23.567  -1.865  1.00  30.76   7
ATOM   1986  C    ARG  1082     24.446  17.479  -4.124  1.00  50.75   6
ATOM   1987  O    ARG  1082     24.501  17.497  -5.355  1.00  50.75   8
ATOM   1988  N    PRO  1083     23.303  17.225  -3.464  1.00  42.97   7
ATOM   1989  CD   PRO  1083     23.155  17.153  -1.995  1.00  16.51   6
ATOM   1990  CA   PRO  1083     22.022  16.983  -4.127  1.00  42.97   6
ATOM   1991  CB   PRO  1083     21.171  16.382  -3.015  1.00  16.51   6
ATOM   1992  CG   PRO  1083     21.665  17.079  -1.805  1.00  16.51   6
ATOM   1993  C    PRO  1083     21.450  18.268  -4.715  1.00  42.97   6
ATOM   1994  O    PRO  1083     21.914  19.353  -4.402  1.00  42.97   8
ATOM   1995  N    SER  1084     20.448  18.132  -5.564  1.00  43.29   7
ATOM   1996  CA   SER  1084     19.842  19.275  -6.217  1.00  43.29   6
ATOM   1997  CB   SER  1084     19.553  18.890  -7.643  1.00  28.32   6
ATOM   1998  OG   SER  1084     18.965  17.607  -7.610  1.00  28.32   8
ATOM   1999  C    SER  1084     18.543  19.679  -5.538  1.00  43.29   6
ATOM   2000  O    SER  1084     17.901  18.858  -4.878  1.00  43.29   8
ATOM   2001  N    PHE  1085     18.148  20.934  -5.723  1.00  22.83   7
ATOM   2002  CA   PHE  1085     16.913  21.427  -5.128  1.00  22.83   6
ATOM   2003  CB   PHE  1085     16.688  22.881  -5.538  1.00   7.27   6
ATOM   2004  CG   PHE  1085     17.599  23.814  -4.858  1.00   7.27   6
ATOM   2005  CD1  PHE  1085     18.487  24.598  -5.588  1.00   7.27   6
ATOM   2006  CD2  PHE  1085     17.592  23.899  -3.476  1.00   7.27   6
ATOM   2007  CE1  PHE  1085     19.356  25.462  -4.949  1.00   7.27   6
ATOM   2008  CE2  PHE  1085     18.454  24.756  -2.819  1.00   7.27   6
ATOM   2009  CZ   PHE  1085     19.341  25.545  -3.560  1.00   7.27   6
ATOM   2010  C    PHE  1085     15.710  20.587  -5.510  1.00  22.83   6
ATOM   2011  O    PHE  1085     14.660  20.668  -4.882  1.00  22.83   8
ATOM   2012  N    ALA  1086     15.878  19.789  -6.553  1.00  45.86   7
ATOM   2013  CA   ALA  1086     14.813  18.919  -7.016  1.00  45.86   6
ATOM   2014  CB   ALA  1086     15.037  18.540  -8.430  1.00  15.16   6
ATOM   2015  C    ALA  1086     14.783  17.674  -6.161  1.00  45.86   6
ATOM   2016  O    ALA  1086     13.720  17.175  -5.815  1.00  45.86   8
ATOM   2017  N    GLN  1087     15.959  17.180  -5.810  1.00  32.39   7
ATOM   2018  CA   GLN  1087     16.020  15.990  -5.000  1.00  32.39   6
ATOM   2019  CB   GLN  1087     17.433  15.386  -5.038  1.00  50.88   6
ATOM   2020  CG   GLN  1087     17.971  15.230  -6.466  1.00  50.88   6
ATOM   2021  CD   GLN  1087     19.290  14.488  -6.552  1.00  50.88   6
ATOM   2022  OE1  GLN  1087     20.221  14.752  -5.790  1.00  50.88   8
ATOM   2023  NE2  GLN  1087     19.389  13.577  -7.510  1.00  50.88   7
ATOM   2024  C    GLN  1087     15.617  16.398  -3.592  1.00  32.39   6
ATOM   2025  O    GLN  1087     14.792  15.737  -2.956  1.00  32.39   8
ATOM   2026  N    ILE  1088     16.177  17.507  -3.116  1.00  19.40   7
ATOM   2027  CA   ILE  1088     15.875  17.997  -1.761  1.00  19.40   6
ATOM   2028  CB   ILE  1088     16.519  19.358  -1.532  1.00  20.50   6
ATOM   2029  CG2  ILE  1088     16.172  19.905  -0.185  1.00  20.50   6
ATOM   2030  CG1  ILE  1088     18.017  19.199  -1.630  1.00  20.50   6
ATOM   2031  CD1  ILE  1088     18.747  20.459  -1.361  1.00  20.50   6
ATOM   2032  C    ILE  1088     14.375  18.102  -1.531  1.00  19.40   6
ATOM   2033  O    ILE  1088     13.852  17.646  -0.514  1.00  19.40   8
ATOM   2034  N    LEU  1089     13.697  18.700  -2.500  1.00  31.43   7
ATOM   2035  CA   LEU  1089     12.262  18.860  -2.452  1.00  31.43   6
ATOM   2036  CB   LEU  1089     11.783  19.531  -3.714  1.00  14.58   6
ATOM   2037  CG   LEU  1089     10.376  20.070  -3.576  1.00  14.58   6
ATOM   2038  CD1  LEU  1089     10.208  20.858  -2.288  1.00  14.58   6
ATOM   2039  CD2  LEU  1089     10.136  20.941  -4.788  1.00  14.58   6
ATOM   2040  C    LEU  1089     11.595  17.509  -2.335  1.00  31.43   6
```

FIG. 3JJ

```
ATOM   2041  O    LEU  1089    10.804  17.270  -1.423  1.00 31.43      8
ATOM   2042  N    VAL  1090    11.920  16.619  -3.265  1.00 26.46      7
ATOM   2043  CA   VAL  1090    11.346  15.288  -3.242  1.00 26.46      6
ATOM   2044  CB   VAL  1090    12.042  14.338  -4.171  1.00 24.17      6
ATOM   2045  CG1  VAL  1090    11.419  12.957  -4.012  1.00 24.17      6
ATOM   2046  CG2  VAL  1090    11.913  14.819  -5.581  1.00 24.17      6
ATOM   2047  C    VAL  1090    11.441  14.697  -1.861  1.00 26.46      6
ATOM   2048  O    VAL  1090    10.476  14.126  -1.362  1.00 26.46      8
ATOM   2049  N    SER  1091    12.600  14.819  -1.235  1.00 24.68      7
ATOM   2050  CA   SER  1091    12.726  14.276   0.094  1.00 24.68      6
ATOM   2051  CB   SER  1091    14.156  14.407   0.599  1.00 45.28      6
ATOM   2052  OG   SER  1091    15.039  13.699  -0.249  1.00 45.28      8
ATOM   2053  C    SER  1091    11.742  14.999   1.006  1.00 24.68      6
ATOM   2054  O    SER  1091    10.796  14.379   1.471  1.00 24.68      8
ATOM   2055  N    LEU  1092    11.919  16.302   1.231  1.00 45.44      7
ATOM   2056  CA   LEU  1092    11.001  17.031   2.112  1.00 45.44      6
ATOM   2057  CB   LEU  1092    11.127  18.557   1.905  1.00 19.86      6
ATOM   2058  CG   LEU  1092    12.518  19.144   2.242  1.00 19.86      6
ATOM   2059  CD1  LEU  1092    12.611  20.594   1.810  1.00 19.86      6
ATOM   2060  CD2  LEU  1092    12.793  19.007   3.728  1.00 19.86      6
ATOM   2061  C    LEU  1092     9.554  16.568   1.918  1.00 45.44      6
ATOM   2062  O    LEU  1092     8.821  16.438   2.891  1.00 45.44      8
ATOM   2063  N    ASN  1093     9.162  16.275   0.678  1.00 44.52      7
ATOM   2064  CA   ASN  1093     7.797  15.820   0.360  1.00 44.52      6
ATOM   2065  CB   ASN  1093     7.578  15.906  -1.147  1.00 34.39      6
ATOM   2066  CG   ASN  1093     7.266  17.302  -1.586  1.00 34.39      6
ATOM   2067  OD1  ASN  1093     7.572  17.705  -2.703  1.00 34.39      8
ATOM   2068  ND2  ASN  1093     6.639  18.061  -0.698  1.00 34.39      7
ATOM   2069  C    ASN  1093     7.501  14.414   0.849  1.00 44.52      6
ATOM   2070  O    ASN  1093     6.437  14.137   1.401  1.00 44.52      8
ATOM   2071  N    ARG  1094     8.458  13.529   0.631  1.00 42.85      7
ATOM   2072  CA   ARG  1094     8.329  12.168   1.074  1.00 42.85      6
ATOM   2073  CB   ARG  1094     9.491  11.353   0.472  1.00 83.86      6
ATOM   2074  CG   ARG  1094    10.129  10.325   1.373  1.00 83.62      6
ATOM   2075  CD   ARG  1094    11.099  10.992   2.328  1.00 83.62      6
ATOM   2076  NE   ARG  1094    11.576  10.076   3.359  1.00 83.62      7
ATOM   2077  CZ   ARG  1094    10.787   9.365   4.163  1.00 83.62      6
ATOM   2078  NH1  ARG  1094     9.466   9.461   4.070  1.00 83.62      7
ATOM   2079  NH2  ARG  1094    11.323   8.549   5.061  1.00 83.62      7
ATOM   2080  C    ARG  1094     8.293  12.166   2.628  1.00 42.85      6
ATOM   2081  O    ARG  1094     7.667  11.308   3.239  1.00 42.85      8
ATOM   2082  N    MET  1095     8.934  13.151   3.253  1.00 51.73      7
ATOM   2083  CA   MET  1095     8.991  13.279   4.712  1.00 51.73      6
ATOM   2084  CB   MET  1095    10.206  14.135   5.109  1.00 28.03      6
ATOM   2085  CG   MET  1095    11.242  13.507   5.999  1.00 28.03      6
ATOM   2086  SD   MET  1095    12.707  14.551   6.044  1.00 28.03     16
ATOM   2087  CE   MET  1095    13.094  14.706   4.302  1.00 28.03      6
ATOM   2088  C    MET  1095     7.757  13.989   5.274  1.00 51.73      6
ATOM   2089  O    MET  1095     7.425  13.870   6.450  1.00 51.73      8
ATOM   2090  N    LEU  1096     7.123  14.763   4.413  1.00 48.50      7
ATOM   2091  CA   LEU  1096     5.981  15.557   4.825  1.00 48.50      6
ATOM   2092  CB   LEU  1096     5.889  16.790   3.951  1.00 41.93      6
ATOM   2093  CG   LEU  1096     6.365  18.048   4.638  1.00 41.93      6
ATOM   2094  CD1  LEU  1096     6.177  19.139   3.616  1.00 41.93      6
ATOM   2095  CD2  LEU  1096     5.593  18.342   5.911  1.00 41.93      6
ATOM   2096  C    LEU  1096     4.663  14.859   4.783  1.00 48.50      6
ATOM   2097  O    LEU  1096     3.747  15.199   5.536  1.00 48.50      8
```

FIG. 3KK

| ATOM | 2098 | N   | GLU | 1097 | 4.537  | 13.900 | 3.890  | 1.00 | 62.96  | 7 |
| ATOM | 2099 | CA  | GLU | 1097 | 3.261  | 13.252 | 3.809  | 1.00 | 63.28  | 6 |
| ATOM | 2100 | CB  | GLU | 1097 | 3.046  | 12.672 | 2.424  | 1.00 | 90.58  | 6 |
| ATOM | 2101 | CG  | GLU | 1097 | 2.625  | 13.708 | 1.449  | 1.00 | 90.58  | 6 |
| ATOM | 2102 | CD  | GLU | 1097 | 2.523  | 13.139 | 0.080  | 1.00 | 90.58  | 6 |
| ATOM | 2103 | OE1 | GLU | 1097 | 3.480  | 12.481 | -0.333 | 1.00 | 90.58  | 8 |
| ATOM | 2104 | OE2 | GLU | 1097 | 1.492  | 13.317 | -0.587 | 1.00 | 90.58  | 8 |
| ATOM | 2105 | C   | GLU | 1097 | 3.099  | 12.216 | 4.892  | 1.00 | 64.94  | 6 |
| ATOM | 2106 | O   | GLU | 1097 | 2.839  | 11.051 | 4.616  | 1.00 | 67.39  | 8 |
| ATOM | 2107 | N   | GLU | 1098 | 3.279  | 12.659 | 6.137  | 1.00 | 99.89  | 7 |
| ATOM | 2108 | CA  | GLU | 1098 | 3.132  | 11.782 | 7.288  | 1.00 | 99.89  | 6 |
| ATOM | 2109 | CB  | GLU | 1098 | 4.342  | 10.880 | 7.434  | 1.00 | 62.46  | 6 |
| ATOM | 2110 | CG  | GLU | 1098 | 4.908  | 10.367 | 6.157  | 1.00 | 62.46  | 6 |
| ATOM | 2111 | CD  | GLU | 1098 | 6.147  | 9.556  | 6.415  | 1.00 | 62.46  | 6 |
| ATOM | 2112 | OE1 | GLU | 1098 | 6.614  | 9.586  | 7.576  | 1.00 | 62.46  | 8 |
| ATOM | 2113 | OE2 | GLU | 1098 | 6.653  | 8.914  | 5.474  | 1.00 | 62.46  | 8 |
| ATOM | 2114 | C   | GLU | 1098 | 2.928  | 12.540 | 8.608  | 1.00 | 99.89  | 6 |
| ATOM | 2115 | O   | GLU | 1098 | 1.962  | 12.277 | 9.312  | 1.00 | 99.89  | 8 |
| ATOM | 2116 | N   | ARG | 1099 | 3.815  | 13.483 | 8.937  | 1.00 | 100.00 | 7 |
| ATOM | 2117 | CA  | ARG | 1099 | 3.735  | 14.251 | 10.201 | 1.00 | 100.00 | 6 |
| ATOM | 2118 | CB  | ARG | 1099 | 2.339  | 14.863 | 10.443 | 1.00 | 95.05  | 6 |
| ATOM | 2119 | CG  | ARG | 1099 | 2.140  | 15.416 | 11.871 | 1.00 | 83.68  | 6 |
| ATOM | 2120 | CD  | ARG | 1099 | 3.239  | 16.413 | 12.239 | 1.00 | 83.68  | 6 |
| ATOM | 2121 | NE  | ARG | 1099 | 3.123  | 16.915 | 13.609 | 1.00 | 83.68  | 7 |
| ATOM | 2122 | CZ  | ARG | 1099 | 3.314  | 18.185 | 13.955 | 1.00 | 83.68  | 6 |
| ATOM | 2123 | NH1 | ARG | 1099 | 3.636  | 19.072 | 13.024 | 1.00 | 83.68  | 7 |
| ATOM | 2124 | NH2 | ARG | 1099 | 3.179  | 18.572 | 15.222 | 1.00 | 83.68  | 7 |
| ATOM | 2125 | C   | ARG | 1099 | 4.083  | 13.322 | 11.354 | 1.00 | 100.00 | 6 |
| ATOM | 2126 | O   | ARG | 1099 | 3.393  | 13.259 | 12.370 | 1.00 | 100.00 | 8 |
| ATOM | 2127 | N   | LYS | 1100 | 5.153  | 12.570 | 11.174 | 1.00 | 88.41  | 7 |
| ATOM | 2128 | CA  | LYS | 1100 | 5.572  | 11.681 | 12.224 | 1.00 | 88.41  | 6 |
| ATOM | 2129 | CB  | LYS | 1100 | 6.250  | 10.454 | 11.641 | 1.00 | 87.41  | 6 |
| ATOM | 2130 | CG  | LYS | 1100 | 5.322  | 9.628  | 10.762 | 1.00 | 87.41  | 6 |
| ATOM | 2131 | CD  | LYS | 1100 | 3.984  | 9.336  | 11.456 | 1.00 | 87.41  | 6 |
| ATOM | 2132 | CE  | LYS | 1100 | 4.165  | 8.742  | 12.861 | 1.00 | 59.92  | 6 |
| ATOM | 2133 | NZ  | LYS | 1100 | 4.852  | 7.411  | 12.877 | 1.00 | 59.92  | 7 |
| ATOM | 2134 | C   | LYS | 1100 | 6.519  | 12.453 | 13.123 | 1.00 | 88.41  | 6 |
| ATOM | 2135 | O   | LYS | 1100 | 7.597  | 11.969 | 13.470 | 1.00 | 88.41  | 8 |
| ATOM | 2136 | N   | THR | 1101 | 6.112  | 13.672 | 13.472 | 1.00 | 100.00 | 7 |
| ATOM | 2137 | CA  | THR | 1101 | 6.892  | 14.519 | 14.356 | 1.00 | 100.00 | 6 |
| ATOM | 2138 | CB  | THR | 1101 | 6.795  | 13.996 | 15.811 | 1.00 | 100.00 | 6 |
| ATOM | 2139 | OG1 | THR | 1101 | 5.426  | 14.034 | 16.239 | 1.00 | 90.24  | 8 |
| ATOM | 2140 | CG2 | THR | 1101 | 7.652  | 14.836 | 16.750 | 1.00 | 90.24  | 6 |
| ATOM | 2141 | C   | THR | 1101 | 8.362  | 14.565 | 13.927 | 1.00 | 100.00 | 6 |
| ATOM | 2142 | O   | THR | 1101 | 9.219  | 13.923 | 14.541 | 1.00 | 100.00 | 8 |
| ATOM | 2143 | N   | TYR | 1102 | 8.655  | 15.300 | 12.862 | 1.00 | 39.18  | 7 |
| ATOM | 2144 | CA  | TYR | 1102 | 10.042 | 15.411 | 12.416 | 1.00 | 39.18  | 6 |
| ATOM | 2145 | CB  | TYR | 1102 | 10.106 | 15.624 | 10.912 | 1.00 | 91.13  | 6 |
| ATOM | 2146 | CG  | TYR | 1102 | 9.798  | 14.391 | 10.132 | 1.00 | 60.67  | 6 |
| ATOM | 2147 | CD1 | TYR | 1102 | 8.500  | 14.112 | 9.717  | 1.00 | 60.67  | 6 |
| ATOM | 2148 | CE1 | TYR | 1102 | 8.222  | 12.956 | 9.006  | 1.00 | 60.67  | 6 |
| ATOM | 2149 | CD2 | TYR | 1102 | 10.809 | 13.487 | 9.821  | 1.00 | 60.67  | 6 |
| ATOM | 2150 | CE2 | TYR | 1102 | 10.544 | 12.338 | 9.120  | 1.00 | 60.67  | 6 |
| ATOM | 2151 | CZ  | TYR | 1102 | 9.256  | 12.078 | 8.711  | 1.00 | 60.67  | 6 |
| ATOM | 2152 | OH  | TYR | 1102 | 9.019  | 10.950 | 7.978  | 1.00 | 60.67  | 8 |
| ATOM | 2153 | C   | TYR | 1102 | 10.781 | 16.549 | 13.102 | 1.00 | 39.18  | 6 |
| ATOM | 2154 | O   | TYR | 1102 | 12.003 | 16.594 | 13.090 | 1.00 | 39.18  | 8 |

FIG. 3LL

| | | | | | | | | | |
|---|---|---|---|---|---|---|---|---|---|
| ATOM | 2155 | N | VAL | 1103 | 10.028 | 17.469 | 13.690 | 1.00 80.69 | 7 |
| ATOM | 2156 | CA | VAL | 1103 | 10.614 | 18.614 | 14.370 | 1.00 80.69 | 6 |
| ATOM | 2157 | CB | VAL | 1103 | 10.585 | 19.857 | 13.466 | 1.00 82.85 | 6 |
| ATOM | 2158 | CG1 | VAL | 1103 | 11.221 | 21.042 | 14.165 | 1.00 25.69 | 6 |
| ATOM | 2159 | CG2 | VAL | 1103 | 11.310 | 19.563 | 12.172 | 1.00 25.69 | 6 |
| ATOM | 2160 | C | VAL | 1103 | 9.791 | 18.892 | 15.611 | 1.00 80.69 | 6 |
| ATOM | 2161 | O | VAL | 1103 | 8.677 | 19.395 | 15.529 | 1.00 80.69 | 8 |
| ATOM | 2162 | N | ASN | 1104 | 10.345 | 18.570 | 16.767 | 1.00 61.67 | 7 |
| ATOM | 2163 | CA | ASN | 1104 | 9.624 | 18.773 | 18.003 | 1.00 61.67 | 6 |
| ATOM | 2164 | CB | ASN | 1104 | 10.315 | 18.015 | 19.112 | 1.00 93.99 | 6 |
| ATOM | 2165 | CG | ASN | 1104 | 9.344 | 17.404 | 20.054 | 1.00 53.82 | 6 |
| ATOM | 2166 | OD1 | ASN | 1104 | 8.643 | 18.111 | 20.791 | 1.00 53.82 | 8 |
| ATOM | 2167 | ND2 | ASN | 1104 | 9.261 | 16.076 | 20.028 | 1.00 53.82 | 7 |
| ATOM | 2168 | C | ASN | 1104 | 9.470 | 20.240 | 18.395 | 1.00 61.67 | 6 |
| ATOM | 2169 | O | ASN | 1104 | 10.453 | 20.966 | 18.484 | 1.00 61.67 | 8 |
| ATOM | 2170 | N | THR | 1105 | 8.233 | 20.675 | 18.625 | 1.00 43.79 | 7 |
| ATOM | 2171 | CA | THR | 1105 | 7.960 | 22.059 | 19.024 | 1.00 43.79 | 6 |
| ATOM | 2172 | CB | THR | 1105 | 7.081 | 22.763 | 18.002 | 1.00 95.52 | 6 |
| ATOM | 2173 | OG1 | THR | 1105 | 5.888 | 22.001 | 17.786 | 1.00 51.15 | 8 |
| ATOM | 2174 | CG2 | THR | 1105 | 7.835 | 22.923 | 16.700 | 1.00 51.15 | 6 |
| ATOM | 2175 | C | THR | 1105 | 7.231 | 22.045 | 20.350 | 1.00 43.79 | 6 |
| ATOM | 2176 | O | THR | 1105 | 6.598 | 23.024 | 20.754 | 1.00 43.79 | 8 |
| ATOM | 2177 | N | THR | 1106 | 7.338 | 20.905 | 21.016 | 1.00 47.73 | 7 |
| ATOM | 2178 | CA | THR | 1106 | 6.683 | 20.671 | 22.281 | 1.00 47.73 | 6 |
| ATOM | 2179 | CB | THR | 1106 | 5.850 | 19.415 | 22.236 | 1.00 24.03 | 6 |
| ATOM | 2180 | OG1 | THR | 1106 | 4.835 | 19.542 | 21.237 | 1.00 24.03 | 8 |
| ATOM | 2181 | CG2 | THR | 1106 | 5.222 | 19.167 | 23.580 | 1.00 24.03 | 6 |
| ATOM | 2182 | C | THR | 1106 | 7.676 | 20.434 | 23.372 | 1.00 47.73 | 6 |
| ATOM | 2183 | O | THR | 1106 | 8.742 | 19.880 | 23.129 | 1.00 47.73 | 8 |
| ATOM | 2184 | N | LEU | 1107 | 7.311 | 20.833 | 24.583 | 1.00 64.31 | 7 |
| ATOM | 2185 | CA | LEU | 1107 | 8.174 | 20.612 | 25.723 | 1.00 64.31 | 6 |
| ATOM | 2186 | CB | LEU | 1107 | 8.207 | 21.803 | 26.637 | 1.00 96.32 | 6 |
| ATOM | 2187 | CG | LEU | 1107 | 8.957 | 22.900 | 25.957 | 1.00 40.62 | 6 |
| ATOM | 2188 | CD1 | LEU | 1107 | 7.919 | 23.838 | 25.432 | 1.00 40.62 | 6 |
| ATOM | 2189 | CD2 | LEU | 1107 | 9.864 | 23.587 | 26.914 | 1.00 40.62 | 6 |
| ATOM | 2190 | C | LEU | 1107 | 7.795 | 19.433 | 26.564 | 1.00 64.31 | 6 |
| ATOM | 2191 | O | LEU | 1107 | 6.801 | 19.458 | 27.281 | 1.00 64.31 | 8 |
| ATOM | 2192 | N | TYR | 1108 | 8.708 | 18.463 | 26.384 | 1.00 94.02 | 7 |
| ATOM | 2193 | CA | TYR | 1108 | 8.405 | 17.305 | 27.238 | 1.00 94.02 | 6 |
| ATOM | 2194 | CB | TYR | 1108 | 8.596 | 16.009 | 26.448 | 1.00 99.65 | 6 |
| ATOM | 2195 | CG | TYR | 1108 | 7.705 | 15.929 | 25.207 | 1.00 78.77 | 6 |
| ATOM | 2196 | CD1 | TYR | 1108 | 7.913 | 14.643 | 24.404 | 1.00 78.77 | 6 |
| ATOM | 2197 | CD2 | TYR | 1108 | 6.212 | 15.974 | 25.538 | 1.00 78.77 | 6 |
| ATOM | 2198 | C | TYR | 1108 | 9.340 | 17.291 | 28.449 | 1.00 94.02 | 6 |
| ATOM | 2199 | O | TYR | 1108 | 8.922 | 16.976 | 29.574 | 1.00 94.02 | 8 |
| ATOM | 2200 | N | GLU | 1109 | 10.796 | 17.582 | 27.521 | 1.00 92.55 | 7 |
| ATOM | 2201 | CA | GLU | 1109 | 11.496 | 17.815 | 28.793 | 1.00 92.55 | 6 |
| ATOM | 2202 | CB | GLU | 1109 | 11.234 | 16.655 | 29.755 | 1.00 95.82 | 6 |
| ATOM | 2203 | C | GLU | 1109 | 13.002 | 17.927 | 28.549 | 1.00 92.55 | 6 |
| ATOM | 2204 | O | GLU | 1109 | 13.672 | 16.935 | 28.226 | 1.00 92.55 | 8 |
| ATOM | 2205 | N | LYS | 1110 | 13.581 | 19.231 | 28.669 | 1.00 54.62 | 7 |
| ATOM | 2206 | CA | LYS | 1110 | 14.995 | 19.556 | 28.430 | 1.00 54.62 | 6 |
| ATOM | 2207 | CB | LYS | 1110 | 15.850 | 18.294 | 28.564 | 1.00100.00 | 6 |
| ATOM | 2208 | CG | LYS | 1110 | 16.129 | 17.914 | 30.020 | 1.00 99.80 | 6 |
| ATOM | 2209 | CD | LYS | 1110 | 17.313 | 16.956 | 30.171 | 1.00 99.80 | 6 |
| ATOM | 2210 | CE | LYS | 1110 | 17.333 | 16.240 | 31.523 | 1.00 99.80 | 6 |
| ATOM | 2211 | NZ | LYS | 1110 | 18.525 | 15.400 | 31.710 | 1.00 99.80 | 7 |

FIG. 3MM

| | | | | | | | | | | |
|---|---|---|---|---|---|---|---|---|---|---|
| ATOM | 2212 | C | LYS | 1110 | 15.168 | 20.134 | 27.023 | 1.00 | 54.62 | 6 |
| ATOM | 2213 | O | LYS | 1110 | 15.875 | 19.561 | 26.181 | 1.00 | 54.62 | 8 |
| ATOM | 2214 | N | PHE | 1111 | 14.506 | 21.258 | 26.825 | 1.00 | 53.78 | 7 |
| ATOM | 2215 | CA | PHE | 1111 | 14.527 | 21.994 | 25.551 | 1.00 | 53.78 | 6 |
| ATOM | 2216 | CB | PHE | 1111 | 13.134 | 22.558 | 25.259 | 1.00 | 97.53 | 6 |
| ATOM | 2217 | CG | PHE | 1111 | 12.847 | 22.718 | 23.764 | 1.00 | 42.19 | 6 |
| ATOM | 2218 | CD1 | PHE | 1111 | 12.368 | 21.631 | 23.023 | 1.00 | 42.19 | 6 |
| ATOM | 2219 | CD2 | PHE | 1111 | 13.062 | 23.951 | 23.140 | 1.00 | 42.19 | 6 |
| ATOM | 2220 | CE1 | PHE | 1111 | 12.104 | 21.779 | 21.655 | 1.00 | 42.19 | 6 |
| ATOM | 2221 | CE2 | PHE | 1111 | 12.798 | 24.100 | 21.773 | 1.00 | 42.19 | 6 |
| ATOM | 2222 | CZ | PHE | 1111 | 12.318 | 23.013 | 21.031 | 1.00 | 42.19 | 6 |
| ATOM | 2223 | C | PHE | 1111 | 15.528 | 23.149 | 25.640 | 1.00 | 53.78 | 6 |
| ATOM | 2224 | O | PHE | 1111 | 15.647 | 23.812 | 26.681 | 1.00 | 53.78 | 8 |
| ATOM | 2225 | N | THR | 1112 | 16.171 | 23.593 | 24.331 | 1.00 | 41.67 | 7 |
| ATOM | 2226 | CA | THR | 1112 | 17.246 | 24.596 | 24.296 | 1.00 | 41.67 | 6 |
| ATOM | 2227 | CB | THR | 1112 | 18.609 | 23.900 | 24.280 | 1.00 | 81.18 | 6 |
| ATOM | 2228 | OG1 | THR | 1112 | 18.657 | 22.952 | 23.224 | 1.00 | 45.38 | 8 |
| ATOM | 2229 | CG2 | THR | 1112 | 18.915 | 23.153 | 25.579 | 1.00 | 45.38 | 6 |
| ATOM | 2230 | C | THR | 1112 | 17.113 | 25.461 | 23.041 | 1.00 | 41.67 | 6 |
| ATOM | 2231 | O | THR | 1112 | 16.476 | 25.063 | 22.055 | 1.00 | 41.67 | 8 |
| ATOM | 2232 | N | TYR | 1113 | 17.727 | 26.628 | 23.125 | 1.00 | 88.60 | 7 |
| ATOM | 2233 | CA | TYR | 1113 | 17.729 | 27.614 | 22.034 | 1.00 | 88.60 | 6 |
| ATOM | 2234 | CB | TYR | 1113 | 16.857 | 28.816 | 22.408 | 1.00 | 72.51 | 6 |
| ATOM | 2235 | CG | TYR | 1113 | 15.375 | 28.464 | 22.561 | 1.00 | 11.65 | 6 |
| ATOM | 2236 | CD1 | TYR | 1113 | 14.778 | 28.484 | 23.827 | 1.00 | 11.65 | 6 |
| ATOM | 2237 | CE1 | TYR | 1113 | 13.422 | 28.166 | 23.967 | 1.00 | 11.65 | 6 |
| ATOM | 2238 | CD2 | TYR | 1113 | 14.614 | 28.124 | 21.435 | 1.00 | 11.65 | 6 |
| ATOM | 2239 | CE2 | TYR | 1113 | 13.258 | 27.806 | 21.575 | 1.00 | 11.65 | 6 |
| ATOM | 2240 | CZ | TYR | 1113 | 12.662 | 27.827 | 22.842 | 1.00 | 11.65 | 6 |
| ATOM | 2241 | OH | TYR | 1113 | 11.344 | 27.518 | 22.978 | 1.00 | 11.65 | 8 |
| ATOM | 2242 | C | TYR | 1113 | 19.155 | 28.108 | 21.772 | 1.00 | 88.60 | 6 |
| ATOM | 2243 | O | TYR | 1113 | 20.133 | 27.378 | 21.991 | 1.00 | 88.60 | 8 |
| ATOM | 2244 | N | ALA | 1114 | 19.217 | 29.344 | 21.309 | 1.00 | 62.73 | 7 |
| ATOM | 2245 | CA | ALA | 1114 | 20.484 | 30.020 | 20.989 | 1.00 | 62.73 | 6 |
| ATOM | 2246 | CB | ALA | 1114 | 21.530 | 28.992 | 20.552 | 1.00 | 7.22 | 6 |
| ATOM | 2247 | C | ALA | 1114 | 20.268 | 31.024 | 19.854 | 1.00 | 62.73 | 6 |
| ATOM | 2248 | O | ALA | 1114 | 20.108 | 30.642 | 18.685 | 1.00 | 62.73 | 8 |
| ATOM | 2249 | N | GLY | 1115 | 20.271 | 32.287 | 20.241 | 1.00 | 60.96 | 7 |
| ATOM | 2250 | CA | GLY | 1115 | 20.078 | 33.409 | 19.310 | 1.00 | 60.96 | 6 |
| ATOM | 2251 | C | GLY | 1115 | 21.034 | 34.552 | 19.657 | 1.00 | 60.96 | 6 |
| ATOM | 2252 | O | GLY | 1115 | 20.817 | 35.296 | 20.625 | 1.00 | 60.96 | 8 |
| ATOM | 2253 | N | ILE | 1116 | 22.069 | 34.651 | 18.843 | 1.00 | 82.32 | 7 |
| ATOM | 2254 | CA | ILE | 1116 | 23.110 | 35.679 | 18.992 | 1.00 | 82.32 | 6 |
| ATOM | 2255 | CB | ILE | 1116 | 22.488 | 37.073 | 18.892 | 1.00 | 68.50 | 6 |
| ATOM | 2256 | C | ILE | 1116 | 23.796 | 35.537 | 20.352 | 1.00 | 82.32 | 6 |
| ATOM | 2257 | O | ILE | 1116 | 24.984 | 35.192 | 20.436 | 1.00 | 82.32 | 8 |
| ATOM | 2258 | OXT | ILE | 1116 | 23.443 | 36.522 | 21.208 | 1.00 | 64.86 | 8 |
| TER | | | | | | | | | | |
| HETATM | 2259 | C29 | TEM | 1 | 14.137 | 43.777 | -1.896 | 1.00 | 87.75 | 6 |
| HETATM | 2260 | C130 | TEM | 1 | 15.517 | 44.384 | -2.200 | 1.00 | 92.68 | 9 |
| HETATM | 2261 | C31 | TEM | 1 | 13.532 | 43.986 | -0.603 | 1.00 | 84.61 | 6 |
| HETATM | 2262 | C32 | TEM | 1 | 10.062 | 43.539 | 1.417 | 1.00 | 72.29 | 6 |
| HETATM | 2263 | C28 | TEM | 1 | 13.152 | 42.505 | -7.029 | 1.00 | 92.68 | 6 |
| HETATM | 2264 | C8 | TEM | 1 | 11.669 | 44.356 | 4.626 | 1.00 | 64.60 | 6 |
| HETATM | 2265 | C9 | TEM | 1 | 12.234 | 43.146 | 5.418 | 1.00 | 62.65 | 6 |
| HETATM | 2266 | C10 | TEM | 1 | 12.979 | 43.794 | 6.609 | 1.00 | 61.60 | 6 |
| HETATM | 2267 | C11 | TEM | 1 | 13.328 | 45.233 | 6.175 | 1.00 | 61.11 | 6 |

FIG. 3NN

```
HETATM  2268  C12  TEM      1      12.788  45.420   4.740  1.00 62.68      6
HETATM  2269  C13  TEM      1      12.175  43.912   2.185  1.00 71.00      6
HETATM  2270  N7   TEM      1      11.303  44.043   3.228  1.00 67.78      7
HETATM  2271  N1   TEM      1       8.672  43.004  -0.559  1.00 73.02      7
HETATM  2272  C2   TEM      1       8.784  43.270   0.784  1.00 71.64      6
HETATM  2273  N3   TEM      1       7.669  43.306   1.546  1.00 71.42      7
HETATM  2274  C4   TEM      1       7.718  43.568   2.851  1.00 69.68      6
HETATM  2275  N5   TEM      1       8.853  43.811   3.473  1.00 68.84      7
HETATM  2276  C6   TEM      1      10.030  43.817   2.820  1.00 69.92      6
HETATM  2277  C14  TEM      1      11.530  43.630   1.036  1.00 75.68      6
HETATM  2278  O22  TEM      1      13.956  40.236  -4.115  1.00 92.68      8
HETATM  2279  C23  TEM      1      13.420  41.285  -6.355  1.00 92.68      6
HETATM  2280  C24  TEM      1      12.844  40.071  -6.856  1.00 92.68      6
HETATM  2281  C25  TEM      1      12.014  40.102  -8.027  1.00 92.68      6
HETATM  2282  C26  TEM      1      11.757  41.334  -8.689  1.00 92.68      6
HETATM  2283  C27  TEM      1      12.330  42.534  -8.187  1.00 92.68      6
HETATM  2284  O21  TEM      1      15.786  41.592  -5.276  1.00 92.68      8
HETATM  2285  C15  TEM      1      12.216  43.429  -0.313  1.00 80.63      6
HETATM  2286  C16  TEM      1      11.576  42.675  -1.308  1.00 83.45      6
HETATM  2287  C17  TEM      1      12.141  42.492  -2.551  1.00 87.27      6
HETATM  2288  C18  TEM      1      13.399  43.018  -2.887  1.00 88.78      6
HETATM  2289  N19  TEM      1      13.818  42.732  -4.220  1.00 90.27      7
HETATM  2290  S20  TEM      1      14.444  41.335  -4.875  1.00 92.68     16
ATOM    2291  S    SO4      2      25.361  40.893  -8.736  1.00 15.55     16
ATOM    2292  O1   SO4      2      26.331  39.742  -8.499  1.00 20.26      8
ATOM    2293  O2   SO4      2      25.230  41.131 -10.222  1.00 12.30      8
ATOM    2294  O3   SO4      2      23.982  40.607  -8.171  1.00 16.39      8
ATOM    2295  O4   SO4      2      25.930  42.110  -8.051  1.00 17.72      8
END
```

FIG. 300

```
ATOM      1   N    VAL A 818      77.669  47.027   2.354  1.00 20.00
ATOM      2   CA   VAL A 818      76.422  47.479   1.690  1.00 20.00
ATOM      3   C    VAL A 818      75.257  46.471   1.737  1.00 20.00
ATOM      4   O    VAL A 818      75.361  45.363   2.335  1.00 20.00
ATOM      5   CB   VAL A 818      76.716  47.863   0.250  1.00 20.00
ATOM      9   N    LEU A 819      74.145  46.870   1.095  1.00 20.00
ATOM     10   CA   LEU A 819      72.922  46.055   1.058  1.00 20.00
ATOM     11   C    LEU A 819      72.341  45.959  -0.347  1.00 20.00
ATOM     12   O    LEU A 819      71.187  46.223  -0.571  1.00 20.00
ATOM     13   CB   LEU A 819      71.897  46.637   2.052  1.00 20.00
ATOM     14   CG   LEU A 819      70.399  46.340   1.987  1.00 20.00
ATOM     15   CD1  LEU A 819      70.026  45.327   3.039  1.00 20.00
ATOM     16   CD2  LEU A 819      69.612  47.643   2.186  1.00 20.00
ATOM     18   N    ASP A 820      73.165  45.565  -1.294  1.00 20.00
ATOM     19   CA   ASP A 820      72.758  45.427  -2.685  1.00 20.00
ATOM     20   C    ASP A 820      71.419  45.961  -3.188  1.00 20.00
ATOM     21   O    ASP A 820      70.510  45.182  -3.445  1.00 20.00
ATOM     22   CB   ASP A 820      72.867  43.971  -3.103  1.00 20.00
ATOM     23   CG   ASP A 820      72.637  43.799  -4.570  1.00 20.00
ATOM     24   OD1  ASP A 820      72.617  42.622  -5.045  1.00 20.00
ATOM     25   OD2  ASP A 820      72.468  44.861  -5.242  1.00 20.00
ATOM     27   N    TRP A 821      71.336  47.280  -3.390  1.00 20.00
ATOM     28   CA   TRP A 821      70.128  47.958  -3.916  1.00 20.00
ATOM     29   C    TRP A 821      69.296  47.063  -4.814  1.00 20.00
ATOM     30   O    TRP A 821      68.077  47.237  -4.938  1.00 20.00
ATOM     31   CB   TRP A 821      70.479  49.190  -4.782  1.00 20.00
ATOM     32   CG   TRP A 821      69.336  50.211  -4.771  1.00 20.00
ATOM     33   CD1  TRP A 821      68.872  50.892  -3.675  1.00 20.00
ATOM     34   CD2  TRP A 821      68.465  50.552  -5.841  1.00 20.00
ATOM     35   NE1  TRP A 821      67.753  51.628  -4.001  1.00 20.00
ATOM     36   CE2  TRP A 821      67.482  51.435  -5.325  1.00 20.00
ATOM     37   CE3  TRP A 821      68.408  50.201  -7.177  1.00 20.00
ATOM     38   CZ2  TRP A 821      66.462  51.963  -6.104  1.00 20.00
ATOM     39   CZ3  TRP A 821      67.382  50.730  -7.962  1.00 20.00
ATOM     40   CH2  TRP A 821      66.430  51.597  -7.420  1.00 20.00
ATOM     43   N    ASN A 822      69.999  46.156  -5.498  1.00 20.00
ATOM     44   CA   ASN A 822      69.370  45.213  -6.404  1.00 20.00
ATOM     45   C    ASN A 822      67.947  44.823  -5.911  1.00 20.00
ATOM     46   O    ASN A 822      67.000  44.734  -6.707  1.00 20.00
ATOM     47   CB   ASN A 822      70.291  43.986  -6.531  1.00 20.00
ATOM     48   CG   ASN A 822      69.610  42.766  -7.181  1.00 20.00
ATOM     49   OD1  ASN A 822      69.287  42.766  -8.393  1.00 20.00
ATOM     50   ND2  ASN A 822      69.406  41.706  -6.377  1.00 20.00
ATOM     54   N    ASP A 823      67.778  44.632  -4.602  1.00 20.00
ATOM     55   CA   ASP A 823      66.472  44.212  -4.129  1.00 20.00
ATOM     56   C    ASP A 823      65.921  44.808  -2.847  1.00 20.00
ATOM     57   O    ASP A 823      66.179  44.295  -1.758  1.00 20.00
ATOM     58   CB   ASP A 823      66.454  42.681  -4.008  1.00 20.00
ATOM     60   N    ILE A 824      65.166  45.894  -2.988  1.00 20.00
ATOM     61   CA   ILE A 824      64.480  46.524  -1.859  1.00 20.00
ATOM     62   C    ILE A 824      63.021  46.501  -2.412  1.00 20.00
ATOM     63   O    ILE A 824      62.776  46.906  -3.570  1.00 20.00
ATOM     64   CB   ILE A 824      64.955  48.019  -1.586  1.00 20.00
ATOM     65   CG1  ILE A 824      65.666  48.576  -2.803  1.00 20.00
ATOM     66   CG2  ILE A 824      65.845  48.113  -0.382  1.00 20.00
ATOM     67   CD1  ILE A 824      67.135  48.549  -2.681  1.00 20.00
```

FIG. 4A

```
ATOM    69  N   LYS A 825      62.077  45.969  -1.626  1.00 20.00
ATOM    70  CA  LYS A 825      60.645  45.921  -2.029  1.00 20.00
ATOM    71  C   LYS A 825      59.922  47.060  -1.266  1.00 20.00
ATOM    72  O   LYS A 825      59.578  46.946  -0.097  1.00 20.00
ATOM    73  CB  LYS A 825      60.043  44.561  -1.696  1.00 20.00
ATOM    75  N   PHE A 826      59.696  48.147  -1.988  1.00 20.00
ATOM    76  CA  PHE A 826      59.153  49.401  -1.462  1.00 20.00
ATOM    77  C   PHE A 826      57.643  49.569  -1.593  1.00 20.00
ATOM    78  O   PHE A 826      57.160  50.073  -2.593  1.00 20.00
ATOM    79  CB  PHE A 826      59.882  50.481  -2.224  1.00 20.00
ATOM    80  CG  PHE A 826      60.298  50.013  -3.604  1.00 20.00
ATOM    81  CD1 PHE A 826      59.336  49.841  -4.613  1.00 20.00
ATOM    82  CD2 PHE A 826      61.611  49.711  -3.887  1.00 20.00
ATOM    83  CE1 PHE A 826      59.675  49.383  -5.876  1.00 20.00
ATOM    84  CE2 PHE A 826      61.960  49.249  -5.145  1.00 20.00
ATOM    85  CZ  PHE A 826      60.984  49.086  -6.144  1.00 20.00
ATOM    87  N   GLN A 827      56.919  49.173  -0.550  1.00 20.00
ATOM    88  CA  GLN A 827      55.459  49.206  -0.491  1.00 20.00
ATOM    89  C   GLN A 827      54.788  50.547  -0.268  1.00 20.00
ATOM    90  O   GLN A 827      54.134  51.071  -1.177  1.00 20.00
ATOM    91  CB  GLN A 827      54.978  48.268   0.591  1.00 20.00
ATOM    92  CG  GLN A 827      56.111  47.581   1.340  1.00 20.00
ATOM    93  CD  GLN A 827      56.511  46.315   0.637  1.00 20.00
ATOM    94  OE1 GLN A 827      56.636  45.253   1.256  1.00 20.00
ATOM    95  NE2 GLN A 827      56.688  46.410  -0.675  1.00 20.00
ATOM    99  N   ASP A 828      54.918  51.103   0.928  1.00 20.00
ATOM   100  CA  ASP A 828      54.261  52.360   1.165  1.00 20.00
ATOM   101  C   ASP A 828      54.815  53.309   2.231  1.00 20.00
ATOM   102  O   ASP A 828      55.694  52.973   3.033  1.00 20.00
ATOM   103  CB  ASP A 828      52.856  52.049   1.499  1.00 20.00
ATOM   104  CG  ASP A 828      52.783  50.948   2.460  1.00 20.00
ATOM   105  OD1 ASP A 828      52.099  49.943   2.182  1.00 20.00
ATOM   106  OD2 ASP A 828      53.439  51.088   3.504  1.00 20.00
ATOM   108  N   VAL A 829      54.278  54.522   2.216  1.00 20.00
ATOM   109  CA  VAL A 829      54.681  55.525   3.158  1.00 20.00
ATOM   110  C   VAL A 829      54.405  54.794   4.471  1.00 20.00
ATOM   111  O   VAL A 829      53.373  54.176   4.562  1.00 20.00
ATOM   112  CB  VAL A 829      53.772  56.742   2.971  1.00 20.00
ATOM   114  N   ILE A 830      55.298  54.759   5.453  1.00 20.00
ATOM   115  CA  ILE A 830      54.911  54.062   6.686  1.00 20.00
ATOM   116  C   ILE A 830      54.690  55.170   7.627  1.00 20.00
ATOM   117  O   ILE A 830      55.296  55.229   8.696  1.00 20.00
ATOM   118  CB  ILE A 830      56.004  53.170   7.366  1.00 20.00
ATOM   119  CG1 ILE A 830      56.458  52.054   6.437  1.00 20.00
ATOM   120  CG2 ILE A 830      55.435  52.493   8.636  1.00 20.00
ATOM   121  CD1 ILE A 830      57.626  51.361   6.996  1.00 20.00
ATOM   123  N   GLY A 831      53.802  56.059   7.244  1.00 20.00
ATOM   124  CA  GLY A 831      53.588  57.205   8.087  1.00 20.00
ATOM   125  C   GLY A 831      54.694  58.162   7.693  1.00 20.00
ATOM   126  O   GLY A 831      55.359  57.972   6.691  1.00 20.00
ATOM   128  N   GLU A 832      54.888  59.180   8.505  1.00 20.00
ATOM   129  CA  GLU A 832      55.889  60.205   8.260  1.00 20.00
ATOM   130  C   GLU A 832      57.146  59.876   7.452  1.00 20.00
ATOM   131  O   GLU A 832      57.220  58.893   6.667  1.00 20.00
ATOM   132  CB  GLU A 832      56.346  60.832   9.592  1.00 20.00
ATOM   133  CG  GLU A 832      56.473  62.337   9.489  1.00 20.00
ATOM   134  CD  GLU A 832      55.501  62.908   8.468  1.00 20.00
```

FIG. 4B

| ATOM | 135 | OE1 | GLU | A | 832 | 54.643 | 63.721 | 8.897 | 1.00 | 20.00 |
| ATOM | 136 | OE2 | GLU | A | 832 | 55.599 | 62.524 | 7.266 | 1.00 | 20.00 |
| ATOM | 138 | N | GLY | A | 833 | 58.134 | 60.754 | 7.680 | 1.00 | 20.00 |
| ATOM | 139 | CA | GLY | A | 833 | 59.440 | 60.670 | 7.054 | 1.00 | 20.00 |
| ATOM | 140 | C | GLY | A | 833 | 60.222 | 61.871 | 7.561 | 1.00 | 20.00 |
| ATOM | 141 | O | GLY | A | 833 | 60.606 | 61.957 | 8.770 | 1.00 | 20.00 |
| ATOM | 143 | N | ASN | A | 834 | 60.380 | 62.816 | 6.621 | 1.00 | 20.00 |
| ATOM | 144 | CA | ASN | A | 834 | 61.123 | 64.085 | 6.772 | 1.00 | 20.00 |
| ATOM | 145 | C | ASN | A | 834 | 62.555 | 63.797 | 7.139 | 1.00 | 20.00 |
| ATOM | 146 | O | ASN | A | 834 | 62.796 | 63.133 | 8.141 | 1.00 | 20.00 |
| ATOM | 147 | CB | ASN | A | 834 | 60.584 | 65.052 | 7.859 | 1.00 | 20.00 |
| ATOM | 148 | CG | ASN | A | 834 | 61.664 | 66.125 | 8.258 | 1.00 | 20.00 |
| ATOM | 149 | OD1 | ASN | A | 834 | 61.998 | 66.999 | 7.444 | 1.00 | 20.00 |
| ATOM | 150 | ND2 | ASN | A | 834 | 62.224 | 66.022 | 9.491 | 1.00 | 20.00 |
| ATOM | 154 | N | PHE | A | 835 | 63.474 | 64.373 | 6.355 | 1.00 | 20.00 |
| ATOM | 155 | CA | PHE | A | 835 | 64.922 | 64.216 | 6.526 | 1.00 | 20.00 |
| ATOM | 156 | C | PHE | A | 835 | 64.972 | 63.040 | 7.488 | 1.00 | 20.00 |
| ATOM | 157 | O | PHE | A | 835 | 65.560 | 63.063 | 8.616 | 1.00 | 20.00 |
| ATOM | 158 | CB | PHE | A | 835 | 65.545 | 65.547 | 7.028 | 1.00 | 20.00 |
| ATOM | 159 | CG | PHE | A | 835 | 65.828 | 66.560 | 5.895 | 1.00 | 20.00 |
| ATOM | 160 | CD1 | PHE | A | 835 | 65.442 | 67.913 | 6.013 | 1.00 | 20.00 |
| ATOM | 161 | CD2 | PHE | A | 835 | 66.534 | 66.176 | 4.742 | 1.00 | 20.00 |
| ATOM | 162 | CE1 | PHE | A | 835 | 65.761 | 68.870 | 5.004 | 1.00 | 20.00 |
| ATOM | 163 | CE2 | PHE | A | 835 | 66.859 | 67.138 | 3.725 | 1.00 | 20.00 |
| ATOM | 164 | CZ | PHE | A | 835 | 66.469 | 68.482 | 3.867 | 1.00 | 20.00 |
| ATOM | 166 | N | GLY | A | 836 | 64.251 | 62.029 | 6.984 | 1.00 | 20.00 |
| ATOM | 167 | CA | GLY | A | 836 | 64.025 | 60.759 | 7.647 | 1.00 | 20.00 |
| ATOM | 168 | C | GLY | A | 836 | 62.817 | 60.226 | 6.884 | 1.00 | 20.00 |
| ATOM | 169 | O | GLY | A | 836 | 61.874 | 59.661 | 7.452 | 1.00 | 20.00 |
| ATOM | 171 | N | GLN | A | 837 | 62.827 | 60.432 | 5.571 | 1.00 | 20.00 |
| ATOM | 172 | CA | GLN | A | 837 | 61.720 | 59.959 | 4.749 | 1.00 | 20.00 |
| ATOM | 173 | C | GLN | A | 837 | 61.471 | 58.496 | 5.132 | 1.00 | 20.00 |
| ATOM | 174 | O | GLN | A | 837 | 62.278 | 57.647 | 4.742 | 1.00 | 20.00 |
| ATOM | 175 | CB | GLN | A | 837 | 62.112 | 60.066 | 3.253 | 1.00 | 20.00 |
| ATOM | 176 | CG | GLN | A | 837 | 63.459 | 60.807 | 2.984 | 1.00 | 20.00 |
| ATOM | 177 | CD | GLN | A | 837 | 63.541 | 61.552 | 1.605 | 1.00 | 20.00 |
| ATOM | 178 | OE1 | GLN | A | 837 | 64.298 | 62.539 | 1.447 | 1.00 | 20.00 |
| ATOM | 179 | NE2 | GLN | A | 837 | 62.786 | 61.053 | 0.607 | 1.00 | 20.00 |
| ATOM | 183 | N | VAL | A | 838 | 60.400 | 58.162 | 5.872 | 1.00 | 20.00 |
| ATOM | 184 | CA | VAL | A | 838 | 60.233 | 56.718 | 6.211 | 1.00 | 20.00 |
| ATOM | 185 | C | VAL | A | 838 | 59.296 | 55.833 | 5.400 | 1.00 | 20.00 |
| ATOM | 186 | O | VAL | A | 838 | 58.143 | 55.705 | 5.734 | 1.00 | 20.00 |
| ATOM | 187 | CB | VAL | A | 838 | 59.824 | 56.442 | 7.659 | 1.00 | 20.00 |
| ATOM | 188 | CG1 | VAL | A | 838 | 60.786 | 55.456 | 8.230 | 1.00 | 20.00 |
| ATOM | 189 | CG2 | VAL | A | 838 | 59.760 | 57.703 | 8.475 | 1.00 | 20.00 |
| ATOM | 191 | N | LEU | A | 839 | 59.820 | 55.181 | 4.373 | 1.00 | 20.00 |
| ATOM | 192 | CA | LEU | A | 839 | 59.031 | 54.306 | 3.542 | 1.00 | 20.00 |
| ATOM | 193 | C | LEU | A | 839 | 58.983 | 52.882 | 4.069 | 1.00 | 20.00 |
| ATOM | 194 | O | LEU | A | 839 | 59.676 | 52.547 | 5.015 | 1.00 | 20.00 |
| ATOM | 195 | CB | LEU | A | 839 | 59.566 | 54.385 | 2.111 | 1.00 | 20.00 |
| ATOM | 196 | CG | LEU | A | 839 | 58.912 | 55.608 | 1.396 | 1.00 | 20.00 |
| ATOM | 197 | CD1 | LEU | A | 839 | 58.295 | 56.545 | 2.426 | 1.00 | 20.00 |
| ATOM | 198 | CD2 | LEU | A | 839 | 59.886 | 56.367 | 0.533 | 1.00 | 20.00 |
| ATOM | 200 | N | LYS | A | 840 | 58.119 | 52.049 | 3.503 | 1.00 | 20.00 |
| ATOM | 201 | CA | LYS | A | 840 | 58.031 | 50.646 | 3.945 | 1.00 | 20.00 |
| ATOM | 202 | C | LYS | A | 840 | 58.687 | 49.724 | 2.927 | 1.00 | 20.00 |
| ATOM | 203 | O | LYS | A | 840 | 58.645 | 49.971 | 1.725 | 1.00 | 20.00 |

FIG. 4C

```
ATOM    204  CB   LYS A 840      56.577  50.198   4.145  1.00 20.00
ATOM    205  CG   LYS A 840      56.445  49.166   5.251  1.00 20.00
ATOM    206  CD   LYS A 840      55.843  47.830   4.789  1.00 20.00
ATOM    207  CE   LYS A 840      55.173  47.110   5.960  1.00 20.00
ATOM    208  NZ   LYS A 840      56.154  46.444   6.801  1.00 20.00
ATOM    213  N    ALA A 841      59.302  48.650   3.383  1.00 20.00
ATOM    214  CA   ALA A 841      59.929  47.798   2.393  1.00 20.00
ATOM    215  C    ALA A 841      60.199  46.360   2.787  1.00 20.00
ATOM    216  O    ALA A 841      60.460  46.044   3.971  1.00 20.00
ATOM    217  CB   ALA A 841      61.224  48.462   1.884  1.00 20.00
ATOM    219  N    ARG A 842      60.111  45.506   1.759  1.00 20.00
ATOM    220  CA   ARG A 842      60.347  44.075   1.824  1.00 20.00
ATOM    221  C    ARG A 842      61.797  43.918   1.340  1.00 20.00
ATOM    222  O    ARG A 842      62.105  43.967   0.158  1.00 20.00
ATOM    223  CB   ARG A 842      59.365  43.360   0.902  1.00 20.00
ATOM    225  N    ILE A 843      62.688  43.746   2.293  1.00 20.00
ATOM    226  CA   ILE A 843      64.113  43.638   2.034  1.00 20.00
ATOM    227  C    ILE A 843      64.747  42.223   2.205  1.00 20.00
ATOM    228  O    ILE A 843      64.527  41.503   3.201  1.00 20.00
ATOM    229  CB   ILE A 843      64.846  44.662   2.928  1.00 20.00
ATOM    230  CG1  ILE A 843      65.867  45.411   2.103  1.00 20.00
ATOM    231  CG2  ILE A 843      65.469  43.996   4.130  1.00 20.00
ATOM    232  CD1  ILE A 843      66.176  44.779   0.772  1.00 20.00
ATOM    234  N    LYS A 844      65.549  41.837   1.226  1.00 20.00
ATOM    235  CA   LYS A 844      66.190  40.551   1.273  1.00 20.00
ATOM    236  C    LYS A 844      67.652  40.641   1.709  1.00 20.00
ATOM    237  O    LYS A 844      68.540  40.820   0.869  1.00 20.00
ATOM    238  CB   LYS A 844      66.093  39.875  -0.111  1.00 20.00
ATOM    240  N    LYS A 845      67.897  40.510   3.014  1.00 20.00
ATOM    241  CA   LYS A 845      69.261  40.516   3.545  1.00 20.00
ATOM    242  C    LYS A 845      69.917  39.112   3.335  1.00 20.00
ATOM    243  O    LYS A 845      69.306  38.060   3.678  1.00 20.00
ATOM    244  CB   LYS A 845      69.255  40.857   5.035  1.00 20.00
ATOM    246  N    ASP A 846      71.148  39.140   2.765  1.00 20.00
ATOM    247  CA   ASP A 846      72.022  37.977   2.481  1.00 20.00
ATOM    248  C    ASP A 846      71.224  36.671   2.559  1.00 20.00
ATOM    249  O    ASP A 846      71.231  35.953   3.581  1.00 20.00
ATOM    250  CB   ASP A 846      73.214  37.987   3.484  1.00 20.00
ATOM    251  CG   ASP A 846      74.448  37.141   3.002  1.00 20.00
ATOM    252  OD1  ASP A 846      74.788  37.167   1.784  1.00 20.00
ATOM    253  OD2  ASP A 846      75.078  36.450   3.869  1.00 20.00
ATOM    255  N    GLY A 847      70.497  36.405   1.476  1.00 20.00
ATOM    256  CA   GLY A 847      69.670  35.206   1.405  1.00 20.00
ATOM    257  C    GLY A 847      68.642  35.071   2.527  1.00 20.00
ATOM    258  O    GLY A 847      68.972  34.604   3.636  1.00 20.00
ATOM    260  N    LEU A 848      67.406  35.481   2.198  1.00 20.00
ATOM    261  CA   LEU A 848      66.192  35.495   3.049  1.00 20.00
ATOM    262  C    LEU A 848      65.707  36.956   3.333  1.00 20.00
ATOM    263  O    LEU A 848      66.470  37.844   3.751  1.00 20.00
ATOM    264  CB   LEU A 848      66.402  34.666   4.318  1.00 20.00
ATOM    265  CG   LEU A 848      66.559  35.338   5.653  1.00 20.00
ATOM    266  CD1  LEU A 848      66.241  34.369   6.804  1.00 20.00
ATOM    267  CD2  LEU A 848      68.011  35.849   5.755  1.00 20.00
ATOM    269  N    ARG A 849      64.434  37.188   3.011  1.00 20.00
ATOM    270  CA   ARG A 849      63.793  38.491   3.149  1.00 20.00
ATOM    271  C    ARG A 849      63.495  38.916   4.576  1.00 20.00
ATOM    272  O    ARG A 849      63.795  38.195   5.542  1.00 20.00
```

FIG. 4D

```
ATOM    273  CB  ARG A 849      62.465  38.508   2.388  1.00 20.00
ATOM    274  CG  ARG A 849      62.570  38.136   0.936  1.00 20.00
ATOM    275  CD  ARG A 849      61.348  38.648   0.182  1.00 20.00
ATOM    276  NE  ARG A 849      61.060  37.918  -1.060  1.00 20.00
ATOM    277  CZ  ARG A 849      60.337  36.795  -1.117  1.00 20.00
ATOM    278  NH1 ARG A 849      59.833  36.281   0.018  1.00 20.00
ATOM    279  NH2 ARG A 849      60.113  36.198  -2.308  1.00 20.00
ATOM    286  N   MET A 850      62.903  40.112   4.678  1.00 20.00
ATOM    287  CA  MET A 850      62.466  40.710   5.938  1.00 20.00
ATOM    288  C   MET A 850      61.786  42.087   5.756  1.00 20.00
ATOM    289  O   MET A 850      61.816  42.702   4.694  1.00 20.00
ATOM    290  CB  MET A 850      63.628  40.814   6.953  1.00 20.00
ATOM    291  CG  MET A 850      65.005  41.061   6.376  1.00 20.00
ATOM    292  SD  MET A 850      66.205  41.855   7.507  1.00 20.00
ATOM    293  CE  MET A 850      66.021  40.869   9.036  1.00 20.00
ATOM    295  N   ASP A 851      61.105  42.523   6.800  1.00 20.00
ATOM    296  CA  ASP A 851      60.477  43.812   6.787  1.00 20.00
ATOM    297  C   ASP A 851      61.586  44.780   7.213  1.00 20.00
ATOM    298  O   ASP A 851      62.559  44.403   7.904  1.00 20.00
ATOM    299  CB  ASP A 851      59.381  43.909   7.855  1.00 20.00
ATOM    300  CG  ASP A 851      58.154  43.076   7.546  1.00 20.00
ATOM    301  OD1 ASP A 851      57.886  42.769   6.352  1.00 20.00
ATOM    302  OD2 ASP A 851      57.452  42.744   8.545  1.00 20.00
ATOM    304  N   ALA A 852      61.366  46.044   6.842  1.00 20.00
ATOM    305  CA  ALA A 852      62.230  47.173   7.161  1.00 20.00
ATOM    306  C   ALA A 852      61.483  48.457   6.814  1.00 20.00
ATOM    307  O   ALA A 852      60.631  48.480   5.902  1.00 20.00
ATOM    308  CB  ALA A 852      63.507  47.092   6.332  1.00 20.00
ATOM    310  N   ALA A 853      61.774  49.522   7.546  1.00 20.00
ATOM    311  CA  ALA A 853      61.205  50.818   7.189  1.00 20.00
ATOM    312  C   ALA A 853      62.439  51.427   6.518  1.00 20.00
ATOM    313  O   ALA A 853      63.529  50.919   6.771  1.00 20.00
ATOM    314  CB  ALA A 853      60.812  51.581   8.418  1.00 20.00
ATOM    316  N   ILE A 854      62.300  52.470   5.685  1.00 20.00
ATOM    317  CA  ILE A 854      63.436  53.072   4.960  1.00 20.00
ATOM    318  C   ILE A 854      63.501  54.570   5.142  1.00 20.00
ATOM    319  O   ILE A 854      62.478  55.156   5.413  1.00 20.00
ATOM    320  CB  ILE A 854      63.313  52.777   3.457  1.00 20.00
ATOM    321  CG1 ILE A 854      63.527  51.284   3.195  1.00 20.00
ATOM    322  CG2 ILE A 854      64.353  53.554   2.664  1.00 20.00
ATOM    323  CD1 ILE A 854      64.906  50.722   3.717  1.00 20.00
ATOM    325  N   LYS A 855      64.699  55.189   5.023  1.00 20.00
ATOM    326  CA  LYS A 855      64.901  56.684   5.158  1.00 20.00
ATOM    327  C   LYS A 855      65.800  57.286   4.079  1.00 20.00
ATOM    328  O   LYS A 855      65.740  56.867   2.946  1.00 20.00
ATOM    329  CB  LYS A 855      65.417  57.088   6.580  1.00 20.00
ATOM    330  CG  LYS A 855      66.949  57.267   6.792  1.00 20.00
ATOM    331  CD  LYS A 855      67.333  57.776   8.262  1.00 20.00
ATOM    332  CE  LYS A 855      68.597  57.022   8.917  1.00 20.00
ATOM    333  NZ  LYS A 855      69.828  57.804   9.506  1.00 20.00
ATOM    338  N   ARG A 856      66.573  58.311   4.439  1.00 20.00
ATOM    339  CA  ARG A 856      67.569  59.035   3.573  1.00 20.00
ATOM    340  C   ARG A 856      66.957  60.199   2.856  1.00 20.00
ATOM    341  O   ARG A 856      66.375  60.027   1.793  1.00 20.00
ATOM    342  CB  ARG A 856      68.288  58.135   2.533  1.00 20.00
ATOM    343  CG  ARG A 856      69.278  58.948   1.706  1.00 20.00
ATOM    344  CD  ARG A 856      68.965  58.943   0.179  1.00 20.00
```

FIG. 4E

```
ATOM  345  NE   ARG A 856     68.880  60.276  -0.435  1.00 20.00
ATOM  346  CZ   ARG A 856     68.623  60.497  -1.732  1.00 20.00
ATOM  347  NH1  ARG A 856     68.425  59.484  -2.568  1.00 20.00
ATOM  348  NH2  ARG A 856     68.555  61.750  -2.204  1.00 20.00
ATOM  355  N    MET A 857     67.166  61.381   3.446  1.00 20.00
ATOM  356  CA   MET A 857     66.581  62.674   2.991  1.00 20.00
ATOM  357  C    MET A 857     67.495  63.831   2.508  1.00 20.00
ATOM  358  O    MET A 857     68.427  64.269   3.254  1.00 20.00
ATOM  359  CB   MET A 857     65.682  63.220   4.125  1.00 20.00
ATOM  360  CG   MET A 857     64.287  63.699   3.730  1.00 20.00
ATOM  361  SD   MET A 857     62.819  63.037   4.735  1.00 20.00
ATOM  362  CE   MET A 857     61.431  64.067   3.876  1.00 20.00
ATOM  363  OXT  MET A 857     67.199  64.316   1.383  1.00 20.00
ATOM  365  N    ASP A 864     77.202  66.313  -0.527  1.00 20.00
ATOM  366  CA   ASP A 864     77.838  67.381  -1.394  1.00 20.00
ATOM  367  C    ASP A 864     78.591  68.418  -0.580  1.00 20.00
ATOM  368  O    ASP A 864     79.619  68.925  -1.043  1.00 20.00
ATOM  369  CB   ASP A 864     76.768  68.105  -2.272  1.00 20.00
ATOM  373  N    ASP A 865     78.090  68.727   0.620  1.00 20.00
ATOM  374  CA   ASP A 865     78.709  69.760   1.436  1.00 20.00
ATOM  375  C    ASP A 865     78.128  69.958   2.819  1.00 20.00
ATOM  376  O    ASP A 865     78.844  70.418   3.695  1.00 20.00
ATOM  377  CB   ASP A 865     78.665  71.087   0.683  1.00 20.00
ATOM  379  N    HIS A 866     76.832  69.683   3.014  1.00 20.00
ATOM  380  CA   HIS A 866     76.223  69.807   4.364  1.00 20.00
ATOM  381  C    HIS A 866     76.425  68.436   4.955  1.00 20.00
ATOM  382  O    HIS A 866     76.537  68.227   6.178  1.00 20.00
ATOM  383  CB   HIS A 866     74.699  70.145   4.303  1.00 20.00
ATOM  384  CG   HIS A 866     73.836  69.068   3.706  1.00 20.00
ATOM  385  ND1  HIS A 866     73.511  69.036   2.360  1.00 20.00
ATOM  386  CD2  HIS A 866     73.145  68.054   4.285  1.00 20.00
ATOM  387  CE1  HIS A 866     72.653  68.054   2.140  1.00 20.00
ATOM  388  NE2  HIS A 866     72.416  67.443   3.290  1.00 20.00
ATOM  392  N    ARG A 867     76.481  67.523   3.992  1.00 20.00
ATOM  393  CA   ARG A 867     76.682  66.101   4.167  1.00 20.00
ATOM  394  C    ARG A 867     77.752  65.727   5.193  1.00 20.00
ATOM  395  O    ARG A 867     78.957  65.919   4.933  1.00 20.00
ATOM  396  CB   ARG A 867     77.059  65.491   2.804  1.00 20.00
ATOM  397  CG   ARG A 867     78.073  66.314   2.001  1.00 20.00
ATOM  398  CD   ARG A 867     79.548  66.134   2.438  1.00 20.00
ATOM  399  NE   ARG A 867     80.417  67.048   1.682  1.00 20.00
ATOM  400  CZ   ARG A 867     81.270  67.924   2.231  1.00 20.00
ATOM  401  NH1  ARG A 867     81.391  68.025   3.566  1.00 20.00
ATOM  402  NH2  ARG A 867     81.977  68.729   1.428  1.00 20.00
ATOM  409  N    ASP A 868     77.304  65.205   6.345  1.00 20.00
ATOM  410  CA   ASP A 868     78.197  64.729   7.417  1.00 20.00
ATOM  411  C    ASP A 868     77.784  63.290   7.881  1.00 20.00
ATOM  412  O    ASP A 868     77.720  62.981   9.089  1.00 20.00
ATOM  413  CB   ASP A 868     78.199  65.733   8.593  1.00 20.00
ATOM  414  CG   ASP A 868     77.414  65.248   9.815  1.00 20.00
ATOM  415  OD1  ASP A 868     76.266  64.747   9.611  1.00 20.00
ATOM  416  OD2  ASP A 868     77.931  65.385  10.971  1.00 20.00
ATOM  418  N    PHE A 869     77.560  62.391   6.921  1.00 20.00
ATOM  419  CA   PHE A 869     77.119  61.033   7.261  1.00 20.00
ATOM  420  C    PHE A 869     78.080  59.895   6.841  1.00 20.00
ATOM  421  O    PHE A 869     78.526  59.819   5.663  1.00 20.00
ATOM  422  CB   PHE A 869     75.738  60.806   6.625  1.00 20.00
```

FIG. 4F

```
ATOM    423  CG  PHE A 869      75.685  61.221   5.199  1.00 20.00
ATOM    424  CD1 PHE A 869      75.561  62.560   4.861  1.00 20.00
ATOM    425  CD2 PHE A 869      75.848  60.286   4.190  1.00 20.00
ATOM    426  CE1 PHE A 869      75.612  62.955   3.509  1.00 20.00
ATOM    427  CE2 PHE A 869      75.896  60.680   2.838  1.00 20.00
ATOM    428  CZ  PHE A 869      75.779  62.022   2.496  1.00 20.00
ATOM    430  N   ALA A 870      78.350  59.018   7.812  1.00 20.00
ATOM    431  CA  ALA A 870      79.231  57.831   7.715  1.00 20.00
ATOM    432  C   ALA A 870      79.352  57.560   9.172  1.00 20.00
ATOM    433  O   ALA A 870      78.350  57.359   9.840  1.00 20.00
ATOM    434  CB  ALA A 870      80.624  58.132   7.160  1.00 20.00
ATOM    436  N   GLY A 871      80.558  57.601   9.698  1.00 20.00
ATOM    437  CA  GLY A 871      80.674  57.344  11.112  1.00 20.00
ATOM    438  C   GLY A 871      79.343  57.592  11.791  1.00 20.00
ATOM    439  O   GLY A 871      78.672  56.648  12.170  1.00 20.00
ATOM    441  N   GLU A 872      78.958  58.864  11.901  1.00 20.00
ATOM    442  CA  GLU A 872      77.690  59.258  12.529  1.00 20.00
ATOM    443  C   GLU A 872      76.698  58.115  12.297  1.00 20.00
ATOM    444  O   GLU A 872      76.096  57.579  13.241  1.00 20.00
ATOM    445  CB  GLU A 872      77.178  60.602  11.939  1.00 20.00
ATOM    446  CG  GLU A 872      76.581  60.552  10.530  1.00 20.00
ATOM    447  CD  GLU A 872      75.027  60.750  10.507  1.00 20.00
ATOM    448  OE1 GLU A 872      74.433  60.770   9.383  1.00 20.00
ATOM    449  OE2 GLU A 872      74.405  60.881  11.596  1.00 20.00
ATOM    451  N   LEU A 873      76.545  57.753  11.028  1.00 20.00
ATOM    452  CA  LEU A 873      75.726  56.633  10.649  1.00 20.00
ATOM    453  C   LEU A 873      76.593  55.505  11.273  1.00 20.00
ATOM    454  O   LEU A 873      76.715  55.463  12.500  1.00 20.00
ATOM    455  CB  LEU A 873      75.658  56.527   9.101  1.00 20.00
ATOM    457  N   GLU A 874      77.195  54.620  10.458  1.00 20.00
ATOM    458  CA  GLU A 874      78.069  53.539  10.975  1.00 20.00
ATOM    459  C   GLU A 874      77.903  53.535  12.468  1.00 20.00
ATOM    460  O   GLU A 874      76.948  52.968  12.998  1.00 20.00
ATOM    461  CB  GLU A 874      79.526  53.831  10.639  1.00 20.00
ATOM    463  N   VAL A 875      78.838  54.222  13.116  1.00 20.00
ATOM    464  CA  VAL A 875      78.847  54.419  14.567  1.00 20.00
ATOM    465  C   VAL A 875      77.770  53.658  15.342  1.00 20.00
ATOM    466  O   VAL A 875      78.065  52.892  16.266  1.00 20.00
ATOM    467  CB  VAL A 875      78.756  55.961  14.897  1.00 20.00
ATOM    469  N   LEU A 876      76.520  53.887  14.966  1.00 20.00
ATOM    470  CA  LEU A 876      75.408  53.237  15.630  1.00 20.00
ATOM    471  C   LEU A 876      75.957  51.873  16.004  1.00 20.00
ATOM    472  O   LEU A 876      75.727  51.387  17.126  1.00 20.00
ATOM    473  CB  LEU A 876      74.208  53.192  14.684  1.00 20.00
ATOM    474  CG  LEU A 876      73.839  54.662  14.399  1.00 20.00
ATOM    475  CD1 LEU A 876      73.193  54.792  13.055  1.00 20.00
ATOM    476  CD2 LEU A 876      72.942  55.198  15.481  1.00 20.00
ATOM    478  N   CYS A 877      76.744  51.320  15.071  1.00 20.00
ATOM    479  CA  CYS A 877      77.459  50.027  15.212  1.00 20.00
ATOM    480  C   CYS A 877      77.658  49.645  16.685  1.00 20.00
ATOM    481  O   CYS A 877      77.099  48.656  17.205  1.00 20.00
ATOM    482  CB  CYS A 877      78.855  50.137  14.546  1.00 20.00
ATOM    483  SG  CYS A 877      79.630  51.894  14.438  1.00 20.00
ATOM    485  N   LYS A 878      78.447  50.496  17.337  1.00 20.00
ATOM    486  CA  LYS A 878      78.789  50.363  18.762  1.00 20.00
ATOM    487  C   LYS A 878      77.629  49.811  19.612  1.00 20.00
ATOM    488  O   LYS A 878      77.847  49.438  20.805  1.00 20.00
```

FIG. 4G

```
ATOM    489  CB  LYS A 878      79.260  51.733  19.351  1.00 20.00
ATOM    490  CG  LYS A 878      80.718  52.114  19.017  1.00 20.00
ATOM    491  CD  LYS A 878      81.321  52.986  20.114  1.00 20.00
ATOM    492  CE  LYS A 878      81.612  54.418  19.609  1.00 20.00
ATOM    493  NZ  LYS A 878      81.754  54.601  18.098  1.00 20.00
ATOM    498  N   LEU A 879      76.427  49.792  19.000  1.00 20.00
ATOM    499  CA  LEU A 879      75.203  49.320  19.634  1.00 20.00
ATOM    500  C   LEU A 879      74.179  49.039  18.584  1.00 20.00
ATOM    501  O   LEU A 879      73.068  49.544  18.652  1.00 20.00
ATOM    502  CB  LEU A 879      74.620  50.336  20.651  1.00 20.00
ATOM    503  CG  LEU A 879      74.799  51.863  20.603  1.00 20.00
ATOM    504  CD1 LEU A 879      75.966  52.280  21.461  1.00 20.00
ATOM    505  CD2 LEU A 879      75.015  52.321  19.200  1.00 20.00
ATOM    507  N   GLY A 880      74.546  48.227  17.597  1.00 20.00
ATOM    508  CA  GLY A 880      73.551  47.899  16.578  1.00 20.00
ATOM    509  C   GLY A 880      72.345  47.314  17.330  1.00 20.00
ATOM    510  O   GLY A 880      71.296  47.906  17.464  1.00 20.00
ATOM    512  N   HIS A 881      72.545  46.101  17.820  1.00 20.00
ATOM    513  CA  HIS A 881      71.575  45.353  18.572  1.00 20.00
ATOM    514  C   HIS A 881      71.402  46.024  19.917  1.00 20.00
ATOM    515  O   HIS A 881      71.758  47.183  20.106  1.00 20.00
ATOM    516  CB  HIS A 881      72.059  43.906  18.744  1.00 20.00
ATOM    517  CG  HIS A 881      71.015  42.958  19.255  1.00 20.00
ATOM    518  ND1 HIS A 881      69.952  42.520  18.485  1.00 20.00
ATOM    519  CD2 HIS A 881      70.877  42.349  20.464  1.00 20.00
ATOM    520  CE1 HIS A 881      69.207  41.691  19.197  1.00 20.00
ATOM    521  NE2 HIS A 881      69.746  41.566  20.402  1.00 20.00
ATOM    525  N   HIS A 882      70.870  45.217  20.817  1.00 20.00
ATOM    526  CA  HIS A 882      70.420  45.429  22.177  1.00 20.00
ATOM    527  C   HIS A 882      68.935  45.241  21.763  1.00 20.00
ATOM    528  O   HIS A 882      68.440  45.758  20.724  1.00 20.00
ATOM    529  CB  HIS A 882      70.704  46.804  22.806  1.00 20.00
ATOM    530  CG  HIS A 882      70.491  46.812  24.295  1.00 20.00
ATOM    531  ND1 HIS A 882      69.252  46.654  24.868  1.00 20.00
ATOM    532  CD2 HIS A 882      71.365  46.839  25.325  1.00 20.00
ATOM    533  CE1 HIS A 882      69.373  46.579  26.183  1.00 20.00
ATOM    534  NE2 HIS A 882      70.645  46.686  26.486  1.00 20.00
ATOM    538  N   PRO A 883      68.210  44.463  22.547  1.00 20.00
ATOM    539  CA  PRO A 883      66.820  44.253  22.152  1.00 20.00
ATOM    540  C   PRO A 883      66.019  45.510  22.212  1.00 20.00
ATOM    541  O   PRO A 883      65.100  45.685  21.439  1.00 20.00
ATOM    542  CB  PRO A 883      66.309  43.176  23.108  1.00 20.00
ATOM    543  CG  PRO A 883      67.285  43.129  24.211  1.00 20.00
ATOM    544  CD  PRO A 883      68.560  43.829  23.819  1.00 20.00
ATOM    545  N   ASN A 884      66.414  46.408  23.098  1.00 20.00
ATOM    546  CA  ASN A 884      65.710  47.650  23.263  1.00 20.00
ATOM    547  C   ASN A 884      66.169  48.856  22.439  1.00 20.00
ATOM    548  O   ASN A 884      65.801  49.977  22.723  1.00 20.00
ATOM    549  CB  ASN A 884      65.672  47.898  24.749  1.00 20.00
ATOM    550  CG  ASN A 884      65.444  46.594  25.498  1.00 20.00
ATOM    551  OD1 ASN A 884      65.835  46.388  26.649  1.00 20.00
ATOM    552  ND2 ASN A 884      64.817  45.687  24.802  1.00 20.00
ATOM    556  N   ILE A 885      66.917  48.603  21.375  1.00 20.00
ATOM    557  CA  ILE A 885      67.391  49.655  20.482  1.00 20.00
ATOM    558  C   ILE A 885      67.205  49.202  19.020  1.00 20.00
ATOM    559  O   ILE A 885      67.847  48.251  18.589  1.00 20.00
ATOM    560  CB  ILE A 885      68.930  50.021  20.761  1.00 20.00
```

FIG. 4H

```
ATOM    561  CG1 ILE A 885      69.032  50.962  21.954  1.00 20.00
ATOM    562  CG2 ILE A 885      69.529  50.830  19.639  1.00 20.00
ATOM    563  CD1 ILE A 885      70.397  51.213  22.385  1.00 20.00
ATOM    565  N   ILE A 886      66.325  49.886  18.282  1.00 20.00
ATOM    566  CA  ILE A 886      66.030  49.608  16.871  1.00 20.00
ATOM    567  C   ILE A 886      67.338  49.271  16.206  1.00 20.00
ATOM    568  O   ILE A 886      68.363  49.491  16.788  1.00 20.00
ATOM    569  CB  ILE A 886      65.331  50.854  16.183  1.00 20.00
ATOM    570  CG1 ILE A 886      63.806  50.758  16.349  1.00 20.00
ATOM    571  CG2 ILE A 886      65.568  50.868  14.691  1.00 20.00
ATOM    572  CD1 ILE A 886      63.134  49.624  15.492  1.00 20.00
ATOM    574  N   ASN A 887      67.347  48.757  14.990  1.00 20.00
ATOM    575  CA  ASN A 887      68.628  48.381  14.442  1.00 20.00
ATOM    576  C   ASN A 887      68.846  48.692  13.013  1.00 20.00
ATOM    577  O   ASN A 887      67.889  48.902  12.273  1.00 20.00
ATOM    578  CB  ASN A 887      68.827  46.892  14.597  1.00 20.00
ATOM    579  CG  ASN A 887      70.276  46.512  14.731  1.00 20.00
ATOM    580  OD1 ASN A 887      71.015  46.382  13.725  1.00 20.00
ATOM    581  ND2 ASN A 887      70.702  46.315  15.979  1.00 20.00
ATOM    585  N   LEU A 888      70.118  48.684  12.604  1.00 20.00
ATOM    586  CA  LEU A 888      70.417  48.950  11.203  1.00 20.00
ATOM    587  C   LEU A 888      70.410  47.641  10.469  1.00 20.00
ATOM    588  O   LEU A 888      71.128  46.705  10.852  1.00 20.00
ATOM    589  CB  LEU A 888      71.799  49.586  11.000  1.00 20.00
ATOM    590  CG  LEU A 888      72.125  49.333   9.517  1.00 20.00
ATOM    591  CD1 LEU A 888      71.290  50.292   8.712  1.00 20.00
ATOM    592  CD2 LEU A 888      73.594  49.451   9.207  1.00 20.00
ATOM    594  N   LEU A 889      69.617  47.531   9.425  1.00 20.00
ATOM    595  CA  LEU A 889      69.676  46.284   8.712  1.00 20.00
ATOM    596  C   LEU A 889      70.630  46.494   7.567  1.00 20.00
ATOM    597  O   LEU A 889      71.830  46.369   7.746  1.00 20.00
ATOM    598  CB  LEU A 889      68.310  45.906   8.247  1.00 20.00
ATOM    599  CG  LEU A 889      67.451  45.554   9.465  1.00 20.00
ATOM    600  CD1 LEU A 889      66.321  44.719   8.913  1.00 20.00
ATOM    601  CD2 LEU A 889      68.201  44.811  10.568  1.00 20.00
ATOM    603  N   GLY A 890      70.114  46.838   6.396  1.00 20.00
ATOM    604  CA  GLY A 890      70.971  47.127   5.254  1.00 20.00
ATOM    605  C   GLY A 890      71.310  48.613   5.048  1.00 20.00
ATOM    606  O   GLY A 890      71.237  49.441   5.951  1.00 20.00
ATOM    608  N   ALA A 891      71.684  48.930   3.819  1.00 20.00
ATOM    609  CA  ALA A 891      72.084  50.262   3.393  1.00 20.00
ATOM    610  C   ALA A 891      72.437  50.082   1.907  1.00 20.00
ATOM    611  O   ALA A 891      72.299  48.965   1.361  1.00 20.00
ATOM    612  CB  ALA A 891      73.296  50.706   4.166  1.00 20.00
ATOM    614  N   CYS A 892      72.908  51.153   1.262  1.00 20.00
ATOM    615  CA  CYS A 892      73.258  51.085  -0.166  1.00 20.00
ATOM    616  C   CYS A 892      73.174  52.468  -0.776  1.00 20.00
ATOM    617  O   CYS A 892      72.263  53.232  -0.453  1.00 20.00
ATOM    618  CB  CYS A 892      72.277  50.171  -0.952  1.00 20.00
ATOM    619  SG  CYS A 892      72.953  48.465  -1.345  1.00 20.00
ATOM    621  N   GLU A 893      74.089  52.785  -1.680  1.00 20.00
ATOM    622  CA  GLU A 893      74.062  54.101  -2.298  1.00 20.00
ATOM    623  C   GLU A 893      73.386  54.004  -3.637  1.00 20.00
ATOM    624  O   GLU A 893      73.956  53.509  -4.616  1.00 20.00
ATOM    625  CB  GLU A 893      75.483  54.655  -2.463  1.00 20.00
ATOM    626  CG  GLU A 893      76.613  53.751  -1.900  1.00 20.00
ATOM    627  CD  GLU A 893      77.227  52.860  -2.966  1.00 20.00
```

FIG. 4I

```
ATOM    628  OE1 GLU A 893      76.831  52.998  -4.151  1.00 20.00
ATOM    629  OE2 GLU A 893      78.105  52.033  -2.612  1.00 20.00
ATOM    631  N   HIS A 894      72.140  54.427  -3.684  1.00 20.00
ATOM    632  CA  HIS A 894      71.437  54.382  -4.949  1.00 20.00
ATOM    633  C   HIS A 894      71.690  55.786  -5.419  1.00 20.00
ATOM    634  O   HIS A 894      71.305  56.755  -4.750  1.00 20.00
ATOM    635  CB  HIS A 894      69.937  54.149  -4.753  1.00 20.00
ATOM    636  CG  HIS A 894      69.133  54.328  -6.003  1.00 20.00
ATOM    637  ND1 HIS A 894      67.767  54.494  -5.990  1.00 20.00
ATOM    638  CD2 HIS A 894      69.510  54.413  -7.301  1.00 20.00
ATOM    639  CE1 HIS A 894      67.332  54.680  -7.223  1.00 20.00
ATOM    640  NE2 HIS A 894      68.369  54.634  -8.037  1.00 20.00
ATOM    644  N   ARG A 895      72.366  55.873  -6.556  1.00 20.00
ATOM    645  CA  ARG A 895      72.768  57.132  -7.151  1.00 20.00
ATOM    646  C   ARG A 895      71.873  58.311  -6.767  1.00 20.00
ATOM    647  O   ARG A 895      70.654  58.317  -7.001  1.00 20.00
ATOM    648  CB  ARG A 895      72.910  56.904  -8.643  1.00 20.00
ATOM    649  CG  ARG A 895      73.918  55.775  -8.856  1.00 20.00
ATOM    650  CD  ARG A 895      73.482  54.825  -9.910  1.00 20.00
ATOM    651  NE  ARG A 895      74.001  55.309 -11.176  1.00 20.00
ATOM    652  CZ  ARG A 895      73.609  54.881 -12.370  1.00 20.00
ATOM    653  NH1 ARG A 895      72.657  53.926 -12.469  1.00 20.00
ATOM    654  NH2 ARG A 895      74.183  55.416 -13.460  1.00 20.00
ATOM    661  N   GLY A 896      72.510  59.315  -6.177  1.00 20.00
ATOM    662  CA  GLY A 896      71.781  60.441  -5.654  1.00 20.00
ATOM    663  C   GLY A 896      71.963  60.040  -4.207  1.00 20.00
ATOM    664  O   GLY A 896      72.194  58.860  -3.967  1.00 20.00
ATOM    666  N   TYR A 897      71.919  60.962  -3.254  1.00 20.00
ATOM    667  CA  TYR A 897      72.066  60.604  -1.839  1.00 20.00
ATOM    668  C   TYR A 897      71.643  59.133  -1.531  1.00 20.00
ATOM    669  O   TYR A 897      70.959  58.507  -2.336  1.00 20.00
ATOM    670  CB  TYR A 897      71.195  61.548  -1.039  1.00 20.00
ATOM    671  CG  TYR A 897      71.828  62.224   0.128  1.00 20.00
ATOM    672  CD1 TYR A 897      73.097  62.810   0.030  1.00 20.00
ATOM    673  CD2 TYR A 897      71.116  62.358   1.321  1.00 20.00
ATOM    674  CE1 TYR A 897      73.638  63.526   1.108  1.00 20.00
ATOM    675  CE2 TYR A 897      71.641  63.069   2.402  1.00 20.00
ATOM    676  CZ  TYR A 897      72.894  63.650   2.290  1.00 20.00
ATOM    677  OH  TYR A 897      73.381  64.361   3.369  1.00 20.00
ATOM    680  N   LEU A 898      72.001  58.564  -0.369  1.00 20.00
ATOM    681  CA  LEU A 898      71.571  57.163  -0.196  1.00 20.00
ATOM    682  C   LEU A 898      71.131  56.437   1.099  1.00 20.00
ATOM    683  O   LEU A 898      71.759  56.483   2.161  1.00 20.00
ATOM    684  CB  LEU A 898      72.542  56.240  -0.990  1.00 20.00
ATOM    686  N   TYR A 899      70.041  55.704   0.830  1.00 20.00
ATOM    687  CA  TYR A 899      69.162  54.833   1.624  1.00 20.00
ATOM    688  C   TYR A 899      69.544  53.804   2.665  1.00 20.00
ATOM    689  O   TYR A 899      70.411  52.969   2.445  1.00 20.00
ATOM    690  CB  TYR A 899      68.268  54.076   0.657  1.00 20.00
ATOM    691  CG  TYR A 899      67.523  54.943  -0.339  1.00 20.00
ATOM    692  CD1 TYR A 899      68.208  55.776  -1.209  1.00 20.00
ATOM    693  CD2 TYR A 899      66.163  54.790  -0.522  1.00 20.00
ATOM    694  CE1 TYR A 899      67.574  56.407  -2.238  1.00 20.00
ATOM    695  CE2 TYR A 899      65.514  55.429  -1.564  1.00 20.00
ATOM    696  CZ  TYR A 899      66.225  56.235  -2.431  1.00 20.00
ATOM    697  OH  TYR A 899      65.602  56.841  -3.510  1.00 20.00
ATOM    700  N   LEU A 900      68.814  53.814   3.775  1.00 20.00
```

FIG. 4J

```
ATOM    701  CA  LEU A 900      69.047  52.841   4.845  1.00 20.00
ATOM    702  C   LEU A 900      67.805  51.988   5.149  1.00 20.00
ATOM    703  O   LEU A 900      66.645  52.459   5.109  1.00 20.00
ATOM    704  CB  LEU A 900      69.455  53.522   6.147  1.00 20.00
ATOM    705  CG  LEU A 900      70.810  54.184   6.259  1.00 20.00
ATOM    706  CD1 LEU A 900      71.404  54.368   4.864  1.00 20.00
ATOM    707  CD2 LEU A 900      70.624  55.498   7.033  1.00 20.00
ATOM    709  N   ALA A 901      68.083  50.739   5.495  1.00 20.00
ATOM    710  CA  ALA A 901      67.043  49.813   5.811  1.00 20.00
ATOM    711  C   ALA A 901      67.113  49.495   7.275  1.00 20.00
ATOM    712  O   ALA A 901      67.828  48.577   7.670  1.00 20.00
ATOM    713  CB  ALA A 901      67.221  48.564   5.003  1.00 20.00
ATOM    715  N   ILE A 902      66.372  50.260   8.078  1.00 20.00
ATOM    716  CA  ILE A 902      66.310  50.058   9.513  1.00 20.00
ATOM    717  C   ILE A 902      65.367  48.888   9.812  1.00 20.00
ATOM    718  O   ILE A 902      64.702  48.383   8.917  1.00 20.00
ATOM    719  CB  ILE A 902      65.801  51.315  10.167  1.00 20.00
ATOM    720  CG1 ILE A 902      66.882  52.398  10.058  1.00 20.00
ATOM    721  CG2 ILE A 902      65.308  51.006  11.556  1.00 20.00
ATOM    722  CD1 ILE A 902      67.878  52.583  11.280  1.00 20.00
ATOM    724  N   GLU A 903      65.322  48.439  11.057  1.00 20.00
ATOM    725  CA  GLU A 903      64.435  47.350  11.465  1.00 20.00
ATOM    726  C   GLU A 903      62.997  47.870  11.692  1.00 20.00
ATOM    727  O   GLU A 903      62.713  48.559  12.662  1.00 20.00
ATOM    728  CB  GLU A 903      64.973  46.703  12.746  1.00 20.00
ATOM    729  CG  GLU A 903      63.985  45.965  13.580  1.00 20.00
ATOM    730  CD  GLU A 903      64.471  45.766  15.006  1.00 20.00
ATOM    731  OE1 GLU A 903      63.971  44.875  15.725  1.00 20.00
ATOM    732  OE2 GLU A 903      65.365  46.509  15.425  1.00 20.00
ATOM    734  N   TYR A 904      62.115  47.514  10.767  1.00 20.00
ATOM    735  CA  TYR A 904      60.707  47.846  10.758  1.00 20.00
ATOM    736  C   TYR A 904      59.985  47.328  11.989  1.00 20.00
ATOM    737  O   TYR A 904      60.054  46.149  12.240  1.00 20.00
ATOM    738  CB  TYR A 904      60.078  47.204   9.521  1.00 20.00
ATOM    739  CG  TYR A 904      58.553  47.146   9.537  1.00 20.00
ATOM    740  CD1 TYR A 904      57.795  48.150   8.920  1.00 20.00
ATOM    741  CD2 TYR A 904      57.868  46.125  10.188  1.00 20.00
ATOM    742  CE1 TYR A 904      56.420  48.136   8.955  1.00 20.00
ATOM    743  CE2 TYR A 904      56.498  46.115  10.223  1.00 20.00
ATOM    744  CZ  TYR A 904      55.779  47.128   9.602  1.00 20.00
ATOM    745  OH  TYR A 904      54.405  47.149   9.622  1.00 20.00
ATOM    748  N   ALA A 905      59.270  48.183  12.727  1.00 20.00
ATOM    749  CA  ALA A 905      58.503  47.772  13.931  1.00 20.00
ATOM    750  C   ALA A 905      56.987  47.506  13.620  1.00 20.00
ATOM    751  O   ALA A 905      56.395  48.128  12.744  1.00 20.00
ATOM    752  CB  ALA A 905      58.649  48.816  14.976  1.00 20.00
ATOM    754  N   PRO A 906      56.341  46.572  14.317  1.00 20.00
ATOM    755  CA  PRO A 906      54.949  46.394  13.918  1.00 20.00
ATOM    756  C   PRO A 906      53.803  46.643  14.902  1.00 20.00
ATOM    757  O   PRO A 906      52.992  45.748  15.150  1.00 20.00
ATOM    758  CB  PRO A 906      54.958  44.937  13.468  1.00 20.00
ATOM    759  CG  PRO A 906      55.981  44.280  14.584  1.00 20.00
ATOM    760  CD  PRO A 906      56.719  45.482  15.227  1.00 20.00
ATOM    761  N   HIS A 907      53.729  47.841  15.450  1.00 20.00
ATOM    762  CA  HIS A 907      52.655  48.251  16.349  1.00 20.00
ATOM    763  C   HIS A 907      52.966  49.700  16.468  1.00 20.00
ATOM    764  O   HIS A 907      52.865  50.262  17.534  1.00 20.00
```

FIG. 4K

```
ATOM    765  CB   HIS A 907      52.745  47.577  17.714  1.00 20.00
ATOM    766  CG   HIS A 907      52.656  46.090  17.650  1.00 20.00
ATOM    767  ND1  HIS A 907      53.753  45.272  17.799  1.00 20.00
ATOM    768  CD2  HIS A 907      51.622  45.274  17.350  1.00 20.00
ATOM    769  CE1  HIS A 907      53.404  44.018  17.593  1.00 20.00
ATOM    770  NE2  HIS A 907      52.116  43.993  17.318  1.00 20.00
ATOM    774  N    GLY A 908      53.411  50.280  15.365  1.00 20.00
ATOM    775  CA   GLY A 908      53.733  51.676  15.348  1.00 20.00
ATOM    776  C    GLY A 908      54.622  52.111  16.486  1.00 20.00
ATOM    777  O    GLY A 908      55.525  51.381  16.887  1.00 20.00
ATOM    779  N    ASN A 909      54.338  53.284  17.054  1.00 20.00
ATOM    780  CA   ASN A 909      55.183  53.854  18.094  1.00 20.00
ATOM    781  C    ASN A 909      54.590  53.912  19.463  1.00 20.00
ATOM    782  O    ASN A 909      53.409  54.064  19.616  1.00 20.00
ATOM    783  CB   ASN A 909      55.545  55.270  17.672  1.00 20.00
ATOM    784  CG   ASN A 909      54.346  56.201  17.669  1.00 20.00
ATOM    785  OD1  ASN A 909      54.409  57.315  17.192  1.00 20.00
ATOM    786  ND2  ASN A 909      53.260  55.738  18.210  1.00 20.00
ATOM    790  N    LEU A 910      55.414  53.878  20.482  1.00 20.00
ATOM    791  CA   LEU A 910      54.872  53.913  21.808  1.00 20.00
ATOM    792  C    LEU A 910      53.703  54.890  21.927  1.00 20.00
ATOM    793  O    LEU A 910      52.760  54.647  22.669  1.00 20.00
ATOM    794  CB   LEU A 910      55.949  54.257  22.797  1.00 20.00
ATOM    795  CG   LEU A 910      55.456  54.079  24.220  1.00 20.00
ATOM    796  CD1  LEU A 910      54.921  52.676  24.488  1.00 20.00
ATOM    797  CD2  LEU A 910      56.617  54.427  25.133  1.00 20.00
ATOM    799  N    LEU A 911      53.725  56.005  21.219  1.00 20.00
ATOM    800  CA   LEU A 911      52.578  56.862  21.381  1.00 20.00
ATOM    801  C    LEU A 911      51.408  56.200  20.656  1.00 20.00
ATOM    802  O    LEU A 911      50.700  55.442  21.275  1.00 20.00
ATOM    803  CB   LEU A 911      52.820  58.302  20.863  1.00 20.00
ATOM    804  CG   LEU A 911      51.958  59.498  21.354  1.00 20.00
ATOM    805  CD1  LEU A 911      51.738  59.517  22.855  1.00 20.00
ATOM    806  CD2  LEU A 911      52.645  60.737  20.917  1.00 20.00
ATOM    808  N    ASP A 912      51.219  56.459  19.371  1.00 20.00
ATOM    809  CA   ASP A 912      50.117  55.895  18.642  1.00 20.00
ATOM    810  C    ASP A 912      49.646  54.540  19.121  1.00 20.00
ATOM    811  O    ASP A 912      48.468  54.225  19.083  1.00 20.00
ATOM    812  CB   ASP A 912      50.461  55.849  17.181  1.00 20.00
ATOM    813  CG   ASP A 912      50.214  57.151  16.498  1.00 20.00
ATOM    814  OD1  ASP A 912      50.507  57.259  15.304  1.00 20.00
ATOM    815  OD2  ASP A 912      49.725  58.089  17.141  1.00 20.00
ATOM    817  N    PHE A 913      50.572  53.703  19.562  1.00 20.00
ATOM    818  CA   PHE A 913      50.168  52.405  20.098  1.00 20.00
ATOM    819  C    PHE A 913      49.397  52.903  21.287  1.00 20.00
ATOM    820  O    PHE A 913      48.236  53.231  21.164  1.00 20.00
ATOM    821  CB   PHE A 913      51.355  51.585  20.547  1.00 20.00
ATOM    822  CG   PHE A 913      51.010  50.182  20.847  1.00 20.00
ATOM    823  CD1  PHE A 913      50.511  49.365  19.866  1.00 20.00
ATOM    824  CD2  PHE A 913      51.133  49.688  22.122  1.00 20.00
ATOM    825  CE1  PHE A 913      50.141  48.088  20.152  1.00 20.00
ATOM    826  CE2  PHE A 913      50.760  48.418  22.407  1.00 20.00
ATOM    827  CZ   PHE A 913      50.263  47.619  21.418  1.00 20.00
ATOM    829  N    LEU A 914      50.059  53.031  22.416  1.00 20.00
ATOM    830  CA   LEU A 914      49.400  53.584  23.572  1.00 20.00
ATOM    831  C    LEU A 914      48.080  54.304  23.288  1.00 20.00
ATOM    832  O    LEU A 914      47.102  54.093  23.985  1.00 20.00
```

FIG. 4L

```
ATOM    833  CB   LEU A 914      50.342  54.549  24.244  1.00 20.00
ATOM    834  CG   LEU A 914      51.146  53.995  25.410  1.00 20.00
ATOM    835  CD1  LEU A 914      52.130  55.080  25.953  1.00 20.00
ATOM    836  CD2  LEU A 914      50.142  53.501  26.466  1.00 20.00
ATOM    838  N    ARG A 915      48.006  55.139  22.265  1.00 20.00
ATOM    839  CA   ARG A 915      46.736  55.841  22.041  1.00 20.00
ATOM    840  C    ARG A 915      45.650  54.970  21.526  1.00 20.00
ATOM    841  O    ARG A 915      44.569  54.984  22.054  1.00 20.00
ATOM    842  CB   ARG A 915      46.896  57.078  21.141  1.00 20.00
ATOM    843  CG   ARG A 915      46.687  58.379  21.885  1:00 20.00
ATOM    844  CD   ARG A 915      47.528  59.415  21.256  1.00 20.00
ATOM    845  NE   ARG A 915      48.215  60.347  22.169  1.00 20.00
ATOM    846  CZ   ARG A 915      48.763  61.482  21.760  1.00 20.00
ATOM    847  NH1  ARG A 915      48.709  61.835  20.494  1.00 20.00
ATOM    848  NH2  ARG A 915      49.383  62.240  22.602  1.00 20.00
ATOM    855  N    LYS A 916      45.943  54.219  20.485  1.00 20.00
ATOM    856  CA   LYS A 916      45.019  53.242  19.890  1.00 20.00
ATOM    857  C    LYS A 916      44.681  52.169  20.920  1.00 20.00
ATOM    858  O    LYS A 916      44.275  51.109  20.561  1.00 20.00
ATOM    859  CB   LYS A 916      45.714  52.563  18.676  1.00 20.00
ATOM    860  CG   LYS A 916      45.988  51.000  18.704  1.00 20.00
ATOM    861  CD   LYS A 916      46.802  50.408  19.888  1.00 20.00
ATOM    862  CE   LYS A 916      46.861  48.841  19.822  1.00 20.00
ATOM    863  NZ   LYS A 916      46.225  47.974  20.937  1.00 20.00
ATOM    868  N    SER A 917      44.851  52.438  22.196  1.00 20.00
ATOM    869  CA   SER A 917      44.597  51.466  23.204  1.00 20.00
ATOM    870  C    SER A 917      43.641  52.011  24.233  1.00 20.00
ATOM    871  O    SER A 917      43.501  51.444  25.330  1.00 20.00
ATOM    872  CB   SER A 917      45.891  51.147  23.883  1.00 20.00
ATOM    873  OG   SER A 917      45.843  51.568  25.227  1.00 20.00
ATOM    876  N    ARG A 918      43.014  53.138  23.902  1.00 20.00
ATOM    877  CA   ARG A 918      42.041  53.822  24.775  1.00 20.00
ATOM    878  C    ARG A 918      40.816  53.359  24.014  1.00 20.00
ATOM    879  O    ARG A 918      40.523  53.883  22.951  1.00 20.00
ATOM    880  CB   ARG A 918      42.260  55.365  24.669  1.00 20.00
ATOM    881  CG   ARG A 918      43.138  56.036  25.794  1.00 20.00
ATOM    882  CD   ARG A 918      43.547  57.502  25.488  1.00 20.00
ATOM    883  NE   ARG A 918      44.494  57.982  26.502  1.00 20.00
ATOM    884  CZ   ARG A 918      44.777  59.260  26.795  1.00 20.00
ATOM    885  NH1  ARG A 918      44.211  60.289  26.165  1.00 20.00
ATOM    886  NH2  ARG A 918      45.625  59.523  27.777  1.00 20.00
ATOM    893  N    VAL A 919      40.135  52.333  24.507  1.00 20.00
ATOM    894  CA   VAL A 919      39.009  51.770  23.757  1.00 20.00
ATOM    895  C    VAL A 919      37.733  52.382  24.202  1.00 20.00
ATOM    896  O    VAL A 919      36.750  52.427  23.450  1.00 20.00
ATOM    897  CB   VAL A 919      38.925  50.198  23.861  1.00 20.00
ATOM    898  CG1  VAL A 919      40.218  49.603  23.459  1.00 20.00
ATOM    899  CG2  VAL A 919      38.550  49.746  25.275  1.00 20.00
ATOM    901  N    LEU A 920      37.736  52.861  25.432  1.00 20.00
ATOM    902  CA   LEU A 920      36.569  53.542  25.895  1.00 20.00
ATOM    903  C    LEU A 920      36.303  54.630  24.864  1.00 20.00
ATOM    904  O    LEU A 920      35.276  55.259  24.906  1.00 20.00
ATOM    905  CB   LEU A 920      36.815  54.146  27.236  1.00 20.00
ATOM    906  CG   LEU A 920      35.641  54.652  28.011  1.00 20.00
ATOM    907  CD1  LEU A 920      35.060  53.567  28.831  1.00 20.00
ATOM    908  CD2  LEU A 920      36.155  55.768  28.901  1.00 20.00
ATOM    910  N    GLU A 921      37.224  54.824  23.926  1.00 20.00
```

FIG. 4M

```
ATOM    911  CA  GLU A 921      37.081  55.783  22.850  1.00 20.00
ATOM    912  C   GLU A 921      37.413  55.109  21.541  1.00 20.00
ATOM    913  O   GLU A 921      37.205  55.677  20.469  1.00 20.00
ATOM    914  CB  GLU A 921      38.047  56.940  23.011  1.00 20.00
ATOM    915  CG  GLU A 921      38.258  57.743  21.736  1.00 20.00
ATOM    916  CD  GLU A 921      39.404  58.696  21.848  1.00 20.00
ATOM    917  OE1 GLU A 921      39.875  58.879  22.982  1.00 20.00
ATOM    918  OE2 GLU A 921      39.836  59.261  20.825  1.00 20.00
ATOM    920  N   THR A 922      37.936  53.893  21.615  1.00 20.00
ATOM    921  CA  THR A 922      38.309  53.178  20.413  1.00 20.00
ATOM    922  C   THR A 922      37.429  51.960  20.078  1.00 20.00
ATOM    923  O   THR A 922      37.502  51.387  18.963  1.00 20.00
ATOM    924  CB  THR A 922      39.742  52.728  20.559  1.00 20.00
ATOM    925  OG1 THR A 922      40.441  53.058  19.366  1.00 20.00
ATOM    926  CG2 THR A 922      39.824  51.214  20.816  1.00 20.00
ATOM    929  N   ASP A 923      36.617  51.575  21.074  1.00 20.00
ATOM    930  CA  ASP A 923      35.712  50.423  21.026  1.00 20.00
ATOM    931  C   ASP A 923      34.972  50.387  22.350  1.00 20.00
ATOM    932  O   ASP A 923      35.259  49.550  23.203  1.00 20.00
ATOM    933  CB  ASP A 923      36.494  49.119  20.905  1.00 20.00
ATOM    934  CG  ASP A 923      35.879  48.142  19.909  1.00 20.00
ATOM    935  OD1 ASP A 923      35.624  48.553  18.745  1.00 20.00
ATOM    936  OD2 ASP A 923      35.669  46.956  20.271  1.00 20.00
ATOM    938  N   PRO A 924      34.042  51.323  22.577  1.00 20.00
ATOM    939  CA  PRO A 924      33.362  51.211  23.874  1.00 20.00
ATOM    940  C   PRO A 924      32.544  49.923  24.176  1.00 20.00
ATOM    941  O   PRO A 924      32.172  49.720  25.342  1.00 20.00
ATOM    942  CB  PRO A 924      32.540  52.506  23.953  1.00 20.00
ATOM    943  CG  PRO A 924      33.214  53.417  22.960  1.00 20.00
ATOM    944  CD  PRO A 924      33.600  52.512  21.841  1.00 20.00
ATOM    945  N   ALA A 925      32.276  49.078  23.156  1.00 20.00
ATOM    946  CA  ALA A 925      31.551  47.770  23.326  1.00 20.00
ATOM    947  C   ALA A 925      32.438  46.878  24.193  1.00 20.00
ATOM    948  O   ALA A 925      32.016  46.274  25.190  1.00 20.00
ATOM    949  CB  ALA A 925      31.328  47.103  21.992  1.00 20.00
ATOM    951  N   PHE A 926      33.695  46.843  23.771  1.00 20.00
ATOM    952  CA  PHE A 926      34.782  46.173  24.431  1.00 20.00
ATOM    953  C   PHE A 926      34.885  46.856  25.745  1.00 20.00
ATOM    954  O   PHE A 926      34.896  46.269  26.772  1.00 20.00
ATOM    955  CB  PHE A 926      36.058  46.460  23.667  1.00 20.00
ATOM    956  CG  PHE A 926      37.046  45.347  23.693  1.00 20.00
ATOM    957  CD1 PHE A 926      37.164  44.511  22.599  1.00 20.00
ATOM    958  CD2 PHE A 926      37.810  45.127  24.825  1.00 20.00
ATOM    959  CE1 PHE A 926      38.003  43.493  22.630  1.00 20.00
ATOM    960  CE2 PHE A 926      38.661  44.107  24.881  1.00 20.00
ATOM    961  CZ  PHE A 926      38.773  43.272  23.786  1.00 20.00
ATOM    963  N   ALA A 927      35.024  48.154  25.681  1.00 20.00
ATOM    964  CA  ALA A 927      35.084  48.926  26.885  1.00 20.00
ATOM    965  C   ALA A 927      34.165  48.337  27.956  1.00 20.00
ATOM    966  O   ALA A 927      34.695  47.721  28.843  1.00 20.00
ATOM    967  CB  ALA A 927      34.717  50.348  26.587  1.00 20.00
ATOM    969  N   ILE A 928      32.825  48.502  27.887  1.00 20.00
ATOM    970  CA  ILE A 928      31.935  47.945  28.958  1.00 20.00
ATOM    971  C   ILE A 928      31.760  46.437  29.001  1.00 20.00
ATOM    972  O   ILE A 928      31.464  45.883  30.050  1.00 20.00
ATOM    973  CB  ILE A 928      30.395  48.487  29.019  1.00 20.00
ATOM    974  CG1 ILE A 928      30.081  49.486  27.941  1.00 20.00
```

FIG. 4N

| | | | | | | | | |
|---|---|---|---|---|---|---|---|---|
| ATOM | 975 | CG2 | ILE A 928 | 30.098 | 49.114 | 30.414 | 1.00 | 20.00 |
| ATOM | 976 | CD1 | ILE A 928 | 29.952 | 50.862 | 28.545 | 1.00 | 20.00 |
| ATOM | 978 | N | ALA A 929 | 31.895 | 45.782 | 27.860 | 1.00 | 20.00 |
| ATOM | 979 | CA | ALA A 929 | 31.747 | 44.356 | 27.867 | 1.00 | 20.00 |
| ATOM | 980 | C | ALA A 929 | 32.803 | 43.844 | 28.804 | 1.00 | 20.00 |
| ATOM | 981 | O | ALA A 929 | 32.525 | 43.055 | 29.667 | 1.00 | 20.00 |
| ATOM | 982 | CB | ALA A 929 | 31.946 | 43.823 | 26.510 | 1.00 | 20.00 |
| ATOM | 984 | N | ASN A 930 | 34.010 | 44.358 | 28.642 | 1.00 | 20.00 |
| ATOM | 985 | CA | ASN A 930 | 35.181 | 44.009 | 29.429 | 1.00 | 20.00 |
| ATOM | 986 | C | ASN A 930 | 35.448 | 44.882 | 30.665 | 1.00 | 20.00 |
| ATOM | 987 | O | ASN A 930 | 36.191 | 44.496 | 31.566 | 1.00 | 20.00 |
| ATOM | 988 | CB | ASN A 930 | 36.397 | 44.067 | 28.511 | 1.00 | 20.00 |
| ATOM | 989 | CG | ASN A 930 | 36.628 | 42.771 | 27.745 | 1.00 | 20.00 |
| ATOM | 990 | OD1 | ASN A 930 | 37.333 | 41.876 | 28.220 | 1.00 | 20.00 |
| ATOM | 991 | ND2 | ASN A 930 | 36.046 | 42.671 | 26.547 | 1.00 | 20.00 |
| ATOM | 995 | N | SER A 931 | 34.847 | 46.063 | 30.695 | 1.00 | 20.00 |
| ATOM | 996 | CA | SER A 931 | 35.050 | 47.041 | 31.768 | 1.00 | 20.00 |
| ATOM | 997 | C | SER A 931 | 36.531 | 47.527 | 31.922 | 1.00 | 20.00 |
| ATOM | 998 | O | SER A 931 | 37.074 | 47.556 | 33.020 | 1.00 | 20.00 |
| ATOM | 999 | CB | SER A 931 | 34.541 | 46.453 | 33.084 | 1.00 | 20.00 |
| ATOM | 1000 | OG | SER A 931 | 34.196 | 45.103 | 32.879 | 1.00 | 20.00 |
| ATOM | 1003 | N | THR A 932 | 37.155 | 47.931 | 30.815 | 1.00 | 20.00 |
| ATOM | 1004 | CA | THR A 932 | 38.545 | 48.392 | 30.821 | 1.00 | 20.00 |
| ATOM | 1005 | C | THR A 932 | 38.800 | 49.536 | 29.872 | 1.00 | 20.00 |
| ATOM | 1006 | O | THR A 932 | 38.184 | 49.614 | 28.803 | 1.00 | 20.00 |
| ATOM | 1007 | CB | THR A 932 | 39.525 | 47.299 | 30.451 | 1.00 | 20.00 |
| ATOM | 1008 | OG1 | THR A 932 | 38.971 | 46.481 | 29.417 | 1.00 | 20.00 |
| ATOM | 1009 | CG2 | THR A 932 | 39.832 | 46.479 | 31.663 | 1.00 | 20.00 |
| ATOM | 1012 | N | ALA A 933 | 39.747 | 50.384 | 30.287 | 1.00 | 20.00 |
| ATOM | 1013 | CA | ALA A 933 | 40.179 | 51.608 | 29.597 | 1.00 | 20.00 |
| ATOM | 1014 | C | ALA A 933 | 41.172 | 51.417 | 28.495 | 1.00 | 20.00 |
| ATOM | 1015 | O | ALA A 933 | 41.155 | 52.134 | 27.513 | 1.00 | 20.00 |
| ATOM | 1016 | CB | ALA A 933 | 40.778 | 52.547 | 30.597 | 1.00 | 20.00 |
| ATOM | 1018 | N | SER A 934 | 42.086 | 50.480 | 28.709 | 1.00 | 20.00 |
| ATOM | 1019 | CA | SER A 934 | 43.134 | 50.131 | 27.749 | 1.00 | 20.00 |
| ATOM | 1020 | C | SER A 934 | 43.001 | 48.645 | 27.512 | 1.00 | 20.00 |
| ATOM | 1021 | O | SER A 934 | 42.431 | 47.966 | 28.337 | 1.00 | 20.00 |
| ATOM | 1022 | CB | SER A 934 | 44.511 | 50.396 | 28.374 | 1.00 | 20.00 |
| ATOM | 1023 | OG | SER A 934 | 45.494 | 50.638 | 27.386 | 1.00 | 20.00 |
| ATOM | 1026 | N | THR A 935 | 43.497 | 48.150 | 26.380 | 1.00 | 20.00 |
| ATOM | 1027 | CA | THR A 935 | 43.529 | 46.701 | 26.144 | 1.00 | 20.00 |
| ATOM | 1028 | C | THR A 935 | 44.801 | 46.297 | 26.814 | 1.00 | 20.00 |
| ATOM | 1029 | O | THR A 935 | 45.015 | 45.118 | 27.082 | 1.00 | 20.00 |
| ATOM | 1030 | CB | THR A 935 | 43.768 | 46.312 | 24.783 | 1.00 | 20.00 |
| ATOM | 1031 | OG1 | THR A 935 | 44.892 | 47.021 | 24.325 | 1.00 | 20.00 |
| ATOM | 1032 | CG2 | THR A 935 | 42.571 | 46.583 | 23.961 | 1.00 | 20.00 |
| ATOM | 1035 | N | LEU A 936 | 45.640 | 47.301 | 27.070 | 1.00 | 20.00 |
| ATOM | 1036 | CA | LEU A 936 | 46.897 | 47.138 | 27.735 | 1.00 | 20.00 |
| ATOM | 1037 | C | LEU A 936 | 46.640 | 46.822 | 29.174 | 1.00 | 20.00 |
| ATOM | 1038 | O | LEU A 936 | 45.579 | 47.010 | 29.666 | 1.00 | 20.00 |
| ATOM | 1039 | CB | LEU A 936 | 47.699 | 48.413 | 27.635 | 1.00 | 20.00 |
| ATOM | 1040 | CG | LEU A 936 | 47.921 | 49.086 | 26.273 | 1.00 | 20.30 |
| ATOM | 1041 | CD1 | LEU A 936 | 49.058 | 50.134 | 26.370 | 1.00 | 20.00 |
| ATOM | 1042 | CD2 | LEU A 936 | 48.250 | 48.029 | 25.238 | 1.00 | 20.00 |
| ATOM | 1044 | N | SER A 937 | 47.652 | 46.322 | 29.841 | 1.00 | 20.00 |
| ATOM | 1045 | CA | SER A 937 | 47.576 | 45.961 | 31.232 | 1.00 | 20.00 |
| ATOM | 1046 | C | SER A 937 | 48.521 | 46.834 | 32.054 | 1.00 | 20.00 |

FIG. 40

```
ATOM   1047  O    SER A 937      49.291  47.608  31.519  1.00 20.00
ATOM   1048  CB   SER A 937      47.988  44.501  31.384  1.00 20.00
ATOM   1049  OG   SER A 937      48.630  44.257  32.628  1.00 20.00
ATOM   1052  N    SER A 938      48.458  46.695  33.365  1.00 20.00
ATOM   1053  CA   SER A 938      49.319  47.433  34.239  1.00 20.00
ATOM   1054  C    SER A 938      50.724  46.904  33.957  1.00 20.00
ATOM   1055  O    SER A 938      51.686  47.668  33.847  1.00 20.00
ATOM   1056  CB   SER A 938      48.900  47.177  35.683  1.00 20.00
ATOM   1057  OG   SER A 938      50.012  47.071  36.555  1.00 20.00
ATOM   1060  N    GLN A 939      50.849  45.587  33.812  1.00 20.00
ATOM   1061  CA   GLN A 939      52.165  45.002  33.522  1.00 20.00
ATOM   1062  C    GLN A 939      52.709  45.435  32.165  1.00 20.00
ATOM   1063  O    GLN A 939      53.831  45.917  32.073  1.00 20.00
ATOM   1064  CB   GLN A 939      52.138  43.465  33.608  1.00 20.00
ATOM   1065  CG   GLN A 939      52.298  42.909  35.046  1.00 20.00
ATOM   1066  CD   GLN A 939      53.756  42.716  35.473  1.00 20.00
ATOM   1067  OE1  GLN A 939      54.595  42.185  34.711  1.00 20.00
ATOM   1068  NE2  GLN A 939      54.065  43.139  36.700  1.00 20.00
ATOM   1072  N    GLN A 940      51.932  45.294  31.111  1.00 20.00
ATOM   1073  CA   GLN A 940      52.445  45.696  29.813  1.00 20.00
ATOM   1074  C    GLN A 940      53.040  47.092  29.913  1.00 20.00
ATOM   1075  O    GLN A 940      53.944  47.477  29.163  1.00 20.00
ATOM   1076  CB   GLN A 940      51.330  45.696  28.788  1.00 20.00
ATOM   1077  CG   GLN A 940      51.695  46.374  27.506  1.00 20.00
ATOM   1078  CD   GLN A 940      52.703  45.592  26.720  1.00 20.00
ATOM   1079  OE1  GLN A 940      52.680  45.571  25.496  1.00 20.00
ATOM   1080  NE2  GLN A 940      53.591  44.934  27.418  1.00 20.00
ATOM   1084  N    LEU A 941      52.523  47.832  30.887  1.00 20.00
ATOM   1085  CA   LEU A 941      52.918  49.212  31.110  1.00 20.00
ATOM   1086  C    LEU A 941      54.285  49.397  31.744  1.00 20.00
ATOM   1087  O    LEU A 941      55.074  50.181  31.231  1.00 20.00
ATOM   1088  CB   LEU A 941      51.855  49.924  31.933  1.00 20.00
ATOM   1089  CG   LEU A 941      50.700  50.500  31.161  1.00 20.00
ATOM   1090  CD1  LEU A 941      50.187  51.653  31.924  1.00 20.00
ATOM   1091  CD2  LEU A 941      51.139  50.904  29.785  1.00 20.00
ATOM   1093  N    LEU A 942      54.571  48.720  32.848  1.00 20.00
ATOM   1094  CA   LEU A 942      55.882  48.863  33.431  1.00 20.00
ATOM   1095  C    LEU A 942      56.822  48.204  32.440  1.00 20.00
ATOM   1096  O    LEU A 942      57.987  48.583  32.283  1.00 20.00
ATOM   1097  CB   LEU A 942      55.955  48.147  34.756  1.00 20.00
ATOM   1098  CG   LEU A 942      54.731  48.399  35.609  1.00 20.00
ATOM   1099  CD1  LEU A 942      54.907  47.676  36.943  1.00 20.00
ATOM   1100  CD2  LEU A 942      54.526  49.936  35.793  1.00 20.00
ATOM   1102  N    HIS A 943      56.309  47.201  31.761  1.00 20.00
ATOM   1103  CA   HIS A 943      57.127  46.548  30.800  1.00 20.00
ATOM   1104  C    HIS A 943      57.754  47.596  29.894  1.00 20.00
ATOM   1105  O    HIS A 943      58.969  47.781  29.936  1.00 20.00
ATOM   1106  CB   HIS A 943      56.302  45.586  29.997  1.00 20.00
ATOM   1107  CG   HIS A 943      56.549  44.159  30.350  1.00 20.00
ATOM   1108  ND1  HIS A 943      56.709  43.732  31.649  1.00 20.00
ATOM   1109  CD2  HIS A 943      56.634  43.054  29.582  1.00 20.00
ATOM   1110  CE1  HIS A 943      56.881  42.427  31.670  1.00 20.00
ATOM   1111  NE2  HIS A 943      56.841  41.994  30.427  1.00 20.00
ATOM   1115  N    PHE A 944      56.929  48.278  29.084  1.00 20.00
ATOM   1116  CA   PHE A 944      57.396  49.327  28.162  1.00 20.00
ATOM   1117  C    PHE A 944      58.366  50.354  28.831  1.00 20.00
ATOM   1118  O    PHE A 944      59.368  50.775  28.249  1.00 20.00
```

FIG. 4P

```
ATOM   1119  CB   PHE A 944      56.205  50.071  27.619  1.00 20.00
ATOM   1120  CG   PHE A 944      55.484  49.372  26.515  1.00 20.00
ATOM   1121  CD1  PHE A 944      54.116  49.207  26.572  1.00 20.00
ATOM   1122  CD2  PHE A 944      56.130  49.020  25.368  1.00 20.00
ATOM   1123  CE1  PHE A 944      53.432  48.727  25.515  1.00 20.00
ATOM   1124  CE2  PHE A 944      55.433  48.534  24.300  1.00 20.00
ATOM   1125  CZ   PHE A 944      54.096  48.393  24.375  1.00 20.00
ATOM   1127  N    ALA A 945      58.055  50.749  30.057  1.00 20.00
ATOM   1128  CA   ALA A 945      58.919  51.639  30.792  1.00 20.00
ATOM   1129  C    ALA A 945      60.323  51.010  31.013  1.00 20.00
ATOM   1130  O    ALA A 945      61.349  51.690  30.906  1.00 20.00
ATOM   1131  CB   ALA A 945      58.292  51.974  32.101  1.00 20.00
ATOM   1133  N    ALA A 946      60.373  49.710  31.297  1.00 20.00
ATOM   1134  CA   ALA A 946      61.650  49.043  31.547  1.00 20.00
ATOM   1135  C    ALA A 946      62.466  48.605  30.330  1.00 20.00
ATOM   1136  O    ALA A 946      63.646  48.331  30.434  1.00 20.00
ATOM   1137  CB   ALA A 946      61.418  47.872  32.429  1.00 20.00
ATOM   1139  N    ASP A 947      61.823  48.486  29.188  1.00 20.00
ATOM   1140  CA   ASP A 947      62.532  48.106  27.998  1.00 20.00
ATOM   1141  C    ASP A 947      63.351  49.335  27.765  1.00 20.00
ATOM   1142  O    ASP A 947      64.564  49.273  27.560  1.00 20.00
ATOM   1143  CB   ASP A 947      61.560  47.930  26.849  1.00 20.00
ATOM   1144  CG   ASP A 947      61.242  46.473  26.549  1.00 20.00
ATOM   1145  OD1  ASP A 947      61.770  45.561  27.247  1.00 20.00
ATOM   1146  OD2  ASP A 947      60.447  46.255  25.595  1.00 20.00
ATOM   1148  N    VAL A 948      62.640  50.465  27.811  1.00 20.00
ATOM   1149  CA   VAL A 948      63.203  51.808  27.624  1.00 20.00
ATOM   1150  C    VAL A 948      64.337  52.099  28.598  1.00 20.00
ATOM   1151  O    VAL A 948      65.360  52.539  28.177  1.00 20.00
ATOM   1152  CB   VAL A 948      62.108  52.917  27.776  1.00 20.00
ATOM   1153  CG1  VAL A 948      62.712  54.286  27.666  1.00 20.00
ATOM   1154  CG2  VAL A 948      61.121  52.784  26.722  1.00 20.00
ATOM   1156  N    ALA A 949      64.166  51.850  29.886  1.00 20.00
ATOM   1157  CA   ALA A 949      65.243  52.135  30.812  1.00 20.00
ATOM   1158  C    ALA A 949      66.449  51.321  30.460  1.00 20.00
ATOM   1159  O    ALA A 949      67.578  51.738  30.669  1.00 20.00
ATOM   1160  CB   ALA A 949      64.850  51.822  32.209  1.00 20.00
ATOM   1162  N    ARG A 950      66.212  50.134  29.928  1.00 20.00
ATOM   1163  CA   ARG A 950      67.293  49.254  29.578  1.00 20.00
ATOM   1164  C    ARG A 950      68.005  49.853  28.406  1.00 20.00
ATOM   1165  O    ARG A 950      69.110  50.330  28.534  1.00 20.00
ATOM   1166  CB   ARG A 950      66.762  47.872  29.240  1.00 20.00
ATOM   1167  CG   ARG A 950      67.029  46.827  30.351  1.00 20.00
ATOM   1168  CD   ARG A 950      67.033  45.384  29.809  1.00 20.00
ATOM   1169  NE   ARG A 950      65.891  45.157  28.900  1.00 20.00
ATOM   1170  CZ   ARG A 950      64.646  44.807  29.260  1.00 20.00
ATOM   1171  NH1  ARG A 950      64.301  44.610  30.522  1.00 20.00
ATOM   1172  NH2  ARG A 950      63.726  44.693  28.323  1.00 20.00
ATOM   1179  N    GLY A 951      67.390  49.844  27.248  1.00 20.00
ATOM   1180  CA   GLY A 951      68.105  50.427  26.146  1.00 20.00
ATOM   1181  C    GLY A 951      68.769  51.722  26.564  1.00 20.00
ATOM   1182  O    GLY A 951      69.885  52.024  26.163  1.00 20.00
ATOM   1184  N    MET A 952      68.080  52.500  27.386  1.00 20.00
ATOM   1185  CA   MET A 952      68.605  53.787  27.807  1.00 20.00
ATOM   1186  C    MET A 952      69.952  53.633  28.437  1.00 20.00
ATOM   1187  O    MET A 952      70.949  53.969  27.845  1.00 20.00
ATOM   1188  CB   MET A 952      67.659  54.492  28.797  1.00 20.00
```

FIG. 4Q

```
ATOM   1189  CG   MET A 952      67.289  55.894  28.400  1.00 20.00
ATOM   1190  SD   MET A 952      67.360  56.078  26.632  1.00 20.00
ATOM   1191  CE   MET A 952      68.656  57.374  26.554  1.00 20.00
ATOM   1193  N    ASP A 953      69.903  53.096  29.648  1.00 20.00
ATOM   1194  CA   ASP A 953      70.999  52.819  30.539  1.00 20.00
ATOM   1195  C    ASP A 953      72.126  52.077  29.948  1.00 20.00
ATOM   1196  O    ASP A 953      73.077  51.814  30.608  1.00 20.00
ATOM   1197  CB   ASP A 953      70.496  52.036  31.733  1.00 20.00
ATOM   1198  CG   ASP A 953      71.538  51.117  32.295  1.00 20.00
ATOM   1199  OD1  ASP A 953      72.241  51.480  33.245  1.00 20.00
ATOM   1200  OD2  ASP A 953      71.672  50.004  31.785  1.00 20.00
ATOM   1202  N    TYR A 954      72.025  51.743  28.692  1.00 20.00
ATOM   1203  CA   TYR A 954      73.060  51.020  28.034  1.00 20.00
ATOM   1204  C    TYR A 954      73.930  52.011  27.324  1.00 20.00
ATOM   1205  O    TYR A 954      75.135  51.833  27.254  1.00 20.00
ATOM   1206  CB   TYR A 954      72.416  50.047  27.070  1.00 20.00
ATOM   1207  CG   TYR A 954      73.330  49.432  26.068  1.00 20.00
ATOM   1208  CD1  TYR A 954      74.294  48.485  26.442  1.00 20.00
ATOM   1209  CD2  TYR A 954      73.181  49.719  24.734  1.00 20.00
ATOM   1210  CE1  TYR A 954      75.071  47.839  25.483  1.00 20.00
ATOM   1211  CE2  TYR A 954      73.947  49.082  23.779  1.00 20.00
ATOM   1212  CZ   TYR A 954      74.883  48.136  24.153  1.00 20.00
ATOM   1213  OH   TYR A 954      75.525  47.442  23.152  1.00 20.00
ATOM   1216  N    LEU A 955      73.286  53.052  26.786  1.00 20.00
ATOM   1217  CA   LEU A 955      73.908  54.184  26.069  1.00 20.00
ATOM   1218  C    LEU A 955      74.356  55.110  27.176  1.00 20.00
ATOM   1219  O    LEU A 955      75.441  55.609  27.207  1.00 20.00
ATOM   1220  CB   LEU A 955      72.863  54.943  25.265  1.00 20.00
ATOM   1221  CG   LEU A 955      72.005  54.277  24.181  1.00 20.00
ATOM   1222  CD1  LEU A 955      70.489  54.637  24.288  1.00 20.00
ATOM   1223  CD2  LEU A 955      72.573  54.751  22.838  1.00 20.00
ATOM   1225  N    SER A 956      73.465  55.311  28.113  1.00 20.00
ATOM   1226  CA   SER A 956      73.699  56.176  29.209  1.00 20.00
ATOM   1227  C    SER A 956      74.985  55.783  29.829  1.00 20.00
ATOM   1228  O    SER A 956      75.557  56.555  30.600  1.00 20.00
ATOM   1229  CB   SER A 956      72.534  56.068  30.172  1.00 20.00
ATOM   1230  OG   SER A 956      72.960  56.102  31.513  1.00 20.00
ATOM   1233  N    GLN A 957      75.468  54.594  29.495  1.00 20.00
ATOM   1234  CA   GLN A 957      76.755  54.097  30.040  1.00 20.00
ATOM   1235  C    GLN A 957      77.824  54.054  28.959  1.00 20.00
ATOM   1236  O    GLN A 957      78.985  54.213  29.208  1.00 20.00
ATOM   1237  CB   GLN A 957      76.591  52.703  30.617  1.00 20.00
ATOM   1238  CG   GLN A 957      75.563  52.626  31.692  1.00 20.00
ATOM   1239  CD   GLN A 957      76.088  51.882  32.875  1.00 20.00
ATOM   1240  OE1  GLN A 957      77.083  52.314  33.492  1.00 20.00
ATOM   1241  NE2  GLN A 957      75.447  50.747  33.215  1.00 20.00
ATOM   1245  N    LYS A 958      77.396  53.827  27.747  1.00 20.00
ATOM   1246  CA   LYS A 958      78.273  53.813  26.622  1.00 20.00
ATOM   1247  C    LYS A 958      78.801  55.275  26.542  1.00 20.00
ATOM   1248  O    LYS A 958      79.643  55.627  25.704  1.00 20.00
ATOM   1249  CB   LYS A 958      77.427  53.440  25.379  1.00 20.00
ATOM   1250  CG   LYS A 958      78.110  52.552  24.355  1.00 20.00
ATOM   1251  CD   LYS A 958      78.715  51.303  25.011  1.00 20.00
ATOM   1252  CE   LYS A 958      77.845  50.099  24.743  1.00 20.00
ATOM   1253  NZ   LYS A 958      77.570  50.041  23.271  1.00 20.00
ATOM   1258  N    GLN A 959      78.268  56.108  27.438  1.00 20.00
ATOM   1259  CA   GLN A 959      78.526  57.551  27.543  1.00 20.00
```

FIG. 4R

```
ATOM   1260  C    GLN A 959      77.366  58.361  26.838  1.00 20.00
ATOM   1261  O    GLN A 959      76.848  59.327  27.401  1.00 20.00
ATOM   1262  CB   GLN A 959      79.901  57.893  26.973  1.00 20.00
ATOM   1263  CG   GLN A 959      80.490  59.183  27.492  1.00 20.00
ATOM   1264  CD   GLN A 959      80.934  59.114  28.944  1.00 20.00
ATOM   1265  OE1  GLN A 959      81.840  58.313  29.295  1.00 20.00
ATOM   1266  NE2  GLN A 959      80.332  59.979  29.811  1.00 20.00
ATOM   1270  N    PHE A 960      76.937  57.940  25.649  1.00 20.00
ATOM   1271  CA   PHE A 960      75.828  58.582  24.898  1.00 20.00
ATOM   1272  C    PHE A 960      74.667  59.365  25.618  1.00 20.00
ATOM   1273  O    PHE A 960      74.110  58.916  26.628  1.00 20.00
ATOM   1274  CB   PHE A 960      75.189  57.528  23.985  1.00 20.00
ATOM   1275  CG   PHE A 960      76.070  57.067  22.851  1.00 20.00
ATOM   1276  CD1  PHE A 960      76.570  55.766  22.818  1.00 20.00
ATOM   1277  CD2  PHE A 960      76.367  57.901  21.792  1.00 20.00
ATOM   1278  CE1  PHE A 960      77.349  55.308  21.743  1.00 20.00
ATOM   1279  CE2  PHE A 960      77.148  57.442  20.720  1.00 20.00
ATOM   1280  CZ   PHE A 960      77.636  56.142  20.704  1.00 20.00
ATOM   1282  N    ILE A 961      74.308  60.532  25.068  1.00 20.00
ATOM   1283  CA   ILE A 961      73.212  61.377  25.623  1.00 20.00
ATOM   1284  C    ILE A 961      72.076  61.460  24.611  1.00 20.00
ATOM   1285  O    ILE A 961      72.341  61.698  23.434  1.00 20.00
ATOM   1286  CB   ILE A 961      73.631  62.832  25.918  1.00 20.00
ATOM   1287  CG1  ILE A 961      74.862  62.886  26.840  1.00 20.00
ATOM   1288  CG2  ILE A 961      72.489  63.547  26.600  1.00 20.00
ATOM   1289  CD1  ILE A 961      75.935  63.855  26.373  1.00 20.00
ATOM   1291  N    HIS A 962      70.821  61.314  25.049  1.00 20.00
ATOM   1292  CA   HIS A 962      69.704  61.307  24.088  1.00 20.00
ATOM   1293  C    HIS A 962      69.158  62.604  23.535  1.00 20.00
ATOM   1294  O    HIS A 962      69.296  62.872  22.344  1.00 20.00
ATOM   1295  CB   HIS A 962      68.515  60.516  24.641  1.00 20.00
ATOM   1296  CG   HIS A 962      67.658  59.896  23.580  1.00 20.00
ATOM   1297  ND1  HIS A 962      67.259  58.586  23.621  1.00 20.00
ATOM   1298  CD2  HIS A 962      67.192  60.388  22.416  1.00 20.00
ATOM   1299  CE1  HIS A 962      66.589  58.290  22.528  1.00 20.00
ATOM   1300  NE2  HIS A 962      66.538  59.369  21.780  1.00 20.00
ATOM   1304  N    ARG A 963      68.502  63.363  24.413  1.00 20.00
ATOM   1305  CA   ARG A 963      67.848  64.665  24.122  1.00 20.00
ATOM   1306  C    ARG A 963      66.653  64.636  23.125  1.00 20.00
ATOM   1307  O    ARG A 963      66.561  65.380  22.147  1.00 20.00
ATOM   1308  CB   ARG A 963      68.909  65.724  23.726  1.00 20.00
ATOM   1309  CG   ARG A 963      69.366  65.645  22.334  1.00 20.00
ATOM   1310  CD   ARG A 963      70.710  66.180  22.216  1.00 20.00
ATOM   1311  NE   ARG A 963      71.391  65.521  21.127  1.00 20.00
ATOM   1312  CZ   ARG A 963      71.002  65.603  19.873  1.00 20.00
ATOM   1313  NH1  ARG A 963      69.946  66.323  19.584  1.00 20.00
ATOM   1314  NH2  ARG A 963      71.648  64.941  18.925  1.00 20.00
ATOM   1321  N    ASN A 964      65.705  63.767  23.408  1.00 20.00
ATOM   1322  CA   ASN A 964      64.536  63.623  22.545  1.00 20.00
ATOM   1323  C    ASN A 964      63.904  62.262  22.803  1.00 20.00
ATOM   1324  O    ASN A 964      63.497  61.558  21.890  1.00 20.00
ATOM   1325  CB   ASN A 964      64.890  63.763  21.054  1.00 20.00
ATOM   1326  CG   ASN A 964      63.647  63.940  20.206  1.00 20.00
ATOM   1327  OD1  ASN A 964      62.565  64.079  20.780  1.00 20.00
ATOM   1328  ND2  ASN A 964      63.769  63.939  18.866  1.00 20.00
ATOM   1332  N    LEU A 965      63.861  61.914  24.081  1.00 20.00
ATOM   1333  CA   LEU A 965      63.291  60.665  24.546  1.00 20.00
```

FIG. 4S

| ATOM | 1334 | C   | LEU | A | 965 | 61.884 | 61.116 | 24.926 | 1.00 | 20.00 |
| ATOM | 1335 | O   | LEU | A | 965 | 61.701 | 62.119 | 25.629 | 1.00 | 20.00 |
| ATOM | 1336 | CB  | LEU | A | 965 | 64.079 | 60.172 | 25.769 | 1.00 | 20.00 |
| ATOM | 1337 | CG  | LEU | A | 965 | 64.292 | 58.716 | 26.189 | 1.00 | 20.00 |
| ATOM | 1338 | CD1 | LEU | A | 965 | 64.689 | 57.802 | 25.040 | 1.00 | 20.00 |
| ATOM | 1339 | CD2 | LEU | A | 965 | 65.320 | 58.728 | 27.276 | 1.00 | 20.00 |
| ATOM | 1341 | N   | ALA | A | 966 | 60.905 | 60.381 | 24.412 | 1.00 | 20.00 |
| ATOM | 1342 | CA  | ALA | A | 966 | 59.511 | 60.666 | 24.605 | 1.00 | 20.00 |
| ATOM | 1343 | C   | ALA | A | 966 | 58.812 | 59.674 | 23.677 | 1.00 | 20.00 |
| ATOM | 1344 | O   | ALA | A | 966 | 59.379 | 59.250 | 22.667 | 1.00 | 20.00 |
| ATOM | 1345 | CB  | ALA | A | 966 | 59.244 | 62.056 | 24.189 | 1.00 | 20.00 |
| ATOM | 1347 | N   | ALA | A | 967 | 57.581 | 59.320 | 24.014 | 1.00 | 20.00 |
| ATOM | 1348 | CA  | ALA | A | 967 | 56.826 | 58.358 | 23.242 | 1.00 | 20.00 |
| ATOM | 1349 | C   | ALA | A | 967 | 56.842 | 58.489 | 21.740 | 1.00 | 20.00 |
| ATOM | 1350 | O   | ALA | A | 967 | 57.050 | 57.521 | 21.044 | 1.00 | 20.00 |
| ATOM | 1351 | CB  | ALA | A | 967 | 55.375 | 58.306 | 23.721 | 1.00 | 20.00 |
| ATOM | 1353 | N   | ARG | A | 968 | 56.606 | 59.671 | 21.205 | 1.00 | 20.00 |
| ATOM | 1354 | CA  | ARG | A | 968 | 56.580 | 59.697 | 19.759 | 1.00 | 20.00 |
| ATOM | 1355 | C   | ARG | A | 968 | 57.802 | 59.015 | 19.160 | 1.00 | 20.00 |
| ATOM | 1356 | O   | ARG | A | 968 | 57.751 | 58.532 | 18.041 | 1.00 | 20.00 |
| ATOM | 1357 | CB  | ARG | A | 968 | 56.455 | 61.123 | 19.226 | 1.00 | 20.00 |
| ATOM | 1358 | CG  | ARG | A | 968 | 57.264 | 62.162 | 19.987 | 1.00 | 20.00 |
| ATOM | 1359 | CD  | ARG | A | 968 | 57.684 | 63.354 | 19.087 | 1.00 | 20.00 |
| ATOM | 1360 | NE  | ARG | A | 968 | 58.467 | 64.376 | 19.784 | 1.00 | 20.00 |
| ATOM | 1361 | CZ  | ARG | A | 968 | 58.098 | 64.982 | 20.904 | 1.00 | 20.00 |
| ATOM | 1362 | NH1 | ARG | A | 968 | 56.937 | 64.698 | 21.492 | 1.00 | 20.00 |
| ATOM | 1363 | NH2 | ARG | A | 968 | 58.929 | 65.828 | 21.473 | 1.00 | 20.00 |
| ATOM | 1370 | N   | ASN | A | 969 | 58.881 | 58.913 | 19.931 | 1.00 | 20.00 |
| ATOM | 1371 | CA  | ASN | A | 969 | 60.122 | 58.388 | 19.383 | 1.00 | 20.00 |
| ATOM | 1372 | C   | ASN | A | 969 | 60.608 | 57.008 | 19.754 | 1.00 | 20.00 |
| ATOM | 1373 | O   | ASN | A | 969 | 61.716 | 56.647 | 19.413 | 1.00 | 20.00 |
| ATOM | 1374 | CB  | ASN | A | 969 | 61.232 | 59.407 | 19.630 | 1.00 | 20.00 |
| ATOM | 1375 | CG  | ASN | A | 969 | 60.873 | 60.787 | 19.118 | 1.00 | 20.00 |
| ATOM | 1376 | OD1 | ASN | A | 969 | 60.733 | 61.724 | 19.892 | 1.00 | 20.00 |
| ATOM | 1377 | ND2 | ASN | A | 969 | 60.702 | 60.910 | 17.802 | 1.00 | 20.00 |
| ATOM | 1381 | N   | ILE | A | 970 | 59.775 | 56.249 | 20.443 | 1.00 | 20.00 |
| ATOM | 1382 | CA  | ILE | A | 970 | 60.073 | 54.912 | 20.851 | 1.00 | 20.00 |
| ATOM | 1383 | C   | ILE | A | 970 | 59.153 | 54.057 | 20.034 | 1.00 | 20.00 |
| ATOM | 1384 | O   | ILE | A | 970 | 58.006 | 54.384 | 19.930 | 1.00 | 20.00 |
| ATOM | 1385 | CB  | ILE | A | 970 | 59.717 | 54.770 | 22.294 | 1.00 | 20.00 |
| ATOM | 1386 | CG1 | ILE | A | 970 | 60.699 | 55.565 | 23.110 | 1.00 | 20.00 |
| ATOM | 1387 | CG2 | ILE | A | 970 | 59.730 | 53.328 | 22.724 | 1.00 | 20.00 |
| ATOM | 1388 | CD1 | ILE | A | 970 | 60.800 | 55.095 | 24.515 | 1.00 | 20.00 |
| ATOM | 1390 | N   | LEU | A | 971 | 59.626 | 52.971 | 19.435 | 1.00 | 20.00 |
| ATOM | 1391 | CA  | LEU | A | 971 | 58.733 | 52.086 | 18.656 | 1.00 | 20.00 |
| ATOM | 1392 | C   | LEU | A | 971 | 58.290 | 50.891 | 19.444 | 1.00 | 20.00 |
| ATOM | 1393 | O   | LEU | A | 971 | 58.776 | 50.653 | 20.523 | 1.00 | 20.00 |
| ATOM | 1394 | CB  | LEU | A | 971 | 59.422 | 51.582 | 17.418 | 1.00 | 20.00 |
| ATOM | 1395 | CG  | LEU | A | 971 | 59.930 | 52.837 | 16.785 | 1.00 | 20.00 |
| ATOM | 1396 | CD1 | LEU | A | 971 | 61.161 | 52.652 | 16.019 | 1.00 | 20.00 |
| ATOM | 1397 | CD2 | LEU | A | 971 | 58.844 | 53.290 | 15.909 | 1.00 | 20.00 |
| ATOM | 1399 | N   | VAL | A | 972 | 57.305 | 50.171 | 18.929 | 1.00 | 20.00 |
| ATOM | 1400 | CA  | VAL | A | 972 | 56.894 | 48.941 | 19.594 | 1.00 | 20.00 |
| ATOM | 1401 | C   | VAL | A | 972 | 57.044 | 47.883 | 18.541 | 1.00 | 20.00 |
| ATOM | 1402 | O   | VAL | A | 972 | 56.221 | 47.793 | 17.661 | 1.00 | 20.00 |
| ATOM | 1403 | CB  | VAL | A | 972 | 55.492 | 48.932 | 20.043 | 1.00 | 20.00 |
| ATOM | 1404 | CG1 | VAL | A | 972 | 55.224 | 47.588 | 20.632 | 1.00 | 20.00 |

FIG. 4T

| | | | | | | | | |
|---|---|---|---|---|---|---|---|---|
| ATOM | 1405 | CG2 | VAL | A | 972 | 55.264 | 50.012 | 21.107 | 1.00 20.00 |
| ATOM | 1407 | N | GLY | A | 973 | 58.127 | 47.106 | 18.614 | 1.00 20.00 |
| ATOM | 1408 | CA | GLY | A | 973 | 58.375 | 46.109 | 17.614 | 1.00 20.00 |
| ATOM | 1409 | C | GLY | A | 973 | 58.065 | 44.685 | 17.980 | 1.00 20.00 |
| ATOM | 1410 | O | GLY | A | 973 | 57.370 | 44.393 | 18.927 | 1.00 20.00 |
| ATOM | 1412 | N | GLU | A | 974 | 58.612 | 43.793 | 17.178 | 1.00 20.00 |
| ATOM | 1413 | CA | GLU | A | 974 | 58.445 | 42.383 | 17.357 | 1.00 20.00 |
| ATOM | 1414 | C | GLU | A | 974 | 58.379 | 41.981 | 18.795 | 1.00 20.00 |
| ATOM | 1415 | O | GLU | A | 974 | 59.246 | 42.274 | 19.572 | 1.00 20.00 |
| ATOM | 1416 | CB | GLU | A | 974 | 59.568 | 41.648 | 16.671 | 1.00 20.00 |
| ATOM | 1417 | CG | GLU | A | 974 | 59.187 | 41.010 | 15.343 | 1.00 20.00 |
| ATOM | 1418 | CD | GLU | A | 974 | 57.698 | 41.173 | 14.936 | 1.00 20.00 |
| ATOM | 1419 | OE1 | GLU | A | 974 | 56.763 | 40.870 | 15.733 | 1.00 20.00 |
| ATOM | 1420 | OE2 | GLU | A | 974 | 57.467 | 41.592 | 13.780 | 1.00 20.00 |
| ATOM | 1422 | N | ASN | A | 975 | 57.305 | 41.316 | 19.147 | 1.00 20.00 |
| ATOM | 1423 | CA | ASN | A | 975 | 57.119 | 40.830 | 20.483 | 1.00 20.00 |
| ATOM | 1424 | C | ASN | A | 975 | 56.741 | 41.832 | 21.554 | 1.00 20.00 |
| ATOM | 1425 | O | ASN | A | 975 | 56.811 | 41.544 | 22.758 | 1.00 20.00 |
| ATOM | 1426 | CB | ASN | A | 975 | 58.333 | 40.006 | 20.864 | 1.00 20.00 |
| ATOM | 1427 | CG | ASN | A | 975 | 58.189 | 38.519 | 20.428 | 1.00 20.00 |
| ATOM | 1428 | OD1 | ASN | A | 975 | 58.243 | 37.639 | 21.263 | 1.00 20.00 |
| ATOM | 1429 | ND2 | ASN | A | 975 | 57.988 | 38.266 | 19.136 | 1.00 20.00 |
| ATOM | 1433 | N | TYR | A | 976 | 56.299 | 43.003 | 21.103 | 1.00 20.00 |
| ATOM | 1434 | CA | TYR | A | 976 | 55.839 | 44.047 | 21.988 | 1.00 20.00 |
| ATOM | 1435 | C | TYR | A | 976 | 56.946 | 44.589 | 22.839 | 1.00 20.00 |
| ATOM | 1436 | O | TYR | A | 976 | 56.797 | 44.863 | 24.016 | 1.00 20.00 |
| ATOM | 1437 | CB | TYR | A | 976 | 54.684 | 43.498 | 22.830 | 1.00 20.00 |
| ATOM | 1438 | CG | TYR | A | 976 | 53.466 | 43.191 | 21.993 | 1.00 20.00 |
| ATOM | 1439 | CD1 | TYR | A | 976 | 52.878 | 41.927 | 22.017 | 1.00 20.00 |
| ATOM | 1440 | CD2 | TYR | A | 976 | 52.939 | 44.157 | 21.112 | 1.00 20.00 |
| ATOM | 1441 | CE1 | TYR | A | 976 | 51.801 | 41.624 | 21.182 | 1.00 20.00 |
| ATOM | 1442 | CE2 | TYR | A | 976 | 51.874 | 43.870 | 20.279 | 1.00 20.00 |
| ATOM | 1443 | CZ | TYR | A | 976 | 51.306 | 42.604 | 20.307 | 1.00 20.00 |
| ATOM | 1444 | OH | TYR | A | 976 | 50.273 | 42.291 | 19.427 | 1.00 20.00 |
| ATOM | 1447 | N | VAL | A | 977 | 58.070 | 44.787 | 22.191 | 1.00 20.00 |
| ATOM | 1448 | CA | VAL | A | 977 | 59.260 | 45.295 | 22.845 | 1.00 20.00 |
| ATOM | 1449 | C | VAL | A | 977 | 59.536 | 46.766 | 22.497 | 1.00 20.00 |
| ATOM | 1450 | O | VAL | A | 977 | 59.446 | 47.195 | 21.355 | 1.00 20.00 |
| ATOM | 1451 | CB | VAL | A | 977 | 60.514 | 44.377 | 22.485 | 1.00 20.00 |
| ATOM | 1452 | CG1 | VAL | A | 977 | 61.768 | 44.854 | 23.182 | 1.00 20.00 |
| ATOM | 1453 | CG2 | VAL | A | 977 | 60.230 | 42.943 | 22.890 | 1.00 20.00 |
| ATOM | 1455 | N | ALA | A | 978 | 59.839 | 47.529 | 23.525 | 1.00 20.00 |
| ATOM | 1456 | CA | ALA | A | 978 | 60.174 | 48.898 | 23.328 | 1.00 20.00 |
| ATOM | 1457 | C | ALA | A | 978 | 61.434 | 48.921 | 22.476 | 1.00 20.00 |
| ATOM | 1458 | O | ALA | A | 978 | 62.242 | 48.026 | 22.527 | 1.00 20.00 |
| ATOM | 1459 | CB | ALA | A | 978 | 60.423 | 49.546 | 24.643 | 1.00 20.00 |
| ATOM | 1461 | N | LYS | A | 979 | 61.597 | 49.926 | 21.653 | 1.00 20.00 |
| ATOM | 1462 | CA | LYS | A | 979 | 62.791 | 50.005 | 20.864 | 1.00 20.00 |
| ATOM | 1463 | C | LYS | A | 979 | 63.098 | 51.476 | 20.826 | 1.00 20.00 |
| ATOM | 1464 | O | LYS | A | 979 | 62.263 | 52.262 | 20.387 | 1.00 20.00 |
| ATOM | 1465 | CB | LYS | A | 979 | 62.551 | 49.492 | 19.448 | 1.00 20.00 |
| ATOM | 1466 | CG | LYS | A | 979 | 62.076 | 48.043 | 19.369 | 1.00 20.00 |
| ATOM | 1467 | CD | LYS | A | 979 | 63.115 | 47.009 | 19.864 | 1.00 20.00 |
| ATOM | 1468 | CE | LYS | A | 979 | 63.866 | 46.343 | 18.708 | 1.00 20.00 |
| ATOM | 1469 | NZ | LYS | A | 979 | 63.212 | 45.122 | 18.253 | 1.00 20.00 |
| ATOM | 1474 | N | ILE | A | 980 | 64.274 | 51.873 | 21.302 | 1.00 20.00 |
| ATOM | 1475 | CA | ILE | A | 980 | 64.615 | 53.287 | 21.240 | 1.00 20.00 |

FIG. 4U

```
ATOM   1476  C    ILE A 980      65.131  53.691  19.858  1.00 20.00
ATOM   1477  O    ILE A 980      65.938  53.004  19.233  1.00 20.00
ATOM   1478  CB   ILE A 980      65.671  53.665  22.263  1.00 20.00
ATOM   1479  CG1  ILE A 980      65.205  53.311  23.667  1.00 20.00
ATOM   1480  CG2  ILE A 980      65.943  55.135  22.173  1.00 20.00
ATOM   1481  CD1  ILE A 980      66.262  53.521  24.730  1.00 20.00
ATOM   1483  N    ALA A 981      64.629  54.815  19.383  1.00 20.00
ATOM   1484  CA   ALA A 981      65.038  55.342  18.097  1.00 20.00
ATOM   1485  C    ALA A 981      65.244  56.854  18.141  1.00 20.00
ATOM   1486  O    ALA A 981      65.039  57.530  19.172  1.00 20.00
ATOM   1487  CB   ALA A 981      64.024  55.024  17.060  1.00 20.00
ATOM   1489  N    ASP A 982      65.610  57.362  16.973  1.00 20.00
ATOM   1490  CA   ASP A 982      65.888  58.763  16.721  1.00 20.00
ATOM   1491  C    ASP A 982      66.653  59.517  17.801  1.00 20.00
ATOM   1492  O    ASP A 982      66.041  60.135  18.684  1.00 20.00
ATOM   1493  CB   ASP A 982      64.620  59.527  16.416  1.00 20.00
ATOM   1494  CG   ASP A 982      64.911  60.946  16.122  1.00 20.00
ATOM   1495  OD1  ASP A 982      65.455  61.240  15.031  1.00 20.00
ATOM   1496  OD2  ASP A 982      64.626  61.766  16.998  1.00 20.00
ATOM   1498  N    PHE A 983      67.988  59.525  17.706  1.00 20.00
ATOM   1499  CA   PHE A 983      68.770  60.223  18.733  1.00 20.00
ATOM   1500  C    PHE A 983      70.123  60.755  18.312  1.00 20.00
ATOM   1501  O    PHE A 983      70.565  60.712  17.155  1.00 20.00
ATOM   1502  CB   PHE A 983      69.001  59.327  19.948  1.00 20.00
ATOM   1503  CG   PHE A 983      69.411  57.928  19.589  1.00 20.00
ATOM   1504  CD1  PHE A 983      68.856  57.280  18.452  1.00 20.00
ATOM   1505  CD2  PHE A 983      70.310  57.244  20.375  1.00 20.00
ATOM   1506  CE1  PHE A 983      69.181  55.987  18.106  1.00 20.00
ATOM   1507  CE2  PHE A 983      70.648  55.939  20.044  1.00 20.00
ATOM   1508  CZ   PHE A 983      70.075  55.308  18.895  1.00 20.00
ATOM   1510  N    GLY A 984      70.797  61.274  19.305  1.00 20.00
ATOM   1511  CA   GLY A 984      72.082  61.799  19.010  1.00 20.00
ATOM   1512  C    GLY A 984      73.058  60.661  18.913  1.00 20.00
ATOM   1513  O    GLY A 984      72.980  59.633  19.633  1.00 20.00
ATOM   1515  N    LEU A 985      73.978  60.846  17.977  1.00 20.00
ATOM   1516  CA   LEU A 985      75.055  59.913  17.812  1.00 20.00
ATOM   1517  C    LEU A 985      76.044  60.741  18.669  1.00 20.00
ATOM   1518  O    LEU A 985      77.236  60.872  18.323  1.00 20.00
ATOM   1519  CB   LEU A 985      75.483  59.871  16.342  1.00 20.00
ATOM   1520  CG   LEU A 985      75.093  58.770  15.337  1.00 20.00
ATOM   1521  CD1  LEU A 985      75.645  57.463  15.830  1.00 20.00
ATOM   1522  CD2  LEU A 985      73.579  58.659  15.129  1.00 20.00
ATOM   1524  N    SER A 986      75.561  61.306  19.786  1.00 20.00
ATOM   1525  CA   SER A 986      76.443  62.118  20.611  1.00 20.00
ATOM   1526  C    SER A 986      76.926  61.629  21.970  1.00 20.00
ATOM   1527  O    SER A 986      76.169  61.709  22.937  1.00 20.00
ATOM   1528  CB   SER A 986      75.850  63.504  20.815  1.00 20.00
ATOM   1529  OG   SER A 986      76.764  64.504  20.379  1.00 20.00
ATOM   1532  N    ARG A 987      78.189  61.152  22.037  1.00 20.00
ATOM   1533  CA   ARG A 987      78.763  60.709  23.306  1.00 20.00
ATOM   1534  C    ARG A 987      79.511  61.893  23.794  1.00 20.00
ATOM   1535  O    ARG A 987      80.191  62.578  23.059  1.00 20.00
ATOM   1536  CB   ARG A 987      79.752  59.525  23.214  1.00 20.00
ATOM   1537  CG   ARG A 987      79.583  58.534  22.078  1.00 20.00
ATOM   1538  CD   ARG A 987      80.953  58.120  21.459  1.00 20.00
ATOM   1539  NE   ARG A 987      81.908  57.509  22.396  1.00 20.00
ATOM   1540  CZ   ARG A 987      82.932  56.731  22.021  1.00 20.00
```

FIG. 4V

```
ATOM   1541  NH1  ARG A 987      83.127  56.473  20.738  1.00 20.00
ATOM   1542  NH2  ARG A 987      83.761  56.206  22.936  1.00 20.00
ATOM   1549  N    GLY A 988      79.387  62.122  25.068  1.00 20.00
ATOM   1550  CA   GLY A 988      80.028  63.260  25.633  1.00 20.00
ATOM   1551  C    GLY A 988      79.480  63.223  27.024  1.00 20.00
ATOM   1552  O    GLY A 988      79.050  62.151  27.453  1.00 20.00
ATOM   1554  N    GLN A 989      79.521  64.369  27.704  1.00 20.00
ATOM   1555  CA   GLN A 989      79.020  64.579  29.053  1.00 20.00
ATOM   1556  C    GLN A 989      78.115  65.864  29.062  1.00 20.00
ATOM   1557  O    GLN A 989      77.565  66.257  30.075  1.00 20.00
ATOM   1558  CB   GLN A 989      80.219  64.739  29.974  1.00 20.00
ATOM   1559  CG   GLN A 989      79.924  65.292  31.348  1.00 20.00
ATOM   1560  CD   GLN A 989      81.068  66.095  31.985  1.00 20.00
ATOM   1561  OE1  GLN A 989      81.783  66.897  31.332  1.00 20.00
ATOM   1562  NE2  GLN A 989      81.233  65.891  33.273  1.00 20.00
ATOM   1566  N    GLU A 990      77.933  66.496  27.908  1.00 20.00
ATOM   1567  CA   GLU A 990      77.185  67.704  27.889  1.00 20.00
ATOM   1568  C    GLU A 990      76.348  68.030  26.675  1.00 20.00
ATOM   1569  O    GLU A 990      75.199  68.420  26.836  1.00 20.00
ATOM   1570  CB   GLU A 990      78.134  68.853  28.117  1.00 20.00
ATOM   1571  CG   GLU A 990      78.194  69.367  29.499  1.00 20.00
ATOM   1572  CD   GLU A 990      79.467  68.991  30.151  1.00 20.00
ATOM   1573  OE1  GLU A 990      80.437  68.623  29.443  1.00 20.00
ATOM   1574  OE2  GLU A 990      79.486  69.061  31.387  1.00 20.00
ATOM   1576  N    VAL A 991      76.878  67.895  25.469  1.00 20.00
ATOM   1577  CA   VAL A 991      76.098  68.270  24.274  1.00 20.00
ATOM   1578  C    VAL A 991      75.373  69.616  24.400  1.00 20.00
ATOM   1579  O    VAL A 991      74.538  69.823  25.274  1.00 20.00
ATOM   1580  CB   VAL A 991      74.965  67.324  23.910  1.00 20.00
ATOM   1581  CG1  VAL A 991      74.620  67.527  22.479  1.00 20.00
ATOM   1582  CG2  VAL A 991      75.323  65.922  24.159  1.00 20.00
ATOM   1584  N    TYR A 992      75.674  70.528  23.504  1.00 20.00
ATOM   1585  CA   TYR A 992      74.997  71.780  23.514  1.00 20.00
ATOM   1586  C    TYR A 992      74.389  71.784  22.118  1.00 20.00
ATOM   1587  O    TYR A 992      75.036  71.437  21.138  1.00 20.00
ATOM   1588  CB   TYR A 992      76.003  72.945  23.687  1.00 20.00
ATOM   1589  CG   TYR A 992      75.520  74.227  23.027  1.00 20.00
ATOM   1590  CD1  TYR A 992      74.579  75.023  23.654  1.00 20.00
ATOM   1591  CD2  TYR A 992      75.804  74.487  21.702  1.00 20.00
ATOM   1592  CE1  TYR A 992      73.939  75.989  22.987  1.00 20.00
ATOM   1593  CE2  TYR A 992      75.160  75.453  21.044  1.00 20.00
ATOM   1594  CZ   TYR A 992      74.218  76.200  21.690  1.00 20.00
ATOM   1595  OH   TYR A 992      73.552  77.196  21.023  1.00 20.00
ATOM   1598  N    VAL A 993      73.131  72.161  22.020  1.00 20.00
ATOM   1599  CA   VAL A 993      72.482  72.226  20.712  1.00 20.00
ATOM   1600  C    VAL A 993      71.311  73.168  21.008  1.00 20.00
ATOM   1601  O    VAL A 993      70.748  73.116  22.101  1.00 20.00
ATOM   1602  CB   VAL A 993      72.102  70.746  20.159  1.00 20.00
ATOM   1603  CG1  VAL A 993      71.570  69.843  21.226  1.00 20.00
ATOM   1604  CG2  VAL A 993      71.121  70.843  19.076  1.00 20.00
ATOM   1606  N    LYS A 994      70.990  74.076  20.082  1.00 20.00
ATOM   1607  CA   LYS A 994      69.917  75.099  20.335  1.00 20.00
ATOM   1608  C    LYS A 994      69.171  75.616  19.093  1.00 20.00
ATOM   1609  O    LYS A 994      69.784  76.097  18.105  1.00 20.00
ATOM   1610  CB   LYS A 994      70.508  76.336  21.083  1.00 20.00
ATOM   1611  CG   LYS A 994      69.513  77.422  21.498  1.00 20.00
ATOM   1612  CD   LYS A 994      69.827  78.812  20.847  1.00 20.00
```

FIG. 4W

| | | | | | | | | |
|---|---|---|---|---|---|---|---|---|
| ATOM | 1613 | CE | LYS | A | 994 | 69.627 | 80.017 | 21.856 | 1.00 20.00 |
| ATOM | 1614 | NZ | LYS | A | 994 | 70.649 | 81.165 | 21.795 | 1.00 20.00 |
| ATOM | 1619 | N | LYS | A | 995 | 67.841 | 75.573 | 19.202 | 1.00 20.00 |
| ATOM | 1620 | CA | LYS | A | 995 | 66.914 | 75.962 | 18.132 | 1.00 20.00 |
| ATOM | 1621 | C | LYS | A | 995 | 65.884 | 74.827 | 18.184 | 1.00 20.00 |
| ATOM | 1622 | O | LYS | A | 995 | 65.303 | 74.470 | 17.139 | 1.00 20.00 |
| ATOM | 1623 | CB | LYS | A | 995 | 67.633 | 75.996 | 16.736 | 1.00 20.00 |
| ATOM | 1624 | OXT | LYS | A | 995 | 65.718 | 74.295 | 19.306 | 1.00 20.00 |
| ATOM | 1626 | N | PRO | A | 001 | 59.536 | 69.751 | 22.343 | 1.00 20.00 |
| ATOM | 1627 | CA | PRO | A | 001 | 60.339 | 69.285 | 23.473 | 1.00 20.00 |
| ATOM | 1628 | C | PRO | A | 001 | 60.137 | 70.032 | 24.772 | 1.00 20.00 |
| ATOM | 1629 | O | PRO | A | 001 | 60.361 | 69.470 | 25.821 | 1.00 20.00 |
| ATOM | 1630 | CB | PRO | A | 001 | 61.803 | 69.328 | 23.049 | 1.00 20.00 |
| ATOM | 1631 | CG | PRO | A | 001 | 61.735 | 69.311 | 21.525 | 1.00 20.00 |
| ATOM | 1632 | CD | PRO | A | 001 | 60.238 | 69.446 | 21.080 | 1.00 20.00 |
| ATOM | 1635 | N | VAL | A | 002 | 59.712 | 71.287 | 24.728 | 1.00 20.00 |
| ATOM | 1636 | CA | VAL | A | 002 | 59.503 | 72.082 | 25.958 | 1.00 20.00 |
| ATOM | 1637 | C | VAL | A | 002 | 58.748 | 71.338 | 27.019 | 1.00 20.00 |
| ATOM | 1638 | O | VAL | A | 002 | 58.868 | 71.595 | 28.206 | 1.00 20.00 |
| ATOM | 1639 | CB | VAL | A | 002 | 58.690 | 73.333 | 25.706 | 1.00 20.00 |
| ATOM | 1640 | CG1 | VAL | A | 002 | 58.862 | 74.285 | 26.868 | 1.00 20.00 |
| ATOM | 1641 | CG2 | VAL | A | 002 | 59.105 | 73.960 | 24.419 | 1.00 20.00 |
| ATOM | 1643 | N | ARG | A | 003 | 57.939 | 70.406 | 26.586 | 1.00 20.00 |
| ATOM | 1644 | CA | ARG | A | 003 | 57.158 | 69.637 | 27.519 | 1.00 20.00 |
| ATOM | 1645 | C | ARG | A | 003 | 57.966 | 68.497 | 28.085 | 1.00 20.00 |
| ATOM | 1646 | O | ARG | A | 003 | 57.686 | 68.013 | 29.163 | 1.00 20.00 |
| ATOM | 1647 | CB | ARG | A | 003 | 55.943 | 69.145 | 26.797 | 1.00 20.00 |
| ATOM | 1648 | CG | ARG | A | 003 | 55.600 | 70.041 | 25.655 | 1.00 20.00 |
| ATOM | 1649 | CD | ARG | A | 003 | 54.176 | 69.825 | 25.386 | 1.00 20.00 |
| ATOM | 1650 | NE | ARG | A | 003 | 53.404 | 70.556 | 26.347 | 1.00 20.00 |
| ATOM | 1651 | CZ | ARG | A | 003 | 52.340 | 71.236 | 25.991 | 1.00 20.00 |
| ATOM | 1652 | NH1 | ARG | A | 003 | 52.002 | 71.218 | 24.710 | 1.00 20.00 |
| ATOM | 1653 | NH2 | ARG | A | 003 | 51.653 | 71.922 | 26.889 | 1.00 20.00 |
| ATOM | 1660 | N | TRP | A | 004 | 58.998 | 68.136 | 27.340 | 1.00 20.00 |
| ATOM | 1661 | CA | TRP | A | 004 | 59.930 | 67.076 | 27.691 | 1.00 20.00 |
| ATOM | 1662 | C | TRP | A | 004 | 61.183 | 67.519 | 28.368 | 1.00 20.00 |
| ATOM | 1663 | O | TRP | A | 004 | 61.602 | 66.921 | 29.361 | 1.00 20.00 |
| ATOM | 1664 | CB | TRP | A | 004 | 60.293 | 66.257 | 26.452 | 1.00 20.00 |
| ATOM | 1665 | CG | TRP | A | 004 | 59.275 | 65.242 | 26.277 | 1.00 20.00 |
| ATOM | 1666 | CD1 | TRP | A | 004 | 59.163 | 64.113 | 27.004 | 1.00 20.00 |
| ATOM | 1667 | CD2 | TRP | A | 004 | 58.027 | 65.395 | 25.588 | 1.00 20.00 |
| ATOM | 1668 | NE1 | TRP | A | 004 | 57.932 | 63.567 | 26.839 | 1.00 20.00 |
| ATOM | 1669 | CE2 | TRP | A | 004 | 57.208 | 64.336 | 25.976 | 1.00 20.00 |
| ATOM | 1670 | CE3 | TRP | A | 004 | 57.518 | 66.339 | 24.696 | 1.00 20.00 |
| ATOM | 1671 | CZ2 | TRP | A | 004 | 55.911 | 64.185 | 25.506 | 1.00 20.00 |
| ATOM | 1672 | CZ3 | TRP | A | 004 | 56.192 | 66.185 | 24.224 | 1.00 20.00 |
| ATOM | 1673 | CH2 | TRP | A | 004 | 55.426 | 65.126 | 24.632 | 1.00 20.00 |
| ATOM | 1676 | N | MET | A | 005 | 61.767 | 68.590 | 27.874 | 1.00 20.00 |
| ATOM | 1677 | CA | MET | A | 005 | 63.025 | 69.060 | 28.428 | 1.00 20.00 |
| ATOM | 1678 | C | MET | A | 005 | 63.185 | 69.238 | 29.950 | 1.00 20.00 |
| ATOM | 1679 | O | MET | A | 005 | 62.268 | 69.013 | 30.733 | 1.00 20.00 |
| ATOM | 1680 | CB | MET | A | 005 | 63.433 | 70.335 | 27.699 | 1.00 20.00 |
| ATOM | 1681 | CG | MET | A | 005 | 64.246 | 70.052 | 26.452 | 1.00 20.00 |
| ATOM | 1682 | SD | MET | A | 005 | 63.856 | 71.198 | 25.171 | 1.00 20.00 |
| ATOM | 1683 | CE | MET | A | 005 | 64.138 | 72.700 | 26.081 | 1.00 20.00 |
| ATOM | 1685 | N | ALA | A | 006 | 64.402 | 69.581 | 30.358 | 1.00 20.00 |
| ATOM | 1686 | CA | ALA | A | 006 | 64.714 | 69.835 | 31.765 | 1.00 20.00 |

FIG. 4X

```
ATOM   1687  C    ALA A 006      65.147  71.295  31.859  1.00 20.00
ATOM   1688  O    ALA A 006      65.854  71.804  30.965  1.00 20.00
ATOM   1689  CB   ALA A 006      65.819  68.944  32.215  1.00 20.00
ATOM   1691  N    ILE A 007      64.694  71.961  32.930  1.00 20.00
ATOM   1692  CA   ILE A 007      64.982  73.368  33.167  1.00 20.00
ATOM   1693  C    ILE A 007      66.361  73.633  32.607  1.00 20.00
ATOM   1694  O    ILE A 007      66.500  74.388  31.663  1.00 20.00
ATOM   1695  CB   ILE A 007      64.876  73.725  34.674  1.00 20.00
ATOM   1696  CG1  ILE A 007      65.897  72.943  35.501  1.00 20.00
ATOM   1697  CG2  ILE A 007      63.518  73.339  35.193  1.00 20.00
ATOM   1698  CD1  ILE A 007      66.781  73.773  36.516  1.00 20.00
ATOM   1700  N    GLU A 008      67.361  72.921  33.131  1.00 20.00
ATOM   1701  CA   GLU A 008      68.768  73.052  32.719  1.00 20.00
ATOM   1702  C    GLU A 008      68.886  73.301  31.217  1.00 20.00
ATOM   1703  O    GLU A 008      69.401  74.319  30.811  1.00 20.00
ATOM   1704  CB   GLU A 008      69.565  71.799  33.174  1.00 20.00
ATOM   1705  CG   GLU A 008      69.424  70.540  32.296  1.00 20.00
ATOM   1706  CD   GLU A 008      69.290  69.267  33.131  1.00 20.00
ATOM   1707  OE1  GLU A 008      69.605  69.369  34.325  1.00 20.00
ATOM   1708  OE2  GLU A 008      68.867  68.187  32.613  1.00 20.00
ATOM   1710  N    SER A 009      68.388  72.388  30.384  1.00 20.00
ATOM   1711  CA   SER A 009      68.456  72.641  28.947  1.00 20.00
ATOM   1712  C    SER A 009      67.387  73.630  28.440  1.00 20.00
ATOM   1713  O    SER A 009      67.491  74.109  27.327  1.00 20.00
ATOM   1714  CB   SER A 009      68.424  71.329  28.129  1.00 20.00
ATOM   1715  OG   SER A 009      67.325  70.511  28.426  1.00 20.00
ATOM   1718  N    LEU A 010      66.361  73.915  29.246  1.00 20.00
ATOM   1719  CA   LEU A 010      65.328  74.909  28.869  1.00 20.00
ATOM   1720  C    LEU A 010      66.043  76.294  28.797  1.00 20.00
ATOM   1721  O    LEU A 010      65.881  77.047  27.816  1.00 20.00
ATOM   1722  CB   LEU A 010      64.213  74.966  29.928  1.00 20.00
ATOM   1723  CG   LEU A 010      62.880  74.229  29.760  1.00 20.00
ATOM   1724  CD1  LEU A 010      61.863  75.034  30.483  1.00 20.00
ATOM   1725  CD2  LEU A 010      62.459  74.066  28.330  1.00 20.00
ATOM   1727  N    ASN A 011      66.825  76.577  29.854  1.00 20.00
ATOM   1728  CA   ASN A 011      67.663  77.762  30.020  1.00 20.00
ATOM   1729  C    ASN A 011      68.799  77.692  28.983  1.00 20.00
ATOM   1730  O    ASN A 011      68.799  78.348  27.914  1.00 20.00
ATOM   1731  CB   ASN A 011      68.303  77.725  31.386  1.00 20.00
ATOM   1732  CG   ASN A 011      67.325  77.469  32.474  1.00 20.00
ATOM   1733  OD1  ASN A 011      66.150  77.759  32.316  1.00 20.00
ATOM   1734  ND2  ASN A 011      67.791  76.929  33.607  1.00 20.00
ATOM   1738  N    TYR A 012      69.774  76.859  29.325  1.00 20.00
ATOM   1739  CA   TYR A 012      70.918  76.611  28.481  1.00 20.00
ATOM   1740  C    TYR A 012      70.488  75.487  27.544  1.00 20.00
ATOM   1741  O    TYR A 012      69.908  74.499  28.020  1.00 20.00
ATOM   1742  CB   TYR A 012      72.047  76.179  29.370  1.00 20.00
ATOM   1743  CG   TYR A 012      71.787  76.590  30.784  1.00 20.00
ATOM   1744  CD1  TYR A 012      71.854  75.680  31.809  1.00 20.00
ATOM   1745  CD2  TYR A 012      71.474  77.879  31.097  1.00 20.00
ATOM   1746  CE1  TYR A 012      71.619  76.047  33.097  1.00 20.00
ATOM   1747  CE2  TYR A 012      71.246  78.242  32.357  1.00 20.00
ATOM   1748  CZ   TYR A 012      71.321  77.328  33.361  1.00 20.00
ATOM   1749  OH   TYR A 012      71.143  77.709  34.668  1.00 20.00
ATOM   1752  N    SER A 013      70.711  75.615  26.235  1.00 20.00
ATOM   1753  CA   SER A 013      70.309  74.544  25.335  1.00 20.00
ATOM   1754  C    SER A 013      71.274  73.385  25.467  1.00 20.00
```

FIG. 4Y

```
ATOM   1755  O    SER A 013      71.810  72.898  24.464  1.00 20.00
ATOM   1756  CB   SER A 013      70.291  75.025  23.898  1.00 20.00
ATOM   1757  OG   SER A 013      70.122  76.432  23.813  1.00 20.00
ATOM   1760  N    VAL A 014      71.469  72.957  26.713  1.00 20.00
ATOM   1761  CA   VAL A 014      72.378  71.890  27.084  1.00 20.00
ATOM   1762  C    VAL A 014      71.711  70.603  27.571  1.00 20.00
ATOM   1763  O    VAL A 014      70.895  70.613  28.493  1.00 20.00
ATOM   1764  CB   VAL A 014      73.316  72.316  28.230  1.00 20.00
ATOM   1765  CG1  VAL A 014      74.335  73.331  27.748  1.00 20.00
ATOM   1766  CG2  VAL A 014      72.490  72.849  29.394  1.00 20.00
ATOM   1768  N    TYR A 015      72.100  69.472  27.009  1.00 20.00
ATOM   1769  CA   TYR A 015      71.502  68.235  27.446  1.00 20.00
ATOM   1770  C    TYR A 015      72.543  67.266  28.029  1.00 20.00
ATOM   1771  O    TYR A 015      73.619  67.072  27.494  1.00 20.00
ATOM   1772  CB   TYR A 015      70.783  67.599  26.252  1.00 20.00
ATOM   1773  CG   TYR A 015      69.875  68.533  25.477  1.00 20.00
ATOM   1774  CD1  TYR A 015      70.194  68.918  24.179  1.00 20.00
ATOM   1775  CD2  TYR A 015      68.665  68.975  26.022  1.00 20.00
ATOM   1776  CE1  TYR A 015      69.334  69.718  23.416  1.00 20.00
ATOM   1777  CE2  TYR A 015      67.782  69.778  25.286  1.00 20.00
ATOM   1778  CZ   TYR A 015      68.116  70.150  23.968  1.00 20.00
ATOM   1779  OH   TYR A 015      67.249  70.935  23.209  1.00 20.00
ATOM   1782  N    THR A 016      72.253  66.679  29.161  1.00 20.00
ATOM   1783  CA   THR A 016      73.172  65.695  29.673  1.00 20.00
ATOM   1784  C    THR A 016      72.464  64.347  29.834  1.00 20.00
ATOM   1785  O    THR A 016      71.573  63.995  29.086  1.00 20.00
ATOM   1786  CB   THR A 016      73.717  66.097  31.000  1.00 20.00
ATOM   1787  OG1  THR A 016      72.692  66.000  31.993  1.00 20.00
ATOM   1788  CG2  THR A 016      74.253  67.455  30.909  1.00 20.00
ATOM   1791  N    THR A 017      72.891  63.584  30.818  1.00 20.00
ATOM   1792  CA   THR A 017      72.235  62.339  31.031  1.00 20.00
ATOM   1793  C    THR A 017      71.021  62.785  31.819  1.00 20.00
ATOM   1794  O    THR A 017      69.889  62.570  31.364  1.00 20.00
ATOM   1795  CB   THR A 017      73.112  61.308  31.826  1.00 20.00
ATOM   1796  OG1  THR A 017      73.546  60.286  30.931  1.00 20.00
ATOM   1797  CG2  THR A 017      72.315  60.660  32.954  1.00 20.00
ATOM   1800  N    ASN A 018      71.265  63.454  32.958  1.00 20.00
ATOM   1801  CA   ASN A 018      70.189  63.934  33.825  1.00 20.00
ATOM   1802  C    ASN A 018      69.025  64.568  33.108  1.00 20.00
ATOM   1803  O    ASN A 018      67.937  64.530  33.636  1.00 20.00
ATOM   1804  CB   ASN A 018      70.696  64.904  34.868  1.00 20.00
ATOM   1805  CG   ASN A 018      71.785  64.331  35.676  1.00 20.00
ATOM   1806  OD1  ASN A 018      71.761  64.412  36.887  1.00 20.00
ATOM   1807  ND2  ASN A 018      72.767  63.734  35.013  1.00 20.00
ATOM   1811  N    SER A 019      69.247  65.184  31.948  1.00 20.00
ATOM   1812  CA   SER A 019      68.132  65.740  31.199  1.00 20.00
ATOM   1813  C    SER A 019      67.362  64.513  30.704  1.00 20.00
ATOM   1814  O    SER A 019      66.145  64.414  30.875  1.00 20.00
ATOM   1815  CB   SER A 019      68.613  66.544  30.006  1.00 20.00
ATOM   1816  OG   SER A 019      69.999  66.633  30.051  1.00 20.00
ATOM   1819  N    ASP A 020      68.110  63.583  30.104  1.00 20.00
ATOM   1820  CA   ASP A 020      67.596  62.309  29.604  1.00 20.00
ATOM   1821  C    ASP A 020      66.784  61.679  30.741  1.00 20.00
ATOM   1822  O    ASP A 020      65.672  61.194  30.543  1.00 20.00
ATOM   1823  CB   ASP A 020      68.767  61.388  29.217  1.00 20.00
ATOM   1824  CG   ASP A 020      69.154  61.484  27.729  1.00 20.00
ATOM   1825  OD1  ASP A 020      68.649  62.363  26.979  1.00 20.00
```

FIG. 4Z

| | | | | | | | | |
|---|---|---|---|---|---|---|---|---|
| ATOM | 1826 | OD2 | ASP | A | 020 | 69.992 | 60.673 | 27.292 | 1.00 20.00 |
| ATOM | 1828 | N | VAL | A | 021 | 67.294 | 61.728 | 31.955 | 1.00 20.00 |
| ATOM | 1829 | CA | VAL | A | 021 | 66.522 | 61.083 | 32.960 | 1.00 20.00 |
| ATOM | 1830 | C | VAL | A | 021 | 65.300 | 61.826 | 33.326 | 1.00 20.00 |
| ATOM | 1831 | O | VAL | A | 021 | 64.372 | 61.212 | 33.879 | 1.00 20.00 |
| ATOM | 1832 | CB | VAL | A | 021 | 67.316 | 60.766 | 34.204 | 1.00 20.00 |
| ATOM | 1833 | CG1 | VAL | A | 021 | 66.471 | 60.862 | 35.417 | 1.00 20.00 |
| ATOM | 1834 | CG2 | VAL | A | 021 | 67.803 | 59.362 | 34.110 | 1.00 20.00 |
| ATOM | 1836 | N | TRP | A | 022 | 65.290 | 63.135 | 33.035 | 1.00 20.00 |
| ATOM | 1837 | CA | TRP | A | 022 | 64.157 | 64.016 | 33.326 | 1.00 20.00 |
| ATOM | 1838 | C | TRP | A | 022 | 63.051 | 63.699 | 32.319 | 1.00 20.00 |
| ATOM | 1839 | O | TRP | A | 022 | 61.948 | 63.268 | 32.629 | 1.00 20.00 |
| ATOM | 1840 | CB | TRP | A | 022 | 64.596 | 65.468 | 33.160 | 1.00 20.00 |
| ATOM | 1841 | CG | TRP | A | 022 | 63.439 | 66.467 | 33.254 | 1.00 20.00 |
| ATOM | 1842 | CD1 | TRP | A | 022 | 62.437 | 66.648 | 32.337 | 1.00 20.00 |
| ATOM | 1843 | CD2 | TRP | A | 022 | 63.161 | 67.366 | 34.322 | 1.00 20.00 |
| ATOM | 1844 | NE1 | TRP | A | 022 | 61.576 | 67.578 | 32.767 | 1.00 20.00 |
| ATOM | 1845 | CE2 | TRP | A | 022 | 61.985 | 68.049 | 33.984 | 1.00 20.00 |
| ATOM | 1846 | CE3 | TRP | A | 022 | 63.791 | 67.662 | 35.529 | 1.00 20.00 |
| ATOM | 1847 | CZ2 | TRP | A | 022 | 61.413 | 69.029 | 34.815 | 1.00 20.00 |
| ATOM | 1848 | CZ3 | TRP | A | 022 | 63.237 | 68.626 | 36.355 | 1.00 20.00 |
| ATOM | 1849 | CH2 | TRP | A | 022 | 62.052 | 69.303 | 35.992 | 1.00 20.00 |
| ATOM | 1852 | N | SER | A | 023 | 63.407 | 63.969 | 31.084 | 1.00 20.00 |
| ATOM | 1853 | CA | SER | A | 023 | 62.591 | 63.721 | 29.928 | 1.00 20.00 |
| ATOM | 1854 | C | SER | A | 023 | 61.978 | 62.316 | 30.007 | 1.00 20.00 |
| ATOM | 1855 | O | SER | A | 023 | 60.863 | 62.092 | 29.540 | 1.00 20.00 |
| ATOM | 1856 | CB | SER | A | 023 | 63.497 | 63.860 | 28.709 | 1.00 20.00 |
| ATOM | 1857 | OG | SER | A | 023 | 62.747 | 63.795 | 27.527 | 1.00 20.00 |
| ATOM | 1860 | N | TYR | A | 024 | 62.731 | 61.390 | 30.617 | 1.00 20.00 |
| ATOM | 1861 | CA | TYR | A | 024 | 62.361 | 59.980 | 30.801 | 1.00 20.00 |
| ATOM | 1862 | C | TYR | A | 024 | 60.980 | 59.761 | 31.454 | 1.00 20.00 |
| ATOM | 1863 | O | TYR | A | 024 | 60.137 | 58.991 | 30.967 | 1.00 20.00 |
| ATOM | 1864 | CB | TYR | A | 024 | 63.436 | 59.307 | 31.627 | 1.00 20.00 |
| ATOM | 1865 | CG | TYR | A | 024 | 63.129 | 57.866 | 31.859 | 1.00 20.00 |
| ATOM | 1866 | CD1 | TYR | A | 024 | 63.276 | 56.948 | 30.849 | 1.00 20.00 |
| ATOM | 1867 | CD2 | TYR | A | 024 | 62.479 | 57.473 | 33.019 | 1.00 20.00 |
| ATOM | 1868 | CE1 | TYR | A | 024 | 62.766 | 55.706 | 30.979 | 1.00 20.00 |
| ATOM | 1869 | CE2 | TYR | A | 024 | 61.962 | 56.236 | 33.157 | 1.00 20.00 |
| ATOM | 1870 | CZ | TYR | A | 024 | 62.099 | 55.365 | 32.135 | 1.00 20.00 |
| ATOM | 1871 | OH | TYR | A | 024 | 61.517 | 54.160 | 32.263 | 1.00 20.00 |
| ATOM | 1874 | N | GLY | A | 025 | 60.803 | 60.436 | 32.583 | 1.00 20.00 |
| ATOM | 1875 | CA | GLY | A | 025 | 59.558 | 60.427 | 33.311 | 1.00 20.00 |
| ATOM | 1876 | C | GLY | A | 025 | 58.477 | 61.257 | 32.614 | 1.00 20.00 |
| ATOM | 1877 | O | GLY | A | 025 | 57.365 | 61.290 | 33.058 | 1.00 20.00 |
| ATOM | 1879 | N | VAL | A | 026 | 58.747 | 61.974 | 31.544 | 1.00 20.00 |
| ATOM | 1880 | CA | VAL | A | 026 | 57.596 | 62.614 | 30.980 | 1.00 20.00 |
| ATOM | 1881 | C | VAL | A | 026 | 57.057 | 61.313 | 30.484 | 1.00 20.00 |
| ATOM | 1882 | O | VAL | A | 026 | 56.006 | 60.906 | 30.923 | 1.00 20.00 |
| ATOM | 1883 | CB | VAL | A | 026 | 57.889 | 63.625 | 29.823 | 1.00 20.00 |
| ATOM | 1884 | CG1 | VAL | A | 026 | 56.583 | 64.258 | 29.328 | 1.00 20.00 |
| ATOM | 1885 | CG2 | VAL | A | 026 | 58.746 | 64.717 | 30.327 | 1.00 20.00 |
| ATOM | 1887 | N | LEU | A | 027 | 57.843 | 60.639 | 29.632 | 1.00 20.00 |
| ATOM | 1888 | CA | LEU | A | 027 | 57.535 | 59.273 | 29.064 | 1.00 20.00 |
| ATOM | 1889 | C | LEU | A | 027 | 56.767 | 58.278 | 30.014 | 1.00 20.00 |
| ATOM | 1890 | O | LEU | A | 027 | 55.745 | 57.736 | 29.702 | 1.00 20.00 |
| ATOM | 1891 | CB | LEU | A | 027 | 58.852 | 58.615 | 28.663 | 1.00 20.00 |
| ATOM | 1892 | CG | LEU | A | 027 | 58.843 | 57.551 | 27.579 | 1.00 20.00 |

FIG. 4AA

```
ATOM   1893  CD1  LEU A 027     58.238  58.171  26.367  1.00 20.00
ATOM   1894  CD2  LEU A 027     60.239  57.031  27.287  1.00 20.00
ATOM   1896  N    LEU A 028     57.333  58.031  31.171  1.00 20.00
ATOM   1897  CA   LEU A 028     56.723  57.188  32.128  1.00 20.00
ATOM   1898  C    LEU A 028     55.330  57.638  32.349  1.00 20.00
ATOM   1899  O    LEU A 028     54.428  56.817  32.517  1.00 20.00
ATOM   1900  CB   LEU A 028     57.455  57.281  33.427  1.00 20.00
ATOM   1901  CG   LEU A 028     56.778  56.395  34.430  1.00 20.00
ATOM   1902  CD1  LEU A 028     56.765  55.005  33.926  1.00 20.00
ATOM   1903  CD2  LEU A 028     57.488  56.475  35.740  1.00 20.00
ATOM   1905  N    TRP A 029     55.148  58.961  32.409  1.00 20.00
ATOM   1906  CA   TRP A 029     53.820  59.578  32.612  1.00 20.00
ATOM   1907  C    TRP A 029     53.028  59.464  31.295  1.00 20.00
ATOM   1908  O    TRP A 029     51.869  59.142  31.301  1.00 20.00
ATOM   1909  CB   TRP A 029     54.010  61.029  33.088  1.00 20.00
ATOM   1910  CG   TRP A 029     52.746  61.841  33.293  1.00 20.00
ATOM   1911  CD1  TRP A 029     52.207  62.275  34.483  1.00 20.00
ATOM   1912  CD2  TRP A 029     51.934  62.381  32.271  1.00 20.00
ATOM   1913  NE1  TRP A 029     51.113  63.057  34.241  1.00 20.00
ATOM   1914  CE2  TRP A 029     50.925  63.138  32.892  1.00 20.00
ATOM   1915  CE3  TRP A 029     51.962  62.298  30.886  1.00 20.00
ATOM   1916  CZ2  TRP A 029     49.975  63.798  32.185  1.00 20.00
ATOM   1917  CZ3  TRP A 029     51.018  62.951  30.186  1.00 20.00
ATOM   1918  CH2  TRP A 029     50.030  63.701  30.830  1.00 20.00
ATOM   1921  N    GLU A 030     53.684  59.695  30.166  1.00 20.00
ATOM   1922  CA   GLU A 030     53.067  59.537  28.861  1.00 20.00
ATOM   1923  C    GLU A 030     52.592  58.103  28.823  1.00 20.00
ATOM   1924  O    GLU A 030     51.775  57.758  27.982  1.00 20.00
ATOM   1925  CB   GLU A 030     54.099  59.616  27.737  1.00 20.00
ATOM   1926  CG   GLU A 030     54.380  60.917  27.071  1.00 20.00
ATOM   1927  CD   GLU A 030     55.162  60.706  25.771  1.00 20.00
ATOM   1928  OE1  GLU A 030     55.818  59.668  25.665  1.00 20.00
ATOM   1929  OE2  GLU A 030     55.144  61.535  24.838  1.00 20.00
ATOM   1931  N    ILE A 031     53.124  57.260  29.711  1.00 20.00
ATOM   1932  CA   ILE A 031     52.839  55.820  29.680  1.00 20.00
ATOM   1933  C    ILE A 031     51.803  55.305  30.628  1.00 20.00
ATOM   1934  O    ILE A 031     50.931  54.585  30.219  1.00 20.00
ATOM   1935  CB   ILE A 031     54.192  54.974  29.833  1.00 20.00
ATOM   1936  CG1  ILE A 031     54.803  54.722  28.459  1.00 20.00
ATOM   1937  CG2  ILE A 031     53.964  53.607  30.495  1.00 20.00
ATOM   1938  CD1  ILE A 031     56.144  54.104  28.543  1.00 20.00
ATOM   1940  N    VAL A 032     51.893  55.672  31.892  1.00 20.00
ATOM   1941  CA   VAL A 032     50.918  55.223  32.895  1.00 20.00
ATOM   1942  C    VAL A 032     49.618  55.914  32.620  1.00 20.00
ATOM   1943  O    VAL A 032     48.706  55.811  33.412  1.00 20.00
ATOM   1944  CB   VAL A 032     51.306  55.664  34.327  1.00 20.00
ATOM   1945  CG1  VAL A 032     50.610  56.932  34.667  1.00 20.00
ATOM   1946  CG2  VAL A 032     50.962  54.602  35.333  1.00 20.00
ATOM   1948  N    SER A 033     49.552  56.605  31.493  1.00 20.00
ATOM   1949  CA   SER A 033     48.413  57.405  31.146  1.00 20.00
ATOM   1950  C    SER A 033     47.776  57.027  29.850  1.00 20.00
ATOM   1951  O    SER A 033     46.634  57.396  29.585  1.00 20.00
ATOM   1952  CB   SER A 033     48.828  58.889  31.116  1.00 20.00
ATOM   1953  OG   SER A 033     49.492  59.239  29.905  1.00 20.00
ATOM   1956  N    LEU A 034     48.513  56.329  29.019  1.00 20.00
ATOM   1957  CA   LEU A 034     47.975  55.904  27.758  1.00 20.00
ATOM   1958  C    LEU A 034     47.939  57.037  26.801  1.00 20.00
```

FIG. 4BB

```
ATOM   1959  O    LEU A 034      46.917  57.357  26.219  1.00 20.00
ATOM   1960  CB   LEU A 034      46.580  55.366  27.923  1.00 20.00
ATOM   1961  CG   LEU A 034      46.208  54.020  28.500  1.00 20.00
ATOM   1962  CD1  LEU A 034      46.074  54.041  29.977  1.00 20.00
ATOM   1963  CD2  LEU A 034      44.892  53.709  27.900  1.00 20.00
ATOM   1965  N    GLY A 035      49.091  57.663  26.658  1.00 20.00
ATOM   1966  CA   GLY A 035      49.248  58.759  25.715  1.00 20.00
ATOM   1967  C    GLY A 035      48.581  60.112  25.920  1.00 20.00
ATOM   1968  O    GLY A 035      48.145  60.734  24.947  1.00 20.00
ATOM   1970  N    GLY A 036      48.511  60.580  27.156  1.00 20.00
ATOM   1971  CA   GLY A 036      47.902  61.874  27.364  1.00 20.00
ATOM   1972  C    GLY A 036      48.981  62.925  27.245  1.00 20.00
ATOM   1973  O    GLY A 036      50.097  62.697  27.759  1.00 20.00
ATOM   1975  N    THR A 037      48.692  64.027  26.543  1.00 20.00
ATOM   1976  CA   THR A 037      49.656  65.126  26.400  1.00 20.00
ATOM   1977  C    THR A 037      50.114  65.691  27.757  1.00 20.00
ATOM   1978  O    THR A 037      49.289  65.966  28.616  1.00 20.00
ATOM   1979  CB   THR A 037      49.038  66.308  25.664  1.00 20.00
ATOM   1980  OG1  THR A 037      49.457  66.326  24.301  1.00 20.00
ATOM   1981  CG2  THR A 037      49.447  67.597  26.327  1.00 20.00
ATOM   1984  N    PRO A 038      51.445  65.866  27.966  1.00 20.00
ATOM   1985  CA   PRO A 038      51.925  66.416  29.237  1.00 20.00
ATOM   1986  C    PRO A 038      51.674  67.919  29.265  1.00 20.00
ATOM   1987  O    PRO A 038      51.812  68.570  28.264  1.00 20.00
ATOM   1988  CB   PRO A 038      53.401  66.083  29.223  1.00 20.00
ATOM   1989  CG   PRO A 038      53.573  65.116  28.170  1.00 20.00
ATOM   1990  CD   PRO A 038      52.592  65.497  27.134  1.00 20.00
ATOM   1991  N    TYR A 039      51.296  68.471  30.407  1.00 20.00
ATOM   1992  CA   TYR A 039      51.040  69.900  30.494  1.00 20.00
ATOM   1993  C    TYR A 039      49.928  70.255  29.514  1.00 20.00
ATOM   1994  O    TYR A 039      50.174  71.011  28.551  1.00 20.00
ATOM   1995  CB   TYR A 039      52.317  70.678  30.156  1.00 20.00
ATOM   1996  CG   TYR A 039      53.492  70.254  31.016  1.00 20.00
ATOM   1997  CD1  TYR A 039      54.593  69.571  30.470  1.00 20.00
ATOM   1998  CD2  TYR A 039      53.456  70.437  32.381  1.00 20.00
ATOM   1999  CE1  TYR A 039      55.586  69.088  31.288  1.00 20.00
ATOM   2000  CE2  TYR A 039      54.438  69.966  33.188  1.00 20.00
ATOM   2001  CZ   TYR A 039      55.489  69.290  32.656  1.00 20.00
ATOM   2002  OH   TYR A 039      56.405  68.759  33.532  1.00 20.00
ATOM   2005  N    CYS A 040      48.713  69.706  29.757  1.00 20.00
ATOM   2006  CA   CYS A 040      47.536  69.943  28.893  1.00 20.00
ATOM   2007  C    CYS A 040      46.861  71.241  29.251  1.00 20.00
ATOM   2008  O    CYS A 040      46.426  71.456  30.371  1.00 20.00
ATOM   2009  CB   CYS A 040      46.518  68.779  28.952  1.00 20.00
ATOM   2010  SG   CYS A 040      45.587  68.439  27.332  1.00 20.00
ATOM   2012  N    GLY A 041      46.773  72.105  28.261  1.00 20.00
ATOM   2013  CA   GLY A 041      46.197  73.417  28.496  1.00 20.00
ATOM   2014  C    GLY A 041      47.251  74.257  29.222  1.00 20.00
ATOM   2015  O    GLY A 041      46.977  74.928  30.241  1.00 20.00
ATOM   2017  N    MET A 042      48.480  74.184  28.727  1.00 20.00
ATOM   2018  CA   MET A 042      49.542  74.920  29.347  1.00 20.00
ATOM   2019  C    MET A 042      50.391  75.508  28.241  1.00 20.00
ATOM   2020  O    MET A 042      50.540  74.944  27.173  1.00 20.00
ATOM   2021  CB   MET A 042      50.321  73.990  30.253  1.00 20.00
ATOM   2022  CG   MET A 042      50.038  74.150  31.721  1.00 20.00
ATOM   2023  SD   MET A 042      51.637  74.393  32.551  1.00 20.00
ATOM   2024  CE   MET A 042      51.370  73.664  34.142  1.00 20.00
```

FIG. 4CC

| ATOM | 2026 | N   | THR | A | 043 | 50.915 | 76.686 | 28.463 | 1.00 | 20.00 |
|------|------|-----|-----|---|-----|--------|--------|--------|------|-------|
| ATOM | 2027 | CA  | THR | A | 043 | 51.699 | 77.320 | 27.418 | 1.00 | 20.00 |
| ATOM | 2028 | C   | THR | A | 043 | 53.137 | 77.204 | 27.856 | 1.00 | 20.00 |
| ATOM | 2029 | O   | THR | A | 043 | 53.479 | 77.409 | 29.047 | 1.00 | 20.00 |
| ATOM | 2030 | CB  | THR | A | 043 | 51.356 | 78.827 | 27.279 | 1.00 | 20.00 |
| ATOM | 2031 | OG1 | THR | A | 043 | 51.534 | 79.465 | 28.565 | 1.00 | 20.00 |
| ATOM | 2032 | CG2 | THR | A | 043 | 49.905 | 79.033 | 26.760 | 1.00 | 20.00 |
| ATOM | 2035 | N   | CYS | A | 044 | 53.977 | 76.862 | 26.885 | 1.00 | 20.00 |
| ATOM | 2036 | CA  | CYS | A | 044 | 55.388 | 76.714 | 27.139 | 1.00 | 20.00 |
| ATOM | 2037 | C   | CYS | A | 044 | 55.681 | 77.866 | 28.075 | 1.00 | 20.00 |
| ATOM | 2038 | O   | CYS | A | 044 | 55.836 | 77.638 | 29.269 | 1.00 | 20.00 |
| ATOM | 2039 | CB  | CYS | A | 044 | 56.128 | 76.779 | 25.814 | 1.00 | 20.00 |
| ATOM | 2040 | SG  | CYS | A | 044 | 55.373 | 75.549 | 24.616 | 1.00 | 20.00 |
| ATOM | 2042 | N   | ALA | A | 045 | 55.664 | 79.092 | 27.554 | 1.00 | 20.00 |
| ATOM | 2043 | CA  | ALA | A | 045 | 55.893 | 80.306 | 28.342 | 1.00 | 20.00 |
| ATOM | 2044 | C   | ALA | A | 045 | 55.536 | 80.155 | 29.809 | 1.00 | 20.00 |
| ATOM | 2045 | O   | ALA | A | 045 | 56.216 | 80.636 | 30.700 | 1.00 | 20.00 |
| ATOM | 2046 | CB  | ALA | A | 045 | 55.082 | 81.416 | 27.760 | 1.00 | 20.00 |
| ATOM | 2048 | N   | GLU | A | 046 | 54.429 | 79.482 | 30.050 | 1.00 | 20.00 |
| ATOM | 2049 | CA  | GLU | A | 046 | 53.961 | 79.269 | 31.390 | 1.00 | 20.00 |
| ATOM | 2050 | C   | GLU | A | 046 | 54.902 | 78.299 | 32.100 | 1.00 | 20.00 |
| ATOM | 2051 | O   | GLU | A | 046 | 55.309 | 78.558 | 33.243 | 1.00 | 20.00 |
| ATOM | 2052 | CB  | GLU | A | 046 | 52.556 | 78.738 | 31.281 | 1.00 | 20.00 |
| ATOM | 2053 | CG  | GLU | A | 046 | 51.601 | 79.002 | 32.429 | 1.00 | 20.00 |
| ATOM | 2054 | CD  | GLU | A | 046 | 50.437 | 78.036 | 32.341 | 1.00 | 20.00 |
| ATOM | 2055 | OE1 | GLU | A | 046 | 50.182 | 77.380 | 33.378 | 1.00 | 20.00 |
| ATOM | 2056 | OE2 | GLU | A | 046 | 49.814 | 77.940 | 31.222 | 1.00 | 20.00 |
| ATOM | 2058 | N   | LEU | A | 047 | 55.251 | 77.192 | 31.437 | 1.00 | 20.00 |
| ATOM | 2059 | CA  | LEU | A | 047 | 56.203 | 76.207 | 32.001 | 1.00 | 20.00 |
| ATOM | 2060 | C   | LEU | A | 047 | 57.470 | 76.893 | 32.593 | 1.00 | 20.00 |
| ATOM | 2061 | O   | LEU | A | 047 | 57.712 | 76.853 | 33.805 | 1.00 | 20.00 |
| ATOM | 2062 | CB  | LEU | A | 047 | 56.639 | 75.203 | 30.914 | 1.00 | 20.00 |
| ATOM | 2063 | CG  | LEU | A | 047 | 55.895 | 73.858 | 30.885 | 1.00 | 20.00 |
| ATOM | 2064 | CD1 | LEU | A | 047 | 56.520 | 72.889 | 29.922 | 1.00 | 20.00 |
| ATOM | 2065 | CD2 | LEU | A | 047 | 55.884 | 73.280 | 32.256 | 1.00 | 20.00 |
| ATOM | 2067 | N   | TYR | A | 048 | 58.254 | 77.503 | 31.694 | 1.00 | 20.00 |
| ATOM | 2068 | CA  | TYR | A | 048 | 59.463 | 78.267 | 31.974 | 1.00 | 20.00 |
| ATOM | 2069 | C   | TYR | A | 048 | 59.499 | 78.978 | 33.311 | 1.00 | 20.00 |
| ATOM | 2070 | O   | TYR | A | 048 | 60.325 | 78.669 | 34.188 | 1.00 | 20.00 |
| ATOM | 2071 | CB  | TYR | A | 048 | 59.684 | 79.343 | 30.919 | 1.00 | 20.00 |
| ATOM | 2072 | CG  | TYR | A | 048 | 60.217 | 78.874 | 29.611 | 1.00 | 20.00 |
| ATOM | 2073 | CD1 | TYR | A | 048 | 59.370 | 78.692 | 28.518 | 1.00 | 20.00 |
| ATOM | 2074 | CD2 | TYR | A | 048 | 61.570 | 78.629 | 29.459 | 1.00 | 20.00 |
| ATOM | 2075 | CE1 | TYR | A | 048 | 59.868 | 78.263 | 27.278 | 1.00 | 20.00 |
| ATOM | 2076 | CE2 | TYR | A | 048 | 62.094 | 78.206 | 28.248 | 1.00 | 20.00 |
| ATOM | 2077 | CZ  | TYR | A | 048 | 61.250 | 78.013 | 27.141 | 1.00 | 20.00 |
| ATOM | 2078 | OH  | TYR | A | 048 | 61.799 | 77.541 | 25.930 | 1.00 | 20.00 |
| ATOM | 2081 | N   | GLU | A | 049 | 58.601 | 79.954 | 33.446 | 1.00 | 20.00 |
| ATOM | 2082 | CA  | GLU | A | 049 | 58.527 | 80.725 | 34.680 | 1.00 | 20.00 |
| ATOM | 2083 | C   | GLU | A | 049 | 58.074 | 79.756 | 35.720 | 1.00 | 20.00 |
| ATOM | 2084 | O   | GLU | A | 049 | 58.417 | 79.886 | 36.903 | 1.00 | 20.00 |
| ATOM | 2085 | CB  | GLU | A | 049 | 57.485 | 81.840 | 34.592 | 1.00 | 20.00 |
| ATOM | 2086 | CG  | GLU | A | 049 | 57.233 | 82.519 | 35.947 | 1.00 | 20.00 |
| ATOM | 2087 | CD  | GLU | A | 049 | 55.761 | 82.820 | 36.314 | 1.00 | 20.00 |
| ATOM | 2088 | OE1 | GLU | A | 049 | 54.860 | 82.700 | 35.453 | 1.00 | 20.00 |
| ATOM | 2089 | OE2 | GLU | A | 049 | 55.540 | 83.185 | 37.497 | 1.00 | 20.00 |
| ATOM | 2091 | N   | LYS | A | 050 | 57.277 | 78.791 | 35.243 | 1.00 | 20.00 |

FIG. 4DD

```
ATOM   2092  CA   LYS A 050      56.683  77.749  36.092  1.00 20.00
ATOM   2093  C    LYS A 050      57.625  76.655  36.652  1.00 20.00
ATOM   2094  O    LYS A 050      58.038  76.747  37.789  1.00 20.00
ATOM   2095  CB   LYS A 050      55.465  77.116  35.362  1.00 20.00
ATOM   2097  N    LEU A 051      57.965  75.640  35.880  1.00 20.00
ATOM   2098  CA   LEU A 051      58.854  74.592  36.398  1.00 20.00
ATOM   2099  C    LEU A 051      59.828  75.002  37.553  1.00 20.00
ATOM   2100  O    LEU A 051      59.835  74.350  38.608  1.00 20.00
ATOM   2101  CB   LEU A 051      59.655  73.957  35.239  1.00 20.00
ATOM   2102  CG   LEU A 051      58.981  72.988  34.248  1.00 20.00
ATOM   2103  CD1  LEU A 051      57.669  72.566  34.798  1.00 20.00
ATOM   2104  CD2  LEU A 051      58.796  73.609  32.875  1.00 20.00
ATOM   2106  N    PRO A 052      60.673  76.050  37.346  1.00 20.00
ATOM   2107  CA   PRO A 052      61.652  76.601  38.292  1.00 20.00
ATOM   2108  C    PRO A 052      61.323  76.418  39.750  1.00 20.00
ATOM   2109  O    PRO A 052      61.675  75.396  40.337  1.00 20.00
ATOM   2110  CB   PRO A 052      61.724  78.053  37.895  1.00 20.00
ATOM   2111  CG   PRO A 052      61.556  78.008  36.389  1.00 20.00
ATOM   2112  CD   PRO A 052      60.771  76.762  36.051  1.00 20.00
ATOM   2113  N    GLN A 053      60.706  77.399  40.394  1.00 20.00
ATOM   2114  CA   GLN A 053      60.319  77.126  41.783  1.00 20.00
ATOM   2115  C    GLN A 053      58.915  76.531  41.498  1.00 20.00
ATOM   2116  O    GLN A 053      58.116  76.198  42.386  1.00 20.00
ATOM   2117  CB   GLN A 053      60.274  78.414  42.664  1.00 20.00
ATOM   2119  N    GLY A 054      58.649  76.413  40.208  1.00 20.00
ATOM   2120  CA   GLY A 054      57.454  75.745  39.784  1.00 20.00
ATOM   2121  C    GLY A 054      57.520  74.261  40.190  1.00 20.00
ATOM   2122  O    GLY A 054      58.564  73.730  40.654  1.00 20.00
ATOM   2124  N    TYR A 055      56.363  73.629  40.002  1.00 20.00
ATOM   2125  CA   TYR A 055      56.081  72.268  40.370  1.00 20.00
ATOM   2126  C    TYR A 055      56.216  71.476  39.095  1.00 20.00
ATOM   2127  O    TYR A 055      56.762  72.008  38.153  1.00 20.00
ATOM   2128  CB   TYR A 055      54.647  72.256  40.889  1.00 20.00
ATOM   2129  CG   TYR A 055      53.604  72.330  39.754  1.00 20.00
ATOM   2130  CD1  TYR A 055      52.634  71.309  39.604  1.00 20.00
ATOM   2131  CD2  TYR A 055      53.685  73.316  38.749  1.00 20.00
ATOM   2132  CE1  TYR A 055      51.805  71.283  38.478  1.00 20.00
ATOM   2133  CE2  TYR A 055      52.863  73.280  37.642  1.00 20.00
ATOM   2134  CZ   TYR A 055      51.928  72.264  37.501  1.00 20.00
ATOM   2135  OH   TYR A 055      51.114  72.171  36.375  1.00 20.00
ATOM   2138  N    ARG A 056      55.738  70.232  39.048  1.00 20.00
ATOM   2139  CA   ARG A 056      55.828  69.422  37.821  1.00 20.00
ATOM   2140  C    ARG A 056      54.504  68.699  37.494  1.00 20.00
ATOM   2141  O    ARG A 056      53.471  69.052  38.098  1.00 20.00
ATOM   2142  CB   ARG A 056      56.926  68.379  37.948  1.00 20.00
ATOM   2143  CG   ARG A 056      57.175  67.962  39.357  1.00 20.00
ATOM   2144  CD   ARG A 056      58.538  68.505  39.833  1.00 20.00
ATOM   2145  NE   ARG A 056      59.319  69.142  38.760  1.00 20.00
ATOM   2146  CZ   ARG A 056      60.182  70.114  38.982  1.00 20.00
ATOM   2147  NH1  ARG A 056      60.367  70.542  40.201  1.00 20.00
ATOM   2148  NH2  ARG A 056      60.839  70.655  37.996  1.00 20.00
ATOM   2155  N    LEU A 057      54.531  67.705  36.565  1.00 20.00
ATOM   2156  CA   LEU A 057      53.312  66.955  36.203  1.00 20.00
ATOM   2157  C    LEU A 057      52.643  66.257  37.370  1.00 20.00
ATOM   2158  O    LEU A 057      53.221  65.587  38.191  1.00 20.00
ATOM   2159  CB   LEU A 057      53.519  65.955  35.071  1.00 20.00
ATOM   2160  CG   LEU A 057      53.850  66.384  33.632  1.00 20.00
```

FIG. 4EE

```
ATOM   2161  CD1 LEU A 057      54.504  65.224  32.920  1.00 20.00
ATOM   2162  CD2 LEU A 057      52.669  66.811  32.830  1.00 20.00
ATOM   2164  N   GLU A 058      51.357  66.515  37.390  1.00 20.00
ATOM   2165  CA  GLU A 058      50.325  66.093  38.333  1.00 20.00
ATOM   2166  C   GLU A 058      50.078  64.562  38.297  1.00 20.00
ATOM   2167  O   GLU A 058      50.013  63.978  37.216  1.00 20.00
ATOM   2168  CB  GLU A 058      49.091  66.872  37.885  1.00 20.00
ATOM   2169  CG  GLU A 058      48.798  66.637  36.334  1.00 20.00
ATOM   2170  CD  GLU A 058      49.565  67.548  35.341  1.00 20.00
ATOM   2171  OE1 GLU A 058      50.058  68.604  35.777  1.00 20.00
ATOM   2172  OE2 GLU A 058      49.657  67.227  34.128  1.00 20.00
ATOM   2174  N   LYS A 059      49.906  63.915  39.448  1.00 20.00
ATOM   2175  CA  LYS A 059      49.693  62.458  39.420  1.00 20.00
ATOM   2176  C   LYS A 059      48.502  61.929  38.655  1.00 20.00
ATOM   2177  O   LYS A 059      47.366  62.213  38.971  1.00 20.00
ATOM   2178  CB  LYS A 059      49.607  61.825  40.814  1.00 20.00
ATOM   2179  CG  LYS A 059      49.383  60.289  40.717  1.00 20.00
ATOM   2180  CD  LYS A 059      49.519  59.551  42.056  1.00 20.00
ATOM   2181  CE  LYS A 059      48.286  59.754  42.979  1.00 20.00
ATOM   2182  NZ  LYS A 059      47.400  58.540  43.161  1.00 20.00
ATOM   2187  N   PRO A 060      48.753  61.095  37.662  1.00 20.00
ATOM   2188  CA  PRO A 060      47.615  60.576  36.931  1.00 20.00
ATOM   2189  C   PRO A 060      46.646  59.848  37.873  1.00 20.00
ATOM   2190  O   PRO A 060      47.048  59.234  38.860  1.00 20.00
ATOM   2191  CB  PRO A 060      48.260  59.643  35.923  1.00 20.00
ATOM   2192  CG  PRO A 060      49.662  60.187  35.751  1.00 20.00
ATOM   2193  CD  PRO A 060      50.018  60.555  37.147  1.00 20.00
ATOM   2194  N   LEU A 061      45.371  59.984  37.543  1.00 20.00
ATOM   2195  CA  LEU A 061      44.236  59.426  38.245  1.00 20.00
ATOM   2196  C   LEU A 061      44.496  58.098  38.924  1.00 20.00
ATOM   2197  O   LEU A 061      44.187  57.890  40.123  1.00 20.00
ATOM   2198  CB  LEU A 061      43.055  59.243  37.248  1.00 20.00
ATOM   2199  CG  LEU A 061      42.994  59.507  35.690  1.00 20.00
ATOM   2200  CD1 LEU A 061      44.393  59.876  35.050  1.00 20.00
ATOM   2201  CD2 LEU A 061      42.384  58.237  35.000  1.00 20.00
ATOM   2203  N   ASN A 062      45.075  57.203  38.117  1.00 20.00
ATOM   2204  CA  ASN A 062      45.378  55.820  38.502  1.00 20.00
ATOM   2205  C   ASN A 062      46.840  55.286  38.537  1.00 20.00
ATOM   2206  O   ASN A 062      47.079  54.209  37.999  1.00 20.00
ATOM   2207  CB  ASN A 062      44.591  54.958  37.559  1.00 20.00
ATOM   2208  CG  ASN A 062      44.675  55.478  36.220  1.00 20.00
ATOM   2209  OD1 ASN A 062      45.731  55.960  35.816  1.00 20.00
ATOM   2210  ND2 ASN A 062      43.590  55.443  35.504  1.00 20.00
ATOM   2214  N   CYS A 063      47.812  56.005  39.100  1.00 20.00
ATOM   2215  CA  CYS A 063      49.165  55.418  39.205  1.00 20.00
ATOM   2216  C   CYS A 063      49.155  55.124  40.645  1.00 20.00
ATOM   2217  O   CYS A 063      48.285  55.550  41.377  1.00 20.00
ATOM   2218  CB  CYS A 063      50.364  56.362  39.046  1.00 20.00
ATOM   2219  SG  CYS A 063      50.817  56.807  37.453  1.00 20.00
ATOM   2221  N   ASP A 064      50.186  54.449  41.067  1.00 20.00
ATOM   2222  CA  ASP A 064      50.291  54.106  42.448  1.00 20.00
ATOM   2223  C   ASP A 064      51.455  54.945  42.917  1.00 20.00
ATOM   2224  O   ASP A 064      52.521  54.903  42.319  1.00 20.00
ATOM   2225  CB  ASP A 064      50.558  52.601  42.552  1.00 20.00
ATOM   2226  CG  ASP A 064      50.951  52.180  43.945  1.00 20.00
ATOM   2227  OD1 ASP A 064      50.078  51.628  44.664  1.00 20.00
ATOM   2228  OD2 ASP A 064      52.131  52.394  44.309  1.00 20.00
```

FIG. 4FF

```
ATOM   2230  N    ASP A 065      51.259  55.718  43.973  1.00 20.00
ATOM   2231  CA   ASP A 065      52.332  56.577  44.460  1.00 20.00
ATOM   2232  C    ASP A 065      53.733  56.051  44.341  1.00 20.00
ATOM   2233  O    ASP A 065      54.642  56.860  44.332  1.00 20.00
ATOM   2234  CB   ASP A 065      52.062  57.029  45.875  1.00 20.00
ATOM   2235  CG   ASP A 065      50.937  58.020  45.923  1.00 20.00
ATOM   2236  OD1  ASP A 065      50.842  58.814  44.958  1.00 20.00
ATOM   2237  OD2  ASP A 065      50.136  58.013  46.883  1.00 20.00
ATOM   2239  N    GLU A 066      53.918  54.734  44.222  1.00 20.00
ATOM   2240  CA   GLU A 066      55.255  54.179  44.049  1.00 20.00
ATOM   2241  C    GLU A 066      55.670  54.466  42.600  1.00 20.00
ATOM   2242  O    GLU A 066      56.854  54.554  42.311  1.00 20.00
ATOM   2243  CB   GLU A 066      55.315  52.656  44.363  1.00 20.00
ATOM   2244  CG   GLU A 066      54.520  52.182  45.635  1.00 20.00
ATOM   2245  CD   GLU A 066      54.944  50.804  46.237  1.00 20.00
ATOM   2246  OE1  GLU A 066      54.716  50.604  47.469  1.00 20.00
ATOM   2247  OE2  GLU A 066      55.494  49.937  45.496  1.00 20.00
ATOM   2249  N    VAL A 067      54.726  54.592  41.671  1.00 20.00
ATOM   2250  CA   VAL A 067      55.092  54.941  40.293  1.00 20.00
ATOM   2251  C    VAL A 067      55.224  56.462  40.180  1.00 20.00
ATOM   2252  O    VAL A 067      56.000  56.986  39.410  1.00 20.00
ATOM   2253  CB   VAL A 067      54.055  54.487  39.279  1.00 20.00
ATOM   2254  CG1  VAL A 067      54.600  54.593  37.857  1.00 20.00
ATOM   2255  CG2  VAL A 067      53.657  53.116  39.597  1.00 20.00
ATOM   2257  N    TYR A 068      54.460  57.189  40.948  1.00 20.00
ATOM   2258  CA   TYR A 068      54.614  58.609  40.861  1.00 20.00
ATOM   2259  C    TYR A 068      55.973  59.018  41.455  1.00 20.00
ATOM   2260  O    TYR A 068      56.712  59.819  40.831  1.00 20.00
ATOM   2261  CB   TYR A 068      53.489  59.313  41.595  1.00 20.00
ATOM   2262  CG   TYR A 068      53.361  60.752  41.220  1.00 20.00
ATOM   2263  CD1  TYR A 068      53.128  61.124  39.920  1.00 20.00
ATOM   2264  CD2  TYR A 068      53.490  61.746  42.186  1.00 20.00
ATOM   2265  CE1  TYR A 068      53.031  62.478  39.603  1.00 20.00
ATOM   2266  CE2  TYR A 068      53.395  63.060  41.887  1.00 20.00
ATOM   2267  CZ   TYR A 068      53.171  63.435  40.612  1.00 20.00
ATOM   2268  OH   TYR A 068      53.121  64.768  40.328  1.00 20.00
ATOM   2271  N    ASP A 069      56.315  58.503  42.647  1.00 20.00
ATOM   2272  CA   ASP A 069      57.609  58.859  43.214  1.00 20.00
ATOM   2273  C    ASP A 069      58.773  58.615  42.263  1.00 20.00
ATOM   2274  O    ASP A 069      59.744  59.344  42.299  1.00 20.00
ATOM   2275  CB   ASP A 069      57.969  58.107  44.464  1.00 20.00
ATOM   2276  CG   ASP A 069      59.422  58.423  44.879  1.00 20.00
ATOM   2277  OD1  ASP A 069      60.352  57.615  44.540  1.00 20.00
ATOM   2278  OD2  ASP A 069      59.635  59.510  45.509  1.00 20.00
ATOM   2280  N    LEU A 070      58.720  57.565  41.452  1.00 20.00
ATOM   2281  CA   LEU A 070      59.809  57.334  40.528  1.00 20.00
ATOM   2282  C    LEU A 070      59.790  58.516  39.558  1.00 20.00
ATOM   2283  O    LEU A 070      60.802  59.127  39.276  1.00 20.00
ATOM   2284  CB   LEU A 070      59.609  56.013  39.765  1.00 20.00
ATOM   2285  CG   LEU A 070      60.747  55.706  38.780  1.00 20.00
ATOM   2286  CD1  LEU A 070      61.879  55.168  39.574  1.00 20.00
ATOM   2287  CD2  LEU A 070      60.351  54.769  37.681  1.00 20.00
ATOM   2289  N    MET A 071      58.597  58.816  39.073  1.00 20.00
ATOM   2290  CA   MET A 071      58.336  59.892  38.116  1.00 20.00
ATOM   2291  C    MET A 071      59.004  61.168  38.549  1.00 20.00
ATOM   2292  O    MET A 071      59.698  61.796  37.776  1.00 20.00
ATOM   2293  CB   MET A 071      56.818  60.169  38.000  1.00 20.00
```

FIG. 4GG

```
ATOM   2294  CG   MET A 071      56.219  59.904  36.636  1.00 20.00
ATOM   2295  SD   MET A 071      54.409  59.761  36.764  1.00 20.00
ATOM   2296  CE   MET A 071      53.977  58.683  35.467  1.00 20.00
ATOM   2298  N    ARG A 072      58.797  61.527  39.803  1.00 20.00
ATOM   2299  CA   ARG A 072      59.303  62.762  40.345  1.00 20.00
ATOM   2300  C    ARG A 072      60.739  62.807  40.778  1.00 20.00
ATOM   2301  O    ARG A 072      61.312  63.884  40.945  1.00 20.00
ATOM   2302  CB   ARG A 072      58.412  63.145  41.499  1.00 20.00
ATOM   2303  CG   ARG A 072      56.978  63.140  41.074  1.00 20.00
ATOM   2304  CD   ARG A 072      56.500  64.539  41.064  1.00 20.00
ATOM   2305  NE   ARG A 072      56.642  65.063  42.415  1.00 20.00
ATOM   2306  CZ   ARG A 072      56.484  66.337  42.720  1.00 20.00
ATOM   2307  NH1  ARG A 072      56.181  67.175  41.753  1.00 20.00
ATOM   2308  NH2  ARG A 072      56.642  66.771  43.968  1.00 20.00
ATOM   2315  N    GLN A 073      61.325  61.647  41.011  1.00 20.00
ATOM   2316  CA   GLN A 073      62.717  61.652  41.387  1.00 20.00
ATOM   2317  C    GLN A 073      63.481  61.931  40.084  1.00 20.00
ATOM   2318  O    GLN A 073      64.658  62.267  40.105  1.00 20.00
ATOM   2319  CB   GLN A 073      63.124  60.316  41.973  1.00 20.00
ATOM   2320  CG   GLN A 073      63.076  60.211  43.490  1.00 20.00
ATOM   2321  CD   GLN A 073      63.603  58.852  43.962  1.00 20.00
ATOM   2322  OE1  GLN A 073      63.853  58.641  45.159  1.00 20.00
ATOM   2323  NE2  GLN A 073      63.792  57.925  43.008  1.00 20.00
ATOM   2327  N    CYS A 074      62.819  61.805  38.947  1.00 20.00
ATOM   2328  CA   CYS A 074      63.503  62.093  37.720  1.00 20.00
ATOM   2329  C    CYS A 074      63.403  63.601  37.500  1.00 20.00
ATOM   2330  O    CYS A 074      64.073  64.148  36.642  1.00 20.00
ATOM   2331  CB   CYS A 074      62.847  61.361  36.524  1.00 20.00
ATOM   2332  SG   CYS A 074      62.746  59.548  36.564  1.00 20.00
ATOM   2334  N    TRP A 075      62.555  64.268  38.277  1.00 20.00
ATOM   2335  CA   TRP A 075      62.311  65.708  38.110  1.00 20.00
ATOM   2336  C    TRP A 075      62.906  66.552  39.231  1.00 20.00
ATOM   2337  O    TRP A 075      62.503  67.692  39.466  1.00 20.00
ATOM   2338  CB   TRP A 075      60.797  65.977  38.037  1.00 20.00
ATOM   2339  CG   TRP A 075      60.090  65.403  36.830  1.00 20.00
ATOM   2340  CD1  TRP A 075      60.586  65.308  35.565  1.00 20.00
ATOM   2341  CD2  TRP A 075      58.768  64.834  36.789  1.00 20.00
ATOM   2342  NE1  TRP A 075      59.669  64.720  34.751  1.00 20.00
ATOM   2343  CE2  TRP A 075      58.542  64.416  35.468  1.00 20.00
ATOM   2344  CE3  TRP A 075      57.755  64.634  37.742  1.00 20.00
ATOM   2345  CZ2  TRP A 075      57.343  63.808  35.062  1.00 20.00
ATOM   2346  CZ3  TRP A 075      56.551  64.024  37.331  1.00 20.00
ATOM   2347  CH2  TRP A 075      56.366  63.624  36.002  1.00 20.00
ATOM   2350  N    ARG A 076      63.865  65.959  39.934  1.00 20.00
ATOM   2351  CA   ARG A 076      64.533  66.625  41.024  1.00 20.00
ATOM   2352  C    ARG A 076      65.304  67.793  40.364  1.00 20.00
ATOM   2353  O    ARG A 076      65.983  67.586  39.347  1.00 20.00
ATOM   2354  CB   ARG A 076      65.462  65.607  41.699  1.00 20.00
ATOM   2355  CG   ARG A 076      64.890  64.932  42.981  1.00 20.00
ATOM   2356  CD   ARG A 076      65.230  63.413  43.072  1.00 20.00
ATOM   2357  NE   ARG A 076      64.997  62.813  44.416  1.00 20.00
ATOM   2358  CZ   ARG A 076      65.490  61.630  44.835  1.00 20.00
ATOM   2359  NH1  ARG A 076      66.258  60.880  44.037  1.00 20.00
ATOM   2360  NH2  ARG A 076      65.231  61.211  46.069  1.00 20.00
ATOM   2367  N    GLU A 077      65.178  69.014  40.895  1.00 20.00
ATOM   2368  CA   GLU A 077      65.885  70.155  40.318  1.00 20.00
ATOM   2369  C    GLU A 077      67.310  69.773  39.983  1.00 20.00
```

FIG. 4HH

```
ATOM   2370  O    GLU A 077      67.613  69.364  38.878  1.00 20.00
ATOM   2371  CB   GLU A 077      65.889  71.343  41.278  1.00 20.00
ATOM   2373  N    LYS A 078      68.184  69.910  40.953  1.00 20.00
ATOM   2374  CA   LYS A 078      69.573  69.583  40.764  1.00 20.00
ATOM   2375  C    LYS A 078      69.811  68.228  40.037  1.00 20.00
ATOM   2376  O    LYS A 078      69.850  67.194  40.664  1.00 20.00
ATOM   2377  CB   LYS A 078      70.225  69.573  42.138  1.00 20.00
ATOM   2378  CG   LYS A 078      69.346  70.070  43.275  1.00 20.00
ATOM   2379  CD   LYS A 078      70.069  69.962  44.591  1.00 20.00
ATOM   2380  CE   LYS A 078      69.301  70.580  45.713  1.00 20.00
ATOM   2381  NZ   LYS A 078      69.362  69.789  47.005  1.00 20.00
ATOM   2386  N    PRO A 079      70.050  68.234  38.721  1.00 20.00
ATOM   2387  CA   PRO A 079      70.261  66.980  38.006  1.00 20.00
ATOM   2388  C    PRO A 079      70.943  65.885  38.771  1.00 20.00
ATOM   2389  O    PRO A 079      70.451  64.770  38.811  1.00 20.00
ATOM   2390  CB   PRO A 079      71.059  67.370  36.772  1.00 20.00
ATOM   2391  CG   PRO A 079      70.896  68.782  36.633  1.00 20.00
ATOM   2392  CD   PRO A 079      70.218  69.385  37.832  1.00 20.00
ATOM   2393  N    TYR A 080      72.085  66.172  39.382  1.00 20.00
ATOM   2394  CA   TYR A 080      72.804  65.132  40.133  1.00 20.00
ATOM   2395  C    TYR A 080      71.975  64.531  41.286  1.00 20.00
ATOM   2396  O    TYR A 080      72.444  63.680  42.014  1.00 20.00
ATOM   2397  CB   TYR A 080      74.139  65.707  40.640  1.00 20.00
ATOM   2398  CG   TYR A 080      74.006  66.804  41.677  1.00 20.00
ATOM   2399  CD1  TYR A 080      74.086  66.521  43.022  1.00 20.00
ATOM   2400  CD2  TYR A 080      73.757  68.117  41.304  1.00 20.00
ATOM   2401  CE1  TYR A 080      73.915  67.500  43.955  1.00 20.00
ATOM   2402  CE2  TYR A 080      73.588  69.104  42.245  1.00 20.00
ATOM   2403  CZ   TYR A 080      73.664  68.784  43.562  1.00 20.00
ATOM   2404  OH   TYR A 080      73.475  69.749  44.512  1.00 20.00
ATOM   2407  N    GLU A 081      70.743  65.007  41.436  1.00 20.00
ATOM   2408  CA   GLU A 081      69.817  64.540  42.462  1.00 20.00
ATOM   2409  C    GLU A 081      68.878  63.538  41.797  1.00 20.00
ATOM   2410  O    GLU A 081      68.205  62.751  42.451  1.00 20.00
ATOM   2411  CB   GLU A 081      69.025  65.709  43.038  1.00 20.00
ATOM   2412  CG   GLU A 081      69.358  66.053  44.505  1.00 20.00
ATOM   2413  CD   GLU A 081      68.385  67.067  45.106  1.00 20.00
ATOM   2414  OE1  GLU A 081      68.518  67.413  46.316  1.00 20.00
ATOM   2415  OE2  GLU A 081      67.485  67.510  44.342  1.00 20.00
ATOM   2417  N    ARG A 082      68.875  63.582  40.471  1.00 20.00
ATOM   2418  CA   ARG A 082      68.097  62.678  39.655  1.00 20.00
ATOM   2419  C    ARG A 082      68.622  61.223  39.710  1.00 20.00
ATOM   2420  O    ARG A 082      69.814  60.963  39.981  1.00 20.00
ATOM   2421  CB   ARG A 082      68.085  63.174  38.218  1.00 20.00
ATOM   2422  CG   ARG A 082      66.784  63.856  37.837  1.00 20.00
ATOM   2423  CD   ARG A 082      66.836  65.398  37.781  1.00 20.00
ATOM   2424  NE   ARG A 082      67.235  65.908  36.451  1.00 20.00
ATOM   2425  CZ   ARG A 082      67.427  67.194  36.163  1.00 20.00
ATOM   2426  NH1  ARG A 082      67.258  68.107  37.101  1.00 20.00
ATOM   2427  NH2  ARG A 082      67.805  67.552  34.947  1.00 20.00
ATOM   2434  N    PRO A 083      67.725  60.237  39.513  1.00 20.00
ATOM   2435  CA   PRO A 083      68.223  58.866  39.554  1.00 20.00
ATOM   2436  C    PRO A 083      69.042  58.596  38.310  1.00 20.00
ATOM   2437  O    PRO A 083      69.594  59.505  37.688  1.00 20.00
ATOM   2438  CB   PRO A 083      66.942  58.037  39.582  1.00 20.00
ATOM   2439  CG   PRO A 083      65.877  58.981  40.016  1.00 20.00
ATOM   2440  CD   PRO A 083      66.265  60.243  39.330  1.00 20.00
```

FIG. 4II

```
ATOM   2441  N    SER A 084      69.110  57.327  37.952  1.00 20.00
ATOM   2442  CA   SER A 084      69.825  56.896  36.760  1.00 20.00
ATOM   2443  C    SER A 084      69.131  55.647  36.225  1.00 20.00
ATOM   2444  O    SER A 084      68.707  54.760  36.990  1.00 20.00
ATOM   2445  CB   SER A 084      71.283  56.583  37.087  1.00 20.00
ATOM   2446  OG   SER A 084      71.397  55.714  38.182  1.00 20.00
ATOM   2449  N    PHE A 085      69.014  55.585  34.905  1.00 20.00
ATOM   2450  CA   PHE A 085      68.378  54.457  34.249  1.00 20.00
ATOM   2451  C    PHE A 085      68.808  53.087  34.761  1.00 20.00
ATOM   2452  O    PHE A 085      68.185  52.089  34.478  1.00 20.00
ATOM   2453  CB   PHE A 085      68.633  54.555  32.762  1.00 20.00
ATOM   2454  CG   PHE A 085      68.121  55.805  32.170  1.00 20.00
ATOM   2455  CD1  PHE A 085      68.888  56.546  31.303  1.00 20.00
ATOM   2456  CD2  PHE A 085      66.866  56.277  32.507  1.00 20.00
ATOM   2457  CE1  PHE A 085      68.402  57.738  30.784  1.00 20.00
ATOM   2458  CE2  PHE A 085      66.395  57.456  31.995  1.00 20.00
ATOM   2459  CZ   PHE A 085      67.160  58.174  31.140  1.00 20.00
ATOM   2461  N    ALA A 086      69.890  53.030  35.509  1.00 20.00
ATOM   2462  CA   ALA A 086      70.327  51.757  35.993  1.00 20.00
ATOM   2463  C    ALA A 086      69.505  51.422  37.206  1.00 20.00
ATOM   2464  O    ALA A 086      69.064  50.291  37.352  1.00 20.00
ATOM   2465  CB   ALA A 086      71.777  51.807  36.323  1.00 20.00
ATOM   2467  N    GLN A 087      69.266  52.398  38.071  1.00 20.00
ATOM   2468  CA   GLN A 087      68.494  52.121  39.266  1.00 20.00
ATOM   2469  C    GLN A 087      66.956  52.163  39.068  1.00 20.00
ATOM   2470  O    GLN A 087      66.195  51.560  39.846  1.00 20.00
ATOM   2471  CB   GLN A 087      68.936  53.074  40.388  1.00 20.00
ATOM   2472  CG   GLN A 087      69.565  54.391  39.973  1.00 20.00
ATOM   2473  CD   GLN A 087      70.381  55.057  41.121  1.00 20.00
ATOM   2474  OE1  GLN A 087      71.123  56.032  40.897  1.00 20.00
ATOM   2475  NE2  GLN A 087      70.244  54.536  42.341  1.00 20.00
ATOM   2479  N    ILE A 088      66.533  52.883  38.025  1.00 20.00
ATOM   2480  CA   ILE A 088      65.126  53.054  37.686  1.00 20.00
ATOM   2481  C    ILE A 088      64.687  51.697  37.241  1.00 20.00
ATOM   2482  O    ILE A 088      63.649  51.196  37.639  1.00 20.00
ATOM   2483  CB   ILE A 088      64.938  54.057  36.496  1.00 20.00
ATOM   2484  CG1  ILE A 088      64.769  55.490  37.007  1.00 20.00
ATOM   2485  CG2  ILE A 088      63.729  53.684  35.655  1.00 20.00
ATOM   2486  CD1  ILE A 088      65.373  56.556  36.035  1.00 20.00
ATOM   2488  N    LEU A 089      65.515  51.128  36.379  1.00 20.00
ATOM   2489  CA   LEU A 089      65.313  49.789  35.843  1.00 20.00
ATOM   2490  C    LEU A 089      65.060  48.826  36.994  1.00 20.00
ATOM   2491  O    LEU A 089      64.018  48.175  37.061  1.00 20.00
ATOM   2492  CB   LEU A 089      66.540  49.336  35.092  1.00 20.00
ATOM   2493  CG   LEU A 089      66.547  47.848  34.823  1.00 20.00
ATOM   2494  CD1  LEU A 089      65.147  47.379  34.407  1.00 20.00
ATOM   2495  CD2  LEU A 089      67.545  47.575  33.708  1.00 20.00
ATOM   2497  N    VAL A 090      66.004  48.748  37.908  1.00 20.00
ATOM   2498  CA   VAL A 090      65.821  47.903  39.051  1.00 20.00
ATOM   2499  C    VAL A 090      64.572  48.276  39.816  1.00 20.00
ATOM   2500  O    VAL A 090      64.276  47.684  40.843  1.00 20.00
ATOM   2501  CB   VAL A 090      66.998  48.040  39.968  1.00 20.00
ATOM   2502  CG1  VAL A 090      66.566  48.001  41.390  1.00 20.00
ATOM   2503  CG2  VAL A 090      68.012  46.942  39.655  1.00 20.00
ATOM   2505  N    SER A 091      63.807  49.232  39.295  1.00 20.00
ATOM   2506  CA   SER A 091      62.626  49.777  39.990  1.00 20.00
ATOM   2507  C    SER A 091      61.224  49.394  39.462  1.00 20.00
```

FIG. 4JJ

```
ATOM  2508  O    SER A 091      60.265  49.286  40.228  1.00 20.00
ATOM  2509  CB   SER A 091      62.780  51.317  40.030  1.00 20.00
ATOM  2510  OG   SER A 091      63.064  51.756  41.334  1.00 20.00
ATOM  2513  N    LEU A 092      61.125  49.264  38.146  1.00 20.00
ATOM  2514  CA   LEU A 092      59.906  48.874  37.485  1.00 20.00
ATOM  2515  C    LEU A 092      59.997  47.345  37.496  1.00 20.00
ATOM  2516  O    LEU A 092      58.987  46.643  37.662  1.00 20.00
ATOM  2517  CB   LEU A 092      59.941  49.394  36.065  1.00 20.00
ATOM  2518  CG   LEU A 092      60.797  50.625  35.992  1.00 20.00
ATOM  2519  CD1  LEU A 092      60.882  51.169  34.601  1.00 20.00
ATOM  2520  CD2  LEU A 092      60.174  51.616  36.871  1.00 20.00
ATOM  2522  N    ASN A 093      61.243  46.886  37.306  1.00 20.00
ATOM  2523  CA   ASN A 093      61.699  45.495  37.299  1.00 20.00
ATOM  2524  C    ASN A 093      61.214  44.889  38.582  1.00 20.00
ATOM  2525  O    ASN A 093      60.803  43.724  38.635  1.00 20.00
ATOM  2526  CB   ASN A 093      63.206  45.466  37.438  1.00 20.00
ATOM  2527  CG   ASN A 093      63.927  44.920  36.244  1.00 20.00
ATOM  2528  OD1  ASN A 093      65.126  44.666  36.350  1.00 20.00
ATOM  2529  ND2  ASN A 093      63.245  44.739  35.117  1.00 20.00
ATOM  2533  N    ARG A 094      61.344  45.693  39.631  1.00 20.00
ATOM  2534  CA   ARG A 094      60.992  45.309  40.985  1.00 20.00
ATOM  2535  C    ARG A 094      59.515  45.614  41.318  1.00 20.00
ATOM  2536  O    ARG A 094      59.112  45.717  42.468  1.00 20.00
ATOM  2537  CB   ARG A 094      61.954  46.010  41.937  1.00 20.00
ATOM  2538  CG   ARG A 094      61.850  45.571  43.339  1.00 20.00
ATOM  2539  CD   ARG A 094      62.088  46.747  44.262  1.00 20.00
ATOM  2540  NE   ARG A 094      61.170  46.917  45.403  1.00 20.00
ATOM  2541  CZ   ARG A 094      59.842  47.007  45.328  1.00 20.00
ATOM  2542  NH1  ARG A 094      59.224  46.948  44.164  1.00 20.00
ATOM  2543  NH2  ARG A 094      59.129  47.209  46.438  1.00 20.00
ATOM  2550  N    MET A 095      58.710  45.750  40.278  1.00 20.00
ATOM  2551  CA   MET A 095      57.306  46.018  40.421  1.00 20.00
ATOM  2552  C    MET A 095      56.723  44.944  39.527  1.00 20.00
ATOM  2553  O    MET A 095      55.597  44.512  39.706  1.00 20.00
ATOM  2554  CB   MET A 095      56.967  47.406  39.870  1.00 20.00
ATOM  2555  CG   MET A 095      57.240  48.556  40.822  1.00 20.00
ATOM  2556  SD   MET A 095      56.618  50.279  40.365  1.00 20.00
ATOM  2557  CE   MET A 095      56.509  50.955  42.056  1.00 20.00
ATOM  2559  N    LEU A 096      57.495  44.509  38.551  1.00 20.00
ATOM  2560  CA   LEU A 096      57.034  43.476  37.646  1.00 20.00
ATOM  2561  C    LEU A 096      56.931  42.034  38.341  1.00 20.00
ATOM  2562  O    LEU A 096      56.594  40.999  37.738  1.00 20.00
ATOM  2563  CB   LEU A 096      57.960  43.493  36.401  1.00 20.00
ATOM  2564  CG   LEU A 096      57.892  44.684  35.421  1.00 20.00
ATOM  2565  CD1  LEU A 096      58.856  44.515  34.311  1.00 20.00
ATOM  2566  CD2  LEU A 096      56.523  44.804  34.819  1.00 20.00
ATOM  2568  N    GLU A 097      57.181  41.981  39.633  1.00 20.00
ATOM  2569  CA   GLU A 097      57.102  40.734  40.327  1.00 20.00
ATOM  2570  C    GLU A 097      56.396  40.934  41.642  1.00 20.00
ATOM  2571  O    GLU A 097      57.064  41.042  42.664  1.00 20.00
ATOM  2572  CB   GLU A 097      58.499  40.252  40.606  1.00 20.00
ATOM  2573  CG   GLU A 097      59.459  40.519  39.475  1.00 20.00
ATOM  2574  CD   GLU A 097      60.327  39.305  39.212  1.00 20.00
ATOM  2575  OE1  GLU A 097      60.756  38.703  40.228  1.00 20.00
ATOM  2576  OE2  GLU A 097      60.564  38.961  38.022  1.00 20.00
ATOM  2578  N    GLU A 098      55.062  41.010  41.622  1.00 20.00
ATOM  2579  CA   GLU A 098      54.192  41.177  42.823  1.00 20.00
```

FIG. 4KK

```
ATOM  2580  C    GLU A 098    52.812  41.404  42.219  1.00 20.00
ATOM  2581  C    GLU A 098    51.765  41.462  42.905  1.00 20.00
ATOM  2582  CB   GLU A 098    54.514  42.433  43.686  1.00 20.00
ATOM  2583  CG   GLU A 098    55.726  43.286  43.421  1.00 20.00
ATOM  2584  CD   GLU A 098    56.655  43.318  44.654  1.00 20.00
ATOM  2585  OE1  GLU A 098    56.157  43.414  45.803  1.00 20.00
ATOM  2586  OE2  GLU A 098    57.903  43.232  44.488  1.00 20.00
ATOM  2588  N    ARG A 099    52.872  41.529  40.898  1.00 20.00
ATOM  2589  CA   ARG A 099    51.725  41.820  40.069  1.00 20.00
ATOM  2590  C    ARG A 099    50.664  42.484  40.859  1.00 20.00
ATOM  2591  O    ARG A 099    49.536  41.992  40.902  1.00 20.00
ATOM  2592  CB   ARG A 099    51.107  40.600  39.385  1.00 20.00
ATOM  2593  CG   ARG A 099    50.252  41.009  38.173  1.00 20.00
ATOM  2594  CD   ARG A 099    49.462  42.327  38.402  1.00 20.00
ATOM  2595  NE   ARG A 099    48.780  42.813  37.193  1.00 20.00
ATOM  2596  CZ   ARG A 099    48.995  44.001  36.614  1.00 20.00
ATOM  2597  NH1  ARG A 099    49.888  44.858  37.132  1.00 20.00
ATOM  2598  NH2  ARG A 099    48.348  44.319  35.492  1.00 20.00
ATOM  2605  N    LYS A 100    51.012  43.593  41.491  1.00 20.00
ATOM  2606  CA   LYS A 100    49.996  44.273  42.208  1.00 20.00
ATOM  2607  C    LYS A 100    49.233  45.314  41.412  1.00 20.00
ATOM  2608  O    LYS A 100    48.414  46.009  41.961  1.00 20.00
ATOM  2609  CB   LYS A 100    50.568  44.887  43.452  1.00 20.00
ATOM  2610  CG   LYS A 100    49.723  44.455  44.606  1.00 20.00
ATOM  2611  CD   LYS A 100    48.746  43.295  44.135  1.00 20.00
ATOM  2612  CE   LYS A 100    47.476  43.250  44.951  1.00 20.00
ATOM  2613  NZ   LYS A 100    47.799  42.986  46.386  1.00 20.00
ATOM  2618  N    THR A 101    49.448  45.372  40.107  1.00 20.00
ATOM  2619  CA   THR A 101    48.825  46.402  39.284  1.00 20.00
ATOM  2620  C    THR A 101    49.208  47.748  39.873  1.00 20.00
ATOM  2621  O    THR A 101    48.788  48.131  40.984  1.00 20.00
ATOM  2622  CB   THR A 101    47.325  46.313  39.223  1.00 20.00
ATOM  2623  OG1  THR A 101    46.859  45.424  40.224  1.00 20.00
ATOM  2624  CG2  THR A 101    46.913  45.840  37.852  1.00 20.00
ATOM  2627  N    TYR A 102    50.025  48.453  39.098  1.00 20.00
ATOM  2628  CA   TYR A 102    50.547  49.712  39.515  1.00 20.00
ATOM  2629  C    TYR A 102    49.870  50.826  38.785  1.00 20.00
ATOM  2630  O    TYR A 102    49.661  51.891  39.342  1.00 20.00
ATOM  2631  CB   TYR A 102    52.040  49.684  39.310  1.00 20.00
ATOM  2632  CG   TYR A 102    52.744  48.940  40.406  1.00 20.00
ATOM  2633  CD1  TYR A 102    53.416  47.744  40.169  1.00 20.00
ATOM  2634  CD2  TYR A 102    52.769  49.460  41.663  1.00 20.00
ATOM  2635  CE1  TYR A 102    54.090  47.122  41.160  1.00 20.00
ATOM  2636  CE2  TYR A 102    53.430  48.852  42.653  1.00 20.00
ATOM  2637  CZ   TYR A 102    54.102  47.691  42.416  1.00 20.00
ATOM  2638  OH   TYR A 102    54.846  47.188  43.470  1.00 20.00
ATOM  2641  N    VAL A 103    49.568  50.591  37.524  1.00 20.00
ATOM  2642  CA   VAL A 103    48.790  51.544  36.741  1.00 20.00
ATOM  2643  C    VAL A 103    47.512  50.735  36.788  1.00 20.00
ATOM  2644  O    VAL A 103    47.571  49.547  37.137  1.00 20.00
ATOM  2645  CB   VAL A 103    49.121  51.597  35.265  1.00 20.00
ATOM  2646  CG1  VAL A 103    48.387  52.783  34.645  1.00 20.00
ATOM  2647  CG2  VAL A 103    50.633  51.634  35.049  1.00 20.00
ATOM  2649  N    ASN A 104    46.380  51.336  36.420  1.00 20.00
ATOM  2650  CA   ASN A 104    45.109  50.645  36.473  1.00 20.00
ATOM  2651  C    ASN A 104    44.386  51.023  35.231  1.00 20.00
ATOM  2652  O    ASN A 104    44.569  52.110  34.731  1.00 20.00
```

FIG. 4LL

```
ATOM   2653  CB   ASN A 104      44.360  51.089  37.714  1.00 20.00
ATOM   2654  CG   ASN A 104      42.863  51.071  37.544  1.00 20.00
ATOM   2655  OD1  ASN A 104      42.348  51.013  36.431  1.00 20.00
ATOM   2656  ND2  ASN A 104      42.149  51.139  38.666  1.00 20.00
ATOM   2660  N    THR A 105      43.545  50.137  34.732  1.00 20.00
ATOM   2661  CA   THR A 105      42.855  50.390  33.490  1.00 20.00
ATOM   2662  C    THR A 105      41.412  49.870  33.596  1.00 20.00
ATOM   2663  O    THR A 105      40.678  49.783  32.593  1.00 20.00
ATOM   2664  CB   THR A 105      43.627  49.686  32.341  1.00 20.00
ATOM   2665  OG1  THR A 105      44.293  48.501  32.839  1.00 20.00
ATOM   2666  CG2  THR A 105      44.686  50.595  31.792  1.00 20.00
ATOM   2669  N    THR A 106      41.013  49.565  34.831  1.00 20.00
ATOM   2670  CA   THR A 106      39.701  49.048  35.173  1.00 20.00
ATOM   2671  C    THR A 106      38.588  50.103  35.353  1.00 20.00
ATOM   2672  O    THR A 106      38.818  51.077  36.038  1.00 20.00
ATOM   2673  CB   THR A 106      39.850  48.258  36.473  1.00 20.00
ATOM   2674  OG1  THR A 106      39.615  46.869  36.226  1.00 20.00
ATOM   2675  CG2  THR A 106      38.902  48.779  37.552  1.00 20.00
ATOM   2678  N    LEU A 107      37.383  49.891  34.775  1.00 20.00
ATOM   2679  CA   LEU A 107      36.229  50.816  34.903  1.00 20.00
ATOM   2680  C    LEU A 107      35.437  50.546  36.199  1.00 20.00
ATOM   2681  O    LEU A 107      35.067  49.413  36.473  1.00 20.00
ATOM   2682  CB   LEU A 107      35.279  50.655  33.739  1.00 20.00
ATOM   2683  CG   LEU A 107      35.798  50.744  32.313  1.00 20.00
ATOM   2684  CD1  LEU A 107      34.625  50.728  31.345  1.00 20.00
ATOM   2685  CD2  LEU A 107      36.667  51.987  32.120  1.00 20.00
ATOM   2687  N    TYR A 108      35.176  51.583  36.998  1.00 20.00
ATOM   2688  CA   TYR A 108      34.436  51.444  38.260  1.00 20.00
ATOM   2689  C    TYR A 108      33.529  52.660  38.590  1.00 20.00
ATOM   2690  O    TYR A 108      33.124  52.843  39.767  1.00 20.00
ATOM   2691  CB   TYR A 108      35.417  51.219  39.419  1.00 20.00
ATOM   2692  CG   TYR A 108      36.234  49.960  39.165  1.00 20.00
ATOM   2693  CD1  TYR A 108      37.446  49.725  40.176  1.00 20.00
ATOM   2694  CD2  TYR A 108      35.201  48.850  39.201  1.00 20.00
ATOM   2696  N    GLU A 109      33.228  53.475  37.565  1.00 20.00
ATOM   2697  CA   GLU A 109      32.363  54.664  37.691  1.00 20.00
ATOM   2698  C    GLU A 109      33.115  55.935  37.364  1.00 20.00
ATOM   2699  O    GLU A 109      34.039  56.360  38.093  1.00 20.00
ATOM   2700  CB   GLU A 109      31.764  54.786  39.092  1.00 20.00
ATOM   2702  N    LYS A 110      32.723  56.590  36.284  1.00 20.00
ATOM   2703  CA   LYS A 110      33.431  57.801  35.968  1.00 20.00
ATOM   2704  C    LYS A 110      34.879  57.443  35.586  1.00 20.00
ATOM   2705  O    LYS A 110      35.653  56.902  36.366  1.00 20.00
ATOM   2706  CB   LYS A 110      33.373  58.742  37.176  1.00 20.00
ATOM   2707  CG   LYS A 110      32.211  58.399  38.165  1.00 20.00
ATOM   2708  CD   LYS A 110      31.414  59.597  38.754  1.00 20.00
ATOM   2709  CE   LYS A 110      30.154  59.092  39.514  1.00 20.00
ATOM   2710  NZ   LYS A 110      30.320  58.678  40.967  1.00 20.00
ATOM   2715  N    PHE A 111      35.184  57.675  34.324  1.00 20.00
ATOM   2716  CA   PHE A 111      36.489  57.460  33.833  1.00 20.00
ATOM   2717  C    PHE A 111      36.665  58.179  32.520  1.00 20.00
ATOM   2718  O    PHE A 111      36.065  57.840  31.494  1.00 20.00
ATOM   2719  CB   PHE A 111      36.842  55.994  33.658  1.00 20.00
ATOM   2720  CG   PHE A 111      38.193  55.795  33.013  1.00 20.00
ATOM   2721  CD1  PHE A 111      39.337  55.675  33.772  1.00 20.00
ATOM   2722  CD2  PHE A 111      38.332  55.861  31.657  1.00 20.00
ATOM   2723  CE1  PHE A 111      40.601  55.639  33.171  1.00 20.00
```

FIG. 4MM

| | | | | | | | | |
|---|---|---|---|---|---|---|---|---|
| ATOM | 2724 | CE2 | PHE A 111 | 39.575 | 55.824 | 31.077 | 1.00 | 20.00 |
| ATOM | 2725 | CZ | PHE A 111 | 40.706 | 55.717 | 31.830 | 1.00 | 20.00 |
| ATOM | 2727 | N | THR A 112 | 37.540 | 59.180 | 32.584 | 1.00 | 20.00 |
| ATOM | 2728 | CA | THR A 112 | 37.904 | 59.997 | 31.457 | 1.00 | 20.00 |
| ATOM | 2729 | C | THR A 112 | 39.374 | 59.703 | 31.350 | 1.00 | 20.00 |
| ATOM | 2730 | O | THR A 112 | 39.967 | 59.297 | 32.329 | 1.00 | 20.00 |
| ATOM | 2731 | CB | THR A 112 | 37.686 | 61.487 | 31.794 | 1.00 | 20.00 |
| ATOM | 2732 | OG1 | THR A 112 | 36.780 | 61.598 | 32.899 | 1.00 | 20.00 |
| ATOM | 2733 | CG2 | THR A 112 | 37.079 | 62.216 | 30.623 | 1.00 | 20.00 |
| ATOM | 2736 | N | TYR A 113 | 39.926 | 59.880 | 30.153 | 1.00 | 20.00 |
| ATOM | 2737 | CA | TYR A 113 | 41.339 | 59.706 | 29.866 | 1.00 | 20.00 |
| ATOM | 2738 | C | TYR A 113 | 42.092 | 61.000 | 30.123 | 1.00 | 20.00 |
| ATOM | 2739 | O | TYR A 113 | 41.837 | 61.669 | 31.105 | 1.00 | 20.00 |
| ATOM | 2740 | CB | TYR A 113 | 41.520 | 59.320 | 28.433 | 1.00 | 20.00 |
| ATOM | 2741 | CG | TYR A 113 | 41.095 | 57.923 | 28.236 | 1.00 | 20.00 |
| ATOM | 2742 | CD1 | TYR A 113 | 40.063 | 57.606 | 27.346 | 1.00 | 20.00 |
| ATOM | 2743 | CD2 | TYR A 113 | 41.699 | 56.879 | 28.960 | 1.00 | 20.00 |
| ATOM | 2744 | CE1 | TYR A 113 | 39.641 | 56.300 | 27.178 | 1.00 | 20.00 |
| ATOM | 2745 | CE2 | TYR A 113 | 41.283 | 55.573 | 28.792 | 1.00 | 20.00 |
| ATOM | 2746 | CZ | TYR A 113 | 40.251 | 55.291 | 27.894 | 1.00 | 20.00 |
| ATOM | 2747 | OH | TYR A 113 | 39.853 | 53.992 | 27.670 | 1.00 | 20.00 |
| ATOM | 2750 | N | ALA A 114 | 42.958 | 61.423 | 29.201 | 1.00 | 20.00 |
| ATOM | 2751 | CA | ALA A 114 | 43.754 | 62.605 | 29.511 | 1.00 | 20.00 |
| ATOM | 2752 | C | ALA A 114 | 43.947 | 63.838 | 28.571 | 1.00 | 20.00 |
| ATOM | 2753 | O | ALA A 114 | 43.604 | 64.944 | 28.952 | 1.00 | 20.00 |
| ATOM | 2754 | CB | ALA A 114 | 45.129 | 62.109 | 30.025 | 1.00 | 20.00 |
| ATOM | 2756 | N | GLY A 115 | 44.491 | 63.670 | 27.377 | 1.00 | 20.00 |
| ATOM | 2757 | CA | GLY A 115 | 44.727 | 64.815 | 26.532 | 1.00 | 20.00 |
| ATOM | 2758 | C | GLY A 115 | 44.350 | 64.834 | 25.059 | 1.00 | 20.00 |
| ATOM | 2759 | O | GLY A 115 | 45.029 | 64.291 | 24.173 | 1.00 | 20.00 |
| ATOM | 2761 | N | ILE A 116 | 43.220 | 65.504 | 24.838 | 1.00 | 20.00 |
| ATOM | 2762 | CA | ILE A 116 | 42.609 | 65.779 | 23.527 | 1.00 | 20.00 |
| ATOM | 2763 | C | ILE A 116 | 41.516 | 64.772 | 23.037 | 1.00 | 20.00 |
| ATOM | 2764 | O | ILE A 116 | 41.123 | 63.952 | 23.880 | 1.00 | 20.00 |
| ATOM | 2765 | CB | ILE A 116 | 43.744 | 65.993 | 22.469 | 1.00 | 20.00 |
| ATOM | 2766 | OXT | ILE A 116 | 41.049 | 64.815 | 21.867 | 1.00 | 20.00 |
| TER | | | | | | | | |
| HETATM | 1 | C1 | INH3A 1 | 58.776 | 51.045 | 11.645 | 0.00 | 0.00 |
| HETATM | 2 | N2 | INH3A 1 | 58.172 | 52.218 | 11.841 | 0.00 | 0.00 |
| HETATM | 3 | C3 | INH3A 1 | 58.936 | 53.310 | 12.056 | 0.00 | 0.00 |
| HETATM | 4 | C4 | INH3A 1 | 60.320 | 53.244 | 12.077 | 0.00 | 0.00 |
| HETATM | 5 | C5 | INH3A 1 | 60.887 | 51.924 | 11.859 | 0.00 | 0.00 |
| HETATM | 6 | N6 | INH3A 1 | 60.101 | 50.854 | 11.646 | 0.00 | 0.00 |
| HETATM | 8 | N8 | INH3A 1 | 58.497 | 54.604 | 12.288 | 0.00 | 0.00 |
| HETATM | 9 | C9 | INH3A 1 | 59.673 | 55.293 | 12.446 | 0.00 | 0.00 |
| HETATM | 10 | C10 | INH3A 1 | 60.842 | 54.525 | 12.326 | 0.00 | 0.00 |
| HETATM | 12 | N13 | INH3A 1 | 62.289 | 51.734 | 11.876 | 0.00 | 0.00 |
| HETATM | 13 | C14 | INH3A 1 | 62.258 | 54.972 | 12.430 | 0.00 | 0.00 |
| HETATM | 14 | C16 | INH3A 1 | 57.098 | 55.079 | 12.339 | 0.00 | 0.00 |
| HETATM | 15 | C17 | INH3A 1 | 63.049 | 54.530 | 13.477 | 0.00 | 0.00 |
| HETATM | 16 | C18 | INH3A 1 | 64.374 | 54.941 | 13.612 | 0.00 | 0.00 |
| HETATM | 17 | C19 | INH3A 1 | 64.935 | 55.815 | 12.687 | 0.00 | 0.00 |
| HETATM | 18 | C20 | INH3A 1 | 64.131 | 56.249 | 11.643 | 0.00 | 0.00 |
| HETATM | 19 | C21 | INH3A 1 | 62.810 | 55.841 | 11.508 | 0.00 | 0.00 |
| HETATM | 23 | N25 | INH3A 1 | 66.225 | 56.236 | 12.788 | 0.00 | 0.00 |
| HETATM | 24 | S26 | INH3A 1 | 66.995 | 56.113 | 14.217 | 0.00 | 0.00 |
| HETATM | 25 | O27 | INH3A 1 | 65.999 | 55.773 | 15.187 | 0.00 | 0.00 |

FIG. 4NN

```
HETATM   26  O28 INH3A   1      67.770  57.301  14.420  0.00  0.00
HETATM   27  C29 INH3A   1      68.100  54.741  14.032  0.00  0.00
HETATM   28  C30 INH3A   1      69.041  54.751  13.007  0.00  0.00
HETATM   29  C31 INH3A   1      69.873  53.654  12.825  0.00  0.00
HETATM   30  C32 INH3A   1      69.740  52.566  13.674  0.00  0.00
HETATM   31  C33 INH3A   1      68.801  52.539  14.696  0.00  0.00
HETATM   32  C34 INH3A   1      67.972  53.639  14.872  0.00  0.00
HETATM   37  F39 INH3A   1      70.540  51.507  13.502  0.00  0.00
HETATM   39  F41 INH3A   1      64.638  57.094  10.735  0.00  0.00
HETATM   40  C42 INH3A   1      56.781  55.784  13.669  0.00  0.00
HETATM   41  C43 INH3A   1      55.311  56.219  13.720  0.00  0.00
HETATM   42  C44 INH3A   1      54.962  57.130  12.528  0.00  0.00
HETATM   43  C45 INH3A   1      55.278  56.419  11.202  0.00  0.00
HETATM   44  C46 INH3A   1      56.748  55.981  11.144  0.00  0.00
HETATM   53  C55 INH3A   1      53.385  58.715  13.548  0.00  0.00
HETATM   54  C56 INH3A   1      51.998  59.356  13.419  0.00  0.00
HETATM   55  N57 INH3A   1      50.930  58.353  13.520  0.00  0.00
HETATM   56  C58 INH3A   1      51.136  57.302  12.516  0.00  0.00
HETATM   57  C59 INH3A   1      52.522  56.662  12.658  0.00  0.00
HETATM   58  N60 INH3A   1      53.588  57.668  12.536  0.00  0.00
HETATM   68  C70 INH3A   1      49.599  58.958  13.416  0.00  0.00
TER
```

FIG. 400

```
CRYST     86.000   86.000  112.000  90.00   90.00   90.00 P42212
SCALE1     0.01163  0.00000  0.00000          0.00000
SCALE2     0.00000  0.01163  0.00000          0.00000
SCALE3     0.00000  0.00000  0.00893          0.00000
ATOM      1  N   PRO A 817       8.606  38.803   6.968  1.00 63.06
ATOM      2  CA  PRO A 817       9.750  39.629   6.436  1.00 62.53
ATOM      3  C   PRO A 817      10.180  38.953   5.133  1.00 62.97
ATOM      4  O   PRO A 817      10.749  37.851   5.149  1.00 59.85
ATOM      5  CB  PRO A 817      10.807  39.752   7.499  1.00 62.45
ATOM      6  N   VAL A 818       9.794  39.542   3.998  1.00 63.22
ATOM      7  CA  VAL A 818      10.112  38.916   2.711  1.00 66.18
ATOM      8  C   VAL A 818      11.172  39.708   1.952  1.00 67.24
ATOM      9  O   VAL A 818      11.086  40.927   1.837  1.00 68.73
ATOM     10  CB  VAL A 818       8.866  38.691   1.843  1.00 66.96
ATOM     11  CG1 VAL A 818       9.133  37.632   0.770  1.00 67.29
ATOM     12  CG2 VAL A 818       7.637  38.224   2.629  1.00 66.80
ATOM     13  N   LEU A 819      12.192  39.014   1.464  1.00 67.40
ATOM     14  CA  LEU A 819      13.300  39.569   0.705  1.00 67.89
ATOM     15  C   LEU A 819      13.445  38.938  -0.680  1.00 68.53
ATOM     16  O   LEU A 819      13.179  37.750  -0.875  1.00 67.98
ATOM     17  CB  LEU A 819      14.589  39.374   1.493  1.00 67.17
ATOM     18  N   ASP A 820      13.854  39.728  -1.668  1.00 70.32
ATOM     19  CA  ASP A 820      13.962  39.181  -3.018  1.00 74.15
ATOM     20  C   ASP A 820      15.382  38.826  -3.421  1.00 75.07
ATOM     21  O   ASP A 820      16.390  39.377  -2.978  1.00 74.87
ATOM     22  CB  ASP A 820      13.314  40.147  -4.017  1.00 76.15
ATOM     23  CG  ASP A 820      13.968  41.518  -4.054  1.00 78.23
ATOM     24  OD1 ASP A 820      14.712  41.846  -3.092  1.00 79.04
ATOM     25  OD2 ASP A 820      13.712  42.246  -5.051  1.00 78.55
ATOM     26  N   TRP A 821      15.489  37.870  -4.336  1.00 77.12
ATOM     27  CA  TRP A 821      16.794  37.480  -4.871  1.00 80.00
ATOM     28  C   TRP A 821      17.288  38.671  -5.674  1.00 80.90
ATOM     29  O   TRP A 821      16.560  39.677  -5.750  1.00 82.56
ATOM     30  CB  TRP A 821      16.640  36.237  -5.738  1.00 81.50
ATOM     31  CG  TRP A 821      17.979  35.683  -6.126  1.00 84.29
ATOM     32  CD1 TRP A 821      18.770  36.052  -7.174  1.00 85.04
ATOM     33  CD2 TRP A 821      18.686  34.639  -5.443  1.00 85.54
ATOM     34  NE1 TRP A 821      19.932  35.323  -7.184  1.00 85.91
ATOM     35  CE2 TRP A 821      19.895  34.435  -6.138  1.00 86.16
ATOM     36  CE3 TRP A 821      18.402  33.854  -4.317  1.00 85.72
ATOM     37  CZ2 TRP A 821      20.822  33.474  -5.736  1.00 86.76
ATOM     38  CZ3 TRP A 821      19.317  32.899  -3.914  1.00 86.12
ATOM     39  CH2 TRP A 821      20.513  32.723  -4.632  1.00 86.81
ATOM     40  N   ASN A 822      18.490  38.703  -6.220  1.00 80.99
ATOM     41  CA  ASN A 822      18.941  39.868  -6.995  1.00 81.52
ATOM     42  C   ASN A 822      18.729  41.071  -6.079  1.00 80.56
ATOM     43  O   ASN A 822      18.110  42.084  -6.381  1.00 81.67
ATOM     44  CB  ASN A 822      18.164  39.937  -8.312  1.00 83.00
ATOM     45  CG  ASN A 822      19.059  40.084  -9.532  1.00 84.08
ATOM     46  OD1 ASN A 822      20.168  40.617  -9.420  1.00 84.25
ATOM     47  ND2 ASN A 822      18.581  39.608 -10.679  1.00 84.49
ATOM     48  N   ASP A 823      19.204  40.923  -4.856  1.00 78.69
ATOM     49  CA  ASP A 823      19.120  41.815  -3.723  1.00 76.89
ATOM     50  C   ASP A 823      19.874  41.123  -2.568  1.00 74.92
ATOM     51  O   ASP A 823      19.952  41.542  -1.417  1.00 75.11
ATOM     52  CB  ASP A 823      17.695  42.112  -3.299  1.00 77.66
ATOM     53  CG  ASP A 823      17.306  43.572  -3.217  1.00 78.83
```

FIG. 5A

| | | | | | | | | | |
|---|---|---|---|---|---|---|---|---|---|
| ATOM | 54 | OD1 | ASP | A | 823 | 17.885 | 44.406 | -3.955 | 1.00 79.53 |
| ATOM | 55 | OD2 | ASP | A | 823 | 16.391 | 43.945 | -2.444 | 1.00 78.52 |
| ATOM | 56 | N | ILE | A | 824 | 20.438 | 39.973 | -2.919 | 1.00 71.67 |
| ATOM | 57 | CA | ILE | A | 824 | 21.270 | 39.189 | -2.030 | 1.00 69.30 |
| ATOM | 58 | C | ILE | A | 824 | 22.624 | 39.046 | -2.750 | 1.00 67.35 |
| ATOM | 59 | O | ILE | A | 824 | 22.678 | 38.352 | -3.770 | 1.00 65.47 |
| ATOM | 60 | CB | ILE | A | 824 | 20.744 | 37.783 | -1.696 | 1.00 69.43 |
| ATOM | 61 | CG1 | ILE | A | 824 | 19.356 | 37.733 | -1.074 | 1.00 69.93 |
| ATOM | 62 | CG2 | ILE | A | 824 | 21.752 | 37.046 | -0.820 | 1.00 69.07 |
| ATOM | 63 | CD1 | ILE | A | 824 | 19.156 | 38.009 | 0.386 | 1.00 71.48 |
| ATOM | 64 | N | LYS | A | 825 | 23.649 | 39.735 | -2.252 | 1.00 65.03 |
| ATOM | 65 | CA | LYS | A | 825 | 24.977 | 39.581 | -2.829 | 1.00 63.66 |
| ATOM | 66 | C | LYS | A | 825 | 25.810 | 38.677 | -1.903 | 1.00 62.88 |
| ATOM | 67 | O | LYS | A | 825 | 26.290 | 39.103 | -0.850 | 1.00 60.46 |
| ATOM | 68 | CB | LYS | A | 825 | 25.688 | 40.893 | -3.082 | 1.00 63.33 |
| ATOM | 69 | N | PHE | A | 826 | 25.952 | 37.420 | -2.315 | 1.00 62.22 |
| ATOM | 70 | CA | PHE | A | 826 | 26.745 | 36.434 | -1.595 | 1.00 63.65 |
| ATOM | 71 | C | PHE | A | 826 | 28.243 | 36.752 | -1.654 | 1.00 64.85 |
| ATOM | 72 | O | PHE | A | 826 | 28.806 | 36.978 | -2.738 | 1.00 65.98 |
| ATOM | 73 | CB | PHE | A | 826 | 26.535 | 35.019 | -2.151 | 1.00 63.23 |
| ATOM | 74 | CG | PHE | A | 826 | 25.242 | 34.324 | -1.828 | 1.00 63.28 |
| ATOM | 75 | CD1 | PHE | A | 826 | 24.194 | 34.262 | -2.742 | 1.00 63.47 |
| ATOM | 76 | CD2 | PHE | A | 826 | 25.068 | 33.738 | -0.587 | 1.00 62.78 |
| ATOM | 77 | CE1 | PHE | A | 826 | 23.013 | 33.606 | -2.421 | 1.00 63.26 |
| ATOM | 78 | CE2 | PHE | A | 826 | 23.893 | 33.090 | -0.261 | 1.00 63.76 |
| ATOM | 79 | CZ | PHE | A | 826 | 22.859 | 33.026 | -1.183 | 1.00 63.42 |
| ATOM | 80 | N | GLN | A | 827 | 28.933 | 36.771 | -0.514 | 1.00 64.73 |
| ATOM | 81 | CA | GLN | A | 827 | 30.359 | 37.048 | -0.474 | 1.00 63.67 |
| ATOM | 82 | C | GLN | A | 827 | 31.182 | 35.763 | -0.387 | 1.00 62.27 |
| ATOM | 83 | O | GLN | A | 827 | 31.703 | 35.217 | -1.356 | 1.00 61.84 |
| ATOM | 84 | CB | GLN | A | 827 | 30.736 | 37.884 | 0.748 | 1.00 65.45 |
| ATOM | 85 | CG | GLN | A | 827 | 29.641 | 38.676 | 1.428 | 1.00 69.14 |
| ATOM | 86 | CD | GLN | A | 827 | 29.805 | 40.166 | 1.185 | 1.00 71.09 |
| ATOM | 87 | OE1 | GLN | A | 827 | 29.364 | 40.617 | 0.124 | 1.00 72.36 |
| ATOM | 88 | NE2 | GLN | A | 827 | 30.442 | 40.865 | 2.124 | 1.00 71.89 |
| ATOM | 89 | N | ASP | A | 828 | 31.371 | 35.286 | 0.838 | 1.00 61.57 |
| ATOM | 90 | CA | ASP | A | 828 | 32.237 | 34.122 | 1.034 | 1.00 62.37 |
| ATOM | 91 | C | ASP | A | 828 | 31.576 | 33.071 | 1.883 | 1.00 61.37 |
| ATOM | 92 | O | ASP | A | 828 | 30.330 | 32.899 | 1.910 | 1.00 63.34 |
| ATOM | 93 | CB | ASP | A | 828 | 33.605 | 34.623 | 1.532 | 1.00 63.30 |
| ATOM | 94 | CG | ASP | A | 828 | 33.536 | 35.073 | 2.977 | 1.00 65.22 |
| ATOM | 95 | OD1 | ASP | A | 828 | 34.629 | 35.346 | 3.505 | 1.00 66.32 |
| ATOM | 96 | OD2 | ASP | A | 828 | 32.418 | 35.135 | 3.513 | 1.00 67.27 |
| ATOM | 97 | N | VAL | A | 829 | 32.332 | 32.174 | 2.503 | 1.00 59.16 |
| ATOM | 98 | CA | VAL | A | 829 | 31.820 | 31.095 | 3.339 | 1.00 56.81 |
| ATOM | 99 | C | VAL | A | 829 | 32.101 | 31.413 | 4.805 | 1.00 57.13 |
| ATOM | 100 | O | VAL | A | 829 | 33.252 | 31.767 | 5.119 | 1.00 57.41 |
| ATOM | 101 | CB | VAL | A | 829 | 32.462 | 29.753 | 2.948 | 1.00 55.58 |
| ATOM | 102 | CG1 | VAL | A | 829 | 32.035 | 28.658 | 3.909 | 1.00 55.56 |
| ATOM | 103 | CG2 | VAL | A | 829 | 32.111 | 29.383 | 1.513 | 1.00 55.17 |
| ATOM | 104 | N | ILE | A | 830 | 31.106 | 31.314 | 5.693 | 1.00 56.36 |
| ATOM | 105 | CA | ILE | A | 830 | 31.360 | 31.613 | 7.108 | 1.00 54.69 |
| ATOM | 106 | C | ILE | A | 830 | 31.971 | 30.371 | 7.750 | 1.00 54.51 |
| ATOM | 107 | O | ILE | A | 830 | 32.927 | 30.411 | 8.507 | 1.00 54.88 |
| ATOM | 108 | CB | ILE | A | 830 | 30.170 | 32.157 | 7.898 | 1.00 52.84 |
| ATOM | 109 | CG1 | ILE | A | 830 | 29.780 | 33.560 | 7.374 | 1.00 52.48 |
| ATOM | 110 | CG2 | ILE | A | 830 | 30.518 | 32.300 | 9.375 | 1.00 51.14 |

FIG. 5B

```
ATOM  111  CD1  ILE A 830    28.389  34.012   7.808  1.00 52.01
ATOM  112  N    GLY A 831    31.431  29.232   7.376  1.00 54.93
ATOM  113  CA   GLY A 831    31.949  27.959   7.866  1.00 57.73
ATOM  114  C    GLY A 831    30.703  27.066   7.878  1.00 60.30
ATOM  115  O    GLY A 831    29.687  27.433   7.281  1.00 59.66
ATOM  116  N    GLU A 832    30.811  25.963   8.594  1.00 62.36
ATOM  117  CA   GLU A 832    29.649  25.080   8.634  1.00 65.54
ATOM  118  C    GLU A 832    28.918  25.256   9.956  1.00 67.03
ATOM  119  O    GLU A 832    29.525  25.480  10.982  1.00 65.58
ATOM  120  CB   GLU A 832    30.079  23.647   8.389  1.00 65.24
ATOM  121  CG   GLU A 832    29.979  22.748   9.615  1.00 64.68
ATOM  122  CD   GLU A 832    30.771  21.493   9.247  1.00 65.38
ATOM  123  OE1  GLU A 832    31.871  21.394   9.838  1.00 65.15
ATOM  124  OE2  GLU A 832    30.232  20.771   8.386  1.00 64.01
ATOM  125  N    GLY A 833    27.605  25.128   9.870  1.00 71.16
ATOM  126  CA   GLY A 833    26.741  25.268  11.048  1.00 75.85
ATOM  127  C    GLY A 833    25.973  23.945  11.138  1.00 79.10
ATOM  128  O    GLY A 833    26.489  22.959  11.666  1.00 80.05
ATOM  129  N    ASN A 834    24.750  23.982  10.627  1.00 80.77
ATOM  130  CA   ASN A 834    23.887  22.807  10.614  1.00 82.57
ATOM  131  C    ASN A 834    23.055  22.917   9.332  1.00 82.72
ATOM  132  O    ASN A 834    22.709  24.047   8.973  1.00 83.47
ATOM  133  CB   ASN A 834    22.974  22.712  11.826  1.00 83.64
ATOM  134  CG   ASN A 834    23.565  22.227  13.122  1.00 84.87
ATOM  135  OD1  ASN A 834    23.040  22.476  14.214  1.00 85.57
ATOM  136  ND2  ASN A 834    24.692  21.516  13.114  1.00 85.28
ATOM  137  N    PHE A 835    22.813  21.799   8.663  1.00 82.37
ATOM  138  CA   PHE A 835    22.018  21.747   7.436  1.00 81.44
ATOM  139  C    PHE A 835    22.770  22.311   6.227  1.00 79.71
ATOM  140  O    PHE A 835    22.207  22.742   5.221  1.00 80.02
ATOM  141  CB   PHE A 835    20.656  22.423   7.609  1.00 81.62
ATOM  142  N    GLY A 836    24.093  22.257   6.306  1.00 77.25
ATOM  143  CA   GLY A 836    25.011  22.771   5.308  1.00 73.64
ATOM  144  C    GLY A 836    25.714  24.008   5.875  1.00 70.61
ATOM  145  O    GLY A 836    25.485  24.453   7.008  1.00 71.32
ATOM  146  N    GLN A 837    26.589  24.607   5.081  1.00 67.00
ATOM  147  CA   GLN A 837    27.288  25.779   5.584  1.00 64.94
ATOM  148  C    GLN A 837    26.303  26.943   5.749  1.00 61.14
ATOM  149  O    GLN A 837    25.079  26.947   5.627  1.00 62.09
ATOM  150  CB   GLN A 837    28.510  26.214   4.782  1.00 65.56
ATOM  151  CG   GLN A 837    28.323  26.175   3.277  1.00 68.22
ATOM  152  CD   GLN A 837    28.499  24.771   2.717  1.00 70.10
ATOM  153  OE1  GLN A 837    27.540  23.989   2.498  1.00 71.35
ATOM  154  NE2  GLN A 837    29.776  24.447   2.508  1.00 69.74
ATOM  155  N    VAL A 838    26.949  27.991   6.223  1.00 56.19
ATOM  156  CA   VAL A 838    26.368  29.284   6.530  1.00 52.12
ATOM  157  C    VAL A 838    27.166  30.196   5.612  1.00 51.49
ATOM  158  O    VAL A 838    28.401  30.088   5.669  1.00 50.02
ATOM  159  CB   VAL A 838    26.657  29.586   8.002  1.00 50.54
ATOM  160  CG1  VAL A 838    26.258  30.989   8.386  1.00 48.67
ATOM  161  CG2  VAL A 838    25.974  28.553   8.890  1.00 48.75
ATOM  162  N    LEU A 839    26.512  30.915   4.719  1.00 50.28
ATOM  163  CA   LEU A 839    27.308  31.782   3.831  1.00 48.12
ATOM  164  C    LEU A 839    27.210  33.217   4.324  1.00 48.21
ATOM  165  O    LEU A 839    26.364  33.580   5.139  1.00 46.74
ATOM  166  CB   LEU A 839    26.831  31.625   2.395  1.00 47.75
ATOM  167  CG   LEU A 839    26.828  30.229   1.803  1.00 48.45
```

FIG. 5C

```
ATOM    168  CD1 LEU A 839      26.155  30.260   0.433  1.00 47.96
ATOM    169  CD2 LEU A 839      28.160  29.519   1.717  1.00 44.56
ATOM    170  N   LYS A 840      28.053  34.107   3.847  1.00 47.52
ATOM    171  CA  LYS A 840      27.984  35.508   4.234  1.00 48.47
ATOM    172  C   LYS A 840      27.434  36.369   3.109  1.00 49.26
ATOM    173  O   LYS A 840      27.837  36.150   1.960  1.00 49.21
ATOM    174  CB  LYS A 840      29.393  35.943   4.654  1.00 48.66
ATOM    175  CG  LYS A 840      29.320  37.059   5.668  1.00 49.85
ATOM    176  CD  LYS A 840      29.716  38.398   5.125  1.00 49.60
ATOM    177  CE  LYS A 840      29.768  39.457   6.225  1.00 50.13
ATOM    178  NZ  LYS A 840      31.184  39.749   6.580  1.00 51.35
ATOM    179  N   ALA A 841      26.486  37.270   3.389  1.00 51.52
ATOM    180  CA  ALA A 841      25.968  38.108   2.312  1.00 53.29
ATOM    181  C   ALA A 841      25.768  39.564   2.726  1.00 54.51
ATOM    182  O   ALA A 841      25.753  39.914   3.903  1.00 54.20
ATOM    183  CB  ALA A 841      24.641  37.503   1.837  1.00 52.47
ATOM    184  N   ARG A 842      25.564  40.398   1.714  1.00 57.16
ATOM    185  CA  ARG A 842      25.154  41.784   1.915  1.00 60.23
ATOM    186  C   ARG A 842      23.699  41.667   1.451  1.00 61.88
ATOM    187  O   ARG A 842      23.499  41.023   0.416  1.00 63.40
ATOM    188  CB  ARG A 842      25.900  42.835   1.119  1.00 61.09
ATOM    189  CG  ARG A 842      27.301  43.137   1.622  1.00 62.77
ATOM    190  CD  ARG A 842      27.258  43.791   2.995  1.00 63.72
ATOM    191  NE  ARG A 842      26.985  45.231   2.928  1.00 64.65
ATOM    192  CZ  ARG A 842      26.963  45.986   4.017  1.00 65.52
ATOM    193  NH1 ARG A 842      26.724  47.291   4.022  1.00 65.78
ATOM    194  NH2 ARG A 842      27.158  45.436   5.214  1.00 66.80
ATOM    195  N   ILE A 843      22.745  42.047   2.281  1.00 63.86
ATOM    196  CA  ILE A 843      21.322  41.935   1.983  1.00 66.38
ATOM    197  C   ILE A 843      20.610  43.284   2.150  1.00 69.29
ATOM    198  O   ILE A 843      20.337  43.810   3.233  1.00 72.01
ATOM    199  CB  ILE A 843      20.524  40.846   2.715  1.00 64.76
ATOM    200  CG1 ILE A 843      20.218  41.134   4.182  1.00 63.75
ATOM    201  CG2 ILE A 843      21.198  39.477   2.638  1.00 65.06
ATOM    202  CD1 ILE A 843      19.030  40.372   4.733  1.00 61.60
ATOM    203  N   LYS A 844      20.274  43.844   0.975  1.00 70.72
ATOM    204  CA  LYS A 844      19.599  45.144   0.939  1.00 72.14
ATOM    205  C   LYS A 844      18.157  45.087   1.427  1.00 73.85
ATOM    206  O   LYS A 844      17.234  44.834   0.650  1.00 74.26
ATOM    207  CB  LYS A 844      19.596  45.771  -0.449  1.00 71.35
ATOM    208  N   LYS A 845      17.931  45.392   2.697  1.00 75.42
ATOM    209  CA  LYS A 845      16.580  45.403   3.262  1.00 77.81
ATOM    210  C   LYS A 845      16.190  46.868   3.403  1.00 80.30
ATOM    211  O   LYS A 845      16.751  47.630   4.197  1.00 79.71
ATOM    212  CB  LYS A 845      16.528  44.624   4.561  1.00 77.32
ATOM    213  CG  LYS A 845      15.188  44.450   5.231  1.00 76.89
ATOM    214  CD  LYS A 845      15.318  43.734   6.572  1.00 76.27
ATOM    215  CE  LYS A 845      13.956  43.469   7.205  1.00 75.52
ATOM    216  NZ  LYS A 845      14.066  42.788   8.521  1.00 74.44
ATOM    217  N   ASP A 846      15.243  47.333   2.610  1.00 82.92
ATOM    218  CA  ASP A 846      14.674  48.627   2.374  1.00 84.85
ATOM    219  C   ASP A 846      15.649  49.493   1.560  1.00 85.22
ATOM    220  O   ASP A 846      15.804  49.302   0.353  1.00 85.44
ATOM    221  CB  ASP A 846      14.070  49.395   3.514  1.00 86.44
ATOM    222  CG  ASP A 846      14.770  49.744   4.790  1.00 87.92
ATOM    223  OD1 ASP A 846      15.058  50.942   5.029  1.00 88.52
ATOM    224  OD2 ASP A 846      15.044  48.819   5.599  1.00 89.21
```

FIG. 5D

| ATOM | 225 | N | GLY | A | 847 | 16.337 | 50.395 | 2.231 | 1.00 | 85.08 |
| ATOM | 226 | CA | GLY | A | 847 | 17.317 | 51.266 | 1.590 | 1.00 | 83.96 |
| ATOM | 227 | C | GLY | A | 847 | 18.593 | 51.154 | 2.430 | 1.00 | 83.43 |
| ATOM | 228 | O | GLY | A | 847 | 19.555 | 51.871 | 2.210 | 1.00 | 84.91 |
| ATOM | 229 | N | LEU | A | 848 | 18.493 | 50.239 | 3.396 | 1.00 | 81.24 |
| ATOM | 230 | CA | LEU | A | 848 | 19.634 | 49.951 | 4.250 | 1.00 | 78.49 |
| ATOM | 231 | C | LEU | A | 848 | 20.311 | 48.732 | 3.617 | 1.00 | 76.61 |
| ATOM | 232 | O | LEU | A | 848 | 19.608 | 47.760 | 3.340 | 1.00 | 76.98 |
| ATOM | 233 | CB | LEU | A | 848 | 19.195 | 49.564 | 5.658 | 1.00 | 78.88 |
| ATOM | 234 | CG | LEU | A | 848 | 18.312 | 50.582 | 6.388 | 1.00 | 79.08 |
| ATOM | 235 | CD1 | LEU | A | 848 | 17.346 | 49.858 | 7.312 | 1.00 | 79.29 |
| ATOM | 236 | CD2 | LEU | A | 848 | 19.184 | 51.563 | 7.157 | 1.00 | 79.32 |
| ATOM | 237 | N | ARG | A | 849 | 21.592 | 48.863 | 3.326 | 1.00 | 73.72 |
| ATOM | 238 | CA | ARG | A | 849 | 22.332 | 47.696 | 2.850 | 1.00 | 70.15 |
| ATOM | 239 | C | ARG | A | 849 | 22.830 | 47.095 | 4.175 | 1.00 | 67.06 |
| ATOM | 240 | O | ARG | A | 849 | 23.153 | 47.922 | 5.036 | 1.00 | 65.85 |
| ATOM | 241 | CB | ARG | A | 849 | 23.493 | 48.031 | 1.941 | 1.00 | 71.56 |
| ATOM | 242 | CG | ARG | A | 849 | 23.308 | 47.798 | 0.452 | 1.00 | 72.96 |
| ATOM | 243 | CD | ARG | A | 849 | 24.483 | 46.995 | -0.110 | 1.00 | 74.22 |
| ATOM | 244 | NE | ARG | A | 849 | 25.606 | 47.792 | -0.586 | 1.00 | 75.64 |
| ATOM | 245 | CZ | ARG | A | 849 | 26.848 | 47.399 | -0.871 | 1.00 | 75.22 |
| ATOM | 246 | NH1 | ARG | A | 849 | 27.183 | 46.121 | -0.715 | 1.00 | 73.54 |
| ATOM | 247 | NH2 | ARG | A | 849 | 27.739 | 48.290 | -1.305 | 1.00 | 74.94 |
| ATOM | 248 | N | MET | A | 850 | 22.777 | 45.781 | 4.369 | 1.00 | 63.25 |
| ATOM | 249 | CA | MET | A | 850 | 23.293 | 45.285 | 5.655 | 1.00 | 59.28 |
| ATOM | 250 | C | MET | A | 850 | 23.898 | 43.883 | 5.493 | 1.00 | 55.95 |
| ATOM | 251 | O | MET | A | 850 | 23.690 | 43.197 | 4.494 | 1.00 | 56.07 |
| ATOM | 252 | CB | MET | A | 850 | 22.245 | 45.279 | 6.757 | 1.00 | 58.62 |
| ATOM | 253 | CG | MET | A | 850 | 21.296 | 44.096 | 6.631 | 1.00 | 59.21 |
| ATOM | 254 | SD | MET | A | 850 | 19.724 | 44.280 | 7.443 | 1.00 | 59.73 |
| ATOM | 255 | CE | MET | A | 850 | 20.128 | 44.922 | 9.049 | 1.00 | 59.43 |
| ATOM | 256 | N | ASP | A | 851 | 24.651 | 43.563 | 6.548 | 1.00 | 51.79 |
| ATOM | 257 | CA | ASP | A | 851 | 25.299 | 42.268 | 6.600 | 1.00 | 48.61 |
| ATOM | 258 | C | ASP | A | 851 | 24.332 | 41.192 | 7.084 | 1.00 | 45.57 |
| ATOM | 259 | O | ASP | A | 851 | 23.630 | 41.457 | 8.086 | 1.00 | 42.14 |
| ATOM | 260 | CB | ASP | A | 851 | 26.379 | 42.285 | 7.697 | 1.00 | 50.01 |
| ATOM | 261 | CG | ASP | A | 851 | 27.669 | 42.933 | 7.256 | 1.00 | 50.84 |
| ATOM | 262 | OD1 | ASP | A | 851 | 28.043 | 42.801 | 6.057 | 1.00 | 51.87 |
| ATOM | 263 | OD2 | ASP | A | 851 | 28.272 | 43.563 | 8.144 | 1.00 | 50.81 |
| ATOM | 264 | N | ALA | A | 852 | 24.472 | 39.961 | 6.632 | 1.00 | 45.45 |
| ATOM | 265 | CA | ALA | A | 852 | 23.622 | 38.884 | 7.138 | 1.00 | 42.89 |
| ATOM | 266 | C | ALA | A | 852 | 24.373 | 37.570 | 7.066 | 1.00 | 42.71 |
| ATOM | 267 | O | ALA | A | 852 | 25.336 | 37.518 | 6.303 | 1.00 | 43.78 |
| ATOM | 268 | CB | ALA | A | 852 | 22.397 | 38.727 | 6.261 | 1.00 | 41.61 |
| ATOM | 269 | N | ALA | A | 853 | 23.847 | 36.577 | 7.785 | 1.00 | 43.18 |
| ATOM | 270 | CA | ALA | A | 853 | 24.394 | 35.222 | 7.668 | 1.00 | 43.19 |
| ATOM | 271 | C | ALA | A | 853 | 23.300 | 34.446 | 6.931 | 1.00 | 45.23 |
| ATOM | 272 | O | ALA | A | 853 | 22.122 | 34.570 | 7.296 | 1.00 | 45.40 |
| ATOM | 273 | CB | ALA | A | 853 | 24.725 | 34.651 | 9.043 | 1.00 | 43.45 |
| ATOM | 274 | N | ILE | A | 854 | 23.599 | 33.717 | 5.863 | 1.00 | 45.69 |
| ATOM | 275 | CA | ILE | A | 854 | 22.561 | 33.051 | 5.093 | 1.00 | 46.79 |
| ATOM | 276 | C | ILE | A | 854 | 22.583 | 31.537 | 5.228 | 1.00 | 50.11 |
| ATOM | 277 | O | ILE | A | 854 | 23.643 | 30.913 | 5.101 | 1.00 | 51.97 |
| ATOM | 278 | CB | ILE | A | 854 | 22.686 | 33.334 | 3.581 | 1.00 | 45.28 |
| ATOM | 279 | CG1 | ILE | A | 854 | 22.754 | 34.819 | 3.268 | 1.00 | 45.20 |
| ATOM | 280 | CG2 | ILE | A | 854 | 21.553 | 32.685 | 2.794 | 1.00 | 45.13 |
| ATOM | 281 | CD1 | ILE | A | 854 | 21.509 | 35.654 | 3.433 | 1.00 | 45.48 |

FIG. 5E

| | | | | | | | | | |
|---|---|---|---|---|---|---|---|---|---|
| ATOM | 282 | N | LYS | A | 855 | 21.408 | 30.949 | 5.453 | 1.00 51.72 |
| ATOM | 283 | CA | LYS | A | 855 | 21.355 | 29.474 | 5.425 | 1.00 54.33 |
| ATOM | 284 | C | LYS | A | 855 | 20.240 | 29.052 | 4.458 | 1.00 55.89 |
| ATOM | 285 | O | LYS | A | 855 | 19.276 | 29.786 | 4.205 | 1.00 52.41 |
| ATOM | 286 | CB | LYS | A | 855 | 21.271 | 28.892 | 6.808 | 1.00 55.64 |
| ATOM | 287 | CG | LYS | A | 855 | 19.914 | 28.834 | 7.487 | 1.00 58.25 |
| ATOM | 288 | CD | LYS | A | 855 | 20.052 | 28.092 | 8.807 | 1.00 59.55 |
| ATOM | 289 | CE | LYS | A | 855 | 18.987 | 27.027 | 9.025 | 1.00 60.12 |
| ATOM | 290 | NZ | LYS | A | 855 | 19.484 | 26.165 | 10.151 | 1.00 60.89 |
| ATOM | 291 | N | ARG | A | 856 | 20.386 | 27.871 | 3.871 | 1.00 59.82 |
| ATOM | 292 | CA | ARG | A | 856 | 19.419 | 27.341 | 2.915 | 1.00 63.71 |
| ATOM | 293 | C | ARG | A | 856 | 18.809 | 26.009 | 3.309 | 1.00 66.24 |
| ATOM | 294 | O | ARG | A | 856 | 19.456 | 25.004 | 3.565 | 1.00 66.29 |
| ATOM | 295 | CB | ARG | A | 856 | 20.126 | 27.258 | 1.555 | 1.00 63.38 |
| ATOM | 296 | N | MET | A | 857 | 17.486 | 25.951 | 3.418 | 1.00 69.77 |
| ATOM | 297 | CA | MET | A | 857 | 16.718 | 24.748 | 3.728 | 1.00 73.04 |
| ATOM | 298 | C | MET | A | 857 | 15.960 | 24.381 | 2.447 | 1.00 75.83 |
| ATOM | 299 | O | MET | A | 857 | 16.149 | 25.126 | 1.472 | 1.00 77.44 |
| ATOM | 300 | CB | MET | A | 857 | 15.761 | 24.965 | 4.887 | 1.00 72.49 |
| ATOM | 301 | N | LYS | A | 858 | 15.174 | 23.321 | 2.404 | 1.00 78.15 |
| ATOM | 302 | CA | LYS | A | 858 | 14.449 | 22.985 | 1.184 | 1.00 80.35 |
| ATOM | 303 | C | LYS | A | 858 | 13.181 | 22.168 | 1.417 | 1.00 81.76 |
| ATOM | 304 | O | LYS | A | 858 | 13.118 | 21.298 | 2.282 | 1.00 82.29 |
| ATOM | 305 | CB | LYS | A | 858 | 15.320 | 22.196 | 0.212 | 1.00 80.34 |
| ATOM | 306 | N | GLU | A | 859 | 12.171 | 22.427 | 0.593 | 1.00 82.86 |
| ATOM | 307 | CA | GLU | A | 859 | 10.905 | 21.705 | 0.631 | 1.00 83.98 |
| ATOM | 308 | C | GLU | A | 859 | 10.372 | 21.378 | 2.024 | 1.00 84.84 |
| ATOM | 309 | O | GLU | A | 859 | 9.465 | 20.540 | 2.160 | 1.00 85.54 |
| ATOM | 310 | CB | GLU | A | 859 | 11.040 | 20.388 | -0.143 | 1.00 83.34 |
| TER | | | | | | | | | |
| ATOM | 311 | N | ASP | B | 868 | 3.887 | 24.257 | 9.102 | 1.00 74.33 |
| ATOM | 312 | CA | ASP | B | 868 | 4.969 | 23.506 | 9.742 | 1.00 73.45 |
| ATOM | 313 | C | ASP | B | 868 | 6.151 | 24.465 | 9.894 | 1.00 72.92 |
| ATOM | 314 | O | ASP | B | 868 | 6.215 | 25.236 | 10.848 | 1.00 72.75 |
| ATOM | 315 | CB | ASP | B | 868 | 5.345 | 22.276 | 8.927 | 1.00 73.09 |
| ATOM | 316 | N | PHE | B | 869 | 6.973 | 24.491 | 8.845 | 1.00 71.93 |
| ATOM | 317 | CA | PHE | B | 869 | 8.128 | 25.356 | 8.739 | 1.00 71.39 |
| ATOM | 318 | C | PHE | B | 869 | 7.722 | 26.812 | 8.514 | 1.00 69.85 |
| ATOM | 319 | O | PHE | B | 869 | 8.507 | 27.721 | 8.789 | 1.00 68.53 |
| ATOM | 320 | CB | PHE | B | 869 | 9.086 | 24.894 | 7.635 | 1.00 72.16 |
| ATOM | 321 | N | ALA | B | 870 | 6.485 | 27.041 | 8.084 | 1.00 68.66 |
| ATOM | 322 | CA | ALA | B | 870 | 6.008 | 28.412 | 7.917 | 1.00 67.79 |
| ATOM | 323 | C | ALA | B | 870 | 5.699 | 28.972 | 9.300 | 1.00 66.69 |
| ATOM | 324 | O | ALA | B | 870 | 5.914 | 30.142 | 9.612 | 1.00 67.76 |
| ATOM | 325 | CB | ALA | B | 870 | 4.786 | 28.421 | 7.009 | 1.00 67.73 |
| ATOM | 326 | N | GLY | B | 871 | 5.125 | 28.124 | 10.156 | 1.00 64.74 |
| ATOM | 327 | CA | GLY | B | 871 | 4.746 | 28.539 | 11.506 | 1.00 63.48 |
| ATOM | 328 | C | GLY | B | 871 | 5.968 | 28.696 | 12.407 | 1.00 63.38 |
| ATOM | 329 | O | GLY | B | 871 | 6.078 | 29.586 | 13.241 | 1.00 62.27 |
| ATOM | 330 | N | GLU | B | 872 | 6.936 | 27.789 | 12.259 | 1.00 63.08 |
| ATOM | 331 | CA | GLU | B | 872 | 8.163 | 27.830 | 13.033 | 1.00 62.41 |
| ATOM | 332 | C | GLU | B | 872 | 8.870 | 29.166 | 12.865 | 1.00 59.48 |
| ATOM | 333 | O | GLU | B | 872 | 9.299 | 29.759 | 13.849 | 1.00 59.18 |
| ATOM | 334 | CB | GLU | B | 872 | 9.104 | 26.684 | 12.627 | 1.00 64.92 |
| ATOM | 335 | CG | GLU | B | 872 | 8.756 | 25.334 | 13.218 | 1.00 67.28 |
| ATOM | 336 | CD | GLU | B | 872 | 9.191 | 24.093 | 12.474 | 1.00 68.33 |
| ATOM | 337 | OE1 | GLU | B | 872 | 8.848 | 22.953 | 12.910 | 1.00 69.51 |

FIG. 5F

```
ATOM  338  OE2  GLU B 872      9.882  24.117  11.435  1.00 69.53
ATOM  339  N    LEU B 873      9.004  29.664  11.648  1.00 57.71
ATOM  340  CA   LEU B 873      9.635  30.916  11.312  1.00 55.15
ATOM  341  C    LEU B 873      8.988  32.099  12.034  1.00 55.46
ATOM  342  O    LEU B 873      9.656  33.045  12.483  1.00 53.19
ATOM  343  CB   LEU B 873      9.629  31.206   9.816  1.00 54.80
ATOM  344  CG   LEU B 873     10.436  30.326   8.876  1.00 56.52
ATOM  345  CD1  LEU B 873     10.416  30.920   7.466  1.00 56.98
ATOM  346  CD2  LEU B 873     11.886  30.139   9.305  1.00 57.06
ATOM  347  N    GLU B 874      7.663  32.055  12.083  1.00 53.38
ATOM  348  CA   GLU B 874      6.839  33.058  12.743  1.00 53.73
ATOM  349  C    GLU B 874      7.208  33.198  14.215  1.00 50.89
ATOM  350  O    GLU B 874      7.431  34.279  14.773  1.00 48.19
ATOM  351  CB   GLU B 874      5.379  32.579  12.639  1.00 57.54
ATOM  352  CG   GLU B 874      4.388  33.300  13.533  1.00 61.33
ATOM  353  CD   GLU B 874      3.007  32.638  13.433  1.00 64.62
ATOM  354  OE1  GLU B 874      2.075  33.216  14.045  1.00 66.21
ATOM  355  OE2  GLU B 874      2.876  31.577  12.771  1.00 64.60
ATOM  356  N    VAL B 875      7.278  32.004  14.839  1.00 48.16
ATOM  357  CA   VAL B 875      7.665  31.965  16.266  1.00 47.64
ATOM  358  C    VAL B 875      9.051  32.599  16.426  1.00 46.85
ATOM  359  O    VAL B 875      9.211  33.498  17.257  1.00 45.14
ATOM  360  CB   VAL B 875      7.523  30.545  16.799  1.00 47.78
ATOM  361  CG1  VAL B 875      8.477  30.264  17.946  1.00 48.21
ATOM  362  CG2  VAL B 875      6.077  30.272  17.240  1.00 47.41
ATOM  363  N    LEU B 876     10.000  32.278  15.538  1.00 47.87
ATOM  364  CA   LEU B 876     11.348  32.838  15.552  1.00 50.02
ATOM  365  C    LEU B 876     11.435  34.322  15.245  1.00 50.20
ATOM  366  O    LEU B 876     12.285  34.988  15.845  1.00 51.04
ATOM  367  CB   LEU B 876     12.308  32.074  14.611  1.00 48.16
ATOM  368  CG   LEU B 876     12.598  30.663  15.159  1.00 49.64
ATOM  369  CD1  LEU B 876     13.303  29.816  14.116  1.00 48.69
ATOM  370  CD2  LEU B 876     13.407  30.766  16.452  1.00 51.42
ATOM  371  N    CYS B 877     10.607  34.849  14.358  1.00 50.72
ATOM  372  CA   CYS B 877     10.638  36.276  14.029  1.00 51.41
ATOM  373  C    CYS B 877     10.130  37.090  15.215  1.00 50.29
ATOM  374  O    CYS B 877     10.630  38.171  15.550  1.00 49.69
ATOM  375  CB   CYS B 877      9.777  36.555  12.788  1.00 53.49
ATOM  376  SG   CYS B 877      9.320  38.304  12.668  1.00 56.75
ATOM  377  N    LYS B 878      9.155  36.480  15.922  1.00 49.77
ATOM  378  CA   LYS B 878      8.602  37.082  17.122  1.00 49.11
ATOM  379  C    LYS B 878      9.567  37.033  18.298  1.00 47.30
ATOM  380  O    LYS B 878      9.418  37.925  19.128  1.00 47.68
ATOM  381  CB   LYS B 878      7.284  36.415  17.561  1.00 51.27
ATOM  382  CG   LYS B 878      6.097  36.821  16.728  1.00 53.14
ATOM  383  CD   LYS B 878      5.072  35.740  16.473  1.00 55.56
ATOM  384  CE   LYS B 878      4.132  35.453  17.638  1.00 55.88
ATOM  385  NZ   LYS B 878      3.445  34.138  17.433  1.00 57.41
ATOM  386  N    LEU B 879     10.495  36.091  18.403  1.00 44.23
ATOM  387  CA   LEU B 879     11.388  36.049  19.550  1.00 42.64
ATOM  388  C    LEU B 879     12.665  36.881  19.317  1.00 41.06
ATOM  389  O    LEU B 879     13.291  37.300  20.264  1.00 39.35
ATOM  390  CB   LEU B 879     11.857  34.606  19.819  1.00 41.39
ATOM  391  CG   LEU B 879     10.790  33.580  20.246  1.00 40.34
ATOM  392  CD1  LEU B 879     11.327  32.180  20.076  1.00 40.43
ATOM  393  CD2  LEU B 879     10.378  33.826  21.693  1.00 40.68
ATOM  394  N    GLY B 880     12.974  37.194  18.075  1.00 40.80
```

FIG. 5G

```
ATOM    395  CA  GLY B 880      14.164  37.870  17.686  1.00 42.66
ATOM    396  C   GLY B 880      14.499  39.226  18.185  1.00 43.75
ATOM    397  O   GLY B 880      15.698  39.526  18.103  1.00 46.29
ATOM    398  N   HIS B 881      13.580  40.053  18.637  1.00 42.86
ATOM    399  CA  HIS B 881      13.759  41.403  19.105  1.00 43.65
ATOM    400  C   HIS B 881      14.619  41.378  20.370  1.00 39.48
ATOM    401  O   HIS B 881      15.539  42.203  20.446  1.00 43.05
ATOM    402  CB  HIS B 881      12.417  42.127  19.236  1.00 47.39
ATOM    403  CG  HIS B 881      11.628  42.051  20.490  1.00 50.98
ATOM    404  ND1 HIS B 881      10.412  41.442  20.685  1.00 53.62
ATOM    405  CD2 HIS B 881      11.944  42.576  21.711  1.00 53.62
ATOM    406  CE1 HIS B 881      10.057  41.591  21.975  1.00 55.27
ATOM    407  NE2 HIS B 881      10.966  42.286  22.647  1.00 55.05
ATOM    408  N   HIS B 882      14.422  40.401  21.250  1.00 35.00
ATOM    409  CA  HIS B 882      15.234  40.280  22.473  1.00 33.75
ATOM    410  C   HIS B 882      16.695  40.394  22.053  1.00 29.63
ATOM    411  O   HIS B 882      17.099  39.702  21.115  1.00 32.51
ATOM    412  CB  HIS B 882      14.977  38.947  23.240  1.00 29.31
ATOM    413  CG  HIS B 882      15.458  39.007  24.665  1.00 28.91
ATOM    414  ND1 HIS B 882      16.739  38.861  25.208  1.00 28.25
ATOM    415  CD2 HIS B 882      14.687  39.334  25.705  1.00 27.99
ATOM    416  CE1 HIS B 882      16.623  39.049  26.523  1.00 28.98
ATOM    417  NE2 HIS B 882      15.346  39.333  26.866  1.00 26.63
ATOM    418  N   PRO B 883      17.468  41.252  22.659  1.00 31.32
ATOM    419  CA  PRO B 883      18.882  41.398  22.375  1.00 31.40
ATOM    420  C   PRO B 883      19.687  40.158  22.658  1.00 32.62
ATOM    421  O   PRO B 883      20.700  39.965  21.941  1.00 36.70
ATOM    422  CB  PRO B 883      19.206  42.672  23.123  1.00 30.55
ATOM    423  CG  PRO B 883      18.433  42.543  24.437  1.00 33.27
ATOM    424  CD  PRO B 883      17.096  42.064  23.858  1.00 31.21
ATOM    425  N   ASN B 884      19.290  39.189  23.448  1.00 33.73
ATOM    426  CA  ASN B 884      19.999  37.942  23.685  1.00 32.47
ATOM    427  C   ASN B 884      19.496  36.811  22.823  1.00 34.37
ATOM    428  O   ASN B 884      19.901  35.659  23.051  1.00 34.65
ATOM    429  CB  ASN B 884      19.952  37.596  25.173  1.00 33.46
ATOM    430  CG  ASN B 884      20.404  38.649  26.117  1.00 36.23
ATOM    431  OD1 ASN B 884      20.011  39.181  27.122  1.00 37.73
ATOM    432  ND2 ASN B 884      21.749  38.992  25.840  1.00 32.70
ATOM    433  N   ILE B 885      18.623  37.014  21.825  1.00 32.48
ATOM    434  CA  ILE B 885      18.185  36.032  20.859  1.00 34.12
ATOM    435  C   ILE B 885      18.587  36.426  19.455  1.00 32.76
ATOM    436  O   ILE B 885      18.359  37.539  18.982  1.00 33.37
ATOM    437  CB  ILE B 885      16.662  35.743  21.004  1.00 33.83
ATOM    438  CG1 ILE B 885      16.442  35.119  22.402  1.00 35.22
ATOM    439  CG2 ILE B 885      16.088  34.847  19.922  1.00 33.58
ATOM    440  CD1 ILE B 885      14.970  34.840  22.653  1.00 38.35
ATOM    441  N   ILE B 886      19.261  35.557  18.697  1.00 34.99
ATOM    442  CA  ILE B 886      19.694  35.965  17.333  1.00 37.58
ATOM    443  C   ILE B 886      18.478  36.272  16.468  1.00 39.01
ATOM    444  O   ILE B 886      17.526  35.459  16.453  1.00 38.20
ATOM    445  CB  ILE B 886      20.693  34.967  16.752  1.00 38.15
ATOM    446  CG1 ILE B 886      21.549  35.590  15.622  1.00 40.28
ATOM    447  CG2 ILE B 886      19.985  33.776  16.206  1.00 38.96
ATOM    448  CD1 ILE B 886      22.675  36.445  16.190  1.00 39.25
ATOM    449  N   ASN B 887      18.472  37.380  15.731  1.00 38.67
ATOM    450  CA  ASN B 887      17.268  37.824  15.016  1.00 40.23
ATOM    451  C   ASN B 887      17.116  37.485  13.560  1.00 40.18
```

FIG. 5H

```
ATOM    452  O    ASN B 887      18.061  37.480  12.780  1.00 41.35
ATOM    453  CB   ASN B 887      17.153  39.347  15.231  1.00 40.41
ATOM    454  CG   ASN B 887      15.888  39.999  14.697  1.00 40.25
ATOM    455  OD1  ASN B 887      15.961  41.166  14.290  1.00 39.53
ATOM    456  ND2  ASN B 887      14.746  39.340  14.692  1.00 38.70
ATOM    457  N    LEU B 888      15.891  37.146  13.147  1.00 42.05
ATOM    458  CA   LEU B 888      15.624  36.781  11.744  1.00 43.89
ATOM    459  C    LEU B 888      15.501  38.053  10.900  1.00 44.52
ATOM    460  O    LEU B 888      14.790  38.957  11.351  1.00 42.69
ATOM    461  CB   LEU B 888      14.321  35.988  11.680  1.00 45.35
ATOM    462  CG   LEU B 888      13.675  35.835  10.310  1.00 46.44
ATOM    463  CD1  LEU B 888      14.617  35.185   9.322  1.00 47.08
ATOM    464  CD2  LEU B 888      12.393  35.011  10.433  1.00 48.74
ATOM    465  N    LEU B 889      16.221  38.160   9.785  1.00 46.33
ATOM    466  CA   LEU B 889      16.106  39.377   9.004  1.00 48.96
ATOM    467  C    LEU B 889      15.178  39.162   7.822  1.00 48.91
ATOM    468  O    LEU B 889      14.331  40.055   7.642  1.00 52.61
ATOM    469  CB   LEU B 889      17.407  40.091   8.621  1.00 52.03
ATOM    470  CG   LEU B 889      18.022  40.806   9.850  1.00 54.44
ATOM    471  CD1  LEU B 889      18.709  39.713  10.624  1.00 56.62
ATOM    472  CD2  LEU B 889      19.053  41.862   9.535  1.00 56.92
ATOM    473  N    GLY B 890      15.192  38.056   7.122  1.00 48.86
ATOM    474  CA   GLY B 890      14.281  37.806   6.027  1.00 49.19
ATOM    475  C    GLY B 890      14.348  36.393   5.478  1.00 51.62
ATOM    476  O    GLY B 890      15.216  35.581   5.811  1.00 49.54
ATOM    477  N    ALA B 891      13.367  36.080   4.619  1.00 52.67
ATOM    478  CA   ALA B 891      13.339  34.779   3.956  1.00 55.84
ATOM    479  C    ALA B 891      13.195  35.036   2.454  1.00 58.68
ATOM    480  O    ALA B 891      12.782  36.128   2.056  1.00 60.04
ATOM    481  CB   ALA B 891      12.292  33.826   4.471  1.00 54.13
ATOM    482  N    CYS B 892      13.681  34.109   1.646  1.00 61.71
ATOM    483  CA   CYS B 892      13.618  34.248   0.200  1.00 64.65
ATOM    484  C    CYS B 892      13.505  32.847  -0.403  1.00 67.70
ATOM    485  O    CYS B 892      14.279  31.955  -0.046  1.00 68.56
ATOM    486  CB   CYS B 892      14.817  34.942  -0.412  1.00 63.99
ATOM    487  SG   CYS B 892      14.859  34.973  -2.216  1.00 64.16
ATOM    488  N    GLU B 893      12.506  32.682  -1.262  1.00 70.26
ATOM    489  CA   GLU B 893      12.337  31.411  -1.965  1.00 72.47
ATOM    490  C    GLU B 893      12.959  31.542  -3.354  1.00 72.44
ATOM    491  O    GLU B 893      12.603  32.421  -4.134  1.00 72.20
ATOM    492  CB   GLU B 893      10.873  30.991  -2.027  1.00 74.16
ATOM    493  CG   GLU B 893      10.291  30.437  -0.736  1.00 76.17
ATOM    494  CD   GLU B 893       8.789  30.210  -0.801  1.00 77.74
ATOM    495  OE1  GLU B 893       8.126  30.906  -1.611  1.00 78.37
ATOM    496  OE2  GLU B 893       8.230  29.357  -0.069  1.00 78.86
ATOM    497  N    HIS B 894      13.922  30.697  -3.677  1.00 73.54
ATOM    498  CA   HIS B 894      14.594  30.700  -4.977  1.00 74.67
ATOM    499  C    HIS B 894      14.847  29.255  -5.401  1.00 74.91
ATOM    500  O    HIS B 894      15.025  28.386  -4.542  1.00 74.35
ATOM    501  CB   HIS B 894      15.857  31.531  -4.919  1.00 75.48
ATOM    502  CG   HIS B 894      16.558  31.697  -6.225  1.00 76.90
ATOM    503  ND1  HIS B 894      17.369  30.719  -6.752  1.00 77.63
ATOM    504  CD2  HIS B 894      16.587  32.733  -7.097  1.00 77.64
ATOM    505  CE1  HIS B 894      17.880  31.150  -7.893  1.00 78.14
ATOM    506  NE2  HIS B 894      17.433  32.377  -8.119  1.00 77.87
ATOM    507  N    ARG B 895      14.774  28.959  -6.699  1.00 74.84
ATOM    508  CA   ARG B 895      14.865  27.593  -7.214  1.00 73.98
```

FIG. 5I

| ATOM | 509 | C | ARG | B | 895 | 14.001 | 26.742 | -6.281 | 1.00 | 74.16 |
| --- | --- | --- | --- | --- | --- | --- | --- | --- | --- | --- |
| ATOM | 510 | O | ARG | B | 895 | 12.911 | 27.249 | -5.967 | 1.00 | 74.67 |
| ATOM | 511 | CB | ARG | B | 895 | 16.262 | 27.053 | -7.367 | 1.00 | 74.14 |
| ATOM | 512 | N | GLY | B | 896 | 14.429 | 25.597 | -5.769 | 1.00 | 73.62 |
| ATOM | 513 | CA | GLY | B | 896 | 13.554 | 24.843 | -4.878 | 1.00 | 74.58 |
| ATOM | 514 | C | GLY | B | 896 | 13.801 | 24.946 | -3.383 | 1.00 | 75.31 |
| ATOM | 515 | O | GLY | B | 896 | 13.362 | 24.085 | -2.599 | 1.00 | 74.62 |
| ATOM | 516 | N | TYR | B | 897 | 14.568 | 25.958 | -2.952 | 1.00 | 75.55 |
| ATOM | 517 | CA | TYR | B | 897 | 14.937 | 26.107 | -1.551 | 1.00 | 75.78 |
| ATOM | 518 | C | TYR | B | 897 | 14.498 | 27.408 | -0.882 | 1.00 | 73.41 |
| ATOM | 519 | O | TYR | B | 897 | 14.296 | 28.420 | -1.548 | 1.00 | 73.50 |
| ATOM | 520 | CB | TYR | B | 897 | 16.466 | 26.038 | -1.444 | 1.00 | 78.25 |
| ATOM | 521 | CG | TYR | B | 897 | 17.225 | 24.811 | -1.836 | 1.00 | 80.53 |
| ATOM | 522 | CD1 | TYR | B | 897 | 17.259 | 24.356 | -3.145 | 1.00 | 81.37 |
| ATOM | 523 | CD2 | TYR | B | 897 | 17.982 | 24.114 | -0.898 | 1.00 | 81.11 |
| ATOM | 524 | CE1 | TYR | B | 897 | 17.983 | 23.232 | -3.498 | 1.00 | 82.95 |
| ATOM | 525 | CE2 | TYR | B | 897 | 18.712 | 22.994 | -1.247 | 1.00 | 82.00 |
| ATOM | 526 | CZ | TYR | B | 897 | 18.723 | 22.542 | -2.554 | 1.00 | 82.42 |
| ATOM | 527 | N | LEU | B | 898 | 14.434 | 27.417 | 0.450 | 1.00 | 70.37 |
| ATOM | 528 | CA | LEU | B | 898 | 14.132 | 28.667 | 1.172 | 1.00 | 68.25 |
| ATOM | 529 | C | LEU | B | 898 | 15.407 | 29.218 | 1.794 | 1.00 | 66.94 |
| ATOM | 530 | O | LEU | B | 898 | 16.271 | 28.530 | 2.340 | 1.00 | 67.22 |
| ATOM | 531 | CB | LEU | B | 898 | 12.957 | 28.443 | 2.089 | 1.00 | 67.63 |
| ATOM | 532 | CG | LEU | B | 898 | 12.979 | 28.839 | 3.549 | 1.00 | 66.92 |
| ATOM | 533 | CD1 | LEU | B | 898 | 11.612 | 29.212 | 4.063 | 1.00 | 67.30 |
| ATOM | 534 | CD2 | LEU | B | 898 | 13.492 | 27.667 | 4.393 | 1.00 | 67.72 |
| ATOM | 535 | N | TYR | B | 899 | 15.648 | 30.512 | 1.585 | 1.00 | 65.23 |
| ATOM | 536 | CA | TYR | B | 899 | 16.871 | 31.191 | 2.019 | 1.00 | 61.95 |
| ATOM | 537 | C | TYR | B | 899 | 16.601 | 32.001 | 3.262 | 1.00 | 60.81 |
| ATOM | 538 | O | TYR | B | 899 | 15.646 | 32.797 | 3.247 | 1.00 | 61.40 |
| ATOM | 539 | CB | TYR | B | 899 | 17.291 | 31.923 | 0.733 | 1.00 | 62.33 |
| ATOM | 540 | CG | TYR | B | 899 | 17.999 | 31.028 | -0.267 | 1.00 | 63.29 |
| ATOM | 541 | CD1 | TYR | B | 899 | 17.347 | 30.060 | -1.018 | 1.00 | 63.92 |
| ATOM | 542 | CD2 | TYR | B | 899 | 19.373 | 31.154 | -0.439 | 1.00 | 63.86 |
| ATOM | 543 | CE1 | TYR | B | 899 | 18.025 | 29.235 | -1.897 | 1.00 | 64.75 |
| ATOM | 544 | CE2 | TYR | B | 899 | 20.078 | 30.345 | -1.317 | 1.00 | 64.65 |
| ATOM | 545 | CZ | TYR | B | 899 | 19.395 | 29.384 | -2.041 | 1.00 | 65.94 |
| ATOM | 546 | OH | TYR | B | 899 | 20.089 | 28.577 | -2.918 | 1.00 | 66.41 |
| ATOM | 547 | N | LEU | B | 900 | 17.269 | 31.750 | 4.397 | 1.00 | 56.58 |
| ATOM | 548 | CA | LEU | B | 900 | 17.006 | 32.506 | 5.625 | 1.00 | 52.46 |
| ATOM | 549 | C | LEU | B | 900 | 18.209 | 33.421 | 5.892 | 1.00 | 50.69 |
| ATOM | 550 | O | LEU | B | 900 | 19.359 | 33.002 | 5.834 | 1.00 | 49.63 |
| ATOM | 551 | CB | LEU | B | 900 | 16.742 | 31.664 | 6.859 | 1.00 | 52.94 |
| ATOM | 552 | CG | LEU | B | 900 | 15.786 | 30.472 | 6.845 | 1.00 | 53.46 |
| ATOM | 553 | CD1 | LEU | B | 900 | 16.449 | 29.204 | 6.312 | 1.00 | 53.02 |
| ATOM | 554 | CD2 | LEU | B | 900 | 15.211 | 30.153 | 8.224 | 1.00 | 53.76 |
| ATOM | 555 | N | ALA | B | 901 | 17.923 | 34.696 | 6.093 | 1.00 | 48.07 |
| ATOM | 556 | CA | ALA | B | 901 | 18.972 | 35.699 | 6.337 | 1.00 | 44.87 |
| ATOM | 557 | C | ALA | B | 901 | 18.893 | 36.119 | 7.800 | 1.00 | 42.43 |
| ATOM | 558 | O | ALA | B | 901 | 17.895 | 36.689 | 8.253 | 1.00 | 41.24 |
| ATOM | 559 | CB | ALA | B | 901 | 18.777 | 36.899 | 5.429 | 1.00 | 43.13 |
| ATOM | 560 | N | ILE | B | 902 | 19.919 | 35.717 | 8.532 | 1.00 | 42.59 |
| ATOM | 561 | CA | ILE | B | 902 | 20.012 | 35.929 | 9.979 | 1.00 | 40.02 |
| ATOM | 562 | C | ILE | B | 902 | 20.926 | 37.088 | 10.334 | 1.00 | 40.16 |
| ATOM | 563 | O | ILE | B | 902 | 21.844 | 37.413 | 9.586 | 1.00 | 41.22 |
| ATOM | 564 | CB | ILE | B | 902 | 20.561 | 34.648 | 10.635 | 1.00 | 39.22 |
| ATOM | 565 | CG1 | ILE | B | 902 | 19.781 | 33.405 | 10.190 | 1.00 | 41.67 |

FIG. 5J

| | | | | | | | | | |
|---|---|---|---|---|---|---|---|---|---|
| ATOM | 566 | CG2 | ILE | B | 902 | 20.538 | 34.742 | 12.152 | 1.00 38.02 |
| ATOM | 567 | CD1 | ILE | B | 902 | 18.288 | 33.542 | 10.392 | 1.00 44.70 |
| ATOM | 568 | N   | GLU | B | 903 | 20.702 | 37.692 | 11.498 | 1.00 38.24 |
| ATOM | 569 | CA  | GLU | B | 903 | 21.487 | 38.756 | 12.058 | 1.00 36.51 |
| ATOM | 570 | C   | GLU | B | 903 | 22.929 | 38.231 | 12.121 | 1.00 37.45 |
| ATOM | 571 | O   | GLU | B | 903 | 23.188 | 37.096 | 12.569 | 1.00 37.05 |
| ATOM | 572 | CB  | GLU | B | 903 | 20.984 | 39.024 | 13.484 | 1.00 36.53 |
| ATOM | 573 | CG  | GLU | B | 903 | 21.936 | 39.865 | 14.343 | 1.00 39.44 |
| ATOM | 574 | CD  | GLU | B | 903 | 21.384 | 40.070 | 15.735 | 1.00 40.57 |
| ATOM | 575 | OE1 | GLU | B | 903 | 21.848 | 40.909 | 16.534 | 1.00 39.27 |
| ATOM | 576 | OE2 | GLU | B | 903 | 20.387 | 39.361 | 16.065 | 1.00 39.59 |
| ATOM | 577 | N   | TYR | B | 904 | 23.817 | 39.039 | 11.558 | 1.00 36.26 |
| ATOM | 578 | CA  | TYR | B | 904 | 25.236 | 38.729 | 11.507 | 1.00 38.11 |
| ATOM | 579 | C   | TYR | B | 904 | 25.923 | 39.016 | 12.842 | 1.00 36.13 |
| ATOM | 580 | O   | TYR | B | 904 | 25.810 | 40.085 | 13.447 | 1.00 36.04 |
| ATOM | 581 | CB  | TYR | B | 904 | 25.870 | 39.456 | 10.293 | 1.00 38.03 |
| ATOM | 582 | CG  | TYR | B | 904 | 27.340 | 39.121 | 10.159 | 1.00 39.56 |
| ATOM | 583 | CD1 | TYR | B | 904 | 27.790 | 37.827 | 9.900  | 1.00 40.02 |
| ATOM | 584 | CD2 | TYR | B | 904 | 28.296 | 40.122 | 10.364 | 1.00 39.80 |
| ATOM | 585 | CE1 | TYR | B | 904 | 29.154 | 37.532 | 9.822  | 1.00 40.07 |
| ATOM | 586 | CE2 | TYR | B | 904 | 29.641 | 39.846 | 10.258 | 1.00 39.30 |
| ATOM | 587 | CZ  | TYR | B | 904 | 30.043 | 38.571 | 9.994  | 1.00 38.67 |
| ATOM | 588 | OH  | TYR | B | 904 | 31.395 | 38.341 | 9.943  | 1.00 42.02 |
| ATOM | 589 | N   | ALA | B | 905 | 26.565 | 37.994 | 13.427 | 1.00 33.70 |
| ATOM | 590 | CA  | ALA | B | 905 | 27.351 | 38.148 | 14.629 | 1.00 34.04 |
| ATOM | 591 | C   | ALA | B | 905 | 28.807 | 38.331 | 14.173 | 1.00 34.59 |
| ATOM | 592 | O   | ALA | B | 905 | 29.422 | 37.413 | 13.631 | 1.00 34.61 |
| ATOM | 593 | CB  | ALA | B | 905 | 27.272 | 36.924 | 15.544 | 1.00 31.52 |
| ATOM | 594 | N   | PRO | B | 906 | 29.362 | 39.523 | 14.313 | 1.00 37.23 |
| ATOM | 595 | CA  | PRO | B | 906 | 30.702 | 39.735 | 13.790 | 1.00 36.90 |
| ATOM | 596 | C   | PRO | B | 906 | 31.854 | 39.167 | 14.554 | 1.00 37.30 |
| ATOM | 597 | O   | PRO | B | 906 | 32.998 | 39.226 | 14.071 | 1.00 37.05 |
| ATOM | 598 | CB  | PRO | B | 906 | 30.757 | 41.248 | 13.601 | 1.00 38.72 |
| ATOM | 599 | CG  | PRO | B | 906 | 29.641 | 41.840 | 14.378 | 1.00 39.46 |
| ATOM | 600 | CD  | PRO | B | 906 | 28.736 | 40.738 | 14.854 | 1.00 35.60 |
| ATOM | 601 | N   | HIS | B | 907 | 31.720 | 38.652 | 15.767 | 1.00 35.76 |
| ATOM | 602 | CA  | HIS | B | 907 | 32.810 | 38.072 | 16.515 | 1.00 34.45 |
| ATOM | 603 | C   | HIS | B | 907 | 32.768 | 36.551 | 16.532 | 1.00 33.29 |
| ATOM | 604 | O   | HIS | B | 907 | 33.420 | 36.044 | 17.429 | 1.00 36.68 |
| ATOM | 605 | CB  | HIS | B | 907 | 32.793 | 38.614 | 17.971 | 1.00 32.90 |
| ATOM | 606 | CG  | HIS | B | 907 | 32.706 | 40.082 | 17.966 | 1.00 33.20 |
| ATOM | 607 | ND1 | HIS | B | 907 | 33.802 | 40.846 | 17.590 | 1.00 35.03 |
| ATOM | 608 | CD2 | HIS | B | 907 | 31.727 | 40.985 | 18.200 | 1.00 31.98 |
| ATOM | 609 | CE1 | HIS | B | 907 | 33.497 | 42.128 | 17.610 | 1.00 33.06 |
| ATOM | 610 | NE2 | HIS | B | 907 | 32.241 | 42.248 | 18.017 | 1.00 33.02 |
| ATOM | 611 | N   | GLY | B | 908 | 32.021 | 35.804 | 15.757 | 1.00 30.48 |
| ATOM | 612 | CA  | GLY | B | 908 | 32.010 | 34.380 | 15.765 | 1.00 32.68 |
| ATOM | 613 | C   | GLY | B | 908 | 31.084 | 33.774 | 16.838 | 1.00 31.58 |
| ATOM | 614 | O   | GLY | B | 908 | 30.218 | 34.407 | 17.431 | 1.00 28.30 |
| ATOM | 615 | N   | ASN | B | 909 | 31.300 | 32.477 | 17.068 | 1.00 27.49 |
| ATOM | 616 | CA  | ASN | B | 909 | 30.550 | 31.793 | 18.108 | 1.00 24.09 |
| ATOM | 617 | C   | ASN | B | 909 | 31.321 | 32.036 | 19.407 | 1.00 25.93 |
| ATOM | 618 | O   | ASN | B | 909 | 32.485 | 32.498 | 19.367 | 1.00 28.49 |
| ATOM | 619 | CB  | ASN | B | 909 | 30.241 | 30.343 | 17.894 | 1.00 26.09 |
| ATOM | 620 | CG  | ASN | B | 909 | 31.306 | 29.286 | 17.946 | 1.00 28.79 |
| ATOM | 621 | OD1 | ASN | B | 909 | 31.088 | 28.055 | 17.867 | 1.00 30.89 |
| ATOM | 622 | ND2 | ASN | B | 909 | 32.526 | 29.772 | 18.045 | 1.00 25.36 |

FIG. 5K

```
ATOM    523  N    LEU B 910      30.721  31.746  20.545  1.00 23.98
ATOM    524  CA   LEU B 910      31.369  32.013  21.809  1.00 24.27
ATOM    525  C    LEU B 910      32.494  31.025  22.149  1.00 28.34
ATOM    526  O    LEU B 910      33.475  31.482  22.740  1.00 28.22
ATOM    527  CB   LEU B 910      30.268  31.885  22.850  1.00 22.33
ATOM    528  CG   LEU B 910      30.701  31.957  24.327  1.00 23.69
ATOM    529  CD1  LEU B 910      31.394  33.213  24.683  1.00 22.29
ATOM    530  CD2  LEU B 910      29.417  31.790  25.166  1.00 21.57
ATOM    631  N    LEU B 911      32.290  29.750  21.805  1.00 27.95
ATOM    632  CA   LEU B 911      33.380  28.801  22.034  1.00 25.73
ATOM    633  C    LEU B 911      34.638  29.295  21.337  1.00 27.49
ATOM    634  O    LEU B 911      35.676  29.359  22.043  1.00 26.42
ATOM    635  CB   LEU B 911      33.003  27.396  21.533  1.00 27.05
ATOM    636  CG   LEU B 911      34.062  26.292  21.771  1.00 25.84
ATOM    637  CD1  LEU B 911      34.319  26.301  23.302  1.00 20.85
ATOM    638  CD2  LEU B 911      33.505  24.899  21.410  1.00 23.88
ATOM    639  N    ASP B 912      34.686  29.509  20.034  1.00 27.48
ATOM    640  CA   ASP B 912      35.832  30.077  19.341  1.00 30.26
ATOM    641  C    ASP B 912      36.323  31.426  19.869  1.00 31.88
ATOM    642  O    ASP B 912      37.540  31.676  19.938  1.00 29.65
ATOM    643  CB   ASP B 912      35.557  30.313  17.848  1.00 30.57
ATOM    644  CG   ASP B 912      35.339  29.102  16.995  1.00 34.53
ATOM    645  OD1  ASP B 912      34.882  29.274  15.841  1.00 37.84
ATOM    646  OD2  ASP B 912      35.663  27.975  17.416  1.00 37.21
ATOM    647  N    PHE B 913      35.440  32.298  20.355  1.00 31.78
ATOM    648  CA   PHE B 913      35.763  33.564  20.967  1.00 29.21
ATOM    649  C    PHE B 913      36.507  33.319  22.291  1.00 30.28
ATOM    650  O    PHE B 913      37.612  33.931  22.463  1.00 27.63
ATOM    651  CB   PHE B 913      34.591  34.492  21.208  1.00 27.45
ATOM    652  CG   PHE B 913      34.831  35.958  21.499  1.00 29.93
ATOM    653  CD1  PHE B 913      35.060  36.840  20.461  1.00 28.75
ATOM    654  CD2  PHE B 913      34.910  36.415  22.816  1.00 27.43
ATOM    655  CE1  PHE B 913      35.313  38.202  20.715  1.00 28.06
ATOM    656  CE2  PHE B 913      35.188  37.763  23.068  1.00 29.46
ATOM    657  CZ   PHE B 913      35.379  38.643  22.029  1.00 28.47
ATOM    658  N    LEU B 914      36.054  32.404  23.151  1.00 26.55
ATOM    659  CA   LEU B 914      36.844  32.188  24.365  1.00 31.20
ATOM    660  C    LEU B 914      38.154  31.425  24.075  1.00 30.42
ATOM    661  O    LEU B 914      39.065  31.539  24.890  1.00 29.64
ATOM    662  CB   LEU B 914      36.133  31.379  25.440  1.00 32.99
ATOM    663  CG   LEU B 914      34.718  31.897  25.858  1.00 32.39
ATOM    664  CD1  LEU B 914      33.745  30.794  26.190  1.00 31.43
ATOM    665  CD2  LEU B 914      34.981  32.805  27.062  1.00 27.44
ATOM    666  N    ARG B 915      38.196  30.595  23.029  1.00 28.43
ATOM    667  CA   ARG B 915      39.414  29.824  22.755  1.00 29.31
ATOM    668  C    ARG B 915      40.498  30.753  22.149  1.00 32.00
ATOM    669  O    ARG B 915      41.692  30.583  22.478  1.00 33.32
ATOM    670  CB   ARG B 915      39.157  28.572  21.911  1.00 25.22
ATOM    671  CG   ARG B 915      38.723  27.348  22.800  1.00 24.37
ATOM    672  CD   ARG B 915      38.161  26.209  21.957  1.00 24.35
ATOM    673  NE   ARG B 915      37.642  25.132  22.889  1.00 26.89
ATOM    674  CZ   ARG B 915      37.100  24.031  22.346  1.00 25.09
ATOM    675  NH1  ARG B 915      37.054  23.901  21.016  1.00 24.19
ATOM    676  NH2  ARG B 915      36.588  23.111  23.194  1.00 23.94
ATOM    677  N    LYS B 916      40.164  31.751  21.372  1.00 34.12
ATOM    678  CA   LYS B 916      40.980  32.736  20.705  1.00 35.63
ATOM    679  C    LYS B 916      41.664  33.693  21.683  1.00 36.01
```

FIG. 5L

| | | | | | | | | | |
|---|---|---|---|---|---|---|---|---|---|
| ATOM | 680 | O | LYS | B | 916 | 42.762 | 34.252 | 21.536 | 1.00 36.61 |
| ATOM | 681 | CB | LYS | B | 916 | 40.287 | 33.552 | 19.615 | 1.00 34.37 |
| ATOM | 682 | CG | LYS | B | 916 | 40.129 | 32.825 | 18.298 | 1.00 42.16 |
| ATOM | 683 | CD | LYS | B | 916 | 39.443 | 33.575 | 17.172 | 1.00 44.43 |
| ATOM | 684 | CE | LYS | B | 916 | 38.756 | 32.732 | 16.114 | 1.00 47.47 |
| ATOM | 685 | NZ | LYS | B | 916 | 37.371 | 33.261 | 15.814 | 1.00 51.77 |
| ATOM | 686 | N | SER | B | 917 | 40.991 | 33.857 | 22.786 | 1.00 33.46 |
| ATOM | 687 | CA | SER | B | 917 | 41.419 | 34.647 | 23.937 | 1.00 32.01 |
| ATOM | 688 | C | SER | B | 917 | 42.545 | 34.012 | 24.721 | 1.00 32.62 |
| ATOM | 689 | O | SER | B | 917 | 43.188 | 34.725 | 25.520 | 1.00 27.96 |
| ATOM | 690 | CB | SER | B | 917 | 40.117 | 34.800 | 24.689 | 1.00 31.09 |
| ATOM | 691 | OG | SER | B | 917 | 40.057 | 34.497 | 26.054 | 1.00 33.24 |
| ATOM | 692 | N | ARG | B | 918 | 42.926 | 32.735 | 24.574 | 1.00 33.26 |
| ATOM | 693 | CA | ARG | B | 918 | 43.911 | 32.087 | 25.401 | 1.00 29.88 |
| ATOM | 694 | C | ARG | B | 918 | 45.341 | 32.471 | 24.927 | 1.00 33.33 |
| ATOM | 695 | O | ARG | B | 918 | 46.072 | 31.782 | 24.226 | 1.00 34.36 |
| ATOM | 696 | CB | ARG | B | 918 | 43.750 | 30.570 | 25.487 | 1.00 30.84 |
| ATOM | 697 | CG | ARG | B | 918 | 42.350 | 30.118 | 25.969 | 1.00 31.53 |
| ATOM | 698 | CD | ARG | B | 918 | 42.301 | 28.655 | 26.234 | 1.00 31.59 |
| ATOM | 699 | NE | ARG | B | 918 | 41.373 | 27.771 | 26.776 | 1.00 30.40 |
| ATOM | 700 | CZ | ARG | B | 918 | 41.314 | 26.510 | 27.146 | 1.00 27.78 |
| ATOM | 701 | NH1 | ARG | B | 918 | 42.579 | 25.901 | 27.032 | 1.00 24.30 |
| ATOM | 702 | NH2 | ARG | B | 918 | 40.359 | 25.804 | 27.635 | 1.00 24.57 |
| ATOM | 703 | N | VAL | B | 919 | 45.792 | 33.639 | 25.388 | 1.00 29.19 |
| ATOM | 704 | CA | VAL | B | 919 | 46.914 | 34.362 | 24.991 | 1.00 31.89 |
| ATOM | 705 | C | VAL | B | 919 | 48.324 | 33.779 | 25.390 | 1.00 33.48 |
| ATOM | 706 | O | VAL | B | 919 | 49.318 | 34.428 | 25.239 | 1.00 42.15 |
| ATOM | 707 | CB | VAL | B | 919 | 47.064 | 35.854 | 25.366 | 1.00 30.88 |
| ATOM | 708 | CG1 | VAL | B | 919 | 46.027 | 36.669 | 24.602 | 1.00 34.82 |
| ATOM | 709 | CG2 | VAL | B | 919 | 46.881 | 36.061 | 26.852 | 1.00 31.88 |
| ATOM | 710 | N | LEU | B | 920 | 48.272 | 32.609 | 25.986 | 1.00 31.42 |
| ATOM | 711 | CA | LEU | B | 920 | 49.386 | 31.803 | 26.310 | 1.00 32.43 |
| ATOM | 712 | C | LEU | B | 920 | 49.646 | 30.949 | 25.049 | 1.00 33.59 |
| ATOM | 713 | O | LEU | B | 920 | 50.874 | 30.754 | 24.757 | 1.00 34.43 |
| ATOM | 714 | CB | LEU | B | 920 | 49.363 | 30.892 | 27.516 | 1.00 26.98 |
| ATOM | 715 | CG | LEU | B | 920 | 49.473 | 31.646 | 28.827 | 1.00 28.45 |
| ATOM | 716 | CD1 | LEU | B | 920 | 49.060 | 30.712 | 29.911 | 1.00 24.11 |
| ATOM | 717 | CD2 | LEU | B | 920 | 50.899 | 32.259 | 29.084 | 1.00 24.38 |
| ATOM | 718 | N | GLU | B | 921 | 48.560 | 30.587 | 24.414 | 1.00 33.03 |
| ATOM | 719 | CA | GLU | B | 921 | 48.691 | 29.839 | 23.163 | 1.00 34.88 |
| ATOM | 720 | C | GLU | B | 921 | 48.686 | 30.741 | 21.960 | 1.00 36.44 |
| ATOM | 721 | O | GLU | B | 921 | 49.468 | 30.532 | 21.028 | 1.00 37.60 |
| ATOM | 722 | CB | GLU | B | 921 | 47.526 | 28.797 | 23.034 | 1.00 36.48 |
| ATOM | 723 | CG | GLU | B | 921 | 47.367 | 28.228 | 21.636 | 1.00 39.16 |
| ATOM | 724 | CD | GLU | B | 921 | 46.213 | 27.255 | 21.414 | 1.00 43.37 |
| ATOM | 725 | OE1 | GLU | B | 921 | 45.489 | 26.854 | 22.357 | 1.00 41.90 |
| ATOM | 726 | OE2 | GLU | B | 921 | 46.044 | 26.848 | 20.222 | 1.00 42.19 |
| ATOM | 727 | N | THR | B | 922 | 47.772 | 31.738 | 21.886 | 1.00 33.22 |
| ATOM | 728 | CA | THR | B | 922 | 47.684 | 32.482 | 20.652 | 1.00 33.16 |
| ATOM | 729 | C | THR | B | 922 | 48.566 | 33.711 | 20.605 | 1.00 33.32 |
| ATOM | 730 | O | THR | B | 922 | 48.787 | 34.124 | 19.452 | 1.00 33.82 |
| ATOM | 731 | CB | THR | B | 922 | 46.212 | 32.897 | 20.346 | 1.00 33.96 |
| ATOM | 732 | OG1 | THR | B | 922 | 45.814 | 33.744 | 21.415 | 1.00 33.38 |
| ATOM | 733 | CG2 | THR | B | 922 | 45.288 | 31.667 | 20.363 | 1.00 35.79 |
| ATOM | 734 | N | ASP | B | 923 | 49.134 | 34.252 | 21.645 | 1.00 34.17 |
| ATOM | 735 | CA | ASP | B | 923 | 50.099 | 35.410 | 21.445 | 1.00 33.90 |
| ATOM | 736 | C | ASP | B | 923 | 50.855 | 35.464 | 22.736 | 1.00 31.06 |

FIG. 5M

```
ATOM    737  O    ASP B 923      50.593  36.342  23.567  1.00 27.46
ATOM    738  CB   ASP B 923      49.307  36.710  21.268  1.00 37.04
ATOM    739  CG   ASP B 923      50.153  37.937  20.960  1.00 41.38
ATOM    740  OD1  ASP B 923      49.577  39.035  20.699  1.00 39.51
ATOM    741  OD2  ASP B 923      51.412  37.813  20.986  1.00 38.37
ATOM    742  N    PRO B 924      51.732  34.505  23.057  1.00 30.87
ATOM    743  CA   PRO B 924      52.373  34.348  24.339  1.00 29.10
ATOM    744  C    PRO B 924      53.219  35.487  24.884  1.00 30.48
ATOM    745  O    PRO B 924      53.451  35.658  26.081  1.00 36.16
ATOM    746  CB   PRO B 924      53.266  33.088  24.160  1.00 29.12
ATOM    747  CG   PRO B 924      53.404  32.976  22.696  1.00 30.23
ATOM    748  CD   PRO B 924      52.076  33.382  22.137  1.00 31.39
ATOM    749  N    ALA B 925      53.613  36.368  24.008  1.00 26.00
ATOM    750  CA   ALA B 925      54.366  37.598  24.150  1.00 32.47
ATOM    751  C    ALA B 925      53.543  38.653  24.869  1.00 29.57
ATOM    752  O    ALA B 925      53.787  39.195  25.935  1.00 30.49
ATOM    753  CB   ALA B 925      54.773  38.221  22.799  1.00 31.57
ATOM    754  N    PHE B 926      52.319  38.825  24.295  1.00 29.73
ATOM    755  CA   PHE B 926      51.269  39.710  24.838  1.00 29.93
ATOM    756  C    PHE B 926      51.056  39.489  26.342  1.00 26.49
ATOM    757  C    PHE B 926      50.877  40.391  27.189  1.00 33.60
ATOM    758  CB   PHE B 926      49.990  39.510  24.004  1.00 33.75
ATOM    759  CG   PHE B 926      48.853  40.282  24.610  1.00 35.41
ATOM    760  CD1  PHE B 926      48.530  41.563  24.201  1.00 35.32
ATOM    761  CD2  PHE B 926      48.148  39.708  25.665  1.00 35.43
ATOM    762  CE1  PHE B 926      47.510  42.237  24.860  1.00 37.62
ATOM    763  CE2  PHE B 926      47.135  40.390  26.312  1.00 40.82
ATOM    764  CZ   PHE B 926      46.803  41.649  25.884  1.00 37.83
ATOM    765  N    ALA B 927      50.917  38.202  26.616  1.00 30.01
ATOM    766  CA   ALA B 927      50.632  37.486  27.815  1.00 28.56
ATOM    767  C    ALA B 927      51.656  37.637  28.900  1.00 29.51
ATOM    768  O    ALA B 927      51.289  37.839  30.056  1.00 30.25
ATOM    769  CB   ALA B 927      50.513  35.973  27.565  1.00 32.88
ATOM    770  N    ILE B 928      52.948  37.452  28.535  1.00 31.84
ATOM    771  CA   ILE B 928      54.019  37.696  29.494  1.00 33.06
ATOM    772  C    ILE B 928      54.111  39.221  29.662  1.00 31.39
ATOM    773  O    ILE B 928      54.206  39.681  30.804  1.00 32.12
ATOM    774  CB   ILE B 928      55.354  37.042  29.050  1.00 34.86
ATOM    775  CG1  ILE B 928      56.448  37.311  30.077  1.00 36.35
ATOM    776  CG2  ILE B 928      55.833  37.483  27.689  1.00 36.48
ATOM    777  CD1  ILE B 928      56.235  36.372  31.274  1.00 40.48
ATOM    778  N    ALA B 929      53.998  40.026  28.623  1.00 32.07
ATOM    779  CA   ALA B 929      54.114  41.493  28.884  1.00 35.07
ATOM    780  C    ALA B 929      52.935  42.038  29.650  1.00 32.88
ATOM    781  O    ALA B 929      53.152  42.885  30.515  1.00 32.96
ATOM    782  CB   ALA B 929      54.276  42.286  27.584  1.00 38.44
ATOM    783  N    ASN B 930      51.737  41.363  29.538  1.00 32.01
ATOM    784  CA   ASN B 930      50.624  41.923  30.307  1.00 32.62
ATOM    785  C    ASN B 930      50.458  41.157  31.604  1.00 32.33
ATOM    786  O    ASN B 930      49.549  41.509  32.315  1.00 30.28
ATOM    787  CB   ASN B 930      49.305  41.975  29.564  1.00 30.21
ATOM    788  CG   ASN B 930      49.462  43.166  28.612  1.00 34.16
ATOM    789  OD1  ASN B 930      49.104  44.224  29.139  1.00 35.09
ATOM    790  ND2  ASN B 930      49.997  42.925  27.434  1.00 33.29
ATOM    791  N    SER B 931      51.284  40.126  31.740  1.00 31.40
ATOM    792  CA   SER B 931      51.064  39.195  32.863  1.00 34.73
ATOM    793  C    SER B 931      49.616  38.647  32.909  1.00 31.81
```

FIG. 5N

| | | | | | | | | | |
|---|---|---|---|---|---|---|---|---|---|
| ATOM | 794 | O   | SER | B | 931 | 48.946 | 38.522 | 33.960 | 1.00 28.51 |
| ATOM | 795 | CB  | SER | B | 931 | 51.539 | 39.966 | 34.083 | 1.00 36.38 |
| ATOM | 796 | OG  | SER | B | 931 | 51.372 | 39.137 | 35.239 | 1.00 44.81 |
| ATOM | 797 | N   | THR | B | 932 | 49.066 | 38.367 | 31.708 | 1.00 31.32 |
| ATOM | 798 | CA  | THR | B | 932 | 47.681 | 37.822 | 31.741 | 1.00 33.33 |
| ATOM | 799 | C   | THR | B | 932 | 47.532 | 36.490 | 31.036 | 1.00 31.10 |
| ATOM | 800 | O   | THR | B | 932 | 48.276 | 36.141 | 30.127 | 1.00 30.68 |
| ATOM | 801 | CB  | THR | B | 932 | 46.678 | 38.870 | 31.263 | 1.00 33.87 |
| ATOM | 802 | OG1 | THR | B | 932 | 45.316 | 38.426 | 31.576 | 1.00 33.49 |
| ATOM | 803 | CG2 | THR | B | 932 | 46.692 | 39.109 | 29.757 | 1.00 33.71 |
| ATOM | 804 | N   | ALA | B | 933 | 46.529 | 35.668 | 31.389 | 1.00 31.61 |
| ATOM | 805 | CA  | ALA | B | 933 | 46.226 | 34.431 | 30.705 | 1.00 29.07 |
| ATOM | 806 | C   | ALA | B | 933 | 45.091 | 34.589 | 29.655 | 1.00 30.40 |
| ATOM | 807 | O   | ALA | B | 933 | 44.908 | 33.676 | 28.853 | 1.00 28.66 |
| ATOM | 808 | CB  | ALA | B | 933 | 45.737 | 33.378 | 31.703 | 1.00 27.24 |
| ATOM | 809 | N   | SER | B | 934 | 44.450 | 35.779 | 29.587 | 1.00 26.77 |
| ATOM | 810 | CA  | SER | B | 934 | 43.413 | 36.013 | 28.587 | 1.00 28.62 |
| ATOM | 811 | C   | SER | B | 934 | 43.192 | 37.464 | 28.195 | 1.00 27.31 |
| ATOM | 812 | O   | SER | B | 934 | 43.323 | 38.417 | 28.980 | 1.00 27.55 |
| ATOM | 813 | CB  | SER | B | 934 | 42.064 | 35.455 | 29.162 | 1.00 26.81 |
| ATOM | 814 | OG  | SER | B | 934 | 40.981 | 35.744 | 28.323 | 1.00 27.56 |
| ATOM | 815 | N   | THR | B | 935 | 42.820 | 37.745 | 26.944 | 1.00 27.99 |
| ATOM | 816 | CA  | THR | B | 935 | 42.439 | 39.110 | 26.578 | 1.00 29.68 |
| ATOM | 817 | C   | THR | B | 935 | 41.160 | 39.524 | 27.282 | 1.00 31.68 |
| ATOM | 818 | O   | THR | B | 935 | 40.842 | 40.718 | 27.320 | 1.00 33.62 |
| ATOM | 819 | CB  | THR | B | 935 | 42.242 | 39.350 | 25.075 | 1.00 28.76 |
| ATOM | 820 | OG1 | THR | B | 935 | 41.506 | 38.262 | 24.505 | 1.00 29.66 |
| ATOM | 821 | CG2 | THR | B | 935 | 43.525 | 39.478 | 24.287 | 1.00 30.80 |
| ATOM | 822 | N   | LEU | B | 936 | 40.343 | 38.579 | 27.771 | 1.00 30.00 |
| ATOM | 823 | CA  | LEU | B | 936 | 39.018 | 38.902 | 28.323 | 1.00 31.45 |
| ATOM | 824 | C   | LEU | B | 936 | 39.137 | 39.093 | 29.820 | 1.00 29.86 |
| ATOM | 825 | O   | LEU | B | 936 | 39.947 | 38.339 | 30.364 | 1.00 28.85 |
| ATOM | 826 | CB  | LEU | B | 936 | 38.171 | 37.634 | 28.127 | 1.00 35.21 |
| ATOM | 827 | CG  | LEU | B | 936 | 37.312 | 37.342 | 26.944 | 1.00 38.52 |
| ATOM | 828 | CD1 | LEU | B | 936 | 37.602 | 38.053 | 25.641 | 1.00 42.04 |
| ATOM | 829 | CD2 | LEU | B | 936 | 37.181 | 35.833 | 26.689 | 1.00 40.21 |
| ATOM | 830 | N   | SER | B | 937 | 38.381 | 39.888 | 30.508 | 1.00 28.66 |
| ATOM | 831 | CA  | SER | B | 937 | 38.427 | 39.976 | 31.975 | 1.00 27.30 |
| ATOM | 832 | C   | SER | B | 937 | 37.373 | 39.107 | 32.612 | 1.00 25.12 |
| ATOM | 833 | O   | SER | B | 937 | 36.444 | 38.641 | 31.960 | 1.00 29.26 |
| ATOM | 834 | CB  | SER | B | 937 | 38.164 | 41.408 | 32.478 | 1.00 28.29 |
| ATOM | 835 | OG  | SER | B | 937 | 36.753 | 41.746 | 32.275 | 1.00 26.99 |
| ATOM | 836 | N   | SER | B | 938 | 37.382 | 38.946 | 33.936 | 1.00 23.75 |
| ATOM | 837 | CA  | SER | B | 938 | 36.444 | 38.301 | 34.738 | 1.00 25.14 |
| ATOM | 838 | C   | SER | B | 938 | 34.982 | 38.781 | 34.508 | 1.00 29.67 |
| ATOM | 839 | O   | SER | B | 938 | 33.973 | 38.052 | 34.324 | 1.00 28.12 |
| ATOM | 840 | CB  | SER | B | 938 | 36.842 | 38.693 | 36.180 | 1.00 25.42 |
| ATOM | 841 | OG  | SER | B | 938 | 35.935 | 37.879 | 36.971 | 1.00 31.24 |
| ATOM | 842 | N   | GLN | B | 939 | 34.834 | 40.109 | 34.487 | 1.00 27.93 |
| ATOM | 843 | CA  | GLN | B | 939 | 33.576 | 40.797 | 34.290 | 1.00 30.16 |
| ATOM | 844 | C   | GLN | B | 939 | 33.036 | 40.463 | 32.911 | 1.00 26.11 |
| ATOM | 845 | O   | GLN | B | 939 | 31.840 | 40.271 | 32.714 | 1.00 28.65 |
| ATOM | 846 | CB  | GLN | B | 939 | 33.784 | 42.330 | 34.312 | 1.00 33.19 |
| ATOM | 847 | CG  | GLN | B | 939 | 33.442 | 43.229 | 35.457 | 1.00 40.59 |
| ATOM | 848 | CD  | GLN | B | 939 | 32.130 | 43.133 | 36.180 | 1.00 39.70 |
| ATOM | 849 | OE1 | GLN | B | 939 | 31.005 | 43.468 | 35.831 | 1.00 47.06 |
| ATOM | 850 | NE2 | GLN | B | 939 | 32.185 | 42.646 | 37.424 | 1.00 42.39 |

FIG. 50

```
ATOM    851  N    GLN B 940      33.893  40.437  31.879  1.00 28.10
ATOM    852  CA   GLN B 940      33.294  39.992  30.590  1.00 26.42
ATOM    853  C    GLN B 940      32.792  38.510  30.608  1.00 27.93
ATOM    854  O    GLN B 940      31.699  38.213  30.003  1.00 24.42
ATOM    855  CB   GLN B 940      34.237  40.315  29.474  1.00 28.32
ATOM    856  CG   GLN B 940      33.821  39.728  28.138  1.00 30.12
ATOM    857  CD   GLN B 940      32.714  40.351  27.341  1.00 32.84
ATOM    858  OE1  GLN B 940      32.980  40.952  26.293  1.00 32.97
ATOM    859  NE2  GLN B 940      31.444  40.215  27.742  1.00 32.92
ATOM    860  N    LEU B 941      33.469  37.651  31.370  1.00 26.91
ATOM    861  CA   LEU B 941      32.909  36.258  31.443  1.00 28.19
ATOM    862  C    LEU B 941      31.589  36.301  32.198  1.00 29.57
ATOM    863  O    LEU B 941      30.678  35.590  31.730  1.00 30.43
ATOM    864  CB   LEU B 941      33.906  35.296  32.049  1.00 25.27
ATOM    865  CG   LEU B 941      35.315  35.323  31.415  1.00 32.42
ATOM    866  CD1  LEU B 941      36.323  34.485  32.227  1.00 31.29
ATOM    867  CD2  LEU B 941      35.341  34.767  30.010  1.00 31.88
ATOM    868  N    LEU B 942      31.450  37.064  33.293  1.00 30.31
ATOM    869  CA   LEU B 942      30.167  37.145  33.968  1.00 32.16
ATOM    870  C    LEU B 942      29.036  37.749  33.115  1.00 31.83
ATOM    871  O    LEU B 942      27.922  37.185  33.174  1.00 33.88
ATOM    872  CB   LEU B 942      30.243  37.957  35.236  1.00 31.72
ATOM    873  CG   LEU B 942      31.083  37.434  36.382  1.00 33.04
ATOM    874  CD1  LEU B 942      31.284  38.550  37.417  1.00 33.30
ATOM    875  CD2  LEU B 942      30.573  36.187  36.999  1.00 35.60
ATOM    876  N    HIS B 943      29.333  38.722  32.292  1.00 30.14
ATOM    877  CA   HIS B 943      28.489  39.305  31.307  1.00 32.55
ATOM    878  C    HIS B 943      27.988  38.261  30.293  1.00 33.04
ATOM    879  O    HIS B 943      26.773  38.281  29.997  1.00 29.13
ATOM    880  CB   HIS B 943      29.051  40.525  30.513  1.00 31.92
ATOM    881  CG   HIS B 943      28.919  41.826  31.219  1.00 34.62
ATOM    882  ND1  HIS B 943      29.954  42.688  31.481  1.00 36.03
ATOM    883  CD2  HIS B 943      27.832  42.442  31.778  1.00 38.05
ATOM    884  CE1  HIS B 943      29.547  43.737  32.168  1.00 35.60
ATOM    885  NE2  HIS B 943      28.245  43.626  32.354  1.00 37.32
ATOM    886  N    PHE B 944      28.860  37.419  29.710  1.00 30.43
ATOM    887  CA   PHE B 944      28.322  36.430  28.793  1.00 30.42
ATOM    888  C    PHE B 944      27.361  35.447  29.480  1.00 28.35
ATOM    889  O    PHE B 944      26.297  35.095  28.948  1.00 27.55
ATOM    890  CB   PHE B 944      29.414  35.601  28.129  1.00 29.40
ATOM    891  CG   PHE B 944      30.259  36.326  27.143  1.00 28.28
ATOM    892  CD1  PHE B 944      31.639  36.118  27.152  1.00 28.85
ATOM    893  CD2  PHE B 944      29.764  37.193  26.200  1.00 27.36
ATOM    894  CE1  PHE B 944      32.429  36.783  26.230  1.00 31.22
ATOM    895  CE2  PHE B 944      30.528  37.861  25.279  1.00 30.76
ATOM    896  CZ   PHE B 944      31.863  37.640  25.305  1.00 29.54
ATOM    897  N    ALA B 945      27.661  35.064  30.707  1.00 28.20
ATOM    898  CA   ALA B 945      26.737  34.232  31.526  1.00 27.06
ATOM    899  C    ALA B 945      25.389  34.896  31.781  1.00 28.16
ATOM    900  O    ALA B 945      24.305  34.272  31.603  1.00 29.72
ATOM    901  CB   ALA B 945      27.424  33.982  32.882  1.00 22.24
ATOM    902  N    ALA B 946      25.348  36.185  32.154  1.00 28.40
ATOM    903  CA   ALA B 946      24.058  36.906  32.424  1.00 26.80
ATOM    904  C    ALA B 946      23.326  37.071  31.128  1.00 26.73
ATOM    905  C    ALA B 946      22.095  36.826  30.960  1.00 33.16
ATOM    906  CB   ALA B 946      24.422  38.268  33.049  1.00 27.29
ATOM    907  N    ASP B 947      24.021  37.501  30.077  1.00 25.12
```

FIG. 5P

```
ATOM    908  CA  ASP B 947      23.361  37.562  28.793  1.00 27.64
ATOM    909  C   ASP B 947      22.653  36.217  28.522  1.00 30.15
ATOM    910  O   ASP B 947      21.423  36.331  28.285  1.00 32.77
ATOM    911  CB  ASP B 947      24.158  37.947  27.594  1.00 32.32
ATOM    912  CG  ASP B 947      24.798  39.318  27.538  1.00 37.39
ATOM    913  OD1 ASP B 947      24.327  40.283  28.209  1.00 38.95
ATOM    914  OD2 ASP B 947      25.817  39.462  26.816  1.00 38.99
ATOM    915  N   VAL B 948      23.225  35.043  28.511  1.00 24.93
ATOM    916  CA  VAL B 948      22.519  33.824  28.235  1.00 26.37
ATOM    917  C   VAL B 948      21.319  33.657  29.150  1.00 26.38
ATOM    918  O   VAL B 948      20.273  33.241  28.688  1.00 28.00
ATOM    919  CB  VAL B 948      23.423  32.575  28.375  1.00 23.63
ATOM    920  CG1 VAL B 948      22.711  31.247  28.218  1.00 28.41
ATOM    921  CG2 VAL B 948      24.500  32.621  27.306  1.00 24.29
ATOM    922  N   ALA B 949      21.496  33.853  30.472  1.00 25.90
ATOM    923  CA  ALA B 949      20.489  33.633  31.449  1.00 24.76
ATOM    924  C   ALA B 949      19.254  34.514  31.245  1.00 29.82
ATOM    925  O   ALA B 949      18.125  33.995  31.478  1.00 29.12
ATOM    926  CB  ALA B 949      21.105  33.945  32.833  1.00 21.23
ATOM    927  N   ARG B 950      19.483  35.753  30.814  1.00 29.05
ATOM    928  CA  ARG B 950      18.417  36.711  30.563  1.00 29.74
ATOM    929  C   ARG B 950      17.681  36.245  29.315  1.00 30.35
ATOM    930  O   ARG B 950      16.454  36.156  29.291  1.00 32.30
ATOM    931  CB  ARG B 950      18.943  38.135  30.331  1.00 29.04
ATOM    932  CG  ARG B 950      17.857  39.209  30.253  1.00 29.74
ATOM    933  CD  ARG B 950      18.484  40.540  29.840  1.00 33.11
ATOM    934  NE  ARG B 950      19.702  40.789  30.623  1.00 36.26
ATOM    935  CZ  ARG B 950      20.973  41.064  30.349  1.00 36.47
ATOM    936  NH1 ARG B 950      21.905  41.281  31.276  1.00 34.51
ATOM    937  NH2 ARG B 950      21.378  41.083  29.088  1.00 37.31
ATOM    938  N   GLY B 951      18.419  35.817  28.306  1.00 29.52
ATOM    939  CA  GLY B 951      17.811  35.222  27.135  1.00 30.22
ATOM    940  C   GLY B 951      16.981  34.005  27.518  1.00 31.96
ATOM    941  O   GLY B 951      15.802  33.895  27.083  1.00 30.42
ATOM    942  N   MET B 952      17.505  33.082  28.235  1.00 31.58
ATOM    943  CA  MET B 952      16.833  31.858  28.668  1.00 31.52
ATOM    944  C   MET B 952      15.593  32.060  29.545  1.00 31.14
ATOM    945  O   MET B 952      14.692  31.277  29.453  1.00 32.05
ATOM    946  CB  MET B 952      17.728  30.817  29.348  1.00 32.91
ATOM    947  CG  MET B 952      18.601  29.963  28.470  1.00 28.12
ATOM    948  SD  MET B 952      17.803  29.220  27.056  1.00 28.47
ATOM    949  CE  MET B 952      16.601  28.118  27.850  1.00 24.09
ATOM    950  N   ASP B 953      15.540  32.991  30.425  1.00 33.12
ATOM    951  CA  ASP B 953      14.479  33.295  31.364  1.00 35.52
ATOM    952  C   ASP B 953      13.331  33.873  30.536  1.00 34.51
ATOM    953  O   ASP B 953      12.167  33.463  30.579  1.00 34.88
ATOM    954  CB  ASP B 953      14.959  34.196  32.470  1.00 37.38
ATOM    955  CG  ASP B 953      13.886  35.033  33.182  1.00 38.60
ATOM    956  OD1 ASP B 953      13.235  34.579  34.136  1.00 38.16
ATOM    957  OD2 ASP B 953      13.774  36.209  32.830  1.00 39.51
ATOM    958  N   TYR B 954      13.741  34.680  29.561  1.00 34.22
ATOM    959  CA  TYR B 954      12.764  35.208  28.602  1.00 33.92
ATOM    960  C   TYR B 954      12.083  34.027  27.920  1.00 35.03
ATOM    961  O   TYR B 954      10.854  33.911  27.879  1.00 33.83
ATOM    962  CB  TYR B 954      13.457  36.158  27.672  1.00 36.04
ATOM    963  CG  TYR B 954      12.621  36.621  26.523  1.00 40.14
ATOM    964  CD1 TYR B 954      11.489  37.372  26.834  1.00 42.51
```

FIG. 5Q

```
ATOM    965  CD2 TYR B 954      12.873  36.322  25.202  1.00 40.08
ATOM    966  CE1 TYR B 954      10.587  37.819  25.869  1.00 45.17
ATOM    967  CE2 TYR B 954      12.012  36.762  24.225  1.00 44.28
ATOM    968  CZ  TYR B 954      10.893  37.541  24.548  1.00 45.99
ATOM    969  OH  TYR B 954      10.043  37.968  23.564  1.00 46.72
ATOM    970  N   LEU B 955      12.809  33.080  27.399  1.00 34.55
ATOM    971  CA  LEU B 955      12.388  31.912  26.704  1.00 34.31
ATOM    972  C   LEU B 955      11.690  30.956  27.654  1.00 32.95
ATOM    973  O   LEU B 955      10.537  30.633  27.336  1.00 36.79
ATOM    974  CB  LEU B 955      13.431  31.053  26.006  1.00 34.82
ATOM    975  CG  LEU B 955      14.032  31.673  24.757  1.00 30.87
ATOM    976  CD1 LEU B 955      15.304  30.976  24.341  1.00 31.55
ATOM    977  CD2 LEU B 955      13.075  31.726  23.592  1.00 32.89
ATOM    978  N   SER B 956      12.231  30.620  28.798  1.00 33.38
ATOM    979  CA  SER B 956      11.489  29.672  29.609  1.00 34.02
ATOM    980  C   SER B 956      10.214  30.243  30.247  1.00 34.18
ATOM    981  O   SER B 956       9.393  29.419  30.652  1.00 30.24
ATOM    982  CB  SER B 956      12.469  29.126  30.630  1.00 33.64
ATOM    983  OG  SER B 956      12.613  30.134  31.586  1.00 37.17
ATOM    984  N   GLN B 957      10.032  31.530  30.438  1.00 32.94
ATOM    985  CA  GLN B 957       8.852  32.137  31.059  1.00 37.57
ATOM    986  C   GLN B 957       7.675  32.048  30.084  1.00 36.65
ATOM    987  O   GLN B 957       6.518  31.962  30.443  1.00 36.69
ATOM    988  CB  GLN B 957       9.101  33.516  31.671  1.00 39.36
ATOM    989  CG  GLN B 957       9.819  33.491  33.028  1.00 43.44
ATOM    990  CD  GLN B 957      10.305  34.801  33.581  1.00 47.63
ATOM    991  OE1 GLN B 957      10.420  35.138  34.789  1.00 48.94
ATOM    992  NE2 GLN B 957      10.736  35.802  32.807  1.00 50.75
ATOM    993  N   LYS B 958       7.937  31.933  28.792  1.00 37.29
ATOM    994  CA  LYS B 958       7.068  31.649  27.696  1.00 36.90
ATOM    995  C   LYS B 958       6.830  30.166  27.402  1.00 39.87
ATOM    996  O   LYS B 958       6.248  29.735  26.407  1.00 41.16
ATOM    997  CB  LYS B 958       7.554  32.393  26.439  1.00 40.75
ATOM    998  CG  LYS B 958       7.237  33.882  26.545  1.00 42.57
ATOM    999  CD  LYS B 958       7.853  34.666  25.399  1.00 44.52
ATOM   1000  CE  LYS B 958       6.950  35.852  25.045  1.00 49.59
ATOM   1001  NZ  LYS B 958       7.755  36.850  24.277  1.00 50.56
ATOM   1002  N   GLN B 959       7.238  29.272  28.275  1.00 38.89
ATOM   1003  CA  GLN B 959       7.191  27.826  28.340  1.00 39.77
ATOM   1004  C   GLN B 959       7.985  27.154  27.246  1.00 36.45
ATOM   1005  O   GLN B 959       7.889  25.977  26.904  1.00 34.64
ATOM   1006  CB  GLN B 959       5.729  27.298  28.353  1.00 42.27
ATOM   1007  CG  GLN B 959       5.062  27.411  29.706  1.00 47.02
ATOM   1008  CD  GLN B 959       3.550  27.270  29.700  1.00 52.44
ATOM   1009  OE1 GLN B 959       2.905  27.301  30.787  1.00 54.64
ATOM   1010  NE2 GLN B 959       2.888  27.133  28.539  1.00 51.33
ATOM   1011  N   PHE B 960       8.932  27.911  26.701  1.00 35.89
ATOM   1012  CA  PHE B 960       9.764  27.490  25.601  1.00 34.12
ATOM   1013  C   PHE B 960      11.017  26.758  26.168  1.00 34.10
ATOM   1014  O   PHE B 960      11.310  27.045  27.320  1.00 36.77
ATOM   1015  CB  PHE B 960      10.127  28.752  24.850  1.00 38.30
ATOM   1016  CG  PHE B 960       9.381  29.131  23.626  1.00 37.64
ATOM   1017  CD1 PHE B 960       8.691  30.350  23.577  1.00 39.17
ATOM   1018  CD2 PHE B 960       9.322  28.313  22.534  1.00 37.83
ATOM   1019  CE1 PHE B 960       7.970  30.753  22.460  1.00 36.50
ATOM   1020  CE2 PHE B 960       8.612  28.711  21.415  1.00 38.89
ATOM   1021  CZ  PHE B 960       7.938  29.930  21.372  1.00 38.28
```

FIG. 5R

| | | | | | | | | | |
|---|---|---|---|---|---|---|---|---|---|
| ATOM | 1022 | N | ILE | B | 961 | 11.301 | 25.645 | 25.515 | 1.00 32.04 |
| ATOM | 1023 | CA | ILE | B | 961 | 12.386 | 24.751 | 25.913 | 1.00 35.73 |
| ATOM | 1024 | C | ILE | B | 961 | 13.444 | 24.628 | 24.816 | 1.00 35.82 |
| ATOM | 1025 | O | ILE | B | 961 | 13.170 | 24.025 | 23.764 | 1.00 36.60 |
| ATOM | 1026 | CB | ILE | B | 961 | 11.866 | 23.322 | 26.185 | 1.00 37.85 |
| ATOM | 1027 | CG1 | ILE | B | 961 | 10.658 | 23.219 | 27.079 | 1.00 39.27 |
| ATOM | 1028 | CG2 | ILE | B | 961 | 12.985 | 22.443 | 26.741 | 1.00 41.20 |
| ATOM | 1029 | CD1 | ILE | B | 961 | 10.666 | 23.505 | 28.545 | 1.00 39.36 |
| ATOM | 1030 | N | HIS | B | 962 | 14.751 | 24.959 | 25.030 | 1.00 33.60 |
| ATOM | 1031 | CA | HIS | B | 962 | 15.736 | 24.996 | 23.975 | 1.00 31.29 |
| ATOM | 1032 | C | HIS | B | 962 | 16.435 | 23.705 | 23.604 | 1.00 30.82 |
| ATOM | 1033 | O | HIS | B | 962 | 16.658 | 23.371 | 22.425 | 1.00 29.73 |
| ATOM | 1034 | CB | HIS | B | 962 | 16.674 | 26.099 | 24.539 | 1.00 31.33 |
| ATOM | 1035 | CG | HIS | B | 962 | 17.589 | 26.596 | 23.457 | 1.00 33.97 |
| ATOM | 1036 | ND1 | HIS | B | 962 | 17.135 | 26.808 | 22.169 | 1.00 33.33 |
| ATOM | 1037 | CD2 | HIS | B | 962 | 18.913 | 26.881 | 23.499 | 1.00 33.27 |
| ATOM | 1038 | CE1 | HIS | B | 962 | 18.200 | 27.242 | 21.492 | 1.00 35.73 |
| ATOM | 1039 | NE2 | HIS | B | 962 | 19.289 | 27.260 | 22.251 | 1.00 29.66 |
| ATOM | 1040 | N | ARG | B | 963 | 16.968 | 23.006 | 24.598 | 1.00 30.47 |
| ATOM | 1041 | CA | ARG | B | 963 | 17.746 | 21.769 | 24.471 | 1.00 33.00 |
| ATOM | 1042 | C | ARG | B | 963 | 19.194 | 21.923 | 23.997 | 1.00 36.77 |
| ATOM | 1043 | O | ARG | B | 963 | 19.889 | 20.887 | 24.004 | 1.00 39.62 |
| ATOM | 1044 | CB | ARG | B | 963 | 17.204 | 20.679 | 23.551 | 1.00 32.77 |
| ATOM | 1045 | CG | ARG | B | 963 | 15.815 | 20.172 | 23.935 | 1.00 31.62 |
| ATOM | 1046 | CD | ARG | B | 963 | 15.128 | 19.404 | 22.847 | 1.00 31.53 |
| ATOM | 1047 | NE | ARG | B | 963 | 15.025 | 19.871 | 21.521 | 1.00 33.88 |
| ATOM | 1048 | CZ | ARG | B | 963 | 15.726 | 19.662 | 20.419 | 1.00 37.97 |
| ATOM | 1049 | NH1 | ARG | B | 963 | 16.808 | 18.841 | 20.421 | 1.00 37.50 |
| ATOM | 1050 | NH2 | ARG | B | 963 | 15.341 | 20.285 | 19.289 | 1.00 37.35 |
| ATOM | 1051 | N | ASN | B | 964 | 19.655 | 23.009 | 23.398 | 1.00 36.17 |
| ATOM | 1052 | CA | ASN | B | 964 | 20.974 | 23.021 | 22.816 | 1.00 38.69 |
| ATOM | 1053 | C | ASN | B | 964 | 21.926 | 24.070 | 23.372 | 1.00 36.17 |
| ATOM | 1054 | O | ASN | B | 964 | 22.772 | 24.513 | 22.610 | 1.00 37.84 |
| ATOM | 1055 | CB | ASN | B | 964 | 20.798 | 23.344 | 21.298 | 1.00 41.85 |
| ATOM | 1056 | CG | ASN | B | 964 | 20.079 | 22.173 | 20.634 | 1.00 46.78 |
| ATOM | 1057 | OD1 | ASN | B | 964 | 20.319 | 21.037 | 21.043 | 1.00 49.94 |
| ATOM | 1058 | ND2 | ASN | B | 964 | 19.184 | 22.496 | 19.688 | 1.00 48.13 |
| ATOM | 1059 | N | LEU | B | 965 | 21.795 | 24.534 | 24.570 | 1.00 32.14 |
| ATOM | 1060 | CA | LEU | B | 965 | 22.546 | 25.569 | 25.189 | 1.00 33.80 |
| ATOM | 1061 | C | LEU | B | 965 | 23.994 | 25.064 | 25.398 | 1.00 36.44 |
| ATOM | 1062 | O | LEU | B | 965 | 24.144 | 24.390 | 26.421 | 1.00 40.41 |
| ATOM | 1063 | CB | LEU | B | 965 | 22.086 | 25.960 | 26.578 | 1.00 31.51 |
| ATOM | 1064 | CG | LEU | B | 965 | 20.940 | 26.943 | 26.863 | 1.00 30.06 |
| ATOM | 1065 | CD1 | LEU | B | 965 | 20.731 | 26.975 | 28.363 | 1.00 26.70 |
| ATOM | 1066 | CD2 | LEU | B | 965 | 21.491 | 28.298 | 26.403 | 1.00 29.20 |
| ATOM | 1067 | N | ALA | B | 966 | 24.919 | 25.275 | 24.490 | 1.00 31.71 |
| ATOM | 1068 | CA | ALA | B | 966 | 26.340 | 24.956 | 24.701 | 1.00 29.62 |
| ATOM | 1069 | C | ALA | B | 966 | 27.144 | 26.139 | 24.175 | 1.00 27.97 |
| ATOM | 1070 | O | ALA | B | 966 | 26.676 | 26.823 | 23.232 | 1.00 24.99 |
| ATOM | 1071 | CB | ALA | B | 966 | 26.737 | 23.681 | 23.960 | 1.00 24.98 |
| ATOM | 1072 | N | ALA | B | 967 | 28.451 | 26.232 | 24.492 | 1.00 28.41 |
| ATOM | 1073 | CA | ALA | B | 967 | 29.236 | 27.348 | 23.991 | 1.00 25.71 |
| ATOM | 1074 | C | ALA | B | 967 | 29.357 | 27.432 | 22.481 | 1.00 28.11 |
| ATOM | 1075 | O | ALA | B | 967 | 29.291 | 28.561 | 21.897 | 1.00 26.71 |
| ATOM | 1076 | CB | ALA | B | 967 | 30.515 | 27.596 | 24.725 | 1.00 28.93 |
| ATOM | 1077 | N | ARG | B | 968 | 29.406 | 26.364 | 21.727 | 1.00 30.03 |
| ATOM | 1078 | CA | ARG | B | 968 | 29.407 | 26.477 | 20.257 | 1.00 30.09 |

FIG. 5S

| | | | | | | | | | |
|---|---|---|---|---|---|---|---|---|---|
| ATOM | 1079 | C   | ARG | B | 968 | 28.100 | 27.003 | 19.677 | 1.00 30.62 |
| ATOM | 1080 | O   | ARG | B | 968 | 28.131 | 27.362 | 18.476 | 1.00 31.68 |
| ATOM | 1081 | CB  | ARG | B | 968 | 29.753 | 25.111 | 19.610 | 1.00 29.15 |
| ATOM | 1082 | CG  | ARG | B | 968 | 28.695 | 24.044 | 19.886 | 1.00 31.62 |
| ATOM | 1083 | CD  | ARG | B | 968 | 28.941 | 22.658 | 19.226 | 1.00 35.47 |
| ATOM | 1084 | NE  | ARG | B | 968 | 27.817 | 21.807 | 19.703 | 1.00 38.33 |
| ATOM | 1085 | CZ  | ARG | B | 968 | 27.827 | 21.154 | 20.851 | 1.00 40.05 |
| ATOM | 1086 | NH1 | ARG | B | 968 | 28.897 | 21.164 | 21.633 | 1.00 42.72 |
| ATOM | 1087 | NH2 | ARG | B | 968 | 26.834 | 20.421 | 21.322 | 1.00 43.32 |
| ATOM | 1088 | N   | ASN | B | 969 | 26.979 | 27.025 | 20.436 | 1.00 28.92 |
| ATOM | 1089 | CA  | ASN | B | 969 | 25.710 | 27.429 | 19.810 | 1.00 29.20 |
| ATOM | 1090 | C   | ASN | B | 969 | 25.291 | 28.803 | 20.297 | 1.00 30.35 |
| ATOM | 1091 | O   | ASN | B | 969 | 24.086 | 29.145 | 20.204 | 1.00 30.32 |
| ATOM | 1092 | CB  | ASN | B | 969 | 24.598 | 26.375 | 20.098 | 1.00 25.04 |
| ATOM | 1093 | CG  | ASN | B | 969 | 24.914 | 25.020 | 19.495 | 1.00 30.26 |
| ATOM | 1094 | OD1 | ASN | B | 969 | 25.378 | 24.869 | 18.361 | 1.00 32.57 |
| ATOM | 1095 | ND2 | ASN | B | 969 | 24.648 | 23.886 | 20.172 | 1.00 28.51 |
| ATOM | 1096 | N   | ILE | B | 970 | 26.257 | 29.496 | 20.910 | 1.00 27.55 |
| ATOM | 1097 | CA  | ILE | B | 970 | 26.015 | 30.841 | 21.418 | 1.00 28.82 |
| ATOM | 1098 | C   | ILE | B | 970 | 26.802 | 31.795 | 20.505 | 1.00 29.55 |
| ATOM | 1099 | O   | ILE | B | 970 | 27.963 | 31.487 | 20.196 | 1.00 27.59 |
| ATOM | 1100 | CB  | ILE | B | 970 | 26.412 | 31.038 | 22.895 | 1.00 26.22 |
| ATOM | 1101 | CG1 | ILE | B | 970 | 25.618 | 30.198 | 23.893 | 1.00 25.70 |
| ATOM | 1102 | CG2 | ILE | B | 970 | 26.312 | 32.536 | 23.261 | 1.00 21.48 |
| ATOM | 1103 | CD1 | ILE | B | 970 | 24.088 | 30.263 | 23.734 | 1.00 23.69 |
| ATOM | 1104 | N   | LEU | B | 971 | 26.208 | 32.904 | 20.028 | 1.00 29.96 |
| ATOM | 1105 | CA  | LEU | B | 971 | 26.961 | 33.826 | 19.172 | 1.00 30.19 |
| ATOM | 1106 | C   | LEU | B | 971 | 27.438 | 35.090 | 19.845 | 1.00 31.70 |
| ATOM | 1107 | O   | LEU | B | 971 | 26.784 | 35.584 | 20.761 | 1.00 33.46 |
| ATOM | 1108 | CB  | LEU | B | 971 | 26.085 | 34.128 | 17.930 | 1.00 30.67 |
| ATOM | 1109 | CG  | LEU | B | 971 | 25.855 | 32.975 | 16.964 | 1.00 34.15 |
| ATOM | 1110 | CD1 | LEU | B | 971 | 24.695 | 33.281 | 15.982 | 1.00 33.06 |
| ATOM | 1111 | CD2 | LEU | B | 971 | 27.122 | 32.553 | 16.185 | 1.00 30.70 |
| ATOM | 1112 | N   | VAL | B | 972 | 28.541 | 35.731 | 19.447 | 1.00 30.83 |
| ATOM | 1113 | CA  | VAL | B | 972 | 29.044 | 36.982 | 20.037 | 1.00 32.48 |
| ATOM | 1114 | C   | VAL | B | 972 | 28.758 | 38.104 | 19.005 | 1.00 30.36 |
| ATOM | 1115 | O   | VAL | B | 972 | 29.405 | 38.186 | 17.951 | 1.00 31.08 |
| ATOM | 1116 | CB  | VAL | B | 972 | 30.521 | 36.984 | 20.420 | 1.00 32.58 |
| ATOM | 1117 | CG1 | VAL | B | 972 | 30.930 | 38.281 | 21.136 | 1.00 34.22 |
| ATOM | 1118 | CG2 | VAL | B | 972 | 30.871 | 35.785 | 21.333 | 1.00 31.21 |
| ATOM | 1119 | N   | GLY | B | 973 | 27.711 | 38.847 | 19.310 | 1.00 30.33 |
| ATOM | 1120 | CA  | GLY | B | 973 | 27.207 | 39.802 | 18.315 | 1.00 29.88 |
| ATOM | 1121 | C   | GLY | B | 973 | 27.727 | 41.204 | 18.479 | 1.00 32.70 |
| ATOM | 1122 | O   | GLY | B | 973 | 28.585 | 41.451 | 19.329 | 1.00 31.01 |
| ATOM | 1123 | N   | GLU | B | 974 | 27.145 | 42.135 | 17.747 | 1.00 34.65 |
| ATOM | 1124 | CA  | GLU | B | 974 | 27.522 | 43.527 | 17.855 | 1.00 33.72 |
| ATOM | 1125 | C   | GLU | B | 974 | 27.649 | 43.930 | 19.302 | 1.00 33.97 |
| ATOM | 1126 | O   | GLU | B | 974 | 26.870 | 43.530 | 20.180 | 1.00 30.31 |
| ATOM | 1127 | CB  | GLU | B | 974 | 26.420 | 44.367 | 17.187 | 1.00 40.43 |
| ATOM | 1128 | CG  | GLU | B | 974 | 26.557 | 44.283 | 15.649 | 1.00 48.26 |
| ATOM | 1129 | CD  | GLU | B | 974 | 26.317 | 45.679 | 15.071 | 1.00 54.12 |
| ATOM | 1130 | OE1 | GLU | B | 974 | 25.119 | 46.052 | 15.074 | 1.00 56.77 |
| ATOM | 1131 | OE2 | GLU | B | 974 | 27.258 | 46.414 | 14.674 | 1.00 56.47 |
| ATOM | 1132 | N   | ASN | B | 975 | 28.679 | 44.730 | 19.612 | 1.00 32.99 |
| ATOM | 1133 | CA  | ASN | B | 975 | 28.909 | 45.235 | 20.945 | 1.00 32.09 |
| ATOM | 1134 | C   | ASN | B | 975 | 29.202 | 44.081 | 21.877 | 1.00 32.69 |
| ATOM | 1135 | O   | ASN | B | 975 | 29.082 | 44.240 | 23.098 | 1.00 33.59 |

FIG. 5T

```
ATOM   1136  CB   ASN B 975      27.642  46.019  21.385  1.00 36.61
ATOM   1137  CG   ASN B 975      27.446  47.285  20.540  1.00 37.11
ATOM   1138  OD1  ASN B 975      26.276  47.739  20.363  1.00 39.26
ATOM   1139  ND2  ASN B 975      28.530  47.826  20.042  1.00 29.86
ATOM   1140  N    TYR B 976      29.715  42.945  21.379  1.00 32.96
ATOM   1141  CA   TYR B 976      29.974  41.815  22.291  1.00 33.87
ATOM   1142  C    TYR B 976      28.745  41.291  22.977  1.00 33.96
ATOM   1143  O    TYR B 976      28.952  40.845  24.142  1.00 38.50
ATOM   1144  CB   TYR B 976      31.090  42.145  23.319  1.00 32.57
ATOM   1145  CG   TYR B 976      32.316  42.635  22.562  1.00 34.93
ATOM   1146  CD1  TYR B 976      32.643  43.977  22.488  1.00 34.96
ATOM   1147  CD2  TYR B 976      33.064  41.750  21.796  1.00 36.25
ATOM   1148  CE1  TYR B 976      33.734  44.404  21.765  1.00 36.57
ATOM   1149  CE2  TYR B 976      34.151  42.185  21.066  1.00 37.74
ATOM   1150  CZ   TYR B 976      34.469  43.524  21.027  1.00 38.58
ATOM   1151  OH   TYR B 976      35.544  43.988  20.318  1.00 41.08
ATOM   1152  N    VAL B 977      27.498  41.318  22.583  1.00 33.38
ATOM   1153  CA   VAL B 977      26.363  40.804  23.354  1.00 30.29
ATOM   1154  C    VAL B 977      26.160  39.324  23.034  1.00 28.06
ATOM   1155  O    VAL B 977      26.157  38.975  21.853  1.00 30.23
ATOM   1156  CB   VAL B 977      25.135  41.674  23.014  1.00 29.39
ATOM   1157  CG1  VAL B 977      23.846  41.027  23.499  1.00 28.20
ATOM   1158  CG2  VAL B 977      25.284  43.038  23.718  1.00 31.72
ATOM   1159  N    ALA B 978      26.159  38.459  24.028  1.00 27.76
ATOM   1160  CA   ALA B 978      25.975  37.006  23.681  1.00 28.79
ATOM   1161  C    ALA B 978      24.563  36.847  23.132  1.00 31.90
ATOM   1162  O    ALA B 978      23.647  37.514  23.577  1.00 30.56
ATOM   1163  CB   ALA B 978      26.186  36.192  24.917  1.00 25.90
ATOM   1164  N    LYS B 979      24.330  36.043  22.103  1.00 33.62
ATOM   1165  CA   LYS B 979      23.070  35.784  21.463  1.00 31.66
ATOM   1166  C    LYS B 979      22.780  34.287  21.336  1.00 31.79
ATOM   1167  O    LYS B 979      23.561  33.490  20.808  1.00 29.59
ATOM   1168  CB   LYS B 979      23.102  36.390  20.030  1.00 34.05
ATOM   1169  CG   LYS B 979      22.883  37.917  20.237  1.00 38.30
ATOM   1170  CD   LYS B 979      23.149  38.766  19.049  1.00 36.22
ATOM   1171  CE   LYS B 979      23.157  40.252  19.366  1.00 39.70
ATOM   1172  NZ   LYS B 979      21.788  40.833  19.313  1.00 39.24
ATOM   1173  N    ILE B 980      21.643  33.866  21.839  1.00 29.92
ATOM   1174  CA   ILE B 980      21.279  32.444  21.718  1.00 29.31
ATOM   1175  C    ILE B 980      20.877  32.083  20.290  1.00 32.94
ATOM   1176  O    ILE B 980      20.093  32.771  19.620  1.00 34.86
ATOM   1177  CB   ILE B 980      20.142  32.123  22.676  1.00 27.87
ATOM   1178  CG1  ILE B 980      20.564  32.314  24.120  1.00 29.18
ATOM   1179  CG2  ILE B 980      19.778  30.614  22.519  1.00 32.98
ATOM   1180  CD1  ILE B 980      19.477  32.141  25.157  1.00 26.99
ATOM   1181  N    ALA B 981      21.425  30.940  19.843  1.00 33.63
ATOM   1182  CA   ALA B 981      21.100  30.397  18.542  1.00 34.72
ATOM   1183  C    ALA B 981      20.872  28.883  18.597  1.00 36.94
ATOM   1184  O    ALA B 981      20.993  28.205  19.630  1.00 36.37
ATOM   1185  CB   ALA B 981      22.158  30.764  17.532  1.00 32.74
ATOM   1186  N    ASP B 982      20.702  28.316  17.416  1.00 38.89
ATOM   1187  CA   ASP B 982      20.540  26.898  17.122  1.00 38.46
ATOM   1188  C    ASP B 982      19.195  26.448  17.713  1.00 37.99
ATOM   1189  O    ASP B 982      19.092  25.674  18.675  1.00 36.61
ATOM   1190  CB   ASP B 982      21.703  26.016  17.541  1.00 40.25
ATOM   1191  CG   ASP B 982      21.452  24.552  17.184  1.00 43.41
ATOM   1192  OD1  ASP B 982      20.728  24.230  16.205  1.00 46.24
```

FIG. 5U

| ATOM | 1193 | OD2 | ASP | B | 982 | 21.881 | 23.629 | 17.877 | 1.00 | 42.63 |
|------|------|-----|-----|---|-----|--------|--------|--------|------|-------|
| ATOM | 1194 | N | PHE | B | 983 | 18.165 | 27.008 | 17.126 | 1.00 | 36.77 |
| ATOM | 1195 | CA | PHE | B | 983 | 16.782 | 26.774 | 17.503 | 1.00 | 41.16 |
| ATOM | 1196 | C | PHE | B | 983 | 16.065 | 25.567 | 16.890 | 1.00 | 42.48 |
| ATOM | 1197 | O | PHE | B | 983 | 16.087 | 25.257 | 15.684 | 1.00 | 43.89 |
| ATOM | 1198 | CB | PHE | B | 983 | 15.964 | 28.059 | 17.163 | 1.00 | 39.87 |
| ATOM | 1199 | CG | PHE | B | 983 | 16.280 | 29.135 | 18.179 | 1.00 | 39.48 |
| ATOM | 1200 | CD1 | PHE | B | 983 | 15.940 | 28.923 | 19.504 | 1.00 | 38.68 |
| ATOM | 1201 | CD2 | PHE | B | 983 | 16.957 | 30.289 | 17.825 | 1.00 | 39.97 |
| ATOM | 1202 | CE1 | PHE | B | 983 | 16.251 | 29.809 | 20.491 | 1.00 | 37.05 |
| ATOM | 1203 | CE2 | PHE | B | 983 | 17.257 | 31.221 | 18.816 | 1.00 | 40.42 |
| ATOM | 1204 | CZ | PHE | B | 983 | 16.906 | 30.993 | 20.135 | 1.00 | 39.41 |
| ATOM | 1205 | N | GLY | B | 984 | 15.346 | 24.852 | 17.733 | 1.00 | 41.51 |
| ATOM | 1206 | CA | GLY | B | 984 | 14.461 | 23.724 | 17.265 | 1.00 | 41.21 |
| ATOM | 1207 | C | GLY | B | 984 | 13.535 | 23.685 | 18.500 | 1.00 | 40.75 |
| ATOM | 1208 | O | GLY | B | 984 | 13.678 | 22.812 | 19.368 | 1.00 | 40.87 |
| ATOM | 1209 | N | LEU | B | 985 | 12.781 | 24.779 | 18.612 | 1.00 | 38.40 |
| ATOM | 1210 | CA | LEU | B | 985 | 12.020 | 25.010 | 19.826 | 1.00 | 38.54 |
| ATOM | 1211 | C | LEU | B | 985 | 10.844 | 24.053 | 20.021 | 1.00 | 39.23 |
| ATOM | 1212 | O | LEU | B | 985 | 10.331 | 23.451 | 19.099 | 1.00 | 39.81 |
| ATOM | 1213 | CB | LEU | B | 985 | 11.597 | 26.477 | 19.879 | 1.00 | 38.29 |
| ATOM | 1214 | CG | LEU | B | 985 | 12.703 | 27.505 | 20.071 | 1.00 | 39.62 |
| ATOM | 1215 | CD1 | LEU | B | 985 | 12.112 | 28.913 | 19.963 | 1.00 | 41.67 |
| ATOM | 1216 | CD2 | LEU | B | 985 | 13.378 | 27.375 | 21.450 | 1.00 | 40.64 |
| ATOM | 1217 | N | SER | B | 986 | 10.420 | 23.923 | 21.268 | 1.00 | 38.75 |
| ATOM | 1218 | CA | SER | B | 986 | 9.258 | 23.124 | 21.640 | 1.00 | 41.57 |
| ATOM | 1219 | C | SER | B | 986 | 8.618 | 23.946 | 22.764 | 1.00 | 41.04 |
| ATOM | 1220 | O | SER | B | 986 | 9.376 | 24.681 | 23.389 | 1.00 | 40.97 |
| ATOM | 1221 | CB | SER | B | 986 | 9.623 | 21.781 | 22.276 | 1.00 | 41.12 |
| ATOM | 1222 | OG | SER | B | 986 | 10.132 | 20.965 | 21.268 | 1.00 | 44.70 |
| ATOM | 1223 | N | ARG | B | 987 | 7.306 | 23.872 | 22.881 | 1.00 | 41.47 |
| ATOM | 1224 | CA | ARG | B | 987 | 6.579 | 24.634 | 23.849 | 1.00 | 39.96 |
| ATOM | 1225 | C | ARG | B | 987 | 5.664 | 23.672 | 24.592 | 1.00 | 39.46 |
| ATOM | 1226 | O | ARG | B | 987 | 4.928 | 22.897 | 24.001 | 1.00 | 40.85 |
| ATOM | 1227 | CB | ARG | B | 987 | 5.759 | 25.671 | 23.100 | 1.00 | 42.69 |
| ATOM | 1228 | CG | ARG | B | 987 | 5.518 | 26.881 | 23.980 | 1.00 | 43.46 |
| ATOM | 1229 | CD | ARG | B | 987 | 4.820 | 27.932 | 23.102 | 1.00 | 47.12 |
| ATOM | 1230 | NE | ARG | B | 987 | 4.503 | 29.062 | 23.969 | 1.00 | 48.45 |
| ATOM | 1231 | CZ | ARG | B | 987 | 4.042 | 30.245 | 23.498 | 1.00 | 49.30 |
| ATOM | 1232 | NH1 | ARG | B | 987 | 3.859 | 30.446 | 22.195 | 1.00 | 47.75 |
| ATOM | 1233 | NH2 | ARG | B | 987 | 3.820 | 31.126 | 24.461 | 1.00 | 47.10 |
| ATOM | 1234 | N | GLY | B | 988 | 5.803 | 23.678 | 25.895 | 1.00 | 36.84 |
| ATOM | 1235 | CA | GLY | B | 988 | 5.310 | 22.780 | 26.860 | 1.00 | 37.53 |
| ATOM | 1236 | C | GLY | B | 988 | 6.133 | 22.613 | 28.131 | 1.00 | 39.84 |
| ATOM | 1237 | O | GLY | B | 988 | 7.113 | 23.319 | 28.413 | 1.00 | 37.68 |
| ATOM | 1238 | N | GLN | B | 989 | 5.621 | 21.679 | 26.931 | 1.00 | 37.98 |
| ATOM | 1239 | CA | GLN | B | 989 | 6.211 | 21.351 | 30.208 | 1.00 | 36.52 |
| ATOM | 1240 | C | GLN | B | 989 | 7.342 | 20.344 | 29.982 | 1.00 | 36.26 |
| ATOM | 1241 | O | GLN | B | 989 | 8.364 | 20.451 | 30.678 | 1.00 | 35.23 |
| ATOM | 1242 | CB | GLN | B | 989 | 5.134 | 20.856 | 31.154 | 1.00 | 36.36 |
| ATOM | 1243 | CG | GLN | B | 989 | 5.676 | 20.186 | 32.391 | 1.00 | 39.62 |
| ATOM | 1244 | CD | GLN | B | 989 | 4.653 | 19.836 | 33.425 | 1.00 | 39.25 |
| ATOM | 1245 | OE1 | GLN | B | 989 | 4.232 | 20.788 | 34.082 | 1.00 | 42.73 |
| ATOM | 1246 | NE2 | GLN | B | 989 | 4.255 | 18.604 | 33.639 | 1.00 | 40.97 |
| ATOM | 1247 | N | GLU | B | 990 | 7.214 | 19.459 | 28.997 | 1.00 | 33.95 |
| ATOM | 1248 | CA | GLU | B | 990 | 8.362 | 18.545 | 28.745 | 1.00 | 32.76 |
| ATOM | 1249 | C | GLU | B | 990 | 8.318 | 18.162 | 27.281 | 1.00 | 31.62 |

FIG. 5V

```
ATOM   1250  O    GLU B 990       7.134  18.267  26.782  1.00  35.90
ATOM   1251  CB   GLU B 990       8.324  17.321  29.615  1.00  32.06
ATOM   1252  CG   GLU B 990       7.034  16.491  29.549  1.00  34.29
ATOM   1253  CD   GLU B 990       5.855  16.986  30.361  1.00  35.18
ATOM   1254  OE1  GLU B 990       4.741  17.354  29.866  1.00  31.61
ATOM   1255  OE2  GLU B 990       5.907  17.055  31.606  1.00  37.46
ATOM   1256  N    VAL B 991       9.245  17.586  26.636  1.00  28.59
ATOM   1257  CA   VAL B 991       9.254  17.187  25.250  1.00  27.10
ATOM   1258  C    VAL B 991      10.294  16.035  25.123  1.00  34.31
ATOM   1259  O    VAL B 991      11.499  16.047  25.461  1.00  34.01
ATOM   1260  CB   VAL B 991       9.566  18.341  24.297  1.00  27.78
ATOM   1261  CG1  VAL B 991      10.981  18.939  24.577  1.00  28.52
ATOM   1262  CG2  VAL B 991       9.531  17.878  22.827  1.00  26.55
ATOM   1263  N    TYR B 992       9.815  15.116  24.284  1.00  33.22
ATOM   1264  CA   TYR B 992      10.510  13.950  23.872  1.00  35.07
ATOM   1265  C    TYR B 992      11.168  14.196  22.521  1.00  36.09
ATOM   1266  O    TYR B 992      10.453  14.723  21.653  1.00  37.35
ATOM   1267  CB   TYR B 992       9.504  12.750  23.851  1.00  32.12
ATOM   1268  CG   TYR B 992      10.187  11.588  23.154  1.00  34.00
ATOM   1269  CD1  TYR B 992      10.952  10.664  23.855  1.00  35.23
ATOM   1270  CD2  TYR B 992      10.065  11.491  21.767  1.00  34.41
ATOM   1271  CE1  TYR B 992      11.597   9.629  23.205  1.00  34.80
ATOM   1272  CE2  TYR B 992      10.706  10.464  21.115  1.00  35.88
ATOM   1273  CZ   TYR B 992      11.471   9.575  21.830  1.00  37.31
ATOM   1274  OH   TYR B 992      12.090   8.582  21.090  1.00  41.58
ATOM   1275  N    VAL B 993      12.465  13.922  22.409  1.00  35.09
ATOM   1276  CA   VAL B 993      13.166  14.093  21.148  1.00  40.55
ATOM   1277  C    VAL B 993      14.192  12.937  21.077  1.00  44.20
ATOM   1278  O    VAL B 993      14.924  12.698  22.027  1.00  41.10
ATOM   1279  CB   VAL B 993      14.027  15.345  20.884  1.00  40.80
ATOM   1280  CG1  VAL B 993      14.377  15.434  19.397  1.00  41.00
ATOM   1281  CG2  VAL B 993      13.444  16.675  21.308  1.00  40.65
ATOM   1282  N    LYS B 994      14.248  12.280  19.929  1.00  52.91
ATOM   1283  CA   LYS B 994      15.228  11.218  19.681  1.00  59.67
ATOM   1284  C    LYS B 994      16.314  11.668  18.722  1.00  63.50
ATOM   1285  O    LYS B 994      15.968  12.346  17.752  1.00  65.43
ATOM   1286  CB   LYS B 994      14.452  10.051  19.050  1.00  62.12
ATOM   1287  CG   LYS B 994      15.258   9.165  18.114  1.00  64.47
ATOM   1288  CD   LYS B 994      14.523   7.917  17.676  1.00  66.81
ATOM   1289  CE   LYS B 994      14.741   6.737  18.627  1.00  69.22
ATOM   1290  NZ   LYS B 994      16.113   6.131  18.446  1.00  70.28
ATOM   1291  N    LYS B 995      17.568  11.244  18.841  1.00  68.11
ATOM   1292  CA   LYS B 995      18.698  11.497  17.964  1.00  69.33
ATOM   1293  C    LYS B 995      19.277  12.900  17.869  1.00  71.04
ATOM   1294  CB   LYS B 995      18.387  11.058  16.520  1.00  68.75
ATOM   1295  N    THR B 996      19.210  13.731  18.891  1.00  72.92
ATOM   1296  CA   THR B 996      19.849  15.039  18.958  1.00  74.27
ATOM   1297  C    THR B 996      18.897  16.170  18.571  1.00  74.88
ATOM   1298  O    THR B 996      17.742  15.867  18.197  1.00  75.62
ATOM   1299  CB   THR B 996      21.108  15.075  18.098  1.00  74.16
TER
ATOM   1300  N    LEU C1000      24.923  13.250  19.201  1.00  61.56
ATOM   1301  CA   LEU C1000      24.606  13.627  20.610  1.00  60.45
ATOM   1302  C    LEU C1000      25.273  14.888  21.132  1.00  59.31
ATOM   1303  O    LEU C1000      25.926  15.737  20.498  1.00  61.19
ATOM   1304  CB   LEU C1000      25.085  12.439  21.459  1.00  62.33
ATOM   1305  N    PRO C1001      25.106  15.086  22.450  1.00  55.81
```

FIG. 5W

```
ATOM   1306  CA   PRO C1001     25.717  16.238  23.164  1.00 47.68
ATOM   1307  C    PRO C1001     25.633  15.865  24.622  1.00 42.57
ATOM   1308  O    PRO C1001     25.066  16.507  25.497  1.00 42.56
ATOM   1309  CB   PRO C1001     25.055  17.514  22.761  1.00 49.13
ATOM   1310  N    VAL C1002     26.137  14.628  24.881  1.00 39.19
ATOM   1311  CA   VAL C1002     26.105  13.982  26.180  1.00 36.21
ATOM   1312  C    VAL C1002     26.526  14.731  27.414  1.00 32.43
ATOM   1313  O    VAL C1002     25.981  14.707  28.510  1.00 29.30
ATOM   1314  CB   VAL C1002     27.129  12.774  26.075  1.00 38.41
ATOM   1315  CG1  VAL C1002     27.304  12.077  27.400  1.00 36.91
ATOM   1316  CG2  VAL C1002     26.315  11.872  25.131  1.00 39.50
ATOM   1317  N    ARG C1003     27.699  15.354  27.317  1.00 35.49
ATOM   1318  CA   ARG C1003     28.454  16.101  28.310  1.00 34.85
ATOM   1319  C    ARG C1003     27.745  17.378  28.731  1.00 32.80
ATOM   1320  O    ARG C1003     28.073  18.089  29.675  1.00 33.09
ATOM   1321  CB   ARG C1003     29.877  16.407  27.775  1.00 35.57
ATOM   1322  CG   ARG C1003     30.017  15.726  26.418  1.00 40.79
ATOM   1323  CD   ARG C1003     31.524  15.638  26.082  1.00 42.74
ATOM   1324  NE   ARG C1003     32.199  15.018  27.219  1.00 46.61
ATOM   1325  CZ   ARG C1003     33.482  14.536  26.897  1.00 42.40
ATOM   1326  NH1  ARG C1003     33.675  14.646  25.606  1.00 44.69
ATOM   1327  NH2  ARG C1003     34.058  13.991  27.899  1.00 41.82
ATOM   1328  N    TRP C1004     26.753  17.765  27.983  1.00 31.57
ATOM   1329  CA   TRP C1004     25.743  18.792  28.171  1.00 32.26
ATOM   1330  C    TRP C1004     24.352  18.357  28.588  1.00 33.31
ATOM   1331  O    TRP C1004     23.571  19.223  29.047  1.00 32.82
ATOM   1332  CB   TRP C1004     25.513  19.633  26.877  1.00 31.61
ATOM   1333  CG   TRP C1004     26.794  20.424  26.649  1.00 29.75
ATOM   1334  CD1  TRP C1004     27.065  21.659  27.174  1.00 33.83
ATOM   1335  CD2  TRP C1004     27.885  20.016  25.845  1.00 30.53
ATOM   1336  NE1  TRP C1004     28.350  22.036  26.758  1.00 30.12
ATOM   1337  CE2  TRP C1004     28.838  21.058  25.939  1.00 32.87
ATOM   1338  CE3  TRP C1004     28.284  18.907  25.081  1.00 31.33
ATOM   1339  CZ2  TRP C1004     30.114  21.052  25.322  1.00 31.29
ATOM   1340  CZ3  TRP C1004     29.523  18.911  24.457  1.00 31.61
ATOM   1341  CH2  TRP C1004     30.442  19.974  24.537  1.00 31.26
ATOM   1342  N    MET C1005     24.039  17.058  28.523  1.00 31.05
ATOM   1343  CA   MET C1005     22.691  16.644  28.871  1.00 30.92
ATOM   1344  C    MET C1005     22.482  16.372  30.342  1.00 31.46
ATOM   1345  O    MET C1005     23.344  15.779  30.955  1.00 30.88
ATOM   1346  CB   MET C1005     22.425  15.401  28.027  1.00 35.15
ATOM   1347  CG   MET C1005     22.250  15.671  26.542  1.00 35.78
ATOM   1348  SD   MET C1005     22.331  14.145  25.574  1.00 43.66
ATOM   1349  CE   MET C1005     20.582  13.671  25.658  1.00 39.42
ATOM   1350  N    ALA C1006     21.331  16.767  30.898  1.00 30.39
ATOM   1351  CA   ALA C1006     20.980  16.384  32.257  1.00 32.23
ATOM   1352  C    ALA C1006     20.903  14.819  32.255  1.00 29.50
ATOM   1353  O    ALA C1006     20.820  14.243  31.191  1.00 25.95
ATOM   1354  CB   ALA C1006     19.558  16.827  32.686  1.00 32.19
ATOM   1355  N    ILE C1007     21.063  14.271  33.415  1.00 28.66
ATOM   1356  CA   ILE C1007     20.991  12.831  33.717  1.00 34.31
ATOM   1357  C    ILE C1007     19.626  12.254  33.361  1.00 32.33
ATOM   1358  O    ILE C1007     19.539  11.314  32.569  1.00 34.27
ATOM   1359  CB   ILE C1007     21.316  12.831  35.238  1.00 36.74
ATOM   1360  CG1  ILE C1007     22.831  12.539  35.418  1.00 40.16
ATOM   1361  CG2  ILE C1007     20.535  11.850  36.027  1.00 41.55
ATOM   1362  CD1  ILE C1007     23.298  12.738  36.843  1.00 39.53
```

FIG. 5X

| | | | | | | | |
|---|---|---|---|---|---|---|---|
| ATOM | 1363 | N | GLU C1008 | 18.515 | 12.879 | 33.668 | 1.00 32.21 |
| ATOM | 1364 | CA | GLU C1008 | 17.179 | 12.414 | 33.238 | 1.00 30.51 |
| ATOM | 1365 | C | GLU C1008 | 17.097 | 12.390 | 31.725 | 1.00 30.14 |
| ATOM | 1366 | O | GLU C1008 | 16.588 | 11.399 | 31.127 | 1.00 30.02 |
| ATOM | 1367 | CB | GLU C1008 | 16.079 | 13.201 | 33.887 | 1.00 32.29 |
| ATOM | 1368 | CG | GLU C1008 | 15.861 | 14.623 | 33.271 | 1.00 31.03 |
| ATOM | 1369 | CD | GLU C1008 | 16.672 | 15.611 | 34.070 | 1.00 30.62 |
| ATOM | 1370 | OE1 | GLU C1008 | 17.610 | 15.181 | 34.800 | 1.00 33.04 |
| ATOM | 1371 | OE2 | GLU C1008 | 16.405 | 16.824 | 34.011 | 1.00 33.30 |
| ATOM | 1372 | N | SER C1009 | 17.652 | 13.397 | 31.054 | 1.00 28.64 |
| ATOM | 1373 | CA | SER C1009 | 17.665 | 13.395 | 29.574 | 1.00 27.96 |
| ATOM | 1374 | C | SER C1009 | 18.561 | 12.320 | 29.008 | 1.00 32.36 |
| ATOM | 1375 | O | SER C1009 | 18.258 | 11.867 | 27.889 | 1.00 33.49 |
| ATOM | 1376 | CB | SER C1009 | 18.120 | 14.740 | 29.001 | 1.00 27.04 |
| ATOM | 1377 | OG | SER C1009 | 17.266 | 15.856 | 29.232 | 1.00 29.52 |
| ATOM | 1378 | N | LEU C1010 | 19.732 | 11.948 | 29.646 | 1.00 30.58 |
| ATOM | 1379 | CA | LEU C1010 | 20.458 | 10.834 | 29.043 | 1.00 33.82 |
| ATOM | 1380 | C | LEU C1010 | 19.587 | 9.543 | 29.184 | 1.00 34.58 |
| ATOM | 1381 | O | LEU C1010 | 19.600 | 8.647 | 28.340 | 1.00 33.77 |
| ATOM | 1382 | CB | LEU C1010 | 21.835 | 10.478 | 29.678 | 1.00 34.39 |
| ATOM | 1383 | CG | LEU C1010 | 22.839 | 11.659 | 29.618 | 1.00 34.04 |
| ATOM | 1384 | CD1 | LEU C1010 | 23.989 | 11.636 | 30.582 | 1.00 35.06 |
| ATOM | 1385 | CD2 | LEU C1010 | 23.324 | 11.698 | 28.183 | 1.00 34.32 |
| ATOM | 1386 | N | ASN C1011 | 18.894 | 9.423 | 30.317 | 1.00 34.50 |
| ATOM | 1387 | CA | ASN C1011 | 18.175 | 8.188 | 30.585 | 1.00 39.53 |
| ATOM | 1388 | C | ASN C1011 | 16.867 | 8.049 | 29.814 | 1.00 39.46 |
| ATOM | 1389 | O | ASN C1011 | 16.521 | 6.887 | 29.507 | 1.00 41.72 |
| ATOM | 1390 | CB | ASN C1011 | 17.744 | 7.990 | 32.055 | 1.00 37.12 |
| ATOM | 1391 | CG | ASN C1011 | 18.994 | 7.594 | 32.849 | 1.00 40.42 |
| ATOM | 1392 | OD1 | ASN C1011 | 19.913 | 7.055 | 32.211 | 1.00 41.43 |
| ATOM | 1393 | ND2 | ASN C1011 | 18.990 | 7.876 | 34.135 | 1.00 37.03 |
| ATOM | 1394 | N | TYR C1012 | 16.144 | 9.174 | 29.765 | 1.00 36.32 |
| ATOM | 1395 | CA | TYR C1012 | 14.765 | 9.067 | 29.205 | 1.00 33.71 |
| ATOM | 1396 | C | TYR C1012 | 14.644 | 9.864 | 27.929 | 1.00 37.07 |
| ATOM | 1397 | O | TYR C1012 | 13.431 | 9.936 | 27.557 | 1.00 39.06 |
| ATOM | 1398 | CB | TYR C1012 | 13.779 | 9.722 | 30.189 | 1.00 25.11 |
| ATOM | 1399 | CG | TYR C1012 | 13.979 | 9.247 | 31.601 | 1.00 26.79 |
| ATOM | 1400 | CD1 | TYR C1012 | 13.915 | 10.061 | 32.704 | 1.00 28.02 |
| ATOM | 1401 | CD2 | TYR C1012 | 14.199 | 7.868 | 31.824 | 1.00 29.96 |
| ATOM | 1402 | CE1 | TYR C1012 | 14.075 | 9.560 | 33.984 | 1.00 31.07 |
| ATOM | 1403 | CE2 | TYR C1012 | 14.378 | 7.325 | 33.070 | 1.00 30.68 |
| ATOM | 1404 | CZ | TYR C1012 | 14.310 | 8.194 | 34.126 | 1.00 32.85 |
| ATOM | 1405 | OH | TYR C1012 | 14.494 | 7.677 | 35.423 | 1.00 38.60 |
| ATOM | 1406 | N | SER C1013 | 15.568 | 10.695 | 27.480 | 1.00 35.61 |
| ATOM | 1407 | CA | SER C1013 | 15.244 | 11.547 | 26.340 | 1.00 36.12 |
| ATOM | 1408 | C | SER C1013 | 14.080 | 12.522 | 26.555 | 1.00 31.92 |
| ATOM | 1409 | O | SER C1013 | 13.533 | 12.997 | 25.558 | 1.00 29.49 |
| ATOM | 1410 | CB | SER C1013 | 15.021 | 10.764 | 25.075 | 1.00 38.37 |
| ATOM | 1411 | OG | SER C1013 | 16.000 | 9.929 | 24.605 | 1.00 39.85 |
| ATOM | 1412 | N | VAL C1014 | 13.848 | 12.926 | 27.798 | 1.00 34.71 |
| ATOM | 1413 | CA | VAL C1014 | 12.887 | 13.999 | 28.005 | 1.00 34.17 |
| ATOM | 1414 | C | VAL C1014 | 13.761 | 15.212 | 28.406 | 1.00 32.14 |
| ATOM | 1415 | O | VAL C1014 | 14.764 | 15.102 | 29.061 | 1.00 31.92 |
| ATOM | 1416 | CB | VAL C1014 | 11.803 | 13.647 | 29.007 | 1.00 35.91 |
| ATOM | 1417 | CG1 | VAL C1014 | 10.773 | 14.771 | 28.958 | 1.00 35.03 |
| ATOM | 1418 | CG2 | VAL C1014 | 11.129 | 12.316 | 28.672 | 1.00 35.03 |
| ATOM | 1419 | N | TYR C1015 | 13.255 | 16.377 | 27.994 | 1.00 33.31 |

FIG. 5Y

```
ATOM   1420  CA   TYR C1015      13.917  17.662  28.222  1.00  29.96
ATOM   1421  C    TYR C1015      12.870  18.627  28.713  1.00  32.82
ATOM   1422  O    TYR C1015      11.635  18.497  28.361  1.00  33.09
ATOM   1423  CB   TYR C1015      14.268  18.208  26.817  1.00  31.34
ATOM   1424  CG   TYR C1015      15.273  17.339  26.106  1.00  32.85
ATOM   1425  CD1  TYR C1015      14.953  16.293  25.270  1.00  33.14
ATOM   1426  CD2  TYR C1015      16.625  17.556  26.338  1.00  33.80
ATOM   1427  CE1  TYR C1015      15.892  15.497  24.664  1.00  36.71
ATOM   1428  CE2  TYR C1015      17.623  16.791  25.745  1.00  36.63
ATOM   1429  CZ   TYR C1015      17.249  15.758  24.895  1.00  36.99
ATOM   1430  OH   TYR C1015      18.233  15.005  24.325  1.00  37.59
ATOM   1431  N    THR C1016      13.210  19.409  29.691  1.00  29.91
ATOM   1432  CA   THR C1016      12.342  20.393  30.312  1.00  30.08
ATOM   1433  C    THR C1016      13.109  21.700  30.459  1.00  33.68
ATOM   1434  O    THR C1016      14.307  21.752  30.085  1.00  32.46
ATOM   1435  CB   THR C1016      11.986  19.882  31.717  1.00  31.45
ATOM   1436  OG1  THR C1016      13.149  19.778  32.540  1.00  31.21
ATOM   1437  CG2  THR C1016      11.332  18.415  31.720  1.00  29.42
ATOM   1438  N    THR C1017      12.509  22.699  31.141  1.00  31.49
ATOM   1439  CA   THR C1017      13.301  23.863  31.536  1.00  32.10
ATOM   1440  C    THR C1017      14.367  23.447  32.536  1.00  33.86
ATOM   1441  O    THR C1017      15.480  24.004  32.588  1.00  31.99
ATOM   1442  CB   THR C1017      12.396  25.033  32.078  1.00  32.15
ATOM   1443  OG1  THR C1017      11.836  25.456  30.829  1.00  32.91
ATOM   1444  CG2  THR C1017      13.152  26.192  32.675  1.00  30.94
ATOM   1445  N    ASN C1018      14.062  22.468  33.403  1.00  32.36
ATOM   1446  CA   ASN C1018      15.020  21.997  34.372  1.00  34.23
ATOM   1447  C    ASN C1018      16.208  21.329  33.647  1.00  33.65
ATOM   1448  O    ASN C1018      17.326  21.560  34.163  1.00  32.63
ATOM   1449  CB   ASN C1018      14.563  21.089  35.519  1.00  33.92
ATOM   1450  CG   ASN C1018      13.478  21.750  36.390  1.00  36.18
ATOM   1451  OD1  ASN C1018      13.561  22.943  36.772  1.00  33.93
ATOM   1452  ND2  ASN C1018      12.400  20.983  36.687  1.00  31.82
ATOM   1453  N    SER C1019      16.007  20.738  32.468  1.00  30.11
ATOM   1454  CA   SER C1019      17.216  20.101  31.865  1.00  31.68
ATOM   1455  C    SER C1019      18.016  21.121  31.069  1.00  30.62
ATOM   1456  O    SER C1019      19.237  21.110  30.787  1.00  25.61
ATOM   1457  CB   SER C1019      16.668  18.883  31.150  1.00  29.04
ATOM   1458  OG   SER C1019      16.208  19.177  29.829  1.00  30.35
ATOM   1459  N    ASP C1020      17.331  22.228  30.738  1.00  30.23
ATOM   1460  CA   ASP C1020      17.923  23.429  30.164  1.00  27.36
ATOM   1461  C    ASP C1020      18.880  24.034  31.183  1.00  26.47
ATOM   1462  O    ASP C1020      19.935  24.477  30.766  1.00  28.27
ATOM   1463  CB   ASP C1020      16.986  24.536  29.714  1.00  28.00
ATOM   1464  CG   ASP C1020      16.480  24.298  28.328  1.00  28.71
ATOM   1465  OD1  ASP C1020      16.969  23.343  27.647  1.00  31.13
ATOM   1466  OD2  ASP C1020      15.583  24.984  27.876  1.00  32.14
ATOM   1467  N    VAL C1021      18.502  24.085  32.455  1.00  26.65
ATOM   1468  CA   VAL C1021      19.328  24.627  33.497  1.00  26.02
ATOM   1469  C    VAL C1021      20.546  23.742  33.781  1.00  27.12
ATOM   1470  O    VAL C1021      21.575  24.333  34.098  1.00  23.97
ATOM   1471  CB   VAL C1021      18.525  24.925  34.779  1.00  27.32
ATOM   1472  CG1  VAL C1021      19.464  25.263  35.929  1.00  25.33
ATOM   1473  CG2  VAL C1021      17.590  26.138  34.626  1.00  29.37
ATOM   1474  N    TRP C1022      20.461  22.409  33.671  1.00  25.32
ATOM   1475  CA   TRP C1022      21.679  21.587  33.868  1.00  23.28
ATOM   1476  C    TRP C1022      22.664  21.958  32.796  1.00  23.00
```

FIG. 5Z

```
ATOM   1477  O    TRP C1022      23.835  22.338  32.917  1.00  25.36
ATOM   1478  CB   TRP C1022      21.248  20.096  33.625  1.00  25.77
ATOM   1479  CG   TRP C1022      22.434  19.150  33.646  1.00  27.35
ATOM   1480  CD1  TRP C1022      23.411  18.987  32.695  1.00  26.63
ATOM   1481  CD2  TRP C1022      22.685  18.200  34.675  1.00  28.39
ATOM   1482  NE1  TRP C1022      24.267  18.008  33.079  1.00  29.90
ATOM   1483  CE2  TRP C1022      23.840  17.481  34.300  1.00  30.24
ATOM   1484  CE3  TRP C1022      22.041  17.867  35.866  1.00  30.30
ATOM   1485  CZ2  TRP C1022      24.394  16.485  35.090  1.00  32.33
ATOM   1486  CZ3  TRP C1022      22.563  16.816  36.624  1.00  31.39
ATOM   1487  CH2  TRP C1022      23.718  16.151  36.243  1.00  32.10
ATOM   1488  N    SER C1023      22.207  21.928  31.529  1.00  21.23
ATOM   1489  CA   SER C1023      23.068  22.354  30.379  1.00  22.80
ATOM   1490  C    SER C1023      23.618  23.745  30.495  1.00  27.97
ATOM   1491  O    SER C1023      24.829  24.031  30.146  1.00  23.26
ATOM   1492  CB   SER C1023      22.108  21.769  29.326  1.00  24.28
ATOM   1493  OG   SER C1023      21.977  22.454  28.131  1.00  34.21
ATOM   1494  N    TYR C1024      22.810  24.769  30.968  1.00  24.68
ATOM   1495  CA   TYR C1024      23.395  26.101  31.223  1.00  25.91
ATOM   1496  C    TYR C1024      24.614  26.083  32.155  1.00  28.55
ATOM   1497  O    TYR C1024      25.582  26.856  32.091  1.00  26.16
ATOM   1498  CB   TYR C1024      22.317  27.041  31.808  1.00  23.53
ATOM   1499  CG   TYR C1024      22.904  28.385  32.225  1.00  23.34
ATOM   1500  CD1  TYR C1024      22.931  29.409  31.328  1.00  21.89
ATOM   1501  CD2  TYR C1024      23.322  28.564  33.537  1.00  21.62
ATOM   1502  CE1  TYR C1024      23.498  30.640  31.655  1.00  24.95
ATOM   1503  CE2  TYR C1024      23.929  29.791  33.858  1.00  25.56
ATOM   1504  CZ   TYR C1024      23.957  30.795  32.941  1.00  24.77
ATOM   1505  OH   TYR C1024      24.513  32.006  33.282  1.00  29.84
ATOM   1506  N    GLY C1025      24.559  25.263  33.180  1.00  31.16
ATOM   1507  CA   GLY C1025      25.499  24.901  34.180  1.00  28.63
ATOM   1508  C    GLY C1025      26.812  24.444  33.475  1.00  29.18
ATOM   1509  O    GLY C1025      27.826  24.973  33.911  1.00  25.38
ATOM   1510  N    VAL C1026      26.724  23.628  32.431  1.00  30.48
ATOM   1511  CA   VAL C1026      27.848  23.171  31.665  1.00  30.49
ATOM   1512  C    VAL C1026      28.404  24.335  30.867  1.00  30.61
ATOM   1513  O    VAL C1026      29.622  24.566  30.796  1.00  31.75
ATOM   1514  CB   VAL C1026      27.598  21.959  30.748  1.00  29.54
ATOM   1515  CG1  VAL C1026      28.867  21.451  30.040  1.00  26.68
ATOM   1516  CG2  VAL C1026      26.960  20.808  31.527  1.00  28.00
ATOM   1517  N    LEU C1027      27.539  25.107  30.208  1.00  29.76
ATOM   1518  CA   LEU C1027      27.925  26.331  29.524  1.00  27.25
ATOM   1519  C    LEU C1027      28.729  27.263  30.410  1.00  25.12
ATOM   1520  O    LEU C1027      29.764  27.833  30.030  1.00  27.00
ATOM   1521  CB   LEU C1027      26.664  27.044  28.959  1.00  27.55
ATOM   1522  CG   LEU C1027      26.904  28.561  28.667  1.00  27.68
ATOM   1523  CD1  LEU C1027      27.658  28.914  27.434  1.00  28.77
ATOM   1524  CD2  LEU C1027      25.485  29.174  28.511  1.00  29.96
ATOM   1525  N    LEU C1028      28.311  27.500  31.665  1.00  27.12
ATOM   1526  CA   LEU C1028      28.994  28.386  32.576  1.00  26.05
ATOM   1527  C    LEU C1028      30.399  27.853  32.836  1.00  28.29
ATOM   1528  O    LEU C1028      31.296  28.666  32.888  1.00  27.74
ATOM   1529  CB   LEU C1028      28.123  28.576  33.809  1.00  24.95
ATOM   1530  CG   LEU C1028      28.601  29.349  34.990  1.00  26.00
ATOM   1531  CD1  LEU C1028      28.932  30.805  34.567  1.00  26.51
ATOM   1532  CD2  LEU C1028      27.771  29.411  36.264  1.00  23.62
ATOM   1533  N    TRP C1029      30.569  26.514  32.998  1.00  27.52
```

FIG. 5AA

| | | | | | | | | |
|---|---|---|---|---|---|---|---|---|
| ATOM | 1534 | CA | TRP | C1029 | 31.811 | 25.818 | 33.200 | 1.00 25.28 |
| ATOM | 1535 | C | TRP | C1029 | 32.677 | 26.052 | 31.992 | 1.00 24.21 |
| ATOM | 1536 | O | TRP | C1029 | 33.809 | 26.411 | 32.199 | 1.00 28.34 |
| ATOM | 1537 | CB | TRP | C1029 | 31.604 | 24.291 | 33.488 | 1.00 25.52 |
| ATOM | 1538 | CG | TRP | C1029 | 32.875 | 23.609 | 33.873 | 1.00 23.89 |
| ATOM | 1539 | CD1 | TRP | C1029 | 33.316 | 23.467 | 35.159 | 1.00 23.77 |
| ATOM | 1540 | CD2 | TRP | C1029 | 33.901 | 23.125 | 33.013 | 1.00 25.22 |
| ATOM | 1541 | NE1 | TRP | C1029 | 34.566 | 22.870 | 35.125 | 1.00 28.07 |
| ATOM | 1542 | CE2 | TRP | C1029 | 34.922 | 22.645 | 33.819 | 1.00 27.51 |
| ATOM | 1543 | CE3 | TRP | C1029 | 34.013 | 23.005 | 31.620 | 1.00 27.28 |
| ATOM | 1544 | CZ2 | TRP | C1029 | 36.095 | 21.998 | 33.349 | 1.00 30.61 |
| ATOM | 1545 | CZ3 | TRP | C1029 | 35.169 | 22.378 | 31.126 | 1.00 30.99 |
| ATOM | 1546 | CH2 | TRP | C1029 | 36.195 | 21.931 | 31.972 | 1.00 29.91 |
| ATOM | 1547 | N | GLU | C1030 | 32.196 | 26.006 | 30.773 | 1.00 22.75 |
| ATOM | 1548 | CA | GLU | C1030 | 32.865 | 26.380 | 29.590 | 1.00 24.64 |
| ATOM | 1549 | C | GLU | C1030 | 33.291 | 27.882 | 29.553 | 1.00 23.46 |
| ATOM | 1550 | O | GLU | C1030 | 34.433 | 28.114 | 29.047 | 1.00 23.61 |
| ATOM | 1551 | CB | GLU | C1030 | 32.036 | 26.144 | 28.339 | 1.00 22.23 |
| ATOM | 1552 | CG | GLU | C1030 | 31.853 | 24.671 | 28.076 | 1.00 27.85 |
| ATOM | 1553 | CD | GLU | C1030 | 30.969 | 24.399 | 26.881 | 1.00 33.40 |
| ATOM | 1554 | OE1 | GLU | C1030 | 29.767 | 24.531 | 27.111 | 1.00 33.08 |
| ATOM | 1555 | OE2 | GLU | C1030 | 31.477 | 24.088 | 25.792 | 1.00 37.59 |
| ATOM | 1556 | N | ILE | C1031 | 32.413 | 28.784 | 30.027 | 1.00 20.93 |
| ATOM | 1557 | CA | ILE | C1031 | 32.888 | 30.190 | 29.987 | 1.00 23.32 |
| ATOM | 1558 | C | ILE | C1031 | 34.099 | 30.417 | 30.881 | 1.00 24.20 |
| ATOM | 1559 | O | ILE | C1031 | 35.125 | 31.060 | 30.547 | 1.00 25.10 |
| ATOM | 1560 | CB | ILE | C1031 | 31.720 | 31.156 | 30.365 | 1.00 22.53 |
| ATOM | 1561 | CG1 | ILE | C1031 | 30.622 | 31.066 | 29.330 | 1.00 24.20 |
| ATOM | 1562 | CG2 | ILE | C1031 | 32.262 | 32.584 | 30.449 | 1.00 25.77 |
| ATOM | 1563 | CD1 | ILE | C1031 | 29.254 | 31.567 | 29.766 | 1.00 24.02 |
| ATOM | 1564 | N | VAL | C1032 | 34.002 | 30.128 | 32.180 | 1.00 23.96 |
| ATOM | 1565 | CA | VAL | C1032 | 34.923 | 30.263 | 33.255 | 1.00 28.42 |
| ATOM | 1566 | C | VAL | C1032 | 36.251 | 29.547 | 32.943 | 1.00 31.87 |
| ATOM | 1567 | O | VAL | C1032 | 37.324 | 30.118 | 33.157 | 1.00 31.88 |
| ATOM | 1568 | CB | VAL | C1032 | 34.229 | 29.636 | 34.479 | 1.00 31.74 |
| ATOM | 1569 | CG1 | VAL | C1032 | 35.145 | 28.990 | 35.490 | 1.00 35.56 |
| ATOM | 1570 | CG2 | VAL | C1032 | 33.241 | 30.562 | 35.210 | 1.00 29.88 |
| ATOM | 1571 | N | SER | C1033 | 36.236 | 28.433 | 32.262 | 1.00 29.60 |
| ATOM | 1572 | CA | SER | C1033 | 37.352 | 27.612 | 31.846 | 1.00 29.62 |
| ATOM | 1573 | C | SER | C1033 | 37.900 | 28.101 | 30.520 | 1.00 30.68 |
| ATOM | 1574 | O | SER | C1033 | 38.900 | 27.598 | 30.046 | 1.00 30.21 |
| ATOM | 1575 | CB | SER | C1033 | 36.909 | 26.139 | 31.703 | 1.00 30.12 |
| ATOM | 1576 | OG | SER | C1033 | 36.408 | 25.725 | 30.430 | 1.00 30.39 |
| ATOM | 1577 | N | LEU | C1034 | 37.291 | 29.100 | 29.905 | 1.00 28.42 |
| ATOM | 1578 | CA | LEU | C1034 | 37.787 | 29.635 | 28.638 | 1.00 31.98 |
| ATOM | 1579 | C | LEU | C1034 | 37.753 | 28.432 | 27.688 | 1.00 32.37 |
| ATOM | 1580 | O | LEU | C1034 | 38.731 | 27.936 | 27.147 | 1.00 39.15 |
| ATOM | 1581 | CB | LEU | C1034 | 39.205 | 30.261 | 28.704 | 1.00 29.58 |
| ATOM | 1582 | CG | LEU | C1034 | 39.466 | 31.409 | 29.630 | 1.00 28.94 |
| ATOM | 1583 | CD1 | LEU | C1034 | 40.895 | 31.922 | 29.656 | 1.00 30.58 |
| ATOM | 1584 | CD2 | LEU | C1034 | 38.617 | 32.636 | 29.209 | 1.00 26.58 |
| ATOM | 1585 | N | GLY | C1035 | 36.530 | 27.864 | 27.544 | 1.00 28.98 |
| ATOM | 1586 | CA | GLY | C1035 | 36.357 | 26.754 | 26.647 | 1.00 24.56 |
| ATOM | 1587 | C | GLY | C1035 | 37.171 | 25.481 | 26.790 | 1.00 20.81 |
| ATOM | 1588 | O | GLY | C1035 | 37.321 | 24.796 | 25.771 | 1.00 21.90 |
| ATOM | 1589 | N | GLY | C1036 | 37.326 | 24.968 | 27.997 | 1.00 21.82 |
| ATOM | 1590 | CA | GLY | C1036 | 37.834 | 23.629 | 28.239 | 1.00 25.47 |

FIG. 5BB

```
ATOM   1591  C    GLY C1036      36.727  22.590  27.923  1.00 28.57
ATOM   1592  O    GLY C1036      35.562  22.944  28.062  1.00 33.09
ATOM   1593  N    THR C1037      37.098  21.424  27.446  1.00 31.18
ATOM   1594  CA   THR C1037      36.071  20.402  27.101  1.00 31.40
ATOM   1595  C    THR C1037      35.671  19.771  28.411  1.00 29.08
ATOM   1596  O    THR C1037      36.402  19.322  29.267  1.00 28.43
ATOM   1597  CB   THR C1037      36.849  19.362  26.248  1.00 35.25
ATOM   1598  OG1  THR C1037      37.143  19.856  24.934  1.00 34.77
ATOM   1599  CG2  THR C1037      36.056  18.071  26.103  1.00 39.81
ATOM   1600  N    PRO C1038      34.318  19.849  28.643  1.00 28.79
ATOM   1601  CA   PRO C1038      33.748  19.251  29.832  1.00 29.26
ATOM   1602  C    PRO C1038      34.121  17.764  29.891  1.00 30.33
ATOM   1603  O    PRO C1038      34.045  17.064  28.877  1.00 30.70
ATOM   1604  CB   PRO C1038      32.262  19.472  29.632  1.00 29.45
ATOM   1605  CG   PRO C1038      32.146  20.595  28.674  1.00 26.90
ATOM   1606  CD   PRO C1038      33.290  20.373  27.726  1.00 26.24
ATOM   1607  N    TYR C1039      34.507  17.239  31.019  1.00 27.10
ATOM   1608  CA   TYR C1039      34.831  15.865  31.319  1.00 31.51
ATOM   1609  C    TYR C1039      35.958  15.322  30.451  1.00 33.48
ATOM   1610  O    TYR C1039      36.068  14.191  29.947  1.00 32.47
ATOM   1611  CB   TYR C1039      33.580  14.968  31.246  1.00 29.03
ATOM   1612  CG   TYR C1039      32.355  15.453  31.980  1.00 28.35
ATOM   1613  CD1  TYR C1039      31.290  15.997  31.247  1.00 27.58
ATOM   1614  CD2  TYR C1039      32.220  15.368  33.364  1.00 26.44
ATOM   1615  CE1  TYR C1039      30.142  16.486  31.827  1.00 23.25
ATOM   1616  CE2  TYR C1039      31.053  15.846  33.969  1.00 25.69
ATOM   1617  CZ   TYR C1039      30.031  16.398  33.196  1.00 25.31
ATOM   1618  OH   TYR C1039      28.870  16.776  33.851  1.00 28.82
ATOM   1619  N    CYS C1040      36.877  16.276  30.243  1.00 37.16
ATOM   1620  CA   CYS C1040      38.045  16.095  29.389  1.00 38.31
ATOM   1621  C    CYS C1040      38.733  14.821  29.848  1.00 36.75
ATOM   1622  O    CYS C1040      38.962  14.593  31.042  1.00 33.37
ATOM   1623  CB   CYS C1040      38.886  17.360  29.511  1.00 41.12
ATOM   1624  SG   CYS C1040      40.570  17.157  28.904  1.00 52.08
ATOM   1625  N    GLY C1041      38.916  13.899  28.920  1.00 38.90
ATOM   1626  CA   GLY C1041      39.550  12.613  29.230  1.00 43.75
ATOM   1627  C    GLY C1041      38.531  11.489  29.459  1.00 46.25
ATOM   1628  O    GLY C1041      38.940  10.313  29.384  1.00 45.71
ATOM   1629  N    MET C1042      37.288  11.831  29.785  1.00 46.22
ATOM   1630  CA   MET C1042      36.267  10.832  30.078  1.00 47.06
ATOM   1631  C    MET C1042      35.471  10.388  28.874  1.00 47.05
ATOM   1632  O    MET C1042      35.257  11.143  27.937  1.00 47.49
ATOM   1633  CB   MET C1042      35.281  11.343  31.119  1.00 46.72
ATOM   1634  CG   MET C1042      35.944  11.646  32.445  1.00 48.06
ATOM   1635  SD   MET C1042      34.712  11.819  33.734  1.00 51.59
ATOM   1636  CE   MET C1042      33.816  10.274  33.378  1.00 51.12
ATOM   1637  N    THR C1043      35.143   9.097  28.852  1.00 48.58
ATOM   1638  CA   THR C1043      34.359   8.548  27.745  1.00 50.37
ATOM   1639  C    THR C1043      32.867   8.824  27.938  1.00 49.20
ATOM   1640  O    THR C1043      32.469   8.990  29.090  1.00 48.53
ATOM   1641  CB   THR C1043      34.541   7.022  27.715  1.00 49.50
ATOM   1642  OG1  THR C1043      33.825   6.420  28.780  1.00 49.52
ATOM   1643  CG2  THR C1043      36.053   6.740  27.911  1.00 48.66
ATOM   1644  N    CYS C1044      32.090   8.784  26.869  1.00 52.39
ATOM   1645  CA   CYS C1044      30.591   8.992  27.031  1.00 54.39
ATOM   1646  C    CYS C1044      30.054   7.913  27.964  1.00 55.34
ATOM   1647  O    CYS C1044      29.373   8.230  28.952  1.00 56.27
```

FIG. 5CC

```
ATOM   1648  CB  CYS C1044    29.890   9.166  25.699  1.00 54.86
ATOM   1649  SG  CYS C1044    30.275  10.658  24.717  1.00 54.87
ATOM   1650  N   ALA C1045    30.546   6.684  27.883  1.00 53.74
ATOM   1651  CA  ALA C1045    30.276   5.533  28.691  1.00 53.52
ATOM   1652  C   ALA C1045    30.319   5.704  30.200  1.00 52.95
ATOM   1653  O   ALA C1045    29.467   5.296  31.022  1.00 52.64
ATOM   1654  CB  ALA C1045    31.379   4.491  28.321  1.00 54.24
ATOM   1655  N   GLU C1046    31.440   6.277  30.650  1.00 50.91
ATOM   1656  CA  GLU C1046    31.637   6.589  32.076  1.00 48.71
ATOM   1657  C   GLU C1046    30.675   7.673  32.539  1.00 46.60
ATOM   1658  O   GLU C1046    30.237   7.666  33.717  1.00 44.26
ATOM   1659  CB  GLU C1046    33.085   7.002  32.314  1.00 49.93
ATOM   1660  CG  GLU C1046    34.115   6.109  31.628  1.00 53.13
ATOM   1661  CD  GLU C1046    35.513   6.735  31.729  1.00 54.82
ATOM   1662  OE1 GLU C1046    36.134   6.539  32.795  1.00 54.82
ATOM   1663  OE2 GLU C1046    35.963   7.416  30.783  1.00 55.96
ATOM   1664  N   LEU C1047    30.268   8.586  31.614  1.00 45.34
ATOM   1665  CA  LEU C1047    29.331   9.632  32.066  1.00 44.07
ATOM   1666  C   LEU C1047    27.983   9.017  32.439  1.00 42.99
ATOM   1667  O   LEU C1047    27.530   9.215  33.576  1.00 42.01
ATOM   1668  CB  LEU C1047    29.181  10.815  31.111  1.00 45.07
ATOM   1669  CG  LEU C1047    30.430  11.706  30.918  1.00 44.08
ATOM   1670  CD1 LEU C1047    30.038  12.921  30.115  1.00 45.50
ATOM   1671  CD2 LEU C1047    31.071  12.058  32.245  1.00 42.85
ATOM   1672  N   TYR C1048    27.409   8.182  31.588  1.00 43.22
ATOM   1673  CA  TYR C1048    26.213   7.392  31.910  1.00 44.38
ATOM   1674  C   TYR C1048    26.397   6.646  33.245  1.00 44.87
ATOM   1675  O   TYR C1048    25.486   6.717  34.085  1.00 43.82
ATOM   1676  CB  TYR C1048    25.905   6.343  30.853  1.00 44.96
ATOM   1677  CG  TYR C1048    25.256   6.871  29.600  1.00 47.81
ATOM   1678  CD1 TYR C1048    26.033   7.330  28.545  1.00 47.83
ATOM   1679  CD2 TYR C1048    23.852   6.898  29.482  1.00 48.40
ATOM   1680  CE1 TYR C1048    25.436   7.802  27.387  1.00 47.27
ATOM   1681  CE2 TYR C1048    23.246   7.366  28.324  1.00 48.08
ATOM   1682  CZ  TYR C1048    24.075   7.815  27.294  1.00 48.94
ATOM   1683  OH  TYR C1048    23.413   8.274  26.168  1.00 49.94
ATOM   1684  N   GLU C1049    27.591   6.069  33.477  1.00 42.94
ATOM   1685  CA  GLU C1049    27.749   5.400  34.754  1.00 45.35
ATOM   1686  C   GLU C1049    28.155   6.333  35.873  1.00 44.67
ATOM   1687  O   GLU C1049    27.588   6.137  36.975  1.00 45.76
ATOM   1688  CB  GLU C1049    28.683   4.171  34.686  1.00 47.30
ATOM   1689  CG  GLU C1049    30.158   4.453  34.837  1.00 49.28
ATOM   1690  CD  GLU C1049    31.072   3.245  35.050  1.00 50.85
ATOM   1691  OE1 GLU C1049    31.702   2.810  34.042  1.00 51.60
ATOM   1692  OE2 GLU C1049    31.179   2.748  36.200  1.00 49.78
ATOM   1693  N   LYS C1050    29.038   7.320  35.685  1.00 45.45
ATOM   1694  CA  LYS C1050    29.387   8.148  36.861  1.00 46.05
ATOM   1695  C   LYS C1050    28.404   9.253  37.175  1.00 44.76
ATOM   1696  O   LYS C1050    28.099   9.497  38.375  1.00 44.16
ATOM   1697  CB  LYS C1050    30.814   8.668  36.707  1.00 49.41
ATOM   1698  CG  LYS C1050    31.798   7.565  36.380  1.00 52.04
ATOM   1699  CD  LYS C1050    33.285   7.938  36.456  1.00 54.77
ATOM   1700  CE  LYS C1050    34.086   6.629  36.533  1.00 56.01
ATOM   1701  NZ  LYS C1050    35.565   6.819  36.433  1.00 58.90
ATOM   1702  N   LEU C1051    27.733   9.813  36.163  1.00 41.92
ATOM   1703  CA  LEU C1051    26.746  10.866  36.552  1.00 43.18
ATOM   1704  C   LEU C1051    25.759  10.435  37.607  1.00 43.39
```

FIG. 5DD

```
ATOM  1705  O    LEU C1051    25.582  11.062  38.662  1.00 43.64
ATOM  1706  CB   LEU C1051    26.145  11.496  35.307  1.00 43.49
ATOM  1707  CG   LEU C1051    27.096  12.382  34.480  1.00 42.95
ATOM  1708  CD1  LEU C1051    26.331  12.985  33.326  1.00 43.01
ATOM  1709  CD2  LEU C1051    27.702  13.468  35.366  1.00 43.66
ATOM  1710  N    PRO C1052    25.084   9.288  37.475  1.00 45.02
ATOM  1711  CA   PRO C1052    24.140   8.817  38.470  1.00 45.84
ATOM  1712  C    PRO C1052    24.736   8.635  39.839  1.00 47.07
ATOM  1713  O    PRO C1052    24.088   8.826  40.880  1.00 48.20
ATOM  1714  CB   PRO C1052    23.559   7.544  37.854  1.00 45.47
ATOM  1715  CG   PRO C1052    23.652   7.799  36.384  1.00 44.83
ATOM  1716  CD   PRO C1052    25.013   8.487  36.242  1.00 45.28
ATOM  1717  N    GLN C1053    26.006   8.296  40.007  1.00 50.49
ATOM  1718  CA   GLN C1053    26.594   8.130  41.331  1.00 52.45
ATOM  1719  C    GLN C1053    26.921   9.462  41.976  1.00 51.74
ATOM  1720  O    GLN C1053    27.231   9.442  43.175  1.00 51.45
ATOM  1721  CB   GLN C1053    27.798   7.199  41.221  1.00 55.75
ATOM  1722  CG   GLN C1053    27.411   5.794  40.768  1.00 61.04
ATOM  1723  CD   GLN C1053    26.526   5.041  41.743  1.00 64.91
ATOM  1724  OE1  GLN C1053    26.851   4.904  42.948  1.00 66.92
ATOM  1725  NE2  GLN C1053    25.370   4.528  41.286  1.00 65.52
ATOM  1726  N    GLY C1054    26.801  10.624  41.320  1.00 49.79
ATOM  1727  CA   GLY C1054    27.061  11.874  42.052  1.00 46.62
ATOM  1728  C    GLY C1054    28.276  12.597  41.495  1.00 44.62
ATOM  1729  O    GLY C1054    28.683  13.662  41.920  1.00 43.65
ATOM  1730  N    TYR C1055    28.917  12.051  40.482  1.00 45.48
ATOM  1731  CA   TYR C1055    30.099  12.698  39.937  1.00 45.51
ATOM  1732  C    TYR C1055    29.685  13.995  39.214  1.00 44.95
ATOM  1733  O    TYR C1055    28.622  13.976  38.583  1.00 46.39
ATOM  1734  CB   TYR C1055    30.767  11.776  38.932  1.00 45.73
ATOM  1735  CG   TYR C1055    32.055  12.414  38.433  1.00 48.52
ATOM  1736  CD1  TYR C1055    33.235  12.302  39.143  1.00 48.82
ATOM  1737  CD2  TYR C1055    32.045  13.129  37.234  1.00 48.37
ATOM  1738  CE1  TYR C1055    34.401  12.898  38.658  1.00 48.87
ATOM  1739  CE2  TYR C1055    33.178  13.723  36.737  1.00 47.42
ATOM  1740  CZ   TYR C1055    34.354  13.582  37.459  1.00 49.27
ATOM  1741  OH   TYR C1055    35.488  14.170  36.952  1.00 48.77
ATOM  1742  N    ARG C1056    30.485  15.051  39.252  1.00 40.28
ATOM  1743  CA   ARG C1056    30.189  16.276  38.566  1.00 38.71
ATOM  1744  C    ARG C1056    31.481  17.012  38.176  1.00 39.85
ATOM  1745  O    ARG C1056    32.472  16.797  38.879  1.00 42.11
ATOM  1746  CB   ARG C1056    29.407  17.281  39.408  1.00 38.04
ATOM  1747  CG   ARG C1056    27.996  17.004  39.890  1.00 37.78
ATOM  1748  CD   ARG C1056    27.022  16.584  38.810  1.00 34.37
ATOM  1749  NE   ARG C1056    25.677  16.380  39.370  1.00 32.75
ATOM  1750  CZ   ARG C1056    25.172  15.135  39.461  1.00 34.13
ATOM  1751  NH1  ARG C1056    23.934  15.014  39.951  1.00 33.89
ATOM  1752  NH2  ARG C1056    25.884  14.083  39.063  1.00 31.70
ATOM  1753  N    LEU C1057    31.450  17.843  37.130  1.00 37.74
ATOM  1754  CA   LEU C1057    32.615  18.640  36.829  1.00 38.61
ATOM  1755  C    LEU C1057    33.280  19.260  38.062  1.00 37.18
ATOM  1756  O    LEU C1057    32.759  19.829  39.007  1.00 36.18
ATOM  1757  CB   LEU C1057    32.223  19.785  35.886  1.00 39.58
ATOM  1758  CG   LEU C1057    31.870  19.236  34.492  1.00 40.26
ATOM  1759  CD1  LEU C1057    31.190  20.384  33.790  1.00 41.53
ATOM  1760  CD2  LEU C1057    33.089  18.719  33.746  1.00 40.04
ATOM  1761  N    GLU C1058    34.597  19.231  37.962  1.00 38.47
```

FIG. 5EE

```
ATOM   1762  CA   GLU C1058     35.494  19.715  39.003  1.00 40.99
ATOM   1763  C    GLU C1058     35.655  21.237  38.941  1.00 37.60
ATOM   1764  O    GLU C1058     35.665  21.759  37.841  1.00 37.18
ATOM   1765  CB   GLU C1058     36.808  18.952  38.778  1.00 43.93
ATOM   1766  CG   GLU C1058     37.256  18.728  37.367  1.00 49.34
ATOM   1767  CD   GLU C1058     36.540  18.005  36.265  1.00 51.18
ATOM   1768  OE1  GLU C1058     36.583  18.538  35.121  1.00 50.19
ATOM   1769  OE2  GLU C1058     35.931  16.902  36.361  1.00 52.82
ATOM   1770  N    LYS C1059     35.708  21.975  40.005  1.00 35.88
ATOM   1771  CA   LYS C1059     35.948  23.424  39.950  1.00 40.12
ATOM   1772  C    LYS C1059     37.345  23.831  39.473  1.00 41.54
ATOM   1773  O    LYS C1059     38.332  23.431  40.095  1.00 41.88
ATOM   1774  CB   LYS C1059     35.946  23.896  41.417  1.00 39.21
ATOM   1775  CG   LYS C1059     35.984  25.413  41.569  1.00 41.97
ATOM   1776  CD   LYS C1059     35.953  25.810  43.048  1.00 43.62
ATOM   1777  CE   LYS C1059     37.349  25.786  43.641  1.00 43.92
ATOM   1778  NZ   LYS C1059     38.192  26.906  43.099  1.00 44.39
ATOM   1779  N    PRO C1060     37.498  24.651  38.439  1.00 41.99
ATOM   1780  CA   PRO C1060     38.795  25.166  38.040  1.00 42.27
ATOM   1781  C    PRO C1060     39.441  25.920  39.186  1.00 42.45
ATOM   1782  O    PRO C1060     38.840  26.618  39.996  1.00 40.76
ATOM   1783  CB   PRO C1060     38.529  26.115  36.894  1.00 43.06
ATOM   1784  CG   PRO C1060     37.145  25.765  36.416  1.00 41.60
ATOM   1785  CD   PRO C1060     36.408  25.170  37.589  1.00 41.74
ATOM   1786  N    LEU C1061     40.773  25.843  39.287  1.00 44.11
ATOM   1787  CA   LEU C1061     41.557  26.440  40.325  1.00 44.84
ATOM   1788  C    LEU C1061     41.416  27.941  40.443  1.00 44.71
ATOM   1789  O    LEU C1061     41.441  28.470  41.567  1.00 45.26
ATOM   1790  CB   LEU C1061     43.036  26.089  40.055  1.00 48.79
ATOM   1791  CG   LEU C1061     43.314  24.624  40.459  1.00 52.11
ATOM   1792  CD1  LEU C1061     44.673  24.204  39.897  1.00 53.08
ATOM   1793  CD2  LEU C1061     43.288  24.512  41.984  1.00 52.05
ATOM   1794  N    ASN C1062     41.247  28.623  39.321  1.00 44.44
ATOM   1795  CA   ASN C1062     41.112  30.085  39.327  1.00 44.45
ATOM   1796  C    ASN C1062     39.661  30.582  39.363  1.00 44.24
ATOM   1797  O    ASN C1062     39.394  31.757  39.073  1.00 42.70
ATOM   1798  CB   ASN C1062     41.811  30.536  38.059  1.00 47.14
ATOM   1799  CG   ASN C1062     41.018  30.280  36.799  1.00 50.71
ATOM   1800  OD1  ASN C1062     40.297  29.260  36.680  1.00 55.26
ATOM   1801  ND2  ASN C1062     41.160  31.208  35.873  1.00 49.84
ATOM   1802  N    CYS C1063     38.727  29.727  39.787  1.00 40.21
ATOM   1803  CA   CYS C1063     37.312  30.006  39.917  1.00 39.16
ATOM   1804  C    CYS C1063     36.922  30.226  41.375  1.00 40.26
ATOM   1805  O    CYS C1063     37.149  29.298  42.177  1.00 38.11
ATOM   1806  CB   CYS C1063     36.476  28.796  39.430  1.00 36.02
ATOM   1807  SG   CYS C1063     34.684  29.162  39.283  1.00 36.25
ATOM   1808  N    ASP C1064     36.179  31.287  41.675  1.00 39.98
ATOM   1809  CA   ASP C1064     35.704  31.514  43.034  1.00 42.23
ATOM   1810  C    ASP C1064     34.623  30.474  43.367  1.00 43.63
ATOM   1811  O    ASP C1064     33.885  29.998  42.516  1.00 42.13
ATOM   1812  CB   ASP C1064     35.166  32.915  43.277  1.00 44.24
ATOM   1813  CG   ASP C1064     34.744  33.348  44.660  1.00 47.38
ATOM   1814  OD1  ASP C1064     35.591  34.016  45.335  1.00 49.14
ATOM   1815  OD2  ASP C1064     33.594  33.165  45.169  1.00 46.30
ATOM   1816  N    ASP C1065     34.571  30.128  44.646  1.00 44.20
ATOM   1817  CA   ASP C1065     33.681  29.213  45.285  1.00 46.41
ATOM   1818  C    ASP C1065     32.214  29.629  45.059  1.00 46.09
```

FIG. 5FF

```
ATOM   1819  O   ASP C1065      31.383  28.772  44.807  1.00 45.90
ATOM   1820  CB  ASP C1065      33.999  29.111  46.780  1.00 49.84
ATOM   1821  CG  ASP C1065      34.972  28.020  47.179  1.00 54.04
ATOM   1822  OD1 ASP C1065      35.370  27.139  46.384  1.00 54.54
ATOM   1823  OD2 ASP C1065      35.412  27.941  48.364  1.00 56.55
ATOM   1824  N   GLU C1066      31.932  30.931  44.991  1.00 46.33
ATOM   1825  CA  GLU C1066      30.585  31.364  44.699  1.00 46.37
ATOM   1826  C   GLU C1066      30.162  30.946  43.279  1.00 43.58
ATOM   1827  O   GLU C1066      28.974  30.622  43.161  1.00 40.53
ATOM   1828  CB  GLU C1066      30.362  32.870  44.901  1.00 47.78
ATOM   1829  CG  GLU C1066      30.464  33.371  46.327  1.00 51.27
ATOM   1830  CD  GLU C1066      30.147  34.853  46.483  1.00 54.46
ATOM   1831  OE1 GLU C1066      30.977  35.632  47.023  1.00 56.49
ATOM   1832  OE2 GLU C1066      29.039  35.278  46.075  1.00 54.91
ATOM   1833  N   VAL C1067      31.031  31.026  42.267  1.00 40.02
ATOM   1834  CA  VAL C1067      30.592  30.670  40.914  1.00 38.39
ATOM   1835  C   VAL C1067      30.361  29.166  40.750  1.00 38.56
ATOM   1836  O   VAL C1067      29.492  28.741  39.975  1.00 35.01
ATOM   1837  CB  VAL C1067      31.561  31.094  39.797  1.00 37.83
ATOM   1838  CG1 VAL C1067      31.071  30.760  38.416  1.00 34.84
ATOM   1839  CG2 VAL C1067      31.809  32.609  39.878  1.00 39.35
ATOM   1840  N   TYR C1068      31.258  28.419  41.393  1.00 37.89
ATOM   1841  CA  TYR C1068      31.203  26.969  41.346  1.00 38.97
ATOM   1842  C   TYR C1068      29.924  26.510  42.044  1.00 40.70
ATOM   1843  O   TYR C1068      29.265  25.613  41.492  1.00 38.63
ATOM   1844  CB  TYR C1068      32.437  26.278  41.913  1.00 37.20
ATOM   1845  CG  TYR C1068      32.470  24.770  41.798  1.00 35.05
ATOM   1846  CD1 TYR C1068      32.535  24.158  40.556  1.00 34.59
ATOM   1847  CD2 TYR C1068      32.431  23.934  42.903  1.00 35.51
ATOM   1848  CE1 TYR C1068      32.536  22.785  40.405  1.00 33.51
ATOM   1849  CE2 TYR C1068      32.456  22.549  42.800  1.00 33.38
ATOM   1850  CZ  TYR C1068      32.540  22.006  41.540  1.00 33.70
ATOM   1851  OH  TYR C1068      32.545  20.637  41.342  1.00 37.05
ATOM   1852  N   ASP C1069      29.573  27.177  43.159  1.00 42.06
ATOM   1853  CA  ASP C1069      28.316  26.862  43.806  1.00 42.68
ATOM   1854  C   ASP C1069      27.124  27.069  42.869  1.00 40.99
ATOM   1855  O   ASP C1069      26.233  26.193  42.884  1.00 40.08
ATOM   1856  CB  ASP C1069      28.116  27.676  45.094  1.00 47.98
ATOM   1857  CG  ASP C1069      28.983  27.092  46.212  1.00 53.70
ATOM   1858  OD1 ASP C1069      29.487  25.940  46.045  1.00 55.80
ATOM   1859  OD2 ASP C1069      29.161  27.786  47.254  1.00 55.99
ATOM   1860  N   LEU C1070      27.080  28.150  42.087  1.00 36.81
ATOM   1861  CA  LEU C1070      25.977  28.308  41.140  1.00 36.03
ATOM   1862  C   LEU C1070      25.905  27.172  40.123  1.00 34.83
ATOM   1863  O   LEU C1070      24.833  26.703  39.743  1.00 32.57
ATOM   1864  CB  LEU C1070      26.131  29.666  40.472  1.00 33.68
ATOM   1865  CG  LEU C1070      25.095  30.113  39.458  1.00 35.12
ATOM   1866  CD1 LEU C1070      23.674  29.955  40.003  1.00 34.71
ATOM   1867  CD2 LEU C1070      25.391  31.582  39.084  1.00 34.63
ATOM   1868  N   MET C1071      27.036  26.703  39.602  1.00 36.71
ATOM   1869  CA  MET C1071      27.131  25.568  38.706  1.00 37.17
ATOM   1870  C   MET C1071      26.555  24.302  39.372  1.00 36.93
ATOM   1871  O   MET C1071      25.808  23.574  38.735  1.00 36.82
ATOM   1872  CB  MET C1071      28.569  25.145  38.294  1.00 35.35
ATOM   1873  CG  MET C1071      29.354  26.145  37.465  1.00 35.64
ATOM   1874  SD  MET C1071      31.096  25.645  37.207  1.00 32.11
ATOM   1875  CE  MET C1071      31.839  27.209  36.753  1.00 34.27
```

FIG. 5GG

```
ATOM   1876  N   ARG C1072    26.959  23.943  40.580  1.00 36.71
ATOM   1877  CA  ARG C1072    26.550  22.771  41.323  1.00 37.27
ATOM   1878  C   ARG C1072    25.039  22.687  41.557  1.00 36.15
ATOM   1879  O   ARG C1072    24.384  21.638  41.587  1.00 37.31
ATOM   1880  CB  ARG C1072    27.272  22.810  42.713  1.00 39.01
ATOM   1881  CG  ARG C1072    28.773  22.514  42.664  1.00 38.84
ATOM   1882  CD  ARG C1072    29.110  21.260  41.887  1.00 40.99
ATOM   1883  NE  ARG C1072    28.618  20.088  42.608  1.00 45.98
ATOM   1884  CZ  ARG C1072    29.217  19.090  43.239  1.00 46.52
ATOM   1885  NH1 ARG C1072    30.532  18.968  43.255  1.00 44.60
ATOM   1886  NH2 ARG C1072    28.428  18.173  43.842  1.00 46.54
ATOM   1887  N   GLN C1073    24.427  23.832  41.775  1.00 36.36
ATOM   1888  CA  GLN C1073    22.986  24.010  41.934  1.00 36.84
ATOM   1889  C   GLN C1073    22.289  23.680  40.612  1.00 35.17
ATOM   1890  O   GLN C1073    21.240  23.043  40.616  1.00 36.12
ATOM   1891  CB  GLN C1073    22.690  25.436  42.324  1.00 40.62
ATOM   1892  CG  GLN C1073    22.926  25.928  43.737  1.00 44.26
ATOM   1893  CD  GLN C1073    22.601  27.425  43.797  1.00 48.97
ATOM   1894  OE1 GLN C1073    22.895  28.160  44.746  1.00 50.88
ATOM   1895  NE2 GLN C1073    21.954  27.977  42.770  1.00 50.58
ATOM   1896  N   CYS C1074    22.888  23.925  39.463  1.00 34.02
ATOM   1897  CA  CYS C1074    22.346  23.554  38.175  1.00 33.44
ATOM   1898  C   CYS C1074    22.300  22.048  37.953  1.00 32.85
ATOM   1899  O   CYS C1074    21.595  21.573  37.050  1.00 28.15
ATOM   1900  CB  CYS C1074    23.165  24.222  37.052  1.00 32.80
ATOM   1901  SG  CYS C1074    22.926  26.054  36.945  1.00 29.54
ATOM   1902  N   TRP C1075    23.155  21.300  38.651  1.00 34.38
ATOM   1903  CA  TRP C1075    23.323  19.869  38.394  1.00 36.36
ATOM   1904  C   TRP C1075    22.772  19.008  39.538  1.00 37.35
ATOM   1905  O   TRP C1075    23.378  17.961  39.809  1.00 36.14
ATOM   1906  CB  TRP C1075    24.797  19.516  38.184  1.00 31.61
ATOM   1907  CG  TRP C1075    25.554  20.319  37.170  1.00 32.01
ATOM   1908  CD1 TRP C1075    25.035  20.735  35.945  1.00 30.72
ATOM   1909  CD2 TRP C1075    26.905  20.792  37.215  1.00 27.71
ATOM   1910  NE1 TRP C1075    26.028  21.458  35.263  1.00 27.75
ATOM   1911  CE2 TRP C1075    27.165  21.473  36.015  1.00 27.79
ATOM   1912  CE3 TRP C1075    27.923  20.731  38.161  1.00 29.11
ATOM   1913  CZ2 TRP C1075    28.393  22.095  35.707  1.00 27.12
ATOM   1914  CZ3 TRP C1075    29.172  21.338  37.861  1.00 27.92
ATOM   1915  CH2 TRP C1075    29.394  22.010  36.640  1.00 26.04
ATOM   1916  N   ARG C1076    21.729  19.503  40.206  1.00 38.82
ATOM   1917  CA  ARG C1076    21.190  18.763  41.348  1.00 40.61
ATOM   1918  C   ARG C1076    20.509  17.546  40.743  1.00 40.05
ATOM   1919  O   ARG C1076    19.967  17.688  39.634  1.00 40.43
ATOM   1920  CB  ARG C1076    20.272  19.608  42.208  1.00 42.35
ATOM   1921  CG  ARG C1076    20.932  20.378  43.334  1.00 45.64
ATOM   1922  CD  ARG C1076    20.106  21.505  43.893  1.00 49.70
ATOM   1923  NE  ARG C1076    20.769  22.441  44.800  1.00 52.00
ATOM   1924  CZ  ARG C1076    20.478  23.723  45.050  1.00 51.66
ATOM   1925  NH1 ARG C1076    19.508  24.410  44.455  1.00 50.03
ATOM   1926  NH2 ARG C1076    21.238  24.353  45.949  1.00 52.86
ATOM   1927  N   GLU C1077    20.598  16.392  41.374  1.00 41.20
ATOM   1928  CA  GLU C1077    19.944  15.200  40.818  1.00 42.65
ATOM   1929  C   GLU C1077    18.447  15.393  40.555  1.00 38.60
ATOM   1930  O   GLU C1077    17.929  15.043  39.481  1.00 35.94
ATOM   1931  CB  GLU C1077    20.198  13.968  41.695  1.00 45.87
ATOM   1932  CG  GLU C1077    20.013  12.643  40.962  1.00 50.08
```

FIG. 5HH

```
ATOM   1933  CD   GLU C1077    20.183  11.401  41.819  1.00 54.47
ATOM   1934  OE1  GLU C1077    20.561  10.312  41.308  1.00 57.69
ATOM   1935  OE2  GLU C1077    19.955  11.404  43.055  1.00 56.30
ATOM   1936  N    LYS C1078    17.706  15.887  41.503  1.00 39.48
ATOM   1937  CA   LYS C1078    16.243  16.090  41.262  1.00 40.94
ATOM   1938  C    LYS C1078    16.079  17.369  40.455  1.00 40.21
ATOM   1939  O    LYS C1078    16.480  18.449  40.854  1.00 38.01
ATOM   1940  CB   LYS C1078    15.475  16.240  42.568  1.00 43.70
ATOM   1941  CG   LYS C1078    15.829  15.188  43.605  1.00 46.67
ATOM   1942  CD   LYS C1078    15.384  15.538  45.015  1.00 49.04
ATOM   1943  CE   LYS C1078    15.414  14.237  45.826  1.00 53.53
ATOM   1944  NZ   LYS C1078    14.894  14.422  47.213  1.00 55.30
ATOM   1945  N    PRO C1079    15.476  17.282  39.288  1.00 38.88
ATOM   1946  CA   PRO C1079    15.298  18.465  38.451  1.00 39.64
ATOM   1947  C    PRO C1079    14.654  19.621  39.182  1.00 40.23
ATOM   1948  O    PRO C1079    15.091  20.778  39.078  1.00 39.41
ATOM   1949  CB   PRO C1079    14.521  17.924  37.259  1.00 36.96
ATOM   1950  CG   PRO C1079    14.929  16.461  37.199  1.00 35.65
ATOM   1951  CD   PRO C1079    14.988  16.035  38.647  1.00 36.92
ATOM   1952  N    TYR C1080    13.657  19.387  40.028  1.00 41.92
ATOM   1953  CA   TYR C1080    12.882  20.406  40.717  1.00 43.85
ATOM   1954  C    TYR C1080    13.587  21.140  41.824  1.00 43.51
ATOM   1955  O    TYR C1080    13.109  22.140  42.388  1.00 43.12
ATOM   1956  CB   TYR C1080    11.505  19.831  41.176  1.00 45.60
ATOM   1957  CG   TYR C1080    11.697  18.722  42.194  1.00 47.84
ATOM   1958  CD1  TYR C1080    11.973  18.993  43.531  1.00 49.35
ATOM   1959  CD2  TYR C1080    11.636  17.389  41.798  1.00 49.13
ATOM   1960  CE1  TYR C1080    12.146  17.958  44.445  1.00 50.14
ATOM   1961  CE2  TYR C1080    11.806  16.370  42.704  1.00 50.24
ATOM   1962  CZ   TYR C1080    12.058  16.656  44.030  1.00 50.60
ATOM   1963  OH   TYR C1080    12.242  15.597  44.908  1.00 53.21
ATOM   1964  N    GLU C1081    14.799  20.700  42.144  1.00 44.60
ATOM   1965  CA   GLU C1081    15.638  21.420  43.102  1.00 44.07
ATOM   1966  C    GLU C1081    16.559  22.432  42.419  1.00 40.19
ATOM   1967  O    GLU C1081    17.250  23.137  43.126  1.00 37.60
ATOM   1968  CB   GLU C1081    16.508  20.467  43.922  1.00 45.52
ATOM   1969  CG   GLU C1081    15.648  19.808  45.014  1.00 50.79
ATOM   1970  CD   GLU C1081    16.627  18.944  45.789  1.00 54.16
ATOM   1971  OE1  GLU C1081    16.879  19.248  46.968  1.00 58.46
ATOM   1972  OE2  GLU C1081    17.210  17.991  45.250  1.00 55.69
ATOM   1973  N    ARG C1082    16.647  22.458  41.105  1.00 39.28
ATOM   1974  CA   ARG C1082    17.497  23.363  40.367  1.00 37.58
ATOM   1975  C    ARG C1082    16.828  24.740  40.394  1.00 38.63
ATOM   1976  O    ARG C1082    15.612  24.910  40.383  1.00 40.38
ATOM   1977  CB   ARG C1082    17.704  22.926  38.895  1.00 36.08
ATOM   1978  CG   ARG C1082    18.469  21.599  38.779  1.00 36.20
ATOM   1979  CD   ARG C1082    18.609  20.955  37.417  1.00 33.59
ATOM   1980  NE   ARG C1082    18.832  19.501  37.535  1.00 34.00
ATOM   1981  CZ   ARG C1082    18.469  18.515  36.714  1.00 32.08
ATOM   1982  NH1  ARG C1082    17.822  18.762  35.569  1.00 31.72
ATOM   1983  NH2  ARG C1082    18.708  17.204  36.908  1.00 31.86
ATOM   1984  N    PRO C1083    17.667  25.772  40.289  1.00 34.94
ATOM   1985  CA   PRO C1083    17.201  27.135  40.253  1.00 32.78
ATOM   1986  C    PRO C1083    16.556  27.432  38.912  1.00 33.70
ATOM   1987  O    PRO C1083    16.641  26.652  37.947  1.00 31.92
ATOM   1988  CB   PRO C1083    18.446  28.006  40.398  1.00 27.76
ATOM   1989  CG   PRO C1083    19.621  27.077  40.186  1.00 30.28
```

FIG. 5II

```
ATOM   1990  CD   PRO C1083     19.139  25.661  40.404  1.00 32.35
ATOM   1991  N    SER C1084     15.816  28.558  38.933  1.00 31.68
ATOM   1992  CA   SER C1084     15.199  29.032  37.705  1.00 31.93
ATOM   1993  C    SER C1084     16.210  30.014  37.080  1.00 31.48
ATOM   1994  O    SER C1084     17.144  30.514  37.733  1.00 29.39
ATOM   1995  CB   SER C1084     13.873  29.704  38.085  1.00 31.83
ATOM   1996  OG   SER C1084     14.132  31.022  38.595  1.00 32.90
ATOM   1997  N    PHE C1085     16.099  30.275  35.783  1.00 30.49
ATOM   1998  CA   PHE C1085     16.882  31.203  35.046  1.00 31.87
ATOM   1999  C    PHE C1085     16.731  32.620  35.612  1.00 35.04
ATOM   2000  O    PHE C1085     17.778  33.269  35.568  1.00 34.20
ATOM   2001  CB   PHE C1085     16.631  31.270  33.533  1.00 29.72
ATOM   2002  CG   PHE C1085     17.113  30.035  32.829  1.00 29.58
ATOM   2003  CD1  PHE C1085     16.278  29.113  32.259  1.00 27.05
ATOM   2004  CD2  PHE C1085     18.513  29.847  32.765  1.00 28.92
ATOM   2005  CE1  PHE C1085     16.764  28.002  31.606  1.00 29.03
ATOM   2006  CE2  PHE C1085     18.999  28.739  32.078  1.00 31.04
ATOM   2007  CZ   PHE C1085     18.172  27.810  31.537  1.00 29.42
ATOM   2008  N    ALA C1086     15.538  32.967  36.152  1.00 34.52
ATOM   2009  CA   ALA C1086     15.461  34.251  36.811  1.00 36.36
ATOM   2010  C    ALA C1086     16.330  34.297  38.053  1.00 35.05
ATOM   2011  O    ALA C1086     16.940  35.370  38.305  1.00 33.03
ATOM   2012  CB   ALA C1086     13.991  34.579  37.178  1.00 36.02
ATOM   2013  N    GLN C1087     16.403  33.210  38.808  1.00 34.48
ATOM   2014  CA   GLN C1087     17.187  33.187  40.043  1.00 37.34
ATOM   2015  C    GLN C1087     18.692  33.172  39.718  1.00 36.23
ATOM   2016  O    GLN C1087     19.488  33.831  40.397  1.00 34.12
ATOM   2017  CB   GLN C1087     16.898  31.991  40.963  1.00 39.18
ATOM   2018  CG   GLN C1087     15.465  31.766  41.372  1.00 41.60
ATOM   2019  CD   GLN C1087     15.181  30.507  42.185  1.00 41.95
ATOM   2020  OE1  GLN C1087     14.644  30.647  43.307  1.00 43.26
ATOM   2021  NE2  GLN C1087     15.463  29.299  41.755  1.00 38.28
ATOM   2022  N    ILE C1088     19.023  32.489  38.609  1.00 36.91
ATOM   2023  CA   ILE C1088     20.421  32.470  38.143  1.00 34.98
ATOM   2024  C    ILE C1088     20.850  33.891  37.730  1.00 36.64
ATOM   2025  O    ILE C1088     21.994  34.310  37.999  1.00 38.60
ATOM   2026  CB   ILE C1088     20.707  31.497  37.017  1.00 31.65
ATOM   2027  CG1  ILE C1088     20.729  30.014  37.479  1.00 28.80
ATOM   2028  CG2  ILE C1088     22.108  31.715  36.417  1.00 32.45
ATOM   2029  CD1  ILE C1088     20.354  29.149  36.296  1.00 24.89
ATOM   2030  N    LEU C1089     20.006  34.626  37.037  1.00 36.93
ATOM   2031  CA   LEU C1089     20.288  36.010  36.641  1.00 38.78
ATOM   2032  C    LEU C1089     20.504  36.934  37.835  1.00 39.65
ATOM   2033  O    LEU C1089     21.396  37.812  37.840  1.00 38.19
ATOM   2034  CB   LEU C1089     19.192  36.562  35.727  1.00 39.78
ATOM   2035  CG   LEU C1089     19.421  37.938  35.087  1.00 41.64
ATOM   2036  CD1  LEU C1089     20.497  37.892  34.014  1.00 39.98
ATOM   2037  CD2  LEU C1089     18.113  38.470  34.492  1.00 40.00
ATOM   2038  N    VAL C1090     19.730  36.740  38.902  1.00 41.42
ATOM   2039  CA   VAL C1090     19.894  37.611  40.075  1.00 43.28
ATOM   2040  C    VAL C1090     21.247  37.342  40.727  1.00 43.77
ATOM   2041  O    VAL C1090     21.948  38.289  41.115  1.00 45.25
ATOM   2042  CB   VAL C1090     18.759  37.424  41.081  1.00 44.41
ATOM   2043  CG1  VAL C1090     19.139  38.123  42.387  1.00 45.32
ATOM   2044  CG2  VAL C1090     17.422  37.989  40.595  1.00 45.38
ATOM   2045  N    SER C1091     21.634  36.074  40.924  1.00 43.36
ATOM   2046  CA   SER C1091     22.921  35.817  41.543  1.00 45.59
```

FIG. 5JJ

```
ATOM   2047  C    SER C1091      24.044  36.357  40.663  1.00 43.29
ATOM   2048  O    SER C1091      24.987  36.921  41.231  1.00 43.04
ATOM   2049  CB   SER C1091      23.056  34.332  41.946  1.00 48.54
ATOM   2050  OG   SER C1091      22.563  33.588  40.846  1.00 54.84
ATOM   2051  N    LEU C1092      23.971  36.337  39.335  1.00 38.97
ATOM   2052  CA   LEU C1092      25.098  36.849  38.570  1.00 37.84
ATOM   2053  C    LEU C1092      25.118  38.383  38.604  1.00 39.82
ATOM   2054  O    LEU C1092      26.207  38.957  38.627  1.00 35.95
ATOM   2055  CB   LEU C1092      25.098  36.309  37.150  1.00 35.04
ATOM   2056  CG   LEU C1092      25.301  34.789  36.982  1.00 33.88
ATOM   2057  CD1  LEU C1092      24.655  34.383  35.662  1.00 33.07
ATOM   2058  CD2  LEU C1092      26.773  34.446  37.016  1.00 34.04
ATOM   2059  N    ASN C1093      23.942  39.039  38.597  1.00 41.48
ATOM   2060  CA   ASN C1093      23.920  40.525  38.641  1.00 43.61
ATOM   2061  C    ASN C1093      24.527  41.074  39.936  1.00 44.92
ATOM   2062  O    ASN C1093      25.166  42.135  39.946  1.00 44.64
ATOM   2063  CB   ASN C1093      22.509  41.084  38.434  1.00 42.95
ATOM   2064  CG   ASN C1093      21.996  41.095  37.021  1.00 44.32
ATOM   2065  OD1  ASN C1093      20.771  41.140  36.726  1.00 46.00
ATOM   2066  ND2  ASN C1093      22.859  41.098  36.023  1.00 43.94
ATOM   2067  N    ARG C1094      24.374  40.336  41.043  1.00 46.27
ATOM   2068  CA   ARG C1094      24.957  40.724  42.334  1.00 47.34
ATOM   2069  C    ARG C1094      26.473  40.529  42.302  1.00 47.18
ATOM   2070  O    ARG C1094      27.308  41.386  42.683  1.00 48.73
ATOM   2071  CB   ARG C1094      24.207  39.952  43.397  1.00 48.52
ATOM   2072  CG   ARG C1094      24.600  40.135  44.831  1.00 53.04
ATOM   2073  CD   ARG C1094      25.893  39.506  45.266  1.00 55.51
ATOM   2074  NE   ARG C1094      25.811  38.266  46.057  1.00 58.34
ATOM   2075  CZ   ARG C1094      26.945  37.595  46.345  1.00 58.94
ATOM   2076  NH1  ARG C1094      28.144  37.993  45.942  1.00 58.67
ATOM   2077  NH2  ARG C1094      26.892  36.486  47.071  1.00 60.47
ATOM   2078  N    MET C1095      26.945  39.465  41.654  1.00 43.61
ATOM   2079  CA   MET C1095      28.378  39.288  41.439  1.00 41.53
ATOM   2080  C    MET C1095      28.854  40.419  40.535  1.00 37.96
ATOM   2081  O    MET C1095      29.993  40.855  40.670  1.00 39.00
ATOM   2082  CB   MET C1095      28.772  37.969  40.755  1.00 39.83
ATOM   2083  CG   MET C1095      28.636  36.767  41.644  1.00 42.24
ATOM   2084  SD   MET C1095      28.588  35.160  40.819  1.00 43.52
ATOM   2085  CE   MET C1095      29.492  34.284  42.084  1.00 43.64
ATOM   2086  N    LEU C1096      28.128  40.770  39.489  1.00 38.63
ATOM   2087  CA   LEU C1096      28.592  41.811  38.583  1.00 40.32
ATOM   2088  C    LEU C1096      28.726  43.159  39.300  1.00 45.56
ATOM   2089  O    LEU C1096      29.676  43.913  39.027  1.00 43.98
ATOM   2090  CB   LEU C1096      27.705  41.881  37.363  1.00 38.78
ATOM   2091  CG   LEU C1096      27.859  40.853  36.254  1.00 36.87
ATOM   2092  CD1  LEU C1096      26.623  40.917  35.364  1.00 37.20
ATOM   2093  CD2  LEU C1096      29.157  41.041  35.484  1.00 36.07
ATOM   2094  N    GLU C1097      27.840  43.531  40.207  1.00 50.71
ATOM   2095  CA   GLU C1097      27.911  44.809  40.888  1.00 56.21
ATOM   2096  C    GLU C1097      28.997  45.073  41.913  1.00 57.95
ATOM   2097  O    GLU C1097      29.115  46.249  42.308  1.00 58.28
ATOM   2098  CB   GLU C1097      26.511  45.083  41.496  1.00 59.17
ATOM   2099  CG   GLU C1097      25.588  45.556  40.362  1.00 62.97
ATOM   2100  CD   GLU C1097      25.880  46.999  39.984  1.00 65.89
ATOM   2101  OE1  GLU C1097      26.772  47.604  40.633  1.00 67.34
ATOM   2102  OE2  GLU C1097      25.159  47.465  39.064  1.00 68.13
ATOM   2103  N    GLU C1098      29.832  44.134  42.340  1.00 59.64
```

FIG. 5KK

```
ATOM   2104  CA   GLU C1098      30.923  44.413  43.251  1.00 62.30
ATOM   2105  C    GLU C1098      32.317  44.135  42.709  1.00 61.47
ATOM   2106  O    GLU C1098      32.699  43.098  42.165  1.00 63.11
ATOM   2107  CB   GLU C1098      30.721  43.618  44.546  1.00 63.71
ATOM   2108  CG   GLU C1098      30.447  42.141  44.289  1.00 64.85
ATOM   2109  CD   GLU C1098      30.147  41.457  45.616  1.00 66.52
ATOM   2110  OE1  GLU C1098      29.135  41.807  46.262  1.00 67.90
ATOM   2111  OE2  GLU C1098      30.943  40.587  46.021  1.00 67.37
ATOM   2112  N    ARG C1099      33.234  45.047  43.011  1.00 62.10
ATOM   2113  CA   ARG C1099      34.637  45.044  42.675  1.00 60.00
ATOM   2114  C    ARG C1099      35.404  43.736  42.782  1.00 58.76
ATOM   2115  O    ARG C1099      36.433  43.655  42.072  1.00 60.07
ATOM   2116  CB   ARG C1099      35.327  46.048  43.623  1.00 61.21
ATOM   2117  N    LYS C1100      35.024  42.747  43.594  1.00 56.32
ATOM   2118  CA   LYS C1100      35.843  41.536  43.624  1.00 55.34
ATOM   2119  C    LYS C1100      35.881  40.863  42.258  1.00 53.59
ATOM   2120  O    LYS C1100      35.083  41.060  41.366  1.00 53.08
ATOM   2121  CB   LYS C1100      35.416  40.629  44.760  1.00 56.50
ATOM   2122  CG   LYS C1100      34.580  39.418  44.451  1.00 57.25
ATOM   2123  CD   LYS C1100      33.972  38.745  45.669  1.00 57.47
ATOM   2124  CE   LYS C1100      34.923  37.780  46.342  1.00 59.43
ATOM   2125  NZ   LYS C1100      34.265  36.502  46.768  1.00 59.87
ATOM   2126  N    THR C1101      36.911  40.037  42.055  1.00 53.38
ATOM   2127  CA   THR C1101      37.201  39.285  40.840  1.00 48.64
ATOM   2128  C    THR C1101      36.746  37.835  41.057  1.00 46.24
ATOM   2129  O    THR C1101      37.229  37.252  42.047  1.00 45.91
ATOM   2130  CB   THR C1101      38.694  39.327  40.489  1.00 47.56
ATOM   2131  OG1  THR C1101      39.019  40.606  39.939  1.00 46.44
ATOM   2132  CG2  THR C1101      39.094  38.266  39.469  1.00 45.84
ATOM   2133  N    TYR C1102      35.884  37.335  40.167  1.00 41.77
ATOM   2134  CA   TYR C1102      35.366  35.978  40.426  1.00 40.39
ATOM   2135  C    TYR C1102      36.129  34.910  39.691  1.00 40.66
ATOM   2136  O    TYR C1102      36.056  33.736  40.095  1.00 42.76
ATOM   2137  CB   TYR C1102      33.858  35.910  40.100  1.00 38.06
ATOM   2138  CG   TYR C1102      33.074  36.622  41.174  1.00 39.42
ATOM   2139  CD1  TYR C1102      32.812  37.986  41.085  1.00 40.49
ATOM   2140  CD2  TYR C1102      32.609  35.932  42.296  1.00 40.20
ATOM   2141  CE1  TYR C1102      32.107  38.642  42.061  1.00 41.47
ATOM   2142  CE2  TYR C1102      31.904  36.580  43.294  1.00 41.62
ATOM   2143  CZ   TYR C1102      31.672  37.936  43.168  1.00 42.72
ATOM   2144  OH   TYR C1102      30.961  38.602  44.148  1.00 42.88
ATOM   2145  N    VAL C1103      36.753  35.276  38.570  1.00 40.18
ATOM   2146  CA   VAL C1103      37.580  34.400  37.772  1.00 38.79
ATOM   2147  C    VAL C1103      38.963  35.061  37.561  1.00 40.96
ATOM   2148  O    VAL C1103      39.070  36.083  36.864  1.00 41.22
ATOM   2149  CB   VAL C1103      37.038  34.042  36.390  1.00 39.03
ATOM   2150  CG1  VAL C1103      37.961  33.001  35.738  1.00 35.66
ATOM   2151  CG2  VAL C1103      35.597  33.463  36.439  1.00 36.18
ATOM   2152  N    ASN C1104      39.993  34.484  38.154  1.00 41.19
ATOM   2153  CA   ASN C1104      41.366  34.972  38.131  1.00 43.68
ATOM   2154  C    ASN C1104      42.006  34.745  36.765  1.00 42.39
ATOM   2155  O    ASN C1104      42.161  33.569  36.390  1.00 46.58
ATOM   2156  CB   ASN C1104      42.212  34.184  39.143  1.00 44.69
ATOM   2157  CG   ASN C1104      43.661  34.686  39.140  1.00 49.43
ATOM   2158  OD1  ASN C1104      44.630  33.918  38.841  1.00 49.14
ATOM   2159  ND2  ASN C1104      43.739  35.989  39.460  1.00 47.59
ATOM   2160  N    THR C1105      42.337  35.771  36.035  1.00 38.71
```

FIG. 5LL

```
ATOM   2161  CA  THR C1105      42.937  35.664  34.723  1.00 38.30
ATOM   2162  C   THR C1105      44.389  36.105  34.806  1.00 37.67
ATOM   2163  O   THR C1105      44.998  36.087  33.725  1.00 39.99
ATOM   2164  CB  THR C1105      42.272  36.465  33.585  1.00 36.40
ATOM   2165  OG1 THR C1105      42.212  37.883  33.885  1.00 38.39
ATOM   2166  CG2 THR C1105      40.875  35.906  33.439  1.00 35.66
ATOM   2167  N   THR C1106      44.918  36.386  35.989  1.00 39.77
ATOM   2168  CA  THR C1106      46.306  36.915  36.002  1.00 43.19
ATOM   2169  C   THR C1106      47.368  35.852  36.199  1.00 44.10
ATOM   2170  O   THR C1106      47.129  34.854  36.896  1.00 45.27
ATOM   2171  CB  THR C1106      46.445  38.022  37.058  1.00 47.23
ATOM   2172  OG1 THR C1106      46.210  37.460  38.369  1.00 52.99
ATOM   2173  CG2 THR C1106      45.403  39.104  36.949  1.00 45.90
ATOM   2174  N   LEU C1107      48.527  35.962  35.531  1.00 42.56
ATOM   2175  CA  LEU C1107      49.593  34.961  35.679  1.00 44.02
ATOM   2176  C   LEU C1107      50.420  35.168  36.946  1.00 46.86
ATOM   2177  O   LEU C1107      50.888  36.295  37.127  1.00 49.56
ATOM   2178  CB  LEU C1107      50.539  34.986  34.483  1.00 38.92
ATOM   2179  CG  LEU C1107      49.970  34.778  33.106  1.00 37.89
ATOM   2180  CD1 LEU C1107      51.073  34.991  32.082  1.00 39.13
ATOM   2181  CD2 LEU C1107      49.400  33.350  32.925  1.00 34.26
ATOM   2182  N   TYR C1108      50.605  34.176  37.803  1.00 49.68
ATOM   2183  CA  TYR C1108      51.362  34.337  39.032  1.00 53.06
ATOM   2184  C   TYR C1108      52.666  33.527  38.953  1.00 51.34
ATOM   2185  O   TYR C1108      53.677  34.091  38.558  1.00 52.57
ATOM   2186  CB  TYR C1108      50.645  33.861  40.328  1.00 54.61
ATOM   2187  CG  TYR C1108      49.538  34.857  40.622  1.00 56.02
ATOM   2188  CD1 TYR C1108      48.208  34.511  40.387  1.00 56.47
ATOM   2189  CD2 TYR C1108      49.864  36.137  41.055  1.00 56.41
ATOM   2190  CE1 TYR C1108      47.207  35.441  40.597  1.00 56.50
ATOM   2191  CE2 TYR C1108      48.864  37.072  41.271  1.00 57.46
ATOM   2192  CZ  TYR C1108      47.544  36.698  41.044  1.00 57.18
ATOM   2193  OH  TYR C1108      46.577  37.639  41.267  1.00 58.64
ATOM   2194  N   GLU C1109      52.585  32.293  39.382  1.00 50.07
ATOM   2195  CA  GLU C1109      53.718  31.412  39.346  1.00 50.65
ATOM   2196  C   GLU C1109      53.548  30.323  38.275  1.00 48.97
ATOM   2197  O   GLU C1109      54.587  29.965  37.719  1.00 47.87
ATOM   2198  CB  GLU C1109      53.958  30.616  40.626  1.00 53.87
ATOM   2199  CG  GLU C1109      53.835  31.284  41.965  1.00 58.53
ATOM   2200  CD  GLU C1109      54.896  32.352  42.202  1.00 60.45
ATOM   2201  OE1 GLU C1109      56.092  31.991  42.113  1.00 61.68
ATOM   2202  OE2 GLU C1109      54.482  33.514  42.480  1.00 61.69
ATOM   2203  N   LYS C1110      52.345  29.727  38.224  1.00 47.13
ATOM   2204  CA  LYS C1110      52.186  28.577  37.324  1.00 45.74
ATOM   2205  C   LYS C1110      50.816  28.638  36.645  1.00 42.35
ATOM   2206  O   LYS C1110      49.924  29.183  37.270  1.00 41.09
ATOM   2207  CB  LYS C1110      52.400  27.320  38.151  1.00 48.67
ATOM   2208  CG  LYS C1110      52.564  26.005  37.440  1.00 53.26
ATOM   2209  CD  LYS C1110      53.174  24.877  38.287  1.00 56.04
ATOM   2210  CE  LYS C1110      54.685  25.087  38.489  1.00 58.45
ATOM   2211  NZ  LYS C1110      55.447  23.870  38.929  1.00 58.97
ATOM   2212  N   PHE C1111      50.666  28.295  35.359  1.00 37.18
ATOM   2213  CA  PHE C1111      49.325  28.434  34.823  1.00 36.07
ATOM   2214  C   PHE C1111      49.163  27.464  33.658  1.00 33.65
ATOM   2215  O   PHE C1111      49.926  27.605  32.736  1.00 31.39
ATOM   2216  CB  PHE C1111      48.962  29.880  34.438  1.00 36.60
ATOM   2217  CG  PHE C1111      47.531  30.157  34.143  1.00 37.58
```

FIG. 5MM

```
ATOM   2218  CD1  PHE C1111     46.754  30.911  35.026  1.00 40.75
ATOM   2219  CD2  PHE C1111     46.914  29.636  33.009  1.00 37.53
ATOM   2220  CE1  PHE C1111     45.395  31.140  34.795  1.00 40.10
ATOM   2221  CE2  PHE C1111     45.582  29.887  32.758  1.00 37.72
ATOM   2222  CZ   PHE C1111     44.824  30.635  33.643  1.00 38.68
ATOM   2223  N    THR C1112     46.115  26.664  33.719  1.00 28.79
ATOM   2224  CA   THR C1112     47.688  25.828  32.634  1.00 31.45
ATOM   2225  C    THR C1112     46.183  26.063  32.377  1.00 30.94
ATOM   2226  O    THR C1112     45.468  26.129  33.377  1.00 29.01
ATOM   2227  CB   THR C1112     47.744  24.317  33.099  1.00 32.34
ATOM   2228  OG1  THR C1112     49.026  24.124  33.723  1.00 35.99
ATOM   2229  CG2  THR C1112     47.738  23.401  31.909  1.00 32.22
ATOM   2230  N    TYR C1113     45.708  26.099  31.158  1.00 28.73
ATOM   2231  CA   TYR C1113     44.309  26.076  30.840  1.00 28.29
ATOM   2232  C    TYR C1113     43.709  24.640  30.942  1.00 31.34
ATOM   2233  O    TYR C1113     44.388  23.615  30.928  1.00 25.50
ATOM   2234  CB   TYR C1113     44.203  26.353  29.330  1.00 27.79
ATOM   2235  CG   TYR C1113     44.656  27.778  29.016  1.00 29.11
ATOM   2236  CD1  TYR C1113     45.753  27.954  28.181  1.00 30.15
ATOM   2237  CD2  TYR C1113     44.032  28.897  29.544  1.00 27.99
ATOM   2238  CE1  TYR C1113     46.199  29.241  27.868  1.00 31.57
ATOM   2239  CE2  TYR C1113     44.460  30.198  29.201  1.00 30.17
ATOM   2240  CZ   TYR C1113     45.571  30.354  28.371  1.00 30.26
ATOM   2241  OH   TYR C1113     46.068  31.611  28.045  1.00 30.20
ATOM   2242  N    ALA C1114     42.398  24.636  31.120  1.00 29.12
ATOM   2243  CA   ALA C1114     41.638  23.395  31.035  1.00 30.29
ATOM   2244  C    ALA C1114     41.882  22.872  29.625  1.00 30.26
ATOM   2245  O    ALA C1114     41.791  23.661  28.680  1.00 30.70
ATOM   2246  CB   ALA C1114     40.127  23.678  31.199  1.00 30.91
ATOM   2247  N    GLY C1115     42.135  21.544  29.515  1.00 28.43
ATOM   2248  CA   GLY C1115     42.371  21.045  28.199  1.00 30.36
ATOM   2249  C    GLY C1115     41.138  20.933  27.334  1.00 34.03
ATOM   2250  O    GLY C1115     39.913  20.801  27.653  1.00 35.50
ATOM   2251  N    ILE C1116     41.445  21.017  26.046  1.00 35.79
ATOM   2252  CA   ILE C1116     40.554  20.877  24.918  1.00 41.16
ATOM   2253  C    ILE C1116     40.987  19.601  24.199  1.00 48.93
ATOM   2254  CB   ILE C1116     40.660  21.990  23.877  1.00 40.53
ATOM   2255  CG1  ILE C1116     40.332  23.381  24.419  1.00 39.34
ATOM   2256  CG2  ILE C1116     39.797  21.709  22.629  1.00 40.56
ATOM   2257  CD1  ILE C1116     40.844  24.462  23.474  1.00 39.48
ATOM   2258  N    ASP C1117     40.096  18.690  23.816  1.00 56.34
ATOM   2259  CA   ASP C1117     40.671  17.809  22.759  1.00 64.41
ATOM   2260  C    ASP C1117     39.582  17.226  21.862  1.00 67.05
ATOM   2261  O    ASP C1117     38.632  16.639  22.384  1.00 66.11
ATOM   2262  CB   ASP C1117     41.552  16.679  23.243  1.00 66.12
ATOM   2263  CG   ASP C1117     42.980  17.054  23.608  1.00 68.11
ATOM   2264  OD1  ASP C1117     43.730  17.676  22.830  1.00 69.52
ATOM   2265  OD2  ASP C1117     43.216  16.706  24.787  1.00 68.31
ATOM   2266  N    CYS C1118     39.775  17.421  20.548  1.00 71.27
ATOM   2267  CA   CYS C1118     38.800  16.948  19.563  1.00 75.06
ATOM   2268  C    CYS C1118     39.057  17.522  18.165  1.00 77.90
ATOM   2269  CB   CYS C1118     37.387  17.351  19.997  1.00 74.91
ATOM   2270  N    SER C1119     38.094  17.334  17.244  1.00 81.20
ATOM   2271  CA   SER C1119     38.055  17.960  15.924  1.00 83.28
ATOM   2272  C    SER C1119     37.335  17.232  14.787  1.00 84.56
ATOM   2273  O    SER C1119     37.930  16.898  13.740  1.00 85.44
ATOM   2274  CB   SER C1119     39.493  18.300  15.476  1.00 83.21
```

FIG. 5NN

```
ATOM    2275  N    ALA C1120      36.028  16.990  14.863  1.00 85.16
ATOM    2276  CA   ALA C1120      35.171  16.384  13.874  1.00 84.89
ATOM    2277  C    ALA C1120      34.722  14.957  14.213  1.00 85.19
ATOM    2278  O    ALA C1120      33.876  14.494  13.396  1.00 85.38
ATOM    2279  CB   ALA C1120      35.714  16.345  12.447  1.00 84.84
TER
HETATM  2280  C1   IN3 D    1     27.737  34.907  12.224  1.00 40.84
HETATM  2281  N2   IN3 D    1     28.220  33.661  12.185  1.00 40.67
HETATM  2282  C3   IN3 D    1     27.362  32.629  12.233  1.00 40.61
HETATM  2283  C4   IN3 D    1     25.970  32.787  12.323  1.00 41.94
HETATM  2284  C5   IN3 D    1     25.529  34.130  12.362  1.00 41.03
HETATM  2285  N6   IN3 D    1     26.426  35.160  12.315  1.00 40.65
HETATM  2287  N8   IN3 D    1     27.727  31.299  12.203  1.00 42.23
HETATM  2288  C9   IN3 D    1     26.517  30.664  12.312  1.00 42.50
HETATM  2289  C10  IN3 D    1     25.373  31.506  12.348  1.00 44.61
HETATM  2291  N12  IN3 D    1     24.231  34.490  12.467  1.00 43.99
HETATM  2292  C13  IN3 D    1     23.982  30.977  12.436  1.00 47.57
HETATM  2293  C14  IN3 D    1     29.096  30.727  12.190  1.00 42.52
HETATM  2294  C15  IN3 D    1     22.960  31.497  13.194  1.00 50.46
HETATM  2295  C16  IN3 D    1     21.667  30.935  13.250  1.00 51.20
HETATM  2296  C17  IN3 D    1     21.337  29.804  12.531  1.00 51.31
HETATM  2297  C18  IN3 D    1     22.357  29.258  11.751  1.00 51.58
HETATM  2298  C19  IN3 D    1     23.637  29.839  11.712  1.00 51.00
HETATM  2302  N23  IN3 D    1     20.099  29.245  12.581  1.00 52.79
HETATM  2303  S24  IN3 D    1     19.137  29.209  13.847  1.00 53.21
HETATM  2304  O25  IN3 D    1     19.809  29.557  15.058  1.00 54.86
HETATM  2305  O26  IN3 D    1     18.402  27.997  13.940  1.00 52.02
HETATM  2306  C27  IN3 D    1     17.984  30.563  13.554  1.00 59.14
HETATM  2307  C28  IN3 D    1     17.058  30.565  12.515  1.00 62.44
HETATM  2308  C29  IN3 D    1     16.171  31.631  12.344  1.00 63.41
HETATM  2309  C30  IN3 D    1     16.219  32.721  13.201  1.00 61.99
HETATM  2310  C31  IN3 D    1     17.146  32.728  14.233  1.00 61.19
HETATM  2311  C32  IN3 D    1     18.012  31.655  14.412  1.00 59.69
HETATM  2312  CL33 IN3 D    1     17.000  29.190  11.437  1.00 72.20
HETATM  2313  CL34 IN3 D    1     14.971  31.634  11.070  1.00 66.32
HETATM  2317  F38  IN3 D    1     22.188  28.164  10.970  1.00 50.23
HETATM  2318  C39  IN3 D    1     29.429  30.465  13.689  1.00 41.55
HETATM  2319  C40  IN3 D    1     30.719  29.713  13.975  1.00 41.76
HETATM  2320  C41  IN3 D    1     30.922  28.491  13.060  1.00 42.34
HETATM  2321  C42  IN3 D    1     30.611  28.800  11.579  1.00 44.10
HETATM  2322  C43  IN3 D    1     29.231  29.447  11.376  1.00 43.74
HETATM  2331  C52  IN3 D    1     32.457  27.054  14.408  1.00 40.98
HETATM  2332  C53  IN3 D    1     33.702  26.161  14.218  1.00 39.93
HETATM  2333  N54  IN3 D    1     34.865  27.024  14.047  1.00 40.92
HETATM  2334  C55  IN3 D    1     34.719  27.865  12.858  1.00 41.55
HETATM  2335  C56  IN3 D    1     33.437  28.707  12.946  1.00 41.49
HETATM  2336  N57  IN3 D    1     32.249  27.891  13.211  1.00 41.23
HETATM  2346  C67  IN3 D    1     36.230  26.430  14.126  1.00 38.95
TER
ATOM    2355  O    HOH W    1     31.108  33.861  12.284  1.00 32.88
ATOM    2356  O    HOH W    2     26.872  17.118  31.780  1.00 27.53
ATOM    2357  O    HOH W    3     33.552  31.769  15.218  1.00 24.69
ATOM    2358  O    HOH W    4     47.567  25.314  28.603  1.00 31.73
ATOM    2359  O    HOH W    5      2.429  17.063  30.925  1.00 30.32
ATOM    2360  O    HOH W    7     33.908  23.176  25.246  1.00 32.79
ATOM    2361  O    HOH W    8     16.942  20.674  27.837  1.00 29.27
ATOM    2362  O    HOH W    9     41.194  27.270  31.243  1.00 27.50
```

FIG. 500

```
ATOM   2363  O   HOH W   10      36.797  18.417  32.828  1.00 30.03
ATOM   2364  O   HOH W   11      28.851  18.044  36.031  1.00 31.02
ATOM   2365  O   HOH W   12      15.509  25.207  20.371  1.00 36.36
ATOM   2366  O   HOH W   13       9.416  22.554  31.309  1.00 34.74
ATOM   2367  O   HOH W   14      24.583  41.060  16.124  1.00 44.69
ATOM   2368  O   HOH W   15       7.357  41.316  15.797  1.00 65.05
ATOM   2369  O   HOH W   16      40.089  39.018  35.286  1.00 43.58
ATOM   2370  O   HOH W   17      42.573  39.050  31.498  1.00 33.36
ATOM   2371  O   HOH W   18      18.935  40.500  18.279  1.00 34.03
ATOM   2372  O   HOH W   19      13.481  27.068  41.482  1.00 45.27
ATOM   2373  O   HOH W   20      19.798  23.284  27.046  1.00 32.39
ATOM   2374  O   HOH W   22      13.750  26.546  29.238  1.00 33.61
ATOM   2375  O   HOH W   23      15.599  37.531  37.224  1.00 41.73
ATOM   2376  O   HOH W   24      45.162  20.392  30.028  1.00 51.51
ATOM   2377  O   HOH W   25      33.164  26.427  17.812  1.00 30.96
ATOM   2378  O   HOH W   27      25.096  40.967  30.617  1.00 31.07
ATOM   2379  O   HOH W   28      44.306  23.553  33.708  1.00 44.45
ATOM   2380  O   HOH W   29      14.071  17.249  33.601  1.00 32.43
ATOM   2381  O   HOH W   30      30.157  24.039  23.053  1.00 31.23
ATOM   2382  O   HOH W   31      21.111  43.623  15.597  1.00 74.93
ATOM   2383  O   HOH W   33      19.327  17.632  28.859  1.00 33.09
ATOM   2384  O   HOH W   34      13.241  23.665  39.267  1.00 41.89
ATOM   2385  O   HOH W   35      31.519  44.776  18.549  1.00 43.36
ATOM   2386  O   HOH W   36      34.470  39.819  38.307  1.00 52.30
ATOM   2387  O   HOH W   37      19.740  20.765  27.651  1.00 65.54
ATOM   2388  O   HOH W   38      44.917  36.546  20.426  1.00 59.90
ATOM   2389  O   HOH W   40      17.011   9.839  35.866  1.00 47.22
ATOM   2390  O   HOH W   41      38.945  20.370  30.087  1.00 25.50
ATOM   2391  O   HOH W   43      46.179  22.872  28.085  1.00 39.76
ATOM   2392  O   HOH W   44      33.414  46.660  18.569  1.00 52.18
ATOM   2393  O   HOH W   45      25.781  19.393  41.795  1.00 39.77
ATOM   2394  O   HOH W   46      25.879  14.880  30.825  1.00 26.83
ATOM   2395  O   HOH W   47      12.674  31.920  35.287  1.00 41.22
ATOM   2396  O   HOH W   48      36.038  20.519  22.613  1.00 40.75
ATOM   2397  O   HOH W   49       9.232  35.876  28.692  1.00 40.36
ATOM   2398  O   HOH W   50      36.218  20.561  20.320  1.00 41.55
ATOM   2399  O   HOH W   54      27.796  43.597  11.505  1.00 56.18
ATOM   2400  O   HOH W   56      43.257  28.114  21.417  1.00 40.56
ATOM   2401  O   HOH W   57      42.324  44.229  29.443  1.00 56.40
ATOM   2402  O   HOH W   58      31.439  22.023  21.413  1.00 32.43
ATOM   2403  O   HOH W   59      49.313  32.007  37.867  1.00 46.71
ATOM   2404  O   HOH W   60      14.875  35.132  15.522  1.00 39.98
ATOM   2405  O   HOH W   62      20.722   5.005  29.475  1.00 39.73
ATOM   2406  O   HOH W   63      45.974  43.256  29.290  1.00 41.18
ATOM   2407  O   HOH W   64      42.241  38.248  37.028  1.00 43.70
ATOM   2408  O   HOH W   65      32.550  42.002  39.832  1.00 36.99
ATOM   2409  O   HOH W   67      39.110  46.531  21.311  1.00 37.71
ATOM   2410  O   HOH W   68      24.108  20.905  21.953  1.00 53.77
ATOM   2411  O   HOH W   69       1.460  21.994  31.199  1.00 37.30
ATOM   2412  O   HOH W   70      49.466  21.211  34.770  1.00 51.34
ATOM   2413  O   HOH W   71      36.003  21.023  42.825  1.00 40.91
ATOM   2414  O   HOH W   73      22.188  25.684   4.901  1.00 54.10
ATOM   2415  O   HOH W   74      39.079  46.157  42.492  1.00 62.53
ATOM   2416  O   HOH W   75      40.067  30.895  33.482  1.00 47.79
ATOM   2417  O   HOH W   76      46.668  20.370  34.397  1.00 41.58
ATOM   2418  O   HOH W   78      11.682  32.018  39.657  1.00 44.53
ATOM   2419  O   HOH W   79      20.567  30.929  42.014  1.00 56.17
```

FIG. 5PP

```
ATOM   2420  O   HOH W  80     22.313  16.019  43.949  1.00 47.96
ATOM   2421  O   HOH W  83     33.379  32.767  48.175  1.00 44.70
ATOM   2422  O   HOH W  84     28.448  47.110  11.329  1.00 72.32
ATOM   2423  O   HOH W  85     11.988  40.527  14.366  1.00 57.96
ATOM   2424  O   HOH W  86     11.100  37.338  30.951  1.00 55.75
ATOM   2425  O   HOH W  87     32.424  25.662  10.927  1.00 60.85
ATOM   2426  O   HOH W  88     40.553  21.024  36.981  1.00 56.71
ATOM   2427  O   HOH W  89     20.806  40.663  41.692  1.00 49.92
ATOM   2428  O   HOH W  90     23.126  21.071  24.679  1.00 28.98
ATOM   2429  O   HOH W  91     21.847  27.668  22.076  1.00 39.04
ATOM   2430  O   HOH W  92     17.442  12.682  22.568  1.00 42.46
ATOM   2431  O   HOH W  94     10.365  22.725  38.862  1.00 42.24
ATOM   2432  O   HOH W  96     12.915  13.110  35.504  1.00 43.57
ATOM   2433  O   HOH W  97     11.437  18.561  35.709  1.00 49.64
ATOM   2434  O   HOH W  98     18.202  17.009  21.807  1.00 60.40
ATOM   2435  O   HOH W  99     13.090  22.057  22.029  1.00 44.65
ATOM   2436  O   HOH W 100     13.782   3.003  30.101  1.00 45.94
ATOM   2437  O   HOH W 101     37.114  30.510  14.091  1.00 54.40
ATOM   2438  O   HOH W 102     39.281  19.995  32.505  1.00 38.67
ATOM   2439  O   HOH W 103     19.163  41.538  33.907  1.00 49.16
ATOM   2440  O   HOH W 105      8.161  24.650  30.444  1.00 38.87
ATOM   2441  O   HOH W 106     19.044  34.146  43.247  1.00 36.17
ATOM   2442  O   HOH W 107     52.411  29.944  20.957  1.00 47.78
ATOM   2443  O   HOH W 109     40.926  37.945  21.207  1.00 57.61
ATOM   2444  O   HOH W 110     23.910  22.805  45.525  1.00 56.43
ATOM   2445  O   HOH W 111     23.876  43.384  19.810  1.00 29.77
ATOM   2446  O   HOH W 112      6.751  36.672  21.579  1.00 62.88
ATOM   2447  O   HOH W 113     43.463  27.806  35.372  1.00 49.32
ATOM   2448  O   HOH W 114     33.230  32.283  12.794  1.00 37.37
ATOM   2449  O   HOH W 115     39.120  18.996  40.839  1.00 82.49
ATOM   2450  O   HOH W 116     17.786  13.772  37.357  1.00 49.91
ATOM   2451  O   HOH W 117     20.655   9.465  38.822  1.00 43.82
ATOM   2452  O   HOH W 118      7.544  39.794  24.678  1.00 56.43
ATOM   2453  O   HOH W 119     34.363  21.476   9.358  1.00 64.39
ATOM   2454  O   HOH W 120     14.923  37.925  31.147  1.00 51.98
ATOM   2455  O   HOH W 121     14.386  25.644  36.407  1.00 47.28
ATOM   2456  O   HOH W 122     33.578  21.114  23.402  1.00 36.98
ATOM   2457  O   HOH W 123     42.616  19.765  31.993  1.00 46.67
ATOM   2458  O   HOH W 124      0.324  31.122  29.775  1.00 85.67
ATOM   2459  O   HOH W 125     44.223  21.073  33.792  1.00 58.84
ATOM   2460  O   HOH W 126     13.220  29.507  33.957  1.00 42.26
ATOM   2461  O   HOH W 127     24.661   6.250  44.308  1.00 53.58
ATOM   2462  O   HOH W 130     37.555  26.025  18.301  1.00 50.21
ATOM   2463  O   HOH W 131     29.409  15.521  23.790  1.00 37.37
ATOM   2464  O   HOH W 134     37.198  41.960  35.518  1.00 40.19
ATOM   2465  O   HOH W 135     38.741  36.516  21.186  1.00 31.33
ATOM   2466  O   HOH W 136     20.039  45.048  11.998  1.00 67.09
ATOM   2467  O   HOH W 137     44.865  39.383  33.992  1.00 42.87
ATOM   2468  O   HOH W 138     47.499  41.543  34.693  1.00 41.95
ATOM   2469  O   HOH W 139     14.470  39.588  29.214  1.00 39.88
ATOM   2470  O   HOH W 140     25.148  21.128  18.186  1.00 55.16
ATOM   2471  O   HOH W 141     19.506   9.850  24.839  1.00 56.90
ATOM   2472  O   HOH W 142     39.082   7.569  29.845  1.00 50.85
ATOM   2473  O   HOH W 143     37.915   8.580  37.497  1.00 73.18
ATOM   2474  O   HOH W 144     37.234  11.075  36.059  1.00 55.17
ATOM   2475  O   HOH W 145     18.909  16.767  43.975  1.00 45.07
ATOM   2476  O   HOH W 146     53.564  36.062  20.842  1.00 35.39
```

FIG. 5QQ

```
ATOM   2477  O   HOH W 147     21.172  42.848  12.347  1.00 52.85
TER
```

FIG. 5RR

```
ATOM      1  N   VAL A 818      77.717  45.877   1.677  1.00100.00
ATOM      2  CA  VAL A 818      76.698  46.966   1.561  1.00100.00
ATOM      3  C   VAL A 818      75.278  46.411   1.674  1.00100.00
ATOM      4  O   VAL A 818      74.803  46.162   2.781  1.00100.00
ATOM      5  CB  VAL A 818      76.875  47.697   0.239  1.00 68.23
ATOM      9  N   LEU A 819      74.617  46.228   0.530  1.00100.00
ATOM     10  CA  LEU A 819      73.248  45.707   0.456  1.00100.00
ATOM     11  C   LEU A 819      72.629  45.997  -0.918  1.00100.00
ATOM     12  O   LEU A 819      71.622  46.689  -1.003  1.00100.00
ATOM     13  CB  LEU A 819      72.369  46.345   1.536  1.00100.00
ATOM     14  CG  LEU A 819      70.873  46.053   1.525  1.00100.00
ATOM     15  CD1 LEU A 819      70.592  44.975   2.511  1.00100.00
ATOM     16  CD2 LEU A 819      70.078  47.283   1.865  1.00100.00
ATOM     18  N   ASP A 820      73.234  45.474  -1.984  1.00100.00
ATOM     19  CA  ASP A 820      72.753  45.676  -3.359  1.00100.00
ATOM     20  C   ASP A 820      71.292  46.104  -3.464  1.00100.00
ATOM     21  O   ASP A 820      70.399  45.421  -2.983  1.00100.00
ATOM     22  CB  ASP A 820      72.969  44.396  -4.177  1.00 99.21
ATOM     23  CG  ASP A 820      71.872  44.160  -5.218  1.00 99.21
ATOM     24  OD1 ASP A 820      71.584  42.982  -5.509  1.00 99.21
ATOM     25  OD2 ASP A 820      71.303  45.140  -5.750  1.00 99.21
ATOM     27  N   TRP A 821      71.050  47.227  -4.126  1.00 93.11
ATOM     28  CA  TRP A 821      69.694  47.719  -4.268  1.00 93.11
ATOM     29  C   TRP A 821      68.716  46.617  -4.650  1.00 93.11
ATOM     30  O   TRP A 821      67.904  46.199  -3.849  1.00 93.11
ATOM     31  CB  TRP A 821      69.639  48.863  -5.283  1.00 97.87
ATOM     32  CG  TRP A 821      68.703  49.927  -4.847  1.00 97.87
ATOM     33  CD1 TRP A 821      68.605  50.452  -3.597  1.00 97.87
ATOM     34  CD2 TRP A 821      67.667  50.542  -5.622  1.00 97.87
ATOM     35  NE1 TRP A 821      67.567  51.352  -3.537  1.00 97.87
ATOM     36  CE2 TRP A 821      66.974  51.429  -4.766  1.00 97.87
ATOM     37  CE3 TRP A 821      67.255  50.429  -6.949  1.00 97.87
ATOM     38  CZ2 TRP A 821      65.897  52.197  -5.193  1.00 97.87
ATOM     39  CZ3 TRP A 821      66.180  51.192  -7.374  1.00 97.87
ATOM     40  CH2 TRP A 821      65.512  52.065  -6.496  1.00 97.87
ATOM     43  N   ASN A 822      68.798  46.140  -5.896  1.00100.00
ATOM     44  CA  ASN A 822      67.901  45.077  -6.364  1.00100.00
ATOM     45  C   ASN A 822      67.686  43.985  -5.314  1.00100.00
ATOM     46  O   ASN A 822      66.545  43.614  -5.030  1.00100.00
ATOM     47  CB  ASN A 822      68.462  44.410  -7.624  1.00 56.29
ATOM     48  CG  ASN A 822      68.707  42.917  -7.427  1.00 56.29
ATOM     49  OD1 ASN A 822      69.755  42.499  -6.902  1.00 56.29
ATOM     50  ND2 ASN A 822      67.739  42.114  -7.837  1.00 56.29
ATOM     54  N   ASP A 823      68.799  43.469  -4.776  1.00 99.96
ATOM     55  CA  ASP A 823      68.825  42.413  -3.756  1.00 99.96
ATOM     56  C   ASP A 823      67.823  42.654  -2.650  1.00 99.96
ATOM     57  O   ASP A 823      67.545  41.765  -1.846  1.00 99.96
ATOM     58  CB  ASP A 823      70.218  42.308  -3.153  1.00100.00
ATOM     60  N   ILE A 824      67.303  43.875  -2.605  1.00 80.08
ATOM     61  CA  ILE A 824      66.315  44.270  -1.616  1.00 80.08
ATOM     62  C   ILE A 824      64.958  44.392  -2.274  1.00 80.08
ATOM     63  O   ILE A 824      64.703  45.359  -2.973  1.00 80.08
ATOM     64  CB  ILE A 824      66.651  45.641  -0.992  1.00100.00
ATOM     65  CG1 ILE A 824      67.806  45.506   0.009  1.00100.00
ATOM     66  CG2 ILE A 824      65.417  46.206  -0.307  1.00100.00
ATOM     67  CD1 ILE A 824      69.048  44.906  -0.577  1.00100.00
```

FIG. 6A

| | | | | | | | | | |
|---|---|---|---|---|---|---|---|---|---|
| ATOM | 69 | N | LYS | A | 825 | 64.098 | 43.404 | -2.036 | 1.00 99.67 |
| ATOM | 70 | CA | LYS | A | 825 | 62.735 | 43.391 | -2.580 | 1.00 99.67 |
| ATOM | 71 | C | LYS | A | 825 | 61.938 | 44.544 | -1.938 | 1.00 99.67 |
| ATOM | 72 | O | LYS | A | 825 | 61.130 | 44.334 | -1.027 | 1.00 99.67 |
| ATOM | 73 | CB | LYS | A | 825 | 62.056 | 42.021 | -2.286 | 1.00 63.59 |
| ATOM | 75 | N | PHE | A | 826 | 62.171 | 45.762 | -2.420 | 1.00 69.32 |
| ATOM | 76 | CA | PHE | A | 826 | 61.502 | 46.933 | -1.875 | 1.00 69.32 |
| ATOM | 77 | C | PHE | A | 826 | 59.977 | 46.823 | -1.994 | 1.00 69.32 |
| ATOM | 78 | O | PHE | A | 826 | 59.500 | 45.922 | -2.684 | 1.00 69.32 |
| ATOM | 79 | CB | PHE | A | 826 | 62.060 | 48.158 | -2.587 | 1.00 99.11 |
| ATOM | 80 | CG | PHE | A | 826 | 63.558 | 48.351 | -2.376 | 1.00 99.11 |
| ATOM | 81 | CD1 | PHE | A | 826 | 64.470 | 47.961 | -3.343 | 1.00 99.11 |
| ATOM | 82 | CD2 | PHE | A | 826 | 64.045 | 48.959 | -1.215 | 1.00 99.11 |
| ATOM | 83 | CE1 | PHE | A | 826 | 65.839 | 48.178 | -3.157 | 1.00 99.11 |
| ATOM | 84 | CE2 | PHE | A | 826 | 65.418 | 49.179 | -1.027 | 1.00 99.11 |
| ATOM | 85 | CZ | PHE | A | 826 | 66.307 | 48.791 | -1.995 | 1.00 99.11 |
| ATOM | 87 | N | GLN | A | 827 | 59.222 | 47.691 | -1.307 | 1.00 70.60 |
| ATOM | 88 | CA | GLN | A | 827 | 57.728 | 47.659 | -1.347 | 1.00 70.60 |
| ATOM | 89 | C | GLN | A | 827 | 57.010 | 49.023 | -1.173 | 1.00 70.60 |
| ATOM | 90 | O | GLN | A | 827 | 57.401 | 49.946 | -1.874 | 1.00 70.60 |
| ATOM | 91 | CB | GLN | A | 827 | 57.178 | 46.624 | -0.337 | 1.00100.00 |
| ATOM | 92 | CG | GLN | A | 827 | 57.627 | 45.151 | -0.598 | 1.00100.00 |
| ATOM | 93 | CD | GLN | A | 827 | 56.797 | 44.413 | -1.665 | 1.00100.00 |
| ATOM | 94 | OE1 | GLN | A | 827 | 55.642 | 44.036 | -1.433 | 1.00100.00 |
| ATOM | 95 | NE2 | GLN | A | 827 | 57.396 | 44.196 | -2.831 | 1.00100.00 |
| ATOM | 99 | N | ASP | A | 828 | 56.000 | 49.149 | -0.278 | 1.00 99.97 |
| ATOM | 100 | CA | ASP | A | 828 | 55.218 | 50.418 | -0.055 | 1.00 99.97 |
| ATOM | 101 | C | ASP | A | 828 | 55.490 | 51.355 | 1.163 | 1.00 99.97 |
| ATOM | 102 | O | ASP | A | 828 | 56.284 | 51.045 | 2.038 | 1.00 99.97 |
| ATOM | 103 | CB | ASP | A | 828 | 53.723 | 50.128 | 0.010 | 1.00100.00 |
| ATOM | 104 | CG | ASP | A | 828 | 53.034 | 50.839 | 1.214 | 1.00100.00 |
| ATOM | 105 | OD1 | ASP | A | 828 | 52.702 | 52.037 | 1.109 | 1.00100.00 |
| ATOM | 106 | OD2 | ASP | A | 828 | 52.834 | 50.215 | 2.280 | 1.00100.00 |
| ATOM | 108 | N | VAL | A | 829 | 54.787 | 52.494 | 1.212 | 1.00100.00 |
| ATOM | 109 | CA | VAL | A | 829 | 54.900 | 53.488 | 2.295 | 1.00100.00 |
| ATOM | 110 | C | VAL | A | 829 | 54.384 | 53.014 | 3.639 | 1.00100.00 |
| ATOM | 111 | O | VAL | A | 829 | 53.683 | 52.012 | 3.703 | 1.00100.00 |
| ATOM | 112 | CB | VAL | A | 829 | 54.162 | 54.786 | 1.912 | 1.00100.00 |
| ATOM | 114 | N | ILE | A | 830 | 54.726 | 53.770 | 4.695 | 1.00 76.50 |
| ATOM | 115 | CA | ILE | A | 830 | 54.342 | 53.500 | 6.102 | 1.00 76.50 |
| ATOM | 116 | C | ILE | A | 830 | 53.685 | 54.717 | 6.782 | 1.00 76.50 |
| ATOM | 117 | O | ILE | A | 830 | 52.464 | 54.830 | 6.808 | 1.00 76.50 |
| ATOM | 118 | CB | ILE | A | 830 | 55.571 | 53.069 | 6.979 | 1.00 83.02 |
| ATOM | 119 | CG1 | ILE | A | 830 | 55.888 | 51.607 | 6.755 | 1.00 83.02 |
| ATOM | 120 | CG2 | ILE | A | 830 | 55.269 | 53.185 | 8.437 | 1.00 83.02 |
| ATOM | 121 | CD1 | ILE | A | 830 | 57.118 | 51.163 | 7.437 | 1.00 83.02 |
| ATOM | 123 | N | GLY | A | 831 | 54.492 | 55.626 | 7.327 | 1.00100.00 |
| ATOM | 124 | CA | GLY | A | 831 | 53.930 | 56.779 | 8.009 | 1.00100.00 |
| ATOM | 125 | C | GLY | A | 831 | 54.664 | 58.090 | 7.811 | 1.00100.00 |
| ATOM | 126 | O | GLY | A | 831 | 54.659 | 58.963 | 8.677 | 1.00100.00 |
| ATOM | 128 | N | GLU | A | 832 | 55.301 | 58.216 | 6.660 | 1.00 46.31 |
| ATOM | 129 | CA | GLU | A | 832 | 56.045 | 59.418 | 6.271 | 1.00 46.31 |
| ATOM | 130 | C | GLU | A | 832 | 57.586 | 59.215 | 6.265 | 1.00 46.31 |
| ATOM | 131 | O | GLU | A | 832 | 58.101 | 58.149 | 5.892 | 1.00 46.31 |
| ATOM | 132 | CB | GLU | A | 832 | 55.668 | 60.618 | 7.158 | 1.00100.00 |
| ATOM | 133 | CG | GLU | A | 832 | 54.587 | 61.531 | 6.557 | 1.00100.00 |
| ATOM | 134 | CD | GLU | A | 832 | 54.197 | 62.702 | 7.473 | 1.00100.00 |

FIG. 6B

| ATOM | 135 | OE1 | GLU | A | 832 | 52.980 | 62.942 | 7.660 | 1.00 | 100.00 |
|------|-----|-----|-----|---|-----|--------|--------|-------|------|--------|
| ATOM | 136 | OE2 | GLU | A | 832 | 55.107 | 63.387 | 8.002 | 1.00 | 100.00 |
| ATOM | 138 | N | GLY | A | 833 | 58.330 | 60.239 | 6.650 | 1.00 | 100.00 |
| ATOM | 139 | CA | GLY | A | 833 | 59.762 | 60.092 | 6.672 | 1.00 | 100.00 |
| ATOM | 140 | C | GLY | A | 833 | 60.311 | 61.410 | 7.090 | 1.00 | 100.00 |
| ATOM | 141 | O | GLY | A | 833 | 60.675 | 61.601 | 8.251 | 1.00 | 100.00 |
| ATOM | 143 | N | ASN | A | 834 | 60.339 | 62.327 | 6.130 | 1.00 | 87.28 |
| ATOM | 144 | CA | ASN | A | 834 | 60.829 | 63.680 | 6.360 | 1.00 | 87.28 |
| ATOM | 145 | C | ASN | A | 834 | 62.306 | 63.520 | 6.639 | 1.00 | 87.28 |
| ATOM | 146 | O | ASN | A | 834 | 62.684 | 62.859 | 7.613 | 1.00 | 87.28 |
| ATOM | 147 | CB | ASN | A | 834 | 60.114 | 64.306 | 7.570 | 1.00 | 100.00 |
| ATOM | 148 | CG | ASN | A | 834 | 60.641 | 65.685 | 7.932 | 1.00 | 100.00 |
| ATOM | 149 | OD1 | ASN | A | 834 | 61.822 | 65.865 | 8.248 | 1.00 | 100.00 |
| ATOM | 150 | ND2 | ASN | A | 834 | 59.751 | 66.671 | 7.903 | 1.00 | 100.00 |
| ATOM | 154 | N | PHE | A | 835 | 63.131 | 64.125 | 5.782 | 1.00 | 68.16 |
| ATOM | 155 | CA | PHE | A | 835 | 64.561 | 64.036 | 5.925 | 1.00 | 68.16 |
| ATOM | 156 | C | PHE | A | 835 | 64.700 | 62.693 | 6.578 | 1.00 | 68.16 |
| ATOM | 157 | O | PHE | A | 835 | 65.138 | 62.586 | 7.733 | 1.00 | 68.16 |
| ATOM | 158 | CB | PHE | A | 835 | 65.073 | 65.139 | 6.840 | 1.00 | 80.78 |
| ATOM | 159 | CG | PHE | A | 835 | 65.317 | 66.447 | 6.135 | 1.00 | 80.78 |
| ATOM | 160 | CD1 | PHE | A | 835 | 64.950 | 67.651 | 6.733 | 1.00 | 80.78 |
| ATOM | 161 | CD2 | PHE | A | 835 | 65.931 | 66.475 | 4.877 | 1.00 | 80.78 |
| ATOM | 162 | CE1 | PHE | A | 835 | 65.190 | 68.856 | 6.097 | 1.00 | 80.78 |
| ATOM | 163 | CE2 | PHE | A | 835 | 66.178 | 67.689 | 4.226 | 1.00 | 80.78 |
| ATOM | 164 | CZ | PHE | A | 835 | 65.805 | 68.881 | 4.838 | 1.00 | 80.78 |
| ATOM | 166 | N | GLY | A | 836 | 64.226 | 61.691 | 5.832 | 1.00 | 100.00 |
| ATOM | 167 | CA | GLY | A | 836 | 64.252 | 60.304 | 6.257 | 1.00 | 100.00 |
| ATOM | 168 | C | GLY | A | 836 | 62.962 | 59.578 | 5.914 | 1.00 | 100.00 |
| ATOM | 169 | O | GLY | A | 836 | 62.314 | 59.012 | 6.792 | 1.00 | 100.00 |
| ATOM | 171 | N | GLN | A | 837 | 62.599 | 59.565 | 4.636 | 1.00 | 88.37 |
| ATOM | 172 | CA | GLN | A | 837 | 61.356 | 58.915 | 4.214 | 1.00 | 88.37 |
| ATOM | 173 | C | GLN | A | 837 | 61.114 | 57.472 | 4.701 | 1.00 | 88.37 |
| ATOM | 174 | O | GLN | A | 837 | 61.739 | 56.544 | 4.186 | 1.00 | 88.37 |
| ATOM | 175 | CB | GLN | A | 837 | 61.206 | 58.983 | 2.666 | 1.00 | 70.59 |
| ATOM | 176 | CG | GLN | A | 837 | 62.424 | 58.531 | 1.876 | 1.00 | 70.59 |
| ATOM | 177 | CD | GLN | A | 837 | 62.484 | 59.097 | 0.437 | 1.00 | 70.59 |
| ATOM | 178 | OE1 | GLN | A | 837 | 63.560 | 59.517 | -0.041 | 1.00 | 70.59 |
| ATOM | 179 | NE2 | GLN | A | 837 | 61.327 | 59.088 | -0.263 | 1.00 | 70.59 |
| ATOM | 183 | N | VAL | A | 838 | 60.211 | 57.302 | 5.687 | 1.00 | 63.61 |
| ATOM | 184 | CA | VAL | A | 838 | 59.835 | 55.959 | 6.213 | 1.00 | 63.61 |
| ATOM | 185 | C | VAL | A | 838 | 58.710 | 55.222 | 5.481 | 1.00 | 63.61 |
| ATOM | 186 | O | VAL | A | 838 | 57.525 | 55.380 | 5.807 | 1.00 | 63.61 |
| ATOM | 187 | CB | VAL | A | 838 | 59.384 | 55.939 | 7.692 | 1.00 | 61.77 |
| ATOM | 188 | CG1 | VAL | A | 838 | 60.243 | 54.967 | 8.446 | 1.00 | 61.77 |
| ATOM | 189 | CG2 | VAL | A | 838 | 59.418 | 57.290 | 8.292 | 1.00 | 61.77 |
| ATOM | 191 | N | LEU | A | 839 | 59.114 | 54.397 | 4.520 | 1.00 | 100.00 |
| ATOM | 192 | CA | LEU | A | 839 | 58.201 | 53.584 | 3.738 | 1.00 | 100.00 |
| ATOM | 193 | C | LEU | A | 839 | 58.399 | 52.107 | 4.098 | 1.00 | 100.00 |
| ATOM | 194 | O | LEU | A | 839 | 59.473 | 51.694 | 4.507 | 1.00 | 100.00 |
| ATOM | 195 | CB | LEU | A | 839 | 58.464 | 53.783 | 2.244 | 1.00 | 100.00 |
| ATOM | 196 | CG | LEU | A | 839 | 58.836 | 55.168 | 1.719 | 1.00 | 100.00 |
| ATOM | 197 | CD1 | LEU | A | 839 | 58.069 | 56.233 | 2.461 | 1.00 | 100.00 |
| ATOM | 198 | CD2 | LEU | A | 839 | 60.323 | 55.367 | 1.853 | 1.00 | 100.00 |
| ATOM | 200 | N | LYS | A | 840 | 57.352 | 51.315 | 3.969 | 1.00 | 58.16 |
| ATOM | 201 | CA | LYS | A | 840 | 57.459 | 49.901 | 4.259 | 1.00 | 58.16 |
| ATOM | 202 | C | LYS | A | 840 | 58.091 | 49.174 | 3.081 | 1.00 | 58.16 |
| ATOM | 203 | O | LYS | A | 840 | 57.837 | 49.497 | 1.943 | 1.00 | 58.16 |

FIG. 6C

| ATOM | 204 | CB  | LYS A 840 | 56.071 | 49.313 | 4.549  | 1.00 | 67.71  |
| ATOM | 205 | CG  | LYS A 840 | 56.075 | 47.809 | 4.810  | 1.00 | 67.71  |
| ATOM | 206 | CD  | LYS A 840 | 55.274 | 47.391 | 6.047  | 1.00 | 67.71  |
| ATOM | 207 | CE  | LYS A 840 | 55.467 | 45.926 | 6.360  | 1.00 | 67.71  |
| ATOM | 208 | NZ  | LYS A 840 | 56.848 | 45.463 | 6.017  | 1.00 | 67.71  |
| ATOM | 213 | N   | ALA A 841 | 58.916 | 48.176 | 3.344  | 1.00 | 99.75  |
| ATOM | 214 | CA  | ALA A 841 | 59.514 | 47.452 | 2.241  | 1.00 | 99.75  |
| ATOM | 215 | C   | ALA A 841 | 59.845 | 46.037 | 2.620  | 1.00 | 99.75  |
| ATOM | 216 | O   | ALA A 841 | 59.830 | 45.684 | 3.796  | 1.00 | 99.75  |
| ATOM | 217 | CB  | ALA A 841 | 60.748 | 48.152 | 1.771  | 1.00 | 78.22  |
| ATOM | 219 | N   | ARG A 842 | 60.143 | 45.231 | 1.605  | 1.00 | 100.00 |
| ATOM | 220 | CA  | ARG A 842 | 60.499 | 43.832 | 1.798  | 1.00 | 100.00 |
| ATOM | 221 | C   | ARG A 842 | 61.972 | 43.576 | 1.429  | 1.00 | 100.00 |
| ATOM | 222 | O   | ARG A 842 | 62.288 | 43.082 | 0.352  | 1.00 | 100.00 |
| ATOM | 223 | CB  | ARG A 842 | 59.574 | 42.951 | 0.973  | 1.00 | 100.00 |
| ATOM | 225 | N   | ILE A 843 | 62.868 | 43.919 | 2.348  | 1.00 | 100.00 |
| ATOM | 226 | CA  | ILE A 843 | 64.301 | 43.743 | 2.148  | 1.00 | 100.00 |
| ATOM | 227 | C   | ILE A 843 | 64.642 | 42.262 | 2.174  | 1.00 | 100.00 |
| ATOM | 228 | O   | ILE A 843 | 63.952 | 41.488 | 2.844  | 1.00 | 100.00 |
| ATOM | 229 | CB  | ILE A 843 | 65.094 | 44.489 | 3.263  | 1.00 | 99.77  |
| ATOM | 230 | CG1 | ILE A 843 | 65.193 | 45.960 | 2.907  | 1.00 | 99.77  |
| ATOM | 231 | CG2 | ILE A 843 | 66.487 | 43.937 | 3.421  | 1.00 | 99.77  |
| ATOM | 232 | CD1 | ILE A 843 | 63.857 | 46.576 | 2.554  | 1.00 | 99.77  |
| ATOM | 234 | N   | LYS A 844 | 65.691 | 41.882 | 1.435  | 1.00 | 77.20  |
| ATOM | 235 | CA  | LYS A 844 | 66.176 | 40.501 | 1.379  | 1.00 | 77.20  |
| ATOM | 236 | C   | LYS A 844 | 67.635 | 40.390 | 1.854  | 1.00 | 77.20  |
| ATOM | 237 | O   | LYS A 844 | 68.499 | 41.059 | 1.313  | 1.00 | 77.20  |
| ATOM | 238 | CB  | LYS A 844 | 66.063 | 39.973 | -0.045 | 1.00 | 63.87  |
| ATOM | 240 | N   | LYS A 845 | 67.921 | 39.570 | 2.859  | 1.00 | 93.93  |
| ATOM | 241 | CA  | LYS A 845 | 69.313 | 39.419 | 3.302  | 1.00 | 93.93  |
| ATOM | 242 | C   | LYS A 845 | 69.979 | 38.431 | 2.382  | 1.00 | 93.93  |
| ATOM | 243 | O   | LYS A 845 | 69.341 | 37.931 | 1.453  | 1.00 | 93.93  |
| ATOM | 244 | CB  | LYS A 845 | 69.391 | 38.854 | 4.684  | 1.00 | 20.96  |
| ATOM | 246 | N   | ASP A 846 | 71.258 | 38.140 | 2.631  | 1.00 | 72.18  |
| ATOM | 247 | CA  | ASP A 846 | 71.912 | 37.136 | 1.815  | 1.00 | 72.18  |
| ATOM | 248 | C   | ASP A 846 | 70.882 | 36.018 | 2.059  | 1.00 | 72.18  |
| ATOM | 249 | O   | ASP A 846 | 70.861 | 35.389 | 3.129  | 1.00 | 72.18  |
| ATOM | 250 | CB  | ASP A 846 | 73.294 | 36.787 | 2.390  | 1.00 | 100.00 |
| ATOM | 251 | CG  | ASP A 846 | 74.415 | 37.685 | 1.842  | 1.00 | 100.00 |
| ATOM | 252 | OD1 | ASP A 846 | 74.632 | 37.694 | 0.607  | 1.00 | 100.00 |
| ATOM | 253 | OD2 | ASP A 846 | 75.083 | 38.376 | 2.650  | 1.00 | 100.00 |
| ATOM | 255 | N   | GLY A 847 | 69.992 | 35.836 | 1.082  | 1.00 | 99.53  |
| ATOM | 256 | CA  | GLY A 847 | 68.923 | 34.870 | 1.231  | 1.00 | 99.53  |
| ATOM | 257 | C   | GLY A 847 | 68.008 | 35.367 | 2.347  | 1.00 | 99.53  |
| ATOM | 258 | O   | GLY A 847 | 68.509 | 35.974 | 3.302  | 1.00 | 99.53  |
| ATOM | 260 | N   | LEU A 848 | 66.694 | 35.120 | 2.228  | 1.00 | 93.78  |
| ATOM | 261 | CA  | LEU A 848 | 65.670 | 35.542 | 3.212  | 1.00 | 93.78  |
| ATOM | 262 | C   | LEU A 848 | 65.095 | 36.935 | 2.949  | 1.00 | 93.78  |
| ATOM | 263 | O   | LEU A 848 | 65.825 | 37.878 | 2.662  | 1.00 | 93.78  |
| ATOM | 264 | CB  | LEU A 848 | 66.215 | 35.504 | 4.654  | 1.00 | 100.00 |
| ATOM | 265 | CG  | LEU A 848 | 66.931 | 36.752 | 5.223  | 1.00 | 100.00 |
| ATOM | 266 | CD1 | LEU A 848 | 65.937 | 37.849 | 5.552  | 1.00 | 100.00 |
| ATOM | 267 | CD2 | LEU A 848 | 67.719 | 36.377 | 6.472  | 1.00 | 100.00 |
| ATOM | 269 | N   | ARG A 849 | 63.781 | 37.063 | 3.070  | 1.00 | 80.14  |
| ATOM | 270 | CA  | ARG A 849 | 63.127 | 38.347 | 2.855  | 1.00 | 80.14  |
| ATOM | 271 | C   | ARG A 849 | 62.191 | 38.669 | 4.013  | 1.00 | 80.14  |
| ATOM | 272 | O   | ARG A 849 | 61.629 | 37.748 | 4.612  | 1.00 | 80.14  |

FIG. 6D

```
ATOM    273  CB  ARG A 849      62.320  38.327   1.561  1.00 99.23
ATOM    274  CG  ARG A 849      61.390  37.148   1.452  1.00 99.23
ATOM    275  CD  ARG A 849      60.021  37.392   2.081  1.00 99.23
ATOM    276  NE  ARG A 849      59.022  36.466   1.540  1.00 99.23
ATOM    277  CZ  ARG A 849      58.743  35.268   2.050  1.00 99.23
ATOM    278  NH1 ARG A 849      59.379  34.826   3.127  1.00 99.23
ATOM    279  NH2 ARG A 849      57.830  34.504   1.475  1.00 99.23
ATOM    286  N   MET A 850      62.041  39.958   4.350  1.00 26.65
ATOM    287  CA  MET A 850      61.122  40.332   5.425  1.00 26.65
ATOM    288  C   MET A 850      60.680  41.820   5.406  1.00 26.65
ATOM    289  O   MET A 850      60.502  42.468   4.345  1.00 26.65
ATOM    290  CB  MET A 850      61.743  39.999   6.780  1.00 99.56
ATOM    291  CG  MET A 850      63.156  39.475   6.689  1.00 99.56
ATOM    292  SD  MET A 850      64.190  40.566   5.745  1.00 99.56
ATOM    293  CE  MET A 850      65.522  40.771   6.902  1.00 99.56
ATOM    295  N   ASP A 851      60.515  42.341   6.612  1.00 27.82
ATOM    296  CA  ASP A 851      60.156  43.721   6.812  1.00 27.82
ATOM    297  C   ASP A 851      61.331  44.534   7.280  1.00 27.82
ATOM    298  O   ASP A 851      62.056  44.144   8.255  1.00 27.82
ATOM    299  CB  ASP A 851      59.124  43.799   7.903  1.00 16.75
ATOM    300  CG  ASP A 851      58.382  42.570   7.998  1.00 16.75
ATOM    301  OD1 ASP A 851      58.147  42.049   6.837  1.00 16.75
ATOM    302  OD2 ASP A 851      58.079  42.189   9.190  1.00 16.75
ATOM    304  N   ALA A 852      61.420  45.691   6.635  1.00 37.08
ATOM    305  CA  ALA A 852      62.400  46.719   6.887  1.00 37.08
ATOM    306  C   ALA A 852      61.643  48.050   6.795  1.00 37.08
ATOM    307  O   ALA A 852      60.764  48.247   5.950  1.00 37.08
ATOM    308  CB  ALA A 852      63.471  46.663   5.835  1.00100.00
ATOM    310  N   ALA A 853      61.955  48.986   7.663  1.00 97.32
ATOM    311  CA  ALA A 853      61.303  50.269   7.528  1.00 97.32
ATOM    312  C   ALA A 853      62.427  51.046   6.852  1.00 97.32
ATOM    313  O   ALA A 853      63.501  51.201   7.415  1.00 97.32
ATOM    314  CB  ALA A 853      60.947  50.824   8.895  1.00 15.46
ATOM    316  N   ILE A 854      62.187  51.469   5.617  1.00 84.85
ATOM    317  CA  ILE A 854      63.178  52.179   4.810  1.00 84.85
ATOM    318  C   ILE A 854      63.221  53.682   4.985  1.00 84.85
ATOM    319  O   ILE A 854      62.197  54.334   5.006  1.00 84.85
ATOM    320  CB  ILE A 854      62.961  51.895   3.315  1.00 99.86
ATOM    321  CG1 ILE A 854      63.540  50.538   2.948  1.00 99.86
ATOM    322  CG2 ILE A 854      63.622  52.963   2.474  1.00 99.86
ATOM    323  CD1 ILE A 854      63.707  49.610   4.109  1.00 99.86
ATOM    325  N   LYS A 855      64.426  54.228   5.095  1.00100.00
ATOM    326  CA  LYS A 855      64.602  55.666   5.249  1.00100.00
ATOM    327  C   LYS A 855      65.867  56.179   4.602  1.00100.00
ATOM    328  O   LYS A 855      66.915  55.567   4.710  1.00100.00
ATOM    329  CB  LYS A 855      64.640  56.058   6.721  1.00100.00
ATOM    330  CG  LYS A 855      65.352  57.373   6.977  1.00100.00
ATOM    331  CD  LYS A 855      64.912  57.985   8.283  1.00100.00
ATOM    332  CE  LYS A 855      65.371  57.143   9.459  1.00100.00
ATOM    333  NZ  LYS A 855      66.801  57.366   9.812  1.00100.00
ATOM    338  N   ARG A 856      65.751  57.314   3.927  1.00100.00
ATOM    339  CA  ARG A 856      66.881  57.980   3.282  1.00100.00
ATOM    340  C   ARG A 856      66.403  59.192   2.543  1.00100.00
ATOM    341  O   ARG A 856      65.575  59.088   1.631  1.00100.00
ATOM    342  CB  ARG A 856      67.602  57.089   2.279  1.00100.00
ATOM    343  CG  ARG A 856      68.637  57.868   1.462  1.00100.00
ATOM    344  CD  ARG A 856      68.118  58.410   0.090  1.00100.00
```

FIG. 6E

```
ATOM    345  NE   ARG A 856      68.946  59.472  -0.512  1.00100.00
ATOM    346  CZ   ARG A 856      68.938  59.819  -1.801  1.00100.00
ATOM    347  NH1  ARG A 856      68.145  59.210  -2.674  1.00100.00
ATOM    348  NH2  ARG A 856      69.744  60.783  -2.222  1.00100.00
ATOM    355  N    MET A 857      66.951  60.337   2.922  1.00 39.23
ATOM    356  CA   MET A 857      66.567  61.616   2.275  1.00 39.23
ATOM    357  C    MET A 857      67.634  62.754   2.130  1.00 39.23
ATOM    358  O    MET A 857      68.221  63.225   3.157  1.00 39.23
ATOM    359  CB   MET A 857      65.320  62.179   2.983  1.00100.00
ATOM    360  CG   MET A 857      64.305  62.877   2.092  1.00100.00
ATOM    361  SD   MET A 857      63.851  64.409   2.908  1.00100.00
ATOM    362  CE   MET A 857      61.992  64.355   2.935  1.00100.00
ATOM    363  OXT  MET A 857      67.842  63.172   0.963  1.00100.00
ATOM    365  N    ASP A 864      73.761  67.110  -3.548  1.00 99.95
ATOM    366  CA   ASP A 864      74.976  66.819  -4.360  1.00 99.95
ATOM    367  C    ASP A 864      76.224  67.493  -3.781  1.00 99.95
ATOM    368  O    ASP A 864      77.068  68.001  -4.530  1.00 99.95
ATOM    369  CB   ASP A 864      74.765  67.261  -5.839  1.00  2.00
ATOM    373  N    ASP A 865      76.338  67.492  -2.453  1.00100.00
ATOM    374  CA   ASP A 865      77.486  68.080  -1.760  1.00100.00
ATOM    375  C    ASP A 865      77.219  68.112  -0.267  1.00100.00
ATOM    376  O    ASP A 865      77.444  69.131   0.391  1.00100.00
ATOM    377  CB   ASP A 865      77.720  69.454  -2.255  1.00 53.42
ATOM    379  N    HIS A 866      76.752  66.983   0.263  1.00100.00
ATOM    380  CA   HIS A 866      76.397  66.853   1.678  1.00100.00
ATOM    381  C    HIS A 866      76.696  65.441   2.178  1.00100.00
ATOM    382  O    HIS A 866      75.859  64.777   2.805  1.00100.00
ATOM    383  CB   HIS A 866      74.905  67.144   1.848  1.00100.00
ATOM    384  CG   HIS A 866      74.036  66.378   0.896  1.00100.00
ATOM    385  ND1  HIS A 866      73.693  66.857  -0.350  1.00100.00
ATOM    386  CD2  HIS A 866      73.459  65.158   1.003  1.00100.00
ATOM    387  CE1  HIS A 866      72.943  65.965  -0.970  1.00100.00
ATOM    388  NE2  HIS A 866      72.787  64.925  -0.170  1.00100.00
ATOM    392  N    ARG A 867      77.912  64.998   1.913  1.00100.00
ATOM    393  CA   ARG A 867      78.335  63.673   2.300  1.00100.00
ATOM    394  C    ARG A 867      78.856  63.654   3.738  1.00100.00
ATOM    395  O    ARG A 867      80.061  63.597   3.985  1.00100.00
ATOM    396  CB   ARG A 867      79.393  63.206   1.310  1.00 99.71
ATOM    397  CG   ARG A 867      79.185  63.783  -0.098  1.00 99.71
ATOM    398  CD   ARG A 867      79.695  65.213  -0.213  1.00 99.71
ATOM    399  NE   ARG A 867      81.116  65.305   0.115  1.00 99.71
ATOM    400  CZ   ARG A 867      81.604  65.381   1.351  1.00 99.71
ATOM    401  NH1  ARG A 867      80.785  65.378   2.396  1.00 99.71
ATOM    402  NH2  ARG A 867      82.919  65.450   1.540  1.00 99.71
ATOM    409  N    ASP A 868      77.920  63.713   4.683  1.00 88.85
ATOM    410  CA   ASP A 868      78.239  63.706   6.112  1.00 88.85
ATOM    411  C    ASP A 868      77.969  62.278   6.646  1.00 88.85
ATOM    412  O    ASP A 868      78.558  61.850   7.655  1.00 88.85
ATOM    413  CB   ASP A 868      77.368  64.758   6.870  1.00 67.57
ATOM    414  CG   ASP A 868      77.674  66.231   6.460  1.00 67.57
ATOM    415  OD1  ASP A 868      78.671  66.496   5.753  1.00 67.57
ATOM    416  OD2  ASP A 868      76.914  67.142   6.852  1.00 67.57
ATOM    418  N    PHE A 869      77.097  61.545   5.943  1.00100.00
ATOM    419  CA   PHE A 869      76.719  60.176   6.322  1.00100.00
ATOM    420  C    PHE A 869      77.809  59.128   6.086  1.00100.00
ATOM    421  O    PHE A 869      78.433  59.091   5.017  1.00100.00
ATOM    422  CB   PHE A 869      75.431  59.745   5.595  1.00 98.24
```

FIG. 6F

```
ATOM    423  CG  PHE A 869      75.346  60.207   4.164  1.00 98.24
ATOM    424  CD1 PHE A 869      74.434  61.186   3.789  1.00 98.24
ATOM    425  CD2 PHE A 869      76.165  59.652   3.186  1.00 98.24
ATOM    426  CE1 PHE A 869      74.341  61.604   2.457  1.00 98.24
ATOM    427  CE2 PHE A 869      76.078  60.063   1.854  1.00 98.24
ATOM    428  CZ  PHE A 869      75.166  61.038   1.492  1.00 98.24
ATOM    430  N   ALA A 870      78.007  58.287   7.106  1.00100.00
ATOM    431  CA  ALA A 870      79.005  57.205   7.146  1.00100.00
ATOM    432  C   ALA A 870      79.570  57.201   8.564  1.00100.00
ATOM    433  O   ALA A 870      80.736  56.892   8.807  1.00100.00
ATOM    434  CB  ALA A 870      80.131  57.437   6.134  1.00100.00
ATOM    436  N   GLY A 871      78.706  57.575   9.490  1.00100.00
ATOM    437  CA  GLY A 871      79.058  57.626  10.888  1.00100.00
ATOM    438  C   GLY A 871      77.783  57.234  11.591  1.00100.00
ATOM    439  O   GLY A 871      77.802  56.636  12.662  1.00100.00
ATOM    441  N   GLU A 872      76.656  57.592  10.987  1.00100.00
ATOM    442  CA  GLU A 872      75.384  57.210  11.564  1.00100.00
ATOM    443  C   GLU A 872      75.581  55.695  11.584  1.00100.00
ATOM    444  O   GLU A 872      75.628  55.083  12.655  1.00100.00
ATOM    445  CB  GLU A 872      74.200  57.613  10.651  1.00 99.93
ATOM    446  CG  GLU A 872      73.244  58.668  11.260  1.00 99.93
ATOM    447  CD  GLU A 872      71.754  58.458  10.919  1.00 99.93
ATOM    448  OE1 GLU A 872      71.434  57.633  10.040  1.00 99.93
ATOM    449  OE2 GLU A 872      70.894  59.128  11.532  1.00 99.93
ATOM    451  N   LEU A 873      75.773  55.121  10.389  1.00 77.06
ATOM    452  CA  LEU A 873      75.982  53.683  10.215  1.00 77.06
ATOM    453  C   LEU A 873      77.167  53.198  11.046  1.00 77.06
ATOM    454  O   LEU A 873      77.384  51.998  11.180  1.00 77.06
ATOM    455  CB  LEU A 873      76.202  53.366   8.746  1.00 96.97
ATOM    457  N   GLU A 874      77.920  54.142  11.612  1.00 98.87
ATOM    458  CA  GLU A 874      79.091  53.832  12.423  1.00 98.87
ATOM    459  C   GLU A 874      78.740  53.585  13.890  1.00 98.87
ATOM    460  O   GLU A 874      79.072  52.546  14.449  1.00 98.87
ATOM    461  CB  GLU A 874      80.107  54.954  12.306  1.00 56.03
ATOM    463  N   VAL A 875      78.096  54.541  14.543  1.00100.00
ATOM    464  CA  VAL A 875      77.725  54.320  15.936  1.00100.00
ATOM    465  C   VAL A 875      76.577  53.312  15.875  1.00100.00
ATOM    466  O   VAL A 875      76.533  52.370  16.654  1.00100.00
ATOM    467  CB  VAL A 875      77.279  55.629  16.582  1.00100.00
ATOM    469  N   LEU A 876      75.678  53.520  14.911  1.00 63.64
ATOM    470  CA  LEU A 876      74.515  52.662  14.649  1.00 63.64
ATOM    471  C   LEU A 876      74.825  51.155  14.638  1.00 63.64
ATOM    472  O   LEU A 876      73.935  50.359  14.292  1.00 63.64
ATOM    473  CB  LEU A 876      73.914  53.005  13.267  1.00 36.83
ATOM    474  CG  LEU A 876      72.851  54.076  12.997  1.00 36.83
ATOM    475  CD1 LEU A 876      72.028  53.665  11.807  1.00 36.83
ATOM    476  CD2 LEU A 876      71.987  54.260  14.181  1.00 36.83
ATOM    478  N   CYS A 877      76.072  50.786  14.978  1.00 75.85
ATOM    479  CA  CYS A 877      76.570  49.391  14.973  1.00 75.85
ATOM    480  C   CYS A 877      76.791  48.697  16.317  1.00 75.85
ATOM    481  O   CYS A 877      75.965  47.904  16.771  1.00 75.85
ATOM    482  CB  CYS A 877      77.890  49.343  14.202  1.00 82.25
ATOM    483  SG  CYS A 877      78.205  50.859  13.250  1.00 82.25
ATOM    485  N   LYS A 878      77.947  48.968  16.913  1.00100.00
ATOM    486  CA  LYS A 878      78.334  48.400  18.202  1.00100.00
ATOM    487  C   LYS A 878      77.159  48.295  19.186  1.00100.00
ATOM    488  O   LYS A 878      77.237  47.565  20.178  1.00100.00
```

FIG. 6G

```
ATOM    489  CB   LYS A 878      79.460  49.251  18.826  1.00 99.60
ATOM    490  CG   LYS A 878      80.588  49.643  17.842  1.00 99.60
ATOM    491  CD   LYS A 878      80.814  51.160  17.739  1.00 99.60
ATOM    492  CE   LYS A 878      81.033  51.598  16.292  1.00 99.60
ATOM    493  NZ   LYS A 878      82.152  52.567  16.077  1.00 99.60
ATOM    498  N    LEU A 879      76.079  49.024  18.905  1.00 99.14
ATOM    499  CA   LEU A 879      74.905  49.034  19.762  1.00 99.14
ATOM    500  C    LEU A 879      73.664  48.687  18.953  1.00 99.14
ATOM    501  O    LEU A 879      72.574  48.526  19.488  1.00 99.14
ATOM    502  CB   LEU A 879      74.748  50.416  20.401  1.00 99.96
ATOM    503  CG   LEU A 879      74.125  51.546  19.579  1.00 99.96
ATOM    504  CD1  LEU A 879      74.530  52.863  20.154  1.00 99.96
ATOM    505  CD2  LEU A 879      74.555  51.454  18.135  1.00 99.96
ATOM    507  N    GLY A 880      73.840  48.593  17.647  1.00 74.75
ATOM    508  CA   GLY A 880      72.737  48.256  16.775  1.00 74.75
ATOM    509  C    GLY A 880      71.778  47.281  17.406  1.00 74.75
ATOM    510  O    GLY A 880      70.589  47.458  17.285  1.00 74.75
ATOM    512  N    HIS A 881      72.288  46.243  18.067  1.00100.00
ATOM    513  CA   HIS A 881      71.428  45.246  18.700  1.00100.00
ATOM    514  C    HIS A 881      71.274  45.583  20.172  1.00100.00
ATOM    515  O    HIS A 881      71.798  46.571  20.661  1.00100.00
ATOM    516  CB   HIS A 881      71.989  43.818  18.514  1.00 80.74
ATOM    517  CG   HIS A 881      71.360  42.778  19.401  1.00 80.74
ATOM    518  ND1  HIS A 881      70.116  42.234  19.155  1.00 80.74
ATOM    519  CD2  HIS A 881      71.778  42.230  20.573  1.00 80.74
ATOM    520  CE1  HIS A 881      69.792  41.404  20.133  1.00 80.74
ATOM    521  NE2  HIS A 881      70.783  41.384  21.007  1.00 80.74
ATOM    525  N    HIS A 882      70.539  44.718  20.846  1.00  5.03
ATOM    526  CA   HIS A 882      70.126  44.779  22.266  1.00  5.03
ATOM    527  C    HIS A 882      68.572  44.646  22.018  1.00  5.03
ATOM    528  O    HIS A 882      67.998  45.211  20.996  1.00  5.03
ATOM    529  CB   HIS A 882      70.487  46.161  22.887  1.00 36.20
ATOM    530  CG   HIS A 882      70.085  46.316  24.322  1.00 36.20
ATOM    531  ND1  HIS A 882      68.786  46.169  24.753  1.00 36.20
ATOM    532  CD2  HIS A 882      70.816  46.553  25.432  1.00 36.20
ATOM    533  CE1  HIS A 882      68.731  46.302  26.066  1.00 36.20
ATOM    534  NE2  HIS A 882      69.949  46.535  26.504  1.00 36.20
ATOM    538  N    PRO A 883      67.875  43.928  22.885  1.00 18.79
ATOM    539  CA   PRO A 883      66.444  43.868  22.564  1.00 18.79
ATOM    540  C    PRO A 883      65.806  45.252  22.201  1.00 18.79
ATOM    541  O    PRO A 883      65.014  45.404  21.188  1.00 18.79
ATOM    542  CB   PRO A 883      65.804  43.294  23.829  1.00 41.14
ATOM    543  CG   PRO A 883      66.946  43.069  24.810  1.00 41.14
ATOM    544  CD   PRO A 883      68.231  43.209  24.107  1.00 41.14
ATOM    545  N    ASN A 884      66.245  46.252  22.975  1.00 21.27
ATOM    546  CA   ASN A 884      65.656  47.545  22.910  1.00 21.27
ATOM    547  C    ASN A 884      66.055  48.782  22.174  1.00 21.27
ATOM    548  O    ASN A 884      65.930  49.811  22.738  1.00 21.27
ATOM    549  CB   ASN A 884      65.371  47.916  24.332  1.00 47.99
ATOM    550  CG   ASN A 884      64.926  46.747  25.093  1.00 47.99
ATOM    551  OD1  ASN A 884      65.360  46.508  26.173  1.00 47.99
ATOM    552  ND2  ASN A 884      64.055  45.990  24.504  1.00 47.99
ATOM    556  N    ILE A 885      66.421  48.685  20.906  1.00  2.00
ATOM    557  CA   ILE A 885      66.784  49.799  20.139  1.00  2.00
ATOM    558  C    ILE A 885      66.578  49.337  18.712  1.00  2.00
ATOM    559  O    ILE A 885      67.324  48.601  18.278  1.00  2.00
ATOM    560  CB   ILE A 885      68.282  50.142  20.404  1.00  5.30
```

FIG. 6H

| | | | | | | | | | |
|---|---|---|---|---|---|---|---|---|---|
| ATOM | 561 | CG1 | ILE | A | 885 | 68.387 | 50.790 | 21.774 | 1.00 5.30 |
| ATOM | 562 | CG2 | ILE | A | 885 | 68.946 | 51.096 | 19.301 | 1.00 5.30 |
| ATOM | 563 | CD1 | ILE | A | 885 | 69.834 | 51.062 | 22.137 | 1.00 5.30 |
| ATOM | 565 | N | ILE | A | 886 | 65.634 | 49.811 | 17.931 | 1.00 41.79 |
| ATOM | 566 | CA | ILE | A | 886 | 65.528 | 49.296 | 16.564 | 1.00 41.79 |
| ATOM | 567 | C | ILE | A | 886 | 66.883 | 48.887 | 15.937 | 1.00 41.79 |
| ATOM | 568 | O | ILE | A | 886 | 67.899 | 49.217 | 16.450 | 1.00 41.79 |
| ATOM | 569 | CB | ILE | A | 886 | 64.769 | 50.316 | 15.671 | 1.00 97.62 |
| ATOM | 570 | CG1 | ILE | A | 886 | 63.737 | 49.563 | 14.817 | 1.00 97.62 |
| ATOM | 571 | CG2 | ILE | A | 886 | 65.742 | 51.141 | 14.871 | 1.00 97.62 |
| ATOM | 572 | CD1 | ILE | A | 886 | 62.833 | 50.438 | 14.004 | 1.00 97.62 |
| ATOM | 574 | N | ASN | A | 887 | 66.915 | 48.190 | 14.817 | 1.00 58.02 |
| ATOM | 575 | CA | ASN | A | 887 | 68.191 | 47.751 | 14.300 | 1.00 58.02 |
| ATOM | 576 | C | ASN | A | 887 | 68.481 | 48.230 | 12.940 | 1.00 58.02 |
| ATOM | 577 | O | ASN | A | 887 | 67.635 | 48.811 | 12.321 | 1.00 58.02 |
| ATOM | 578 | CB | ASN | A | 887 | 68.237 | 46.228 | 14.269 | 1.00 61.11 |
| ATOM | 579 | CG | ASN | A | 887 | 69.626 | 45.688 | 14.460 | 1.00 61.11 |
| ATOM | 580 | OD1 | ASN | A | 887 | 70.307 | 45.367 | 13.505 | 1.00 61.11 |
| ATOM | 581 | ND2 | ASN | A | 887 | 70.050 | 45.584 | 15.711 | 1.00 61.11 |
| ATOM | 585 | N | LEU | A | 888 | 69.688 | 47.945 | 12.467 | 1.00100.00 |
| ATOM | 586 | CA | LEU | A | 888 | 70.097 | 48.313 | 11.122 | 1.00100.00 |
| ATOM | 587 | C | LEU | A | 888 | 70.158 | 47.037 | 10.282 | 1.00100.00 |
| ATOM | 588 | O | LEU | A | 888 | 71.039 | 46.202 | 10.444 | 1.00100.00 |
| ATOM | 589 | CB | LEU | A | 888 | 71.467 | 48.993 | 11.131 | 1.00100.00 |
| ATOM | 590 | CG | LEU | A | 888 | 72.068 | 49.217 | 9.743 | 1.00100.00 |
| ATOM | 591 | CD1 | LEU | A | 888 | 72.054 | 50.676 | 9.410 | 1.00100.00 |
| ATOM | 592 | CD2 | LEU | A | 888 | 73.475 | 48.686 | 9.699 | 1.00100.00 |
| ATOM | 594 | N | LEU | A | 889 | 69.191 | 46.880 | 9.398 | 1.00 73.18 |
| ATOM | 595 | CA | LEU | A | 889 | 69.128 | 45.721 | 8.530 | 1.00 73.18 |
| ATOM | 596 | C | LEU | A | 889 | 70.044 | 45.860 | 7.290 | 1.00 73.18 |
| ATOM | 597 | O | LEU | A | 889 | 70.737 | 44.920 | 6.926 | 1.00 73.18 |
| ATOM | 598 | CB | LEU | A | 889 | 67.666 | 45.500 | 8.102 | 1.00 10.03 |
| ATOM | 599 | CG | LEU | A | 889 | 66.628 | 44.729 | 9.010 | 1.00 10.03 |
| ATOM | 600 | CD1 | LEU | A | 889 | 66.180 | 43.517 | 8.146 | 1.00 10.03 |
| ATOM | 601 | CD2 | LEU | A | 889 | 67.147 | 44.336 | 10.432 | 1.00 10.03 |
| ATOM | 603 | N | GLY | A | 890 | 70.058 | 47.028 | 6.651 | 1.00100.00 |
| ATOM | 604 | CA | GLY | A | 890 | 70.898 | 47.201 | 5.475 | 1.00100.00 |
| ATOM | 605 | C | GLY | A | 890 | 71.057 | 48.582 | 4.845 | 1.00100.00 |
| ATOM | 606 | O | GLY | A | 890 | 70.515 | 49.581 | 5.319 | 1.00100.00 |
| ATOM | 608 | N | ALA | A | 891 | 71.829 | 48.616 | 3.758 | 1.00 93.61 |
| ATOM | 609 | CA | ALA | A | 891 | 72.124 | 49.833 | 2.992 | 1.00 93.61 |
| ATOM | 610 | C | ALA | A | 891 | 73.125 | 49.438 | 1.929 | 1.00 93.61 |
| ATOM | 611 | O | ALA | A | 891 | 73.999 | 48.626 | 2.223 | 1.00 93.61 |
| ATOM | 612 | CB | ALA | A | 891 | 72.763 | 50.871 | 3.886 | 1.00 28.61 |
| ATOM | 614 | N | CYS | A | 892 | 73.033 | 49.985 | 0.715 | 1.00100.00 |
| ATOM | 615 | CA | CYS | A | 892 | 74.034 | 49.635 | -0.306 | 1.00100.00 |
| ATOM | 616 | C | CYS | A | 892 | 74.789 | 50.793 | -0.956 | 1.00100.00 |
| ATOM | 617 | O | CYS | A | 892 | 75.934 | 51.073 | -0.606 | 1.00100.00 |
| ATOM | 618 | CB | CYS | A | 892 | 73.432 | 48.787 | -1.429 | 1.00100.00 |
| ATOM | 619 | SG | CYS | A | 892 | 74.641 | 48.356 | -2.757 | 1.00100.00 |
| ATOM | 621 | N | GLU | A | 893 | 74.134 | 51.447 | -1.914 | 1.00 85.23 |
| ATOM | 622 | CA | GLU | A | 893 | 74.715 | 52.555 | -2.679 | 1.00 85.23 |
| ATOM | 623 | C | GLU | A | 893 | 73.816 | 52.794 | -3.880 | 1.00 85.23 |
| ATOM | 624 | O | GLU | A | 893 | 74.228 | 52.512 | -5.011 | 1.00 85.23 |
| ATOM | 625 | CB | GLU | A | 893 | 76.108 | 52.176 | -3.222 | 1.00100.00 |
| ATOM | 626 | CG | GLU | A | 893 | 77.267 | 53.065 | -2.785 | 1.00100.00 |
| ATOM | 627 | CD | GLU | A | 893 | 78.487 | 52.246 | -2.386 | 1.00100.00 |

FIG. 6I

```
ATOM    628  OE1 GLU A 893      79.029  51.535  -3.266  1.00100.00
ATOM    629  OE2 GLU A 893      78.893  52.307  -1.197  1.00100.00
ATOM    631  N   HIS A 894      72.602  53.293  -3.664  1.00100.00
ATOM    632  CA  HIS A 894      71.731  53.508  -4.810  1.00100.00
ATOM    633  C   HIS A 894      71.885  54.855  -5.463  1.00100.00
ATOM    634  O   HIS A 894      71.106  55.770  -5.181  1.00100.00
ATOM    635  CB  HIS A 894      70.261  53.338  -4.477  1.00100.00
ATOM    636  CG  HIS A 894      69.370  53.597  -5.652  1.00100.00
ATOM    637  ND1 HIS A 894      68.309  54.476  -5.610  1.00100.00
ATOM    638  CD2 HIS A 894      69.419  53.128  -6.922  1.00100.00
ATOM    639  CE1 HIS A 894      67.743  54.539  -6.802  1.00100.00
ATOM    640  NE2 HIS A 894      68.397  53.729  -7.615  1.00100.00
ATOM    644  N   ARG A 895      72.888  54.950  -6.340  1.00100.00
ATOM    645  CA  ARG A 895      73.176  56.161  -7.090  1.00100.00
ATOM    646  C   ARG A 895      72.331  57.309  -6.481  1.00100.00
ATOM    647  O   ARG A 895      71.194  57.562  -6.910  1.00100.00
ATOM    648  CB  ARG A 895      72.842  55.883  -8.571  1.00 36.65
ATOM    649  CG  ARG A 895      73.711  54.767  -9.229  1.00 36.65
ATOM    650  CD  ARG A 895      73.012  54.079 -10.421  1.00 36.65
ATOM    651  NE  ARG A 895      73.587  54.370 -11.738  1.00 36.65
ATOM    652  CZ  ARG A 895      74.382  53.546 -12.451  1.00 36.65
ATOM    653  NH1 ARG A 895      74.735  52.315 -11.986  1.00 36.65
ATOM    654  NH2 ARG A 895      74.848  53.963 -13.644  1.00 36.65
ATOM    661  N   GLY A 896      72.901  57.979  -5.469  1.00 33.20
ATOM    662  CA  GLY A 896      72.190  59.016  -4.751  1.00 33.20
ATOM    663  C   GLY A 896      71.918  58.455  -3.348  1.00 33.20
ATOM    664  O   GLY A 896      70.779  58.462  -2.847  1.00 33.20
ATOM    666  N   TYR A 897      72.971  57.947  -2.705  1.00 98.45
ATOM    667  CA  TYR A 897      72.864  57.372  -1.356  1.00 98.45
ATOM    668  C   TYR A 897      72.959  55.835  -1.387  1.00 98.45
ATOM    669  O   TYR A 897      73.599  55.240  -2.258  1.00 98.45
ATOM    670  CB  TYR A 897      71.532  57.786  -0.716  1.00100.00
ATOM    671  CG  TYR A 897      71.522  58.208   0.734  1.00100.00
ATOM    672  CD1 TYR A 897      71.152  59.511   1.080  1.00100.00
ATOM    673  CD2 TYR A 897      71.631  57.268   1.756  1.00100.00
ATOM    674  CE1 TYR A 897      70.860  59.866   2.391  1.00100.00
ATOM    675  CE2 TYR A 897      71.345  57.604   3.074  1.00100.00
ATOM    676  CZ  TYR A 897      70.947  58.908   3.389  1.00100.00
ATOM    677  OH  TYR A 897      70.582  59.246   4.682  1.00100.00
ATOM    680  N   LEU A 898      72.293  55.212  -0.419  1.00100.00
ATOM    681  CA  LEU A 898      72.272  53.765  -0.258  1.00100.00
ATOM    682  C   LEU A 898      70.983  53.363   0.469  1.00100.00
ATOM    683  O   LEU A 898      70.810  52.197   0.836  1.00100.00
ATOM    684  CB  LEU A 898      73.495  53.328   0.551  1.00 67.92
ATOM    686  N   TYR A 899      70.097  54.345   0.668  1.00100.00
ATOM    687  CA  TYR A 899      68.813  54.169   1.347  1.00100.00
ATOM    688  C   TYR A 899      68.976  53.434   2.680  1.00100.00
ATOM    689  O   TYR A 899      70.090  53.252   3.153  1.00100.00
ATOM    690  CB  TYR A 899      67.840  53.420   0.434  1.00 99.94
ATOM    691  CG  TYR A 899      67.265  54.259  -0.694  1.00 99.94
ATOM    692  CD1 TYR A 899      67.218  53.770  -2.004  1.00 99.94
ATOM    693  CD2 TYR A 899      66.738  55.531  -0.454  1.00 99.94
ATOM    694  CE1 TYR A 899      66.662  54.519  -3.044  1.00 99.94
ATOM    695  CE2 TYR A 899      66.176  56.295  -1.493  1.00 99.94
ATOM    696  CZ  TYR A 899      66.143  55.778  -2.780  1.00 99.94
ATOM    697  OH  TYR A 899      65.580  56.509  -3.792  1.00 99.94
ATOM    700  N   LEU A 900      67.876  53.017   3.300  1.00 99.32
```

FIG. 6J

| | | | | | | | | | |
|---|---|---|---|---|---|---|---|---|---|
| ATOM | 701 | CA | LEU | A | 900 | 67.987 | 52.305 | 4.573 | 1.00 99.32 |
| ATOM | 702 | C | LEU | A | 900 | 67.119 | 51.071 | 4.770 | 1.00 99.32 |
| ATOM | 703 | O | LEU | A | 900 | 66.306 | 50.702 | 3.933 | 1.00 99.32 |
| ATOM | 704 | CB | LEU | A | 900 | 67.755 | 53.258 | 5.752 | 1.00 72.65 |
| ATOM | 705 | CG | LEU | A | 900 | 68.911 | 53.350 | 6.752 | 1.00 72.65 |
| ATOM | 706 | CD1 | LEU | A | 900 | 70.175 | 52.843 | 6.059 | 1.00 72.65 |
| ATOM | 707 | CD2 | LEU | A | 900 | 69.096 | 54.792 | 7.259 | 1.00 72.65 |
| ATOM | 709 | N | ALA | A | 901 | 67.330 | 50.439 | 5.912 | 1.00 100.00 |
| ATOM | 710 | CA | ALA | A | 901 | 66.617 | 49.244 | 6.288 | 1.00 100.00 |
| ATOM | 711 | C | ALA | A | 901 | 66.802 | 49.053 | 7.774 | 1.00 100.00 |
| ATOM | 712 | O | ALA | A | 901 | 67.774 | 48.484 | 8.231 | 1.00 100.00 |
| ATOM | 713 | CB | ALA | A | 901 | 67.152 | 48.049 | 5.537 | 1.00 100.00 |
| ATOM | 715 | N | ILE | A | 902 | 65.840 | 49.575 | 8.510 | 1.00 33.23 |
| ATOM | 716 | CA | ILE | A | 902 | 65.773 | 49.510 | 9.964 | 1.00 33.23 |
| ATOM | 717 | C | ILE | A | 902 | 64.912 | 48.295 | 10.352 | 1.00 33.23 |
| ATOM | 718 | O | ILE | A | 902 | 63.988 | 47.959 | 9.648 | 1.00 33.23 |
| ATOM | 719 | CB | ILE | A | 902 | 65.130 | 50.817 | 10.474 | 1.00 58.03 |
| ATOM | 720 | CG1 | ILE | A | 902 | 65.930 | 51.992 | 9.960 | 1.00 58.03 |
| ATOM | 721 | CG2 | ILE | A | 902 | 65.107 | 50.870 | 11.955 | 1.00 58.03 |
| ATOM | 722 | CD1 | ILE | A | 902 | 67.193 | 52.207 | 10.738 | 1.00 58.03 |
| ATOM | 724 | N | GLU | A | 903 | 65.256 | 47.622 | 11.440 | 1.00 37.33 |
| ATOM | 725 | CA | GLU | A | 903 | 64.468 | 46.507 | 11.912 | 1.00 37.33 |
| ATOM | 726 | C | GLU | A | 903 | 63.079 | 47.051 | 11.790 | 1.00 37.33 |
| ATOM | 727 | O | GLU | A | 903 | 62.856 | 48.198 | 12.081 | 1.00 37.33 |
| ATOM | 728 | CB | GLU | A | 903 | 64.732 | 46.216 | 13.388 | 1.00 74.67 |
| ATOM | 729 | CG | GLU | A | 903 | 63.667 | 45.362 | 14.022 | 1.00 74.67 |
| ATOM | 730 | CD | GLU | A | 903 | 63.757 | 45.302 | 15.525 | 1.00 74.67 |
| ATOM | 731 | OE1 | GLU | A | 903 | 62.771 | 44.921 | 16.178 | 1.00 74.67 |
| ATOM | 732 | OE2 | GLU | A | 903 | 64.809 | 45.637 | 16.072 | 1.00 74.67 |
| ATOM | 734 | N | TYR | A | 904 | 62.137 | 46.221 | 11.362 | 1.00 98.95 |
| ATOM | 735 | CA | TYR | A | 904 | 60.765 | 46.667 | 11.209 | 1.00 98.95 |
| ATOM | 736 | C | TYR | A | 904 | 59.912 | 46.319 | 12.435 | 1.00 98.95 |
| ATOM | 737 | O | TYR | A | 904 | 59.998 | 45.210 | 12.968 | 1.00 98.95 |
| ATOM | 738 | CB | TYR | A | 904 | 60.187 | 46.064 | 9.939 | 1.00 65.21 |
| ATOM | 739 | CG | TYR | A | 904 | 58.741 | 46.366 | 9.749 | 1.00 65.21 |
| ATOM | 740 | CD1 | TYR | A | 904 | 58.343 | 47.461 | 9.002 | 1.00 65.21 |
| ATOM | 741 | CD2 | TYR | A | 904 | 57.760 | 45.602 | 10.367 | 1.00 65.21 |
| ATOM | 742 | CE1 | TYR | A | 904 | 56.994 | 47.797 | 8.878 | 1.00 65.21 |
| ATOM | 743 | CE2 | TYR | A | 904 | 56.418 | 45.929 | 10.249 | 1.00 65.21 |
| ATOM | 744 | CZ | TYR | A | 904 | 56.046 | 47.029 | 9.500 | 1.00 65.21 |
| ATOM | 745 | OH | TYR | A | 904 | 54.736 | 47.335 | 9.321 | 1.00 65.21 |
| ATOM | 748 | N | ALA | A | 905 | 59.103 | 47.287 | 12.877 | 1.00 44.07 |
| ATOM | 749 | CA | ALA | A | 905 | 58.241 | 47.148 | 14.049 | 1.00 44.07 |
| ATOM | 750 | C | ALA | A | 905 | 56.742 | 46.973 | 13.670 | 1.00 44.07 |
| ATOM | 751 | O | ALA | A | 905 | 56.091 | 47.865 | 13.125 | 1.00 44.07 |
| ATOM | 752 | CB | ALA | A | 905 | 58.459 | 48.326 | 14.943 | 1.00 44.16 |
| ATOM | 754 | N | PRO | A | 906 | 56.169 | 45.798 | 13.983 | 1.00 95.76 |
| ATOM | 755 | CA | PRO | A | 906 | 54.773 | 45.513 | 13.643 | 1.00 95.76 |
| ATOM | 756 | C | PRO | A | 906 | 53.627 | 46.336 | 14.226 | 1.00 95.76 |
| ATOM | 757 | O | PRO | A | 906 | 52.547 | 46.358 | 13.656 | 1.00 95.76 |
| ATOM | 758 | CB | PRO | A | 906 | 54.642 | 44.022 | 13.956 | 1.00 74.50 |
| ATOM | 759 | CG | PRO | A | 906 | 55.605 | 43.816 | 15.072 | 1.00 74.50 |
| ATOM | 760 | CD | PRO | A | 906 | 56.773 | 44.682 | 14.734 | 1.00 74.50 |
| ATOM | 761 | N | HIS | A | 907 | 53.838 | 47.018 | 15.336 | 1.00 75.88 |
| ATOM | 762 | CA | HIS | A | 907 | 52.751 | 47.792 | 15.909 | 1.00 75.88 |
| ATOM | 763 | C | HIS | A | 907 | 52.942 | 49.300 | 15.917 | 1.00 75.88 |
| ATOM | 764 | O | HIS | A | 907 | 52.370 | 49.979 | 16.754 | 1.00 75.88 |

FIG. 6K

```
ATOM    765  CB  HIS A 907     52.491  47.321  17.327  1.00 58.13
ATOM    766  CG  HIS A 907     52.494  45.839  17.465  1.00 58.13
ATOM    767  ND1 HIS A 907     52.400  44.991  16.387  1.00 58.13
ATOM    768  CD2 HIS A 907     52.595  45.049  18.552  1.00 58.13
ATOM    769  CE1 HIS A 907     52.442  43.741  16.805  1.00 58.13
ATOM    770  NE2 HIS A 907     52.563  43.750  18.117  1.00 58.13
ATOM    774  N   GLY A 908     53.744  49.827  15.004  1.00 99.49
ATOM    775  CA  GLY A 908     53.952  51.258  14.965  1.00 99.49
ATOM    776  C   GLY A 908     54.688  51.796  16.168  1.00 99.49
ATOM    777  O   GLY A 908     55.536  51.126  16.736  1.00 99.49
ATOM    779  N   ASN A 909     54.345  53.015  16.565  1.00 37.36
ATOM    780  CA  ASN A 909     54.995  53.672  17.686  1.00 37.36
ATOM    781  C   ASN A 909     54.274  53.675  18.970  1.00 37.36
ATOM    782  O   ASN A 909     53.091  53.524  19.093  1.00 37.36
ATOM    783  CB  ASN A 909     55.422  55.139  17.378  1.00 21.80
ATOM    784  CG  ASN A 909     54.300  56.174  17.594  1.00 21.80
ATOM    785  OD1 ASN A 909     54.091  57.036  16.763  1.00 21.80
ATOM    786  ND2 ASN A 909     53.611  56.094  18.714  1.00 21.80
ATOM    790  N   LEU A 910     55.043  53.958  19.971  1.00  6.05
ATOM    791  CA  LEU A 910     54.505  53.895  21.258  1.00  6.05
ATOM    792  C   LEU A 910     53.372  54.836  21.506  1.00  6.05
ATOM    793  O   LEU A 910     52.558  54.488  22.290  1.00  6.05
ATOM    794  CB  LEU A 910     55.629  53.964  22.304  1.00 22.43
ATOM    795  CG  LEU A 910     55.112  53.756  23.738  1.00 22.43
ATOM    796  CD1 LEU A 910     54.795  52.285  23.989  1.00 22.43
ATOM    797  CD2 LEU A 910     56.128  54.383  24.829  1.00 22.43
ATOM    799  N   LEU A 911     53.269  56.034  20.959  1.00 53.76
ATOM    800  CA  LEU A 911     52.062  56.772  21.333  1.00 53.76
ATOM    801  C   LEU A 911     50.801  56.136  20.690  1.00 53.76
ATOM    802  O   LEU A 911     49.969  55.583  21.406  1.00 53.76
ATOM    803  CB  LEU A 911     52.158  58.265  20.991  1.00  2.16
ATOM    804  CG  LEU A 911     51.350  59.370  21.692  1.00  2.16
ATOM    805  CD1 LEU A 911     51.622  59.513  23.075  1.00  2.16
ATOM    806  CD2 LEU A 911     51.612  60.569  20.997  1.00  2.16
ATOM    808  N   ASP A 912     50.666  56.165  19.363  1.00 37.67
ATOM    809  CA  ASP A 912     49.481  55.594  18.764  1.00 37.67
ATOM    810  C   ASP A 912     49.087  54.287  19.391  1.00 37.67
ATOM    811  O   ASP A 912     48.010  54.116  19.875  1.00 37.67
ATOM    812  CB  ASP A 912     49.652  55.383  17.285  1.00  2.00
ATOM    813  CG  ASP A 912     49.965  56.675  16.516  1.00  2.00
ATOM    814  OD1 ASP A 912     49.929  56.718  15.258  1.00  2.00
ATOM    815  OD2 ASP A 912     50.263  57.647  17.195  1.00  2.00
ATOM    817  N   PHE A 913     49.977  53.341  19.403  1.00 21.37
ATOM    818  CA  PHE A 913     49.659  52.056  19.975  1.00 21.37
ATOM    819  C   PHE A 913     49.216  52.291  21.331  1.00 21.37
ATOM    820  O   PHE A 913     48.338  51.566  21.787  1.00 21.37
ATOM    821  CB  PHE A 913     50.826  51.097  19.956  1.00  2.23
ATOM    822  CG  PHE A 913     50.639  49.861  20.776  1.00  2.23
ATOM    823  CD1 PHE A 913     50.389  48.681  20.185  1.00  2.23
ATOM    824  CD2 PHE A 913     50.826  49.886  22.142  1.00  2.23
ATOM    825  CE1 PHE A 913     50.330  47.610  20.870  1.00  2.23
ATOM    826  CE2 PHE A 913     50.749  48.684  22.902  1.00  2.23
ATOM    827  CZ  PHE A 913     50.503  47.593  22.238  1.00  2.23
ATOM    829  N   LEU A 914     49.753  53.295  22.003  1.00 34.44
ATOM    830  CA  LEU A 914     49.233  53.552  23.340  1.00 34.44
ATOM    831  C   LEU A 914     47.770  54.028  23.202  1.00 34.44
ATOM    832  O   LEU A 914     46.927  53.718  24.017  1.00 34.44
```

FIG. 6L

```
ATOM    833  CB  LEU A 914      50.089  54.600  24.053  1.00 99.33
ATOM    834  CG  LEU A 914      51.192  54.077  24.972  1.00 99.33
ATOM    835  CD1 LEU A 914      52.365  55.032  24.979  1.00 99.33
ATOM    836  CD2 LEU A 914      50.633  53.912  26.367  1.00 99.33
ATOM    838  N   ARG A 915      47.489  54.720  22.111  1.00 38.92
ATOM    839  CA  ARG A 915      46.202  55.332  21.795  1.00 38.92
ATOM    840  C   ARG A 915      45.058  54.463  21.348  1.00 38.92
ATOM    841  O   ARG A 915      43.891  54.728  21.700  1.00 38.92
ATOM    842  CB  ARG A 915      46.422  56.347  20.720  1.00  6.43
ATOM    843  CG  ARG A 915      46.646  57.788  21.276  1.00  6.43
ATOM    844  CD  ARG A 915      47.992  58.402  21.097  1.00  6.43
ATOM    845  NE  ARG A 915      48.094  59.491  22.107  1.00  6.43
ATOM    846  CZ  ARG A 915      48.254  60.805  21.838  1.00  6.43
ATOM    847  NH1 ARG A 915      48.331  61.314  20.610  1.00  6.43
ATOM    848  NH2 ARG A 915      48.468  61.590  22.822  1.00  6.43
ATOM    855  N   LYS A 916      45.399  53.475  20.520  1.00 22.32
ATOM    856  CA  LYS A 916      44.513  52.462  20.007  1.00 22.32
ATOM    857  C   LYS A 916      44.158  51.432  21.156  1.00 22.32
ATOM    858  O   LYS A 916      43.680  50.278  20.864  1.00 22.32
ATOM    859  CB  LYS A 916      45.275  51.740  18.908  1.00 23.97
ATOM    860  CG  LYS A 916      46.735  51.281  19.327  1.00 23.97
ATOM    861  CD  LYS A 916      46.899  50.099  20.472  1.00 23.97
ATOM    862  CE  LYS A 916      46.886  48.726  19.880  1.00 23.97
ATOM    863  NZ  LYS A 916      46.600  48.934  18.374  1.00 23.97
ATOM    868  N   SER A 917      44.387  51.831  22.418  1.00 22.74
ATOM    869  CA  SER A 917      44.179  51.001  23.600  1.00 22.74
ATOM    870  C   SER A 917      43.034  51.499  24.516  1.00 22.74
ATOM    871  O   SER A 917      42.627  50.829  25.545  1.00 22.74
ATOM    872  CB  SER A 917      45.489  50.997  24.415  1.00 34.41
ATOM    873  OG  SER A 917      45.310  50.676  25.795  1.00 34.41
ATOM    876  N   ARG A 918      42.610  52.718  24.199  1.00 59.16
ATOM    877  CA  ARG A 918      41.546  53.402  24.928  1.00 59.16
ATOM    878  C   ARG A 918      40.240  52.937  24.293  1.00 59.16
ATOM    879  O   ARG A 918      39.667  53.636  23.457  1.00 59.16
ATOM    880  CB  ARG A 918      41.724  54.919  24.780  1.00 47.25
ATOM    881  CG  ARG A 918      43.152  55.447  25.013  1.00 47.25
ATOM    882  CD  ARG A 918      43.251  56.981  25.073  1.00 47.25
ATOM    883  NE  ARG A 918      44.063  57.501  26.186  1.00 47.25
ATOM    884  CZ  ARG A 918      44.349  58.794  26.368  1.00 47.25
ATOM    885  NH1 ARG A 918      43.894  59.671  25.521  1.00 47.25
ATOM    886  NH2 ARG A 918      45.092  59.226  27.374  1.00 47.25
ATOM    893  N   VAL A 919      39.829  51.722  24.665  1.00 99.87
ATOM    894  CA  VAL A 919      38.625  51.077  24.148  1.00 99.87
ATOM    895  C   VAL A 919      37.442  52.049  24.208  1.00 99.87
ATOM    896  O   VAL A 919      36.849  52.376  23.191  1.00 99.87
ATOM    897  CB  VAL A 919      38.375  49.713  24.883  1.00 30.60
ATOM    898  CG1 VAL A 919      39.007  48.626  24.110  1.00 30.60
ATOM    899  CG2 VAL A 919      38.949  49.723  26.257  1.00 30.60
ATOM    901  N   LEU A 920      37.111  52.497  25.405  1.00 36.31
ATOM    902  CA  LEU A 920      36.115  53.513  25.648  1.00 36.31
ATOM    903  C   LEU A 920      36.539  54.698  24.811  1.00 36.31
ATOM    904  O   LEU A 920      37.065  55.646  25.312  1.00 36.31
ATOM    905  CB  LEU A 920      36.201  53.928  27.088  1.00 11.95
ATOM    906  CG  LEU A 920      34.951  54.248  27.902  1.00 11.95
ATOM    907  CD1 LEU A 920      34.645  52.948  28.585  1.00 11.95
ATOM    908  CD2 LEU A 920      35.117  55.350  28.954  1.00 11.95
ATOM    910  N   GLU A 921      36.349  54.626  23.518  1.00  9.77
```

FIG. 6M

```
ATOM    911  CA   GLU A 921      36.726  55.656  22.606  1.00   9.77
ATOM    912  C    GLU A 921      36.937  54.877  21.314  1.00   9.77
ATOM    913  O    GLU A 921      36.305  55.139  20.294  1.00   9.77
ATOM    914  CB   GLU A 921      38.009  56.321  23.076  1.00  41.44
ATOM    915  CG   GLU A 921      38.187  57.798  22.646  1.00  41.44
ATOM    916  CD   GLU A 921      39.514  58.054  21.899  1.00  41.44
ATOM    917  OE1  GLU A 921      40.583  58.228  22.581  1.00  41.44
ATOM    918  OE2  GLU A 921      39.465  58.066  20.642  1.00  41.44
ATOM    920  N    THR A 922      37.799  53.864  21.348  1.00  38.88
ATOM    921  CA   THR A 922      38.110  53.051  20.167  1.00  38.88
ATOM    922  C    THR A 922      36.981  52.136  19.842  1.00  38.88
ATOM    923  O    THR A 922      36.505  52.013  18.726  1.00  38.88
ATOM    924  CB   THR A 922      39.174  52.111  20.500  1.00  40.90
ATOM    925  OG1  THR A 922      39.068  51.846  21.908  1.00  40.90
ATOM    926  CG2  THR A 922      40.560  52.671  20.140  1.00  40.90
ATOM    929  N    ASP A 923      36.604  51.443  20.897  1.00  29.76
ATOM    930  CA   ASP A 923      35.585  50.420  20.901  1.00  29.76
ATOM    931  C    ASP A 923      34.964  50.486  22.309  1.00  29.76
ATOM    932  O    ASP A 923      35.466  49.896  23.271  1.00  29.76
ATOM    933  CB   ASP A 923      36.294  49.081  20.662  1.00 100.00
ATOM    934  CG   ASP A 923      35.357  47.934  20.521  1.00 100.00
ATOM    935  OD1  ASP A 923      35.131  47.241  21.517  1.00 100.00
ATOM    936  OD2  ASP A 923      34.854  47.713  19.413  1.00 100.00
ATOM    938  N    PRO A 924      33.906  51.274  22.472  1.00  69.79
ATOM    939  CA   PRO A 924      33.351  51.282  23.821  1.00  69.79
ATOM    940  C    PRO A 924      32.633  49.968  24.194  1.00  69.79
ATOM    941  O    PRO A 924      32.489  49.672  25.371  1.00  69.79
ATOM    942  CB   PRO A 924      32.449  52.516  23.822  1.00  55.89
ATOM    943  CG   PRO A 924      32.843  53.260  22.568  1.00  55.89
ATOM    944  CD   PRO A 924      33.238  52.242  21.601  1.00  55.89
ATOM    945  N    ALA A 925      32.206  49.183  23.199  1.00 100.00
ATOM    946  CA   ALA A 925      31.555  47.887  23.453  1.00 100.00
ATOM    947  C    ALA A 925      32.501  47.062  24.325  1.00 100.00
ATOM    948  O    ALA A 925      32.137  46.651  25.428  1.00 100.00
ATOM    949  CB   ALA A 925      31.278  47.156  22.146  1.00 100.00
ATOM    951  N    PHE A 926      33.704  46.798  23.809  1.00  39.96
ATOM    952  CA   PHE A 926      34.714  46.108  24.576  1.00  39.96
ATOM    953  C    PHE A 926      34.808  46.862  25.859  1.00  39.96
ATOM    954  O    PHE A 926      34.279  46.468  26.851  1.00  39.96
ATOM    955  CB   PHE A 926      36.075  46.145  23.886  1.00  99.37
ATOM    956  CG   PHE A 926      37.128  45.350  24.602  1.00  99.37
ATOM    957  CD1  PHE A 926      37.270  43.990  24.365  1.00  99.37
ATOM    958  CD2  PHE A 926      37.940  45.950  25.560  1.00  99.37
ATOM    959  CE1  PHE A 926      38.192  43.248  25.071  1.00  99.37
ATOM    960  CE2  PHE A 926      38.861  45.217  26.265  1.00  99.37
ATOM    961  CZ   PHE A 926      38.987  43.863  26.023  1.00  99.37
ATOM    963  N    ALA A 927      35.470  47.996  25.823  1.00 100.00
ATOM    964  CA   ALA A 927      35.628  48.798  27.018  1.00 100.00
ATOM    965  C    ALA A 927      34.627  48.539  28.167  1.00 100.00
ATOM    966  O    ALA A 927      35.030  48.490  29.328  1.00 100.00
ATOM    967  CB   ALA A 927      35.611  50.250  26.619  1.00  37.88
ATOM    969  N    ILE A 928      33.343  48.348  27.845  1.00  71.50
ATOM    970  CA   ILE A 928      32.287  48.137  28.866  1.00  71.50
ATOM    971  C    ILE A 928      31.863  46.700  29.164  1.00  71.50
ATOM    972  O    ILE A 928      31.579  46.352  30.301  1.00  71.50
ATOM    973  CB   ILE A 928      30.987  48.939  28.510  1.00  96.87
ATOM    974  CG1  ILE A 928      30.326  49.467  29.787  1.00  96.87
```

FIG. 6N

```
ATOM    975  CG2 ILE A 928      30.008  48.051  27.748  1.00 96.87
ATOM    976  CD1 ILE A 928      28.888  49.846  29.624  1.00 96.87
ATOM    978  N   ALA A 929      31.793  45.881  28.130  1.00100.00
ATOM    979  CA  ALA A 929      31.431  44.498  28.319  1.00100.00
ATOM    980  C   ALA A 929      32.550  43.917  29.163  1.00100.00
ATOM    981  O   ALA A 929      32.326  43.246  30.160  1.00100.00
ATOM    982  CB  ALA A 929      31.367  43.810  26.982  1.00 31.88
ATOM    984  N   ASN A 930      33.767  44.220  28.737  1.00 37.33
ATOM    985  CA  ASN A 930      35.009  43.775  29.380  1.00 37.33
ATOM    986  C   ASN A 930      35.326  44.575  30.614  1.00 37.33
ATOM    987  O   ASN A 930      36.020  44.110  31.496  1.00 37.33
ATOM    988  CB  ASN A 930      36.163  43.843  28.378  1.00 87.25
ATOM    989  CG  ASN A 930      36.469  42.497  27.753  1.00 87.25
ATOM    990  OD1 ASN A 930      37.485  41.865  28.062  1.00 87.25
ATOM    991  ND2 ASN A 930      35.590  42.051  26.865  1.00 87.25
ATOM    995  N   SER A 931      34.828  45.807  30.629  1.00 35.86
ATOM    996  CA  SER A 931      34.968  46.734  31.740  1.00 35.86
ATOM    997  C   SER A 931      36.347  47.321  32.044  1.00 35.86
ATOM    998  O   SER A 931      36.779  47.344  33.211  1.00 35.86
ATOM    999  CB  SER A 931      34.413  46.039  32.992  1.00 47.04
ATOM   1000  OG  SER A 931      34.049  44.700  32.650  1.00 47.04
ATOM   1003  N   THR A 932      37.030  47.813  31.024  1.00 77.19
ATOM   1004  CA  THR A 932      38.346  48.398  31.249  1.00 77.19
ATOM   1005  C   THR A 932      38.655  49.585  30.346  1.00 77.19
ATOM   1006  O   THR A 932      38.224  49.632  29.198  1.00 77.19
ATOM   1007  CB  THR A 932      39.453  47.353  31.056  1.00 99.17
ATOM   1008  OG1 THR A 932      39.813  47.299  29.676  1.00 99.17
ATOM   1009  CG2 THR A 932      38.980  45.991  31.492  1.00 99.17
ATOM   1012  N   ALA A 933      39.376  50.554  30.891  1.00 37.14
ATOM   1013  CA  ALA A 933      39.814  51.734  30.120  1.00 37.14
ATOM   1014  C   ALA A 933      40.655  51.286  28.911  1.00 37.14
ATOM   1015  O   ALA A 933      40.255  51.495  27.792  1.00 37.14
ATOM   1016  CB  ALA A 933      40.625  52.743  31.046  1.00  2.00
ATOM   1018  N   SER A 934      41.814  50.674  29.139  1.00 18.52
ATOM   1019  CA  SER A 934      42.656  50.117  28.038  1.00 18.52
ATOM   1020  C   SER A 934      42.578  48.537  27.897  1.00 18.52
ATOM   1021  O   SER A 934      42.047  47.842  28.815  1.00 18.52
ATOM   1022  CB  SER A 934      44.114  50.415  28.347  1.00 25.65
ATOM   1023  OG  SER A 934      44.983  49.645  27.568  1.00 25.65
ATOM   1026  N   THR A 935      43.162  48.023  26.794  1.00 63.20
ATOM   1027  CA  THR A 935      43.338  46.574  26.529  1.00 63.20
ATOM   1028  C   THR A 935      44.762  46.121  26.957  1.00 63.20
ATOM   1029  O   THR A 935      45.084  44.947  26.871  1.00 63.20
ATOM   1030  CB  THR A 935      43.298  46.147  25.069  1.00 29.40
ATOM   1031  OG1 THR A 935      44.470  46.603  24.393  1.00 29.40
ATOM   1032  CG2 THR A 935      42.095  46.590  24.385  1.00 29.40
ATOM   1035  N   LEU A 936      45.616  47.065  27.349  1.00  6.64
ATOM   1036  CA  LEU A 936      46.959  46.811  27.861  1.00  6.64
ATOM   1037  C   LEU A 936      46.654  46.775  29.277  1.00  6.64
ATOM   1038  O   LEU A 936      45.478  46.916  29.572  1.00  6.64
ATOM   1039  CB  LEU A 936      47.962  47.919  27.602  1.00  2.00
ATOM   1040  CG  LEU A 936      48.129  48.224  26.129  1.00  2.00
ATOM   1041  CD1 LEU A 936      48.725  49.731  25.993  1.00  2.00
ATOM   1042  CD2 LEU A 936      48.953  47.147  25.523  1.00  2.00
ATOM   1044  N   SER A 937      47.638  46.528  30.129  1.00 38.75
ATOM   1045  CA  SER A 937      47.437  46.434  31.555  1.00 38.75
ATOM   1046  C   SER A 937      48.615  47.041  32.342  1.00 38.75
```

FIG. 60

```
ATOM   1047  O   SER A 937      49.664  47.405  31.785  1.00 38.75
ATOM   1048  CB  SER A 937      47.257  44.979  31.954  1.00 80.09
ATOM   1049  OG  SER A 937      48.471  44.274  31.851  1.00 80.09
ATOM   1052  N   SER A 938      48.441  47.158  33.646  1.00 54.88
ATOM   1053  CA  SER A 938      49.489  47.699  34.441  1.00 54.88
ATOM   1054  C   SER A 938      50.807  47.155  33.941  1.00 54.88
ATOM   1055  O   SER A 938      51.696  47.907  33.571  1.00 54.88
ATOM   1056  CB  SER A 938      49.295  47.312  35.887  1.00 69.11
ATOM   1057  OG  SER A 938      50.397  47.773  36.631  1.00 69.11
ATOM   1060  N   GLN A 939      50.906  45.831  33.902  1.00 55.81
ATOM   1061  CA  GLN A 939      52.106  45.148  33.492  1.00 55.81
ATOM   1062  C   GLN A 939      52.644  45.445  32.132  1.00 55.81
ATOM   1063  O   GLN A 939      53.750  45.896  32.027  1.00 55.81
ATOM   1064  CB  GLN A 939      51.924  43.650  33.615  1.00 74.76
ATOM   1065  CG  GLN A 939      52.012  43.126  35.014  1.00 74.76
ATOM   1066  CD  GLN A 939      53.409  42.973  35.514  1.00 74.76
ATOM   1067  OE1 GLN A 939      54.238  42.296  34.906  1.00 74.76
ATOM   1068  NE2 GLN A 939      53.684  43.597  36.648  1.00 74.76
ATOM   1072  N   GLN A 940      51.899  45.176  31.069  1.00 26.74
ATOM   1073  CA  GLN A 940      52.446  45.439  29.736  1.00 26.74
ATOM   1074  C   GLN A 940      52.963  46.884  29.791  1.00 26.74
ATOM   1075  O   GLN A 940      53.929  47.302  29.115  1.00 26.74
ATOM   1076  CB  GLN A 940      51.405  45.313  28.639  1.00 43.63
ATOM   1077  CG  GLN A 940      51.815  46.080  27.393  1.00 43.63
ATOM   1078  CD  GLN A 940      52.444  45.214  26.267  1.00 43.63
ATOM   1079  OE1 GLN A 940      51.734  44.544  25.479  1.00 43.63
ATOM   1080  NE2 GLN A 940      53.756  45.236  26.183  1.00 43.63
ATOM   1084  N   LEU A 941      52.300  47.595  30.698  1.00 30.59
ATOM   1085  CA  LEU A 941      52.514  48.989  30.932  1.00 30.59
ATOM   1086  C   LEU A 941      53.800  49.234  31.599  1.00 30.59
ATOM   1087  O   LEU A 941      54.611  49.971  31.068  1.00 30.59
ATOM   1088  CB  LEU A 941      51.334  49.521  31.709  1.00 27.00
ATOM   1089  CG  LEU A 941      50.344  50.390  30.959  1.00 27.00
ATOM   1090  CD1 LEU A 941      50.253  51.655  31.777  1.00 27.00
ATOM   1091  CD2 LEU A 941      50.770  50.642  29.576  1.00 27.00
ATOM   1093  N   LEU A 942      53.992  48.683  32.768  1.00 26.63
ATOM   1094  CA  LEU A 942      55.284  48.801  33.427  1.00 26.63
ATOM   1095  C   LEU A 942      56.433  48.144  32.573  1.00 26.63
ATOM   1096  O   LEU A 942      57.616  48.326  32.850  1.00 26.63
ATOM   1097  CB  LEU A 942      55.208  48.083  34.741  1.00  3.59
ATOM   1098  CG  LEU A 942      55.275  49.016  35.906  1.00  3.59
ATOM   1099  CD1 LEU A 942      55.141  48.265  37.321  1.00  3.59
ATOM   1100  CD2 LEU A 942      56.635  49.823  35.675  1.00  3.59
ATOM   1102  N   HIS A 943      56.084  47.359  31.562  1.00 54.79
ATOM   1103  CA  HIS A 943      57.101  46.756  30.741  1.00 54.79
ATOM   1104  C   HIS A 943      57.531  47.932  29.905  1.00 54.79
ATOM   1105  O   HIS A 943      58.389  48.665  30.324  1.00 54.79
ATOM   1106  CB  HIS A 943      56.530  45.638  29.852  1.00 38.35
ATOM   1107  CG  HIS A 943      56.799  44.246  30.345  1.00 38.35
ATOM   1108  ND1 HIS A 943      56.846  43.914  31.682  1.00 38.35
ATOM   1109  CD2 HIS A 943      56.988  43.092  29.671  1.00 38.35
ATOM   1110  CE1 HIS A 943      57.050  42.619  31.812  1.00 38.35
ATOM   1111  NE2 HIS A 943      57.143  42.096  30.603  1.00 38.35
ATOM   1115  N   PHE A 944      56.905  48.115  28.741  1.00  4.19
ATOM   1116  CA  PHE A 944      57.172  49.217  27.780  1.00  4.19
ATOM   1117  C   PHE A 944      58.218  50.257  28.412  1.00  4.19
ATOM   1118  O   PHE A 944      59.278  50.592  27.781  1.00  4.19
```

FIG. 6P

```
ATOM  1119  CB   PHE A 944    55.878  49.913  27.509  1.00  28.23
ATOM  1120  CG   PHE A 944    55.036  49.255  26.489  1.00  28.23
ATOM  1121  CD1  PHE A 944    53.632  49.319  26.610  1.00  28.23
ATOM  1122  CD2  PHE A 944    55.605  48.780  25.336  1.00  28.23
ATOM  1123  CE1  PHE A 944    52.813  48.958  25.614  1.00  28.23
ATOM  1124  CE2  PHE A 944    54.769  48.399  24.289  1.00  28.23
ATOM  1125  CZ   PHE A 944    53.342  48.504  24.452  1.00  28.23
ATOM  1127  N    ALA A 945    57.874  50.702  29.637  1.00  24.23
ATOM  1128  CA   ALA A 945    58.742  51.520  30.434  1.00  24.23
ATOM  1129  C    ALA A 945    59.943  50.648  30.375  1.00  24.23
ATOM  1130  O    ALA A 945    60.623  50.707  29.408  1.00  24.23
ATOM  1131  CB   ALA A 945    58.270  51.631  31.839  1.00  16.89
ATOM  1133  N    ALA A 946    60.153  49.775  31.366  1.00  23.93
ATOM  1134  CA   ALA A 946    61.327  48.819  31.493  1.00  23.93
ATOM  1135  C    ALA A 946    62.279  48.525  30.320  1.00  23.93
ATOM  1136  O    ALA A 946    63.460  48.674  30.432  1.00  23.93
ATOM  1137  CB   ALA A 946    60.834  47.495  32.054  1.00  76.24
ATOM  1139  N    ASP A 947    61.796  48.078  29.188  1.00   9.63
ATOM  1140  CA   ASP A 947    62.727  47.858  28.131  1.00   9.63
ATOM  1141  C    ASP A 947    63.169  49.132  27.456  1.00   9.63
ATOM  1142  O    ASP A 947    63.604  49.093  26.290  1.00   9.63
ATOM  1143  CB   ASP A 947    62.145  46.880  27.114  1.00  90.89
ATOM  1144  CG   ASP A 947    61.065  47.493  26.259  1.00  90.89
ATOM  1145  OD1  ASP A 947    60.143  46.747  25.854  1.00  90.89
ATOM  1146  OD2  ASP A 947    61.128  48.707  25.978  1.00  90.89
ATOM  1148  N    VAL A 948    63.024  50.287  28.098  1.00  60.29
ATOM  1149  CA   VAL A 948    63.435  51.532  27.459  1.00  60.29
ATOM  1150  C    VAL A 948    64.572  51.963  28.376  1.00  60.29
ATOM  1151  O    VAL A 948    65.604  52.405  27.907  1.00  60.29
ATOM  1152  CB   VAL A 948    62.213  52.606  27.324  1.00   2.00
ATOM  1153  CG1  VAL A 948    62.752  54.133  26.901  1.00   2.00
ATOM  1154  CG2  VAL A 948    61.348  52.297  26.209  1.00   2.00
ATOM  1156  N    ALA A 949    64.402  51.773  29.686  1.00  12.91
ATOM  1157  CA   ALA A 949    65.448  52.097  30.677  1.00  12.91
ATOM  1158  C    ALA A 949    66.681  51.382  30.188  1.00  12.91
ATOM  1159  O    ALA A 949    67.733  52.000  29.956  1.00  12.91
ATOM  1160  CB   ALA A 949    65.135  51.617  32.017  1.00   2.00
ATOM  1162  N    ARG A 950    66.484  50.078  30.000  1.00  22.64
ATOM  1163  CA   ARG A 950    67.422  49.105  29.537  1.00  22.64
ATOM  1164  C    ARG A 950    68.106  49.588  28.340  1.00  22.64
ATOM  1165  O    ARG A 950    69.275  49.681  28.386  1.00  22.64
ATOM  1166  CB   ARG A 950    66.702  47.783  29.233  1.00  87.27
ATOM  1167  CG   ARG A 950    67.146  46.606  30.102  1.00  87.27
ATOM  1168  CD   ARG A 950    66.806  45.233  29.493  1.00  87.27
ATOM  1169  NE   ARG A 950    65.466  45.208  28.912  1.00  87.27
ATOM  1170  CZ   ARG A 950    64.341  44.977  29.580  1.00  87.27
ATOM  1171  NH1  ARG A 950    64.357  44.746  30.879  1.00  87.27
ATOM  1172  NH2  ARG A 950    63.188  45.019  28.941  1.00  87.27
ATOM  1179  N    GLY A 951    67.435  49.846  27.241  1.00  33.31
ATOM  1180  CA   GLY A 951    68.177  50.360  26.102  1.00  33.31
ATOM  1181  C    GLY A 951    68.720  51.768  26.462  1.00  33.31
ATOM  1182  O    GLY A 951    69.514  52.379  25.745  1.00  33.31
ATOM  1184  N    MET A 952    68.277  52.318  27.588  1.00  48.02
ATOM  1185  CA   MET A 952    68.774  53.615  27.949  1.00  48.02
ATOM  1186  C    MET A 952    70.030  53.440  28.759  1.00  48.02
ATOM  1187  O    MET A 952    70.861  54.316  28.719  1.00  48.02
ATOM  1188  CB   MET A 952    67.721  54.442  28.720  1.00  58.75
```

FIG. 6Q

| | | | | | | | | | |
|---|---|---|---|---|---|---|---|---|---|
| ATOM | 1189 | CG | MET | A | 952 | 67.277 | 55.792 | 28.089 | 1.00 58.75 |
| ATOM | 1190 | SD | MET | A | 952 | 67.797 | 56.265 | 26.390 | 1.00 58.75 |
| ATOM | 1191 | CE | MET | A | 952 | 69.079 | 57.471 | 26.826 | 1.00 58.75 |
| ATOM | 1193 | N | ASP | A | 953 | 70.145 | 52.325 | 29.494 | 1.00 30.83 |
| ATOM | 1194 | CA | ASP | A | 953 | 71.299 | 51.942 | 30.317 | 1.00 30.83 |
| ATOM | 1195 | C | ASP | A | 953 | 72.393 | 51.689 | 29.346 | 1.00 30.83 |
| ATOM | 1196 | O | ASP | A | 953 | 73.521 | 52.078 | 29.523 | 1.00 30.83 |
| ATOM | 1197 | CB | ASP | A | 953 | 71.084 | 50.617 | 30.955 | 1.00 30.69 |
| ATOM | 1198 | CG | ASP | A | 953 | 71.512 | 50.589 | 32.381 | 1.00 30.69 |
| ATOM | 1199 | OD1 | ASP | A | 953 | 71.504 | 51.661 | 32.997 | 1.00 30.69 |
| ATOM | 1200 | OD2 | ASP | A | 953 | 71.838 | 49.485 | 32.907 | 1.00 30.69 |
| ATOM | 1202 | N | TYR | A | 954 | 72.031 | 50.999 | 28.292 | 1.00 19.34 |
| ATOM | 1203 | CA | TYR | A | 954 | 72.952 | 50.630 | 27.239 | 1.00 19.34 |
| ATOM | 1204 | C | TYR | A | 954 | 73.559 | 51.896 | 26.762 | 1.00 19.34 |
| ATOM | 1205 | O | TYR | A | 954 | 74.529 | 52.327 | 27.362 | 1.00 19.34 |
| ATOM | 1206 | CB | TYR | A | 954 | 72.236 | 49.887 | 26.117 | 1.00 37.26 |
| ATOM | 1207 | CG | TYR | A | 954 | 73.181 | 49.115 | 25.244 | 1.00 37.26 |
| ATOM | 1208 | CD1 | TYR | A | 954 | 74.158 | 48.238 | 25.784 | 1.00 37.26 |
| ATOM | 1209 | CD2 | TYR | A | 954 | 73.149 | 49.300 | 23.871 | 1.00 37.26 |
| ATOM | 1210 | CE1 | TYR | A | 954 | 75.072 | 47.594 | 24.942 | 1.00 37.26 |
| ATOM | 1211 | CE2 | TYR | A | 954 | 74.042 | 48.676 | 23.041 | 1.00 37.26 |
| ATOM | 1212 | CZ | TYR | A | 954 | 74.993 | 47.843 | 23.568 | 1.00 37.26 |
| ATOM | 1213 | OH | TYR | A | 954 | 75.859 | 47.367 | 22.645 | 1.00 37.26 |
| ATOM | 1216 | N | LEU | A | 955 | 72.967 | 52.501 | 25.722 | 1.00 49.71 |
| ATOM | 1217 | CA | LEU | A | 955 | 73.404 | 53.781 | 25.150 | 1.00 49.71 |
| ATOM | 1218 | C | LEU | A | 955 | 73.854 | 54.641 | 26.293 | 1.00 49.71 |
| ATOM | 1219 | O | LEU | A | 955 | 74.950 | 55.109 | 26.279 | 1.00 49.71 |
| ATOM | 1220 | CB | LEU | A | 955 | 72.272 | 54.530 | 24.439 | 1.00 17.74 |
| ATOM | 1221 | CG | LEU | A | 955 | 71.456 | 53.937 | 23.292 | 1.00 17.74 |
| ATOM | 1222 | CD1 | LEU | A | 955 | 69.972 | 54.493 | 23.397 | 1.00 17.74 |
| ATOM | 1223 | CD2 | LEU | A | 955 | 71.989 | 54.345 | 21.914 | 1.00 17.74 |
| ATOM | 1225 | N | SER | A | 956 | 73.012 | 54.840 | 27.293 | 1.00 34.64 |
| ATOM | 1226 | CA | SER | A | 956 | 73.430 | 55.663 | 28.404 | 1.00 34.64 |
| ATOM | 1227 | C | SER | A | 956 | 74.843 | 55.350 | 28.778 | 1.00 34.64 |
| ATOM | 1228 | O | SER | A | 956 | 75.701 | 56.218 | 28.579 | 1.00 34.64 |
| ATOM | 1229 | CB | SER | A | 956 | 72.561 | 55.495 | 29.622 | 1.00 37.38 |
| ATOM | 1230 | OG | SER | A | 956 | 73.071 | 56.228 | 30.699 | 1.00 37.38 |
| ATOM | 1233 | N | GLN | A | 957 | 75.134 | 54.188 | 29.321 | 1.00 33.59 |
| ATOM | 1234 | CA | GLN | A | 957 | 76.511 | 53.895 | 29.680 | 1.00 33.59 |
| ATOM | 1235 | C | GLN | A | 957 | 77.379 | 53.837 | 28.410 | 1.00 33.59 |
| ATOM | 1236 | O | GLN | A | 957 | 77.719 | 52.798 | 27.943 | 1.00 33.59 |
| ATOM | 1237 | CB | GLN | A | 957 | 76.583 | 52.568 | 30.455 | 1.00 42.10 |
| ATOM | 1238 | CG | GLN | A | 957 | 76.621 | 52.721 | 32.002 | 1.00 42.10 |
| ATOM | 1239 | CD | GLN | A | 957 | 77.483 | 53.951 | 32.500 | 1.00 42.10 |
| ATOM | 1240 | OE1 | GLN | A | 957 | 78.321 | 54.499 | 31.739 | 1.00 42.10 |
| ATOM | 1241 | NE2 | GLN | A | 957 | 77.274 | 54.367 | 33.780 | 1.00 42.10 |
| ATOM | 1245 | N | LYS | A | 958 | 77.739 | 54.952 | 27.823 | 1.00 99.18 |
| ATOM | 1246 | CA | LYS | A | 958 | 78.543 | 54.854 | 26.620 | 1.00 99.18 |
| ATOM | 1247 | C | LYS | A | 958 | 78.688 | 56.227 | 26.039 | 1.00 99.18 |
| ATOM | 1248 | O | LYS | A | 958 | 79.111 | 56.370 | 24.897 | 1.00 99.18 |
| ATOM | 1249 | CB | LYS | A | 958 | 77.880 | 53.934 | 25.586 | 1.00 99.74 |
| ATOM | 1250 | CG | LYS | A | 958 | 78.545 | 52.582 | 25.404 | 1.00 99.74 |
| ATOM | 1251 | CD | LYS | A | 958 | 77.830 | 51.738 | 24.360 | 1.00 99.74 |
| ATOM | 1252 | CE | LYS | A | 958 | 77.997 | 50.238 | 24.629 | 1.00 99.74 |
| ATOM | 1253 | NZ | LYS | A | 958 | 78.459 | 49.456 | 23.434 | 1.00 99.74 |
| ATOM | 1258 | N | GLN | A | 959 | 78.327 | 57.233 | 26.832 | 1.00 73.45 |
| ATOM | 1259 | CA | GLN | A | 959 | 78.423 | 58.615 | 26.402 | 1.00 73.45 |

FIG. 6R

```
ATOM  1260  C   GLN A 959      77.378  58.947  25.376  1.00  73.45
ATOM  1261  O   GLN A 959      77.493  59.970  24.702  1.00  73.45
ATOM  1262  CB  GLN A 959      79.785  58.882  25.784  1.00  19.35
ATOM  1263  CG  GLN A 959      80.899  58.069  26.399  1.00  19.35
ATOM  1264  CD  GLN A 959      80.957  58.449  27.805  1.00  19.35
ATOM  1265  OE1 GLN A 959      80.252  59.453  28.221  1.00  19.35
ATOM  1266  NE2 GLN A 959      81.763  57.708  28.610  1.00  19.35
ATOM  1270  N   PHE A 960      75.376  58.075  25.242  1.00  36.08
ATOM  1271  CA  PHE A 960      75.312  58.292  24.262  1.00  36.08
ATOM  1272  C   PHE A 960      74.223  59.102  24.958  1.00  36.08
ATOM  1273  O   PHE A 960      73.754  58.762  26.078  1.00  36.08
ATOM  1274  CB  PHE A 960      74.810  56.957  23.718  1.00  85.11
ATOM  1275  CG  PHE A 960      75.670  56.407  22.614  1.00  85.11
ATOM  1276  CD1 PHE A 960      76.531  55.349  22.839  1.00  85.11
ATOM  1277  CD2 PHE A 960      75.656  56.981  21.350  1.00  85.11
ATOM  1278  CE1 PHE A 960      77.361  54.879  21.822  1.00  85.11
ATOM  1279  CE2 PHE A 960      76.493  56.505  20.330  1.00  85.11
ATOM  1280  CZ  PHE A 960      77.338  55.461  20.572  1.00  85.11
ATOM  1282  N   ILE A 961      73.918  60.227  24.300  1.00  30.22
ATOM  1283  CA  ILE A 961      72.939  61.196  24.749  1.00  30.22
ATOM  1284  C   ILE A 961      71.858  61.213  23.713  1.00  30.22
ATOM  1285  O   ILE A 961      72.112  61.420  22.545  1.00  30.22
ATOM  1286  CB  ILE A 961      73.536  62.578  24.911  1.00  71.39
ATOM  1287  CG1 ILE A 961      74.693  62.526  25.899  1.00  71.39
ATOM  1288  CG2 ILE A 961      72.488  63.518  25.442  1.00  71.39
ATOM  1289  CD1 ILE A 961      75.888  63.302  25.476  1.00  71.39
ATOM  1291  N   HIS A 962      70.627  61.034  24.158  1.00  80.58
ATOM  1292  CA  HIS A 962      69.524  60.924  23.236  1.00  80.58
ATOM  1293  C   HIS A 962      68.798  62.196  22.692  1.00  80.58
ATOM  1294  O   HIS A 962      69.179  62.676  21.629  1.00  80.58
ATOM  1295  CB  HIS A 962      68.584  59.904  23.855  1.00  39.42
ATOM  1296  CG  HIS A 962      67.415  59.585  23.008  1.00  39.42
ATOM  1297  ND1 HIS A 962      67.142  58.316  22.575  1.00  39.42
ATOM  1298  CD2 HIS A 962      66.450  60.378  22.499  1.00  39.42
ATOM  1299  CE1 HIS A 962      66.052  58.335  21.832  1.00  39.42
ATOM  1300  NE2 HIS A 962      65.617  59.580  21.772  1.00  39.42
ATOM  1304  N   ARG A 963      67.745  62.694  23.367  1.00  25.62
ATOM  1305  CA  ARG A 963      67.008  63.920  22.979  1.00  25.62
ATOM  1306  C   ARG A 963      65.777  63.852  22.084  1.00  25.62
ATOM  1307  O   ARG A 963      65.762  64.331  20.941  1.00  25.62
ATOM  1308  CB  ARG A 963      67.977  64.955  22.380  1.00  98.75
ATOM  1309  CG  ARG A 963      69.318  65.061  23.081  1.00  98.75
ATOM  1310  CD  ARG A 963      70.230  66.016  22.356  1.00  98.75
ATOM  1311  NE  ARG A 963      70.718  65.501  21.087  1.00  98.75
ATOM  1312  CZ  ARG A 963      70.212  65.832  19.911  1.00  98.75
ATOM  1313  NH1 ARG A 963      69.200  66.680  19.852  1.00  98.75
ATOM  1314  NH2 ARG A 963      70.717  65.321  18.801  1.00  98.75
ATOM  1321  N   ASN A 964      64.738  63.276  22.661  1.00  47.91
ATOM  1322  CA  ASN A 964      63.442  63.070  22.035  1.00  47.91
ATOM  1323  C   ASN A 964      63.235  61.618  22.246  1.00  47.91
ATOM  1324  O   ASN A 964      63.068  60.856  21.302  1.00  47.91
ATOM  1325  CB  ASN A 964      63.453  63.377  20.538  1.00  84.77
ATOM  1326  CG  ASN A 964      62.453  64.459  20.153  1.00  84.77
ATOM  1327  OD1 ASN A 964      61.509  64.768  20.902  1.00  84.77
ATOM  1328  ND2 ASN A 964      62.653  65.039  18.977  1.00  84.77
ATOM  1332  N   LEU A 965      63.366  61.249  23.509  1.00  96.70
ATOM  1333  CA  LEU A 965      63.148  59.897  23.937  1.00  96.70
```

FIG. 6S

```
ATOM   1334  C   LEU A 965      61.836  60.220  24.659  1.00 96.70
ATOM   1335  O   LEU A 965      61.784  60.527  25.833  1.00 96.70
ATOM   1336  CB  LEU A 965      64.352  59.382  24.805  1.00 17.46
ATOM   1337  CG  LEU A 965      64.456  58.589  26.099  1.00 17.46
ATOM   1338  CD1 LEU A 965      65.774  58.784  26.891  1.00 17.46
ATOM   1339  CD2 LEU A 965      63.423  59.114  26.967  1.00 17.46
ATOM   1341  N   ALA A 966      60.794  60.283  23.833  1.00 71.46
ATOM   1342  CA  ALA A 966      59.408  60.534  24.219  1.00 71.46
ATOM   1343  C   ALA A 966      58.601  59.518  23.395  1.00 71.46
ATOM   1344  O   ALA A 966      59.009  59.122  22.314  1.00 71.46
ATOM   1345  CB  ALA A 966      59.005  61.933  23.885  1.00 62.29
ATOM   1347  N   ALA A 967      57.457  59.105  23.908  1.00 34.40
ATOM   1348  CA  ALA A 967      56.641  58.086  23.249  1.00 34.40
ATOM   1349  C   ALA A 967      56.585  58.066  21.726  1.00 34.40
ATOM   1350  O   ALA A 967      56.689  57.011  21.106  1.00 34.40
ATOM   1351  CB  ALA A 967      55.236  58.088  23.807  1.00 31.96
ATOM   1353  N   ARG A 968      56.462  59.208  21.094  1.00  9.59
ATOM   1354  CA  ARG A 968      56.309  59.113  19.678  1.00  9.59
ATOM   1355  C   ARG A 968      57.467  58.532  19.054  1.00  9.59
ATOM   1356  O   ARG A 968      57.335  58.106  17.930  1.00  9.59
ATOM   1357  CB  ARG A 968      55.960  60.480  19.013  1.00 12.36
ATOM   1358  CG  ARG A 968      56.480  61.806  19.751  1.00 12.36
ATOM   1359  CD  ARG A 968      56.426  62.907  18.727  1.00 12.36
ATOM   1360  NE  ARG A 968      57.453  63.898  18.879  1.00 12.36
ATOM   1361  CZ  ARG A 968      57.608  64.568  19.994  1.00 12.36
ATOM   1362  NH1 ARG A 968      56.746  64.307  20.994  1.00 12.36
ATOM   1363  NH2 ARG A 968      58.718  65.297  20.206  1.00 12.36
ATOM   1370  N   ASN A 969      58.511  58.550  19.735  1.00 56.22
ATOM   1371  CA  ASN A 969      59.878  58.043  19.179  1.00 56.22
ATOM   1372  C   ASN A 969      60.309  56.672  19.730  1.00 56.22
ATOM   1373  O   ASN A 969      61.472  56.327  19.673  1.00 56.22
ATOM   1374  CB  ASN A 969      61.011  59.053  19.444  1.00 99.68
ATOM   1375  CG  ASN A 969      60.674  60.482  18.998  1.00 99.68
ATOM   1376  OD1 ASN A 969      60.213  61.303  19.787  1.00 99.68
ATOM   1377  ND2 ASN A 969      60.926  60.780  17.732  1.00 99.68
ATOM   1381  N   ILE A 970      59.351  55.935  20.288  1.00 10.68
ATOM   1382  CA  ILE A 970      59.507  54.683  20.853  1.00 10.68
ATOM   1383  C   ILE A 970      58.651  53.708  20.079  1.00 10.68
ATOM   1384  O   ILE A 970      57.450  53.865  20.060  1.00 10.68
ATOM   1385  CB  ILE A 970      59.003  54.602  22.168  1.00 11.62
ATOM   1386  CG1 ILE A 970      59.808  55.496  23.084  1.00 11.62
ATOM   1387  CG2 ILE A 970      59.191  53.056  22.620  1.00 11.62
ATOM   1388  CD1 ILE A 970      61.263  55.730  22.600  1.00 11.62
ATOM   1390  N   LEU A 971      59.250  52.676  19.496  1.00 31.69
ATOM   1391  CA  LEU A 971      58.519  51.699  18.733  1.00 31.69
ATOM   1392  C   LEU A 971      58.148  50.357  19.369  1.00 31.69
ATOM   1393  O   LEU A 971      58.938  49.792  20.148  1.00 31.69
ATOM   1394  CB  LEU A 971      59.308  51.333  17.535  1.00 17.23
ATOM   1395  CG  LEU A 971      59.702  52.411  16.632  1.00 17.23
ATOM   1396  CD1 LEU A 971      60.981  51.973  16.005  1.00 17.23
ATOM   1397  CD2 LEU A 971      58.629  52.642  15.646  1.00 17.23
ATOM   1399  N   VAL A 972      56.953  49.832  19.017  1.00 20.91
ATOM   1400  CA  VAL A 972      56.655  48.486  19.475  1.00 20.91
ATOM   1401  C   VAL A 972      56.862  47.491  18.389  1.00 20.91
ATOM   1402  O   VAL A 972      56.022  47.375  17.523  1.00 20.91
ATOM   1403  CB  VAL A 972      55.344  48.349  19.953  1.00  9.13
ATOM   1404  CG1 VAL A 972      55.362  47.291  21.081  1.00  9.13
```

FIG. 6T

```
ATOM   1405  CG2 VAL A 972    54.797  49.894  20.467  1.00   9.13
ATOM   1407  N   GLY A 973    58.077  46.873  18.414  1.00  32.46
ATOM   1408  CA  GLY A 973    58.514  45.851  17.466  1.00  32.46
ATOM   1409  C   GLY A 973    58.012  44.434  17.814  1.00  32.46
ATOM   1410  O   GLY A 973    57.324  44.254  18.816  1.00  32.46
ATOM   1412  N   GLU A 974    58.393  43.403  17.055  1.00  22.44
ATOM   1413  CA  GLU A 974    57.846  42.109  17.351  1.00  22.44
ATOM   1414  C   GLU A 974    57.902  41.725  18.793  1.00  22.44
ATOM   1415  O   GLU A 974    58.809  42.041  19.510  1.00  22.44
ATOM   1416  CB  GLU A 974    58.364  41.035  16.394  1.00  65.78
ATOM   1417  CG  GLU A 974    57.385  40.798  15.138  1.00  65.78
ATOM   1418  CD  GLU A 974    55.821  40.585  15.469  1.00  65.78
ATOM   1419  OE1 GLU A 974    55.398  40.463  16.656  1.00  65.78
ATOM   1420  OE2 GLU A 974    55.005  40.540  14.512  1.00  65.78
ATOM   1422  N   ASN A 975    56.767  41.210  19.246  1.00  22.08
ATOM   1423  CA  ASN A 975    56.540  40.717  20.627  1.00  22.08
ATOM   1424  C   ASN A 975    56.037  41.756  21.638  1.00  22.08
ATOM   1425  O   ASN A 975    55.968  41.482  22.844  1.00  22.08
ATOM   1426  CB  ASN A 975    57.810  40.016  21.140  1.00  99.25
ATOM   1427  CG  ASN A 975    58.074  38.679  20.438  1.00  99.25
ATOM   1428  OD1 ASN A 975    58.836  37.859  20.929  1.00  99.25
ATOM   1429  ND2 ASN A 975    57.446  38.465  19.292  1.00  99.25
ATOM   1433  N   TYR A 976    55.656  42.932  21.134  1.00  30.29
ATOM   1434  CA  TYR A 976    55.204  44.013  21.972  1.00  30.29
ATOM   1435  C   TYR A 976    56.427  44.631  22.697  1.00  30.29
ATOM   1436  O   TYR A 976    56.331  45.214  23.759  1.00  30.29
ATOM   1437  CB  TYR A 976    54.157  43.463  22.893  1.00  71.60
ATOM   1438  CG  TYR A 976    53.001  42.961  22.089  1.00  71.60
ATOM   1439  CD1 TYR A 976    52.698  41.611  22.036  1.00  71.60
ATOM   1440  CD2 TYR A 976    52.229  43.840  21.339  1.00  71.60
ATOM   1441  CE1 TYR A 976    51.652  41.145  21.243  1.00  71.60
ATOM   1442  CE2 TYR A 976    51.181  43.390  20.547  1.00  71.60
ATOM   1443  CZ  TYR A 976    50.895  42.043  20.491  1.00  71.60
ATOM   1444  OH  TYR A 976    49.905  41.588  19.655  1.00  71.60
ATOM   1447  N   VAL A 977    57.569  44.513  22.047  1.00  35.58
ATOM   1448  CA  VAL A 977    58.837  44.988  22.597  1.00  35.58
ATOM   1449  C   VAL A 977    59.247  46.367  22.101  1.00  35.58
ATOM   1450  O   VAL A 977    59.495  46.616  20.903  1.00  35.58
ATOM   1451  CB  VAL A 977    59.994  43.975  22.316  1.00  54.29
ATOM   1452  CG1 VAL A 977    61.110  44.134  23.340  1.00  54.29
ATOM   1453  CG2 VAL A 977    59.418  42.533  22.339  1.00  54.29
ATOM   1455  N   ALA A 978    59.355  47.233  23.082  1.00  36.83
ATOM   1456  CA  ALA A 978    59.628  48.594  22.857  1.00  36.83
ATOM   1457  C   ALA A 978    61.086  49.005  22.550  1.00  36.83
ATOM   1458  O   ALA A 978    61.937  48.823  23.380  1.00  36.83
ATOM   1459  CB  ALA A 978    59.142  49.265  24.019  1.00  27.14
ATOM   1461  N   LYS A 979    61.368  49.570  21.374  1.00  42.93
ATOM   1462  CA  LYS A 979    62.704  50.023  21.063  1.00  42.93
ATOM   1463  C   LYS A 979    63.002  51.530  20.907  1.00  42.93
ATOM   1464  O   LYS A 979    62.175  52.352  20.414  1.00  42.93
ATOM   1465  CB  LYS A 979    63.190  49.433  19.798  1.00  32.23
ATOM   1466  CG  LYS A 979    62.273  48.708  19.039  1.00  32.23
ATOM   1467  CD  LYS A 979    62.556  47.230  19.416  1.00  32.23
ATOM   1468  CE  LYS A 979    63.156  46.356  18.275  1.00  32.23
ATOM   1469  NZ  LYS A 979    63.744  45.144  18.883  1.00  32.23
ATOM   1474  N   ILE A 980    64.233  51.887  21.275  1.00   2.00
ATOM   1475  CA  ILE A 980    64.639  53.265  21.099  1.00   2.00
```

FIG. 6U

```
ATOM  1476  C   ILE A 980      65.044  53.446  19.649  1.00  2.00
ATOM  1477  O   ILE A 980      65.191  52.445  18.913  1.00  2.00
ATOM  1478  CB  ILE A 980      65.717  53.649  22.013  1.00 22.25
ATOM  1479  CG1 ILE A 980      65.318  53.372  23.463  1.00 22.25
ATOM  1480  CG2 ILE A 980      65.839  55.073  21.885  1.00 22.25
ATOM  1481  CD1 ILE A 980      66.358  53.040  24.467  1.00 22.25
ATOM  1483  N   ALA A 981      65.129  54.715  19.235  1.00 37.10
ATOM  1484  CA  ALA A 981      65.489  55.166  17.870  1.00 37.10
ATOM  1485  C   ALA A 981      65.426  56.684  17.652  1.00 37.10
ATOM  1486  O   ALA A 981      64.905  57.454  18.494  1.00 37.10
ATOM  1487  CB  ALA A 981      64.634  54.620  16.964  1.00 12.10
ATOM  1489  N   ASP A 982      65.933  57.120  16.508  1.00 81.89
ATOM  1490  CA  ASP A 982      65.907  58.525  16.186  1.00 81.89
ATOM  1491  C   ASP A 982      66.821  59.190  17.201  1.00 81.89
ATOM  1492  O   ASP A 982      66.877  60.416  17.342  1.00 81.89
ATOM  1493  CB  ASP A 982      64.465  59.029  16.284  1.00 22.36
ATOM  1494  CG  ASP A 982      64.352  60.357  16.999  1.00 22.36
ATOM  1495  OD1 ASP A 982      64.517  61.390  16.281  1.00 22.36
ATOM  1496  OD2 ASP A 982      64.112  60.353  18.252  1.00 22.36
ATOM  1498  N   PHE A 983      67.540  58.353  17.922  1.00 90.03
ATOM  1499  CA  PHE A 983      68.502  58.819  18.897  1.00 90.03
ATOM  1500  C   PHE A 983      69.521  59.638  18.083  1.00 90.03
ATOM  1501  O   PHE A 983      69.436  59.728  16.844  1.00 90.03
ATOM  1502  CB  PHE A 983      69.205  57.599  19.489  1.00100.00
ATOM  1503  CG  PHE A 983      69.417  56.489  18.475  1.00100.00
ATOM  1504  CD1 PHE A 983      70.419  56.593  17.502  1.00100.00
ATOM  1505  CD2 PHE A 983      68.567  55.387  18.435  1.00100.00
ATOM  1506  CE1 PHE A 983      70.557  55.624  16.513  1.00100.00
ATOM  1507  CE2 PHE A 983      68.704  54.418  17.449  1.00100.00
ATOM  1508  CZ  PHE A 983      69.698  54.537  16.488  1.00100.00
ATOM  1510  N   GLY A 984      70.493  60.226  18.770  1.00 59.78
ATOM  1511  CA  GLY A 984      71.533  60.957  18.060  1.00 59.78
ATOM  1512  C   GLY A 984      72.821  60.159  18.193  1.00 59.78
ATOM  1513  O   GLY A 984      72.900  59.221  19.019  1.00 59.78
ATOM  1515  N   LEU A 985      73.816  60.488  17.379  1.00 99.32
ATOM  1516  CA  LEU A 985      75.094  59.791  17.454  1.00 99.32
ATOM  1517  C   LEU A 985      75.886  60.603  18.440  1.00 99.32
ATOM  1518  O   LEU A 985      77.068  60.348  18.669  1.00 99.32
ATOM  1519  CB  LEU A 985      75.824  59.786  16.106  1.00100.00
ATOM  1520  CG  LEU A 985      75.453  58.753  15.036  1.00100.00
ATOM  1521  CD1 LEU A 985      74.707  57.590  15.651  1.00100.00
ATOM  1522  CD2 LEU A 985      74.604  59.428  13.971  1.00100.00
ATOM  1524  N   SER A 986      75.211  61.587  19.020  1.00 37.75
ATOM  1525  CA  SER A 986      75.828  62.476  19.989  1.00 37.75
ATOM  1526  C   SER A 986      76.413  61.806  21.210  1.00 37.75
ATOM  1527  O   SER A 986      75.708  61.541  22.143  1.00 37.75
ATOM  1528  CB  SER A 986      74.830  63.525  20.445  1.00 99.91
ATOM  1529  OG  SER A 986      75.198  64.776  19.917  1.00 99.91
ATOM  1532  N   ARG A 987      77.710  61.513  21.216  1.00 63.13
ATOM  1533  CA  ARG A 987      78.285  60.910  22.407  1.00 63.13
ATOM  1534  C   ARG A 987      79.243  61.904  22.979  1.00 63.13
ATOM  1535  O   ARG A 987      80.058  62.476  22.270  1.00 63.13
ATOM  1536  CB  ARG A 987      78.964  59.567  22.132  1.00 87.40
ATOM  1537  CG  ARG A 987      79.870  59.529  20.947  1.00 87.40
ATOM  1538  CD  ARG A 987      81.110  58.722  21.273  1.00 87.40
ATOM  1539  NE  ARG A 987      80.807  57.654  22.217  1.00 87.40
ATOM  1540  CZ  ARG A 987      80.782  56.366  21.898  1.00 87.40
```

FIG. 6V

| ATOM | 1541 | NH1 | ARG A 987 | 81.042 | 55.981 | 20.658 | 1.00 | 87.40 |
| ATOM | 1542 | NH2 | ARG A 987 | 80.506 | 55.463 | 22.824 | 1.00 | 87.40 |
| ATOM | 1549 | N | GLY A 988 | 79.090 | 62.096 | 24.282 | 1.00 | 28.62 |
| ATOM | 1550 | CA | GLY A 988 | 79.833 | 63.044 | 25.072 | 1.00 | 28.62 |
| ATOM | 1551 | C | GLY A 988 | 79.268 | 63.073 | 26.476 | 1.00 | 28.62 |
| ATOM | 1552 | O | GLY A 988 | 78.558 | 62.156 | 26.816 | 1.00 | 28.62 |
| ATOM | 1554 | N | GLN A 989 | 79.612 | 64.094 | 27.270 | 1.00 | 22.70 |
| ATOM | 1555 | CA | GLN A 989 | 79.214 | 64.322 | 28.682 | 1.00 | 22.70 |
| ATOM | 1556 | C | GLN A 989 | 78.188 | 65.518 | 28.775 | 1.00 | 22.70 |
| ATOM | 1557 | O | GLN A 989 | 77.534 | 65.676 | 29.785 | 1.00 | 22.70 |
| ATOM | 1558 | CB | GLN A 989 | 80.449 | 64.647 | 29.536 | 1.00 | 98.73 |
| ATOM | 1559 | CG | GLN A 989 | 80.240 | 64.572 | 31.049 | 1.00 | 98.73 |
| ATOM | 1560 | CD | GLN A 989 | 81.127 | 65.539 | 31.844 | 1.00 | 98.73 |
| ATOM | 1561 | OE1 | GLN A 989 | 81.240 | 66.712 | 31.510 | 1.00 | 98.73 |
| ATOM | 1562 | NE2 | GLN A 989 | 81.746 | 65.043 | 32.901 | 1.00 | 98.73 |
| ATOM | 1566 | N | GLU A 990 | 78.055 | 66.323 | 27.724 | 1.00 | 47.13 |
| ATOM | 1567 | CA | GLU A 990 | 77.173 | 67.478 | 27.725 | 1.00 | 47.13 |
| ATOM | 1568 | C | GLU A 990 | 77.106 | 67.842 | 26.251 | 1.00 | 47.13 |
| ATOM | 1569 | O | GLU A 990 | 78.116 | 67.765 | 25.565 | 1.00 | 47.13 |
| ATOM | 1570 | CB | GLU A 990 | 77.830 | 68.612 | 28.534 | 1.00 | 77.23 |
| ATOM | 1571 | CG | GLU A 990 | 76.950 | 69.834 | 28.830 | 1.00 | 77.23 |
| ATOM | 1572 | CD | GLU A 990 | 76.930 | 70.244 | 30.322 | 1.00 | 77.23 |
| ATOM | 1573 | OE1 | GLU A 990 | 77.431 | 69.468 | 31.165 | 1.00 | 77.23 |
| ATOM | 1574 | OE2 | GLU A 990 | 76.406 | 71.337 | 30.658 | 1.00 | 77.23 |
| ATOM | 1576 | N | VAL A 991 | 75.946 | 68.228 | 25.727 | 1.00 | 24.20 |
| ATOM | 1577 | CA | VAL A 991 | 75.831 | 68.569 | 24.274 | 1.00 | 24.20 |
| ATOM | 1578 | C | VAL A 991 | 75.272 | 69.989 | 24.073 | 1.00 | 24.20 |
| ATOM | 1579 | O | VAL A 991 | 75.089 | 70.682 | 25.017 | 1.00 | 24.20 |
| ATOM | 1580 | CB | VAL A 991 | 74.897 | 67.572 | 23.527 | 1.00 | 55.15 |
| ATOM | 1581 | CG1 | VAL A 991 | 75.197 | 67.520 | 22.035 | 1.00 | 55.15 |
| ATOM | 1582 | CG2 | VAL A 991 | 75.015 | 66.252 | 24.148 | 1.00 | 55.15 |
| ATOM | 1584 | N | TYR A 992 | 75.056 | 70.398 | 22.840 | 1.00 | 53.40 |
| ATOM | 1585 | CA | TYR A 992 | 74.514 | 71.693 | 22.545 | 1.00 | 53.40 |
| ATOM | 1586 | C | TYR A 992 | 73.954 | 71.659 | 21.140 | 1.00 | 53.40 |
| ATOM | 1587 | O | TYR A 992 | 74.678 | 71.455 | 20.177 | 1.00 | 53.40 |
| ATOM | 1588 | CB | TYR A 992 | 75.594 | 72.774 | 22.658 | 1.00 | 83.17 |
| ATOM | 1589 | CG | TYR A 992 | 75.167 | 74.067 | 22.018 | 1.00 | 83.17 |
| ATOM | 1590 | CD1 | TYR A 992 | 74.337 | 74.950 | 22.688 | 1.00 | 83.17 |
| ATOM | 1591 | CD2 | TYR A 992 | 75.452 | 74.316 | 20.694 | 1.00 | 83.17 |
| ATOM | 1592 | CE1 | TYR A 992 | 73.796 | 76.025 | 22.047 | 1.00 | 83.17 |
| ATOM | 1593 | CE2 | TYR A 992 | 74.919 | 75.380 | 20.053 | 1.00 | 83.17 |
| ATOM | 1594 | CZ | TYR A 992 | 74.090 | 76.230 | 20.726 | 1.00 | 83.17 |
| ATOM | 1595 | OH | TYR A 992 | 73.569 | 77.297 | 20.053 | 1.00 | 83.17 |
| ATOM | 1598 | N | VAL A 993 | 72.645 | 71.821 | 21.015 | 1.00 | 100.00 |
| ATOM | 1599 | CA | VAL A 993 | 72.047 | 71.808 | 19.695 | 1.00 | 100.00 |
| ATOM | 1600 | C | VAL A 993 | 70.897 | 72.813 | 19.594 | 1.00 | 100.00 |
| ATOM | 1601 | O | VAL A 993 | 69.736 | 72.514 | 19.912 | 1.00 | 100.00 |
| ATOM | 1602 | CB | VAL A 993 | 71.604 | 70.371 | 19.304 | 1.00 | 80.14 |
| ATOM | 1603 | CG1 | VAL A 993 | 71.422 | 69.529 | 20.538 | 1.00 | 80.14 |
| ATOM | 1604 | CG2 | VAL A 993 | 70.338 | 70.409 | 18.450 | 1.00 | 80.14 |
| ATOM | 1606 | N | LYS A 994 | 71.260 | 74.022 | 19.155 | 1.00 | 83.98 |
| ATOM | 1607 | CA | LYS A 994 | 70.329 | 75.125 | 18.980 | 1.00 | 83.98 |
| ATOM | 1608 | C | LYS A 994 | 69.729 | 74.959 | 17.615 | 1.00 | 83.98 |
| ATOM | 1609 | O | LYS A 994 | 70.421 | 74.538 | 16.688 | 1.00 | 83.98 |
| ATOM | 1610 | CB | LYS A 994 | 71.076 | 76.455 | 19.070 | 1.00 | 100.00 |
| ATOM | 1611 | CG | LYS A 994 | 70.350 | 77.670 | 18.498 | 1.00 | 100.00 |
| ATOM | 1612 | CD | LYS A 994 | 71.347 | 78.789 | 18.226 | 1.00 | 100.00 |

FIG. 6W

```
ATOM   1613  CE   LYS A  994      70.694  80.150  18.153  1.00100.00
ATOM   1614  NZ   LYS A  994      71.425  81.159  18.962  1.00100.00
ATOM   1619  N    LYS A  995      68.446  75.287  17.488  1.00 66.77
ATOM   1620  CA   LYS A  995      67.741  75.142  16.210  1.00 66.77
ATOM   1621  C    LYS A  995      68.023  73.749  15.591  1.00 66.77
ATOM   1622  O    LYS A  995      67.910  73.583  14.358  1.00 66.77
ATOM   1623  CB   LYS A  995      68.167  76.265  15.244  1.00100.00
ATOM   1624  OXT  LYS A  995      68.354  72.815  16.355  1.00100.00
ATOM   1626  N    PRO A1001       61.032  69.682  22.189  1.00 23.57
ATOM   1627  CA   PRO A1001       59.754  69.092  22.679  1.00 23.57
ATOM   1628  C    PRO A1001       59.681  69.765  24.004  1.00 23.57
ATOM   1629  O    PRO A1001       59.857  69.162  25.026  1.00 23.57
ATOM   1630  CB   PRO A1001       59.964  67.607  22.863  1.00 82.24
ATOM   1631  CG   PRO A1001       61.529  67.446  22.804  1.00 82.24
ATOM   1632  CD   PRO A1001       62.179  68.812  22.494  1.00 82.24
ATOM   1635  N    VAL A1002       59.429  71.067  23.965  1.00 14.96
ATOM   1636  CA   VAL A1002       59.401  71.905  25.163  1.00 14.96
ATOM   1637  C    VAL A1002       58.731  71.247  26.277  1.00 14.96
ATOM   1638  O    VAL A1002       58.930  71.607  27.409  1.00 14.96
ATOM   1639  CB   VAL A1002       58.755  73.268  24.833  1.00 66.63
ATOM   1640  CG1  VAL A1002       57.691  73.065  23.764  1.00 66.63
ATOM   1641  CG2  VAL A1002       58.212  73.946  26.088  1.00 66.63
ATOM   1643  N    ARG A1003       57.913  70.256  25.990  1.00 36.10
ATOM   1644  CA   ARG A1003       57.188  69.580  27.054  1.00 36.10
ATOM   1645  C    ARG A1003       57.957  68.409  27.649  1.00 36.10
ATOM   1646  O    ARG A1003       57.762  68.012  28.773  1.00 36.10
ATOM   1647  CB   ARG A1003       55.829  69.195  26.507  1.00 97.10
ATOM   1648  CG   ARG A1003       55.381  70.237  25.495  1.00 97.10
ATOM   1649  CD   ARG A1003       53.974  70.007  25.036  1.00 97.10
ATOM   1650  NE   ARG A1003       53.022  70.432  26.045  1.00 97.10
ATOM   1651  CZ   ARG A1003       51.949  71.153  25.782  1.00 97.10
ATOM   1652  NH1  ARG A1003       51.699  71.527  24.544  1.00 97.10
ATOM   1653  NH2  ARG A1003       51.136  71.493  26.759  1.00 97.10
ATOM   1660  N    TRP A1004       58.902  67.934  26.865  1.00 31.39
ATOM   1661  CA   TRP A1004       59.799  66.858  27.231  1.00 31.39
ATOM   1662  C    TRP A1004       61.031  67.342  27.941  1.00 31.39
ATOM   1663  O    TRP A1004       61.431  66.841  28.992  1.00 31.39
ATOM   1664  CB   TRP A1004       60.117  66.113  25.981  1.00 37.57
ATOM   1665  CG   TRP A1004       59.058  65.128  25.860  1.00 37.57
ATOM   1666  CD1  TRP A1004       59.055  63.870  26.415  1.00 37.57
ATOM   1667  CD2  TRP A1004       57.758  65.324  25.323  1.00 37.57
ATOM   1668  NE1  TRP A1004       57.832  63.290  26.253  1.00 37.57
ATOM   1669  CE2  TRP A1004       57.011  64.149  25.594  1.00 37.57
ATOM   1670  CE3  TRP A1004       57.142  66.370  24.648  1.00 37.57
ATOM   1671  CZ2  TRP A1004       55.683  63.991  25.214  1.00 37.57
ATOM   1672  CZ3  TRP A1004       55.789  66.223  24.252  1.00 37.57
ATOM   1673  CH2  TRP A1004       55.087  65.041  24.541  1.00 37.57
ATOM   1676  N    MET A1005       61.556  68.426  27.391  1.00 10.72
ATOM   1677  CA   MET A1005       62.723  69.067  27.879  1.00 10.72
ATOM   1678  C    MET A1005       62.709  69.405  29.340  1.00 10.72
ATOM   1679  O    MET A1005       61.690  69.822  29.947  1.00 10.72
ATOM   1680  CB   MET A1005       62.983  70.254  27.003  1.00 63.30
ATOM   1681  CG   MET A1005       63.299  69.783  25.632  1.00 63.30
ATOM   1682  SD   MET A1005       63.194  71.078  24.467  1.00 63.30
ATOM   1683  CE   MET A1005       64.494  72.111  25.002  1.00 63.30
ATOM   1685  N    ALA A1006       63.873  69.180  29.939  1.00 13.71
ATOM   1686  CA   ALA A1006       64.092  69.541  31.343  1.00 13.71
```

FIG. 6X

```
ATOM   1687  C    ALA A1006      64.634  71.015  31.321  1.00 13.71
ATOM   1688  O    ALA A1006      64.885  71.575  30.254  1.00 13.71
ATOM   1689  CB   ALA A1006      65.114  68.618  31.976  1.00 44.23
ATOM   1691  N    ILE A1007      64.762  71.597  32.515  1.00 21.54
ATOM   1692  CA   ILE A1007      65.278  72.951  32.738  1.00 21.54
ATOM   1693  C    ILE A1007      66.586  73.324  31.943  1.00 21.54
ATOM   1694  O    ILE A1007      66.528  73.791  30.817  1.00 21.54
ATOM   1695  CB   ILE A1007      65.482  73.137  34.300  1.00 20.90
ATOM   1696  CG1  ILE A1007      66.672  72.188  34.830  1.00 20.90
ATOM   1697  CG2  ILE A1007      64.088  72.800  35.034  1.00 20.90
ATOM   1698  CD1  ILE A1007      67.395  72.474  36.237  1.00 20.90
ATOM   1700  N    GLU A1008      67.752  73.082  32.510  1.00 10.72
ATOM   1701  CA   GLU A1008      69.028  73.410  31.892  1.00 10.72
ATOM   1702  C    GLU A1008      69.066  73.404  30.369  1.00 10.72
ATOM   1703  O    GLU A1008      70.144  73.771  29.757  1.00 10.72
ATOM   1704  CB   GLU A1008      70.098  72.429  32.417  1.00 39.30
ATOM   1705  CG   GLU A1008      69.942  70.977  31.916  1.00 39.30
ATOM   1706  CD   GLU A1008      69.159  70.091  32.896  1.00 39.30
ATOM   1707  OE1  GLU A1008      68.082  70.549  33.382  1.00 39.30
ATOM   1708  OE2  GLU A1008      69.634  68.944  33.178  1.00 39.30
ATOM   1710  N    SER A1009      67.976  72.880  29.764  1.00 31.45
ATOM   1711  CA   SER A1009      67.798  72.791  28.314  1.00 31.45
ATOM   1712  C    SER A1009      66.826  73.844  27.779  1.00 31.45
ATOM   1713  O    SER A1009      67.007  74.396  26.685  1.00 31.45
ATOM   1714  CB   SER A1009      67.286  71.410  27.930  1.00100.00
ATOM   1715  OG   SER A1009      68.088  70.402  28.500  1.00100.00
ATOM   1718  N    LEU A1010      65.745  74.095  28.485  1.00 75.06
ATOM   1719  CA   LEU A1010      64.852  75.103  27.977  1.00 75.06
ATOM   1720  C    LEU A1010      65.758  76.342  27.926  1.00 75.06
ATOM   1721  O    LEU A1010      65.737  77.146  26.989  1.00 75.06
ATOM   1722  CB   LEU A1010      63.675  75.238  28.938  1.00 62.28
ATOM   1723  CG   LEU A1010      62.685  74.078  28.725  1.00 62.28
ATOM   1724  CD1  LEU A1010      61.421  74.394  29.511  1.00 62.28
ATOM   1725  CD2  LEU A1010      62.379  73.854  27.229  1.00 62.28
ATOM   1727  N    ASN A1011      66.597  76.401  28.951  1.00 36.75
ATOM   1728  CA   ASN A1011      67.611  77.389  29.207  1.00 36.75
ATOM   1729  C    ASN A1011      68.761  77.280  28.189  1.00 36.75
ATOM   1730  O    ASN A1011      68.696  77.728  27.006  1.00 36.75
ATOM   1731  CB   ASN A1011      68.174  77.122  30.588  1.00 53.79
ATOM   1732  CG   ASN A1011      67.148  77.215  31.633  1.00 53.79
ATOM   1733  OD1  ASN A1011      66.008  77.430  31.335  1.00 53.79
ATOM   1734  ND2  ASN A1011      67.541  77.071  32.879  1.00 53.79
ATOM   1738  N    TYR A1012      69.810  76.638  28.685  1.00 25.53
ATOM   1739  CA   TYR A1012      71.016  76.422  27.940  1.00 25.53
ATOM   1740  C    TYR A1012      70.747  75.476  26.776  1.00 25.53
ATOM   1741  O    TYR A1012      71.392  75.570  25.756  1.00 25.53
ATOM   1742  CB   TYR A1012      72.118  75.898  28.872  1.00 38.16
ATOM   1743  CG   TYR A1012      71.934  76.312  30.315  1.00 38.16
ATOM   1744  CD1  TYR A1012      72.332  75.491  31.341  1.00 38.16
ATOM   1745  CD2  TYR A1012      71.301  77.512  30.645  1.00 38.16
ATOM   1746  CE1  TYR A1012      72.105  75.841  32.642  1.00 38.16
ATOM   1747  CE2  TYR A1012      71.072  77.863  31.943  1.00 38.16
ATOM   1748  CZ   TYR A1012      71.473  77.028  32.927  1.00 38.16
ATOM   1749  OH   TYR A1012      71.240  77.363  34.217  1.00 38.16
ATOM   1752  N    SER A1013      69.812  74.566  26.863  1.00 71.42
ATOM   1753  CA   SER A1013      69.638  73.752  25.672  1.00 71.42
ATOM   1754  C    SER A1013      70.875  72.864  25.398  1.00 71.42
```

FIG. 6Y

| ATOM | 1755 | O | SER | A1013 | 71.360 | 72.693 | 24.272 | 1.00 | 71.42 |
|------|------|---|-----|-------|--------|--------|--------|------|-------|
| ATOM | 1756 | CB | SER | A1013 | 69.331 | 74.696 | 24.502 | 1.00 | 25.42 |
| ATOM | 1757 | OG | SER | A1013 | 70.477 | 75.126 | 23.819 | 1.00 | 25.42 |
| ATOM | 1760 | N | VAL | A1014 | 71.383 | 72.310 | 26.482 | 1.00 | 66.71 |
| ATOM | 1761 | CA | VAL | A1014 | 72.507 | 71.433 | 26.395 | 1.00 | 66.71 |
| ATOM | 1762 | C | VAL | A1014 | 71.902 | 70.215 | 26.967 | 1.00 | 66.71 |
| ATOM | 1763 | O | VAL | A1014 | 71.255 | 70.283 | 27.994 | 1.00 | 66.71 |
| ATOM | 1764 | CB | VAL | A1014 | 73.745 | 71.888 | 27.263 | 1.00 | 53.96 |
| ATOM | 1765 | CG1 | VAL | A1014 | 74.220 | 73.271 | 26.795 | 1.00 | 53.96 |
| ATOM | 1766 | CG2 | VAL | A1014 | 73.427 | 71.814 | 28.765 | 1.00 | 53.96 |
| ATOM | 1768 | N | TYR | A1015 | 72.067 | 69.104 | 26.273 | 1.00 | 65.68 |
| ATOM | 1769 | CA | TYR | A1015 | 71.511 | 67.861 | 26.751 | 1.00 | 65.68 |
| ATOM | 1770 | C | TYR | A1015 | 72.584 | 66.891 | 27.248 | 1.00 | 65.68 |
| ATOM | 1771 | O | TYR | A1015 | 73.635 | 66.702 | 26.646 | 1.00 | 65.68 |
| ATOM | 1772 | CB | TYR | A1015 | 70.656 | 67.214 | 25.663 | 1.00 | 100.00 |
| ATOM | 1773 | CG | TYR | A1015 | 69.758 | 68.179 | 24.939 | 1.00 | 100.00 |
| ATOM | 1774 | CD1 | TYR | A1015 | 70.148 | 68.741 | 23.734 | 1.00 | 100.00 |
| ATOM | 1775 | CD2 | TYR | A1015 | 68.509 | 68.505 | 25.434 | 1.00 | 100.00 |
| ATOM | 1776 | CE1 | TYR | A1015 | 69.315 | 69.596 | 23.037 | 1.00 | 100.00 |
| ATOM | 1777 | CE2 | TYR | A1015 | 67.664 | 69.364 | 24.740 | 1.00 | 100.00 |
| ATOM | 1778 | CZ | TYR | A1015 | 68.078 | 69.901 | 23.546 | 1.00 | 100.00 |
| ATOM | 1779 | OH | TYR | A1015 | 67.272 | 70.751 | 22.848 | 1.00 | 100.00 |
| ATOM | 1782 | N | THR | A1016 | 72.263 | 66.269 | 28.363 | 1.00 | 55.88 |
| ATOM | 1783 | CA | THR | A1016 | 73.124 | 65.322 | 29.008 | 1.00 | 55.88 |
| ATOM | 1784 | C | THR | A1016 | 72.360 | 64.056 | 29.380 | 1.00 | 55.88 |
| ATOM | 1785 | O | THR | A1016 | 71.164 | 63.996 | 29.243 | 1.00 | 55.88 |
| ATOM | 1786 | CB | THR | A1016 | 73.653 | 65.988 | 30.209 | 1.00 | 30.90 |
| ATOM | 1787 | OG1 | THR | A1016 | 72.699 | 65.891 | 31.280 | 1.00 | 30.90 |
| ATOM | 1788 | CG2 | THR | A1016 | 73.881 | 67.440 | 29.876 | 1.00 | 30.90 |
| ATOM | 1791 | N | THR | A1017 | 73.054 | 63.037 | 29.840 | 1.00 | 99.25 |
| ATOM | 1792 | CA | THR | A1017 | 72.361 | 61.822 | 30.213 | 1.00 | 99.25 |
| ATOM | 1793 | C | THR | A1017 | 71.878 | 62.074 | 31.618 | 1.00 | 99.25 |
| ATOM | 1794 | O | THR | A1017 | 72.112 | 61.294 | 32.534 | 1.00 | 99.25 |
| ATOM | 1795 | CB | THR | A1017 | 73.312 | 60.593 | 30.094 | 1.00 | 32.66 |
| ATOM | 1796 | OG1 | THR | A1017 | 72.893 | 59.789 | 28.972 | 1.00 | 32.66 |
| ATOM | 1797 | CG2 | THR | A1017 | 73.353 | 59.770 | 31.323 | 1.00 | 32.66 |
| ATOM | 1800 | N | ASN | A1018 | 71.185 | 63.198 | 31.786 | 1.00 | 18.01 |
| ATOM | 1801 | CA | ASN | A1018 | 70.687 | 63.569 | 33.141 | 1.00 | 18.01 |
| ATOM | 1802 | C | ASN | A1018 | 69.349 | 64.119 | 32.874 | 1.00 | 18.01 |
| ATOM | 1803 | O | ASN | A1018 | 68.447 | 64.021 | 33.724 | 1.00 | 18.01 |
| ATOM | 1804 | CB | ASN | A1018 | 71.527 | 64.623 | 33.742 | 1.00 | 34.98 |
| ATOM | 1805 | CG | ASN | A1018 | 71.808 | 64.337 | 35.101 | 1.00 | 34.98 |
| ATOM | 1806 | OD1 | ASN | A1018 | 71.282 | 64.966 | 35.982 | 1.00 | 34.98 |
| ATOM | 1807 | ND2 | ASN | A1018 | 72.659 | 63.353 | 35.331 | 1.00 | 34.98 |
| ATOM | 1811 | N | SER | A1019 | 69.294 | 64.679 | 31.656 | 1.00 | 37.97 |
| ATOM | 1812 | CA | SER | A1019 | 68.205 | 65.335 | 30.991 | 1.00 | 37.97 |
| ATOM | 1813 | C | SER | A1019 | 67.811 | 64.369 | 29.862 | 1.00 | 37.97 |
| ATOM | 1814 | O | SER | A1019 | 67.493 | 64.733 | 28.729 | 1.00 | 37.97 |
| ATOM | 1815 | CB | SER | A1019 | 68.737 | 66.641 | 30.420 | 1.00 | 17.17 |
| ATOM | 1816 | OG | SER | A1019 | 69.329 | 66.474 | 29.138 | 1.00 | 17.17 |
| ATOM | 1819 | N | ASP | A1020 | 67.985 | 63.097 | 30.155 | 1.00 | 31.25 |
| ATOM | 1820 | CA | ASP | A1020 | 67.582 | 62.062 | 29.225 | 1.00 | 31.25 |
| ATOM | 1821 | C | ASP | A1020 | 66.669 | 61.475 | 30.328 | 1.00 | 31.25 |
| ATOM | 1822 | O | ASP | A1020 | 65.473 | 61.257 | 30.127 | 1.00 | 31.25 |
| ATOM | 1823 | CB | ASP | A1020 | 68.777 | 61.166 | 28.790 | 1.00 | 31.83 |
| ATOM | 1824 | CG | ASP | A1020 | 69.074 | 61.295 | 27.302 | 1.00 | 31.83 |
| ATOM | 1825 | OD1 | ASP | A1020 | 68.289 | 61.870 | 26.618 | 1.00 | 31.83 |

FIG. 6Z

```
ATOM   1826  OD2 ASP A1020      70.043  60.869  26.709  1.00 31.83
ATOM   1828  N   VAL A1021      67.214  61.357  31.535  1.00 57.04
ATOM   1829  CA  VAL A1021      66.440  60.813  32.614  1.00 57.04
ATOM   1830  C   VAL A1021      65.131  61.522  32.628  1.00 57.04
ATOM   1831  O   VAL A1021      64.091  60.915  32.317  1.00 57.04
ATOM   1832  CB  VAL A1021      67.130  60.987  33.916  1.00 94.63
ATOM   1833  CG1 VAL A1021      66.156  60.813  35.032  1.00 94.63
ATOM   1834  CG2 VAL A1021      68.236  59.965  34.012  1.00 94.63
ATOM   1836  N   TRP A1022      65.189  62.814  32.960  1.00 51.41
ATOM   1837  CA  TRP A1022      64.023  63.696  33.032  1.00 51.41
ATOM   1838  C   TRP A1022      63.002  63.457  31.908  1.00 51.41
ATOM   1839  O   TRP A1022      61.815  63.252  32.147  1.00 51.41
ATOM   1840  CB  TRP A1022      64.519  65.133  33.005  1.00 32.10
ATOM   1841  CG  TRP A1022      63.422  66.227  32.925  1.00 32.10
ATOM   1842  CD1 TRP A1022      62.602  66.469  31.868  1.00 32.10
ATOM   1843  CD2 TRP A1022      63.068  67.160  33.938  1.00 32.10
ATOM   1844  NE1 TRP A1022      61.779  67.469  32.157  1.00 32.10
ATOM   1845  CE2 TRP A1022      62.032  67.931  33.428  1.00 32.10
ATOM   1846  CE3 TRP A1022      63.526  67.420  35.221  1.00 32.10
ATOM   1847  CZ2 TRP A1022      61.408  69.004  34.187  1.00 32.10
ATOM   1848  CZ3 TRP A1022      62.921  68.481  35.978  1.00 32.10
ATOM   1849  CH2 TRP A1022      61.879  69.255  35.453  1.00 32.10
ATOM   1852  N   SER A1023      63.472  63.525  30.671  1.00 66.03
ATOM   1853  CA  SER A1023      62.598  63.263  29.546  1.00 66.03
ATOM   1854  C   SER A1023      61.921  61.955  29.911  1.00 66.03
ATOM   1855  O   SER A1023      60.717  61.903  30.036  1.00 66.03
ATOM   1856  CB  SER A1023      63.414  63.109  28.274  1.00 96.89
ATOM   1857  OG  SER A1023      63.734  64.377  27.752  1.00 96.89
ATOM   1860  N   TYR A1024      62.719  60.909  30.106  1.00 11.41
ATOM   1861  CA  TYR A1024      62.238  59.645  30.472  1.00 11.41
ATOM   1862  C   TYR A1024      60.940  59.597  31.308  1.00 11.41
ATOM   1863  O   TYR A1024      60.018  58.807  30.992  1.00 11.41
ATOM   1864  CB  TYR A1024      63.320  58.871  31.188  1.00 14.38
ATOM   1865  CG  TYR A1024      62.850  57.491  31.472  1.00 14.38
ATOM   1866  CD1 TYR A1024      62.821  56.581  30.474  1.00 14.38
ATOM   1867  CD2 TYR A1024      62.314  57.167  32.733  1.00 14.38
ATOM   1868  CE1 TYR A1024      62.276  55.380  30.688  1.00 14.38
ATOM   1869  CE2 TYR A1024      61.765  55.987  32.993  1.00 14.38
ATOM   1870  CZ  TYR A1024      61.734  55.069  31.972  1.00 14.38
ATOM   1871  OH  TYR A1024      61.197  53.831  32.179  1.00 14.38
ATOM   1874  N   GLY A1025      60.894  60.341  32.397  1.00 29.83
ATOM   1875  CA  GLY A1025      59.678  60.385  33.207  1.00 29.83
ATOM   1876  C   GLY A1025      58.509  61.033  32.430  1.00 29.83
ATOM   1877  O   GLY A1025      57.356  60.716  32.652  1.00 29.83
ATOM   1879  N   VAL A1026      58.762  61.985  31.554  1.00 67.56
ATOM   1880  CA  VAL A1026      57.615  62.466  30.859  1.00 67.56
ATOM   1881  C   VAL A1026      57.199  61.121  30.271  1.00 67.56
ATOM   1882  O   VAL A1026      56.204  60.589  30.705  1.00 67.56
ATOM   1883  CB  VAL A1026      57.975  63.548  29.836  1.00 59.88
ATOM   1884  CG1 VAL A1026      56.872  64.579  29.759  1.00 59.88
ATOM   1885  CG2 VAL A1026      59.232  64.199  30.249  1.00 59.88
ATOM   1887  N   LEU A1027      57.992  60.546  29.354  1.00 31.95
ATOM   1888  CA  LEU A1027      57.703  59.178  28.787  1.00 31.95
ATOM   1889  C   LEU A1027      57.056  58.236  29.865  1.00 31.95
ATOM   1890  O   LEU A1027      55.988  57.621  29.691  1.00 31.95
ATOM   1891  CB  LEU A1027      59.000  58.502  28.304  1.00 37.14
ATOM   1892  CG  LEU A1027      58.894  57.447  27.219  1.00 37.14
```

FIG. 6AA

```
ATOM   1893  CD1  LEU A1027    57.496  57.117  27.007  1.00 37.14
ATOM   1894  CD2  LEU A1027    59.417  57.890  25.930  1.00 37.14
ATOM   1896  N    LEU A1028    57.746  58.125  30.978  1.00  8.77
ATOM   1897  CA   LEU A1028    57.188  57.363  32.009  1.00  8.77
ATOM   1898  C    LEU A1028    55.743  57.749  32.088  1.00  8.77
ATOM   1899  O    LEU A1028    54.947  56.870  31.744  1.00  8.77
ATOM   1900  CB   LEU A1028    57.875  57.508  33.363  1.00 48.45
ATOM   1901  CG   LEU A1028    57.252  56.440  34.294  1.00 48.45
ATOM   1902  CD1  LEU A1028    56.823  55.185  33.534  1.00 48.45
ATOM   1903  CD2  LEU A1028    58.220  56.043  35.333  1.00 48.45
ATOM   1905  N    TRP A1029    55.442  59.029  32.483  1.00 30.07
ATOM   1906  CA   TRP A1029    54.084  59.703  32.660  1.00 30.07
ATOM   1907  C    TRP A1029    53.253  59.613  31.429  1.00 30.07
ATOM   1908  O    TRP A1029    52.118  59.261  31.397  1.00 30.07
ATOM   1909  CB   TRP A1029    54.227  61.222  32.983  1.00  2.92
ATOM   1910  CG   TRP A1029    52.932  62.000  33.312  1.00  2.92
ATOM   1911  CD1  TRP A1029    52.349  62.276  34.582  1.00  2.92
ATOM   1912  CD2  TRP A1029    51.964  62.434  32.334  1.00  2.92
ATOM   1913  NE1  TRP A1029    51.050  62.846  34.369  1.00  2.92
ATOM   1914  CE2  TRP A1029    50.827  62.919  33.011  1.00  2.92
ATOM   1915  CE3  TRP A1029    51.955  62.444  30.937  1.00  2.92
ATOM   1916  CZ2  TRP A1029    49.767  63.362  32.342  1.00  2.92
ATOM   1917  CZ3  TRP A1029    50.836  62.910  30.283  1.00  2.92
ATOM   1918  CH2  TRP A1029    49.791  63.345  30.971  1.00  2.92
ATOM   1921  N    GLU A1030    53.881  60.008  30.382  1.00 26.20
ATOM   1922  CA   GLU A1030    53.292  59.957  29.076  1.00 26.20
ATOM   1923  C    GLU A1030    52.824  58.589  28.725  1.00 26.20
ATOM   1924  O    GLU A1030    52.344  58.417  27.638  1.00 26.20
ATOM   1925  CB   GLU A1030    54.358  60.378  28.077  1.00 24.00
ATOM   1926  CG   GLU A1030    53.879  60.996  26.869  1.00 24.00
ATOM   1927  CD   GLU A1030    54.860  60.718  25.857  1.00 24.00
ATOM   1928  OE1  GLU A1030    55.885  60.279  26.378  1.00 24.00
ATOM   1929  OE2  GLU A1030    54.661  60.907  24.633  1.00 24.00
ATOM   1931  N    ILE A1031    52.969  57.631  29.631  1.00 14.69
ATOM   1932  CA   ILE A1031    52.633  56.216  29.376  1.00 14.69
ATOM   1933  C    ILE A1031    51.704  55.738  30.426  1.00 14.69
ATOM   1934  O    ILE A1031    51.033  54.761  30.203  1.00 14.69
ATOM   1935  CB   ILE A1031    53.923  55.272  29.416  1.00 33.44
ATOM   1936  CG1  ILE A1031    54.294  54.757  28.021  1.00 33.44
ATOM   1937  CG2  ILE A1031    53.671  53.993  30.253  1.00 33.44
ATOM   1938  CD1  ILE A1031    55.762  54.225  27.948  1.00 33.44
ATOM   1940  N    VAL A1032    51.726  56.285  31.621  1.00 14.19
ATOM   1941  CA   VAL A1032    50.676  55.868  32.559  1.00 14.19
ATOM   1942  C    VAL A1032    49.327  56.496  32.011  1.00 14.19
ATOM   1943  O    VAL A1032    48.282  55.823  31.882  1.00 14.19
ATOM   1944  CB   VAL A1032    50.924  56.349  33.944  1.00 41.51
ATOM   1945  CG1  VAL A1032    49.666  56.640  34.596  1.00 41.51
ATOM   1946  CG2  VAL A1032    51.681  55.290  34.704  1.00 41.51
ATOM   1948  N    SER A1033    49.395  57.755  31.625  1.00 31.81
ATOM   1949  CA   SER A1033    48.320  58.505  31.065  1.00 31.81
ATOM   1950  C    SER A1033    47.658  57.730  29.910  1.00 31.81
ATOM   1951  O    SER A1033    46.551  58.079  29.445  1.00 31.81
ATOM   1952  CB   SER A1033    48.895  59.828  30.546  1.00 68.54
ATOM   1953  OG   SER A1033    49.757  59.623  29.445  1.00 68.54
ATOM   1956  N    LEU A1034    48.316  56.686  29.442  1.00  2.00
ATOM   1957  CA   LEU A1034    47.777  55.984  28.298  1.00  2.00
ATOM   1958  C    LEU A1034    47.645  56.833  26.999  1.00  2.00
```

FIG. 6BB

| | | | | | | | |
|---|---|---|---|---|---|---|---|
| ATOM | 1959 | O | LEU A1034 | 46.584 | 56.955 | 26.409 | 1.00 2.00 |
| ATOM | 1960 | CB | LEU A1034 | 46.422 | 55.343 | 28.654 | 1.00 31.43 |
| ATOM | 1961 | CG | LEU A1034 | 46.478 | 53.883 | 29.207 | 1.00 31.43 |
| ATOM | 1962 | CD1 | LEU A1034 | 45.072 | 53.333 | 29.484 | 1.00 31.43 |
| ATOM | 1963 | CD2 | LEU A1034 | 47.244 | 52.988 | 28.207 | 1.00 31.43 |
| ATOM | 1965 | N | GLY A1035 | 48.706 | 57.372 | 26.438 | 1.00 4.53 |
| ATOM | 1966 | CA | GLY A1035 | 48.437 | 58.149 | 25.224 | 1.00 4.53 |
| ATOM | 1967 | C | GLY A1035 | 48.241 | 59.685 | 25.565 | 1.00 4.53 |
| ATOM | 1968 | O | GLY A1035 | 47.964 | 60.498 | 24.649 | 1.00 4.53 |
| ATOM | 1970 | N | GLY A1036 | 48.509 | 60.071 | 26.820 | 1.00 18.31 |
| ATOM | 1971 | CA | GLY A1036 | 48.281 | 61.470 | 27.160 | 1.00 18.31 |
| ATOM | 1972 | C | GLY A1036 | 49.211 | 62.717 | 27.185 | 1.00 18.31 |
| ATOM | 1973 | O | GLY A1036 | 49.988 | 62.881 | 28.181 | 1.00 18.31 |
| ATOM | 1975 | N | THR A1037 | 49.027 | 63.591 | 26.164 | 1.00 48.85 |
| ATOM | 1976 | CA | THR A1037 | 49.733 | 64.890 | 25.939 | 1.00 48.85 |
| ATOM | 1977 | C | THR A1037 | 50.225 | 65.522 | 27.265 | 1.00 48.85 |
| ATOM | 1978 | O | THR A1037 | 49.431 | 65.933 | 28.077 | 1.00 48.85 |
| ATOM | 1979 | CB | THR A1037 | 48.780 | 65.886 | 25.216 | 1.00 25.15 |
| ATOM | 1980 | OG1 | THR A1037 | 48.988 | 65.904 | 23.772 | 1.00 25.15 |
| ATOM | 1981 | CG2 | THR A1037 | 48.993 | 67.215 | 25.789 | 1.00 25.15 |
| ATOM | 1984 | N | PRO A1038 | 51.538 | 65.697 | 27.456 | 1.00 42.23 |
| ATOM | 1985 | CA | PRO A1038 | 51.796 | 66.239 | 28.775 | 1.00 42.23 |
| ATOM | 1986 | C | PRO A1038 | 51.496 | 67.691 | 28.996 | 1.00 42.23 |
| ATOM | 1987 | O | PRO A1038 | 51.359 | 68.450 | 28.057 | 1.00 42.23 |
| ATOM | 1988 | CB | PRO A1038 | 53.271 | 65.779 | 29.048 | 1.00 10.66 |
| ATOM | 1989 | CG | PRO A1038 | 53.679 | 65.007 | 27.861 | 1.00 10.66 |
| ATOM | 1990 | CD | PRO A1038 | 52.809 | 65.456 | 26.765 | 1.00 10.66 |
| ATOM | 1991 | N | TYR A1039 | 51.381 | 68.090 | 30.253 | 1.00 39.67 |
| ATOM | 1992 | CA | TYR A1039 | 51.037 | 69.509 | 30.576 | 1.00 39.67 |
| ATOM | 1993 | C | TYR A1039 | 49.924 | 69.987 | 29.682 | 1.00 39.67 |
| ATOM | 1994 | O | TYR A1039 | 50.172 | 70.931 | 28.955 | 1.00 39.67 |
| ATOM | 1995 | CB | TYR A1039 | 52.256 | 70.457 | 30.375 | 1.00 15.36 |
| ATOM | 1996 | CG | TYR A1039 | 53.503 | 69.958 | 31.103 | 1.00 15.36 |
| ATOM | 1997 | CD1 | TYR A1039 | 54.685 | 69.536 | 30.407 | 1.00 15.36 |
| ATOM | 1998 | CD2 | TYR A1039 | 53.518 | 69.952 | 32.481 | 1.00 15.36 |
| ATOM | 1999 | CE1 | TYR A1039 | 55.790 | 69.157 | 31.105 | 1.00 15.36 |
| ATOM | 2000 | CE2 | TYR A1039 | 54.636 | 69.571 | 33.153 | 1.00 15.36 |
| ATOM | 2001 | CZ | TYR A1039 | 55.737 | 69.191 | 32.449 | 1.00 15.36 |
| ATOM | 2002 | OH | TYR A1039 | 56.737 | 68.889 | 33.251 | 1.00 15.36 |
| ATOM | 2005 | N | CYS A1040 | 48.756 | 69.319 | 29.692 | 1.00 100.00 |
| ATOM | 2006 | CA | CYS A1040 | 47.597 | 69.681 | 28.845 | 1.00 100.00 |
| ATOM | 2007 | C | CYS A1040 | 47.013 | 70.930 | 29.435 | 1.00 100.00 |
| ATOM | 2008 | O | CYS A1040 | 46.711 | 70.987 | 30.625 | 1.00 100.00 |
| ATOM | 2009 | CB | CYS A1040 | 46.507 | 68.566 | 28.832 | 1.00 63.76 |
| ATOM | 2010 | SG | CYS A1040 | 45.039 | 68.722 | 27.619 | 1.00 63.76 |
| ATOM | 2012 | N | GLY A1041 | 46.836 | 71.938 | 28.605 | 1.00 75.53 |
| ATOM | 2013 | CA | GLY A1041 | 46.305 | 73.175 | 29.127 | 1.00 75.53 |
| ATOM | 2014 | C | GLY A1041 | 47.419 | 74.160 | 29.448 | 1.00 75.53 |
| ATOM | 2015 | O | GLY A1041 | 47.217 | 75.358 | 29.342 | 1.00 75.53 |
| ATOM | 2017 | N | MET A1042 | 48.581 | 73.668 | 29.868 | 1.00 27.54 |
| ATOM | 2018 | CA | MET A1042 | 49.666 | 74.553 | 30.126 | 1.00 27.54 |
| ATOM | 2019 | C | MET A1042 | 50.119 | 75.065 | 28.731 | 1.00 27.54 |
| ATOM | 2020 | O | MET A1042 | 50.034 | 74.344 | 27.742 | 1.00 27.54 |
| ATOM | 2021 | CB | MET A1042 | 50.771 | 73.851 | 30.909 | 1.00 47.82 |
| ATOM | 2022 | CG | MET A1042 | 51.032 | 74.460 | 32.298 | 1.00 47.82 |
| ATOM | 2023 | SD | MET A1042 | 52.810 | 74.502 | 32.805 | 1.00 47.82 |
| ATOM | 2024 | CE | MET A1042 | 52.729 | 74.790 | 34.564 | 1.00 47.82 |

FIG. 6CC

```
ATOM   2026  N    THR A1043    50.481  76.351  28.681  1.00 59.25
ATOM   2027  CA   THR A1043    50.918  77.067  27.468  1.00 59.25
ATOM   2028  C    THR A1043    52.434  76.937  27.397  1.00 59.25
ATOM   2029  O    THR A1043    53.084  76.835  28.437  1.00 59.25
ATOM   2030  CB   THR A1043    50.586  78.617  27.528  1.00 62.50
ATOM   2031  OG1  THR A1043    51.070  79.181  28.773  1.00 62.50
ATOM   2032  CG2  THR A1043    49.076  78.877  27.351  1.00 62.50
ATOM   2035  N    CYS A1044    52.997  76.968  26.194  1.00100.00
ATOM   2036  CA   CYS A1044    54.435  76.799  26.060  1.00100.00
ATOM   2037  C    CYS A1044    55.282  77.679  26.975  1.00100.00
ATOM   2038  O    CYS A1044    56.478  77.467  27.100  1.00100.00
ATOM   2039  CB   CYS A1044    54.857  76.963  24.601  1.00 77.67
ATOM   2040  SG   CYS A1044    54.890  75.383  23.687  1.00 77.67
ATOM   2042  N    ALA A1045    54.673  78.663  27.623  1.00100.00
ATOM   2043  CA   ALA A1045    55.425  79.501  28.548  1.00100.00
ATOM   2044  C    ALA A1045    54.810  79.446  29.910  1.00100.00
ATOM   2045  O    ALA A1045    55.455  79.833  30.878  1.00100.00
ATOM   2046  CB   ALA A1045    55.461  80.899  28.107  1.00 35.04
ATOM   2048  N    GLU A1046    53.550  79.023  30.018  1.00 27.64
ATOM   2049  CA   GLU A1046    53.057  78.932  31.346  1.00 27.64
ATOM   2050  C    GLU A1046    54.177  78.018  31.917  1.00 27.64
ATOM   2051  O    GLU A1046    54.507  78.117  33.092  1.00 27.64
ATOM   2052  CB   GLU A1046    51.665  78.264  31.365  1.00 79.70
ATOM   2053  CG   GLU A1046    50.465  79.239  31.521  1.00 79.70
ATOM   2054  CD   GLU A1046    49.180  78.818  30.745  1.00 79.70
ATOM   2055  OE1  GLU A1046    48.058  79.216  31.128  1.00 79.70
ATOM   2056  OE2  GLU A1046    49.264  78.096  29.748  1.00 79.70
ATOM   2058  N    LEU A1047    54.800  77.199  31.050  1.00 83.80
ATOM   2059  CA   LEU A1047    55.871  76.230  31.413  1.00 83.80
ATOM   2060  C    LEU A1047    57.286  76.737  31.646  1.00 83.80
ATOM   2061  O    LEU A1047    57.838  76.529  32.712  1.00 83.80
ATOM   2062  CB   LEU A1047    55.968  75.119  30.368  1.00 39.62
ATOM   2063  CG   LEU A1047    55.167  73.857  30.626  1.00 39.62
ATOM   2064  CD1  LEU A1047    55.186  73.119  29.339  1.00 39.62
ATOM   2065  CD2  LEU A1047    55.697  73.034  31.803  1.00 39.62
ATOM   2067  N    TYR A1048    57.904  77.315  30.615  1.00 32.07
ATOM   2068  CA   TYR A1048    59.235  77.894  30.746  1.00 32.07
ATOM   2069  C    TYR A1048    59.043  78.647  32.109  1.00 32.07
ATOM   2070  O    TYR A1048    59.704  78.383  33.115  1.00 32.07
ATOM   2071  CB   TYR A1048    59.498  78.877  29.566  1.00 14.15
ATOM   2072  CG   TYR A1048    60.160  78.333  28.256  1.00 14.15
ATOM   2073  CD1  TYR A1048    59.401  77.982  27.165  1.00 14.15
ATOM   2074  CD2  TYR A1048    61.563  78.249  28.095  1.00 14.15
ATOM   2075  CE1  TYR A1048    59.969  77.565  25.934  1.00 14.15
ATOM   2076  CE2  TYR A1048    62.137  77.841  26.871  1.00 14.15
ATOM   2077  CZ   TYR A1048    61.359  77.502  25.784  1.00 14.15
ATOM   2078  OH   TYR A1048    61.927  77.135  24.513  1.00 14.15
ATOM   2081  N    GLU A1049    58.053  79.533  32.169  1.00 36.64
ATOM   2082  CA   GLU A1049    57.811  80.267  33.390  1.00 36.64
ATOM   2083  C    GLU A1049    57.770  79.384  34.578  1.00 36.64
ATOM   2084  O    GLU A1049    58.757  79.290  35.320  1.00 36.64
ATOM   2085  CB   GLU A1049    56.500  81.002  33.368  1.00 35.78
ATOM   2086  CG   GLU A1049    56.151  81.544  34.760  1.00 35.78
ATOM   2087  CD   GLU A1049    54.683  81.875  34.899  1.00 35.78
ATOM   2088  OE1  GLU A1049    53.989  82.043  33.858  1.00 35.78
ATOM   2089  OE2  GLU A1049    54.252  81.947  36.060  1.00 35.78
ATOM   2091  N    LYS A1050    56.601  78.737  34.708  1.00 93.85
```

FIG. 6DD

```
ATOM   2092  CA   LYS A1050      56.197  77.839  35.793  1.00 93.85
ATOM   2093  C    LYS A1050      57.046  76.622  36.085  1.00 93.85
ATOM   2094  O    LYS A1050      57.178  76.212  37.231  1.00 93.85
ATOM   2095  CB   LYS A1050      54.752  77.418  35.584  1.00 86.89
ATOM   2097  N    LEU A1051      57.599  76.008  35.063  1.00 40.78
ATOM   2098  CA   LEU A1051      58.458  74.868  35.336  1.00 40.78
ATOM   2099  C    LEU A1051      59.412  75.166  36.508  1.00 40.78
ATOM   2100  O    LEU A1051      59.321  74.483  37.539  1.00 40.78
ATOM   2101  CB   LEU A1051      59.201  74.391  34.072  1.00 66.80
ATOM   2102  CG   LEU A1051      58.984  72.898  33.726  1.00 66.80
ATOM   2103  CD1  LEU A1051      57.754  72.376  34.370  1.00 66.80
ATOM   2104  CD2  LEU A1051      58.875  72.719  32.253  1.00 66.80
ATOM   2106  N    PRO A1052      60.356  76.129  36.369  1.00 42.79
ATOM   2107  CA   PRO A1052      61.299  76.504  37.431  1.00 42.79
ATOM   2108  C    PRO A1052      60.655  76.803  38.741  1.00 42.79
ATOM   2109  O    PRO A1052      61.311  76.783  39.783  1.00 42.79
ATOM   2110  CB   PRO A1052      61.928  77.731  36.906  1.00 29.07
ATOM   2111  CG   PRO A1052      61.952  77.549  35.473  1.00 29.07
ATOM   2112  CD   PRO A1052      60.713  76.805  35.110  1.00 29.07
ATOM   2113  N    GLN A1053      59.365  77.114  38.699  1.00 68.39
ATOM   2114  CA   GLN A1053      58.662  77.426  39.921  1.00 68.39
ATOM   2115  C    GLN A1053      58.823  76.206  40.781  1.00 68.39
ATOM   2116  O    GLN A1053      58.934  76.303  41.999  1.00 68.39
ATOM   2117  CB   GLN A1053      57.200  77.701  39.646  1.00100.00
ATOM   2119  N    GLY A1054      58.852  75.049  40.125  1.00 93.49
ATOM   2120  CA   GLY A1054      59.012  73.776  40.808  1.00 93.49
ATOM   2121  C    GLY A1054      57.849  72.863  40.494  1.00 93.49
ATOM   2122  O    GLY A1054      57.727  71.794  41.065  1.00 93.49
ATOM   2124  N    TYR A1055      57.000  73.311  39.577  1.00 23.98
ATOM   2125  CA   TYR A1055      55.804  72.609  39.141  1.00 23.98
ATOM   2126  C    TYR A1055      56.207  71.481  38.197  1.00 23.98
ATOM   2127  O    TYR A1055      57.062  71.702  37.321  1.00 23.98
ATOM   2128  CB   TYR A1055      54.869  73.579  38.415  1.00 76.79
ATOM   2129  CG   TYR A1055      53.703  72.894  37.769  1.00 76.79
ATOM   2130  CD1  TYR A1055      52.547  72.645  38.480  1.00 76.79
ATOM   2131  CD2  TYR A1055      53.803  72.391  36.479  1.00 76.79
ATOM   2132  CE1  TYR A1055      51.516  71.891  37.927  1.00 76.79
ATOM   2133  CE2  TYR A1055      52.788  71.639  35.913  1.00 76.79
ATOM   2134  CZ   TYR A1055      51.647  71.382  36.644  1.00 76.79
ATOM   2135  OH   TYR A1055      50.677  70.559  36.119  1.00 76.79
ATOM   2138  N    ARG A1056      55.598  70.299  38.398  1.00 28.98
ATOM   2139  CA   ARG A1056      55.836  69.092  37.633  1.00 28.98
ATOM   2140  C    ARG A1056      54.472  68.506  37.281  1.00 28.98
ATOM   2141  O    ARG A1056      53.443  68.997  37.844  1.00 28.98
ATOM   2142  CB   ARG A1056      56.540  68.057  38.504  1.00 43.74
ATOM   2143  CG   ARG A1056      57.930  68.420  39.046  1.00 43.74
ATOM   2144  CD   ARG A1056      58.890  68.928  37.990  1.00 43.74
ATOM   2145  NE   ARG A1056      59.420  70.184  38.476  1.00 43.74
ATOM   2146  CZ   ARG A1056      60.710  70.421  38.632  1.00 43.74
ATOM   2147  NH1  ARG A1056      61.589  69.481  38.326  1.00 43.74
ATOM   2148  NH2  ARG A1056      61.113  71.570  39.153  1.00 43.74
ATOM   2155  N    LEU A1057      54.457  67.425  36.423  1.00  3.73
ATOM   2156  CA   LEU A1057      53.199  66.719  36.037  1.00  3.73
ATOM   2157  C    LEU A1057      52.455  66.273  37.247  1.00  3.73
ATOM   2158  O    LEU A1057      53.013  65.940  38.293  1.00  3.73
ATOM   2159  CB   LEU A1057      53.453  65.540  35.129  1.00 53.30
ATOM   2160  CG   LEU A1057      53.594  65.965  33.659  1.00 53.30
```

FIG. 6EE

```
ATOM   2161  CD1 LEU A1057     54.129  64.770  32.869  1.00 53.30
ATOM   2162  CD2 LEU A1057     52.271  66.541  33.071  1.00 53.30
ATOM   2164  N   GLU A1058     51.138  66.322  37.070  1.00 13.17
ATOM   2165  CA  GLU A1058     50.076  65.947  38.013  1.00 13.17
ATOM   2166  C   GLU A1058     50.122  64.399  38.274  1.00 13.17
ATOM   2167  O   GLU A1058     50.140  63.602  37.310  1.00 13.17
ATOM   2168  CB  GLU A1058     48.779  66.341  37.327  1.00 48.21
ATOM   2169  CG  GLU A1058     48.686  65.807  35.864  1.00 48.21
ATOM   2170  CD  GLU A1058     49.433  66.661  34.827  1.00 48.21
ATOM   2171  OE1 GLU A1058     50.080  67.619  35.269  1.00 48.21
ATOM   2172  OE2 GLU A1058     49.379  66.410  33.589  1.00 48.21
ATOM   2174  N   LYS A1059     50.163  63.947  39.531  1.00 35.98
ATOM   2175  CA  LYS A1059     50.196  62.496  39.689  1.00 35.98
ATOM   2176  C   LYS A1059     49.010  62.039  38.876  1.00 35.98
ATOM   2177  O   LYS A1059     47.980  62.696  38.847  1.00 35.98
ATOM   2178  CB  LYS A1059     50.046  62.040  41.118  1.00 48.90
ATOM   2179  CG  LYS A1059     50.101  60.540  41.194  1.00 48.90
ATOM   2180  CD  LYS A1059     50.190  60.048  42.616  1.00 48.90
ATOM   2181  CE  LYS A1059     48.873  59.367  43.057  1.00 48.90
ATOM   2182  NZ  LYS A1059     48.940  57.857  43.104  1.00 48.90
ATOM   2187  N   PRO A1060     49.129  60.936  38.161  1.00 50.25
ATOM   2188  CA  PRO A1060     47.931  60.601  37.405  1.00 50.25
ATOM   2189  C   PRO A1060     46.928  59.608  37.964  1.00 50.25
ATOM   2190  O   PRO A1060     47.176  58.424  37.967  1.00 50.25
ATOM   2191  CB  PRO A1060     48.504  60.174  36.084  1.00 21.32
ATOM   2192  CG  PRO A1060     50.037  59.963  36.356  1.00 21.32
ATOM   2193  CD  PRO A1060     50.246  60.058  37.817  1.00 21.32
ATOM   2194  N   LEU A1061     45.772  60.120  38.395  1.00 35.93
ATOM   2195  CA  LEU A1061     44.633  59.371  38.985  1.00 35.93
ATOM   2196  C   LEU A1061     44.746  57.870  39.239  1.00 35.93
ATOM   2197  O   LEU A1061     44.731  57.415  40.396  1.00 35.93
ATOM   2198  CB  LEU A1061     43.368  59.617  38.155  1.00 74.38
ATOM   2199  CG  LEU A1061     43.355  59.574  36.617  1.00 74.38
ATOM   2200  CD1 LEU A1061     44.689  59.971  35.997  1.00 74.38
ATOM   2201  CD2 LEU A1061     42.942  58.174  36.185  1.00 74.38
ATOM   2203  N   ASN A1062     44.864  57.145  38.117  1.00 56.10
ATOM   2204  CA  ASN A1062     44.988  55.689  37.947  1.00 56.10
ATOM   2205  C   ASN A1062     46.399  55.281  38.291  1.00 56.10
ATOM   2206  O   ASN A1062     46.855  54.240  37.822  1.00 56.10
ATOM   2207  CB  ASN A1062     44.865  55.366  36.477  1.00 38.56
ATOM   2208  CG  ASN A1062     46.002  56.035  35.686  1.00 38.56
ATOM   2209  OD1 ASN A1062     46.683  56.890  36.256  1.00 38.56
ATOM   2210  ND2 ASN A1062     46.216  55.673  34.397  1.00 38.56
ATOM   2214  N   CYS A1063     47.109  56.092  39.065  1.00 99.97
ATOM   2215  CA  CYS A1063     48.503  55.791  39.376  1.00 99.97
ATOM   2216  C   CYS A1063     48.861  55.613  40.829  1.00 99.97
ATOM   2217  O   CYS A1063     48.362  56.299  41.699  1.00 99.97
ATOM   2218  CB  CYS A1063     49.398  56.891  38.827  1.00 81.22
ATOM   2219  SG  CYS A1063     50.449  56.431  37.527  1.00 81.22
ATOM   2221  N   ASP A1064     49.770  54.691  41.070  1.00 40.11
ATOM   2222  CA  ASP A1064     50.260  54.424  42.405  1.00 40.11
ATOM   2223  C   ASP A1064     51.472  55.243  42.813  1.00 40.11
ATOM   2224  O   ASP A1064     52.454  55.285  42.109  1.00 40.11
ATOM   2225  CB  ASP A1064     50.623  52.961  42.560  1.00 60.57
ATOM   2226  CG  ASP A1064     50.760  52.580  43.992  1.00 60.57
ATOM   2227  OD1 ASP A1064     50.671  53.492  44.844  1.00 60.57
ATOM   2228  OD2 ASP A1064     50.941  51.391  44.292  1.00 60.57
```

FIG. 6FF

| ATOM | 2230 | N   | ASP | A1065 | 51.409 | 55.855 | 43.980 | 1.00 | 46.39 |
| ATOM | 2231 | CA  | ASP | A1065 | 52.499 | 56.662 | 44.508 | 1.00 | 46.39 |
| ATOM | 2232 | C   | ASP | A1065 | 53.384 | 56.043 | 44.229 | 1.00 | 46.39 |
| ATOM | 2233 | O   | ASP | A1065 | 54.869 | 56.717 | 44.124 | 1.00 | 46.39 |
| ATOM | 2234 | CB  | ASP | A1065 | 52.299 | 56.875 | 46.021 | 1.00 | 75.00 |
| ATOM | 2235 | CG  | ASP | A1065 | 51.156 | 57.855 | 46.357 | 1.00 | 75.00 |
| ATOM | 2236 | OD1 | ASP | A1065 | 50.426 | 58.300 | 45.452 | 1.00 | 75.00 |
| ATOM | 2237 | OD2 | ASP | A1065 | 50.988 | 58.179 | 47.550 | 1.00 | 75.00 |
| ATOM | 2239 | N   | GLU | A1066 | 53.951 | 54.742 | 44.107 | 1.00 | 29.06 |
| ATOM | 2240 | CA  | GLU | A1066 | 55.205 | 54.101 | 43.803 | 1.00 | 29.06 |
| ATOM | 2241 | C   | GLU | A1066 | 55.543 | 54.513 | 42.403 | 1.00 | 29.06 |
| ATOM | 2242 | O   | GLU | A1066 | 56.559 | 55.189 | 42.220 | 1.00 | 29.06 |
| ATOM | 2243 | CB  | GLU | A1066 | 55.109 | 52.567 | 43.888 | 1.00 | 46.46 |
| ATOM | 2244 | CG  | GLU | A1066 | 56.488 | 51.877 | 43.895 | 1.00 | 46.46 |
| ATOM | 2245 | CD  | GLU | A1066 | 56.612 | 50.697 | 44.880 | 1.00 | 46.46 |
| ATOM | 2246 | OE1 | GLU | A1066 | 55.711 | 50.554 | 45.759 | 1.00 | 46.46 |
| ATOM | 2247 | OE2 | GLU | A1066 | 57.616 | 49.923 | 44.765 | 1.00 | 46.46 |
| ATOM | 2249 | N   | VAL | A1067 | 54.727 | 54.154 | 41.416 | 1.00 | 32.03 |
| ATOM | 2250 | CA  | VAL | A1067 | 55.023 | 54.533 | 40.036 | 1.00 | 32.03 |
| ATOM | 2251 | C   | VAL | A1067 | 55.293 | 56.054 | 39.731 | 1.00 | 32.03 |
| ATOM | 2252 | O   | VAL | A1067 | 56.029 | 56.405 | 38.812 | 1.00 | 32.03 |
| ATOM | 2253 | CB  | VAL | A1067 | 53.885 | 54.021 | 39.107 | 1.00 | 15.97 |
| ATOM | 2254 | CG1 | VAL | A1067 | 53.965 | 54.642 | 37.618 | 1.00 | 15.97 |
| ATOM | 2255 | CG2 | VAL | A1067 | 53.929 | 52.448 | 39.087 | 1.00 | 15.97 |
| ATOM | 2257 | N   | TYR | A1068 | 54.738 | 56.973 | 40.480 | 1.00 | 40.19 |
| ATOM | 2258 | CA  | TYR | A1068 | 55.001 | 58.328 | 40.091 | 1.00 | 40.19 |
| ATOM | 2259 | C   | TYR | A1068 | 56.057 | 58.982 | 40.941 | 1.00 | 40.19 |
| ATOM | 2260 | O   | TYR | A1068 | 56.899 | 59.755 | 40.422 | 1.00 | 40.19 |
| ATOM | 2261 | CB  | TYR | A1068 | 53.684 | 59.082 | 40.070 | 1.00 | 3.92 |
| ATOM | 2262 | CG  | TYR | A1068 | 53.658 | 60.503 | 40.344 | 1.00 | 3.92 |
| ATOM | 2263 | CD1 | TYR | A1068 | 53.484 | 61.369 | 39.326 | 1.00 | 3.92 |
| ATOM | 2264 | CD2 | TYR | A1068 | 53.650 | 60.958 | 41.607 | 1.00 | 3.92 |
| ATOM | 2265 | CE1 | TYR | A1068 | 53.296 | 62.732 | 39.530 | 1.00 | 3.92 |
| ATOM | 2266 | CE2 | TYR | A1068 | 53.473 | 62.266 | 41.862 | 1.00 | 3.92 |
| ATOM | 2267 | CZ  | TYR | A1068 | 53.311 | 63.163 | 40.812 | 1.00 | 3.92 |
| ATOM | 2268 | OH  | TYR | A1068 | 53.384 | 64.523 | 41.015 | 1.00 | 3.92 |
| ATOM | 2271 | N   | ASP | A1069 | 55.999 | 58.711 | 42.242 | 1.00 | 34.55 |
| ATOM | 2272 | CA  | ASP | A1069 | 57.036 | 59.211 | 43.139 | 1.00 | 34.55 |
| ATOM | 2273 | C   | ASP | A1069 | 58.139 | 58.257 | 42.721 | 1.00 | 34.55 |
| ATOM | 2274 | O   | ASP | A1069 | 58.415 | 57.326 | 43.454 | 1.00 | 34.55 |
| ATOM | 2275 | CB  | ASP | A1069 | 56.639 | 58.964 | 44.588 | 1.00 | 80.97 |
| ATOM | 2276 | CG  | ASP | A1069 | 57.819 | 58.905 | 45.514 | 1.00 | 80.97 |
| ATOM | 2277 | OD1 | ASP | A1069 | 58.968 | 59.094 | 45.061 | 1.00 | 80.97 |
| ATOM | 2278 | OD2 | ASP | A1069 | 57.591 | 58.673 | 46.714 | 1.00 | 80.97 |
| ATOM | 2280 | N   | LEU | A1070 | 58.667 | 58.506 | 41.503 | 1.00 | 4.63 |
| ATOM | 2281 | CA  | LEU | A1070 | 59.682 | 57.806 | 40.729 | 1.00 | 4.63 |
| ATOM | 2282 | C   | LEU | A1070 | 59.701 | 58.504 | 39.408 | 1.00 | 4.63 |
| ATOM | 2283 | O   | LEU | A1070 | 60.763 | 58.899 | 38.932 | 1.00 | 4.63 |
| ATOM | 2284 | CB  | LEU | A1070 | 59.389 | 56.337 | 40.348 | 1.00 | 35.45 |
| ATOM | 2285 | CG  | LEU | A1070 | 60.432 | 56.018 | 39.208 | 1.00 | 35.45 |
| ATOM | 2286 | CD1 | LEU | A1070 | 61.722 | 55.660 | 39.890 | 1.00 | 35.45 |
| ATOM | 2287 | CD2 | LEU | A1070 | 60.081 | 54.914 | 38.223 | 1.00 | 35.45 |
| ATOM | 2289 | N   | MET | A1071 | 58.577 | 58.594 | 38.714 | 1.00 | 33.43 |
| ATOM | 2290 | CA  | MET | A1071 | 58.662 | 59.377 | 37.490 | 1.00 | 33.43 |
| ATOM | 2291 | C   | MET | A1071 | 59.072 | 60.795 | 37.999 | 1.00 | 33.43 |
| ATOM | 2292 | O   | MET | A1071 | 59.717 | 61.547 | 37.301 | 1.00 | 33.43 |
| ATOM | 2293 | CB  | MET | A1071 | 57.328 | 59.425 | 36.716 | 1.00 | 46.26 |

FIG. 6GG

```
ATOM  2294  CG   MET A1071    56.293  60.425  37.126  1.00  46.26
ATOM  2295  SD   MET A1071    54.669  59.634  37.210  1.00  46.26
ATOM  2296  CE   MET A1071    54.450  58.978  35.595  1.00  46.26
ATOM  2298  N    ARG A1072    58.729  61.126  39.238  1.00  27.25
ATOM  2299  CA   ARG A1072    59.114  62.389  39.800  1.00  27.25
ATOM  2300  C    ARG A1072    60.612  62.482  40.123  1.00  27.25
ATOM  2301  O    ARG A1072    61.232  63.557  40.039  1.00  27.25
ATOM  2302  CB   ARG A1072    58.293  62.660  41.064  1.00100.00
ATOM  2303  CG   ARG A1072    56.890  63.206  40.805  1.00100.00
ATOM  2304  CD   ARG A1072    56.900  64.723  40.605  1.00100.00
ATOM  2305  NE   ARG A1072    57.085  65.438  41.861  1.00100.00
ATOM  2306  CZ   ARG A1072    56.517  66.600  42.150  1.00100.00
ATOM  2307  NH1  ARG A1072    55.722  67.184  41.271  1.00100.00
ATOM  2308  NH2  ARG A1072    56.749  67.178  43.315  1.00100.00
ATOM  2315  N    GLN A1073    61.212  61.376  40.533  1.00  63.04
ATOM  2316  CA   GLN A1073    62.625  61.439  40.836  1.00  63.04
ATOM  2317  C    GLN A1073    63.329  61.922  39.571  1.00  63.04
ATOM  2318  O    GLN A1073    64.270  62.702  39.623  1.00  63.04
ATOM  2319  CB   GLN A1073    63.152  60.060  41.233  1.00  85.05
ATOM  2320  CG   GLN A1073    62.417  59.384  42.387  1.00  85.05
ATOM  2321  CD   GLN A1073    63.134  58.127  42.896  1.00  85.05
ATOM  2322  OE1  GLN A1073    62.615  57.410  43.752  1.00  85.05
ATOM  2323  NE2  GLN A1073    64.322  57.859  42.364  1.00  85.05
ATOM  2327  N    CYS A1074    62.838  61.488  38.421  1.00  37.06
ATOM  2328  CA   CYS A1074    63.456  61.841  37.163  1.00  37.06
ATOM  2329  C    CYS A1074    63.305  63.280  36.845  1.00  37.06
ATOM  2330  O    CYS A1074    63.613  63.703  35.747  1.00  37.06
ATOM  2331  CB   CYS A1074    62.838  61.039  36.021  1.00  55.92
ATOM  2332  SG   CYS A1074    62.574  59.373  36.414  1.00  55.92
ATOM  2334  N    TRP A1075    62.780  64.030  37.793  1.00  54.40
ATOM  2335  CA   TRP A1075    62.549  65.443  37.559  1.00  54.40
ATOM  2336  C    TRP A1075    63.051  66.360  38.693  1.00  54.40
ATOM  2337  O    TRP A1075    62.683  67.533  38.757  1.00  54.40
ATOM  2338  CB   TRP A1075    61.055  65.719  37.347  1.00  13.83
ATOM  2339  CG   TRP A1075    60.306  65.009  36.268  1.00  13.83
ATOM  2340  CD1  TRP A1075    60.694  64.793  34.985  1.00  13.83
ATOM  2341  CD2  TRP A1075    58.962  64.566  36.350  1.00  13.83
ATOM  2342  NE1  TRP A1075    59.683  64.256  34.259  1.00  13.83
ATOM  2343  CE2  TRP A1075    58.593  64.109  35.078  1.00  13.83
ATOM  2344  CE3  TRP A1075    58.029  64.518  37.373  1.00  13.83
ATOM  2345  CZ2  TRP A1075    57.303  63.604  34.801  1.00  13.83
ATOM  2346  CZ3  TRP A1075    56.751  64.011  37.074  1.00  13.83
ATOM  2347  CH2  TRP A1075    56.423  63.573  35.814  1.00  13.83
ATOM  2350  N    ARG A1076    63.867  65.842  39.597  1.00  99.49
ATOM  2351  CA   ARG A1076    64.354  66.722  40.635  1.00  99.49
ATOM  2352  C    ARG A1076    64.967  67.872  39.838  1.00  99.49
ATOM  2353  O    ARG A1076    65.185  67.747  38.637  1.00  99.49
ATOM  2354  CB   ARG A1076    65.412  66.011  41.484  1.00  96.28
ATOM  2355  CG   ARG A1076    64.948  64.665  42.026  1.00  96.28
ATOM  2356  CD   ARG A1076    65.966  64.028  42.968  1.00  96.28
ATOM  2357  NE   ARG A1076    65.361  63.411  44.155  1.00  96.28
ATOM  2358  CZ   ARG A1076    65.408  62.110  44.427  1.00  96.28
ATOM  2359  NH1  ARG A1076    66.029  61.286  43.595  1.00  96.28
ATOM  2360  NH2  ARG A1076    64.855  61.635  45.538  1.00  96.28
ATOM  2367  N    GLU A1077    65.200  69.008  40.469  1.00  54.46
ATOM  2368  CA   GLU A1077    65.824  70.107  39.764  1.00  54.46
ATOM  2369  C    GLU A1077    67.293  69.771  39.587  1.00  54.46
```

FIG. 6HH

| | | | | | | | | |
|---|---|---|---|---|---|---|---|---|
| ATOM | 2370 | O | GLU | A1077 | 67.727 | 69.428 | 38.509 | 1.00 54.46 |
| ATOM | 2371 | CB | GLU | A1077 | 65.689 | 71.328 | 40.555 | 1.00 10.55 |
| ATOM | 2373 | N | LYS | A1078 | 68.050 | 69.854 | 40.670 | 1.00 35.40 |
| ATOM | 2374 | CA | LYS | A1078 | 69.476 | 69.542 | 40.642 | 1.00 35.40 |
| ATOM | 2375 | C | LYS | A1078 | 69.746 | 68.345 | 39.704 | 1.00 35.40 |
| ATOM | 2376 | O | LYS | A1078 | 69.592 | 67.215 | 40.099 | 1.00 35.40 |
| ATOM | 2377 | CB | LYS | A1078 | 69.954 | 69.234 | 42.058 | 1.00 95.51 |
| ATOM | 2378 | CG | LYS | A1078 | 70.054 | 70.458 | 42.936 | 1.00 95.51 |
| ATOM | 2379 | CD | LYS | A1078 | 70.070 | 70.094 | 44.414 | 1.00 95.51 |
| ATOM | 2380 | CE | LYS | A1078 | 71.487 | 70.050 | 44.990 | 1.00 95.51 |
| ATOM | 2381 | NZ | LYS | A1078 | 71.575 | 69.341 | 46.309 | 1.00 95.51 |
| ATOM | 2386 | N | PRO | A1079 | 70.230 | 68.582 | 38.481 | 1.00 54.45 |
| ATOM | 2387 | CA | PRO | A1079 | 70.437 | 67.398 | 37.643 | 1.00 54.45 |
| ATOM | 2388 | C | PRO | A1079 | 71.172 | 66.206 | 38.238 | 1.00 54.45 |
| ATOM | 2389 | O | PRO | A1079 | 70.745 | 65.097 | 38.040 | 1.00 54.45 |
| ATOM | 2390 | CB | PRO | A1079 | 71.099 | 67.958 | 36.381 | 1.00 46.70 |
| ATOM | 2391 | CG | PRO | A1079 | 70.732 | 69.385 | 36.376 | 1.00 46.70 |
| ATOM | 2392 | CD | PRO | A1079 | 70.658 | 69.817 | 37.801 | 1.00 46.70 |
| ATOM | 2393 | N | TYR | A1080 | 72.265 | 66.402 | 38.968 | 1.00100.00 |
| ATOM | 2394 | CA | TYR | A1080 | 72.963 | 65.243 | 39.542 | 1.00100.00 |
| ATOM | 2395 | C | TYR | A1080 | 72.128 | 64.578 | 40.621 | 1.00100.00 |
| ATOM | 2396 | O | TYR | A1080 | 72.619 | 63.747 | 41.375 | 1.00100.00 |
| ATOM | 2397 | CB | TYR | A1080 | 74.301 | 65.630 | 40.141 | 1.00 41.54 |
| ATOM | 2398 | CG | TYR | A1080 | 74.194 | 66.859 | 40.985 | 1.00 41.54 |
| ATOM | 2399 | CD1 | TYR | A1080 | 73.912 | 66.774 | 42.320 | 1.00 41.54 |
| ATOM | 2400 | CD2 | TYR | A1080 | 74.316 | 68.109 | 40.422 | 1.00 41.54 |
| ATOM | 2401 | CE1 | TYR | A1080 | 73.757 | 67.883 | 43.061 | 1.00 41.54 |
| ATOM | 2402 | CE2 | TYR | A1080 | 74.158 | 69.220 | 41.161 | 1.00 41.54 |
| ATOM | 2403 | CZ | TYR | A1080 | 73.882 | 69.118 | 42.480 | 1.00 41.54 |
| ATOM | 2404 | OH | TYR | A1080 | 73.778 | 70.273 | 43.233 | 1.00 41.54 |
| ATOM | 2407 | N | GLU | A1081 | 70.870 | 64.982 | 40.712 | 1.00 38.29 |
| ATOM | 2408 | CA | GLU | A1081 | 69.948 | 64.379 | 41.652 | 1.00 38.29 |
| ATOM | 2409 | C | GLU | A1081 | 69.030 | 63.423 | 40.853 | 1.00 38.29 |
| ATOM | 2410 | O | GLU | A1081 | 68.522 | 62.448 | 41.398 | 1.00 38.29 |
| ATOM | 2411 | CB | GLU | A1081 | 69.214 | 65.451 | 42.451 | 1.00 37.33 |
| ATOM | 2412 | CG | GLU | A1081 | 69.927 | 65.679 | 43.797 | 1.00 37.33 |
| ATOM | 2413 | CD | GLU | A1081 | 69.529 | 66.957 | 44.542 | 1.00 37.33 |
| ATOM | 2414 | OE1 | GLU | A1081 | 70.080 | 67.203 | 45.646 | 1.00 37.33 |
| ATOM | 2415 | OE2 | GLU | A1081 | 68.676 | 67.741 | 44.045 | 1.00 37.33 |
| ATOM | 2417 | N | ARG | A1082 | 68.876 | 63.690 | 39.550 | 1.00 35.27 |
| ATOM | 2418 | CA | ARG | A1082 | 68.154 | 62.803 | 38.655 | 1.00 35.27 |
| ATOM | 2419 | C | ARG | A1082 | 68.831 | 61.404 | 38.883 | 1.00 35.27 |
| ATOM | 2420 | O | ARG | A1082 | 69.932 | 61.322 | 39.463 | 1.00 35.27 |
| ATOM | 2421 | CB | ARG | A1082 | 68.336 | 63.260 | 37.216 | 1.00 62.49 |
| ATOM | 2422 | CG | ARG | A1082 | 67.202 | 64.072 | 36.647 | 1.00 62.49 |
| ATOM | 2423 | CD | ARG | A1082 | 67.299 | 65.548 | 36.942 | 1.00 62.49 |
| ATOM | 2424 | NE | ARG | A1082 | 67.442 | 66.375 | 35.737 | 1.00 62.49 |
| ATOM | 2425 | CZ | ARG | A1082 | 67.099 | 67.665 | 35.661 | 1.00 62.49 |
| ATOM | 2426 | NH1 | ARG | A1082 | 66.585 | 68.293 | 36.705 | 1.00 62.49 |
| ATOM | 2427 | NH2 | ARG | A1082 | 67.317 | 68.345 | 34.547 | 1.00 62.49 |
| ATOM | 2434 | N | PRO | A1083 | 68.144 | 60.280 | 38.530 | 1.00 37.62 |
| ATOM | 2435 | CA | PRO | A1083 | 68.732 | 58.945 | 38.729 | 1.00 37.62 |
| ATOM | 2436 | C | PRO | A1083 | 69.270 | 58.328 | 37.461 | 1.00 37.62 |
| ATOM | 2437 | O | PRO | A1083 | 68.905 | 58.780 | 36.414 | 1.00 37.62 |
| ATOM | 2438 | CB | PRO | A1083 | 67.541 | 58.148 | 39.267 | 1.00 40.57 |
| ATOM | 2439 | CG | PRO | A1083 | 66.294 | 59.139 | 39.213 | 1.00 40.57 |
| ATOM | 2440 | CD | PRO | A1083 | 66.721 | 60.125 | 38.171 | 1.00 40.57 |

FIG. 6II

```
ATOM   2441  N    SER A1084      70.157  57.337  37.541  1.00  23.77
ATOM   2442  CA   SER A1084      70.642  56.597  36.339  1.00  23.77
ATOM   2443  C    SER A1084      69.465  55.689  35.826  1.00  23.77
ATOM   2444  O    SER A1084      68.690  55.172  36.633  1.00  23.77
ATOM   2445  CB   SER A1084      71.772  55.617  36.733  1.00   2.00
ATOM   2446  OG   SER A1084      71.518  55.019  38.069  1.00   2.00
ATOM   2449  N    PHE A1085      69.330  55.466  34.520  1.00  44.36
ATOM   2450  CA   PHE A1085      68.272  54.565  34.032  1.00  44.36
ATOM   2451  C    PHE A1085      68.458  53.237  34.801  1.00  44.36
ATOM   2452  O    PHE A1085      67.633  52.852  35.603  1.00  44.36
ATOM   2453  CB   PHE A1085      68.414  54.399  32.529  1.00  95.75
ATOM   2454  CG   PHE A1085      68.175  55.669  31.783  1.00  95.75
ATOM   2455  CD1  PHE A1085      69.088  56.137  30.866  1.00  95.75
ATOM   2456  CD2  PHE A1085      67.036  56.409  32.022  1.00  95.75
ATOM   2457  CE1  PHE A1085      68.863  57.321  30.200  1.00  95.75
ATOM   2458  CE2  PHE A1085      66.807  57.591  31.361  1.00  95.75
ATOM   2459  CZ   PHE A1085      67.713  58.049  30.452  1.00  95.75
ATOM   2461  N    ALA A1086      69.541  52.541  34.541  1.00  35.91
ATOM   2462  CA   ALA A1086      69.894  51.395  35.347  1.00  35.91
ATOM   2463  C    ALA A1086      69.171  51.316  36.743  1.00  35.91
ATOM   2464  O    ALA A1086      68.741  50.223  37.179  1.00  35.91
ATOM   2465  CB   ALA A1086      71.400  51.423  35.580  1.00  44.62
ATOM   2467  N    GLN A1087      69.081  52.427  37.464  1.00  20.15
ATOM   2468  CA   GLN A1087      68.394  52.412  38.732  1.00  20.15
ATOM   2469  C    GLN A1087      66.842  52.338  38.466  1.00  20.15
ATOM   2470  O    GLN A1087      66.039  51.538  39.059  1.00  20.15
ATOM   2471  CB   GLN A1087      68.766  53.690  39.501  1.00  19.20
ATOM   2472  CG   GLN A1087      70.227  53.686  40.069  1.00  19.20
ATOM   2473  CD   GLN A1087      70.563  54.908  40.926  1.00  19.20
ATOM   2474  OE1  GLN A1087      70.927  55.939  40.379  1.00  19.20
ATOM   2475  NE2  GLN A1087      70.473  54.783  42.263  1.00  19.20
ATOM   2479  N    ILE A1088      66.451  53.197  37.550  1.00  25.82
ATOM   2480  CA   ILE A1088      65.088  53.310  37.160  1.00  25.82
ATOM   2481  C    ILE A1088      64.852  51.851  36.847  1.00  25.82
ATOM   2482  O    ILE A1088      63.966  51.300  37.447  1.00  25.82
ATOM   2483  CB   ILE A1088      64.921  54.260  35.919  1.00  17.84
ATOM   2484  CG1  ILE A1088      65.069  55.704  36.340  1.00  17.84
ATOM   2485  CG2  ILE A1088      63.626  53.984  35.170  1.00  17.84
ATOM   2486  CD1  ILE A1088      65.738  56.545  35.203  1.00  17.84
ATOM   2488  N    LEU A1089      65.628  51.205  35.969  1.00  19.62
ATOM   2489  CA   LEU A1089      65.380  49.747  35.692  1.00  19.62
ATOM   2490  C    LEU A1089      65.471  48.746  36.793  1.00  19.62
ATOM   2491  O    LEU A1089      64.899  47.746  36.680  1.00  19.62
ATOM   2492  CB   LEU A1089      66.155  49.127  34.566  1.00   2.73
ATOM   2493  CG   LEU A1089      65.363  47.882  33.978  1.00   2.73
ATOM   2494  CD1  LEU A1089      65.305  47.787  32.425  1.00   2.73
ATOM   2495  CD2  LEU A1089      66.127  46.642  34.338  1.00   2.73
ATOM   2497  N    VAL A1090      66.164  48.988  37.866  1.00  15.82
ATOM   2498  CA   VAL A1090      66.074  47.993  38.898  1.00  15.82
ATOM   2499  C    VAL A1090      64.931  48.400  39.791  1.00  15.82
ATOM   2500  O    VAL A1090      64.700  47.776  40.834  1.00  15.82
ATOM   2501  CB   VAL A1090      67.396  47.811  39.695  1.00   8.61
ATOM   2502  CG1  VAL A1090      67.259  48.053  41.220  1.00   8.61
ATOM   2503  CG2  VAL A1090      67.829  46.397  39.452  1.00   8.61
ATOM   2505  N    SER A1091      64.218  49.451  39.377  1.00  45.24
ATOM   2506  CA   SER A1091      63.073  50.005  40.110  1.00  45.24
ATOM   2507  C    SER A1091      61.708  49.486  39.628  1.00  45.24
```

FIG. 6JJ

| ATOM | 2508 | O   | SER A1091 | 60.764 | 49.305 | 40.422 | 1.00 | 45.24  |
|------|------|-----|-----------|--------|--------|--------|------|--------|
| ATOM | 2509 | CB  | SER A1091 | 63.064 | 51.511 | 39.963 | 1.00 | 46.04  |
| ATOM | 2510 | OG  | SER A1091 | 62.473 | 52.119 | 41.083 | 1.00 | 46.04  |
| ATOM | 2513 | N   | LEU A1092 | 61.582 | 49.317 | 38.318 | 1.00 | 48.10  |
| ATOM | 2514 | CA  | LEU A1092 | 60.336 | 48.814 | 37.772 | 1.00 | 48.10  |
| ATOM | 2515 | C   | LEU A1092 | 60.362 | 47.286 | 37.896 | 1.00 | 48.10  |
| ATOM | 2516 | O   | LEU A1092 | 59.310 | 46.649 | 38.093 | 1.00 | 48.10  |
| ATOM | 2517 | CB  | LEU A1092 | 60.226 | 49.217 | 36.335 | 1.00 | 20.50  |
| ATOM | 2518 | CG  | LEU A1092 | 60.649 | 50.636 | 36.171 | 1.00 | 20.50  |
| ATOM | 2519 | CD1 | LEU A1092 | 61.112 | 50.957 | 34.819 | 1.00 | 20.50  |
| ATOM | 2520 | CD2 | LEU A1092 | 59.492 | 51.389 | 36.445 | 1.00 | 20.50  |
| ATOM | 2522 | N   | ASN A1093 | 61.588 | 46.721 | 37.764 | 1.00 | 21.90  |
| ATOM | 2523 | CA  | ASN A1093 | 61.816 | 45.284 | 37.914 | 1.00 | 21.90  |
| ATOM | 2524 | C   | ASN A1093 | 61.298 | 44.970 | 39.321 | 1.00 | 21.90  |
| ATOM | 2525 | O   | ASN A1093 | 60.506 | 44.064 | 39.515 | 1.00 | 21.90  |
| ATOM | 2526 | CB  | ASN A1093 | 63.301 | 45.010 | 37.802 | 1.00 | 40.34  |
| ATOM | 2527 | CG  | ASN A1093 | 63.756 | 44.903 | 36.364 | 1.00 | 40.34  |
| ATOM | 2528 | OD1 | ASN A1093 | 64.796 | 44.322 | 36.103 | 1.00 | 40.34  |
| ATOM | 2529 | ND2 | ASN A1093 | 62.989 | 45.468 | 35.422 | 1.00 | 40.34  |
| ATOM | 2533 | N   | ARG A1094 | 61.699 | 45.746 | 40.314 | 1.00 | 34.76  |
| ATOM | 2534 | CA  | ARG A1094 | 61.194 | 45.385 | 41.611 | 1.00 | 34.76  |
| ATOM | 2535 | C   | ARG A1094 | 59.685 | 45.221 | 41.451 | 1.00 | 34.76  |
| ATOM | 2536 | O   | ARG A1094 | 59.122 | 44.320 | 42.022 | 1.00 | 34.76  |
| ATOM | 2537 | CB  | ARG A1094 | 61.515 | 46.451 | 42.653 | 1.00 | 99.74  |
| ATOM | 2538 | CG  | ARG A1094 | 61.377 | 45.969 | 44.088 | 1.00 | 99.74  |
| ATOM | 2539 | CD  | ARG A1094 | 59.934 | 46.037 | 44.575 | 1.00 | 99.74  |
| ATOM | 2540 | NE  | ARG A1094 | 59.736 | 47.099 | 45.557 | 1.00 | 99.74  |
| ATOM | 2541 | CZ  | ARG A1094 | 58.550 | 47.590 | 45.907 | 1.00 | 99.74  |
| ATOM | 2542 | NH1 | ARG A1094 | 57.438 | 47.117 | 45.357 | 1.00 | 99.74  |
| ATOM | 2543 | NH2 | ARG A1094 | 58.479 | 48.565 | 46.805 | 1.00 | 99.74  |
| ATOM | 2550 | N   | MET A1095 | 59.045 | 46.073 | 40.640 | 1.00 | 52.46  |
| ATOM | 2551 | CA  | MET A1095 | 57.594 | 46.029 | 40.452 | 1.00 | 52.46  |
| ATOM | 2552 | C   | MET A1095 | 57.136 | 44.721 | 39.781 | 1.00 | 52.46  |
| ATOM | 2553 | O   | MET A1095 | 56.663 | 43.809 | 40.435 | 1.00 | 52.46  |
| ATOM | 2554 | CB  | MET A1095 | 57.151 | 47.287 | 39.683 | 1.00 | 62.45  |
| ATOM | 2555 | CG  | MET A1095 | 57.076 | 48.578 | 40.594 | 1.00 | 62.45  |
| ATOM | 2556 | SD  | MET A1095 | 57.031 | 50.297 | 39.847 | 1.00 | 62.45  |
| ATOM | 2557 | CE  | MET A1095 | 57.509 | 51.299 | 41.162 | 1.00 | 62.45  |
| ATOM | 2559 | N   | LEU A1096 | 57.289 | 44.666 | 38.476 | 1.00 | 14.04  |
| ATOM | 2560 | CA  | LEU A1096 | 57.029 | 43.531 | 37.600 | 1.00 | 14.04  |
| ATOM | 2561 | C   | LEU A1096 | 57.039 | 42.101 | 38.255 | 1.00 | 14.04  |
| ATOM | 2562 | O   | LEU A1096 | 56.575 | 41.148 | 37.638 | 1.00 | 14.04  |
| ATOM | 2563 | CB  | LEU A1096 | 58.046 | 43.560 | 36.441 | 1.00 | 37.25  |
| ATOM | 2564 | CG  | LEU A1096 | 58.047 | 44.610 | 35.300 | 1.00 | 37.25  |
| ATOM | 2565 | CD1 | LEU A1096 | 59.158 | 44.291 | 34.269 | 1.00 | 37.25  |
| ATOM | 2566 | CD2 | LEU A1096 | 56.643 | 44.684 | 34.592 | 1.00 | 37.25  |
| ATOM | 2568 | N   | GLU A1097 | 57.574 | 41.928 | 39.450 | 1.00 | 42.58  |
| ATOM | 2569 | CA  | GLU A1097 | 57.530 | 40.621 | 40.048 | 1.00 | 42.58  |
| ATOM | 2570 | C   | GLU A1097 | 56.651 | 40.690 | 41.296 | 1.00 | 42.58  |
| ATOM | 2571 | O   | GLU A1097 | 57.019 | 40.286 | 42.411 | 1.00 | 42.58  |
| ATOM | 2572 | CB  | GLU A1097 | 58.919 | 40.136 | 40.396 | 1.00 | 100.00 |
| ATOM | 2573 | CG  | GLU A1097 | 59.757 | 39.901 | 39.188 | 1.00 | 100.00 |
| ATOM | 2574 | CD  | GLU A1097 | 60.925 | 40.839 | 39.144 | 1.00 | 100.00 |
| ATOM | 2575 | OE1 | GLU A1097 | 61.083 | 41.611 | 40.117 | 1.00 | 100.00 |
| ATOM | 2576 | OE2 | GLU A1097 | 61.680 | 40.799 | 38.147 | 1.00 | 100.00 |
| ATOM | 2578 | N   | GLU A1098 | 55.454 | 41.211 | 41.108 | 1.00 | 43.50  |
| ATOM | 2579 | CA  | GLU A1098 | 54.540 | 41.313 | 42.226 | 1.00 | 43.50  |

FIG. 6KK

```
ATOM   2580  C    GLU A1098      53.112  41.239  41.679  1.00 43.50
ATOM   2581  O    GLU A1098      52.247  40.533  42.228  1.00 43.50
ATOM   2582  CB   GLU A1098      54.783  42.639  42.970  1.00 60.12
ATOM   2583  CG   GLU A1098      56.233  43.014  43.093  1.00 60.12
ATOM   2584  CD   GLU A1098      56.895  42.498  44.392  1.00 60.12
ATOM   2585  OE1  GLU A1098      56.253  42.586  45.481  1.00 60.12
ATOM   2586  OE2  GLU A1098      58.071  42.019  44.331  1.00 60.12
ATOM   2588  N    ARG A1099      52.896  41.931  40.566  1.00100.00
ATOM   2589  CA   ARG A1099      51.564  42.010  40.005  1.00100.00
ATOM   2590  C    ARG A1099      50.792  42.471  41.232  1.00100.00
ATOM   2591  O    ARG A1099      50.117  41.681  41.899  1.00100.00
ATOM   2592  CB   ARG A1099      51.050  40.643  39.530  1.00 69.49
ATOM   2593  CG   ARG A1099      49.707  40.745  38.761  1.00 69.49
ATOM   2594  CD   ARG A1099      49.883  40.941  37.244  1.00 69.49
ATOM   2595  NE   ARG A1099      49.647  42.326  36.812  1.00 69.49
ATOM   2596  CZ   ARG A1099      49.095  42.672  35.648  1.00 69.49
ATOM   2597  NH1  ARG A1099      48.705  41.740  34.782  1.00 69.49
ATOM   2598  NH2  ARG A1099      48.989  43.951  35.322  1.00 69.49
ATOM   2605  N    LYS A1100      50.957  43.748  41.555  1.00 49.25
ATOM   2606  CA   LYS A1100      50.308  44.328  42.698  1.00 49.25
ATOM   2607  C    LYS A1100      49.232  45.070  42.019  1.00 49.25
ATOM   2608  O    LYS A1100      48.111  45.129  42.502  1.00 49.25
ATOM   2609  CB   LYS A1100      51.247  45.296  43.419  1.00 99.82
ATOM   2610  CG   LYS A1100      50.853  45.635  44.859  1.00 99.82
ATOM   2611  CD   LYS A1100      50.997  44.447  45.815  1.00 99.82
ATOM   2612  CE   LYS A1100      49.635  43.868  46.212  1.00 99.82
ATOM   2613  NZ   LYS A1100      49.247  44.148  47.622  1.00 99.82
ATOM   2618  N    THR A1101      49.603  45.578  40.850  1.00 64.74
ATOM   2619  CA   THR A1101      48.769  46.370  39.946  1.00 64.74
ATOM   2620  C    THR A1101      49.030  47.835  40.194  1.00 64.74
ATOM   2621  O    THR A1101      48.381  48.463  41.014  1.00 64.74
ATOM   2622  CB   THR A1101      47.282  46.080  40.069  1.00100.00
ATOM   2623  OG1  THR A1101      47.083  44.676  40.244  1.00100.00
ATOM   2624  CG2  THR A1101      46.581  46.494  38.801  1.00100.00
ATOM   2627  N    TYR A1102      50.026  48.346  39.472  1.00 78.61
ATOM   2628  CA   TYR A1102      50.462  49.715  39.571  1.00 78.61
ATOM   2629  C    TYR A1102      49.666  50.619  38.672  1.00 78.61
ATOM   2630  O    TYR A1102      49.438  51.753  39.026  1.00 78.61
ATOM   2631  CB   TYR A1102      51.960  49.856  39.210  1.00 42.69
ATOM   2632  CG   TYR A1102      52.910  49.107  40.092  1.00 42.69
ATOM   2633  CD1  TYR A1102      53.228  47.735  39.812  1.00 42.69
ATOM   2634  CD2  TYR A1102      53.356  49.663  41.288  1.00 42.69
ATOM   2635  CE1  TYR A1102      53.926  46.943  40.711  1.00 42.69
ATOM   2636  CE2  TYR A1102      54.061  48.880  42.207  1.00 42.69
ATOM   2637  CZ   TYR A1102      54.327  47.512  41.917  1.00 42.69
ATOM   2638  OH   TYR A1102      54.871  46.698  42.873  1.00 42.69
ATOM   2641  N    VAL A1103      49.233  50.151  37.513  1.00100.00
ATOM   2642  CA   VAL A1103      48.509  51.066  36.650  1.00100.00
ATOM   2643  C    VAL A1103      47.068  50.762  36.293  1.00100.00
ATOM   2644  O    VAL A1103      46.757  50.368  35.175  1.00100.00
ATOM   2645  CB   VAL A1103      49.276  51.325  35.350  1.00100.00
ATOM   2646  CG1  VAL A1103      48.590  52.426  34.565  1.00100.00
ATOM   2647  CG2  VAL A1103      50.694  51.746  35.661  1.00100.00
ATOM   2649  N    ASN A1104      46.191  50.990  37.260  1.00 30.52
ATOM   2650  CA   ASN A1104      44.768  50.802  37.118  1.00 30.52
ATOM   2651  C    ASN A1104      44.245  51.216  35.761  1.00 30.52
ATOM   2652  O    ASN A1104      44.475  52.317  35.289  1.00 30.52
```

FIG. 6LL

```
ATOM   2653  CB   ASN A1104      44.041  51.572  38.171  1.00  63.62
ATOM   2654  CG   ASN A1104      42.646  51.154  38.272  1.00  63.62
ATOM   2655  OD1  ASN A1104      41.934  51.137  37.275  1.00  63.62
ATOM   2656  ND2  ASN A1104      42.224  50.788  39.469  1.00  63.62
ATOM   2660  N    THR A1105      43.519  50.305  35.135  1.00  45.33
ATOM   2661  CA   THR A1105      42.978  50.501  33.817  1.00  45.33
ATOM   2662  C    THR A1105      41.629  49.788  33.751  1.00  45.33
ATOM   2663  O    THR A1105      40.980  49.726  32.734  1.00  45.33
ATOM   2664  CB   THR A1105      43.987  49.959  32.817  1.00  46.03
ATOM   2665  OG1  THR A1105      44.604  48.759  33.328  1.00  46.03
ATOM   2666  CG2  THR A1105      45.083  50.972  32.633  1.00  46.03
ATOM   2669  N    THR A1106      41.199  49.243  34.869  1.00  15.59
ATOM   2670  CA   THR A1106      39.900  48.589  34.956  1.00  15.59
ATOM   2671  C    THR A1106      38.820  49.661  35.289  1.00  15.59
ATOM   2672  O    THR A1106      39.072  50.461  36.167  1.00  15.59
ATOM   2673  CB   THR A1106      39.931  47.514  36.091  1.00  59.09
ATOM   2674  OG1  THR A1106      39.776  46.205  35.525  1.00  59.09
ATOM   2675  CG2  THR A1106      38.827  47.743  37.083  1.00  59.09
ATOM   2678  N    LEU A1107      37.641  49.683  34.662  1.00  27.67
ATOM   2679  CA   LEU A1107      36.613  50.729  35.028  1.00  27.67
ATOM   2680  C    LEU A1107      35.966  50.401  36.392  1.00  27.67
ATOM   2681  O    LEU A1107      34.939  49.735  36.477  1.00  27.67
ATOM   2682  CB   LEU A1107      35.491  50.874  33.967  1.00  39.85
ATOM   2683  CG   LEU A1107      35.834  50.768  32.492  1.00  39.85
ATOM   2684  CD1  LEU A1107      34.611  50.486  31.731  1.00  39.85
ATOM   2685  CD2  LEU A1107      36.500  51.981  31.985  1.00  39.85
ATOM   2687  N    TYR A1108      36.576  50.816  37.480  1.00  99.39
ATOM   2688  CA   TYR A1108      35.969  50.482  38.748  1.00  99.39
ATOM   2689  C    TYR A1108      34.685  51.305  38.878  1.00  99.39
ATOM   2690  O    TYR A1108      33.900  51.097  39.806  1.00  99.39
ATOM   2691  CB   TYR A1108      36.973  50.749  39.872  1.00 100.00
ATOM   2692  CG   TYR A1108      38.383  50.249  39.513  1.00 100.00
ATOM   2693  CD1  TYR A1108      39.286  51.419  39.214  1.00 100.00
ATOM   2694  CD2  TYR A1108      38.945  49.421  40.644  1.00 100.00
ATOM   2696  N    GLU A1109      34.486  52.198  37.899  1.00 100.00
ATOM   2697  CA   GLU A1109      33.341  53.116  37.779  1.00 100.00
ATOM   2698  C    GLU A1109      33.875  54.536  37.598  1.00 100.00
ATOM   2699  O    GLU A1109      34.957  54.846  38.095  1.00 100.00
ATOM   2700  CB   GLU A1109      32.454  53.065  39.001  1.00  76.82
ATOM   2702  N    LYS A1110      33.104  55.390  36.914  1.00 100.00
ATOM   2703  CA   LYS A1110      33.486  56.779  36.626  1.00 100.00
ATOM   2704  C    LYS A1110      34.891  56.830  36.038  1.00 100.00
ATOM   2705  O    LYS A1110      35.858  56.673  36.763  1.00 100.00
ATOM   2706  CB   LYS A1110      33.430  57.631  37.900  1.00  99.15
ATOM   2707  CG   LYS A1110      34.009  56.977  39.152  1.00  99.15
ATOM   2708  CD   LYS A1110      34.718  57.970  40.052  1.00  99.15
ATOM   2709  CE   LYS A1110      34.246  57.852  41.490  1.00  99.15
ATOM   2710  NZ   LYS A1110      33.479  59.054  41.919  1.00  99.15
ATOM   2715  N    PHE A1111      35.030  57.055  34.737  1.00 100.00
ATOM   2716  CA   PHE A1111      36.373  57.068  34.186  1.00 100.00
ATOM   2717  C    PHE A1111      36.824  58.244  33.333  1.00 100.00
ATOM   2718  O    PHE A1111      36.116  58.763  32.487  1.00 100.00
ATOM   2719  CB   PHE A1111      36.685  55.747  33.449  1.00  61.16
ATOM   2720  CG   PHE A1111      38.144  55.601  33.081  1.00  61.16
ATOM   2721  CD1  PHE A1111      39.101  55.397  34.055  1.00  61.16
ATOM   2722  CD2  PHE A1111      38.575  55.820  31.785  1.00  61.16
ATOM   2723  CE1  PHE A1111      40.448  55.431  33.736  1.00  61.16
```

FIG. 6MM

```
ATOM   2724  CE2 PHE A1111     39.917  55.853  31.485  1.00 61.16
ATOM   2725  CZ  PHE A1111     40.845  55.664  32.451  1.00 61.16
ATOM   2727  N   THR A1112     38.080  58.579  33.586  1.00 54.03
ATOM   2728  CA  THR A1112     38.875  59.664  33.030  1.00 54.03
ATOM   2729  C   THR A1112     39.433  59.610  31.628  1.00 54.03
ATOM   2730  O   THR A1112     38.693  59.607  30.694  1.00 54.03
ATOM   2731  CB  THR A1112     40.029  59.942  34.007  1.00100.00
ATOM   2732  OG1 THR A1112     41.181  59.195  33.618  1.00100.00
ATOM   2733  CG2 THR A1112     39.637  59.498  35.430  1.00100.00
ATOM   2736  N   TYR A1113     40.750  59.639  31.504  1.00 39.45
ATOM   2737  CA  TYR A1113     41.514  59.623  30.240  1.00 39.45
ATOM   2738  C   TYR A1113     42.391  60.886  30.057  1.00 39.45
ATOM   2739  O   TYR A1113     42.658  61.611  30.980  1.00 39.45
ATOM   2740  CB  TYR A1113     40.661  59.461  29.000  1.00 60.42
ATOM   2741  CG  TYR A1113     40.682  58.097  28.373  1.00 60.42
ATOM   2742  CD1 TYR A1113     40.003  57.867  27.193  1.00 60.42
ATOM   2743  CD2 TYR A1113     41.168  56.982  29.056  1.00 60.42
ATOM   2744  CE1 TYR A1113     39.776  56.585  26.720  1.00 60.42
ATOM   2745  CE2 TYR A1113     40.938  55.670  28.577  1.00 60.42
ATOM   2746  CZ  TYR A1113     40.231  55.511  27.413  1.00 60.42
ATOM   2747  OH  TYR A1113     39.943  54.290  26.912  1.00 60.42
ATOM   2750  N   ALA A1114     42.852  61.153  28.847  1.00100.00
ATOM   2751  CA  ALA A1114     43.759  62.268  28.741  1.00100.00
ATOM   2752  C   ALA A1114     44.080  62.762  27.312  1.00100.00
ATOM   2753  O   ALA A1114     44.093  63.971  27.052  1.00100.00
ATOM   2754  CB  ALA A1114     45.049  61.857  29.500  1.00 34.32
ATOM   2756  N   GLY A1115     44.317  61.803  26.410  1.00 68.47
ATOM   2757  CA  GLY A1115     44.683  62.024  24.996  1.00 68.47
ATOM   2758  C   GLY A1115     44.399  63.213  24.093  1.00 68.47
ATOM   2759  O   GLY A1115     45.017  63.303  23.036  1.00 68.47
ATOM   2761  N   ILE A1116     43.470  64.088  24.487  1.00100.00
ATOM   2762  CA  ILE A1116     43.066  65.299  23.739  1.00100.00
ATOM   2763  C   ILE A1116     41.700  65.193  23.039  1.00100.00
ATOM   2764  O   ILE A1116     41.049  64.140  23.163  1.00100.00
ATOM   2765  CB  ILE A1116     44.141  65.709  22.727  1.00 87.32
ATOM   2766  OXT ILE A1116     41.280  66.178  22.385  1.00 87.32
TER
HETATM    1  C1  INH I    1    58.113  50.247  12.231  0.00  0.00
HETATM    2  N2  INH I    1    57.524  51.444  12.202  0.00  0.00
HETATM    3  C3  INH I    1    58.303  52.541  12.107  0.00  0.00
HETATM    4  C4  INH I    1    59.686  52.462  12.036  0.00  0.00
HETATM    5  C5  INH I    1    60.234  51.117  12.080  0.00  0.00
HETATM    6  N6  INH I    1    59.434  50.040  12.174  0.00  0.00
HETATM    8  N8  INH I    1    57.877  53.857  12.079  0.00  0.00
HETATM    9  C9  INH I    1    59.057  54.550  11.988  0.00  0.00
HETATM   10  C10 INH I    1    60.219  53.760  11.953  0.00  0.00
HETATM   12  C13 INH I    1    61.633  54.217  11.871  0.00  0.00
HETATM   13  N15 INH I    1    61.632  50.906  12.042  0.00  0.00
HETATM   14  C16 INH I    1    56.477  54.327  12.146  0.00  0.00
HETATM   15  C17 INH I    1    56.258  55.192  13.391  0.00  0.00
HETATM   16  C18 INH I    1    54.809  55.688  13.471  0.00  0.00
HETATM   17  C19 INH I    1    54.371  56.477  12.214  0.00  0.00
HETATM   18  C20 INH I    1    54.670  55.630  10.955  0.00  0.00
HETATM   19  C21 INH I    1    56.121  55.136  10.897  0.00  0.00
HETATM   28  N30 INH I    1    52.949  56.902  12.268  0.00  0.00
HETATM   29  C32 INH I    1    51.997  55.774  12.311  0.00  0.00
HETATM   30  C33 INH I    1    50.531  56.215  12.400  0.00  0.00
```

FIG. 6NN

SEQUENCE LISTING

<160> NUMBER OF SEQ ID NOS: 2

<210> SEQ ID NO 1
<211> LENGTH: 1127
<212> TYPE: PRT
<213> ORGANISM: Homo sapiens

<400> SEQUENCE: 1

```
Met Asp Ser Leu Ala Ser Leu Val Leu Cys Gly Val Ser Leu Leu Leu
 1               5                  10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60
```

```
Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
             85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
        130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
        370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445
```

```
        Asn Ala Pro Asn Val Ile Asp Thr Gly His Asn Phe Ala Val Ile Asn
            450                 455                 460
        Ile Ser Ser Glu Pro Tyr Phe Gly Asp Gly Pro Ile Lys Ser Lys Lys
        465                 470                 475                 480
        Leu Leu Tyr Lys Pro Val Asn His Tyr Glu Ala Trp Gln His Ile Gln
                        485                 490                 495
        Val Thr Asn Glu Ile Val Thr Leu Asn Tyr Leu Glu Pro Arg Thr Glu
                    500                 505                 510
        Tyr Glu Leu Cys Val Gln Leu Val Arg Arg Gly Glu Gly Gly Glu Gly
                515                 520                 525
        His Pro Gly Pro Val Arg Arg Phe Thr Thr Ala Ser Ile Gly Leu Pro
            530                 535                 540
        Pro Pro Arg Gly Leu Asn Leu Leu Pro Lys Ser Gln Thr Thr Leu Asn
        545                 550                 555                 560
        Leu Thr Trp Gln Pro Ile Phe Pro Ser Ser Glu Asp Asp Phe Tyr Val
                        565                 570                 575
        Glu Val Glu Arg Arg Ser Val Gln Lys Ser Asp Gln Gln Asn Ile Lys
                    580                 585                 590
        Val Pro Gly Asn Leu Thr Ser Val Leu Leu Asn Asn Leu His Pro Arg
                595                 600                 605
        Glu Gln Tyr Val Val Arg Ala Arg Val Asn Thr Lys Ala Gln Gly Glu
            610                 615                 620
        Trp Ser Glu Asp Leu Thr Ala Trp Thr Leu Ser Asp Ile Leu Pro Pro
        625                 630                 635                 640
        Gln Pro Glu Asn Ile Lys Ile Ser Asn Ile Thr His Ser Ser Ala Val
                        645                 650                 655
        Ile Ser Trp Thr Ile Leu Asp Gly Tyr Ser Ile Ser Ser Ile Thr Ile
                    660                 665                 670
        Arg Tyr Lys Val Gln Gly Lys Asn Glu Asp Gln His Val Asp Val Lys
                675                 680                 685
        Ile Lys Asn Ala Thr Ile Ile Gln Tyr Gln Leu Lys Gly Leu Glu Pro
            690                 695                 700
        Glu Thr Ala Tyr Gln Val Asp Ile Phe Ala Glu Asn Asn Ile Gly Ser
        705                 710                 715                 720
        Ser Asn Pro Ala Phe Ser His Glu Leu Val Thr Leu Pro Glu Ser Gln
                        725                 730                 735
        Ala Pro Ala Asp Leu Gly Gly Gly Lys Met Leu Leu Ile Ala Ile Leu
                    740                 745                 750
        Gly Ser Ala Gly Met Thr Cys Leu Thr Val Leu Leu Ala Phe Leu Ile
                755                 760                 765
        Ile Leu Gln Leu Lys Arg Ala Asn Val Gln Arg Arg Met Ala Gln Ala
            770                 775                 780
        Phe Gln Asn Val Arg Glu Glu Pro Ala Val Gln Phe Asn Ser Gly Thr
        785                 790                 795                 800
        Leu Ala Leu Asn Arg Lys Val Lys Asn Asn Pro Asp Pro Thr Ile Tyr
                        805                 810                 815
```

```
Pro Val Leu Asp Trp Asn Asp Ile Lys Phe Gln Asp Val Ile Gly Glu
            820                 825                 830
Gly Asn Phe Gly Gln Val Leu Lys Ala Arg Ile Lys Lys Asp Gly Leu
        835                 840                 845
Arg Met Asp Ala Ala Ile Lys Arg Met Lys Glu Tyr Ala Ser Lys Asp
    850                 855                 860
Asp His Arg Asp Phe Ala Gly Glu Leu Glu Val Leu Cys Lys Leu Gly
865                 870                 875                 880
His His Pro Asn Ile Ile Asn Leu Leu Gly Ala Cys Glu His Arg Gly
            885                 890                 895
Tyr Leu Tyr Leu Ala Ile Glu Tyr Ala Pro His Gly Asn Leu Leu Asp
        900                 905                 910
Phe Leu Arg Lys Ser Arg Val Leu Glu Thr Asp Pro Ala Phe Ala Ile
    915                 920                 925
Ala Asn Ser Thr Ala Ser Thr Leu Ser Ser Gln Gln Leu Leu His Phe
930                 935                 940
Ala Ala Asp Val Ala Arg Gly Met Asp Tyr Leu Ser Gln Lys Gln Phe
945                 950                 955                 960
Ile His Arg Asp Leu Ala Ala Arg Asn Ile Leu Val Gly Glu Asn Tyr
            965                 970                 975
Val Ala Lys Ile Ala Asp Phe Gly Leu Ser Arg Gly Gln Glu Val Tyr
        980                 985                 990
Val Lys Lys Thr Met Gly Arg Leu Pro Val Arg Trp Met Ala Ile Glu
    995                 1000                1005
Ser Leu Asn Tyr Ser Val Tyr Thr Thr Asn Ser Asp Val Trp Ser Tyr
    1010                1015                1020
Gly Val Leu Leu Trp Glu Ile Val Ser Leu Gly Gly Thr Pro Tyr Cys
1025                1030                1035                1040
Gly Met Thr Cys Ala Glu Leu Tyr Glu Lys Leu Pro Gln Gly Tyr Arg
            1045                1050                1055
Leu Glu Lys Pro Leu Asn Cys Asp Asp Glu Val Tyr Asp Leu Met Arg
        1060                1065                1070
Gln Cys Trp Arg Glu Lys Pro Tyr Glu Arg Pro Ser Phe Ala Gln Ile
    1075                1080                1085
Leu Val Ser Leu Asn Arg Met Leu Glu Glu Arg Lys Thr Tyr Val Asn
        1090                1095                1100
Thr Thr Leu Tyr Glu Lys Phe Thr Tyr Ala Gly Ile Asp Cys Ser Ala
1105                1110                1115                1120
Glu Glu Ala Ala Phe Ile Gly
            1125

<210> SEQ ID NO 2
<211> LENGTH: 326
<212> TYPE: PRT
<213> ORGANISM: Homo sapiens

<400> SEQUENCE: 2

Ala Leu Asn Arg Lys Val Lys Asn Asn Pro Asp Pro Thr Ile Tyr Pro
1               5                   10                  15
Val Leu Asp Trp Asn Asp Ile Lys Phe Gln Asp Val Ile Gly Glu Gly
            20                  25                  30
Asn Phe Gly Gln Val Leu Lys Ala Arg Ile Lys Lys Asp Gly Leu Arg
        35                  40                  45
```

```
Met Asp Ala Ala Ile Lys Arg Met Lys Glu Tyr Ala Ser Lys Asp Asp
 50                  55                  60

His Arg Asp Phe Ala Gly Glu Leu Glu Val Leu Cys Lys Leu Gly His
 65                  70                  75                  80

His Pro Asn Ile Ile Asn Leu Leu Gly Ala Cys Glu His Arg Gly Tyr
                 85                  90                  95

Leu Tyr Leu Ala Ile Glu Tyr Ala Pro His Gly Asn Leu Leu Asp Phe
                100                 105                 110

Leu Arg Lys Ser Arg Val Leu Glu Thr Asp Pro Ala Phe Ala Ile Ala
                115                 120                 125

Asn Ser Thr Ala Ser Thr Leu Ser Ser Gln Gln Leu Leu His Phe Ala
            130                 135                 140

Ala Asp Val Ala Arg Gly Met Asp Tyr Leu Ser Gln Lys Gln Phe Ile
145                 150                 155                 160

His Arg Asn Leu Ala Ala Arg Asn Ile Leu Val Gly Glu Asn Tyr Val
                165                 170                 175

Ala Lys Ile Ala Asp Phe Gly Leu Ser Arg Gly Gln Glu Val Tyr Val
                180                 185                 190

Lys Lys Thr Met Gly Arg Leu Pro Val Arg Trp Met Ala Ile Glu Ser
            195                 200                 205

Leu Asn Tyr Ser Val Tyr Thr Thr Asn Ser Asp Val Trp Ser Tyr Gly
        210                 215                 220

Val Leu Leu Trp Glu Ile Val Ser Leu Gly Gly Thr Pro Tyr Cys Gly
225                 230                 235                 240

Met Thr Cys Ala Glu Leu Tyr Glu Lys Leu Pro Gln Gly Tyr Arg Leu
                245                 250                 255

Glu Lys Pro Leu Asn Cys Asp Asp Glu Val Tyr Asp Leu Met Arg Gln
            260                 265                 270

Cys Trp Arg Glu Lys Pro Tyr Glu Arg Pro Ser Phe Ala Gln Ile Leu
            275                 280                 285

Val Ser Leu Asn Arg Met Leu Glu Glu Arg Lys Thr Tyr Val Asn Thr
    290                 295                 300

Thr Leu Tyr Glu Lys Phe Thr Tyr Ala Gly Ile Asp Cys Ser Ala Glu
305                 310                 315                 320

Glu Ala Ala Phe Ile Gly
                325
```

METHOD OF IDENTIFYING INHIBITORS OF TIE-2

RELATED APPLICATION

This application claims the benefit of U.S. Provisional Application No. 60/192,920, filed on Mar. 29, 2000. The entire teachings of the above application is incorporated herein by reference.

BACKGROUND OF THE INVENTION

Angiogenesis is a fundamental process by which new blood vessels are formed through sprouting, branching, proliferation, and tubule formation by endothelial cells from existing vasculature. In healthy humans, this neovascularization is under stringent control, normally occurring only during embryonic development, endometrial regulation, breast lactation and wound repair. However, in many pathological conditions, such as rheumatoid arthritis, solid tumors, Kaposi's sarcoma, blindness due to ocular neovascularization, psoriasis and atherosclerosis, disease progression is dependent upon persistent angiogenesis. The vasculature, which is the conduit for drug delivery, is one of the most accessible tissues in the body. Each endothelial cell of tumor vessels is estimated to support 100 to 1,000 neighboring cells, yet in the absence of an angiogenic stimulus endothelial cells typically divide only once every thousand days.

A number of polypeptide growth factors and their associated endothelial cell specific receptors have been discovered which are primarily responsible for the stimulation of endothelial cell growth, differentiation and the establishment of new vasculature. These growth factor receptors include the vascular endothelial growth factor receptors (VEGFR) Flk-1 (mouse), KDR/VEG-FR-2 (human), Flt-1/VEGFR-1, and Flt-4/VEGFR-3. Receptors which are responsible for neovascularizaton also include the receptor tyrosine kinases Tie-1 and Tie-2.

Due to its role in regulating new vascular development, Tie-2 is a potential target for therapies aimed at controlling diseases which depend upon persistent angiogenesis. The development of biochemical assays for Tie-2 has enabled drug discovery to proceed along the pathways of identifying lead Tie-2 inhibitors by high-throughput screening of compound libraries and by testing compounds that mimic substrate structure; however, rational, structure-based design has not been possible up to this point because of the lack of accurate three-dimensional structural data for Tie-2 receptors.

SUMMARY OF THE INVENTION

The present invention relates to a polypeptide which comprises the catalytic domain of Tie-2, a crystalline form of this polypeptide and the use of structural information derived from the crystalline form of the polypeptide for designing and/or identifying potential inhibitors of the binding of one or more native ligands to the catalytic domain of Tie-2.

In one embodiment, the present invention relates to a polypeptide comprising the catalytic domain of TIE-2 and having the amino acid sequence set forth in SEQ ID NO: 2. In another embodiment, the invention relates to a crystalline form of this polypeptide or the polypeptide complexed with a ligand.

In another embodiment, the invention provides a method of determining the three dimensional structure of a crystalline polypeptide comprising the Tie-2 catalytic domain. In one embodiment, the method comprises the steps of (1) obtaining a crystal of the polypeptide comprising the catalytic domain of Tie-2; (2) obtaining x-ray diffraction data for said crystal; and (3) solving the crystal structure of said crystal. The method optionally comprises the additional step of obtaining the polypeptide, with the three dimensional structure to be determined, prior to obtaining the crystal of said peptide.

In another embodiment, the method comprises the steps of (1) obtaining a crystal of the polypeptide comprising the catalytic domain of Tie-2; (2) obtaining x-ray diffraction data for said crystal; and (3) solving the crystal structure of said crystal by using said x-ray diffraction data and the atomic coordinates for the Tie-2 catalytic domain of a second polypeptide. The method optionally comprises the additional step of obtaining the polypeptide, with the three dimensional structure to be determined, prior to obtaining the crystal of said peptide.

The invention further relates to a method for identifying a compound which inhibits the catalytic activity of Tie-2 by, for example, inhibiting the binding of natural substrates such as a tyrosyl polypeptide or protein or ATP, to the catalytic domain of Tie-2. Such a compound is referred to herein as a "Tie-2 inhibitor". The method comprises the steps of (1) using a three-dimensional structure of Tie-2 as defined by the atomic coordinates of the cataytic domain of Tie-2; (2) employing the three dimensional structure to design or select a potential inhibitor; and (3) assessing the ability of the selected compound to inhibit the catalytic activity of Tie-2. The method can also include the step of providing the compound designed or selected in step 2, for example, by synthesizing the compound or obtaining the compound from a compound library. In addition, the method can include the step of assessing the ability of the identified compound to bind to the catalytic domain of Tie-2 and/or assessing the ability of the identified compound to inhibit the binding of a natural ligand of Tie-2.

In another embodiment, the method for identifying a compound which inhibits the catalytic activity of Tie-2, comprises the step of determining the ability of one or more functional groups and/or moieties of the compound, when present in, or bound to, the Tie-2 catalytic domain, to interact with one or more subsites of the Tie-2 catalytic domain. Generally, the Tie-2 catalytic domain is defined by the conserved homologous seqences when compared to other known tyrosine kinases. If the compound is able to interact with a preselected number or set of subsites, or has a calculated interaction energy within a desired or preselected range, the compound is identified as a potential inhibitor of Tie-2.

The invention further provides a method of designing a compound which is a potential inhibitor of the catalytic activity of Tie-2. The method includes the steps of (1) identifying one or more functional groups capable of interacting with one or more subsites of the Tie-2 catalytic domain; and (2) identifying a scaffold which presents the functional group, or functional groups, identified in step 1 in a suitable orientation for interacting with one or more subsites of the Tie-2 catalytic domain. The compound which results from attachment of the identified functional groups or moieties to the identified scaffold is a potential inhibitor of Tie-2. The Tie-2 catalytic domain is, generally, defined by the atomic coordinates of a polypeptide comprising the Tie-2 catalytic domain.

In yet another embodiment, the invention provides compounds which inhibit the catalytic activity of Tie-2 and which fit, or bind to, the Tie-2 catalytic domain. Such compounds typically comprise one or more functional groups which, when the compound is bound in the Tie-2 catalytic domain, interact with one or more subsites of the catalytic domain. Generally, the Tie-2 catalytic domain is defined by the conserved homologous sequence when compared to other known tyrosine kinases. In a particular embodiment, the Tie-2 inhibitor is a compound which is identified or designed by a method of the present invention.

The present invention further provides a method for treating a condition mediated by Tie-2 in a patient. The method comprises administering to the patient a therapeutically or prophylactically effective amount of a compound which inhibits the catalytic activity of Tie-2, such as a Tie-2 inhibitor of the invention, for example, a compound identified as a Tie-2 inhibitor or designed to inhibit Tie-2 by a method of the present invention.

The present invention provides several advantages. For example, the invention provides the first detailed three dimensional structures of the ligand binding domain of a Tie-2 protein. The methods described herein can be used to facilitate formation of Tie-2 crystals which diffract at high resolution. These structures enable the rational development of inhibitors of Tie-2 by permitting the design and/or identification of molecular structures having features which facilitate binding to the Tie-2 binding domain. The methods of use of the structures disclosed herein, thus, permit more rapid discovery of compounds which are potentially useful for the treatment of conditions which are mediated, at least in part, by Tie-2 activity.

BRIEF DESCRIPTION OF THE DRAWINGS

FIG. 1 presents the amino acid sequence of human Tie-2 (SEQ ID NO: 1).

FIG. 2 presents the amino acid sequence which includes the catalytic domain of human Tie-2 from amino acid 802 to amino acid 1124, and has a catalytically inactive point mutation at amino acid 964 (SEQ ID NO: 2).

FIGS. 3A-3OO present the atomic coordinates for SEQ ID NO 2/inhibitor I complex.

FIGS. 4A-4OO present the atomic coordinates for SEQ ID NO 2/inhibitor II complex.

FIGS. 5A-5RR present the atomic coordinates for SEQ ID NO 2/inhibitor III complex.

FIGS. 6A-6NN present the atomic coordinates for SEQ ID NO 2/inhibitor IV complex.

DETAILED DESCRIPTION OF THE INVENTION

Figure 7:
FIG. 7 shows the structure of a prototypical kinase, insulin receptor kinase.
Figure 8:
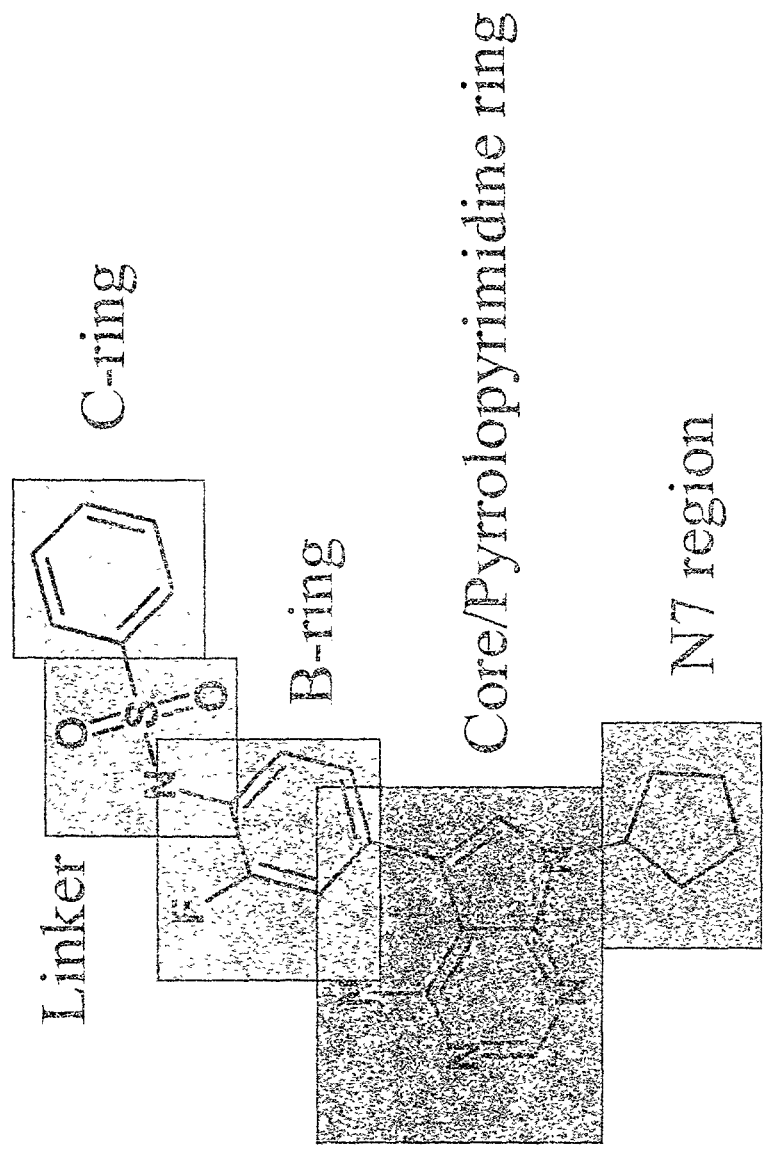
FIG. 8 shows identifies regions of a pyrrolopyrimidine inhibitor (i.e., inhibitor I) which interact with the catalytic domain of Tie-2.

The present invention relates to the x-ray crystallographic study of polypeptides comprising the catalytic domain of Tie-2. The atomic coordinates which result from this study are of use in identifying compounds which fit in the catalytic domain and are, therefore, potential inhibitors of Tie-2. These Tie-2 inhibitors are of use in methods of treating a patient having a condition which is modulated by or dependent upon Tie-2 activity, for example, a condition dependent on persistant angiogenesis.

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, rheumatoid arthritis, retinopathy of prematurity, infantile hemangiomas, psoriasis and atherosclerosis.

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1-20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413-423; Songyang et al., 1994, *Mol. Cell. Biol.* 14:2777-2785; Songyang et al., 1993, *Cell* 72:767-778; and Koch et al., 1991, *Science* 252:668-678; Shoelson, *Curr. Opin. Chem. Biol.* (1997), 1(2), 227-234; Cowburn, *Curr. Opin. Struct. Biol.* (1997), 7(6), 835-838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767-778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767-778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895-898, 1995).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovascularization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence of sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization.

The Examples herein describe the preparation and crystallization of polypeptides comprising the catalytic domain of human Tie-2. As used herein, the term "catalytic domain" refers to a specific module common to all kinases which bind ATP, such as the tyrosyl binding site, the site where ATP binds including the metal-ion binding region, and the site where the phosphoryl transfer occurs. For Tie-2, the catalytic domain is defined by amino acid residues from about residue 828 to about residue 985 of SEQ ID NO: 1, with residues 828-840, 853-855, 872, 873, 876, 879, 880, 885-888, 900, 902-909, 912, 954, 955, 960, 964, 968-971, and 980-985 included in the catalytic domain.

The amino acid sequences of native human Tie-2 (SEQ ID NO: 1) is taken as defined in SWISS-PROT (Ziegler, et al. *Oncogene*, 8:663 (1993)). As described in the Examples, certain of these crystals were examined by x-ray crystallography and atomic coordinates for the peptide were obtained. In certain cases, the polypeptide was unligated, that is, not complexed with a ligand. In other cases, the polypeptide was complexed with a ligand and the atomic coordinates of the ligand bound to the Tie-2 catalytic domain were also obtained.

Tie-2 is subject to autophosphorylation and transphosphorylation by other proteins. Phosphorylation state is a particularly important posttranslational modification to consider. A wild-type construct (i.e., without the D964N mutation) having residues 802-1124 of SEQ ID NO 1 was isolated from an expression system as a singly- or a multiply-phosphorylated species. One singly-phosphorylated species has its phosphate on either Y897 or Y899. In multiply phosphorylated species, phosphorylation can be on combinations of many Y residues on the protein. A diphosphorylated species crystallized in the space group P2(1)2(1)2(1) with the unit cell dimensions of a=54.320 Å, b=75.872 Å, c=78.143 Å, and $\alpha=\beta=\gamma=90.0°$. The term "space group" is a term of art which refers to the collection of symmetry elements of the unit cell of a crystal. Other phosphorylation sites are described in Jones, N., et al., *J. Biol. Chem.* (1999), 274(43):30896.

A catalytically inactive mutant of human Tie-2 (SEQ ID NO 2) was also crystallized. The catalytically inactive mutant had the same sequence as residues 802 to 1124 of human Tie-2 except that residue 964 which is aspartic acid in wild type human Tie-2 was replaced with asparagine. This substitution rendered the mutant catalytically inactive. SEQ ID NO 2 crystallized in the space group C222(1) which had the unit cell dimensions a=75.195 Å, b=116.287 Å, c=95.060 Å, and $\alpha=\beta=\gamma=90.0°$ The atomic coordinates for four crystals of Tie-2/ligand complexes examined by x-ray crystallography are presented in FIGS. 3A-3OO, 4A-4OO, 5A-5RR and 6A-6NN. The term "atomic coordinates" (or "structural coordinates") refers to mathematical coordinates derived from mathematical equations related to the patterns obtained on diffraction of x-rays by atoms (scattering centers) of a crystalline polypeptide comprising a Tie-2 catalytic domain molecule. The diffraction data are used to calculate an electron density map of the repeating unit of the crystal. The electron density maps are used to establish the positions of the individual atoms within the unit cell of the crystal. Atomic coordinates can be transformed as is known in the art to different coordinate systems without affecting the relative positions of the atoms.

In particular, four high resolution crystal structures were obtained for SEQ ID NO 2) complexed with one of four different inhibitors shown below:

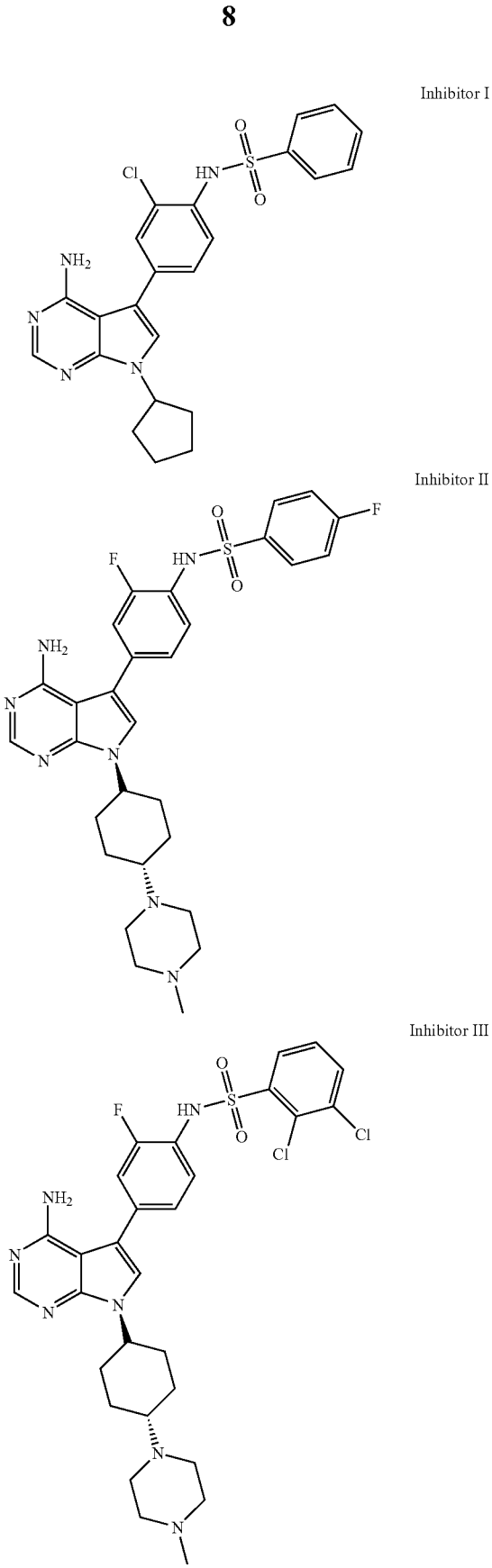

Inhibitor I

Inhibitor II

Inhibitor III

-continued

Inhibitor IV

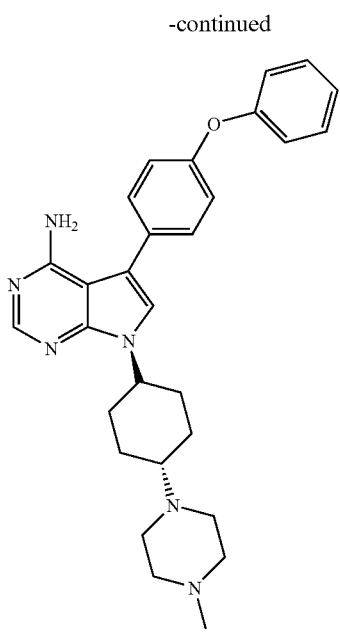

The results of the x-ray crystal structure determination for SEQ ID NO 2, the catalytic domain of human Tie-2, showed the following features:

The overall structure adopted a recognizable kinase fold with an N-terminal lobe and a somewhat larger C-terminal lobe. ATP binding was at the interface of the two lobes with inhibitors also binding in this region. The major secondary structural elements of the N-terminal lobe were a five strand beta sheet and a long alpha helix. The C-terminal lobe was primarily a bundle of alpha helices with a short, two-strand beta sheet near the interface with the N-terminal lobe. FIG. 7 shows a prototypical receptor tyrosine kinase, insulin receptor kinase which highlights the structural features associated with known kinases. The structure of the catalytic domain of Tie-2, shown in FIG. 9 has similar features to this The hinge region connects the N-terminal and C-terminal lobes. The portion of the hinge which forms part of the ATP/inhibitor binding region presents several hydrogen bonding partners. The carbonyl oxygen atoms of E903, A905 and P906 and the backbone amide protons of A905, H907 and G908 were presented into the pocket. The sidechains of L900, I902, Y904 and A905 helped to define the size, shape and nature of the binding pocket.

The purine core binding region was the region where the N-terminal and C-terminal lobes of the protein cooperate to form a flat, predominantly hydrophobic binding region which is the traditional location for the purine ring of ATP in other kinase structures. The residues which contribute to this region included: I830, A853, V838, I886, L971 and A981. Sidechains of residues in the hinge region, I902, Y904 and A905 also contributed hydrophobic character to this region. The carbonyl oxygen of I830 and the amide proton of V838 also presented an interaction site within this region.

By analogy to known kinase structures, the ribose ring of ATP would traditionally occupy an area between G831 in the N-terminal lobe and N909 in the C-terminal lobe called the extended sugar pocket. The backbone amide protons of G831, E832 and N909, the carbonyl oxygen of R968 and the sidechains of E832, N909 and D912 presented hydrogen bond partners.

By analogy to known kinase structures, the γ-phosphate of ATP would occupy an area around the sidechains of residues D964 (N964 in the catalytically inactive mutant, (SEQ ID NO 2). The sidechain of R968 also contributes to this region. The predominant available interaction type was hydrogen bonding, with quite complex coordination possible.

The nucleotide binding loop, or glycine-rich loop, was a flap like loop in the N-terminal lobe which covered the front portion of the ATP binding region. Residues not already described in other binding areas include D828, V829, G833, N834, F835, G836, Q837, L839, and K840. Residues I830, G831, E832 and V838 were also part of this structural element, but have already been included in other binding regions described above. This loop is usually considered to be very flexible and is capable of altering the shape and size of the ATP binding region. Carbonyl oxygen atoms, N834 sidechain atoms and backbone amide protons of G833, N834 and F835 were potentially available for hydrogen bonding. The sidechain atoms of D828 and K840 were available for ionic/hydrogen bonding interactions. The sidechain atoms of V829, I830, F835 and L839 can contribute to hydrophobic interactions.

The early activation loop was a long flexible loop containing at least one residue, the phosphorylation of which, is generally believed to determine the activation state of the protein. The loop begins in the ATP binding site and ends in the C-terminal lobe in the area which most likely corresponds to substrate binding. Residues F983, G984, and L985 form part of the ATP binding site and were also on the N-terminal side of the activation loop. The carboxyl oxygen and amide protons of F983 and G984 and the amide proton of L985 were available for hydrogen bonding and the sidechains of F983 and L985 can contribute to hydrophobic interactions.

K855, by homology to known kinases, is part of the catalytic mechanism of the kinase. The amino group can participate in ionic or hydrogen bond interactions and the methylene groups can contribute to hydrophobic interactions. The sidechain is very mobile.

The distal hydrophobic pocket is is characterized by a buried hydrophobic cavity. This portion of the ATP binding region is not occupied by any ATP atoms in known kinase structures. Residues which contribute to this pocket include L873, L876, L879, I885, L888, Y954, L955, F960 and I980. I886, A981 and F983 from regions already described also contribute hydrophobic interactions to this region. In addition, there was a number of backbone hydrogen bond partners available in this area. These partners included the carbonyl oxygen atoms of I886, L879, and G880. With the apparent disruption of the alpha-C helix, carbonyl oxygen atoms of E872, L873 and L876 may also be available. The backbone amide proton of residues, I886 and L888 were also available in this region.

Several residues contributed to the ATP/inhibitor binding site but do not seem to be part of definable subregion. These residues are I854, E872, N887, I970 and I980. E872 often forms an ionic interaction with the catalytic lysine in known kinase structures. N887 may contribute to the distal hydrophobic pocket. The sidechains of I854, and I970 face away from the ATP pocket, however carbonyl oxygen atoms from these residues as well as I980 were presented towards the binding region.

The structure of the SEQ ID NO 2/inhibitor I complex had the following features:

Final resolution of the structure was 2.8 Å in space group C2221, with final coordinates determined for backbone atoms of residues 818-857, 864-995, 1001-1116.

The pyrrolopyrimidine ring of inhibitor I formed hydrogen bonds to residues in the hinge region and interacts with purine core region. The core of the inhibitor presented a hydrogen bond donor in the form of the amino proton of the 4-NH$_2$ substituent to the carbonyl oxygen of E903. Atom N3 of the pyrimidine ring accepted a hydrogen bond from the backbone N—H of A905. The ring system of the core presented a planar face to residues of both the C-terminal and N-terminal lobes. The residues in these areas present a hydrophobic surface which "sandwiches" the planar core of the inhibitor. Residues involved in this hydrophobic sandwich region include I830, V838, I86, I902 and L971. Atoms N1 and N7 of the inhibitor core faced the solvent exposed mouth of the binding pocket. Atom C6 of the inhibitor faced the long axis of the nucleotide binding loop of the N-terminal lobe of the protein.

The N7 cyclopentane ring of Inhibitor I was directed towards solvent but was still within the protein cavity. This region was described above as the extended sugar pocket. This region was characterized by hydrophobic interactions with primarily I830 and L971. Methylene groups of E832 may also contribute in this fashion.

The phenyl ring attached to C5 of the pyrrolopyrimidine ring was in a predominantly hydrophobic area, generated by residues from the purine core region, the distal hydrophobic pocket and methylene groups from the catalytic lysine, K855. The hydrophobic contacts were with residues V838, I886, I902, L971 and A981. Lysine 855 was highly mobile, so it is also possible that the chlorine atom meta to the pyrrolopyrimidine ring was receiving a hydrogen bond.

The sulfonamide linker made a clear hydrogen bond with an amide proton of D982 and may also make a hydrogen bond to the amide proton of F983.

The terminal phenyl ring was located in the distal hydrophobic pocket. Primary contacts were with L876, I886, L888 and F983.

The structure of the SEQ ID NO 2/inhibitor II, SEQ ID NO 2/inhibitor III and SEQ ID NO 2/inhibitor IV complexes had the following features:

Residues 818-857, 864-995, 1001-1116 have been modeled into the solved structure. A space group P42212 was observed. The overall fold is still a standard kinase catalytic domain fold and the binding regions described above for SEQ ID NO 2/inhibitor I still pertain.

The pyrrolopyrimidine core, B-ring, linker and C-ring of inhibitor II in the SEQ ID NO 2/inhibitor II complex was bound the same way as inhibitor I. In addition, the N-7 cyclohexyl N-methyl piperazinyl group occupied the extended sugar pocket and made a strong ionic interaction with D912.

The pyrrolopyrimidine of inhibitor III binds was bound the same way in the SEQ ID NO 2/inhibitor III complex as inhibitor I. The N-7 cyclohexyl N-methy piperazinyl group occupied the extended sugar pocket and made a strong ionic interaction with D912 as in the SEQ ID NO 2/inhibitor II complex. The B-ring was bound in a similar fashion to inhibitor I, however, the hydrogen bond between halogens, fluorine in this case, and K855 was more clear. The sulfonyl oxygens of the sulfonamide linker made two clear hydrogen bonds to backbone amide protons of D983 and F983. The C-ring occupied the distal hydrophobic pocket with main interactions coming from L876, I886, L888, L900, I902 and F983.

The pyrrolopyrimidine core of inhibitor IV in the SEQ ID NO 2/inhibitor IV complex was bound the same way as inhibitor I. The N-7 cyclohexyl N-methyl piperazinyl group occupies the extended sugar pocket and makes a strong ionic interaction with D912 as in SEQ ID NO 2/inhibitor II. The B-ring binds in a similar fashion to inhibitor I, however there is no halogen atom to act as a potential hydrogen bond partner in inhibitor IV. The oxygen atom of the linker accepted a hydrogen bond from the catalytic lysine, K855. The C-ring of inhibitor IV occupied the distal hydrophobic pocket with main interactions coming from L876, I886, I902 and F983.

Analysis of the three dimensional structure of the Tie-2 catalytic domain has indicated the presence of a number of subsites, each of which includes molecular functional groups capable of interacting with complementary moieties of an inhibitor. Subsites 1 through 9 of the Tie-2 catalytic domain are defined below. A summary of the properties of the chemical moieties present at each subsite is given below. Subsites are characterized below according to the properties of chemical moieties with which they are complementary, or with which they can interact. Such moieties can include hydrogen bond acceptors, such as hydroxyl, amino, ether, thioether, carboxyl, P=O, and carbonyl groups, halogen atoms, such as fluorine, chlorine, bromine and iodine atoms; and other groups including a heteroatom having at least one lone pair of electrons, such as groups containing trivalent phosphorous, di- and tetravalent sulfur, oxygen and nitrogen atoms; hydrogen bond donors, such as hydroxyl, thiol, an amide proton, amine protons, carboxylic acid groups and any of the groups listed under hydrogen atom acceptors to which a hydrogen atom is bonded; hydrophobic groups, such as linear, branched or cyclic alkyl, ether or thioalkyl groups; linear, branched or cyclic alkenyl groups; linear, branched or cyclic alkynyl groups; aryl groups, such as mono- and polycyclic aromatic hydrocarbyl groups and mono- and polycyclic heterocyclic or heteroaryl groups; positively charged groups, such as primary, secondary, tertiary and quaternary ammonium groups, imidazolium and other protonated heteroalkyl and heteroaryl moieties, substituted and unsubstituted guanidinium groups, sulfonium groups and phosphonium groups; and negatively charged groups, such as carboxylate, phenolate, thiolate, sulfonamide, sulfamate, boronate, vanadate, sulfonate, sulfinate, phosphinate, tetrazolate and other heteroaryl anions, heterocyclic N-oxides, and phosphonate groups. A given chemical moiety can contain one or more of these groups.

Subsite 1: Hinge Region

Hydrogen Acceptors: The the backbone carbonyl oxygen of residues E903, A905 and P906 present proton acceptors.

Hydrogen Donors: The backbone amide protons of residues A905, H907 and G908 present proton donors.

Hydrophobic Groups: The sidechains of L900, I902, Y904 and A905 present hydrophobic groups.

Subsite 2: The Purine Core Binding Region

Hydrophobic Groups: Residues I830, A853, V838, I886, L971, A981 and the sidechains of residues I902, Y904, and A905 present hydrophobic groups.

Hydrogen Acceptors: The carbonyl oxygen of I830 presents a proton acceptor.

Hydrogen Donors: The amide proton of V838 presents a proton donor.

Subsite 3: The Extended Sugar Pocket

Hydrogen Acceptors: The backbone carbonyl oxygen of R968 and the sidechain carbonyl oxygen of E832, N909 and D912 present proton acceptors.

Hydrogen Donors: The backbone amide protons of G831, E832 and N909 present proton donors.

Subsite 4: The Extended γ-Phosphate Region
Hydrogen Bonding Groups: Residues D964 (N964 in the catalytically inactive mutant), N969 and D982 present both proton donor and proton acceptor groups.

Subsite 5: The Nucleotide binding Loop
Hydrogen Acceptors: The carbonyl oxygen of the sidechain of residue N834 presents a proton acceptor.
Hydrogen Donors: The backbone amide protons of residues G833, N834 and F835 present proton donors.
Positively Charged Group: The sidechain of K840 presents a positively charged site.
Negatively Charged Group: The sidechain of D828 presents a negatively charged site.
Hydrophobic Groups: The sidechains of V829, I830, F835 and L839 present hydrophobic groups.

Subsite 6: The Early Activation Loop
Hydrogen Acceptors: The backbone carbonyl oxygens of residues F983 and G984 presents a proton acceptor.
Hydrogen Donors: The backbone amide protons of residues F983, G984 and L985 present proton donors.
Hydrophobic Groups: The sidechains of F983 and L985 present hydrophobic groups.

Subsite 7: The Catalytic Lysine
Positively Charged Group: The sidechain of K855 presents a positively charged site.
Hydrophobic Group: The methylene groups of the sidechain of K855 presents a hydrophobic group.

Subsite 8: The Distal Hydrophobic Pocket
Hydrophobic Groups: Residues L873, L876, L879, I885, L888, Y954, L955, F960, I980, I886, A981 and F983 present hydrophobic groups.
Hydrogen Acceptors: The backbone carbonyl oxygens of residues I886, L879, G880, E872, L873 and L876 present proton acceptors.
Hydrogen Donors: The backbone amide protons of residues I886 and L888 present proton donors.

Subsite 9: Miscellaneous interaction sites which contribute to the ATP binding site.
Hydrogen Acceptors: The backbone carbonyl oxygens of residues I854, I970 and I980 present proton acceptors in the ATP binding region.
Negatively Charged Groups: E872 presents a negatively charged group which often forms an ionic bond with the catalytic lysine residue K855.

Figure 9:
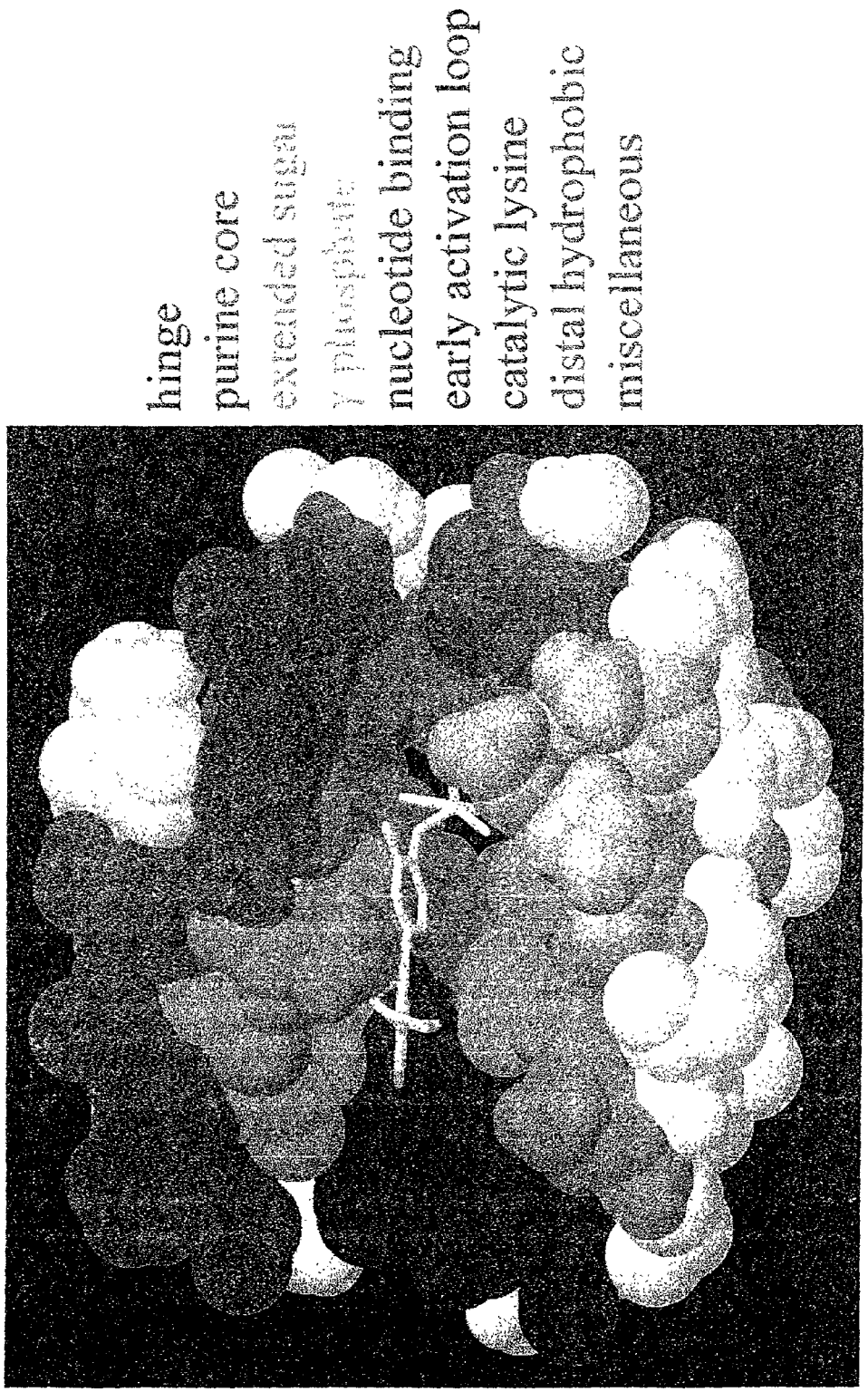
FIG. 9 shows a model of the catalytic domain of Tie-2 bound to inhibitor I. Subsites are shown in different colors.

FIG. 9 provides a model of the catalytic domain of Tie-2 bound to inhibitor I. Subsites 1-9 of the catalytic domain are each depicted in a different color as follows: the hinge region (dark blue), the purine core (light blue), the extended sugar pocket (light purple), the γ-phosphate region (dark yellow), the nucleotide binding loop (red), the early activation loop (dark green), the catalytic lysine (light green), the distal hydrophobic pocket (dark purple), and miscellaneous interaction sites (brown). The inhibitor is depicted in light yellow.

In one embodiment, the present invention provides polypeptides comprising the catalytic domain of Tie-2, crystalline forms of these polypeptides, optionally complexed with a ligand, and the three dimensional structure of the polypeptides, including the three dimensional structure of the Tie-2 catalytic domain. In general, these three dimensional structures are defined by atomic coordinates derived from x-ray crystallographic studies of the polypeptides. The catalytic domain can be unphosphorylated, monophosphorylated or multiply phosphorylated. Phosphorylization typically occurs at tyrosine residues. One monophosphorylated species has a phosphate group on Y897 or Y899.

The polypeptides can include the catalytic domain of Tie-2 from any species, such as a yeast or other unicellular organism, an invertebrate or a vertebrate. Preferably, the polypeptide includes the catalytic domain of a mammalian Tie-2, such as murine Tie-2. More preferably, the polypeptide includes the catalytic domain of human Tie-2. The polypeptides of the invention also includes polypeptides comprising single nucleotide polymorphisms of the catalytic domain of human Tie-2 or murine Tie-2. In one embodiment, the polypeptides of the invention, and crystalline forms thereof, include a sequence which has at least 80% identity to the catalytic domain of human Tie-2 or murine Tie-2.

To determine the percent identity of two amino acid sequences, the sequences are aligned for optimal comparison purposes (e.g., gaps can be introduced in one or both of a first and a second amino acid or nucleic acid sequence for optimal alignment, and non-homologous (dissimilar) sequences can be disregarded for comparison purposes). In a preferred embodiment, the length of a first sequence aligned for comparison purposes is at least 30%, preferably at least 40%, more preferably at least 50%, even more preferably at least 60%, and even more preferably at least 70%, 80%, or 90% of the length of the second sequence. The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient homology so as to perform one or more of the same functions performed by Tie-2 polypeptides described herein by amino acid sequence. Homology for a polypeptide is determined by conservative amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, for example, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg or replacements among the aromatic residues Phe, Tyr and Trp. Guidance concerning which amino acid changes are likely to be phenotypically silent is found in Bowie et al., *Science* 247:1306-1310 (1990).

The comparison of sequences and determination of percent identity and homology between two sequences can be accomplished using a mathematical agorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereaux, J. eds., M. Stockton Press, New York, 1991). In a preferred embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossom 62 matrix or a PAM250 matrix, and a gap weight of, for example, 16, 14, 12, 10, 8, 6, or 4 and a length weight of, for example, 1, 2, 3, 4, 5, or 6. In yet another preferred embodiment, the percent identity between two nucleotide sequences is determined using the GAP program in the GCG software package (Devereaux, J., et al., *Nucleic Acids Res.* 12(1):387 (1984)), using a NWSgapdna.CMP matrix and a gap weight of, for example, 40, 50, 60, 70, or 80 and a length weight of, for example, 1, 2, 3, 4, 5, or 6. In another embodiment, the percent identity between two amino acid or nucleotide sequences is determined using the algorithm of E. Meyers and W. Miller (*CABIOS,* 4:11-17 (1989)) which has been incorporated into the ALIGN program (version 2.0), using, for example, a PAM120 weight residue table, a gap length penalty of 12 and a gap penalty of 4.

The protein sequences of the present invention, for example, amino acids 802-1124 of human Tie-2 (SEQ ID NO 1), can further be used as a "query sequence" to perform a search against databases to, for example, identify other family members or related sequences. Such searches can be performed using the NBLAST and XBLAST programs (version 2.0) of Altschul, et al. (*J. Mol. Biol.* 215:403-10 (1990)). BLAST protein searches can be performed with the XBLAST program, for example, score=50, word length=3, to obtain amino acid sequences homologous to the proteins of the invention. To obtain gapped alignments for comparison purposes, gapped BLAST can be utilized as described in Altshul et al., (*Nucleic Acids Res.* 25(17):3389-3402 (1997)). When utilizing BLAST and gapped BLAST programs, the default parameters of the respective programs (e.g., XBLAST and NBLAST ) can be used as given on Mar. 29, 2000.

Homology for amino acid sequences can be defined in terms of the parameters set by the Advanced Blast search available from NCBI (the National Center for Biotechnology Information. These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found in Altschul, S. F. et al., *Nucleic Acids Res.* 25:3389-3402 (1997).

In one embodiment, the polypeptide includes amino acids 802 to 1124 of SEQ ID NO: 1. Polypeptides can also have amino acids 792 to 1124, 782 to 1124, 772 to 1124, 812 to 1124, 822 to 1124, 832 to 1124, 802 to 1114, 802 to 1104, or 802 to 1094 of SEQ ID NO 1. In another embodiment, the polypeptide can be a catalytically inactive mutant of Tie-2, such as SEQ ID NO 2, wherein the asparagine amino acid at 964 is replaced with an aspartic acid amino acid (designated D964N mutant). Other catalytically inactive mutants include substitution of the asparagine amino acid at 964 with alanine, serine, threonine, or glycine.

In another embodiment, the catalytic domain which is crystallized can have deletions of amino acids from the native sequence. For example, a polypeptide which is suitable for crystallization can include amino acids 802 to 918 of SEQ ID NO 1 fused to amino acids 934 to 1124 of SEQ ID NO 1 or other related "kinase-insert domain" deletions.

The crystalline polypeptide, preferably, further includes a ligand bound to the Tie-2 catalytic domain. The ligand is, preferably, a small (less than about 1500 molecular weight) organic molecule, for example, inhibitor I, II, III, or IV.

In one embodiment, the invention relates to a method of determining the three dimensional structure of a first polypeptide comprising the catalytic domain of a Tie-2 protein. The method includes the steps of (1) obtaining a crystal comprising the first polypeptide; (2) obtaining x-ray diffraction data for said crystal; and (3) using the x-ray diffraction data and the atomic coordinates of a second polypeptide comprising the catalytic domain of a Tie-2 protein to solve the crystal structure of the first polypeptide, thereby determining the three dimensional structure of the first polypeptide. The second polypeptide can include the same Tie-2 catalytic domain as the first polypeptide, or a different Tie-2 catalytic domain. Either or both of the first and second polypeptides can, optionally, be complexed with a ligand. That is, the crystal of the first polypeptide can comprise a complex of the first polypeptide with a ligand. The atomic coordinates of the second polypeptide can, optionally, include the atomic coordinates of a ligand molecule bound to the second polypeptide. The atomic coordinates of the second polypeptide, generally, have been previously obtained, for example, by x-ray crystallographic analysis of a crystal comprising the second polypeptide or a complex of the second polypeptide with a ligand. The atomic coordinates of the second polypeptide can be used to solve the crystal structure using methods known in the art, for example, molecular replacement or isomorphous replacement. Preferably, the second polypeptide comprises the catalytic domain of a mammalin Tie-2, more preferably, human Tie-2. For example the atomic coordinates which can be used include the atomic coordinates presented herein, preferably the atomic coordinates presented in FIGS. 3-7.

The invention also provides a method of identifying a compound which is a potential inhibitor of Tie-2. The method comprises the steps of (1) obtaining a crystal of a polypeptide comprising the catalytic domain of Tie-2; (2) obtaining the atomic coordinates of the polypeptide by x-ray diffraction studies using said crystal; (3) using said atomic coordinates to define the catalytic domain of Tie-2; and (4) identifying a compound which fits the catalytic domain. The method can further include the steps of obtaining, for example, from a compound library, or synthesizing the compound identified in step 4, and assessing the ability of the identified compound to inhibit Tie-2 enzymatic activity.

The polypeptide preferably comprises the catalytic domain of a mammalian Tie-2. More preferably the polypeptide comprises the catalytic domain of human Tie-2. In a preferred embodiment, the polypeptide is a polypeptide of the present invention, as described above.

The polypeptide can be crystallized using methods known in the art, such as the methods described in the Examples, to afford polypeptide crystals which are suitable for x-ray diffraction studies. A crystalline polypeptide/ligand complex can be produced by soaking the resulting crystalline polypeptide in a solution including the ligand. Preferably, the ligand solution is in a solvent in which the polypeptide is insoluble.

The atomic coordinates of the polypeptide (and ligand) can be determined, for example, by x-ray crystallography using methods known in the art. The data obtained from the crystallography can be used to generate atomic coordinates, for example, of the atoms of the polypeptide and ligand, if present. As is known in the art, solution and refinement of the x-ray crystal structure can result in the determination of coordinates for some or all of the non-hydrogen atoms. The atomic coordinates can be used, as is known in the art, to generate a three-dimensional structure of the Tie-2 catalytic domain. This structure can then be used to assess the ability of any given compound, preferably using computer-based methods, to fit into the catalytic domain.

A compound fits into the catalytic domain if it is of a suitable size and shape to physically reside in the catalytic domain, that is, if it has a shape which is complementary to the catalytic domain and can reside in the catalytic domain without significant unfavorable steric or van der Waals interactions. Preferably, the compound includes one or more functional groups and/or moieties which interact with one or more subsites within the catalytic domain. Computational methods for evaluating the ability of a compound to fit into the catalytic domain, as defined by the atomic coordinates of the polypeptide, are known in the art, and representative examples are provided below.

In another embodiment, the method of identifying a potential inhibitor of Tie-2 comprises the step of determining the ability of one or more functional groups and/or moieties of the compound, when present in the Tie-2 catalytic domain, to interact with one or more subsites of the Tie-2 catalytic domain. Preferably, the Tie-2 catalytic domain is defined by the atomic coordinates of a polypeptide comprising the Tie-2 catalytic domain. If the compound is able to interact with a preselected number or set of subsites, the compound is identified as a potential inhibitor of Tie-2.

A functional group or moiety of the compound is said to "interact" with a subsite of the Tie-2 catalytic domain if it participates in an energetically favorable, or stabilizing, interaction with one or more complementary moieties within the subsite. Two chemical moieties are "complementary" if they are capable, when suitably positioned, of participating in an attractive, or stabilizing, interaction, such as an electrostatic or van der Waals interaction. Typically, the attractive interaction is an ion-ion (or salt bridge), ion-dipole, dipole-dipole, hydrogen bond, pi-pi or hydrophobic interaction. For example, a negatively charged moiety and a positively charged moiety are complementary because, if suitably positioned, they can form a salt bridge. Likewise, a hydrogen bond donor and a hydrogen bond acceptor are complementary if suitably positioned.

Typically, an assessment of interactions between the test compound and the Tie-2 catalytic domain may employ computer-based computational methods, such as those known in the art, in which possible interactions of a compound with the protein, as defined by atomic coordinates, are evaluated with respect to interaction strength by calculating the interaction energy upon binding the compound to the protein. Compounds which have calculated interaction energies within a preselected range or which otherwise, in the opinion of the computational chemist employing the method, have the greatest potential as Tie-2 inhibitors, can then be provided, for example, from a compound library or via synthesis, and assayed for the ability to inhibit Tie-2. The interaction energy for a given compound generally depends upon the ability of the compound to interact with one or more subsites within the protein catalytic domain.

In one embodiment, the atomic coordinates used in the method are the atomic coordinates set forth in FIGS. 3A-3OO, 4A-4OO, 5A-5RR and 6A-6NN. It is to be understood that the coordinates set forth in FIGS. 3-6 can be transformed, for example, into a different coordinate system, in ways known to those skilled in the art without substantially changing the three dimensional structure represented thereby.

In certain cases, a moiety of the compound can interact with a subsite via two or more individual interactions. A moiety of the compound and a subsite can interact if they have complementary properties and are positioned in sufficient proximity and in a suitable orientation for a stabilizing interaction to occur. The possible range of distances for the moiety of the compound and the subsite depends upon the distance dependence of the interaction, as is known in the art. For example, a hydrogen bond typically occurs when a hydrogen bond donor atom, which bears a hydrogen atom, and a hydrogen bond acceptor atom are separated by about 2.5 Å and about 3.5 Å. Hydrogen bonds are well known in the art (Pimentel et al., *The Hydrogen Bond,* San Francisco: Freeman (1960)). Generally, the overall interaction, or binding, between the compound and the Tie-2 catalytic domain will depend upon the number and strength of these individual interactions.

The ability of a test compound to interact with one or more subsites of the catalytic domain of Tie-2 can be determined by computationally evaluating interactions between functional groups, or moieties, of the test compound and one or more amino acid side chains in a particular protein subsite, such as subsites 1 to 9 above. Typically, a compound which is capable of participating in stabilizing interactions with a preselected number of subsites, preferably without simultaneously participating in significant destabilizing interactions, is identified as a potential inhibitor of Tie-2. Such a compound will interact with one or more subsites, preferably with two or more subsites and, more preferably, with three or more subsites.

The invention further provides a method of designing a compound which is a potential inhibitor of Tie-2. The method includes the steps of (1) identifying one or more functional groups capable of interacting with one or more subsites of the Tie-2 catalytic domain; and (2) identifying a scaffold which presents the functional group or functional groups identified in step 1 in a suitable orientation for interacting with one or more subsites of the Tie-2 catalytic domain. The compound which results from attachment of the identified functional groups or moieties to the identified scaffold is a potential inhibitor of Tie-2. The Tie-2 catalytic domain is, generally, defined by the conserved homolohous sequence when compared to other known tyrosine kinases, for example, the atomic coordinates set forth in FIGS. 3A-3OO, 4A-4OO, 5A-5RR and 6A-6NN.

Suitable methods, as are known in the art, can be used to identify chemical moieties, fragments or functional groups which are capable of interacting favorably with a particular subsite or set of subsites. These methods include, but are not limited to: interactive molecular graphics; molecular mechanics; conformational analysis; energy evaluation; docking; database searching; pharmacophore modeling; de novo design and property estimation. These methods can also be employed to assemble chemical moieties, fragments or functional groups into a single inhibitor molecule. These same methods can also be used to determine whether a given chemical moiety, fragment or functional group is able to interact favorably with a particular subsite or set of subsites.

In one embodiment, the design of potential human Tie-2 inhibitors begins from the general perspective of three-dimensional shape and electrostatic complementarity for the catalytic domain, encompassing subsites 1-9, and subsequently, interactive molecular modeling techniques can be applied by one skilled in the art to visually inspect the quality of the fit of a candidate inhibitor modeled into the binding site. Suitable visualization programs include INSIGHTII (Molecular Simulations Inc., San Diego, Calif.), QUANTA (Molecular Simulations Inc., San Diego, Calif.), SYBYL (Tripos Inc., St Louis, Mo.), RASMOL (Roger Sayle et al., *Trends Biochem. Sci.* 20: 374-376 (1995)), GRASP (Nicholls et al., *Proteins* 11: 281-289 (1991)), and MIDAS (Ferrin et al., *J. Mol. Graphics* 6:13-27 (1988)).

A further embodiment of the present invention utilizes a database searching program which is capable of scanning a database of small molecules of known three-dimensional structure for candidates which fit into the target protein site. Suitable software programs include CATALYST (Molecular Simulations Inc., San Diego, Calif.), UNITY (Tripos Inc., St Louis, Mo.), FLEXX (Rarey et al., *J. Mol. Biol.* 261: 470-489 (1996)), CHEM-3DBS (Oxford Molecular Group, Oxford, UK), DOCK (Kuntz et al., *J. Mol. Biol* 161: 269-288 (1982)), and MACCS-3D (MDL Information Systems Inc., San Leandro, Calif.). It is not expected that the molecules found in the search will necessarily be leads themselves, since a complete evaluation of all interactions will necessarily be made during the initial search. Rather, it is anticipated that such candidates might act as the framework for further design, providing molecular skeletons to which appropriate atomic replacements can be made. Of course, the chemical complimentary of these molecules can be evaluated, but it is expected that the scaffold, functional groups, linkers and/or monomers may be changed to maximize the electrostatic, hydrogen bonding, and hydrophobic interactions with the enzyme. Goodford (Goodford *J Med Chem* 28:849-857 (1985)) has produced a computer program, GRID, which seeks to determine regions of high affinity for different chemical groups (termed probes) on the molecular surface of the binding site. GRID hence provides a tool for suggesting modifications to known ligands that might enhance binding.

A range of factors, including electrostatic interactions, hydrogen bonding, hydrophobic interactions, desolvation effects, conformational strain or mobility, chelation and cooperative interaction and motions of ligand and enzyme, all influence the binding effect and should be taken into account in attempts to design bioactive inhibitors.

Yet another embodiment of a computer-assisted molecular design method for identifying inhibitors comprises searching for fragments which fit into a binding region subsite and link to a predefined scaffold. The scaffold itself may be identified in such a manner. Programs suitable for the searching of such functional groups and monomers include LUDI (Boehm, *J. Comp. Aid. Mol. Des.* 6:61-78 (1992)), CAVEAT (Bartlett et al. in "Molecular Recognition in Chemical and Biological Problems", special publication of *The Royal Chem. Soc.*, 78:182-196 (1989)) and MCSS (Miranker et al. *Proteins* 11: 29-34 (1991)).

Yet another embodiment of a computer-assisted molecular design method for identifying inhibitors of the subject phosphatase comprises the de novo synthesis of potential inhibitors by algorithmic connection of small molecular fragments that will exhibit the desired structural and electrostatic complementarity with the active site of the enzyme. The methodology employs a large template set of small molecules with are iteratively pieced together in a model of the Tie-2 active site. Programs suitable for this task include GROW (Moon et al. *Proteins* 11:314-328 (1991)) and SPROUT (Gillet et al. *J Comp. Aid. Mol. Des.* 7:127 (1993)).

In yet another embodiment, the suitability of inhibitor candidates can be determined using an empirical scoring function, which can rank the binding affinities for a set of inhibitors. For an example of such a method see Muegge et al. and references therein (Muegge et al., *J Med. Chem.* 42:791-804 (1999)).

Other modeling techniques can be used in accordance with this invention, for example, those described by Cohen et al. (*J. Med. Chem.* 33: 883-894 (1994)); Navia et al. (*Current Opinions in Structural Biology* 2: 202-210 (1992)); Baldwin et al. (*J. Med. Chem.* 32: 2510-2513 (1989)); Appelt et al. (*J. Med. Chem.* 34: 1925-1934 (1991)); and Ealick et al. (*Proc. Nat. Acad. Sci. USA* 88: 11540-11544 (1991)).

A compound which is identified by one of the foregoing methods as a potential inhibitor of Tie-2 can then be obtained, for example, by synthesis or from a compound library, and assessed for the ability to inhibit Tie-2 in vitro. Such an in vitro assay can be performed as is known in the art, for example, by contacting Tie-2 in solution with the test compound in the presence of a substrate for Tie-2. The rate of substrate transformation can be determined in the presence of the test compound and compared with the rate in the absence of the test compound. Suitable assays for Tie-2 biological activity are described in Example 4.

An inhibitor identified or designed by a method of the present invention can be a competitive inhibitor, an uncompetitive inhibitor or a noncompetitive inhibitor. A "competitive" inhibitor is one that inhibits Tie-2 activity by binding fully or partially within the same region of Tie-2, as ATP, thereby directly competing with ATP for the active site of Tie-2. An "uncompetitive" inhibitor inhibits Tie-2 by binding to a different region of the enzyme than ATP. Such inhibitors bind to Tie-2 already bound with ATP and not to the free enzyme. A "non-competitive" inhibitor is one that can bind to either the free or ATP bound form of Tie-2. In some instances, an inhibitor may inhibit the enzymes catalytic activity by impeding the binding of multiple substrates (e.g., ATP and tyrosyl substrates). This may be accomplished by fully or partially occluding multiple substrate binding sites, or by occupying a site which allosterically or conformationally reduces affinities for substrates or blocks product release.

In another embodiment, the present invention provides Tie-2 inhibitors, and methods of use thereof, which are capable of binding to the catalytic domain of Tie-2, for example, compounds which are identified as inhibitors of at least one biological activity of Tie-2 or which are designed by the methods described above to inhibit at least one biological activity of Tie-2. For example, the invention includes compounds which interact with one or more, preferably two or more, and more preferably, three or more of Tie-2 subsites 1 to 9.

In one embodiment, the Tie-2 inhibitor of the invention comprises a moiety or moieties positioned to interact with subsite 1, subsite 2 and, optionally, with at least one other subsite, when present in the Tie-2 catalytic domain. For example, a functional group which can interact with subsite 1 can be a hydrogen bond donor, a hydrogen bond acceptor, or a hydrophobic moiety. A functional group which can interact with subsite 2 can be a hydrophobic group, hydrogen bond donor, or a hydrogen bond acceptor.

In another embodiment, the Tie-2 inhibitor of the invention comprises functional groups positioned to interact with subsites 1, 2 and 3, and, optionally, one or more additional subsites.

The Tie-2 inhibitors of the invention also include compounds having functional groups positioned to interact with subsite 1, subsite 2, subsite 8 and, optionally, one or more additional subsites. In another embodiment, the inhibitor has functional groups positioned to interact with subsite 1, subsite 2, subsite 3, subsite 8, and, optionally, one or more additional subsites.

In other embodiments, the Tie-2 inhibitors of the invention include compounds which have functional groups positioned to interact with the following groups of subsites, each of which can, optionally, include one or more additional subsites: subsites 1, 4, and 5; subsites 1, 2, 7 and 8; subsites 1, 2, 3, 7 and 8; subsites 1, 2, 3, 7 and 8; subsites 1, 2, 4, 6 and 8; subsites 1, 2, 3, 4, 6 and 8; subsites 1, 2, 3, 4, 6 and 8.

A moiety of the inhibitor compound is "positioned to interact" with a given subsite, if, when placed within the Tie-2 catalytic domain, as defined by the atomic coordinates presented in FIGS. 3-6, the moiety is proximal to, and oriented properly relative to, the appropriate amino acid side chains within the subsite.

As indicated in the description of the subsites above, several of subsites 1-9 can potentially interact with two or more types of moieties. For each of the subsites listed below the preferred type of interacting moiety possessed by the potential inhibitor is indicated.

Subsite 1: hydrogen bond donor (E903) and hydrogen bond acceptor (A905).
Subsite 2: hydrophobic, preferably aromatic, moiety (I830, V838, I886, I902 and L971).
Subsite 3: hydrophobic, preferably alkyl, moiety (I830 and L971) and a positively charged moiety (D912).
Subsite 4: hydrogen acceptor moiety (D982 and F938).
Subsite 8: hydrophobic, preferably aromatic, moiety (L876, I886, L888 and F983)

A preferred Tie-2 inhibitor of the invention inhibits Tie-2 enzymatic activity with a Ki of at least about 1 mM, preferably at least about 100 µM and more preferably at least about 10 µM. In another embodiment, a Tie-2 inhibitor binds selectively to a Tie-2 receptor over other tyrosine kinase receptors, such as insulin receptor or Csk, KDR, lck, or zap. In a preferred embodiment, the inhibitor has a $K_i$ 0.1 fold or less for a Tie-2 receptor than for an insulin receptor or Csk. In a more preferred embodiment, the inhibitor has $K_i$ 0.01 fold or less for a Tie-2 receptor than for an insulin receptor or Csk.

In a most preferred embodiment, the inhibitor has an $K_i$ 0.001 fold less or less for a Tie-2 receptor than for an insulin receptor or Csk.

In a preferred embodiment, the Tie-2 inhibitor of the invention comprises two or more of the following when present at, or bound to, the Tie-2 catalytic domain: (a) a hydrogen bond donor positioned to interact with Glu 903 of human Tie-2; (b) a hydrogen bond acceptor positioned to interact with Ala 905 of human Tie-2; (c) a hydrogen bond don or positioned to interact with Ala 905 of human Tie-2; (d) a hydrophobic moiety positioned to interact with one or more of Ile 830, Val 838, Ala 853, Ile 886, Ile 902, Tyr 904, Ala 905 and Leu 971 of human Tie-2; (e) a hydrogen bond donor or positively charged functional group positioned to interact with Asp 912 of human Tie-2; (f) a hydrogen bond donor or hydrogen bond acceptor postioned to interact with Asn 909 of human Tie-2; (g) a hydrophobic moiety positoned to interact with one or more of Val 838, Lys 855, Ile 886, Ile 902, Leu 971 and Ala 981 of human Tie-2; (h) a hydrogen bond acceptor or negatively charged functional group positioned to interact with Lys 855 of human Tie-2; (i) a hydrogen bond acceptor positioned to interact with Asp 982 of human Tie-2; (j) a hydrogen bond acceptor positioned to interact with Phe 983 of human Tie-2; (k) a hydrophobic moiety positioned to interact with one or more of Leu 873, Leu 876, Ile 885, Ile 886, Leu 888, Leu 900, Ile 902, Ala 981 and Phe 983 of human Tie-2; (l) a hydrogen bond donor or positively charged functional group positioned to interact with Asp 982 of human Tie-2; (m) a hydrogen bond donor positioned to interact with Ile 886 of human Tie-2; (n) a hydrogen bond donor positioned to interact with Leu 768 of human Tie-2; (o) a hydrogen bond acceptor positioned to interact with Gly 831 of human Tie-2; (p) a hydrogen bond donor or positively charged functional group positioned to interact with Glu 832 of human Tie-2; (q) a hydrogen bond acceptor or negatively charged functional group positioned to interact with Lys 840 of human Tie-2; (r) a hydrogen bond acceptor or negatively charged functional group positioned to interact with Lys 916 of human Tie-2; (s) a hydrogen bond acceptor or negatively charged functional group positioned to interact with Arg 968 of human Tie-2; (t) a hydrogen bond donor positioned to interact with Arg 968 of human Tie-2.

In preferred embodiments, the Tie-2 inhibitors of the invention comprise (b) and (d); (d) and at least one of (a), (b) and (c); (d) and at least two of (a), (b) and (c); (d) and 110 at least two of (a), (b) and (c), and at least one of (e) and (f); (d) and (g), and at least two of (a), (b) and (c); (d), (g), at least two of (a), (b) and (c) and at least one of (e) and (f); (d), (g), (k), and at least two of (a), (b) and (c); (d), (g), (k), at least one of (e) and (f), at least two of (a), (b), and (c); (d), at least one of (i) and (j) and at least two of (a), (b) and (c); (d) and at least two of (a), (b) and (c), at least one of (e) and (f), and at least one of (i) and (j); (d), (g),(k), at least one of (i) and (j), and at least two of (a), (b) and (c); and (d), (g), (k), at least one of (e) and (f), and at least two of (a), (b) and (c).

Preferred Tie-2 inhibitors of the invention comprise a molecular scaffold or framework, to which the moieties and/or functional groups which interact with the Tie-2 subsites are attached, either directly or via an intervening moiety. The scaffold can be, for example, a peptide or peptide mimetic backbone, a cyclic or polycyclic moiety, such as a monocyclic, bicyclic or tricyclic moiety, and can include one or more hydrocarbonyl or heterocyclic rings. The molecular scaffold presents the attached interacting moieties in the proper configuration or orientation for interaction with the appropriate residues of Tie-2.

Pyrrolopyrimidines, such as inhibitor, I, II, III or IV, are preferred Tie-2 inhibitors. Methods for synthesizing pyrrolopyrimidines are described in PCT application number WO99/21560, the teachings of which are incorporated herein by reference in their entirety. In one embodiment, the inhibitors of the invention do not include the pyrrolopyrimidines represented by structural formula V:

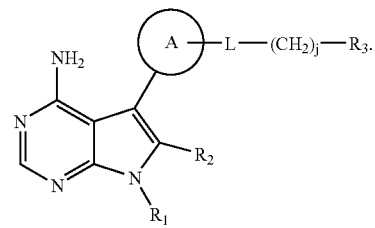

and pharmaceutically acceptable salts thereof, wherein: p1 Ring A is a six membered aromatic ring or a five or six membered heteroaromatic ring which is optionally substituted with one or more substituents selected from the group consisting of a substituted or unsubstituted aliphatic group, a halogen, a substituted or unsubstituted aromatic group, substituted or unsubstituted heteroaromatic group, substituted or unsubstituted cycloalkyl, substituted or unsubstituted heterocycloalkyl, substituted or unsubstituted aralkyl, substituted or unsubstituted heteroaralkyl, cyano, nitro, —NR$_4$R$_5$, —C(O)$_2$H, —OH, a substituted or unsubstituted alkoxycarbonyl, —C(O)$_2$-haloalkyl, a substituted or unsubstituted alkylthio ether, a substituted or unsubstituted alkylsulfoxide, a substituted or unsubstituted alkylsulfone, a substituted or unsubstituted arylthio ether, a substituted or unsubstituted arylsulfoxide, a substituted or unsubstituted arylsulfone, a substituted or unsubstituted alkyl carbonyl, —C(O)-haloalkyl, a substituted or unsubstituted aliphatic ether, a substituted or unsubstituted aromatic ether, carboxamido, tetrazolyl, trifluoromethylsulphonamido, trifluoromethylcarbonylamino, a substituted or unsubstituted alkynyl, a substituted or unsubstituted alkyl amido, a substituted or unsubstituted aryl amido, —NR$_{95}$C(O)R$_{95}$, a substituted or unsubstituted styryl and a substituted or unsubstituted aralkyl amido, wherein R$_{95}$ is an aliphatic group or an aromatic group;

L is —O—; —S—; —S(O)—; —S(O)$_2$—; —N(R)—; —N(C(O)OR)—; —N(C(O)R)—; —N(SO$_2$R); —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)—; —N(R)S(O)$_2$—; —OC(O)N(R)—; —N(R)C(O)N(R)—; —NRC(O)O—; —S(O)N(R)—; —S(O)$_2$N(R)—; N(C(O)R)S(O)—; N(C(O)R)S(O)$_2$—; —N(R)S(O)N(R)—; —N(R)S(O)$_2$N(R)—; —C(O)N(R)C(O)—; —S(O)N(R)C(O)—; —S(O)$_2$N(R)C(O)—; —OS(O)N(R)—; —OS(O)$_2$N(R)—; —N(R)S(O)O—; —N(R)S(O)$_2$O—; —N(R)S(O)C(O)—; —N(R)S(O)$_2$C(O)—; —SON(C(O)R)—; —SO$_2$N(C(O)R)—; —N(R)SON(R)—; —N(R)SO$_2$N(R)—; —C(O)O—; —N(R)P(OR')O—; —N(R)P(OR')-; —N(R)P(O)(OR')O—; —N(R)P(O)(OR')—; —N(C(O)R)P(OR')O—; —N(C(O)R)P(OR')—; —N(C(O)R)P(O)(OR')O— or —N(C(O)R)P(OR')—, wherein R and R' are each, independently, —H, an acyl group, a substituted or unsubstituted aliphatic group, a substituted or unsubstituted aromatic group, a substituted or unsubstituted heteroaromatic group, or a substituted or unsubstituted cycloalkyl group; or L is —R$_b$N(R)S(O)$_2$—, —R$_b$N(R)P(O)—, or —R$_b$N(R)P(O)O—, wherein R$_b$ is an alkylene group which when taken together with the sulphonamide, phosphinamide, or phosphonamide group to which it is bound forms a five or six membered ring fused to ring A; or L is represented by one of the following structural formulas:

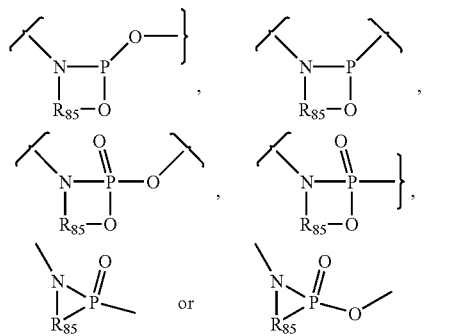

wherein R$_{85}$ taken together with the phosphinamide, or phophonamide is a 5-, 6-, or 7-membered, aromatic, heteroaromatic or heterocycloalkyl ring system;

R$_1$ is a substituted aliphatic group, a substituted cycloalkyl, a substituted bicycloalkyl, a substituted cycloalkenyl, an optionally substituted aromatic group, an optionally substituted heteroaromatic group, an optionally substituted heteroaralkyl, an optionally substituted heterocycloalkyl, an optionally substituted heterobicycloalkyl, an optionally substituted alkylamindo, and optionally substituted arylamido, an optionally substituted —S(O)$_2$-alkyl or optionally substituted —S(O)$_2$-cycloalkyl, a —C(O)-alkyl or an optionally substituted —C(O)-alkyl, provided that when R$_1$ is an aliphatic group or cycloalkyl group, R$_1$ is not exclusively substituted with one or more substitutent selected from the group consisting of hydroxyl and lower alkyl ethers, provided that the heterocycloalkyl is not 2-phenyl-1,3-dioxan-5-yl and provided that an aliphatic group is not substituted exclusively with one or more aliphatic groups, wherein one or more substituent is selected from the group consisting of a substituted or unsubstituted aliphatic group, a substituted or unsubstituted aromatic group, a substituted or unsubstituted heteroaromatic, a substituted or unsubstituted aralkyl, a substituted or unsubstituted heteroaralkyl, a substituted or unsubstituted cycloalkyl, a substituted or unsubstituted heterocycloalkyl, a substituted or unsubstituted aromatic ether, a substituted or unsubstituted aliphatic ether, a substituted or unsubstituted alkoxycarbonyl, a substituted or unsubstituted alkylcarbonyl, a substituted or unsubstituted arylcarbonyl, a substituted or unsubstituted heteroarylcarbonyl, substituted or unsubstituted aryloxycarbonyl, —OH, a substituted or unsubstituted aminocarbonyl, an oxime, a substituted or unsubstituted azabicycloalkyl, heterocycloalkyl, oxo, aldehyde, a substituted or unsubstituted alkyl sulfonamido group, a substituted or unsubstituted aryl sulfonamido group, a substituted or unsubstituted bicycloalkyl, a substituted or unsubstituted heterobicycloalkyl, cyano, —NH2, an alkylamino, ureido, thioureido and -B-E;

B is a substituted or unsubstituted cycloalkyl, a substituted or unsubstituted heterocycloalkyl, a substituted or unsubstituted aromatic, a substituted or unsubstituted heteroaromatic, an alkylene, an aminoalkyl, an alkylenecarbnonyl, or an aminoalkylcarbonyl;

E is a substituted or unsubstituted azacycloalkyl, a substituted or unsubstituted azacycloalkylcarbonyl, a substituted or unsubstituted azacycloalkylsulfonyl, a substituted or unsubstituted azacycloalkylalkyl, a substituted or unsubstituted heteroaryl, a substituted or unsubstituted heteroarylcarbonyl, a substituted or unsubstituted heteroarylsulfonyl, a substituted or unsubstituted heteroaralkyl, a substituted or unsubstituted alkyl sulfonamido, a substituted or unsubstituted aryl sulfonamido, a substituted or unsubstituted bicycloalkyl, a substituted or unsubstituted ureido, a substituted or unsubstituted thioureido or a substituted or unsubstituted aryl;

R$_2$ is —H, a substituted or unsubstituted aliphatic group, a substituted or unsubstituted cycloalkyl, a halogen, —OH, cyano, a substituted or unsubstituted aromatic group, a substituted or unsubstituted heteroaromatic group, a substituted or unsubstituted heterocycloalkyl, a substituted or unsubstituted aralkyl, a substituted or unsubstituted heteroaralkyl, —NR$_4$R$_5$, or —C(O)NR$_4$R$_5$;

R$_3$ is a substituted or unsubstituted aliphatic group, a substituted or unsubstituted alkenyl group, a substituted or unsubstituted cycloalkyl, a substituted or unsubstituted aromatic group, a substituted or unsubstituted heteroaromatic group, or a substituted or unsubstituted heterocycloalkyl;

provided that L is —SN(R)—, —S(O)N(R)—, —S(O)$_2$N (R)—, —N(R)S—, —N(R)S(O)—, —N(R)S(O)$_2$—, —N(R)SN(R')—, —N(R)S(O)N(R')—, or —N(R)S (O)$_2$N(R')— when R$_3$ is a substituted or unsubstituted aliphatic group, a substituted or unsubstituted alkenyl group;

provided that j is 0 when L is —O—, —CH$_2$NR—, —C(O)NR— or —NRC(O)— and R$_3$ is azacycloalkyl or azaheteroaryl; and provided that j is 0 when L is —O— and R$_3$ is phenyl;

R$_4$, R$_5$ and the nitrogen atom together form a 3, 4, 5, 6 or 7-membered, substituted or unsubstituted heterocycloalkyl, substituted or unsubstituted heterobicycloalkyl or a substituted or unsubstituted heteroaromatic; or R$_4$ and R$_5$ are each, independently, —H, azabicycloalkyl, heterocycloalkyl, a substituted or unsubstituted alkyl group or Y-Z;

Y is selected from the group consisting of —C(O)—, —(CH$_2$)$_p$—, —S(O)$_2$—, —C(O)O—, —SO$_2$NH—, —CONH—, (CH$_2$)$_p$O—, —(CH$_2$)$_p$NH—, —(CH$_2$)$_p$ S—, —(CH$_2$)$_p$S(0)—, and —(CH$_2$)$_p$S(O)$_2$—;

p is an integer from 0 to 6;

Z is —H, a substituted or unsubstituted alkyl, substituted or unsubstituted amino, substituted or unsubstituted aryl, substituted or unsubstituted heteroaryl or substituted or unsubstituted heterocycloalkyl group; and j an integer from 0 to 6.

As used herein, aromatic groups include carbocyclic ring systems (e.g. phenyl and cinnamyl) and fused polycyclic aromatic ring systems (e.g. naphthyl and 1,2,3,4-tetrahydronaphthyl). Arromatic groups are also referred to as aryl groups herein.

Heteroaromatic groups, as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring or heteroaryl ring is fused to one or more other heteroaryl rings (e.g., benzo(b)thienyl, benzimidazole, indole, tetrahydroindole, azaindole, indazole, quinoline, imidazopyridine, purine, pyrrolo[2,3-d]pyrimidine, pyrazolo[3,4-d]pyrimidine) and their N-oxides.

An aralkyl group, as used herein, is an aromatic substituent that is linked to a compound by an aliphatic group having from one to about six carbon atoms.

An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

An acyl group, as used herein, is an —C(O)NR$_x$R$_z$, —C(O)OR$_x$, —C(O)R$_x$, in which R$_x$ and R$_z$ are each, independently, —H, a substituted or unsubstituted aliphatic group or a substituted or unsubstituted aromatic group.

As used herein, aliphatic groups include straight chained, branched or cyclic C$_1$-C$_8$ hydrocarbons which are completely saturated or which contain one or more units of unsaturation. A "lower alkyl group" is a saturated aliphatic group having form 1-6 carbon atoms.

Inhibitor I bound to the catalytically inactive mutant of Tie-2 (see FIG. 2 for sequence and FIG. 3 for atomic coordinates) crystallized in the space group C2221. The x-ray crystallographic structure reveiled the following interactions:

The pyrrolopyrimidine ring of the inhibitor I forms hydrogen bonds to residues in the hinge region and interacts with purine core region. The core of the inhibitor presents a hydrogen bond donor in the form of the amino proton of the 4-NH$_2$ substituent to the carbonyl oxygen of E903. Atom N3 of the pyrimidine ring accepts a hydrogen bond from the backbone N—H of A905. The ring system of the core presents a planar face to residues of both the C-terminal and N-terminal lobes. The residues in these areas present a hydrophobic surface which "sandwiches" the planar core of the inhibitor. Residues involved in this hydrophobic sandwich region include I830, V838, I86, I902 and L971. Atoms N1 and N7 of the core face the solvent exposed mouth of the binding pocket. Atom C6 faces the long axis of the nucleotide binding loop of the N-terminal lobe of the protein.

The N7 cyclopentane ring is directed towards solvent but is still within the protein cavity. This region was described above as the extended sugar pocket after the binding mode of the ribose ring of ATP observed in other kinase structures. This region is characterized by hydrophobic interactions with primarily I830 and L971. Methylene groups of E832 may also contribute in this fashion.

The phenyl ring attached to C5 of the pyrrolopyrimidine ring is in a predominantly hydrophobic area, generated by residues from the purine core region, the distal hydrophobic pocket and methylene groups from the catalytic lysine, K855. The hydrophobic contacts are with residues V838, I886, I902, L971 and A981. Lysine 855 is highly mobile, so it is also possible that the Cl atom meta to the pyrrolopyrimidine ring is receiving a hydrogen bond.

The sulfonamide linker makes a clear hydrogen bond with an amide proton of D982 and may also make a hydrogen bond to the amide proton of F983.

The terminal phenyl ring (labelled ring C) is located in the distal hydrophobic pocket. Primary contacts are with L876, I886, L888 and F983.

Inhibitor II bound to the catalytically inactive mutant of Tie-2 (see FIG. 2 for sequence and FIG. 4 for atomic coordinates) crystallized in the space group P42212. The x-ray crystallographic structure reveiled the following additional interactions:

The pyrrolopyrimidine core, B-ring, linker and C-ring bind the same way as inhibitor I. The N-7 cyclohexyl N-methy piperazinyl group occupies the extended sugar pocket and makes a strong ionic interaction with D912.

Inhibitor III bound to the catalytically inactive mutant of Tie-2 (see FIG. 2 for sequence and FIG. 4 for atomic coordinates) crystallized in the space group P42212. The x-ray crystallographic structure reveiled the following additional interactions:

The pyrrolopyrimidine core binds the same way as inhibitor I. The N-7 cyclohexyl N-methy piperazinyl group occupies the extended sugar pocket and makes a strong ionic interaction with D912 as in Tie-2/inhibitor II. The B-ring binds in a similar fashion to inhibitor I, however, the hydrogen bond between a halogen, fluorine in this case, and K855 is more clear. The linker makes two clear hydrogen bonds to backbone amide protons of D983 and F983. The C-ring occupies the distal hydrophobic pocket with main interactions coming from L876, I886, L888, L900, I902 and F983.

Inhibitor IV bound to the catalytically inactive mutant of Tie-2 (see FIG. 2 for sequence and FIG. 4 for atomic coordinates) crystallized in the space group P42212. The x-ray crystallographic structure reveiled the following additional interactions:

The pyrrolopyrimidine core binds the same way as inhibitor I. The N-7 cyclohexyl N-methy piperazinyl group occupies the extended sugar pocket and makes a strong ionic interaction with D912 as in Tie-2/inhibitor II. The B-ring binds in a similar fashion to inhibitor I, however there is no chlorine atom to act as a potential hydrogen bond partner. The linker in this case is an oxygen atom which accepts a hydrogen bond from the catalytic lysine, K855. The C-ring occupies the distal hydrophobic pocket with main interactions coming from L876, I886, I902 and F983.

In one embodiment, the present invention relates to a method of treating a Tie-2-dependent condition in a patient. The method comprises the step of administering to the patient a therapeutically effective amount of a Tie-2 inhibitor as described above. The patient can be any animal, and is, preferably, a mammal and, more preferably, a human.

A "Tie-2-dependent condition" is a disease or medical condition in which the catalytic activity of Tie-2 plays a role, for example, in the development of the disease or condition. For example, in one embodiment, the condition is characterized by excessive vascular proliferation. Tie-2 inhibitors are useful in treating angiogenesis dependent disorders, and disorders involving aberrant endothilial-pereindothelial interactions (e.g., restenosis).

Tie-2 dependent conditions include hyperproliferative disorders, cancer, a cardiovascular condition, an ocular condition, von Hippel Lindau disease, pemphigoid, psoriasis, Paget's disease, polycystic kidney disease, fibrosis, sarcoidosis, cirrhosis, thyroiditis, Osler-Weber-Rendu disease, chronic inflammation, synovitis, inflammatory bowel disease, Crohn's disease, rheumatoid arthritis, osteoarthritis, psoriatic arthritis, an ulcer and sepsis. In addition a Tie-2 inhibitor can be used to decrease fertility in a patient.

Preferred methods of treatment are where the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, malignant ascites, Kaposi's sarcoma, Hodgkin's disease, lymphoma, myeloma or leukemia.

Another preferred method of treatment is where the cardiovascular condition, atherosclerosis, restenosis, ischemia/reperfusion injury, chronic occlusive pulmonary disease, vascular occlusion, carotid obstructive disease, Crow-Fukase (POEMS) syndrome, anemia, ischemia, infarct, vascular leakage disorders.

Yet another preferred method of treatment is where the ocular condition is ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration or microangiopathy.

A Tie-2 inhibitor can also be used in a method of promoting angiogenesis or vasculogenesis. In addition, a Tie-2 inhibitor can be administered with a pro-angiogenic growth factor.

A therapeutically effective amount, as this term is used herein, is an amount which results in partial or complete inhibition of disease progression or symptoms. Such an amount will depend, for example, on the size and gender of the patient, the condition to be treated, the severity of the symptoms and the result sought, and can be determined by one skilled in the art.

The compound of the invention can, optionally, be administered in combination with one or more additional drugs or therapies which, for example, are known for treating and/or alleviating symptoms of the condition mediated by Tie-2. The additional drug can be administered simultaneously with the compound of the invention, or sequentially. For example, the Tie-2 inhibitor can be administered in combination with another anticancer agent, as is known in the art. Additional therapies which may be coadministered would include, for example, radiation therapy, ultraviolet irradiation, hyperthermia, laser irradiation, targeted radionuclides and neutron bombardment.

The invention further provides pharmaceutical compositions comprising one or more of the Tie-2 inhibitors described above. Such compositions comprise a therapeutically (or prophylactically) effective amount of one or more Tie-2 binding inhibitors, as described above, and a pharmaceutically acceptable carrier or excipient. Suitable pharmaceutically acceptable carriers include, but are not limited to, saline, buffered saline, dextrose, water, glycerol, ethanol, and combinations thereof. The carrier and composition can be sterile. The formulation should suit the mode of administration.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, cyclodextrin, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrrolidinone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

The pharmaceutical compositions of the invention can also include an agent which controls release of the Tie-2 inhibitor compound, thereby providing a timed or sustained release composition.

The Tie-2 inhibitor can be administered subcutaneously, intravenously, parenterally, intraperitoneally, intradermally, intramuscularly, intraocularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal, ocular mucosa, intestinal mucosa, bronchial mucosa) administration, nose drops, aerosols, inhalants, nebulizers, eye drops or suppositories can be used. The compounds and agents of this invention can be administered together with other biologically active agents, such as analgesics, anti-inflammatory agents, anesthetics and other agents which can control one or more symptoms or causes of a Tie-2 dependent condition.

In a specific embodiment, it may be desirable to administer the agents of the invention locally to a localized area in need of treatment; this may be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints.

EXAMPLES

Example 1

Protein Purification $(His)_6$Tie-2802-1124, D964N, which contains a TEV protease cleavage peptide, was expressed recombinantly by baculovirus infection of SF-9 cells. Cells were lysed in a buffer containing 20 mM Tris pH 8.0, 137 mM NaCl, 10% glycerol, 1% Triton X-1100, 1 mM ADP, 5 mM $MgCl_2$ and complete protease inhibitor, EDTA-free cocktail from Boehringer Mannhein. The ligand ADP/$Mg^{++}$ was maintained at this concentration in buffers of all subsequent purification steps. The cell lysate was centrifuged and the supernatant was applied to a $Ni^{++}$ chelating sepharose column which had been equilibrated in 50 mM HEPES, pH 7.5, 0.3 M NaCl. Tie-2 was eluted by competition with 100 mM imidazole. The eluted $(His)_6$ Tie-2 was digested with Tev protease and dialyzed against 50 mM HEPES, pH 7.5, 0.25 M NaCl, 5 mM DTT. The dialyzed sample was centrifuged to remove any precipitated protein, and Tie-2 was bound to a MonoQ anion exchange column and eluted with a linear 20 column volume gradient of 0.025-0.2 M NaCl. Typically, differences in the monodispersity of early eluting verses late eluting fractions could be detected using Dynamic Light Scattering (DLS). Sample purity was assessed with SDS-PAGE, native PAGE, and LC/MS total mass analysis. Fractions with similar DLS characteristics were pooled and concentrated to greater than 2 mg/ml using ultrafiltration at −80° C. The ultracentrifuged samples were used in crystallographic experiments described below. Table I lists a range of conditions suitable for crystallization.

Example 2

I. Diphosphorylated Tie-2 802-1124

A. Crystallization Conditions:

Tie-2802-1124 ($2PO_4$) protein was crystallized in a sitting or hanging drop geometry using a vapor diffusion method. The protein concentration was 5 mg/ml, and the well solution was 10% PEG 6,000; 0.1 M HEPES, pH 7.5; 5% MPD (2-methyl-2,4-pentanediol). Drops were set up using equal volumes of protein and well solution containing 500 μM inhibitor. Crystals routinely grew to 0.4 mm×0.1 mm×0.01 mm in about a week. Crystals were of the space group P2(1)2(1)2(1) with unit cell dimensions a=54.320 Å, b=75.872 Å, c=78.143 Å, and α=β=γ=90.0°. Table I list a range of conditions which are suitable for crystallization.

B. Data Collection

Data on ligand bound crystals were collected on a Rigaku RU300 rotating anode generator running at 50 kV 150 mA equipped with an R-Axis II phosphoimage plate detector. X-rays were monochromatized by long mirrors and filtered with a 0.0067 μm Nickel filter. Data were processed and reduced with DENZO and SCALEPACK (Minor, W. 1993). Data were collected to 3.5 Å resolution.

C. Data Processing

Programs in the CCP4 suite (Collaborative Computational Project, Number 4 1994) (tomtz, trunc, cad and ecalc) were used to format and process the data for molecular replacement. The molecular replacement program AMORE (Navaza, J. 1994) was used successfully to find phases for the data set using an initial model. The initial model was composed of the carboxy-terminal portion (residues 566-575 and 592-672) of the FGFR kinase domain trimmed back to poly-Alanine (PDB accession number 1FGK). A second round of AMORE with a more complete model (residues 464-485, 491-500, 505-575 and 592-762) was also performed to confirm the phasing solution.

D. Optimization of Model

Several round of least-squared minimization using CNS (Brunger, A. T. et al., 1998) alternating with manual rebuilding, using the graphics program O, version 6.2.1 (Jones, A., 1997; Kleywegt G. J., 1995) were performed iteratively to improve the model while comparing it to electron density maps generated after each round with coefficients 2fo-fc contoured at a level of 1.0 sigma.

II. Tie-2 (D964N) 802-1124 (SEQ ID NO 2)

A. Crystallization Conditions

Purified Tie-2 (D964N) 802-1124 protein was crystallized in a sitting drop geometry using the vapor diffusion method. The protein concentration was 2.5 mg/ml, and the well solution was 1.0 to 1.5 M ammonium sulfate, 0.1M MES, pH 6.5, 5% dioxane (1,4-dioxane). Drops were set up using equal volumes of protein and well solution containing 100-300 μM inhibitor. Crystals routinely grew to 0.3 mm×0.05 mm×0.01 mm in about 2-3 days. Crystals of Tie-2/inhibitor I were of the space group C222(1) with unit cell dimensions a=75.195 Å, b=116.287 Å, c=95.060 Å and α=β=γ=90.0°. Crystals of the Tie-2/inhibitor II, III or IV complex were of the space group P42212 with unit cell dimensions a=b=86.0 Å, c=112.0 Å and α=β=γ=90.0°.

B. Data Collection

Data on a ligand-bound crystal (Tie-2 (D964N) 802-1124) complexed with inhibitors I, II, III, or IV were collected at the beamline X25 at Brookhaven National Laboratory (Upton, N.Y.) equipped with the Brandeis B4, CCD detector. Data were processed and reduced with DENZO and SCALEPACK (Minor, W. 1993). Data for the Tie-2/inhibitor I complex were collected complete to 2.75 Å resolution, with higher resolution reflections visible to 2.0 Å resolution.

C. Data Processing

Programs in the CCP4 suite (Collaborative Computational Project, Number 4 1994) (tomtz, trunc, cad and ecalc) were used to format and process the data for molecular replacement. The molecular replacement program AMORE (Navaza, J. 1994) was used successfully to find phases for the data set using an initial model. The initial model was composed of the a conservative portion of the FGFR kinase domain (Tie2 residue numbering 818-830, 841-842, 850-857, 866-890, 900-916, 935-981, 1001-1093). The model, mostly poly-Alanine, was trimmed of loop regions which diverged upon superposition of five tyrosine kinase structures (IRK, HCK, SRC, FGFR, and LCK). In addition this model included only those side-chain residues in positions where an identical side-chain was found in the FGFR model.

D. Optimization of Model

Several round of least-squared minimization using CNS (Brunger, A. T. et al., 1998) alternating with manual rebuilding, using the graphics program O, version 6.2 (Jones, A., 1997; Kleywegt G. J., 1995) were performed to iteratively improve the model while comparing it to two electron density maps: one generated with coefficients 2fo-fc contoured at a level of 1.0 sigma and the other generated with coefficients fo-fc contoured at a level of 1.5 sigma.

E. Inhibitor Docking

Inhibitor I was found to be bound to the active site. It was initially docked by hand in O by visually inspecting the electron density maps and adjusting the torsion angles of the inhibitor. Parameter and topology files were generated for CNS using the X-util program xplo2d (Kleywegt G. J. and Jones, T. A. 1997) and modified slightly to properly model chlorine in the inhibitor.

III. Tie-2 (D964N) 802-1124 (SEQ ID NO 2)

A. Crystallization Conditions

The protein (construct Tie-2D964N) was provided in a buffer containing 25 mM HEPES, pH 7.5, 50 mM NaCl, 5 mM MgCl2, 1 mM ADP and 5 mM DTT. The protein concentration was about 2.3 mg/ml as determined with a Coomassie Plus assay, BSA as standard. The inhibitor III was dissolved in DMSO to give a 50 mM stock solution. Stock solution was added to the protein solution for a final inhibitor concentration of 2 mM. Crystallization conditions were screened with Hampton Screen Crystal screen, Crystal screen2, Membfac, Natrix and PEG/ion screen at room temperature and 4° C. Crystals grew with precipitation buffer: 20% PEG 3350, 0,2M tri-Lithium Citrat pH 8,1 (Hampton Screen PEG/ion screen, Nr. 45) sitting or hanging drop: 750 μl buffer in reservoir in the drop typically 1 μl-2 μl protein and 1 μl-2 μl reservoir solution were mixed.

Addition of the following additives (10% by volume to the drop) also yielded crystals:

| | |
|---|---|
| Add. Screen I Nr.:01 | 0.1 M Ba-Chloride |
| Add. Screen I Nr.:03 | 0.1 M Ca-Chloride |
| Add. Screen I Nr.:06 | 0.1 M Mg-Chloride |
| Add. Screen I Nr.:16 | 0.1 M Trimehylamine |
| Add. Screen I Nr.:22 | 30% Ethanol |
| Add. Screen II Nr.:08 | 30% Xylitol |
| Add. Screen II Nr.:13 | 30% 1,5 Diaminopentan-dihydrochloride |
| Add. Screen II Nr.:14 | 30% 1,8 Diaminooctane |
| Add. Screen II Nr.:17 | 0.1 M Hexaaminocobalt-trichloride |
| Add. Screen III Nr.:02 | 1.0 M Cesium-chloride |
| Add. Screen III Nr.:04 | 1.0 M Lihium-chloride |
| Add. Screen III Nr.:06 | 0.5 M Sodium-flouride |
| Add. Screen III Nr.:16 | 40% Acetonitrile |
| Add. Screen III Nr.:18 | 40% n-Propanol |
| Add. Screen Ill Nr.:19 | 5% Ethyl-acetate |
| Add. Screen III Nr.:20 | 40% Acetone |
| Add. Screen III Nr.:21 | 2,5% Dichlormethane |
| Add. Screen III Nr.:22 | 7% n-Butanol |
| Add. Screen III Nr.:24 | 0.1 M 1,4 Dithio-DL-threitol |

B. Data Collection:

Data were measured at the beam line BW 6 of the Max-Planck-Society at DESY, Hamburg.

The crystals were shock cooled to 100 K; cryobuffer was crystallization buffer plus 20-30% glycerol. 213 frames with delta phi=0.25 degrees were collected with a MAR CCD detector, at a crystal detector distance of 120 mm and a wavelength of 1.072 Å.

Crystals are of a tetragonal space group with unit cell dimensions a—b=86.0 Å and c=112.0 Å. The cell dimensions of different crystals vary (for a and b between 85 and 87 Å, for c between 97 and 113). Extinctions indicate the space group P42212 which was confirmed by molecular replacement.

TABLE II

Crystallization conditions for Tie-2/inhibitor complexes.

| Condition | Tie-2 802-1124 D964N | Tie-2 802-1124 (diphosphorylated) |
|---|---|---|
| Protein concentration | 2.5 mg/mL optimal<br>range 1.5-4 mg/mL<br>limits 1.0-5.0 mg/mL | 5 mg/mL optimal<br>range 2.5-10 mg/mL |
| Buffer concentration | 100 mM MES optimal<br>range 50-250 mM<br>Limits 20-300 mM | 100 mM HEPES optimal<br>Range 50-150 mM<br>Limits 20-300 mM |
| pH | 6.5 optimal<br>range 5.5-7.5 | 7.5 optimal<br>range 7.0-7.7<br>limits 6.5-8.0 |
| Buffer Identity | Buffers capable of buffering in a similar pH range expected to give similar results | (same) |
| Precipitant | $(NH_4)_2SO_4$<br>Range 1.0-1.5 M<br>Limits 0.7-1.8 M | 10% PEG 6000 optimal<br>conc. range 5-15%<br>conc. limits 1-20% |

TABLE II-continued

Crystallization conditions for Tie-2/inhibitor complexes.

| Condition | Tie-2 802-1124 D964N | Tie-2 802-1124 (diphosphorylated) |
|---|---|---|
| Additive parameters | 5% 1,4-dioxane optimal range 0-10% (higher concentrations etch the plastic vessel in which the experiment is done; higher concentrations may be possible in a resistant vessel) 1,3-dioxane, similar molecules, or mixtures in various ratios should also give similar results | MW range 4000-8000 MW limits may be much wider 5% MPD (2-Me-2,4-pentanediol) optimal range 0-10% |
| Additive identities | Examples which have been successfully added: 1,5-diaminopentane Glycerol (1-10%) Ethylene glycol (1-10%) Spermidine (10-300 mM) Combinations, in varying ratios, may give similar results | (same) |
| Drop volumes and ratios | 2 μL protein + 2 μL well solution optimal Total volume range: up to 200 μL, assuming a sitting geometry for larger volumes Volume Ratio range: 1 part protein to 0.5-2.0 parts well solution | (same) |
| Well volume (for 4 μL crystallization drop) | Range 500-1000 μL Limits 250 - large volume (limited by the distance between the drop and the surface of the well solution allowed by the vessel geometry, see below) | (same) |
| Drop - well solution distance | 2 cm optimal Range 1-4 cm Limits: 0.1 cm-5 cm | (same) |
| Temperature | room temp optimal (22-25° C.) limits 17-30° C. | (same) |
| Ligands | ADP/$Mg^{2+}$ and analogs Inhibitors: inhibitors I-IV, analogs Expect similar results from ligands that bind reversibly under crystallization conditions with $K_d$ values < 1 mM | (same) |
| Constructs | Variants in amino acid sequence that crystallize in the same space group and unit cell should be considered equivalent Additional constructs would include deletion of unstructured termini as determined by crystal structure of this construct. For example, deletion of the C-terminal 24 residues (leaving 802-1100 has been prepared, which is likely to yield similar results | (same) |
| Posttranslational modification | Variants in posttranslational modification that crystallize in the same space group and unit cell should be considered equivalent | 2 phosphate forms have been crystallized. This protein contains one phosphate on either Y897 or Y899 and one on one of five Tyr residues, at amino acids 1012, 1015, 1024, 1040, and 1048 Other phosphorylated forms may give similar results. A single phosphate species has been observed in which the phosphate is on either Y897 or Y899 has also been isolated. In addition, 3 and 4 phosphate species have been isolated which may crystallize. |
| Space group | C222(1) | P2(1)2(1)2(1) |

TABLE II-continued

Crystallization conditions for Tie-2/inhibitor complexes.

| Condition | Tie-2 802-1124 D964N | Tie-2 802-1124 (diphosphorylated) |
|---|---|---|
| Unit cell | a = 75.195 Å, b = 116.287 Å, c = 95.060 Å<br>Variations of ±2% should be considered equivalent<br>Angles: a = b = c = 90°<br>Observed variations of ±1% should be considered equivalent | a = 54.320 Å, b = 75.872 Å, c = 78.143 Å<br>Variations of ±2% should be considered equivalent<br>Angles: a = b = c = 90°<br>Observed variations of ±1% should be considered equivalent |
| Other crystallization tricks that should give at least equivalent results | Low gravity<br>Temperature oscillations<br>Presence of cryoprotectant (15-25% glycerol added before data collection)<br>Variations in crystallization tray geometry<br>Data collection temperature (range: minus 180 to plus 25° C.) | (same) |

REFERENCES

Brunger, A. T., Adams, P. D., Clore, G. M., DeLano, W. L. Gros, P. Grosse-Kunstleve, R. W., Jiang, J-S., Kuszewski, J., Nigels, M., Pannu, N. S., Read, R. J., Rice, L. M., Simonson, T., and Warren, G. L. (1998) *Acta Cryst., D*54, 905-921.

Collaborative Computational Project, Number 4 (1994) The CCP4 Suite: Programs for Protein Crystallography. *Acta Crys.t D*50, 760-763.

Jones, A. T and Kjeldgaard, M. (1997) Methods in Enzymology 277, 173-208.

Kleywegt G. J. and Jones, T. A. (1997) Methods in Enzymology 277, 525-545.

Kleywegt G. J., (1995) ESF/CCP4 Newsletter 31, 45-50.

Minor, W. XDISPLAYF program, Purdue University (1993)

Navaza, J. (1994) *Acta Cryst. A*50, 157-163.

Example 3

In Vitro Potency Test of Tie-2 Inhibitors

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature.* 373:536-539) by a test compound relative to control.

Human Tie-2 Kinase Production and Purification

The coding sequence for the human Tie-2 intra-cellular domain (aa775-1124) was generated through PCR using cDNAs isolated from human placenta as a template. A poly-His$_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

EGFR Tyrosine Kinase Source

EGFR was purchased from Sigma (Cat # E-3641; 500 units/50 1) and the EGF ligand was acquired from Oncogene Research Products/Calbiochem (Cat # PF011-100).

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology,* 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those skilled in the art. For purposes of determining inhibitor selectivity, a universal PTK substrate (e.g., random copolymer of poly(Glu$_4$ Tyr), 20,000-50,000 MW) was employed together with ATP (typically 5 µM) at concentrations approximately twice the apparent Km in the assay.

The following procedure was used to assay the inhibitory effect of compounds of this invention on Tie-2 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 g/ml in Gibco PBS.

Reaction Buffer: 100 mM Hepes, 20 mM MgCl$_2$, 4 mM MnCl$_2$, 5 mM DTT, 0.02% BSA, 200 µM NaVO$_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 μg/ml. Add 125 μl per well of Corning modified flat bottom high affinity ELISA plates (Corning #25805-96). Add 125 μl PBS to blank wells. Cover with sealing tape and incubate overnight 37° C. Wash 1× with 250 μl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.
Prepare reaction buffer
Prepare enzyme solution so that desired units are in 50 μl, e.g. for KDR make to 1 ng/l for a total of 50 ng per well in the reactions. Store on ice.
Make 4×ATP solution to 20 μM from 100 mM stock in water. Store on ice
Add 50 μl of the enzyme solution per well (typically 5-50 ng enzyme/well depending on the specific activity of the kinase)
Add 25 μl 4×inhibitor
Add 25 μl 4×ATP for inhibitor assay
Incubate for 10 minutes at room temperature
Stop reaction by adding 50 μl 0.05N HCl per well
Wash plate
**Final Concentrations for Reaction: 5 μM ATP, 5% DMSO 3. Antibody Binding Dilute 1 mg/ml aliquot of PY20-HRP (Pierce) antibody (a phosphotyrosine antibody) to 50 ng/ml in 0.1% BSA in PBS by a 2 step dilution (100×, then 200×)
Add 100 μl Ab per well. Incubate 1 hr at room temp. Incubate 1 hr at 4C.
Wash 4× plate 4. Color Reaction Prepare TMB substrate and add 100 μl per well
Monitor OD at 650 nm until 0.6 is reached
Stop with 1M Phosphoric acid. Shake on plate reader.
Read OD immediately at 450 nm
Optimal incubation times and enzyme reaction conditions vary slightly with enzyme preparations and are determined empirically for each lot.

Example 4

Cellular Assay for Determining the Potency of Tie-2 Inhibitors

The following cellular assay can be used to determine the potency of a Tie-2 inhibitor.

"NIH-3T3/hTEK Cell Line:

A retroviral expression vector containing the fill length Tie-2 cDNA, LNCX6 h-TEK, was kindly provided to us by Dr. Kevin Peters. A tumorigenic subline of NIH 3T3 cells was transfected with 10 ig of LNCX6 h-TEK by calcium phosphate precipitation method and selected with 400 ig/ml neomycin. Individual clones were isolated and analyzed for the presence of Tie-2 protein by Western blotting. Maximum expression of Tie-2 was observed in clone #67. Expression of Angiopoietin 1 message has been shown using PCR and an autocrine loop is revealed in the presence of vanadate Cellular Tie-2 Assay:

Tie-2 cellular autophosphorylation was measured using the NIH-3T3/hTEK (hTEK) cell line. Cells were seeded in 96 well plates overnight. The media was removed and cells treated with inhibitor for 20 minutes and phosphotase inhibitor NaVO$_3$ (2 mM) for 15 more minutes. Cells were lysed with RIPA buffer and lysates were immunoprecipitated using a specific a-Tie-2 monoclonal antibody (KP33, provided by Dr. Kevin Peters) and the IP'd protein run on SDS PAGE. The phosphotyrosine level on Tie2 protein were then determined by a-phosphotyrosine antibodies (4G10, Upstate Biotechnology) on Western blots. Films were scanned and % inhibition as compared to untreated control was determined."

Equivalents

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a compound which is a potential inhibitor of a Tie-2 protein, said method comprising the steps of:
   (a) crystallizing a crystal of a polypeptide consisting of the catalytic domain of a Tie-2 protein as defined in FIG. 2;
   (b) obtaining the atomic coordinates of the crystal of the polypeptide;
   (c) using said atomic coordinates to define the active subsites of Tie-2; and
   (d) identifying a compound which binds to one or more active subsites;
   wherein the compound which binds to the active subsite or sites is a potential inhibitor of a Tie-2 protein.

2. The method of claim 1, further comprising the step of:
   (d) assessing the ability of the compound identified in step (c) to inhibit Tie-2.

3. The method of claim 1, wherein the Tie-2 protein is a mammalian protein.

4. The method of claim 2, wherein the Tie-2 protein is a human protein.

5. The method of claim 4, wherein the Tie-2 protein is wild type human Tie-2.

6. The method of claim 1, wherein said crystal further comprises a ligand bound to said catalytic domain.

7. The method of claim 4, wherein the polypeptide comprises amino acids 802-1124 of SEQ ID NO: 1.

8. The method of claim 4, wherein the compound is of the formula:

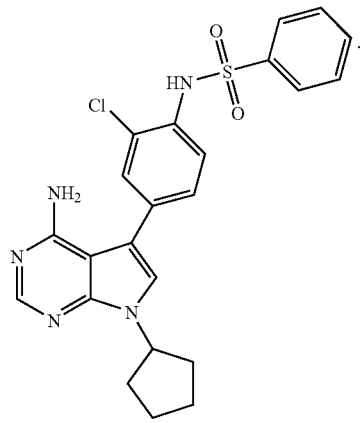

9. The method of claim 8, wherein the crystal has unit cell parameters wherein a is about 96 Å, b is about 118 Å, c is about 78 Å and $\alpha=\beta=\gamma=90°$.

10. The method of claim 4, wherein the compound is of the formula:

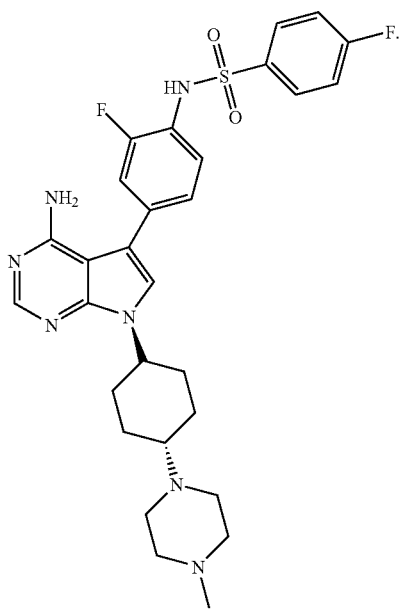

11. The method of claim 10, wherein the crystal has unit cell parameters wherein a and b are about 86.0 Å, c is about 112.0 Å and $\alpha=\beta=\gamma=90°$.

12. The method of claim 4, wherein the compound is of the formula:

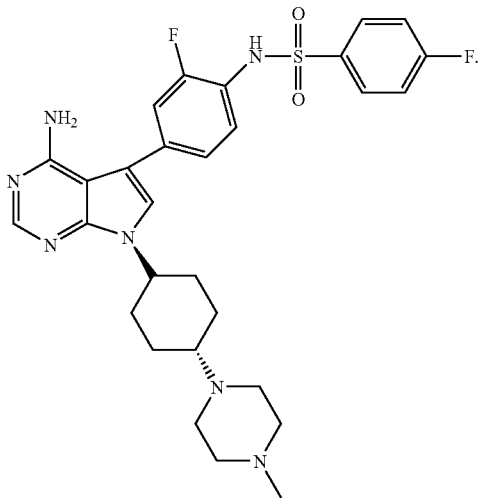

13. The method of claim 12, wherein the crystal has unit cell parameters wherein a and b are about 86.0 Å, and c is about 112 Å and $\alpha=\beta=\gamma=90°$.

14. The method of claim 4, wherein the compound is of the formula:

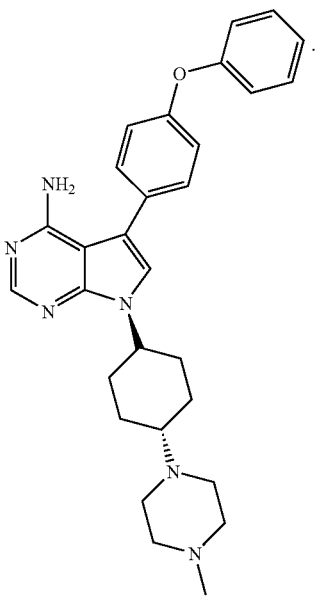

15. The method of claim 14, wherein the crystal has unit cell parameters wherein a and b are about 86.0 Å, and c is about 112 Å and $\alpha=\beta=\gamma=90°$.

* * * * *